US012747245B2

(12) United States Patent
Jaquith

(10) Patent No.: US 12,747,245 B2
(45) **Date of Patent: *Sep. 29, 2026**

150

(54) AP2 ASSOCIATED KINASE 1 INHIBITORS AND USES THEREOF

(71) Applicant: Satellos Bioscience Inc., Toronto (CA)

(72) Inventor: James Brian Jaquith, Cobourg (CA)

(73) Assignee: Satellos Bioscience Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 19/204,186

(22) Filed: May 9, 2025

(65) Prior Publication Data

US 2025/0270222 A1 Aug. 28, 2025

Related U.S. Application Data

(63) Continuation of application No. PCT/US2024/045579, filed on Sep. 6, 2024.

(60) Provisional application No. 63/537,405, filed on Sep. 8, 2023.

(51) Int. Cl.
*C07D 487/04* (2006.01)
*A61K 31/5025* (2006.01)
*A61K 31/519* (2006.01)
*C07D 519/00* (2006.01)

(52) U.S. Cl.
CPC ........ *C07D 487/04* (2013.01); *A61K 31/5025* (2013.01); *A61K 31/519* (2013.01); *C07D 519/00* (2013.01)

(58) Field of Classification Search
CPC .. C07D 487/04; C07D 519/00; A61K 31/519; A61K 31/5025
See application file for complete search history.

(56) References Cited

U.S. PATENT DOCUMENTS

| | | | |
|---|---|---|---|
| 4,522,811 | A | 6/1985 | Eppstein et al. |
| 8,946,415 | B2 | 2/2015 | Bi et al. |
| 8,969,565 | B2 | 3/2015 | Bi et al. |
| 9,403,832 | B2 | 8/2016 | Bi et al. |
| 9,682,982 | B2 | 6/2017 | Bi et al. |
| 9,862,724 | B2 | 1/2018 | Bi et al. |
| 2010/0029657 | A1 | 2/2010 | Levin et al. |
| 2016/0039824 | A1 | 2/2016 | Bi et al. |
| 2017/0129896 | A1 | 5/2017 | Bi et al. |
| 2020/0038485 | A1 | 2/2020 | Rudnicki et al. |
| 2023/0203041 | A1 | 6/2023 | McCarthy et al. |
| 2025/0122207 | A1 | 4/2025 | Jaquith |

FOREIGN PATENT DOCUMENTS

| | | | |
|---|---|---|---|
| WO | WO-2007044401 | A2 | 4/2007 |
| WO | WO-2009108838 | A1 | 9/2009 |
| WO | WO-2010118207 | A1 | 10/2010 |
| WO | WO-2013134036 | A1 | 9/2013 |
| WO | WO-2013134219 | A1 | 9/2013 |
| WO | WO-2013134228 | A1 | 9/2013 |
| WO | WO-2013134336 | A2 | 9/2013 |
| WO | WO-2014022167 | A1 | 2/2014 |
| WO | WO-2014130258 | A1 | 8/2014 |
| WO | WO-2015006100 | A1 | 1/2015 |
| WO | WO-2015026574 | A1 | 2/2015 |
| WO | WO-2015035117 | A1 | 3/2015 |
| WO | WO-2015035167 | A1 | 3/2015 |
| WO | WO-2015038112 | A1 | 3/2015 |
| WO | WO-2015054358 | A1 | 4/2015 |
| WO | WO-2015116060 | A1 | 8/2015 |
| WO | WO-2015116492 | A1 | 8/2015 |
| WO | WO-2015142714 | A1 | 9/2015 |
| WO | WO-2015153720 | A1 | 10/2015 |
| WO | WO-2016022312 | A1 | 2/2016 |
| WO | WO-2016164295 | A2 | 10/2016 |
| WO | WO-2017059085 | A1 | 4/2017 |
| WO | WO-2018098500 | A1 | 5/2018 |
| WO | WO-2021216442 | A1 | 10/2021 |
| WO | WO-2021216454 | A1 | 10/2021 |
| WO | WO-2023134692 | A1 | 7/2023 |
| WO | WO-2023230523 | A1 | 11/2023 |
| WO | WO-2025054448 | A1 | 3/2025 |

OTHER PUBLICATIONS

Kostich, et al., Inhibition of AAK1 Kinase as a Novel Therapeutic Approach to Treat Neuropathic Pain, J. Pharmacol. And Exp. Ther., 358:371-386 (2016) (Year: 2016).*
Charge and Rudnicki, "Cellular and molecular regulation of muscle regeneration." Physiol Rev. Jan. 2004; 84(1): 209-38. doi: 10.1152/physrev.00019.2003.
U.S. Appl. No. 18/868,700, filed Nov. 22, 2024, by Rudnicki; Michael A. et al.
Dumont, N. A., et al., "Dystrophin expression in muscle stem cells regulates their polarity and asymmetric division." Nat Med, 2015. 21(12): p. 1455-1463.

(Continued)

*Primary Examiner* — Erich A Leeser
(74) *Attorney, Agent, or Firm* — COOLEY LLP

(57) ABSTRACT

Provided herein are compounds of Formula (I) having the structure:

(I)

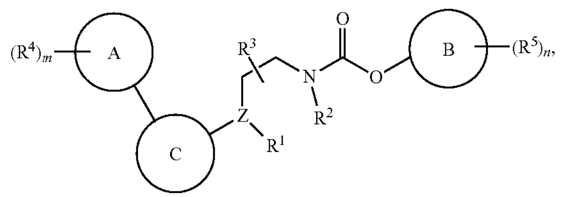

or a pharmaceutically acceptable salt, deuterated form, stereoisomer, or composition thereof, that can be used to treat or manage a disease or a disorder mediated by AAK1 activity, such as a muscular dystrophy, in a subject in need thereof.

37 Claims, No Drawings

(56) References Cited

OTHER PUBLICATIONS

Hammers, D. W., et al., "The D2.mdx mouse as a preclinical model of the skeletal muscle pathology associated with Duchenne muscular dystrophy." Sci Rep. Aug. 21, 2020; 10(1): 14070. doi: 10.1038/s41598-020-70987-y, 12 pages.
Hartz et al., "Discovery, Structure-Activity Relationships, and In Vivo Evaluation of Novel Aryl Amides as Brain Penetrant Adaptor Protein 2-Associated Kinase 1 (AAK1) Inhibitors for the Treatment of Neuropathic Pain." J Med Chem. Aug. 12, 2021; 64(15): 11090-11128. doi: 10.1021/acs.jmedchem.1c00472. Epub Jul. 16, 2021.
Hesselink, "LX9211 A Selective Inhibitor of AAK1 (Adapter-Associated Kinase) for Neuropathic Pain? Some Thoughts on Selectivity and Specificity." Austin Neurol. 2018; 3(1): 1013. 3 pages.
International Preliminary Report on Patentability for PCT Application No. PCT/US2023/067421 mailed Dec. 5, 2024, 8 pages.
International Search Report and Written Opinion for PCT Application No. PCT/US2023/067421 dated Oct. 2, 2023, 12 pages.
International Search Report and Written Opinion for PCT Application No. PCT/US2024/045579 mailed Dec. 20, 2024, 11 pages.
Invitation to pay additional fees for International Application No. PCT/US2024/045579, mailed Oct. 31, 2024, 3 pages.
Kostich, W., et al. "Inhibition of AAK1 Kinase as a Novel Therapeutic Approach to Treat Neuropathic Pain." J Pharmacol Exp Ther. Sep. 2016;358(3):371-86. doi: 10.1124/jpet.116.235333. Epub Jul. 13, 2016.
Martinez-Gualda, B., et al., "A patent review of adaptor associated kinase 1 (AAKI) inhibitors (2013-present)." Expert Opin Ther Pat. Oct. 2021;31(10):911-936. doi:10.1080/13543776.2021.1928637. Epub May 21, 2021.
Seno et al., "Transcriptomic analysis of dystrophin RNAi knockdown reveals a central role for dystrophin in muscle differentiation and contractile apparatus organization." BMC Genomics. Jun. 1, 2010:11:345. doi: 10.1186/1471-2164-11-345, 12 pages.
Swiderski and Lynch, "Murine models of Duchenne muscular dystrophy: is there a best model?" Am J Physiol Cell Physiol. Aug. 1, 2021; 321(2): C409-C412. doi: 10.1152/ajpcell.00212.2021. Epub Jul. 14, 2021.
Verdonck, S., et al. "Synthesis and Structure-Activity Relationships of 3,5-Disubstituted-pyrrolo[2,3- b]pyridines as Inhibitors of Adaptor-Associated Kinase 1 with Antiviral Activity." J Med Chem. Jun. 27, 2019; 62(12): 5810-5831. doi: 10.1021/acs.jmedchem.9b00136. Epub Jun. 12, 2019.
Wang, Y. X., et al., "EGFR-Aurka Signaling Rescues Polarity and Regeneration Defects in Dystrophin-Deficient Muscle Stem Cells by Increasing Asymmetric Divisions." Cell Stem Cell, 2019. 24(3): p. 419-432 e6.
Wells, C., et al., "SGC-AAK1-1: A Chemical Probe Targeting AAK1 and BMP2K." ACS Med Chem Lett. Oct. 23, 2019; 11(3): 340-345. doi: 10.1021/acsmedchemlett.9b00399. eCollection Mar. 12, 2020.

* cited by examiner

AP2 ASSOCIATED KINASE 1 INHIBITORS AND USES THEREOF

CROSS-REFERENCE TO RELATED APPLICATIONS

The present application is a continuation of International Patent Application No. PCT/US2024/045579, filed Sep. 6, 2024, which claims the benefit of priority to U.S. Provisional Application No. 63/537,405, filed Sep. 8, 2023, each of which is incorporated herein by reference in its entirety.

FIELD OF INVENTION

This disclosure relates to compounds and compositions for use in promoting muscle cell/tissue regeneration and treating muscle tissue injuries and muscle diseases, such as muscular dystrophies.

BACKGROUND

Muscular diseases and disorders, both developmental and degenerative, can cause the gradual or sudden loss of muscular function due to the decline or death of muscle cells, as well as lessened muscular development over time. Congenital myopathies are examples of muscular diseases that present these characteristics. Muscular dystrophies, which are a group of muscle diseases caused by one or more genetic mutations, cause progressive weakness and degeneration of skeletal muscles. FDA-approved therapies for treating Duchenne muscular dystrophy are available, but these options are limited to patients with specific mutations in the disease's causative gene and only slow disease progression. Thus, there is a need in the art for new therapies that target different mechanisms, treat the various types of muscle loss, and improve outcomes in broader patient populations, e.g., by regenerating muscle and reversing the level of disability.

SUMMARY OF THE INVENTION

To address these and other unmet needs, the present disclosure provides compounds and compositions useful in treating or managing muscular diseases or disorders, including muscular diseases and disorders that are mediated by AAK1 activity.

In some embodiments, the present disclosure provides a compound of Formula (I):

(I)

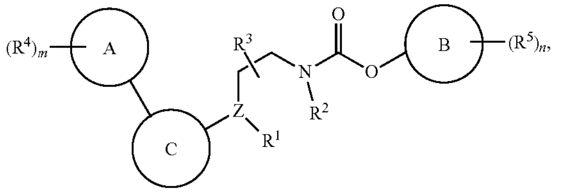

or pharmaceutically acceptable salt, deuterated form, or stereoisomer thereof, wherein:

Ⓐ is phenyl or heteroaryl;

Ⓑ is heterocyclyl;

Ⓒ is

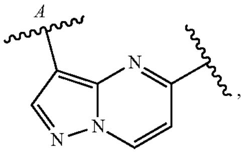,

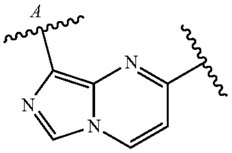, or

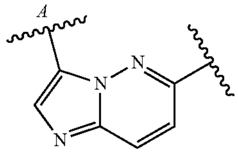;

Z is CH or N;

$R^1$ and $R^2$ are each independently H or $C_{1-6}$ alkyl, or $R^1$ and $R^2$ taken together with the atoms to which they are attached form a 5- or 6-membered heterocyclyl;

$R^3$ is H, halogen, $C_{1-6}$ alkyl, —CN, or —$COR^a$, or an $R^1$ and $R^3$ taken together with the atoms to which they are attached form a 5- or 6-membered heterocyclyl;

each $R^4$ is independently halogen, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, $C_{1-6}$ alkyl, $C_{1-6}$ heteroalkyl, O—$C_{1-6}$ alkyl, heterocyclyl, $C_{1-5}$ alkylene-cycloalkyl, or $C_{1-5}$ alkylene-heterocyclyl, or two $R^5$ form an oxo;

$R^a$ is —OH, —O—($C_{1-6}$ alkyl), —$NH_2$, —NH—($C_{1-6}$ alkyl), or —NH—($C_{1-6}$ alkyl) z;

m is 0, 1, 2, or 3; and n is 0, 1, or 2, provided that the compound is not:

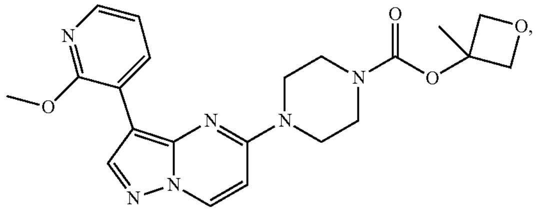

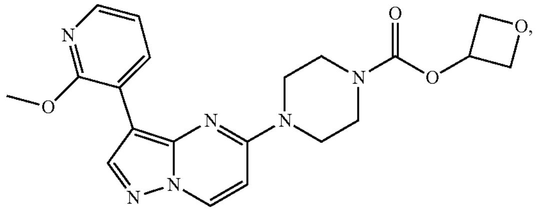

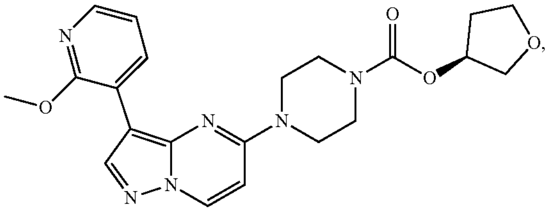

-continued

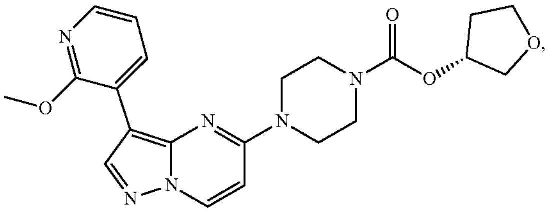

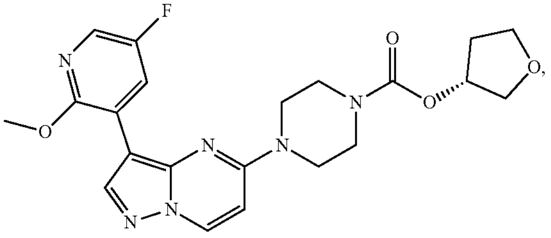

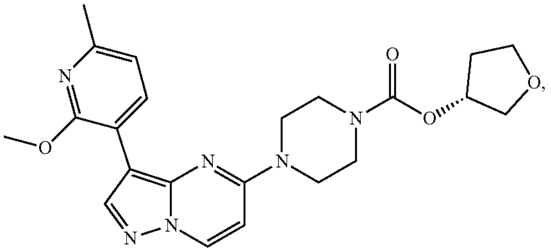

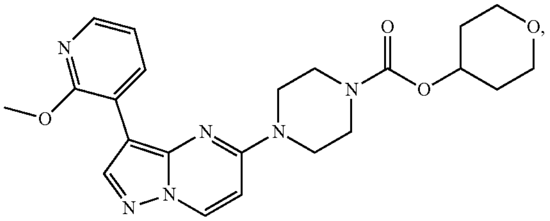

or

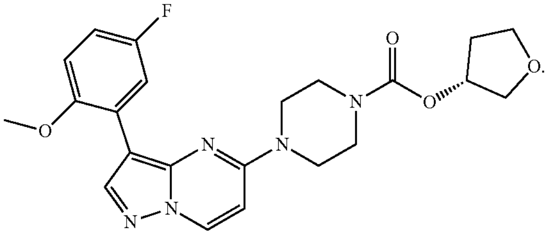

In some embodiments, Ⓒ is

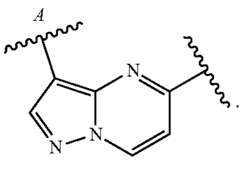

In some embodiments, the present disclosure provides compound of Formula (IA):

(IA)

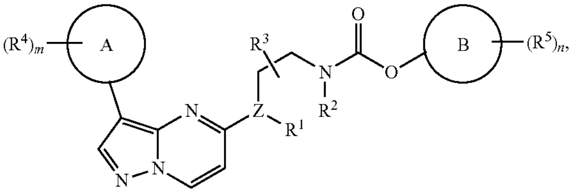

or pharmaceutically acceptable salt, deuterated form, or stereoisomer thereof, wherein:

Ⓐ is phenyl or N-heteroaryl;

Ⓑ is heterocyclyl;

Z is CH or N;

$R^1$ and $R^2$ are each independently H or $C_{1-6}$ alkyl, or an $R^1$ and $R^2$ taken together with the atoms to which they are attached for a 5- or 6-membered heterocyclyl;

$R^3$ is H, halogen, $C_{1-6}$ alkyl, CN, or $COR^a$;

each $R^4$ is independently halogen, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, $C_{1-6}$ alkyl, $C_{1-6}$ heteroalkyl, O—$C_{1-6}$ alkyl, heterocyclyl, $C_{1-5}$ alkylene-cycloalkyl, or $C_{1-5}$ alkylene-heterocyclyl, or two $R^5$ form an oxo;

$R^a$ is —OH, —O—$C_{1-6}$ alkyl, —$NH_2$, —NH—($C_{1-6}$ alkyl), or —N($C_{1-6}$ alkyl)$_2$;

m is 0, 1, 2, or 3; and n is 0, 1, or 2, provided that the compound is not:

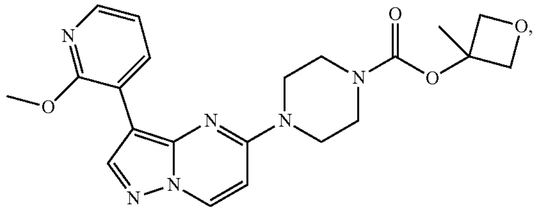

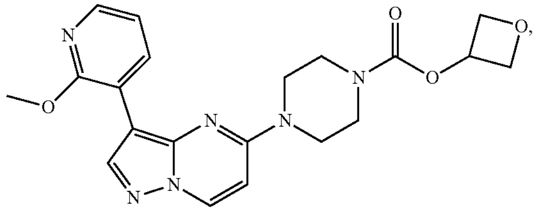

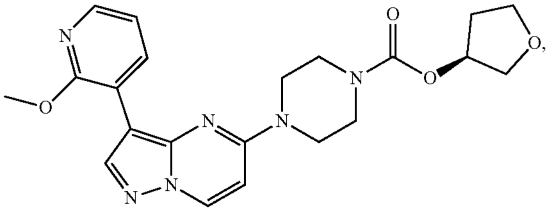

-continued

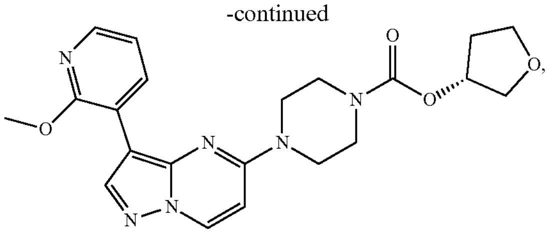

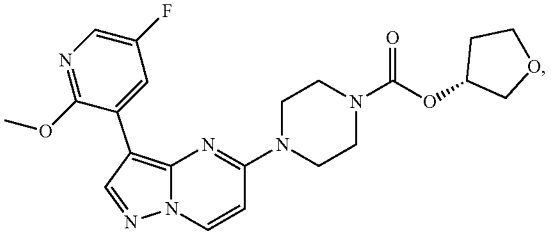

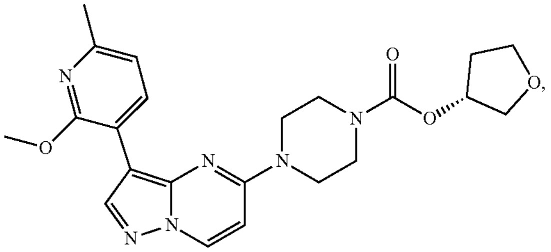

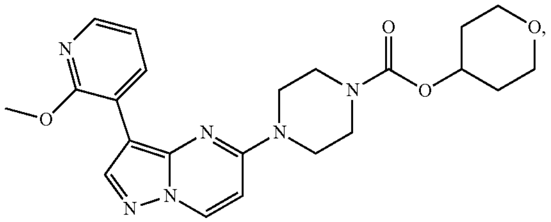

or

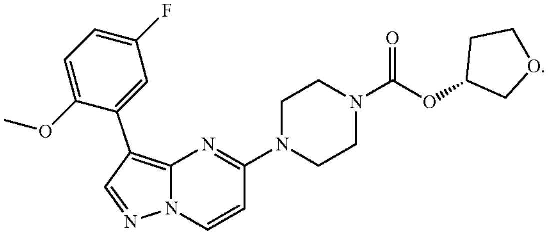

In some embodiments, the present disclosure provides a compound of Formula (IA-1):

(IA-1)

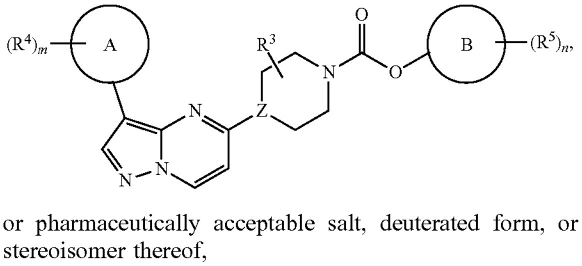

or pharmaceutically acceptable salt, deuterated form, or stereoisomer thereof, wherein:

Ⓐ is phenyl or N-heteroaryl;

Ⓑ is heterocyclyl;

Z is CH or N;

$R^3$ is H, halogen, $C_{1-6}$ alkyl, CN, or $COR^a$;

each $R^4$ is independently halogen, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, alkyl, $C_{1-6}$ heteroalkyl, O—$C_{1-6}$ alkyl, heterocyclyl, $C_{1-5}$ alkylene-cycloalkyl, or $C_{1-5}$ alkylene-heterocyclyl, or two $R^5$ form an oxo;

$R^a$ is —OH, —O—($C_{1-6}$ alkyl), —$NH_2$, —NH—($C_{1-6}$ alkyl), or —N($C_{1-6}$ alkyl)$_2$;

m is 0, 1, 2, or 3; and n is 0, 1, or 2, provided that the compound is not:

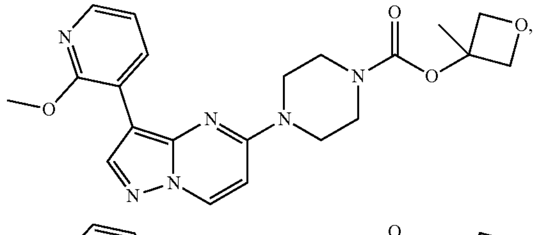

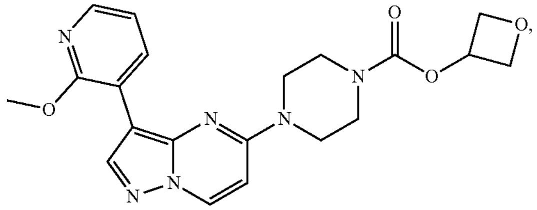

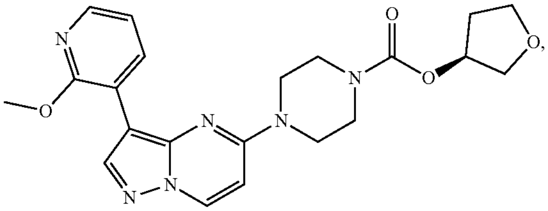

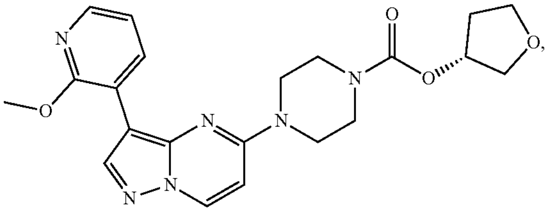

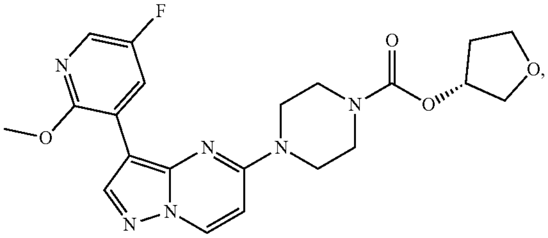

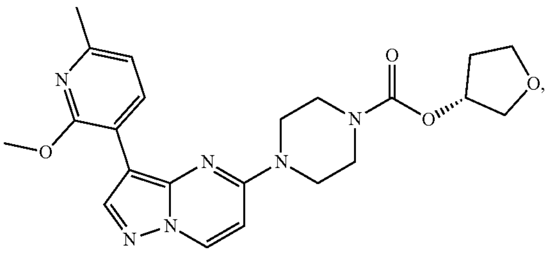

-continued

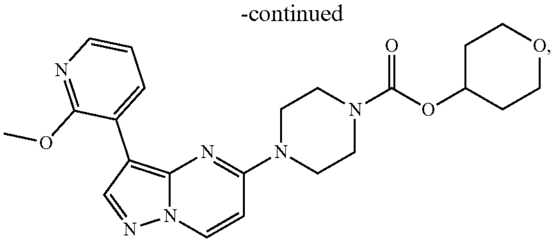

or

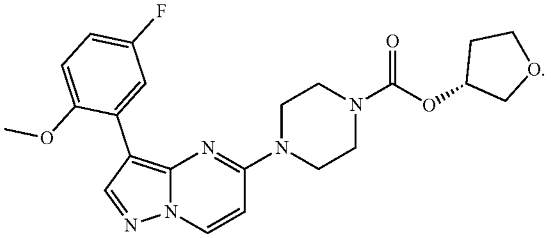

In some embodiments, the present disclosure provides a compound of Formula (IA-2):

(IA-2)

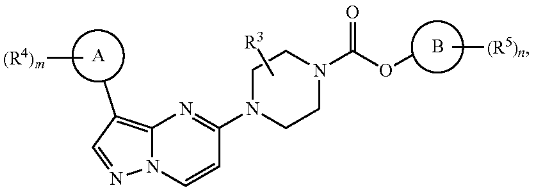

or pharmaceutically acceptable salt, deuterated form, or stereoisomer thereof, wherein:

Ⓐ is phenyl or N-heteroaryl;

Ⓑ is heterocyclyl;

$R^3$ is H, halogen, $C_{1-6}$ alkyl, CN, or $COR^a$;

each $R^4$ is independently halogen, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, $C_{1-6}$ alkyl, $C_{1-6}$ heteroalkyl, O—$C_{1-6}$ alkyl, heterocyclyl, $C_{1-5}$ alkylene-cycloalkyl, or $C_{1-5}$ alkylene-heterocyclyl, or two $R^5$ form an oxo;

$R^a$ is —OH, —O—$C_{1-6}$ alkyl, —$NH_2$, —NH—($C_{1-6}$ alkyl), or —N($C_{1-6}$ alkyl)$_2$;

m is 0, 1, 2, or 3; and n is 0, 1, or 2, provided that the compound is not:

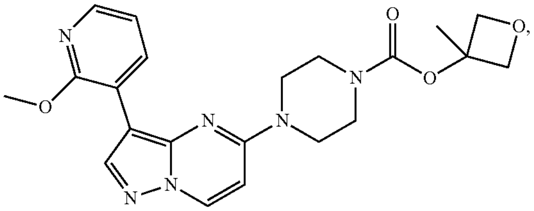

-continued

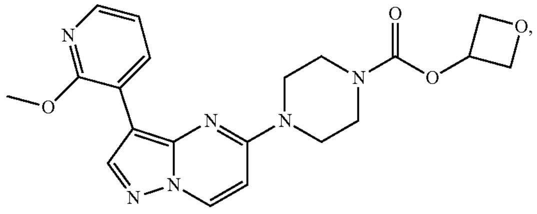

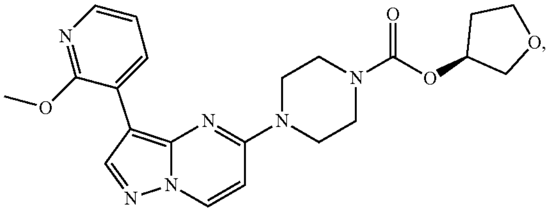

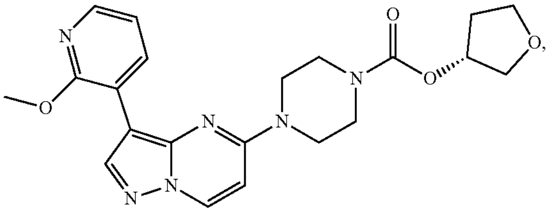

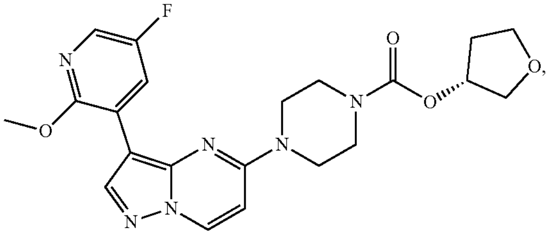

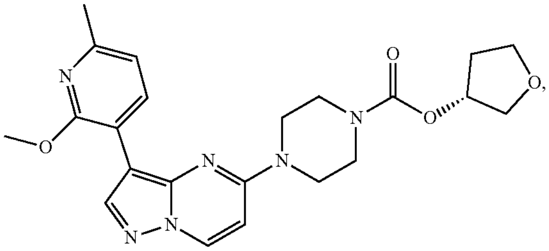

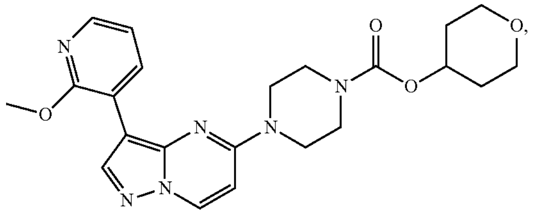

or

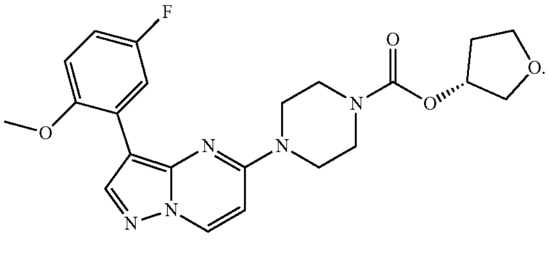

In some embodiments, (A) is:

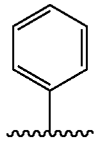, 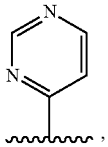, 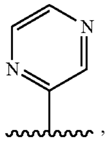, or 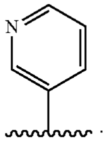.

In come embodiments, the present disclosure provides a compound of Formula (IA-3):

(IA-3)

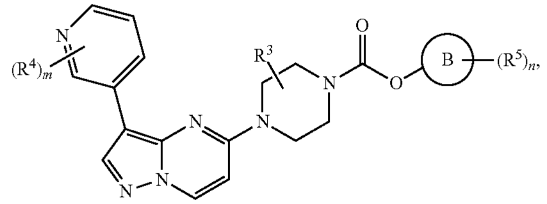

or pharmaceutically acceptable salt, deuterated form, or stereoisomer thereof, wherein:

(B) is heterocyclyl;

$R^3$ is H, halogen, $C_{1-6}$ alkyl, CN, or $COR^a$;

each $R^4$ is independently halogen, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, $C_{1-6}$ alkyl, $C_{1-6}$ heteroalkyl, O—$C_{1-6}$ alkyl, heterocyclyl, $C_{1-5}$ alkylene-cycloalkyl, or $C_{1-5}$ alkylene-heterocyclyl, or two $R^5$ form an oxo;

$R^a$ is —OH, —O—$C_{1-6}$ alkyl, —$NH_2$, —NH—($C_{1-6}$ alkyl), or —N($C_{1-6}$ alkyl)$_2$;

m is 0, 1, 2, or 3; and n is 0, 1, or 2, provided that the compound is not:

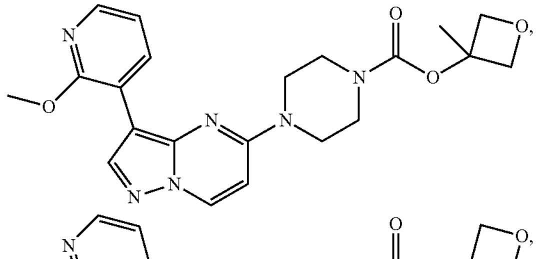

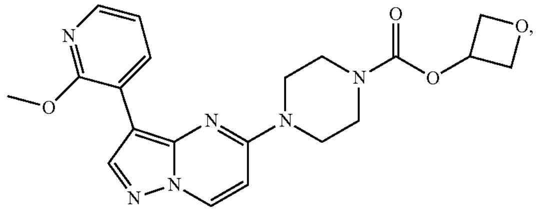

-continued

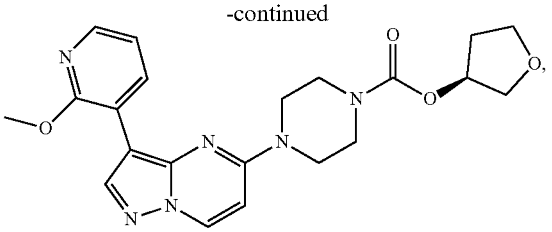

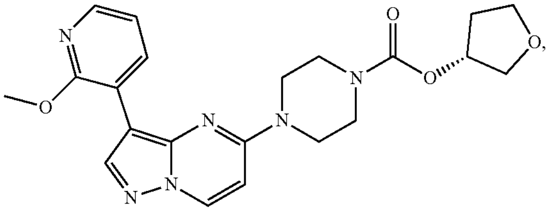

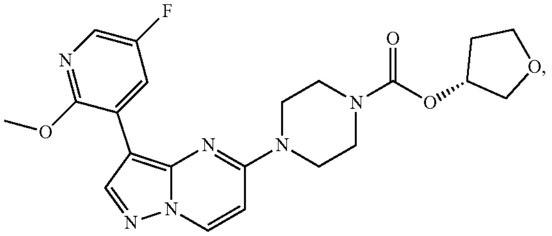

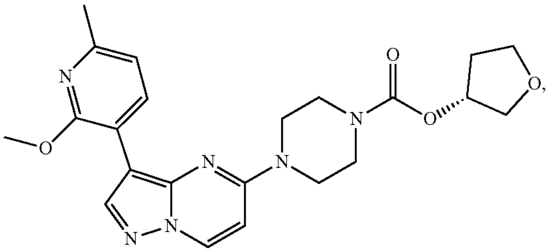

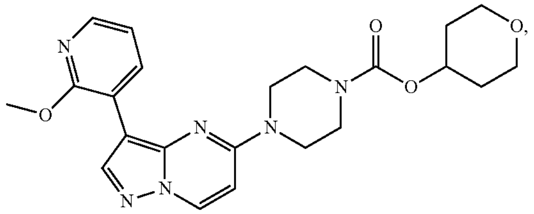 or

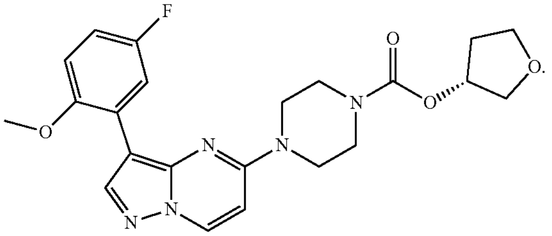

In some embodiments, (B) is N-heterocyclyl or a bicyclic ether. In some embodiments, (B) is N-heterocyclyl. In some embodiments, (B) is

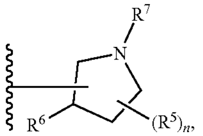

wherein each $R^5$ is independently halogen, $C_{1-6}$ alkyl, $C_{1-6}$ heteroalkyl, O—$C_{1-6}$ alkyl, $C_{1-5}$ alkylene-cycloalkyl, or $C_{1-5}$ alkylene-heterocyclyl, or two $R^5$ taken together form an oxo; $R^6$ is H, $C_{1-6}$ alkyl, $C_{2-6}$ alkenyl, or $C_{2-6}$ alkynyl; $R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, $C_{1-5}$ alkylene-C(O)—NH—($CH_2Ph$), or 4- to 8-membered heterocyclyl; and n is 0, 1, or 2.

In some embodiments, the present disclosure provides a compound of Formula (IA-4):

(IA-4)

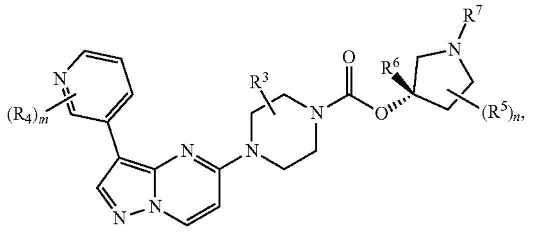

or pharmaceutically acceptable salt or deuterated form thereof, wherein:

$R^3$ is H, halogen, $C_{1-5}$ alkyl, —CN, or —COR$^a$;

each $R^4$ is independently halogen, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently H, halogen, $C_{1-6}$ alkyl, $C_{1-6}$ heteroalkyl, O—$C_{1-6}$ alkyl, $C_{1-5}$ alkylene-cycloalkyl, or $C_{1-5}$ alkylene-heterocyclyl, or two $R^5$ form an oxo;

$R^6$ is H, $C_{1-6}$ alkyl, $C_{2-6}$ alkenyl, or $C_{2-6}$ alkynyl;

$R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl;

$R^a$ is —OH, —O—$C_{1-6}$ alkyl, —$NH_2$, —NH—($C_{1-6}$ alkyl), or —N($C_{1-6}$ alkyl)$_2$;

m is 0, 1, 2, or 3; and n is 0, 1, or 2.

In some embodiments, the present disclosure provides a compound of Formula (IA-5):

(IA-5)

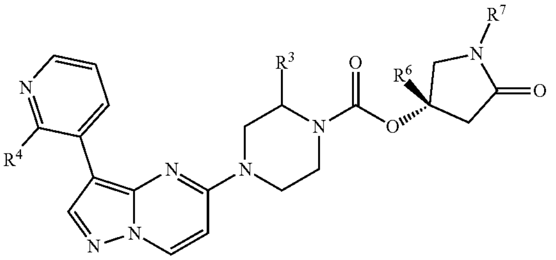

or pharmaceutically acceptable salt or deuterated form thereof, wherein:

$R^3$ is H, halogen, $C_{1-6}$ alkyl, —CN, —C(O)$NH_2$, —C(O)OEt, or —C(O)OH;

$R^4$ is halogen, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

$R^6$ is H, $C_{1-6}$ alkyl, $C_{2-6}$ alkenyl, or $C_{2-6}$ alkynyl; and $R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl.

In some embodiments, the present disclosure provides a compound of Formula (IA-6):

(IA-6)

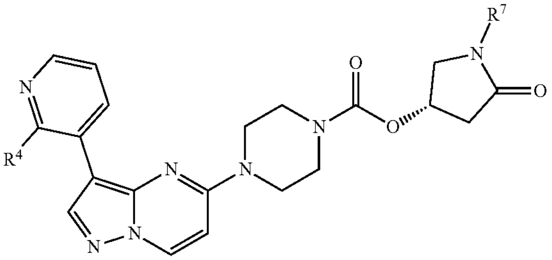

or pharmaceutically acceptable salt or deuterated form thereof, wherein:

$R^4$ is halogen, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl); and $R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl.

In some embodiments, the present disclosure provides a compound of Formula (IB):

(IB)

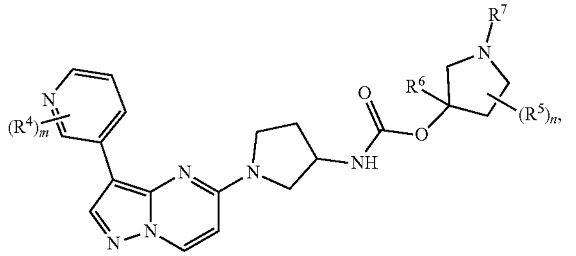

or pharmaceutically acceptable salt or deuterated form thereof, wherein:

each $R^4$ is independently halogen, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently H, halogen, $C_{1-6}$ alkyl, $C_{1-6}$ heteroalkyl, O—$C_{1-6}$ alkyl, $C_{1-5}$ alkylene-cycloalkyl, or $C_{1-5}$ alkylene-heterocyclyl, or two $R^5$ form an oxo;

$R^6$ is H, $C_{1-6}$ alkyl, $C_{2-6}$ alkenyl, or $C_{2-6}$ alkynyl;

$R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2$Ph, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2$Ph), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl;

m is 0; 1, or 2; and n is 0, 1, or 2.

In some embodiments, the present disclosure provides a compound of Formula (IC):

(IC)

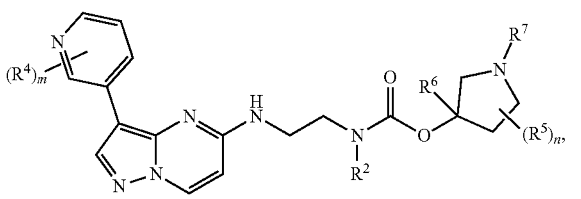

or pharmaceutically acceptable salt or deuterated form thereof, wherein:

$R^2$ is H or $C_{1-6}$ alkyl, or $R^1$ and $R^2$ taken together with the atoms to which they are attached form a 5- or 6-membered heterocyclyl;

each $R^4$ is independently halogen, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently H, halogen, $C_{1-6}$ alkyl, $C_{1-6}$ heteroalkyl, O—$C_{1-6}$ alkyl, $C_{1-5}$ alkylene-cycloalkyl, or $C_{1-5}$ alkylene-heterocyclyl, or two $R^5$ form an oxo;

$R^6$ is H, $C_{1-6}$ alkyl, $C_{2-6}$ alkenyl, or $C_{2-6}$ alkynyl;

$R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2$Ph, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2$Ph), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl;

m is 0, 1, 2, or 3; and n is 0, 1, or 2.

The present disclosure also provides pharmaceutical compositions comprising a compound disclosed herein and one or more pharmaceutically acceptable carriers and/or excipients.

In some embodiments, the present disclosure provides methods of treating or managing a disease or a disorder mediated by AAK1 activity, comprising administering to a subject in need thereof, a compound disclosed herein or a pharmaceutically acceptable salt thereof.

In some embodiments, the present disclosure provides methods of treating or managing a disease or a disorder mediated by AAK1 activity, comprising administering to a subject in need thereof, a pharmaceutical composition disclosed herein.

In some embodiments, the disease or a disorder mediated by AAK1 activity is a muscular dystrophy. In some embodiments, the muscular dystrophy is Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) or a congenital muscular dystrophy.

The present disclosure also provides methods of treating a muscular disease or disorder in a subject in need thereof, comprising administering to the subject, a compound disclosed herein or a pharmaceutically acceptable salt thereof.

In some embodiments, the present disclosure provides methods of treating a muscular disease or disorder in a subject in need thereof are provided, comprising administering to the subject, a pharmaceutical composition disclosed herein.

In some embodiments, the muscular disease or disorder is muscular dystrophy. In some embodiments, the muscular dystrophy is Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) or a congenital muscular dystrophy In some embodiments, the present disclosure provides methods for increasing skeletal muscle tissue growth or regeneration in a subject, comprising administering to the subject a compound disclosed herein or a pharmaceutically acceptable salt thereof.

In some embodiments, the present disclosure provides methods for increasing skeletal muscle tissue growth or regeneration in a subject, comprising administering to the subject a pharmaceutically composition disclosed herein.

In some embodiments, the subject has a mutation of a dystrophin gene.

DETAILED DESCRIPTION

This disclosure provides compounds, compositions and methods for modulating cell signalling pathways and increasing asymmetric division of satellite cells, e.g., to increase or enhance muscle regeneration, or as a therapeutic strategy for a variety of muscle wasting diseases, such as, but not limited to, Duchenne muscular dystrophy (DMD). The compounds, compositions, and methods disclosed herein may similarly be used to increase or stimulate myofiber and/or muscle tissue regeneration.

Adult skeletal muscle has regenerative capability. For example, after acute muscle injury, muscle fibers are repaired and new muscle fibers form within about a week as the result of expansion and differentiation of self-renewing muscle satellite cells. During regeneration, normally quiescent satellite cells are activated to produce daughter myogenic precursor cells, which then form the new muscle fibers. However, the number of satellite cells decreases during ageing, which results in reduced muscle regeneration ability. Additionally, in certain muscle diseases, such as DMD, decreased satellite cell regenerative ability and number results in impaired regeneration and accelerated disease progression.

Satellite cells are a heterogeneous population primarily composed of committed progenitors, together with a small population of muscle stem cells that are capable of long-term self-renewal. Satellite cells undergo two forms of cell division: asymmetric division, in which a major subpopulation of cells generates daughter cells committed to myogenic differentiation, while a small subpopulation of cells give rise to self-renewing daughter cells; and symmetric division, in which one stem cell population generates two identical stem daughter cells. In regenerating muscle, satellite cell symmetric divisions occur mostly in a planar orientation (parallel to the myofiber), whereas asymmetric divisions occur in an apicobasal orientation (perpendicular to the myofiber). Thus, in the context of acute muscle injury, asymmetric satellite cell division generates a stem cell and a transient-amplifying progenitor capable of dividing multiple times to generate a cohort of myogenic precursor cells that differentiate by fusion with existing myofibers or by forming new myofibers, whereas symmetric satellite cell division promotes expansion of satellite stem cells and maintains homeostasis of the stem cell compartment.

Satellite cells are juxtaposed against the myofiber sarcolemma within a cleft that forms the niche beneath the basal lamina. Quiescent satellite cells are polarized and express different adhesion proteins on the basal versus the apical cell surface, which influence quiescence and cell polarity. In healthy satellite cells, dystrophin acts as a scaffolding protein during mitosis to bind Par1b, leading to asymmetric segregation of Pard3 and the PAR complex and apical-basal orientation of the centrosomes prior to mitotic division. Following apical-basal oriented asymmetric division, the committed daughter cell no longer has contact with the basal lamina, while the stem cell in contact with the basal lamina maintains niche interactions to promote a return to quiescence.

Definitions

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and/or "approximately" may be used in conjunction with numerical values and/or ranges. The term "about" is understood to mean those values that are within ±10% of the recited value. Furthermore, the phrases "less than about [a value]" or "greater than about [a value]" should be understood in view of the definition of the term "about" provided herein. The terms "about" and "approximately" may be used interchangeably.

"Alkyl" or "alkyl group" refers to a fully saturated, straight or branched hydrocarbon chain radical, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_8$alkyl. A $C_1$-$C_8$alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_8$alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. In some embodiments, the alkyl disclosed herein is a $C_{1-12}$ alkyl, a $C_{1-6}$ alkyl, a $C_{1-5}$ alkyl, a $C_{1-4}$ alkyl, or a $C_{1-3}$ alkyl. Non-limiting examples of $C_1$-$C_{12}$ alkyl include methyl, ethyl, n-propyl, i-propyl, sec-propyl, n-butyl, I-butyl-, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical. Alkylenes comprising any number of carbon atoms from 1 to 12 are included. In some embodiments, the alkylene disclosed herein is a $C_{1-6}$ alkylene, a $C_{1-5}$ alkylene, a $C_{1-4}$ alkylene, a $C_{1-3}$ alkylene, a $C_{1-2}$ alkylene, or a $C_1$ alkylene. Non-limiting examples of $C_1$-$C_{12}$ alkylene include methylene, ethylene, propylene, n-butylene, ethenylene, propenylene-, n-butenylene, propynylene-, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated-otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. In some embodiments, the alkenyl disclosed herein is a $C_{2-12}$ alkenyl, a $C_{2-6}$ alkenyl, a $C_{2-5}$ alkenyl, a $C_{2-4}$ alkenyl, or a $C_{2-3}$ alkenyl. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Examples of $C_1$-$C_3$ alkyl includes methyl, ethyl, n-propyl, and i-propyl. Examples of $C_1$-$C_4$ alkyl include methyl, ethyl, n-propyl, i-propyl, n-butyl, i-butyl, and sec-butyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl groups comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. In some embodiments, the alkynyl disclosed herein is a $C_{2-12}$ alkynyl, a $C_{2-6}$ alkynyl, a $C_{2-5}$ alkynyl, a $C_{2-4}$ alkynyl, or a $C_{2-3}$ alkynyl. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —$OR_a$ where $R_a$ is an alkyl, alkenyl or alkynyl radical as defined above containing one to twelve carbon atoms. In some embodiments, the alkoxy disclosed herein is a $C_{1-12}$ alkoxy, a $C_{1-6}$ alkoxy, a $C_{1-5}$ alkoxy, a $C_{1-4}$ alkoxy, or a $C_{1-3}$ alkoxy. In some embodiments, the alkoxy is a methoxy, an ethoxy, or an isopropoxy. Unless stated otherwise specifically in the specification, an alkoxy group can be optionally substituted.

"Alkylamino" refers to a radical of the formula —$NHR_a$ or —$NR_aR_a$ where each $R^a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —C(═O) $R^a$ moiety, wherein $R^a$ is an alkyl, alkenyl or alkynyl radical as defined above. A non-limiting example of an alkyl carbonyl is the methyl carbonyl ("acetal") moiety. Alkylcarbonyl groups can also be referred to as "Cw-Cz acyl" where w and z depicts the range of the number of carbons in $R^a$, as defined above. For example, "$C_1$-$C_{10}$ acyl" refers to alkylcarbonyl group as defined above, where $R^a$ is $C_1$-$C_{10}$ alkyl, $C_1$-$C_{10}$ alkenyl, or $C_1$-$C_{10}$ alkynyl radical as defined above. Unless stated otherwise specifically in the specification, an alkyl carbonyl group can be optionally substituted.

"Aryl" refers to a hydrocarbon ring system radical comprising hydrogen, 5 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene-, pyrene, and triphenylene. In some embodiments, the aryl is a $C_{6-14}$ aryl. In some embodiments, the aryl is a $C_{6-12}$ aryl. In some embodiments, the aryl is a phenyl. Unless stated otherwise specifically in the specification, the term "aryl" is meant to include aryl radicals that are optionally substituted. In some embodiments, the aryl as defined herein is substituted with one or more halogen, $C_{1-6}$ alkyl, $C_{1-6}$ alkoxy, $C(O)(C_{1-6}$ alkyl), C(O)(O—$C_{1-6}$ alkyl), CN, $C(O)NH_2$, C(O)NH($C_{1-6}$ alkyl), or C(O)N($C_{1-6}$ alkyl$)_2$.

"Alkylenearyl" refers to a radical of the formula —$R_b$—$R_c$ where $R_b$ is an alkylene, as defined above and $R_c$ is one or more aryl radicals as defined above: Examples include benzyl, diphenylmethyl, and the like. Unless stated otherwise specifically in the specification, an aralkyl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include cycloalkyl, cycloalkenyl and cycloalkynyl as defined herein. In some embodiments, the carbocyclyl is a $C_{3-12}$ carbocyclyl, a $C_{3-8}$ carbocyclyl, or a $C_{3-6}$ carbocyclyl. Unless stated otherwise specifically in the specification, a carbocyclyl group can be optionally substituted.

"Cycloalkyl" refers to a stable nonaromatic monocyclic or polycyclic fully saturated hydrocarbon radical consisting solely of carbon and hydrogen atoms, which can include fused or bridged ring systems, having from three to twenty carbon atoms, for example having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethylbicyclo[2.2.1]heptanyl-, and the like. In some embodiments, the cycloalkyl is a $C_{3-12}$ cycloalkyl, a $C_{3-8}$ cycloalkyl, or a $C_{3-6}$ cycloalkyl. In some embodiments, the cycloalkyl is a cyclopropyl. Unless otherwise stated-specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, for example having from three to ten carbon atoms, and which is attached to the rest of the molecule by a single bond. Monocyclic cycloalkenyl radicals include, for example, cyclopentenyl, cyclohexenyl, cycloheptenyl, cycloctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, for example having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the formula $—R_b—R_d$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2—difluoroethyl, 3—bromo—-2fluoropropyl, 1,2—-dibromoethyl, and the like. In some embodiments, the haloalkyl is $CF_3$, $CHF_2$, $CH_2F$, $CH_2CF_3$, or $CF_2CH_3$. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above that is substituted by one or more halo radicals, as defined above, e.g., 1-fluoropropynyl, 1-fluorobutynyl, and the like. Unless stated otherwise specifically in the specification, a haloalkenyl group can be optionally substituted.

"Heterocyclyl," "heterocyclic ring" or "heterocycle" refers to a stable saturated or unsaturated 3- to 20-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2oxopyrrolidinyl, oxazolidinyl-, piperidinyl, piperazinyl, 4piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl-, 1-oxo-thiomorpholinyl, and 1,1-dioxothiomorpholinyl. In some embodiments, the heterocyclyl is a 3- to 12-membered heterocyclyl, a 4- to 8-membered heterocyclyl, or a 4- to 6-membered heterocyclyl. In some embodiments, the heterocyclyl is a 4-membered heterocyclyl, e.g., an azetidine. In some embodiments, the heterocyclyl includes 1, 2, or 3 heteroatoms selected from the group consisting of N, O, and S. Unless stated otherwise specifically in the specification, a heterocyclyl-group can be optionally substituted. In some embodiments, the heterocyclyl as defined herein is optionally substituted with one or more oxo, $C_{1-6}$ alkyl, $C_{1-6}$ alkoxy, $C(O)(C_{1-6}$ alkyl), C(O)(O—$C_{1-6}$ alkyl), $C(O)NH_2$, $C(O)NH(C_{1-6}$ alkyl), or $C(O)N(C_{1-6}$ alkyl$)_2$.

"N-heterocyclyl" refers to a heterocyclyl radical as defined above containing at least one nitrogen. In some embodiments, the N-heterocyclyl includes, 1, 2, or 3 nitrogen atoms. Unless stated otherwise specifically in the specification, a N-heterocyclyl group can be optionally substituted.

"Alkyleneheterocyclyl" refers to a radical of the formula $—R_b—R_e$ where $R_b$ is an alkylene as defined above and $R_e$ is a heterocyclyl radical as defined above, and if the heterocyclyl is a nitrogen-containing heterocyclyl, the heterocyclyl can be attached to the alkyl, alkenyl, alkynyl radical at the nitrogen atom. Unless stated otherwise specifically in the specification, a heterocyclylalkyl group can be optionally substituted.

"Heteroaryl" refers to a 5 to 20-membered ring system comprising hydrogen atoms, one to nineteen carbon atoms, one to six heteroatoms selected from the group consisting of nitrogen, oxygen and sulfur, at least one aromatic ring, and which is attached to the rest of the molecule by a single bond. For purposes of this disclosure, the heteroaryl can be a monocyclic, bicyclic, tricyclic or tetracyclic ring system, which can include fused or bridged ring systems; and the nitrogen, carbon or sulfur atoms in the heteroaryl can be optionally oxidized; the nitrogen atom can be optionally quaternized-. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). In some embodiments, the heteroaryl is a 5- to 14-membered heteroaryl. In some embodiments, the heteroaryl is a 5- or 6-membered heteroaryl. In some embodiments, the heteroaryl includes 1, 2, or 3 heteroatoms selected from the group consisting of N, O, and S. Unless stated otherwise specifically in the specification, a heteroaryl group can be optionally substituted. In some embodiments, the heteroaryl as defined herein is substituted with one or more halogen, $C_{1-6}$ alkyl, $C_{1-6}$ alkoxy, $C(O)(C_{1-6}$ alkyl), C(O)(O—$C_{1-6}$ alkyl), CN, $C(O)NH_2$, $C(O)NH(C_{1-6}$ alkyl), or $C(O)N(C_{1-6}$ alkyl$)_2$.

"N-heteroaryl" refers to a heteroaryl radical as defined above containing at least one nitrogen and where the point of attachment of the heteroaryl radical to the rest of the molecule is through a nitrogen atom in the heteroaryl radical. In some embodiments, the N-heteroaryl is a 5- or 6-membered N-heteroaryl. In some embodiments, the N-heteroaryl is a 6-membered heteroaryl. Unless stated otherwise specifically in the specification, an N-heteroaryl group can be optionally substituted.

"Alkyleneheteroaryl" refers to a radical of the formula —$R_b$—$R_f$ where $R_b$ is an alkylene as defined above and $R_f$ is a heteroaryl radical as defined above. Unless stated otherwise specifically in the specification, a heteroarylalkyl group can be optionally substituted.

"Thioalkyl" refers to a radical of the formula —$SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the groups described herein (e.g., alkyl, alkenyl, alkynyl, alkoxy, aryl, aralkyl, carbocyclyl, cycloalkyl, cycloalkenyl, cycloalkynyl, haloalkyl, heterocyclyl, and/or heteroaryl) wherein at least one hydrogen atom is replaced by a bond to a non-hydrogen atoms such as, but not limited to: deuterium, a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $NR_gR_h$, $NR_gC(=O)R_h$, $NR_gC(=O)NR_gR_h$, $NR_gC(=O)OR_h$, $NR_gSO_2R_h$, $OC(=O)NR_gR_h$, $OR_g$, $SR_g$, $SOR_g$, $SO_2R_g$, $OSOR_g$, $SO_2OR_g$, $=NSO_2R_g$, and $SO_2NR_gR_h$. "Substituted" also means any of the above groups in which one or more hydrogen atoms are replaced with $C(=O)R_g$, $C(=O)OR_g$, $C(=O)NR_gR_h$, $CH_2SO_2R_g$, $CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol

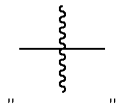

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

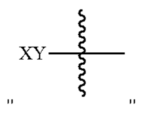

indicates that the chemical entity "XY" is bonded to another chemical entity via the point of attachment bond. Furthermore, the specific point of attachment to the non-depicted chemical entity can be specified by inference. For example, the compound $CH_3$-$R^3$, wherein $R^3$ is H or

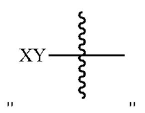

infers that when $R^3$ is "XY", the point of attachment bond is the same bond as the bond by which $R_3$ is depicted as being bonded to $CH_3$.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring can be replaced with a nitrogen atom.

"Geminal" refers to any two substituents (e.g., those described herein such as alkyl, alkenyl, alkynyl, cycloalkyl, heterocycloalkyl, aryl, heteroaryl, etc.) that are attached to the same atom. In some embodiments, geminal substitution refers to substitution on the same carbon atom. The structure

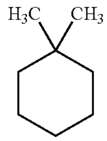

exemplifies geminal methyl substitution on cyclohexane. In some embodiments, the optional substitution is geminal substitution.

"Optional" or "optionally" means that the subsequently described event of circumstances can or cannot occur, and that the description includes instances where said event or circumstance occurs and instances in which it does not. For example, "optionally substituted aryl" means that the aryl radical can or cannot be substituted and that the description includes both substituted aryl radicals and aryl radicals having no substitution.

The compounds of the invention, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)- for amino acids. The present invention is meant to include all such possible isomers, as well as their racemic and optically pure forms whether or not they are specifically depicted herein. Optically active (+ and (−), (R)- and (S)-, or (D)- and (L)-isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. In some embodiments, inorganic salts include ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2diethylaminoethanol, dicyclohexylamine-, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, | piperidine, N—ethyl piperidine, polyamine resins and the like. In particular embodiments, organic bases include isopropylamine, diethylamine, ethanolamine, trimethylamine, dicyclohexylamine, choline and caffeine.

Compounds of the Disclosure

The present disclosure further provides a compound of Formula (A):

(A)

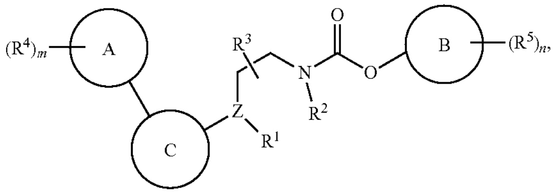

or pharmaceutically acceptable salt, deuterated form, or stereoisomer thereof, wherein:

Ⓐ is phenyl or heteroaryl;

Ⓑ is heterocyclyl;

Ⓒ is

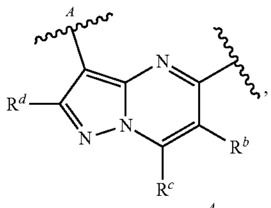

,

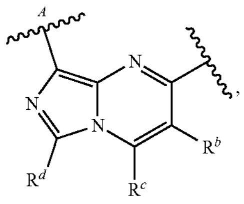

, or

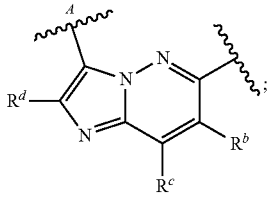

;

Z is CH or N;

$R^1$ and $R^2$ are each independently H or $C_{1-6}$ alkyl, or $R^1$ and $R^2$ taken together with the atoms to which they are attached form a 5- or 6-membered heterocyclyl;

$R^3$ is H, halogen, $C_{1-6}$ alkyl, —CN, or —$COR^a$, or an $R^1$ and $R^3$ taken together with the atoms to which they are attached form a 5- or 6-membered heterocyclyl;

each $R^4$ is independently halogen, —OH, —O—$C_{1-6}$ alkyl, —O—$C_{1-6}$ haloalkyl, —O-cycloalkyl, —O-heterocyclyl, —O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, —$C_{1-6}$ alkyl, $C_{1-6}$ heteroalkyl, —O—$C_{1-6}$ alkyl, heterocyclyl, —$C_{1-5}$ alkylene-cycloalkyl, or —$C_{1-5}$ alkylene-heterocyclyl, or two $R^5$ form an oxo;

$R^a$ is —OH, —O—($C_{1-6}$ alkyl), —$NH_2$, —NH—($C_{1-6}$ alkyl), or —NH—($C_{1-6}$ alkyl)$_2$;

$R_b$, $R^c$, and $R^d$ are each independently H, halogen, —$C_{1-6}$ alkyl, JOH, —O—($C_{1-6}$ alkyl), —$NH_2$, —NH—($C_{1-6}$ alkyl), or —NH—($C_{1-6}$ alkyl)$_2$;

m is 0, 1, 2, or 3; and n is 0, 1, or 2, provided that the compound is not:

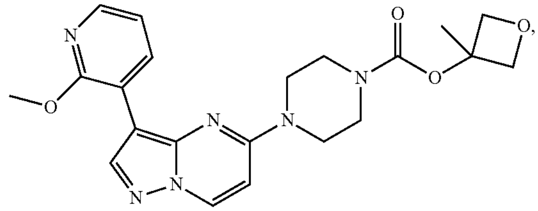

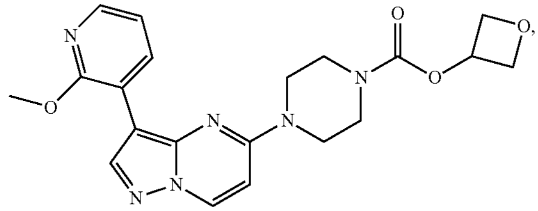

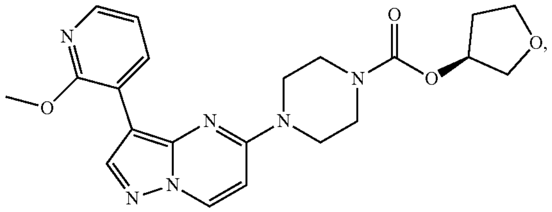

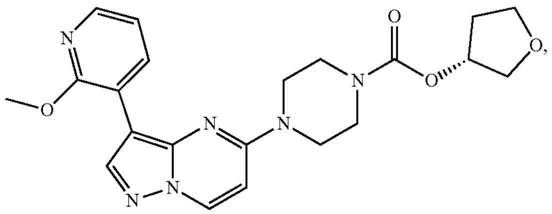

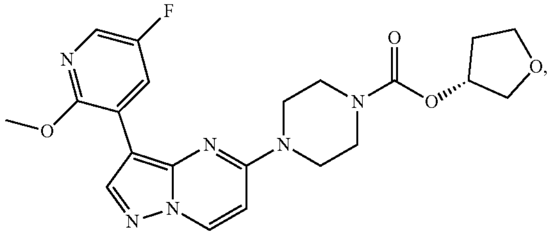

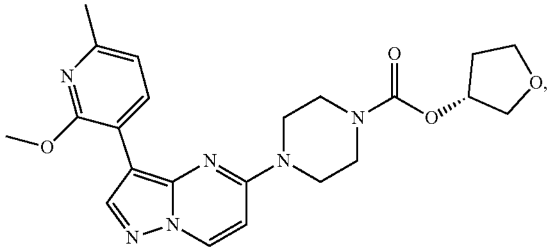

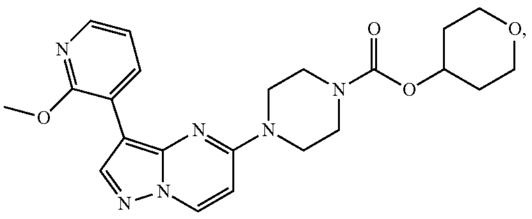

or

-continued

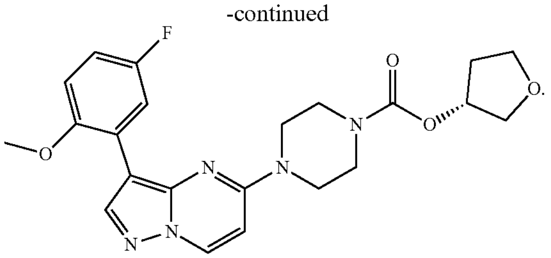

In some embodiments, Ⓒ is

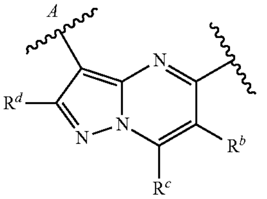

or

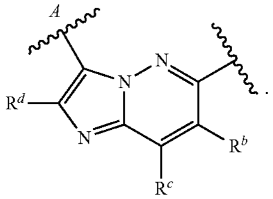

In some embodiments, Ⓒ is

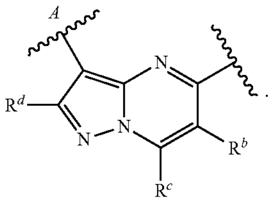

In some embodiments, Ⓒ is

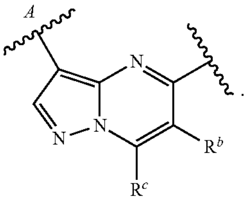

In some embodiments, Ⓒ is

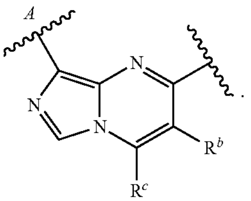

In some embodiments, Ⓒ is

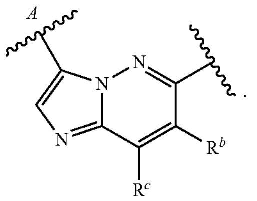

In some embodiments, $R^b$ and $R^c$ are each independently H, halogen, $C_{1-6}$ alkyl, —OH, —O—($C_{1-6}$ alkyl), —$NH_2$, —NH—($C_{1-6}$ alkyl), or —NH—($C_{1-6}$ alkyl)$_2$. In some embodiments, $R^b$ and $R^c$ are each independently H, Cl, F, Me, —OH, —OMe, —$NH_2$, —NHMe, or —$NMe_2$. In some embodiments, $R^b$ and $R^c$ are each independently H, F, —OH, —OMe, or Me. In some embodiments, $R_b$ is H, F, Me, —OH, or —OMe and $R^c$ is H. In some embodiments, $R^b$ is H or F and $R^c$ is H. In some embodiments, $R^b$ is H and $R^c$ is H. In some embodiments, $R^d$ is H or $C_{1-6}$ alkyl. In some embodiments, $R^d$ is H or Me. In some embodiments, $R^d$ is H.

The present disclosure provides a compound of Formula (I):

(I)

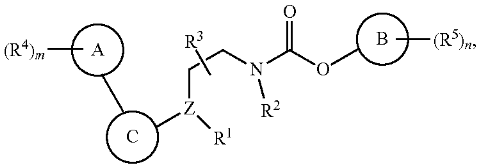

or pharmaceutically acceptable salt, deuterated form, or stereoisomer thereof, wherein:

Ⓐ is phenyl or heteroaryl;

Ⓑ is heterocyclyl;

Ⓒ is

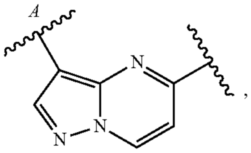

,

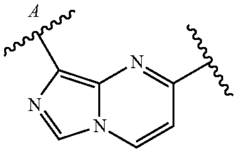

, or

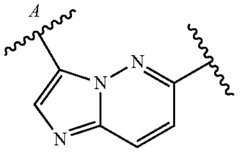

;

Z is CH or N;

$R^1$ and $R^2$ are each independently H or $C_{1-6}$ alkyl, or $R^1$ and $R^2$ taken together with the atoms to which they are attached form a 5- or 6-membered heterocyclyl;

$R^3$ is H, halogen, $C_{1-6}$ alkyl, —CN, or —$COR^a$, or an $R^1$ and $R^3$ taken together with the atoms to which they are attached form a 5- or 6-membered heterocyclyl;

each $R^4$ is independently halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, NH—($C_{1-6}$ alkyl), —N($C_{1-6}$ alkyl)$_2$, —NH-(cycloalkyl), or —NH-(heterocyclyl);

each $R^5$ is independently halogen, $C_{1-6}$ alkyl, $C_{1-6}$ heteroalkyl, O—$C_{1-6}$ alkyl, heterocyclyl, $C_{1-5}$ alkylene-cycloalkyl, or $C_{1-5}$ alkylene-heterocyclyl, or two $R^5$ form an oxo;

$R^a$ is —OH, —O—($C_{1-6}$ alkyl), —$NH_2$, —NH—($C_{1-6}$ alkyl), or —NH—($C_{1-6}$ alkyl)$_2$;

m is 0, 1, 2, or 3; and n is 0, 1, or 2, provided that the compound is not:

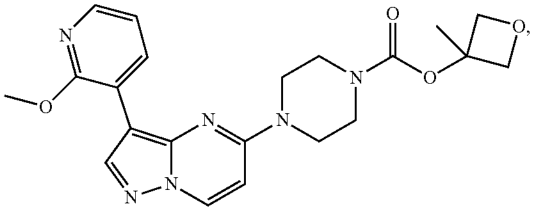

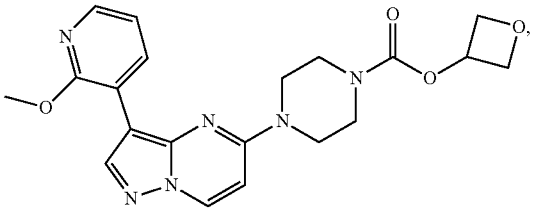

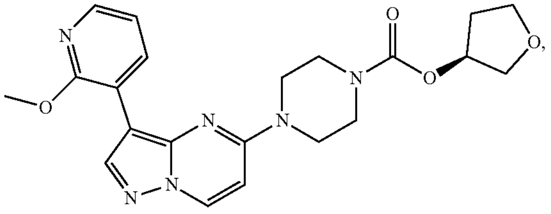

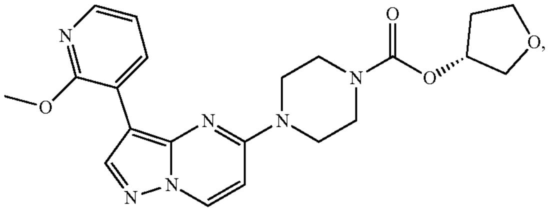

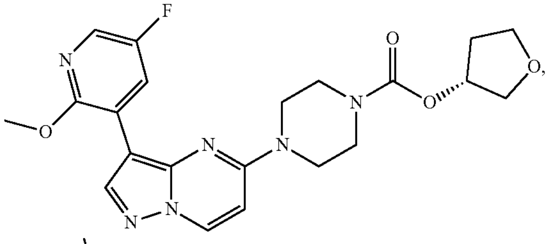

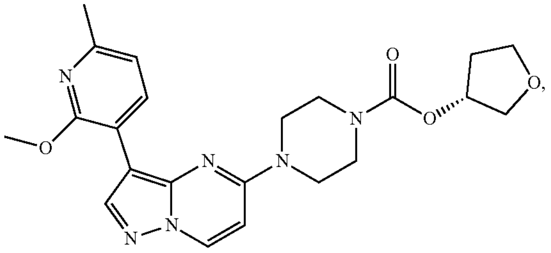

-continued

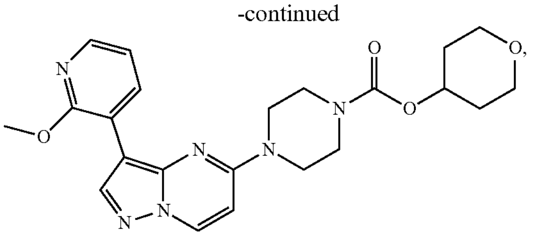

or

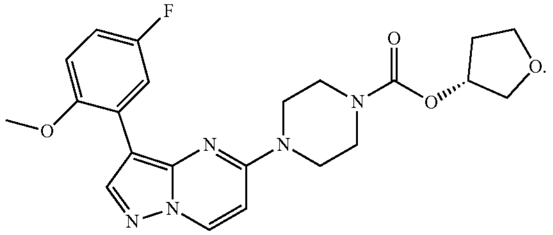

In some embodiments, Ⓒ is

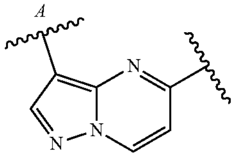

or

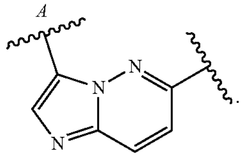

In some embodiments Ⓒ is

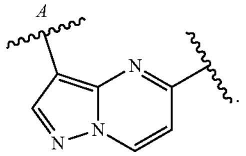

In some embodiments, Ⓒ is

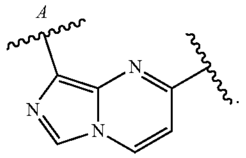

In some embodiments, Ⓒ is

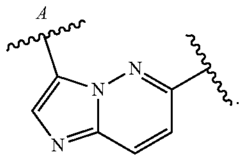

In some embodiments, the present disclosure provides compound of Formula (IA'):

(IA')

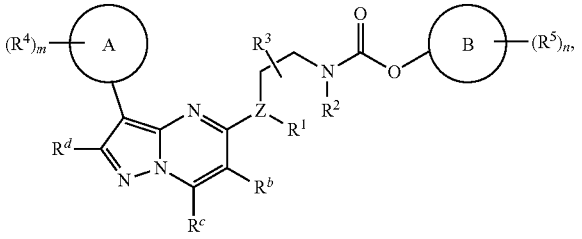

or pharmaceutically acceptable salt, deuterated form, or stereoisomer thereof, wherein:

Ⓐ is phenyl or N-heteroaryl;

Ⓑ is heterocyclyl;

Z is CH or N;

$R^1$ and $R^2$ are each independently H or $C_{1-6}$ alkyl, or an $R^1$ and $R^2$ taken together with the atoms to which they are attached for a 5- or 6-membered heterocyclyl;

$R^3$ is H, halogen, $C_{1-6}$ alkyl, CN, or $COR^a$;

each $R^4$ is independently halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, $C_{1-6}$ alkyl, $C_{1-6}$ heteroalkyl, O—$C_{1-6}$ alkyl, heterocyclyl, $C_{1-5}$ alkylene-cycloalkyl, or $C_{1-5}$ alkylene-heterocyclyl, or two $R^5$ form an oxo;

$R^a$ is —OH, —O—$C_{1-4}$ alkyl, —$NH_2$, —NH—($C_{1-6}$ alkyl), or —N($C_{1-6}$ alkyl)$_2$;

$R^b$, $R^c$, and $R^d$ are each independently H, halogen, $C_{1-6}$ alkyl, —OH, —O—($C_{1-6}$ alkyl), —$NH_2$, —NH—($C_{1-6}$ alkyl), or —NH—($C_{1-6}$ alkyl)$_2$;

m is 0, 1, 2, or 3; and n is 0, 1, or 2, provided that the compound is not:

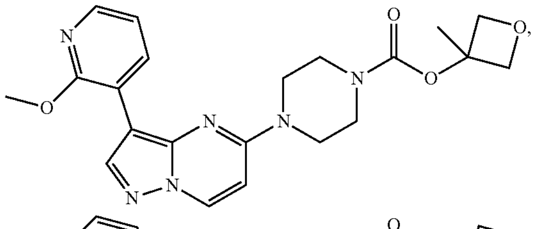

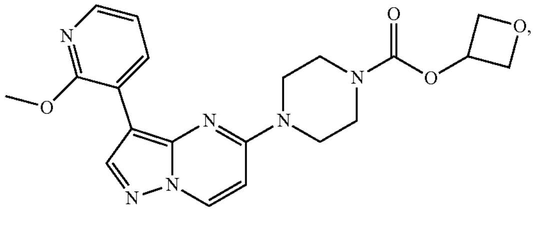

-continued

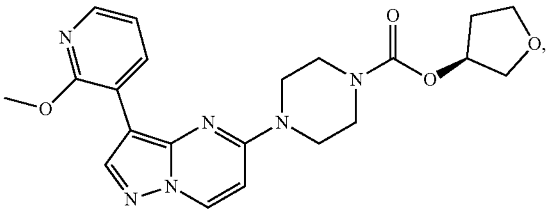

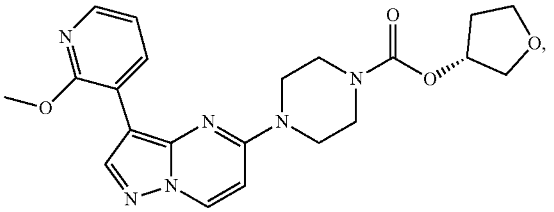

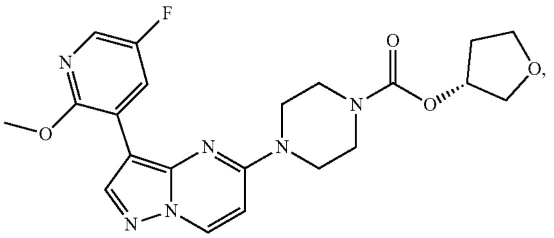

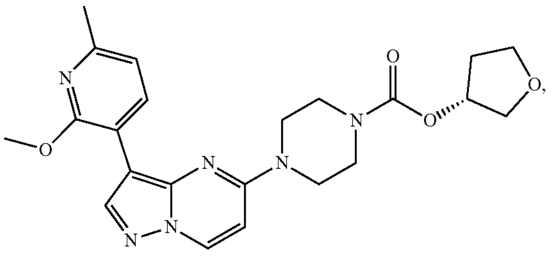

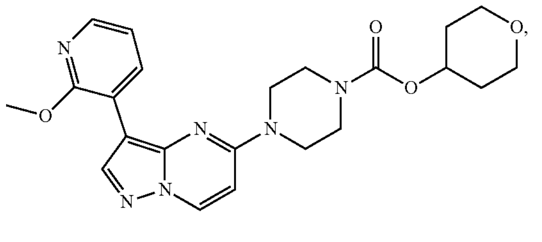

or

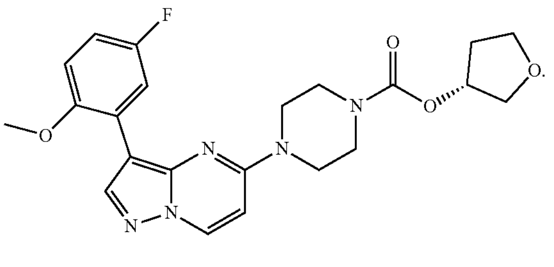

In some embodiments, the present disclosure provides compound of Formula (IA):

(IA)

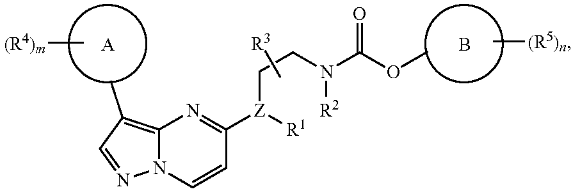

or pharmaceutically acceptable salt, deuterated form, or stereoisomer thereof, wherein:

Ⓐ is phenyl or N-heteroaryl;

Ⓑ is heterocyclyl;

Z is CH or N;

$R^1$ and $R^2$ are each independently H or $C_{1-6}$ alkyl, or an $R^1$ and $R^2$ taken together with the atoms to which they are attached for a 5- or 6-membered heterocyclyl;

$R^3$ is H, halogen, $C_{1-6}$ alkyl, CN, or $COR^a$;

each $R^4$ is independently halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, $C_{1-6}$ alkyl, $C_{1-6}$ heteroalkyl, O—$C_{1-6}$ alkyl, heterocyclyl, $C_{1-5}$ alkylene-cycloalkyl, or $C_{1-5}$ alkylene-heterocyclyl, or two $R^5$ form an oxo;

$R^a$ is —OH, —O—$C_{1-6}$ alkyl, —$NH_2$, —NH—($C_{1-6}$ alkyl), or —N($C_{1-6}$ alkyl)$_2$;

m is 0, 1, 2, or 3; and n is 0, 1, or 2, provided that the compound is not:

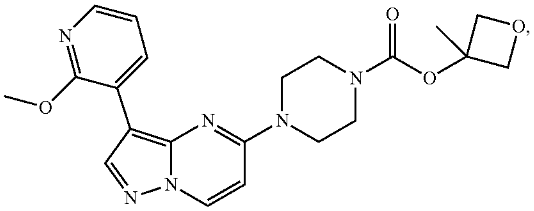

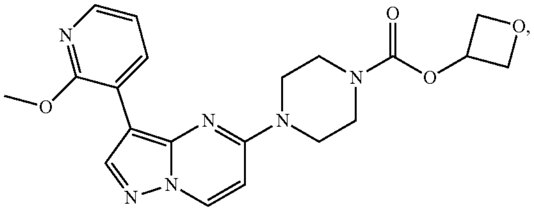

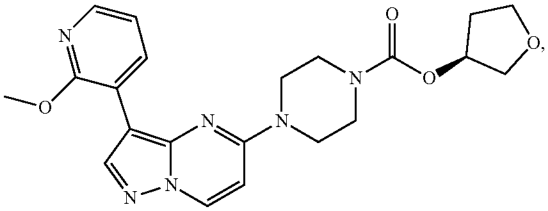

-continued

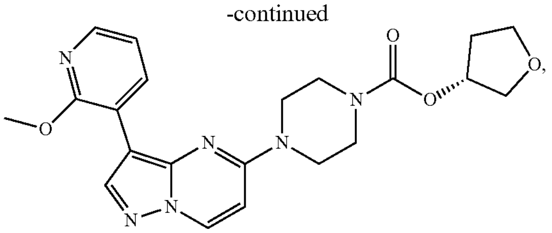

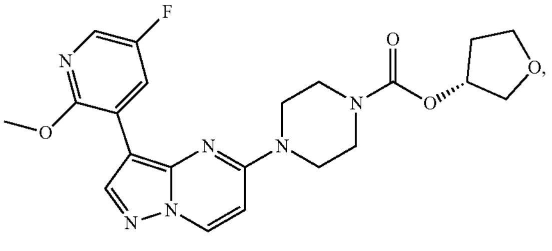

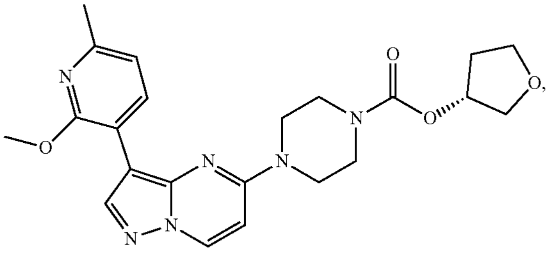

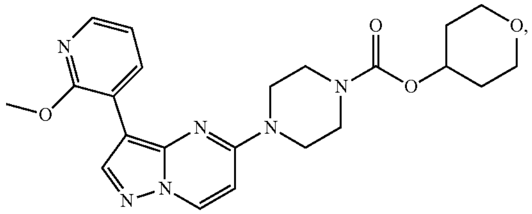

or

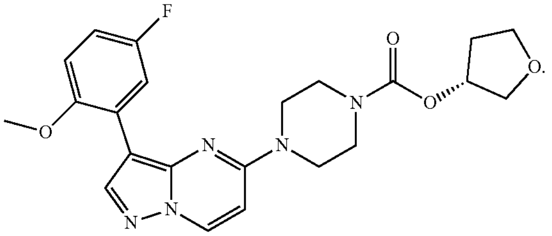

In some embodiments, $R^1$ and $R^3$ taken together with the atoms to which they are attached form a 5-membered heterocyclyl. In some embodiments, the 5-membered heterocyclyl is a pyrrolidinyl. In some embodiments, the 5-membered heterocyclyl is

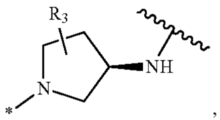

, wherein * represents the point of attachment to Ⓒ. In some embodiments, the 5-membered heterocyclyl is

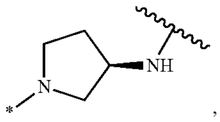 [SMILES: *N[C@@H]1CCN(*)C1], wherein * represents the point of attachment to Ⓒ.

In some embodiments, $R^1$ and $R^2$ taken together with the atoms to which they are attached form a 6-membered heterocyclyl. In some embodiments, the 6-membered heterocyclyl is a piperidinyl or piperazinyl. In some embodiments, the 6-membered heterocyclyl is Ⓒ. wherein * represents the point of attachment to Ⓒ.

In some embodiments, the 6-membered heterocyclyl is a piperidinyl or piperazinyl. In some embodiments, the 6-membered heterocyclyl is

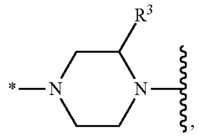

wherein * represents the point of attachment to Ⓒ. In some embodiments, the 6-membered heterocyclyl is

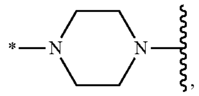 [SMILES: *N1CCN(*)CC1]

wherein * represents the point of attachment to Ⓒ.

In some embodiments, $R^1$ and $R^2$ are each independently H, $C_{1-6}$ alkyl, or —C(O) ($C_{1-6}$ alkyl). In some embodiments, $R^1$ and $R^2$ are each independently H or $C_{1-6}$ alkyl. In some embodiments, $R^1$ and $R^2$ are each independently H, Me, Et, nPr, or iPr. In some embodiments, $R^1$ and $R^2$ are each independently H or Me. In some embodiments, $R^1$ is H and $R^2$ is Me. In some embodiments, $R^1$ is Me and $R^2$ is H. In some embodiments, $R^1$ and $R^2$ are H. In some embodiments, $R^1$ and $R^2$ are Me.

In some embodiments, the present disclosure provides a compound of Formula (IA'-1):

(IA'-1)

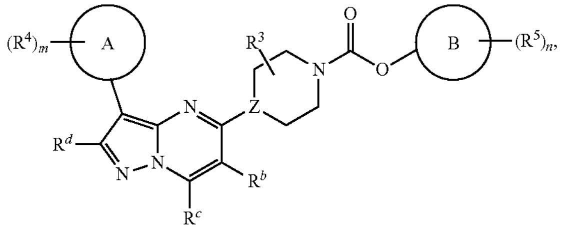

or pharmaceutically acceptable salt, deuterated form, or stereoisomer thereof, wherein:

Ⓐ is phenyl or N-heteroaryl;

Ⓑ is heterocyclyl;

Z is CH or N;

$R^3$ is H, halogen, $C_{1-6}$ alkyl, CN, or $COR^a$;

each $R^4$ is independently halogen, —OH, —O—$C_{1-6}$ alkyl, —O—$C_{1-6}$ haloalkyl, —O-cycloalkyl, —O-heterocyclyl, —O—($C_{1-5}$ alkylene)-cycloalkyl, —O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, alkyl, —$C_{1-6}$ heteroalkyl, —O—$C_{1-6}$ alkyl, heterocyclyl, —$C_{1-5}$ alkylene-cycloalkyl, or —$C_{1-5}$ alkylene-heterocyclyl, or two $R^5$ form an oxo;

$R^a$ is —OH, —O—($C_{1-6}$ alkyl), —$NH_2$, —NH—($C_{1-6}$ alkyl), or —N($C_{1-6}$ alkyl)$_2$;

$R^b$, $R^c$, and $R^d$ are each independently H, halogen, $C_{1-6}$ alkyl, —OH, —O—($C_{1-6}$ alkyl), —$NH_2$, —NH—($C_{1-6}$ alkyl), or —NH—($C_{1-6}$ alkyl)$_2$;

m is 0, 1, 2, or 3; and n is 0, 1, or 2, provided that the compound is not:

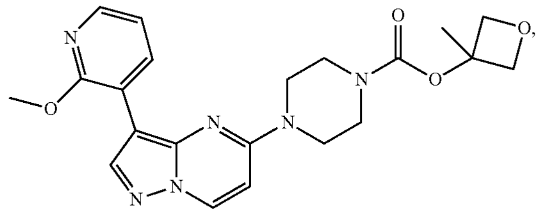

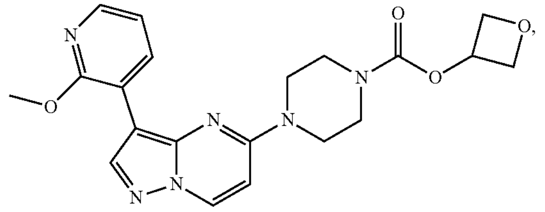

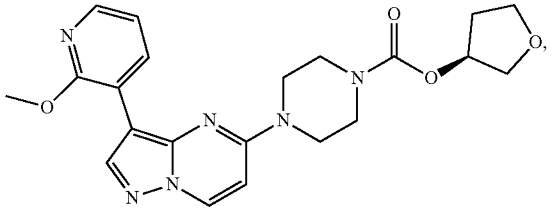

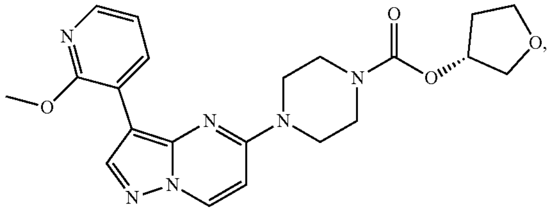

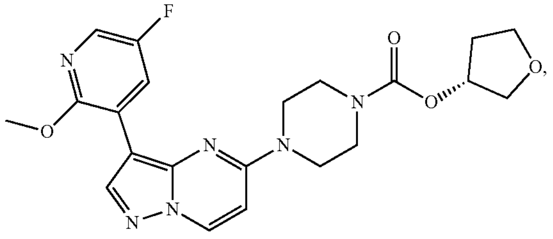

-continued

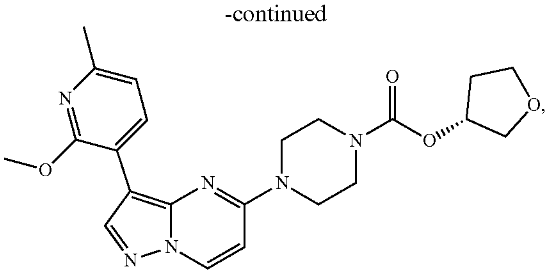

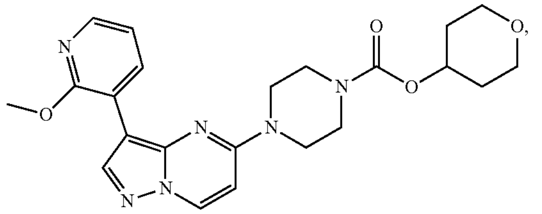

or

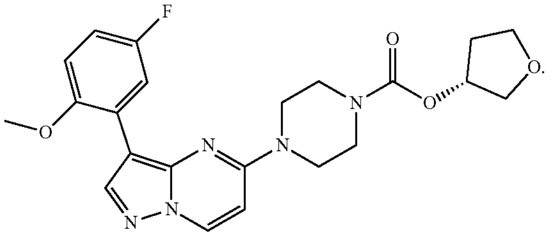

In some embodiments, the present disclosure provides a compound of Formula (IA-1):

(IA-1)

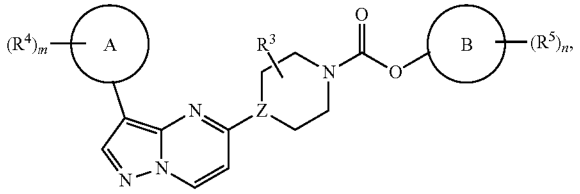

or pharmaceutically acceptable salt, deuterated form, or stereoisomer thereof, wherein:

Ⓐ is phenyl or N-heteroaryl;

Ⓑ is heterocyclyl;

Z is CH or N;

$R^3$ is H, halogen, $C_{1-6}$ alkyl, CN, or $COR^a$;

each $R^4$ is independently halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, NH—($C_{1-6}$ alkyl), —N($C_{1-6}$ alkyl)$_2$, —NH-(cycloalkyl), or —NH-(heterocyclyl);

each $R^5$ is independently halogen, alkyl, $C_{1-6}$ heteroalkyl, O—$C_{1-6}$ alkyl, heterocyclyl, $C_{1-5}$ alkylene-cycloalkyl, or $C_{1-5}$ alkylene-heterocyclyl, or two $R^5$ form an oxo;

$R^a$ is —OH, —O—($C_{1-6}$ alkyl), —$NH_2$, —NH—($C_{1-6}$ alkyl), or —N($C_{1-6}$ alkyl)$_2$;

m is 0, 1, 2, or 3; and n is 0, 1, or 2, provided that the compound is not:

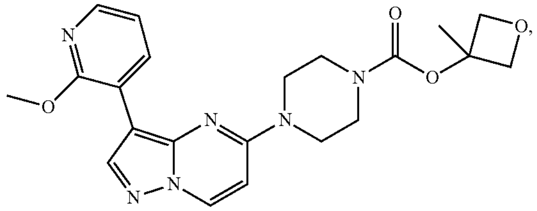

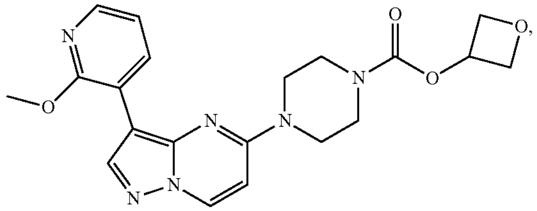

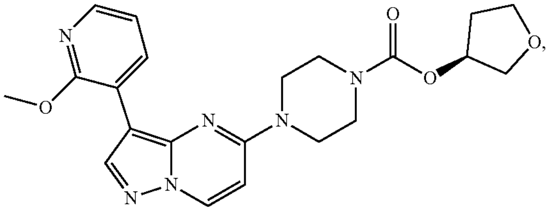

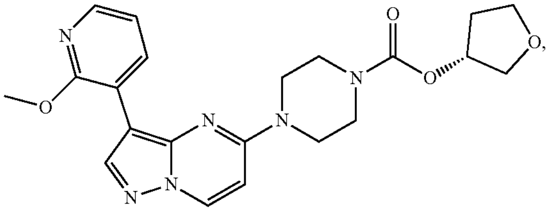

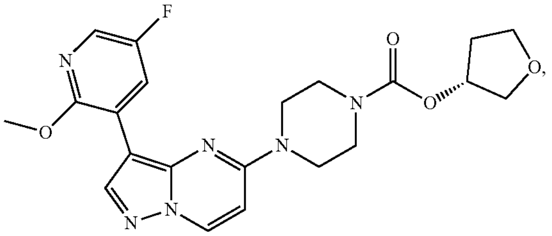

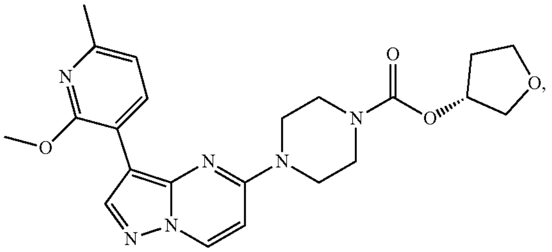

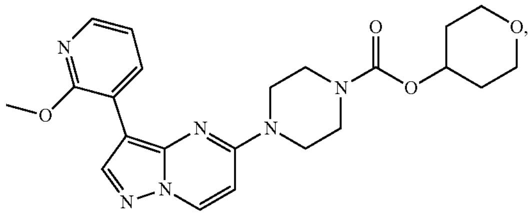

or

-continued

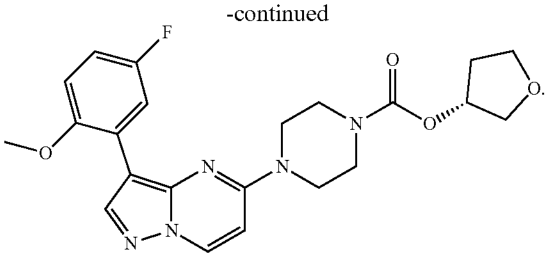

In some embodiments, Z is N. In some embodiments, Z is CH.

In some embodiments, the present disclosure provides a compound of Formula (IA'-2):

(IA'-2)

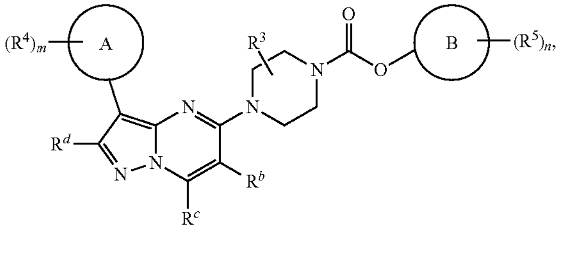

or pharmaceutically acceptable salt, deuterated form, or stereoisomer thereof, wherein:

Ⓐ is phenyl or N-heteroaryl;

Ⓑ is heterocyclyl;

$R^3$ is H, halogen, $C_{1-6}$ alkyl, CN, or $COR^a$;

each $R^4$ is independently halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, $C_{1-6}$ alkyl, $C_{1-6}$ heteroalkyl, O—$C_{1-6}$ alkyl, heterocyclyl, $C_{1-5}$ alkylene-cycloalkyl, or $C_{1-5}$ alkylene-heterocyclyl, or two $R^5$ form an oxo;

$R^a$ is —OH, —O—($C_{1-6}$ alkyl), —$NH_2$, —NH—($C_{1-6}$ alkyl), or —N($C_{1-6}$ alkyl)$_2$;

$R^b$, $R^c$, and $R^d$ are each independently H, halogen, $C_{1-6}$ alkyl, JOH, —O—($C_{1-6}$ alkyl), —$NH_2$, —NH—($C_{1-6}$ alkyl), or —NH—($C_{1-6}$ alkyl)$_2$;

m is 0, 1, 2, or 3; and n is 0, 1, or 2, provided that the compound is not:

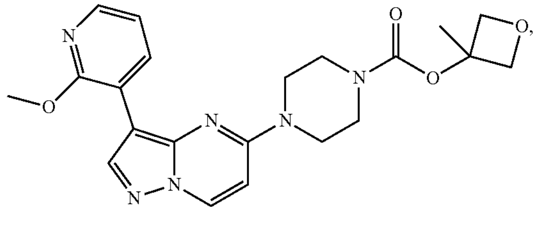

-continued

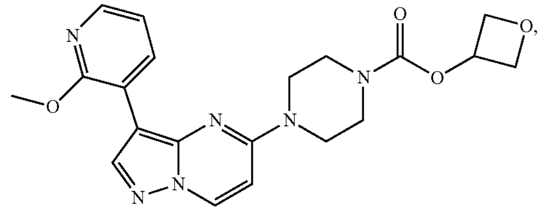

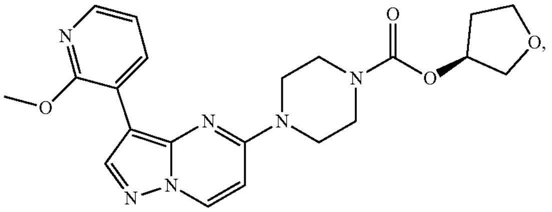

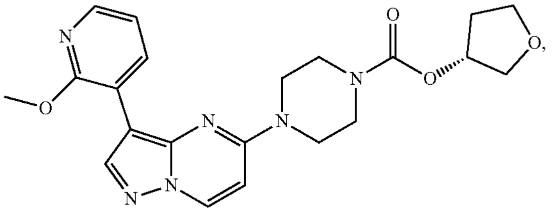

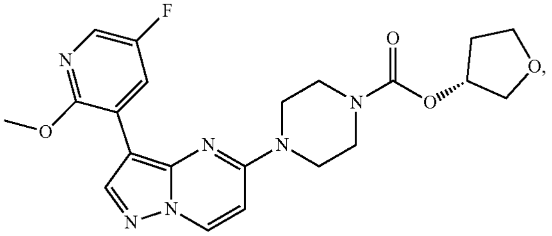

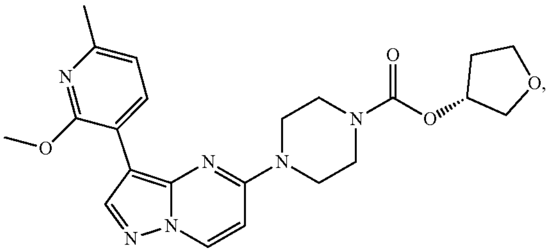

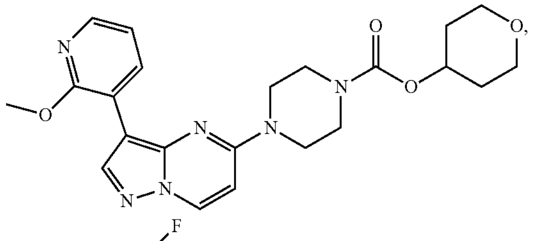

or

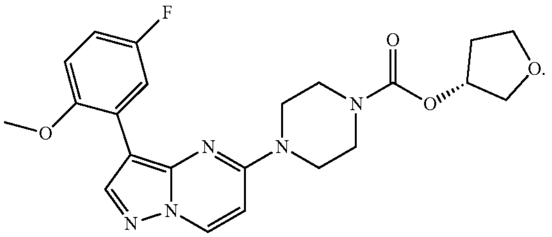

In some embodiments, the present disclosure provides a compound of Formula (IA-2):

(IA-2)

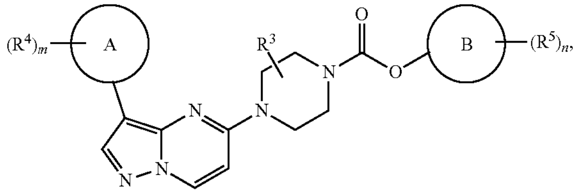

or pharmaceutically acceptable salt, deuterated form, or stereoisomer thereof, wherein:

(A) is phenyl or N-heteroaryl;

(B) is heterocyclyl;

$R^3$ is H, halogen, $C_{1-6}$ alkyl, CN, or $COR^a$;

each $R^4$ is independently halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, $C_{1-6}$ alkyl, $C_{1-6}$ heteroalkyl, O—$C_{1-6}$ alkyl, heterocyclyl, $C_{1-5}$ alkylene-cycloalkyl, or $C_{1-5}$ alkylene-heterocyclyl, or two $R^5$ form an oxo;

$R^a$ is —OH, —O—($C_{1-6}$ alkyl), —$NH_2$, —NH—($C_{1-6}$ alkyl), or —N($C_{1-6}$ alkyl)$_2$;

m is 0, 1, 2, or 3; and n is 0, 1, or 2, provided that the compound is not:

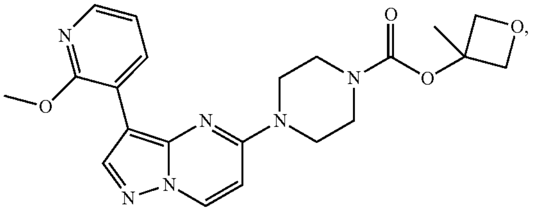

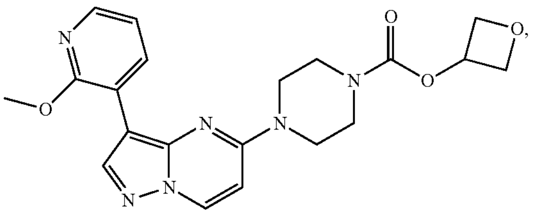

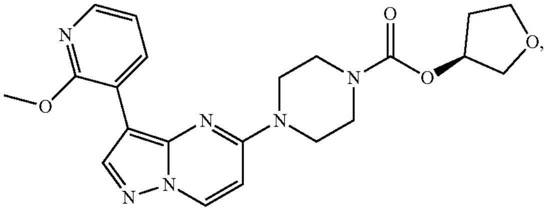

-continued

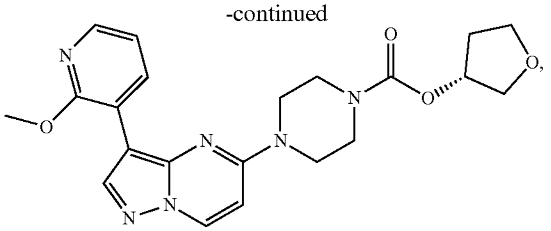

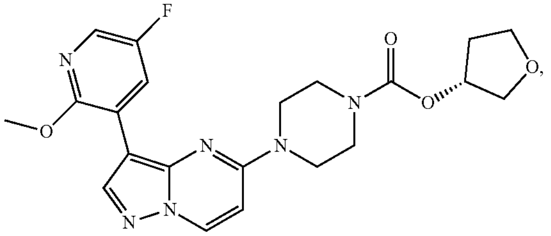

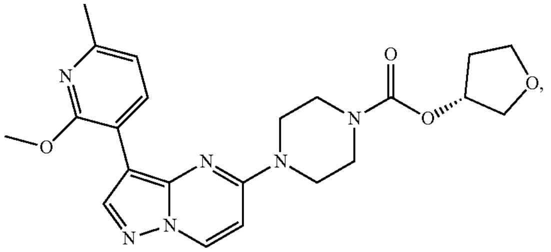

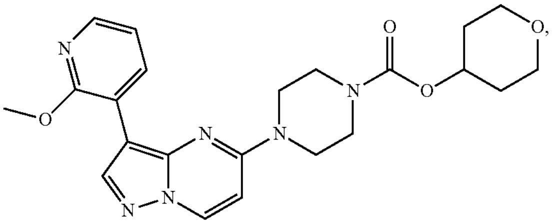 or

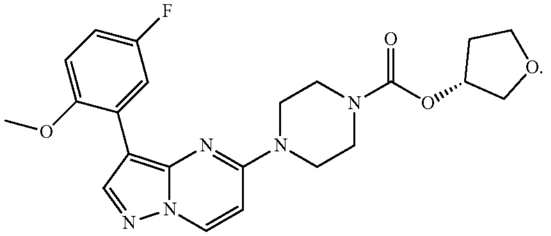

In some embodiments, (A) is 5-membered or 6-membered N-heteroaryl. In some embodiments, (A) is 6-membered N-heteroaryl. In some embodiments, the 5-membered heteroaryl is thiophenyl, oxazolyl, thiazolyl, or imidazolyl. In some embodiments, the 6-membered heteroaryl is a pyridinyl, pyrazinyl, pyrimidinyl, or pyridazinyl. In some embodiments, the 6-membered heteroaryl is a pyridinyl. In some embodiments, the pyridinyl is a 3-pyridinyl.

As noted in the formulas above, (A) can be substituted with 0-3 $R^4$ groups disclosed herein. Accordingly, in some embodiments, (A) is:

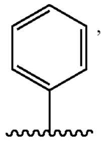, 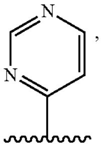, 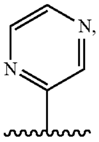, or 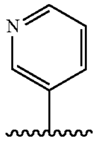.

In some embodiments, Ⓐ is:
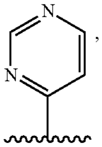, 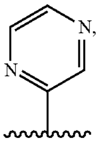 or 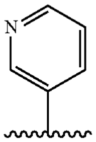.
In some embodiments, when m is 1 or 2,
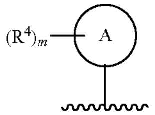
is:
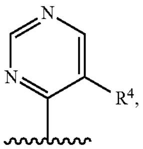 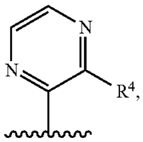 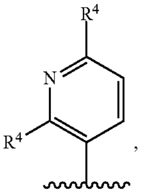, 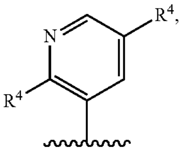 or 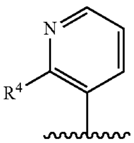.
In some embodiments, when m is 1 or 2,
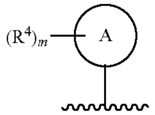
is:
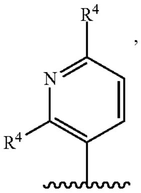, 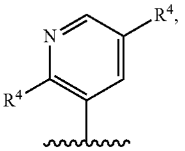 or 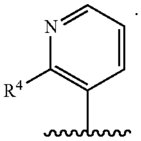.
In some embodiments, when m is 1 or 2,
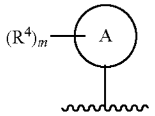
is:
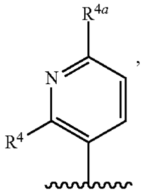, 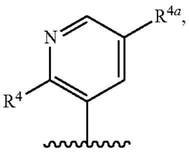 or 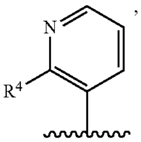,
wherein $R^{4a}$ is H, halogen, $C_{1-6}$ alkyl, or $C_{1-6}$ alkoxy, optionally wherein $R^{4a}$ is H, F, Me, or OMe. In some embodiments, when m is 1 or 2,
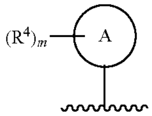
is:
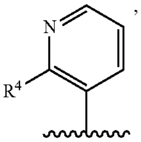, 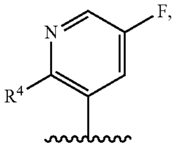 or 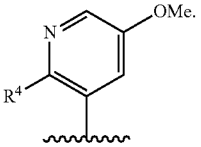
In some embodiments, when m is 1,
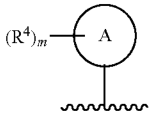
is:
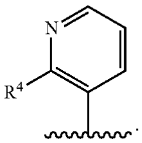.
In some embodiments, when m is 1 or 2,
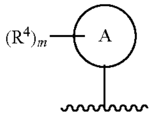

is:

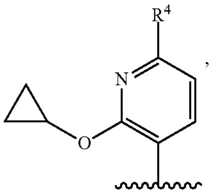

,

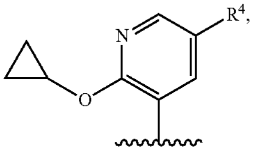

or

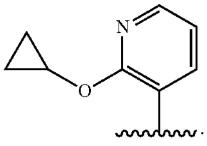

In some embodiments, when m is 1,

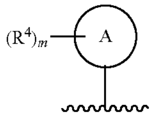

is

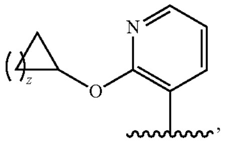

wherein Z is an integer from 1-4. In some embodiments, when m is 2,

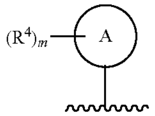

is

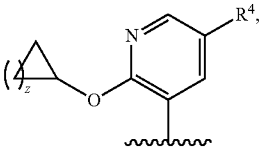

wherein Z is an integer from 1-4. In some embodiments, when m is 1,

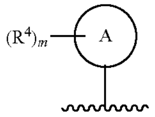

is

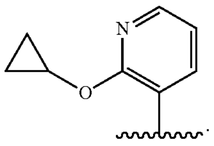

In some embodiments, when m is 2,

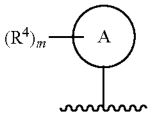

is

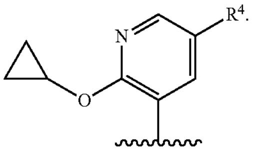

In some embodiments, the present disclosure provides a compound of Formula (IA'-3):

(IA'-3)

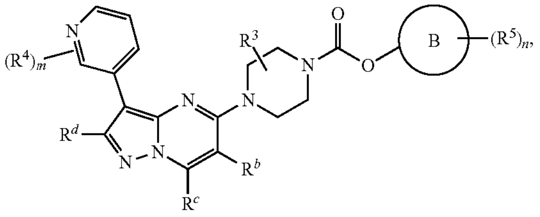

or pharmaceutically acceptable salt, deuterated form, or stereoisomer thereof, wherein:

Ⓑ is heterocyclyl;

$R^3$ is H, halogen, —$C_{1-6}$ alkyl, —CN, or —$COR^a$;

each $R^4$ is independently halogen, —OH, —O—$C_{1-6}$ alkyl, —O—$C_{1-6}$ haloalkyl, —O-cycloalkyl, —O-heterocyclyl, —O—($C_{1-5}$ alkylene)-cycloalkyl, —O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, —$C_{1-6}$ alkyl, —$C_{1-6}$ heteroalkyl, —O—$C_{1-6}$ alkyl, heterocyclyl, —$C_{1-5}$ alkylene-cycloalkyl, or —$C_{1-5}$ alkylene-heterocyclyl, or two $R^5$ form an oxo;

$R^a$ is —OH, —O—($C_{1-6}$ alkyl), —$NH_2$, —NH—($C_{1-6}$ alkyl), or —N($C_{1-6}$ alkyl)$_2$;

$R^b$, $R^c$, and $R^d$ are each independently H, halogen, $C_{1-6}$ alkyl, —OH, —O—($C_{1-6}$ alkyl), —$NH_2$, —NH—($C_{1-6}$ alkyl), or —NH—($C_{1-6}$ alkyl)$_2$;

m is 0, 1, 2, or 3; and n is 0, 1, or 2, provided that the compound is not:

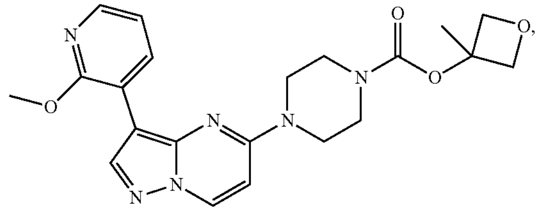

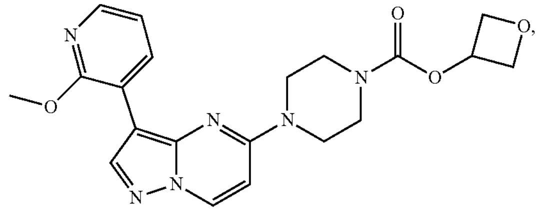

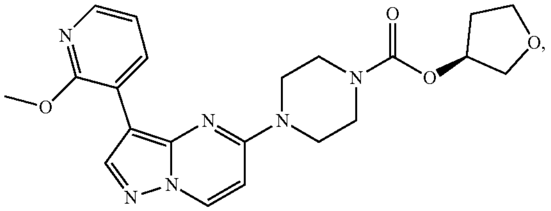

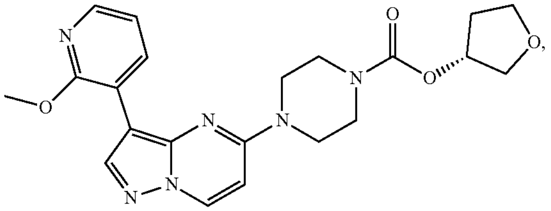

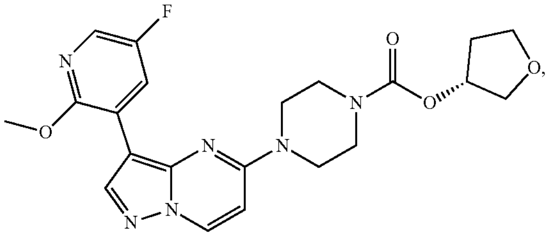

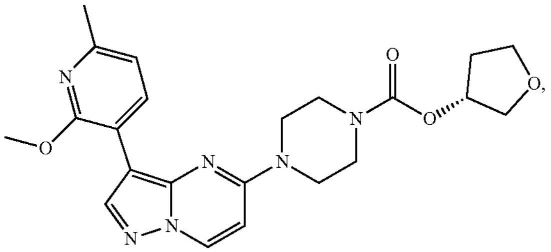

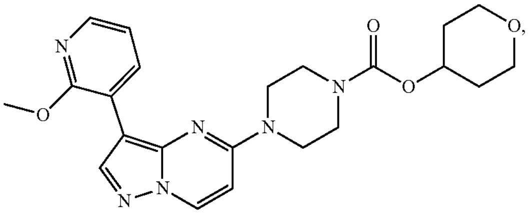

or

-continued

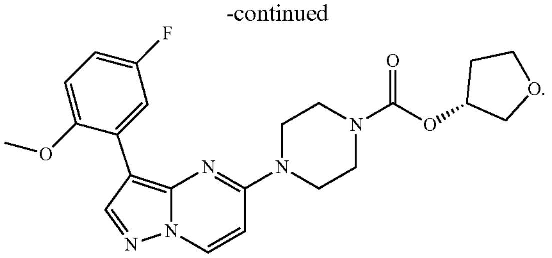

In some embodiments, the present disclosure provides a compound of Formula (IA-3):

(IA-3)

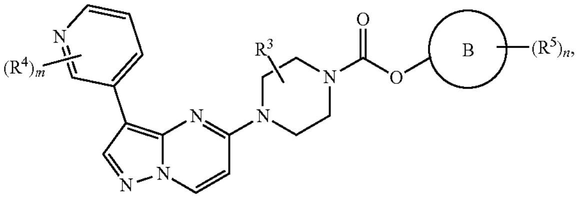

or pharmaceutically acceptable salt, deuterated form, or stereoisomer thereof, wherein:

Ⓑ is heterocyclyl;

$R^3$ is H, halogen, $C_{1-6}$ alkyl, CN, or $COR^a$;

each $R^4$ is independently halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, $C_{1-6}$ alkyl, $C_{1-6}$ heteroalkyl, O—$C_{1-6}$ alkyl, heterocyclyl, $C_{1-5}$ alkylene-cycloalkyl, or $C_{1-5}$ alkylene-heterocyclyl, or two $R^5$ form an oxo;

$R^a$ is —OH, —O—($C_{1-6}$ alkyl), —$NH_2$, —NH—($C_{1-6}$ alkyl), or —N($C_{1-6}$ alkyl)$_2$;

m is 0, 1, 2, or 3; and n is 0, 1, or 2, provided that the compound is not:

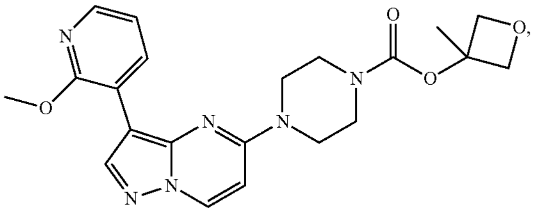

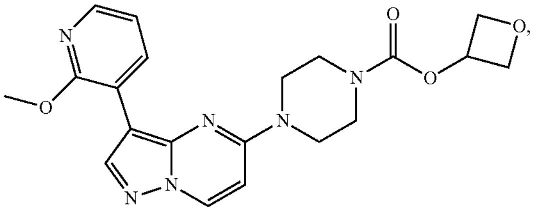

-continued

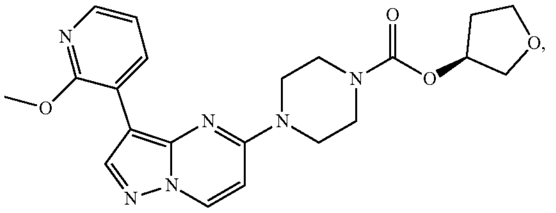

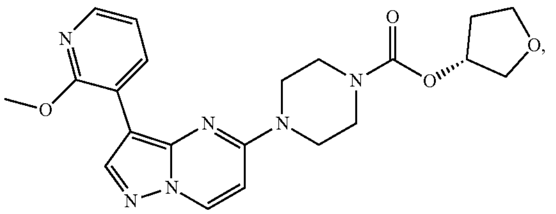

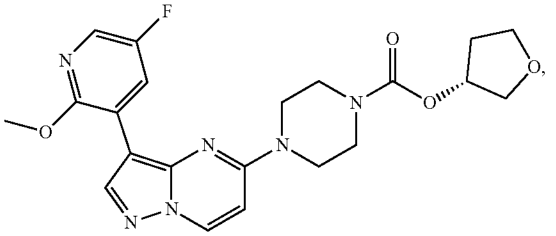

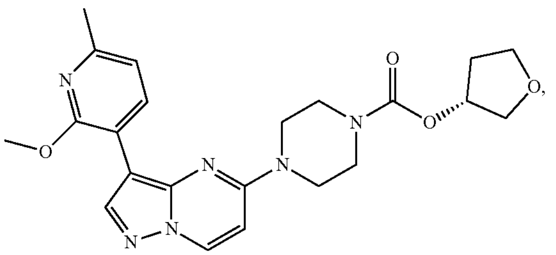

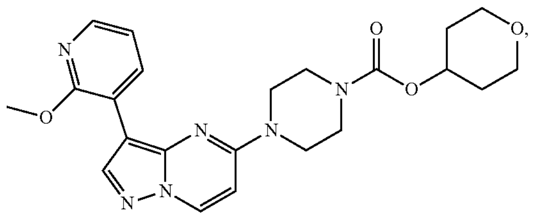

or

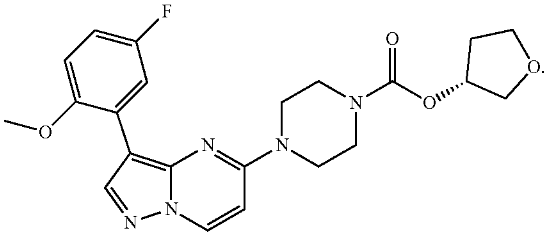

In some embodiments, Ⓑ is N-heterocyclyl or a bicyclic ether. In some embodiments, Ⓑ is N-heterocyclyl or tert-butyl, wherein when Ⓑ is ter-butyl, $R^5$ is absent. In some embodiments, Ⓑ is N-heterocyclyl. In some embodiments, Ⓑ is a 5- to 8-membered N-heterocyclyl. In some embodiments, Ⓑ is a 6-membered N-heterocyclyl. In some embodiments, Ⓑ is a 5-membered N-heterocyclyl. In some embodiments, the N-heterocyclyl is

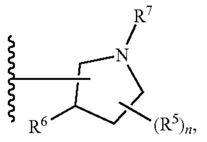

wherein $R^5$, $R^6$, $R^7$, and n are as defined herein. In some embodiments, the N-heterocyclyl is

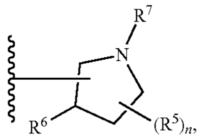

wherein each $R^5$ is independently halogen, $C_{1-6}$ alkyl, $C_{1-6}$ heteroalkyl, O—$C_{1-6}$ alkyl, $C_{1-5}$ alkylene-cycloalkyl, or $C_{1-5}$ alkylene-heterocyclyl, or two $R^5$ taken together form an oxo; $R^6$ is H, $C_{1-6}$ alkyl, $C_{2-6}$ alkenyl, or $C_{2-6}$ alkynyl; $R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, $C_{1-5}$ alkylene-C(O)—NH—($CH_2Ph$), or 4- to 8-membered heterocyclyl; and n is 0, 1, or 2. In some embodiments, two $R^5$ taken together form an oxo. In some embodiments, Ⓑ is a bicyclic ether. In some embodiments, the bicyclic ether is

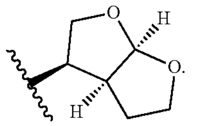 [SMILES: *[C@H]1CO[C@H]2OCC[C@H]21]

In some embodiments, Ⓑ is N-heterocyclyl and the N-heterocyclyl is

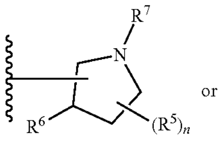

or

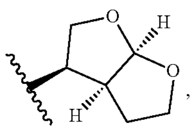

wherein $R^5$, $R^6$, $R^7$, and n are as defined herein.

In some embodiments, Ⓑ is N-heterocyclyl and the N-heterocyclyl is

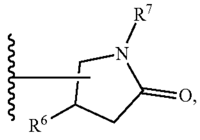

wherein $R^6$ and $R^7$ are as defined herein. In some embodiments, Ⓑ is N-heterocyclyl and the N-heterocyclyl is

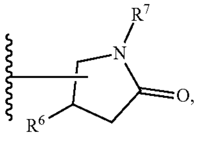

wherein $R^6$ is H, $C_{1-6}$ alkyl, $C_{2-6}$ alkenyl, or $C_{2-6}$ alkynyl; and $R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl. In some embodiments, Ⓑ is N-heterocyclyl and the N-heterocyclyl is

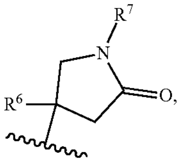

wherein $R^6$ and $R^7$ are as defined herein. In some embodiments, Ⓑ is N-heterocyclyl and the N-heterocyclyl is

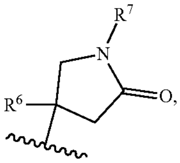

wherein $R^6$ is H, $C_{1-6}$ alkyl, $C_{2-6}$ alkenyl, or $C_{2-6}$ alkynyl; and $R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl.

In some embodiments, Ⓑ is

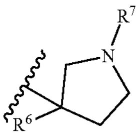 , 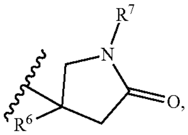

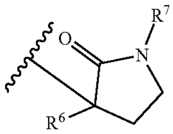 , or 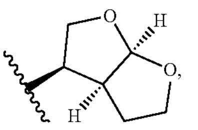

wherein $R^6$ and $R^7$ are as defined herein. In some embodiments, Ⓑ is

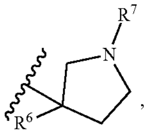 , 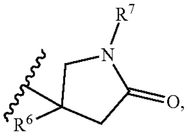 or

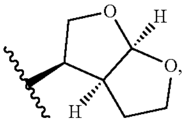

wherein $R^6$ and $R^7$ are as defined herein. In some embodiments, Ⓑ is

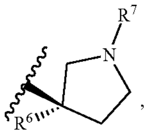 , 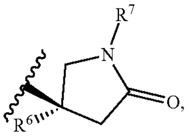 or

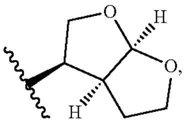

wherein $R^6$ and $R^7$ are as defined herein. In some embodiments, Ⓑ is

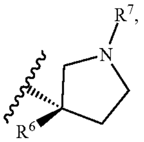 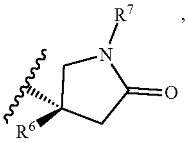 , or

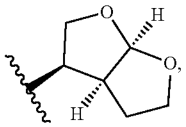

wherein $R^6$ and $R^7$ are as defined herein. In some embodiments, Ⓑ is

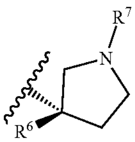 or 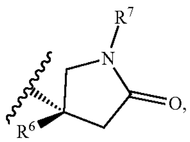

wherein $R^6$ and $R^7$ are as defined herein. In some embodiments, Ⓑ is

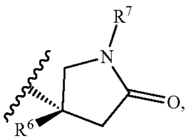

wherein $R^6$ and $R^7$ are as defined herein. In some embodiments, Ⓑ is

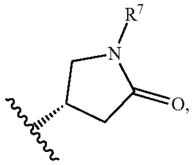

wherein $R^7$ is as defined herein. In some embodiments, Ⓑ is

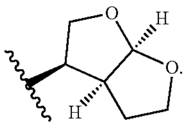 [SMILES: *[C@H]1CO[C@H]2OCC[C@H]21]

In some embodiments,

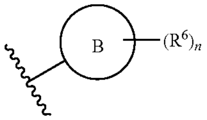

is

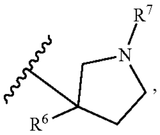
,
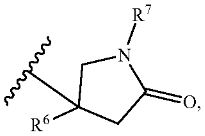

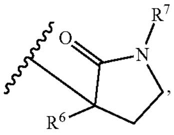
, or
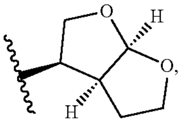

wherein $R^6$ and $R^7$ are as defined herein, or tert-butyl. In some embodiments,

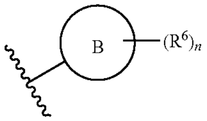

is

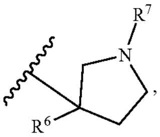
,
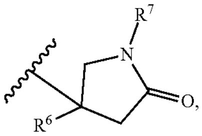
or

-continued

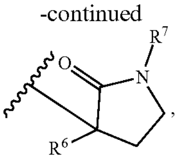

wherein $R^6$ and $R^7$ are as defined herein, or tert-butyl. In some embodiments,

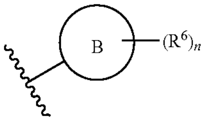

is

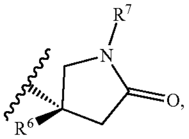

wherein $R^6$ and $R^7$ are as defined herein, or tert-butyl. In some embodiments,

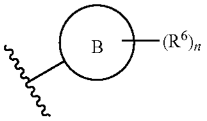

is

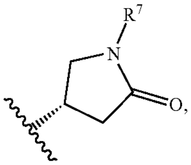

wherein $R_7$ is as defined herein, or tert-butyl.

In some embodiments, the present disclosure provides a compound of Formula (IA'-4):

(IA'-4)

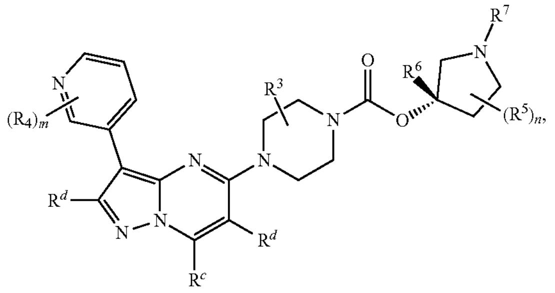

or pharmaceutically acceptable salt or deuterated form thereof, wherein:

$R^3$ is H, halogen, $C_{1-5}$ alkyl, —CN, or —$COR^a$;

each $R^4$ is independently halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently H, halogen, $C_{1-6}$ alkyl, $C_{1-6}$ heteroalkyl, O—$C_{1-6}$ alkyl, $C_{1-5}$ alkylene-cycloalkyl, or $C_{1-5}$ alkylene-heterocyclyl, or two $R^5$ form an oxo;

$R^6$ is H, $C_{1-6}$ alkyl, $C_{2-6}$ alkenyl, or $C_{2-6}$ alkynyl;

$R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2$Ph, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2$Ph), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl;

$R^a$ is —OH, —O—($C_{1-6}$ alkyl), —$NH_2$, —NH—($C_{1-6}$ alkyl), or —N($C_{1-6}$ alkyl)$_2$;

$R^b$, $R^c$, and $R^d$ are each independently H, halogen, $C_{1-6}$ alkyl, —OH, —O—($C_{1-6}$ alkyl), —$NH_2$, —NH—($C_{1-6}$ alkyl), or —NH—($C_{1-6}$ alkyl)$_2$;

m is 0, 1, 2, or 3; and n is 0, 1, or 2.

In some embodiments, the compound of (IA'-4) has the structure:

(IA'-4a)

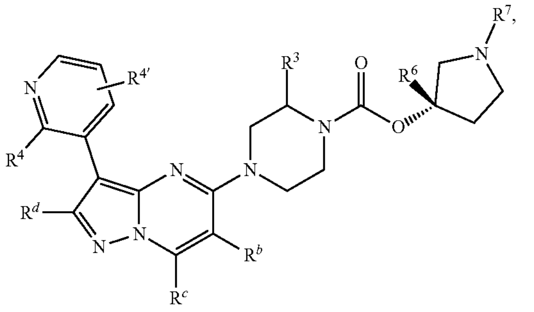

wherein $R^b$, $R^c$, $R^d$, $R^3$, $R^4$, $R^6$, and $R^7$ are as defined herein; and $R^{4'}$ is H, halogen, $C_{1-6}$ alkyl, or $C_{1-6}$ alkoxy.

In some embodiments, $R^{4'}$ is H, F, Me, or OMe.

In some embodiments, the present disclosure provides a compound of Formula (IA-4):

(IA-4)

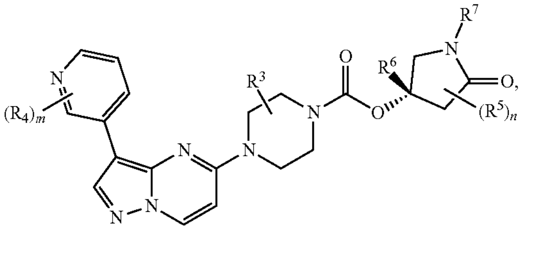

or pharmaceutically acceptable salt or deuterated form thereof, wherein:

$R^3$ is H, halogen, $C_{1-5}$ alkyl, —CN, or —$COR^2$;

each $R^4$ is independently halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently H, halogen, $C_{1-6}$ alkyl, $C_{1-6}$ heteroalkyl, O—$C_{1-6}$ alkyl, $C_{1-5}$ alkylene-cycloalkyl, or $C_{1-5}$ alkylene-heterocyclyl, or two $R^5$ form an oxo;

$R^6$ is H, $C_{1-6}$ alkyl, $C_{2-6}$ alkenyl, or $C_{2-6}$ alkynyl;

$R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2$Ph, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2$Ph), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl;

$R^a$ is —OH, —O—($C_{1-6}$ alkyl), —$NH_2$, —NH—($C_{1-6}$ alkyl), or —N($C_{1-6}$ alkyl)$_2$;

m is 0, 1, 2, or 3; and n is 0, 1, or 2.

In some embodiments, the compound of (IA-4) has the structure:

(IA-4a)

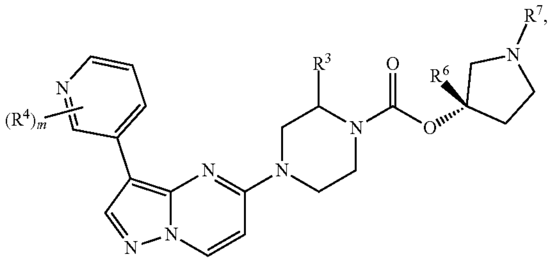

wherein $R^3$, $R^4$, $R^6$, $R^7$, and m are as defined herein.

In some embodiments, $R^a$ is —OH, —O—$C_{1-6}$ alkyl, —$NH_2$, —NH—($C_{1-6}$ alkyl), or —N($C_{1-6}$ alkyl)$_2$. In some embodiments, $R^a$ is —OH, —OMe, —$NH_2$, —NHMe, or —$NMe_2$.

In some embodiments, each $R^4$ is independently halogen, —OH, alkoxy, —O-cycloalkyl, —O-heterocyclyl, —O-aryl, —O-heteroaryl, —NH-(alkyl), —NH-(cycloalkyl), or —NH-(heterocyclyl). In some embodiments, each $R^4$ is independently halogen, —OH, $C_{1-6}$ alkoxy, —O—($C_{3-6}$ cycloalkyl), —O-(3- to 12-membered heterocyclyl), —O—($C_{6-12}$ aryl), —O-(5- to 14-membered heteroaryl), —NH—($C_{1-6}$ alkyl), —NH—($C_{3-6}$ cycloalkyl), or —NH-(3- to 14-membered heterocyclyl). In some embodiments, each $R^4$ is independently halogen, alkoxy, —O-cycloalkyl, —O-heterocyclyl, —O-aryl, —O-heteroaryl, —NH-(alkyl), —NH-(cycloalkyl), or —NH-(heterocyclyl). In some embodiments, each $R^4$ is independently halogen, alkoxy, —O-cycloalkyl, —O-heterocyclyl, —NH-(alkyl), —NH-(cycloalkyl), or —NH-(heterocyclyl). In some embodiments, each $R^4$ is independently halogen, alkoxy, —O-cycloalkyl, —O-heterocyclyl, —O-phenyl, or —O-heteroaryl. In some embodiments, each $R^4$ is independently alkoxy, —O-cycloalkyl, or —O-heterocyclyl. In some embodiments, each $R^4$ is independently-O—($C_{1-5}$ alkyl), —O—($C_{3-6}$ cycloalkyl), —O-(4- to 8-membered heterocyclyl), —NH—($C_{1-5}$ alkyl), —NH—($C_{3-6}$ cycloalkyl), or —NH-(4- to 8-membered heterocyclyl). In some embodiments, each $R^4$ is independently-O—($C_{1-5}$ alkyl), —O—($C_{3-6}$ cycloalkyl), —O-(4- to 8-membered heterocyclyl), —O-phenyl, or O-(5- to 6-membered heteroaryl). In some embodiments, each $R^4$ is independently-O—($C_{1-5}$ alkyl), —O—($C_{3-6}$ cycloalkyl), or —O-(4- to 8-membered heterocyclyl). In some embodiments, each $R^4$ is independently-O—($C_{1-5}$ alkyl), —O—($C_{3-6}$ cycloalkyl), or —O-(4- to 8-membered O-heterocyclyl). In some embodiments, each $R^4$ is —O—($C_{3-6}$ cycloalkyl).

In some embodiments, each $R^4$ is independently:

F, —OH, 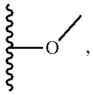,

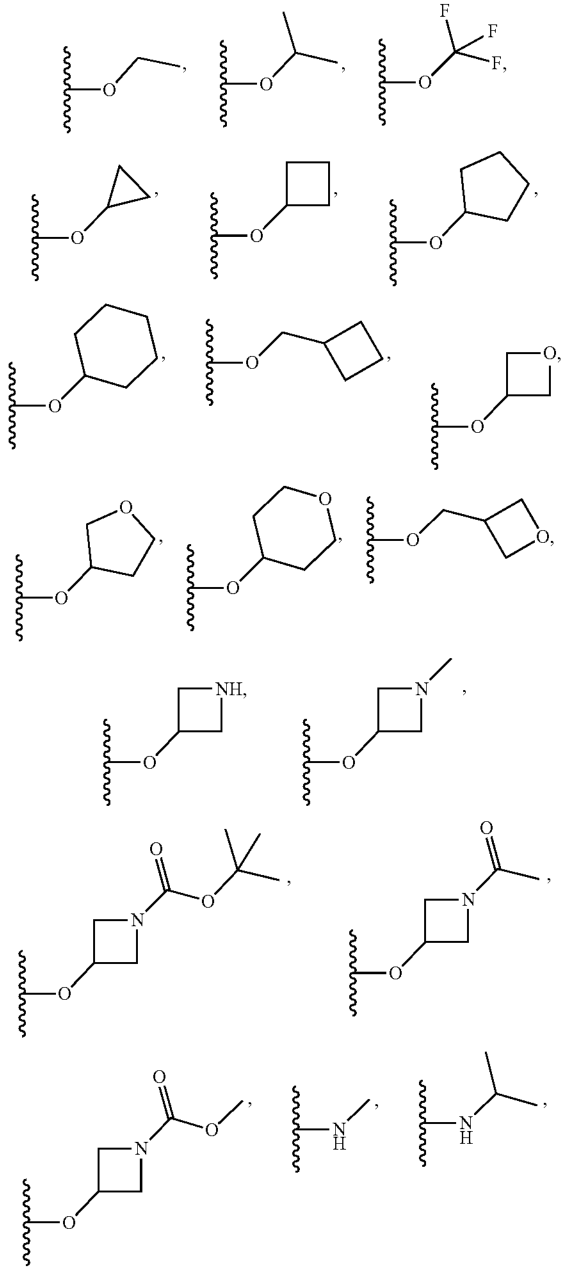

-continued

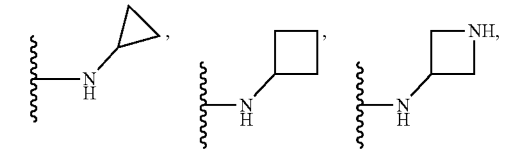

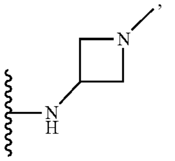

or

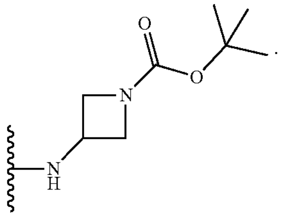

In some embodiments, each $R^4$ is independently:

F, —OH, 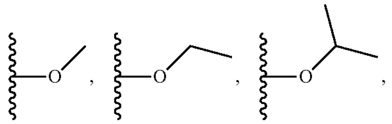

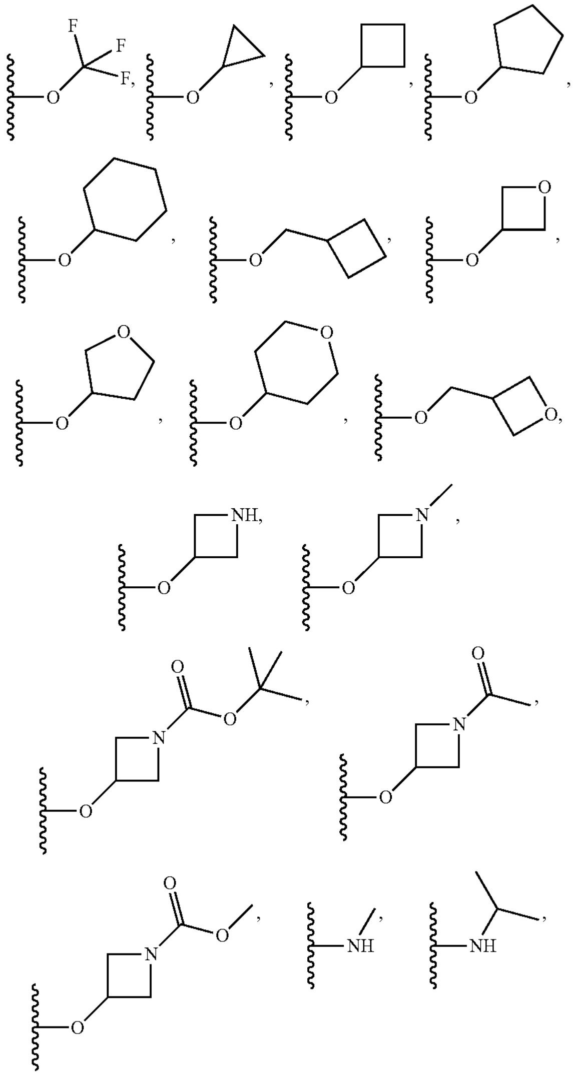

-continued

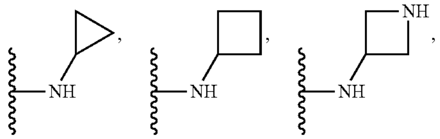

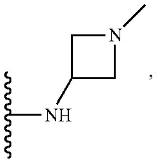

, or

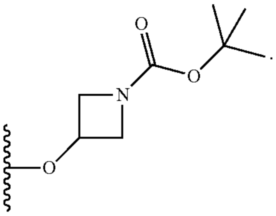

In some embodiments, each $R^4$ is independently:

F, 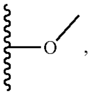 ,

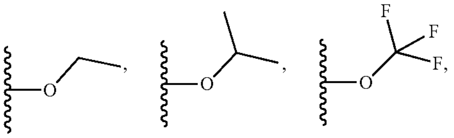

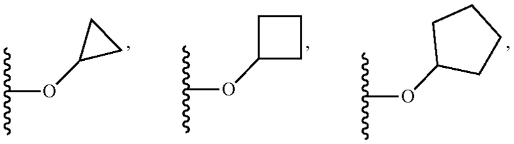

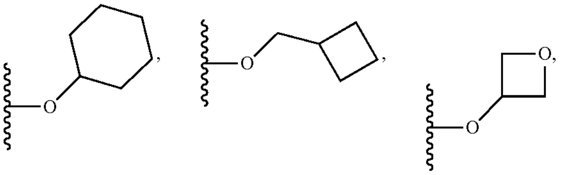

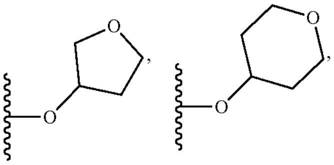

or

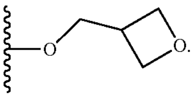

In some embodiments, each $R^4$ is independently:

F, 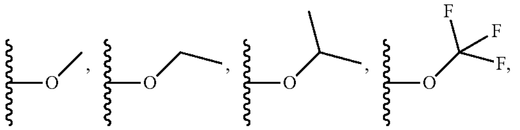

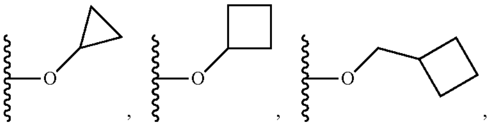

-continued

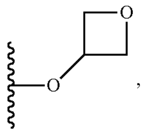

, or

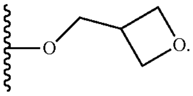

In some embodiments, each $R^4$ is independently —OH,

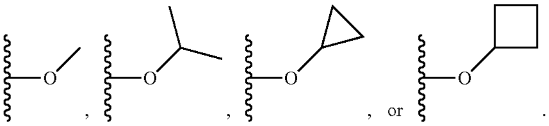

In some embodiments, each $R^4$ is independently

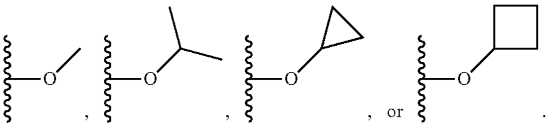

In some embodiments, each $R^4$ is independently

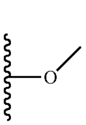

or

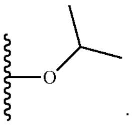 [SMILES: *OC(C)C]

In some embodiments, each $R^4$ is independently

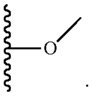

In some embodiments, each $R^4$ is independently

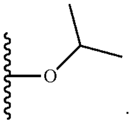

In some embodiments, m is 1 and $R^4$ is:

—OH, 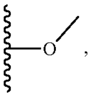 ,

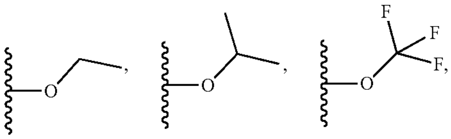

-continued

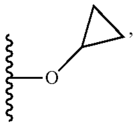, 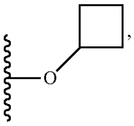,

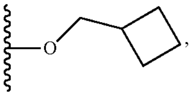, 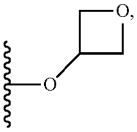

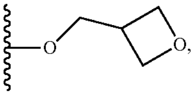

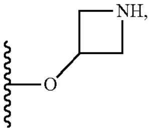 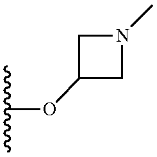,

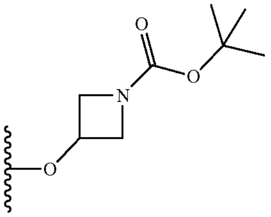, 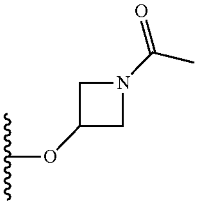.

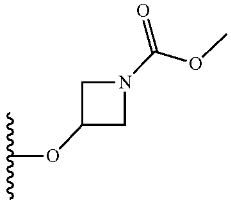, 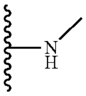, 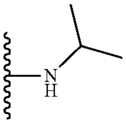,

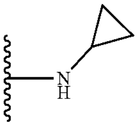, 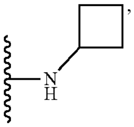, 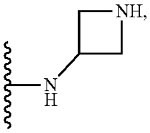

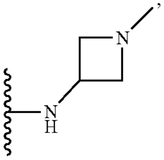, or 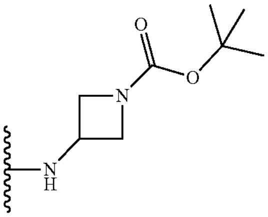.

In some embodiments, m is 1 and $R^4$ is

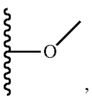, 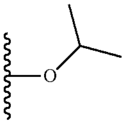, 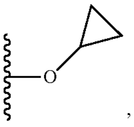, or 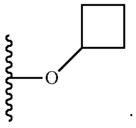.

In some embodiments, m is 1 and $R^4$ is

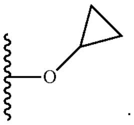 [SMILES: *OC1CC1].

In some embodiments, m is 2, and one $R^4$ is

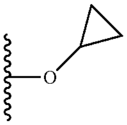 or 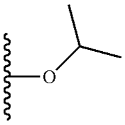

and the other $R^4$ is F, —OMe, or —$OCF_3$. In some embodiments, m is 2, and one $R^4$ is

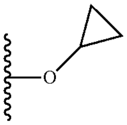 [SMILES: *OC1CC1]

and the other $R^4$ is F, —OMe, or —$OCF_3$. In some embodiments, m is 2, and one $R^4$ is

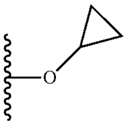 [SMILES: *OC1CC1]

and the other $R^4$ is F or —OMe.

In some embodiments, the present disclosure provides a compound of Formula (IA'-5):

(IA'-5)

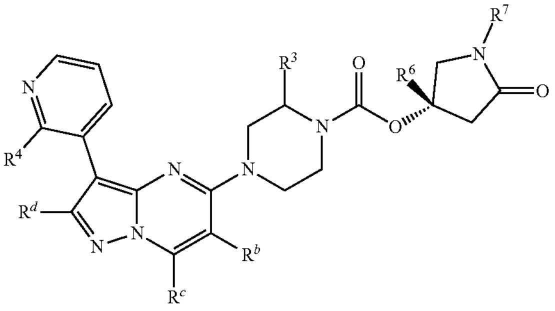

or pharmaceutically acceptable salt or deuterated form thereof, wherein:

$R^b$, $R^c$, and $R^d$ are each independently H, halogen, $C_{1-6}$ alkyl, —OH, —O—($C_{1-6}$ alkyl), —$NH_2$, —NH—($C_{1-6}$ alkyl), or —NH—($C_{1-6}$ alkyl)$_2$;

$R^3$ is H, halogen, $C_{1-6}$ alkyl, —CN, —C(O)$NH_2$, —C(O)OEt, or —C(O)OH;

$R^4$ is halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

$R^6$ is H, $C_{1-6}$ alkyl, $C_{2-6}$ alkenyl, or $C_{2-6}$ alkynyl;

$R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl.

In some embodiments, the present disclosure provides a compound of Formula (IA-5):

(IA-5)

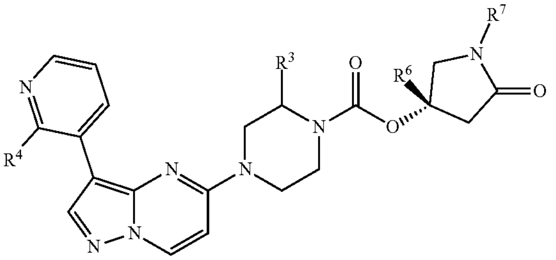

or pharmaceutically acceptable salt or deuterated form thereof, wherein:

$R^3$ is H, halogen, $C_{1-6}$ alkyl, —CN, —C(O)$NH_2$, —C(O)OEt, or —C(O)OH;

$R^4$ is halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

$R^6$ is H, $C_{1-6}$ alkyl, $C_{2-6}$ alkenyl, or $C_{2-6}$ alkynyl; and $R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl.

In some embodiments, the compound of Formula (IA-5) has the structure:

(IA-5a)

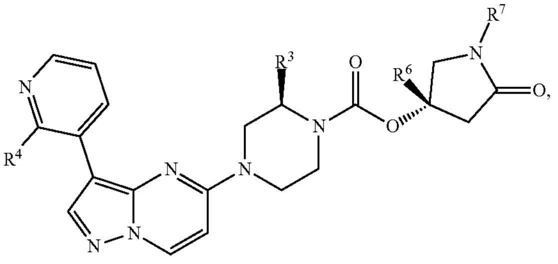

or a pharmaceutically acceptable salt thereof, wherein $R^3$, $R^4$, $R^6$, and $R^7$ are as defined herein.

In some embodiments, the compound of Formula (IA-5) has the structure:

(IA-5b)

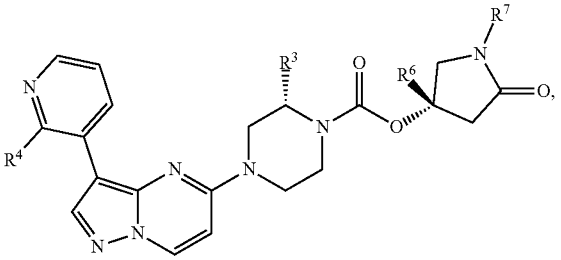

or a pharmaceutically acceptable salt thereof, wherein $R^3$, $R^4$, $R^6$, and $R^7$ are as defined herein.

In some embodiments, the present disclosure provides a compound of Formula (IA'-6):

(IA'-6)

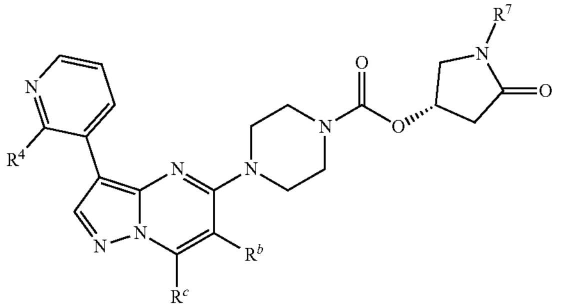

or pharmaceutically acceptable salt or deuterated form thereof, wherein:

$R^b$, $R^c$, and $R^d$ are each independently H, halogen, $C_{1-6}$ alkyl, —OH, —O—($C_{1-6}$ alkyl), —$NH_2$, —NH—($C_{1-6}$ alkyl), or —NH—($C_{1-6}$ alkyl)$_2$;

$R^4$ is halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl); and $R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl.

In some embodiments, the present disclosure provides a compound of Formula (IA-6):

(IA-6)

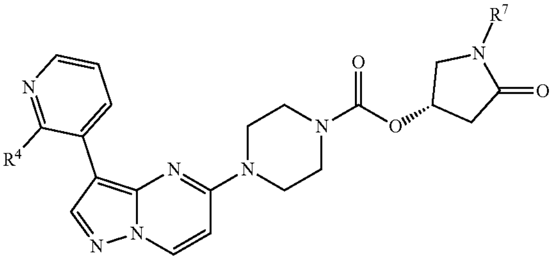

or pharmaceutically acceptable salt or deuterated form thereof, wherein:

$R^4$ is halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl); and $R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl.

In some embodiments, $R^b$ and $R^c$ are each independently H, halogen, —OH, $C_{1-6}$ alkyl, —O—$C_{1-6}$ alkyl, —$NH_2$, —NH—($C_{1-6}$ alkyl), or —N($C_{1-6}$ alkyl)$_2$. In some embodiments, $R_b$ and $R^c$ are each independently H, F, Cl, Me, —OH, —OMe, —$NH_2$, —NHMe, or —$NMe_2$. In some embodiments, $R^b$ and $R^c$ are each independently H, F, Me, —OH, —OMe, or Me. In some embodiments, $R^b$ is H, F, Me, —OH, or —OMe and $R^c$ is H. In some embodiments, $R^b$ is H or F and $R^c$ is H. In some embodiments, $R_b$ is H and $R^c$ is H.

In some embodiments, $R^d$ is H or $C_{1-6}$ alkyl. In some embodiments, $R^d$ is H or Me. In some embodiments, $R^d$ is H.

In some embodiments, $R^3$ is H, $C_{1-5}$ alkyl, —CN, or —C(O) (O—$C_{1-6}$ alkyl). In some embodiments, $R^3$ is H, $C_{1-3}$ alkyl, —CN, or —C(O) (O—$C_{1-3}$ alkyl). In some embodiments, $R^3$ is H, Me, Et, iPr, —C≡CH, —CN, —C(O)OMe, or —C(O)OEt. In some embodiments, $R^3$ is H, Me, —C≡CH, —CN, or —C(O)OEt. In some embodiments, $R^3$ is H, —C≡CH, —CN, or —C(O)OEt. In some embodiments, $R^3$ is H.

In some embodiments, $R^4$ is halogen, —OH, alkoxy, —O-cycloalkyl, —O-heterocyclyl, —O-aryl, —O-heteroaryl, —NH-(alkyl), —NH-(cycloalkyl), or —NH-(heterocyclyl). In some embodiments, $R^4$ is halogen, —OH, $C_{1-6}$ alkoxy, —O—($C_{3-6}$ cycloalkyl), —O-(3- to 12-membered heterocyclyl), —O—($C_{6-12}$ aryl), —O-(5- to 14-membered heteroaryl), —NH—($C_{1-6}$ alkyl), —NH—($C_{3-6}$ cycloalkyl), or —NH-(3- to 12-membered heterocyclyl). In some embodiments, $R^4$ is halogen, alkoxy, —O-cycloalkyl, —O-heterocyclyl, —O-aryl, —O-heteroaryl, —NH-(alkyl), —NH-(cycloalkyl), or —NH-(heterocyclyl). In some embodiments, $R^4$ is halogen, alkoxy, —O-cycloalkyl, —O-heterocyclyl, —NH-(alkyl), —NH-(cycloalkyl), or —NH-(heterocyclyl). In some embodiments, $R^4$ is halogen, alkoxy, —O-cycloalkyl, —O-heterocyclyl, —O-phenyl, or —O-heteroaryl. In some embodiments, $R^4$ is alkoxy, —O-cycloalkyl, or —O-heterocyclyl. In some embodiments, $R^4$ is —O—($C_{1-5}$ alkyl), —O—($C_{3-6}$ cycloalkyl), —O-(4- to 8-membered heterocyclyl), —NH—($C_{1-5}$ alkyl), —NH—($C_{3-6}$ cycloalkyl), or —NH-(4- to 8-membered heterocyclyl). In some embodiments, $R^4$ is —O—($C_{1-5}$ alkyl), —O—($C_{3-6}$ cycloalkyl), —O-(4- to 8-membered heterocyclyl), —O-phenyl, or O-(5- to 6-membered heteroaryl). In some embodiments, $R^4$ is —O—($C_{1-5}$ alkyl), —O—($C_{3-6}$ cycloalkyl), or —O-(4- to 8-membered heterocyclyl). In some embodiments, $R^4$ is —O—($C_{3-6}$ cycloalkyl).

In some embodiments, $R^4$ is:

—OH, 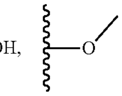 ,

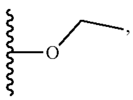 , 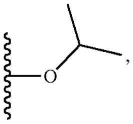 , 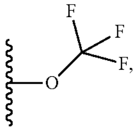 ,

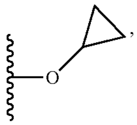 , 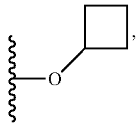 , 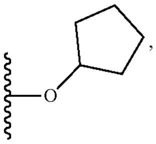 ,

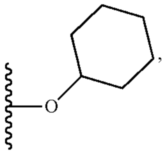 , 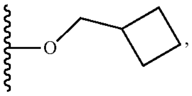 , 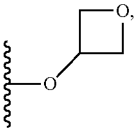 ,

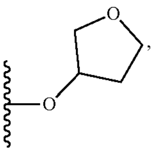 , 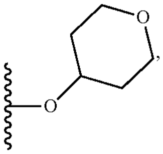 , 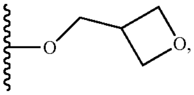 ,

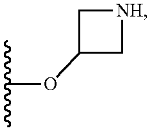 , 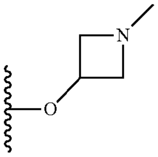 ,

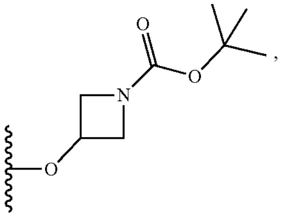 , 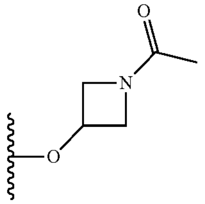 ,

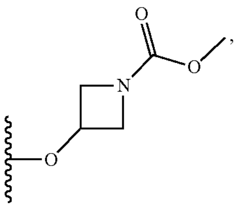 , 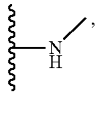 , 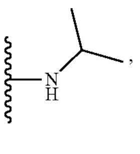 ,

-continued
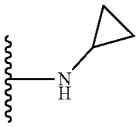,
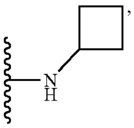,
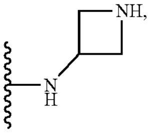
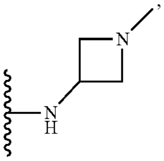, or
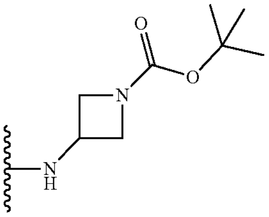.
In some embodiments, $R^4$ is:
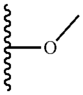,
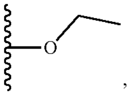,
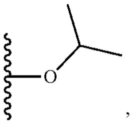,
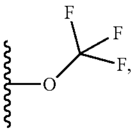
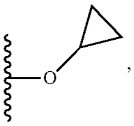,
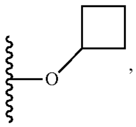,
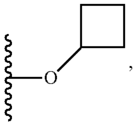,
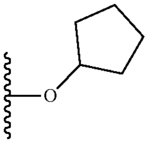,
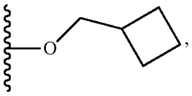,
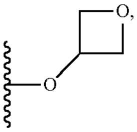
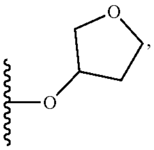,
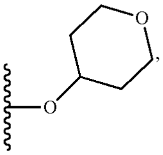, or
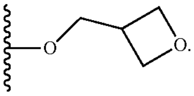
In some embodiments, $R^4$ is:
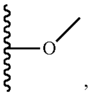 [SMILES: *OC],
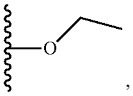,
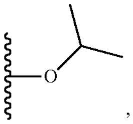,
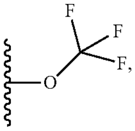
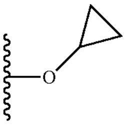,
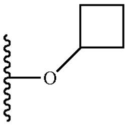,
-continued
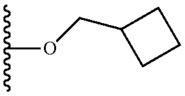,
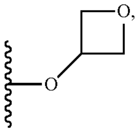, or
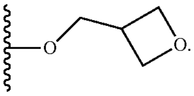
In some embodiments, $R^4$ is —OH,
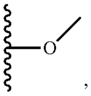,
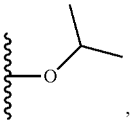,
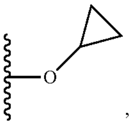, or
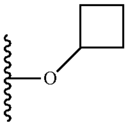.
In some embodiments, $R^4$ is
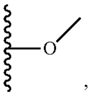,
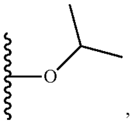,
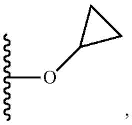, or
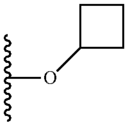.
In some embodiments, $R^4$ is
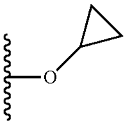 or 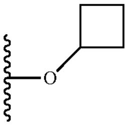.
In some embodiments, $R^4$ is
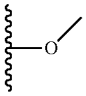 or 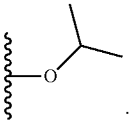.
In some embodiments, $R^4$ is
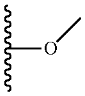.

In some embodiments, $R^4$ is

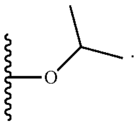

In some embodiments, $R^4$ is

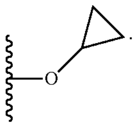 [SMILES: *OC1CC1]

In some embodiments, $R^5$ is each independently H, halogen, $C_{1-6}$ alkyl, O—$C_{1-6}$ alkyl, $C_{1-5}$ alkylene-cycloalkyl, or $C_{1-5}$ alkylene-heterocyclyl, or two $R^5$ form an oxo. In some embodiments, $R^5$ is each independently H, halogen, $C_{1-6}$ alkyl, O—$C_{1-6}$ alkyl, or $C_{1-5}$ alkylene-cycloalkyl, or two $R^5$ form an oxo. In some embodiments, $R^5$ is each independently H, halogen, $C_{1-6}$ alkyl, or O—$C_{1-6}$ alkyl, or two $R^5$ form an oxo. In some embodiments, $R^5$ is each independently H, halogen, or $C_{1-6}$ alkyl, or two $R^5$ form an oxo. In some embodiments, $R^5$ is each independently H or $C_{1-6}$ alkyl, or two $R^5$ form an oxo. In some embodiments, $R^5$ is each independently H or halogen, or two $R^5$ form an oxo. In some embodiments, each $R^5$ is H, or two $R^5$ form an oxo. In some embodiments, each $R^5$ is H. In some embodiments, two $R^5$ form an oxo.

In some embodiments, $R^6$ is H, $C_{1-6}$ alkyl, $C_{2-6}$ alkenyl, or $C_{2-6}$ alkynyl. In some embodiments, $R^6$ is H, $C_{1-6}$ alkyl, or $C_{2-6}$ alkynyl. In some embodiments, $R^6$ is H, $C_{1-2}$ alkyl, $C_{2-3}$ alkenyl, or $C_{2-3}$ alkynyl. In some embodiments, $R^6$ is H, F, Me, Et, CH═$CH_2$, or —C≡CH. In some embodiments, $R^6$ is H, Me, Et, —CH═$CH_2$, or —C≡CH. In some embodiments, $R^6$ is H, Me, Et, or —C≡CH. In some embodiments, $R^6$ is H, Me, or —C≡CH. In some embodiments, $R^6$ is H, Me, or —C≡CH. In some embodiments, $R^6$ is H or Me. In some embodiments, $R^6$ is Me or —C≡CH. In some embodiments, $R^6$ is H. In some embodiments, $R^6$ is Me. In some embodiments, $R^6$ is —C≡CH.

In some embodiments, $R^7$ is H, $C_{1-6}$ alkyl, $C_{1-5}$ alkylene-OH, $C_{1-5}$ alkylene-O—($C_{1-3}$ alkyl), $C_{1-5}$ alkylene-O—$CH_2$Ph, $C_{1-5}$ alkylene-$NH_2$, $C_{1-5}$ alkylene-NH—($C_{1-3}$ alkyl), $C_{1-5}$ alkylene-N($C_{1-3}$ alkyl)$_2$, $C_{1-3}$ alkylene-C(O)—NH—($C_{1-3}$ alkyl), $C_{1-3}$ alkylene-C(O)—$NH_2$, or 4- to 6-membered heterocyclyl. In some embodiments, $R^7$ is H, $CH_3$, $CH_2CH_3$, i-Pr,

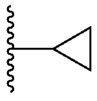,

—$CH_2CH_2$—OH, —$CH_2CH_2$—$OCH_3$, —$CH_2CH_2$—OBn, —$CH_2CH_2$—$NH_2$, —$CH_2CH_2$—NH—($CH_3$), —$CH_2CH_2$—N($CH_3$) 2, —$CH_2$C(O)—$NH_2$, —$CH_2$C(O)—NH—($CH_3$), —$CH_2$C(O)—N($CH_3$)$_2$,

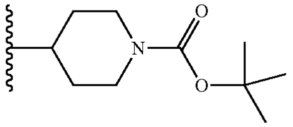,

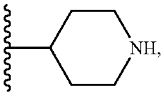 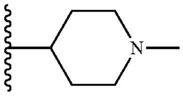,

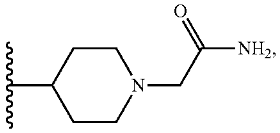 or 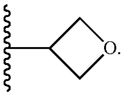

In some embodiments, $R^7$ is H, $C_{1-6}$ alkyl, $C_{3-6}$ cycloalkyl, —$CH_2$—($C_{3-6}$ cycloalkyl), or —$CH_2$-(4- to 6-membered heterocyclyl). In some embodiments, $R^7$ is H, $C_{1-6}$ alkyl, $C_{3-6}$ cycloalkyl, or —$CH_2$—($C_{3-6}$ cycloalkyl). In some embodiments, $R^7$ is H, $C_{1-6}$ alkyl, or $C_{3-6}$ cycloalkyl. In some embodiments, $R^7$ is H or $C_{1-6}$ alkyl. In some embodiments, $R^7$ is H or $C_{1-3}$ alkyl. In some embodiments, $R^7$ is H, Me, Et, n-Pr, or i-Pr. In some embodiments, $R^7$ is H or Me.

In some embodiments, m is 1, 2, or 3. In some embodiments, m is 1 or 2. In some embodiments, m is 1. In some embodiments, m is 2. In some embodiments, m is 3.

In some embodiments, n is 0 or 1. In some embodiments, n is 1 or 2. In some embodiments, n is 0. In some embodiments, n is 1. In some embodiments, n is 2.

In some embodiments of the disclosed compounds, $R^3$ is as defined herein; $R^4$ is

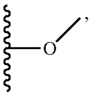, 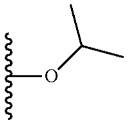, 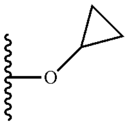,

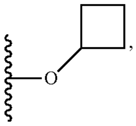, 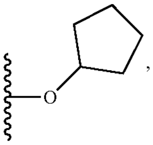, or

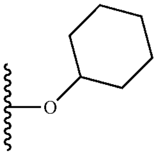;

$R^5$ is H, halogen, or $C_{1-6}$ alkyl, or two $R^5$ taken together with the carbon atom to which they are attached form an oxo; $R^6$ is H, Me, or —C≡CH; $R^7$ is H, $C_{1-6}$ alkyl, $C_{3-6}$ cycloalkyl, or —$CH_2$—($C_{3-6}$ cycloalkyl); m is 1, and n is 0, 1, or 2. In some embodiments, $R^6$ is H.

In some embodiments of the disclosed compounds, $R^3$ is as defined herein; $R^4$ is

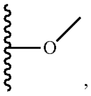, 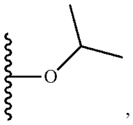, 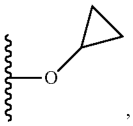, or

-continued

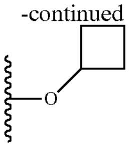

;

$R^5$ is H, halogen, or $C_{1-6}$ alkyl, or two $R^5$ taken together with the carbon atom to which they are attached form an oxo; $R^6$ is H, Me, or —C≡CH; $R^7$ is H, $C_{1-6}$ alkyl, $C_{3-6}$ cycloalkyl, or —$CH_2$—($C_{3-6}$ cycloalkyl); m is 1, and n is 0, 1, or 2. In some embodiments, $R^6$ is H.

In some embodiments of the disclosed compounds, $R^3$ is as defined herein; $R^4$ is

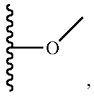 , 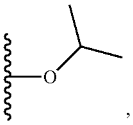 , 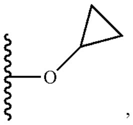 [SMILES: *OC1CC1] , or 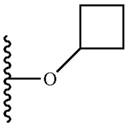 ;

$R^5$ is H, halogen, or $C_{1-6}$ alkyl, or two $R^5$ taken together with the carbon atom to which they are attached form an oxo; $R^6$ is H, Me, or —C≡CH; $R^7$ is H or $C_{1-6}$ alkyl; m is 1, and n is 0, 1, or 2. In some embodiments, $R^6$ is H.

In some embodiments of the disclosed compounds, $R^3$ is as defined herein; $R^4$ is

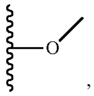 , 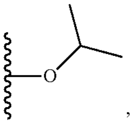 , 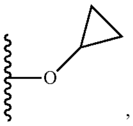 , or 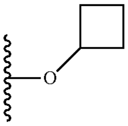 ;

$R^5$ is H, or two $R^5$ taken together with the carbon atom to which they are attached form an oxo; $R^6$ is H, Me, or —C≡CH; $R^7$ is H or $C_{1-6}$ alkyl; m is 1, and n is 0, 1, or 2. In some embodiments, $R^6$ is H.

In some embodiments of the disclosed compounds, $R^3$ is as defined herein; $R^4$ is

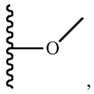 , 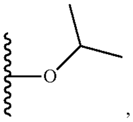 , 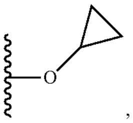 , or 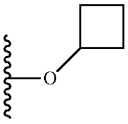 ;

two $R^5$ taken together with the carbon atom to which they are attached form an oxo; $R^6$ is H, Me, or —C≡CH; $R^7$ is H or $C_{1-6}$ alkyl; m is 1, and n is 2. In some embodiments, $R^6$ is H.

In some embodiments of the disclosed compounds, $R^3$ is as defined herein; $R^4$ is

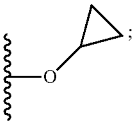 [SMILES: *OC1CC1]

;

$R^5$ is H, halogen, or $C_{1-6}$ alkyl, or two $R^5$ taken together with the carbon atom to which they are attached form an oxo; $R^6$ is H, Me, or —C≡CH; $R^7$ is H, $C_{1-6}$ alkyl, $C_{3-6}$ cycloalkyl, or —$CH_2$—($C_{3-6}$ cycloalkyl); m is 1, and n is 0, 1, or 2. In some embodiments, $R^6$ is H.

In some embodiments of the disclosed compounds, $R^3$ is as defined herein; $R^4$ is

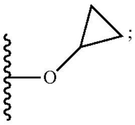

;

$R^5$ is H, halogen, or $C_{1-6}$ alkyl, or two $R^5$ taken together with the carbon atom to which they are attached form an oxo; $R^6$ is H, Me, or —C≡CH; $R^7$ is H or $C_{1-6}$ alkyl; m is 1, and n is 0, 1, or 2. In some embodiments, $R^6$ is H.

In some embodiments of the disclosed compounds, $R^3$ is as defined herein; $R^4$ is

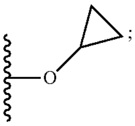 [SMILES: *OC1CC1]

;

$R^5$ is H, or two $R^5$ taken together with the carbon atom to which they are attached form an oxo; $R^6$ is H, Me, or —C≡CH; $R^7$ is H or $C_{1-6}$ alkyl; m is 1, and n is 0, 1, or 2. In some embodiments, $R^6$ is H.

In some embodiments of the disclosed compounds, $R^3$ is as defined herein; $R^4$ is

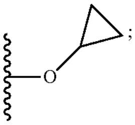 [SMILES: *OC1CC1]

;

two $R^5$ taken together with the carbon atom to which they are attached form an oxo; $R^6$ is H, Me, or —C≡CH; $R^7$ is H or $C_{1-6}$ alkyl; m is 1, and n is 2. In some embodiments, $R^6$ is H.

In some embodiments, the present disclosure provides a compound of Formula (IB):

(IB)

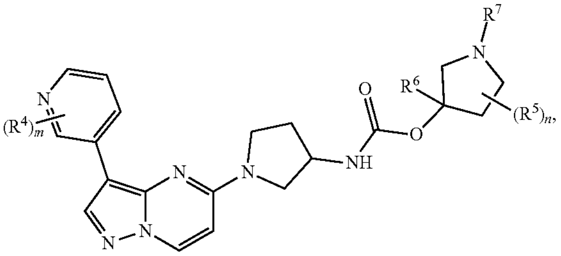

or pharmaceutically acceptable salt or deuterated form thereof, wherein:

each $R^4$ is independently halogen, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently H, halogen, $C_{1-6}$ alkyl, $C_{1-6}$ heteroalkyl, O—$C_{1-6}$ alkyl, $C_{1-5}$ alkylene-cycloalkyl, or $C_{1-5}$ alkylene-heterocyclyl, or two $R^5$ form an oxo;

$R^6$ is H, $C_{1-6}$ alkyl, $C_{2-6}$ alkenyl, or $C_{2-6}$ alkynyl;

$R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl;

m is 0, 1, or 2; and n is 0, 1, or 2.

In some embodiments, the compound of Formula (IB) has the structure:

(IB-1)

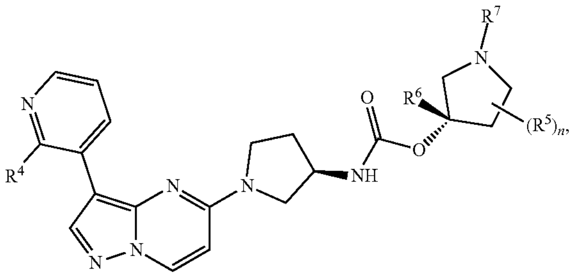

(IB-2)

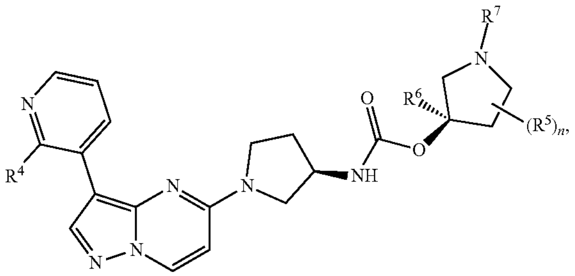

(IB-3)

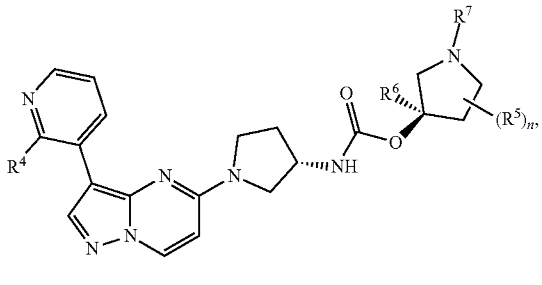

or

-continued (IB-4)

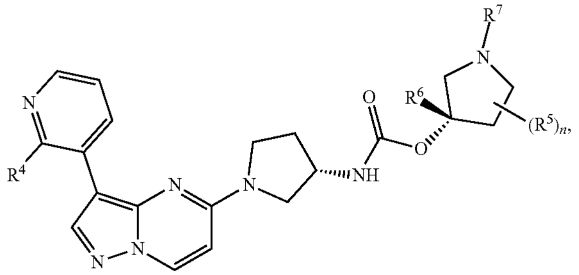

or a pharmaceutically acceptable salt thereof, wherein $R^4$, $R^5$, $R^6$, $R^7$, and n are as defined herein.

In some embodiments, the compound of Formula (IB) has the structure:

(IB-1a)

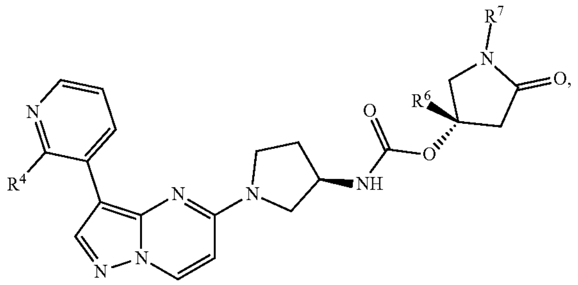

(IB-2a)

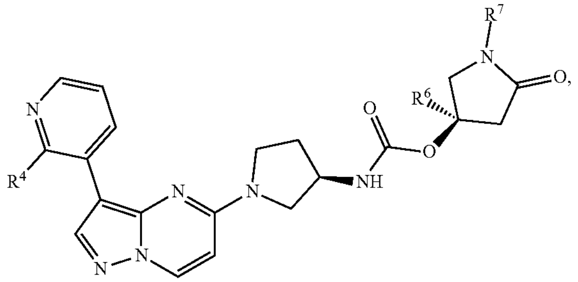

(IB-3a)

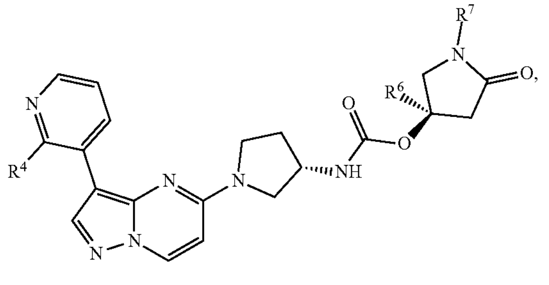

or

-continued (IB-4a)

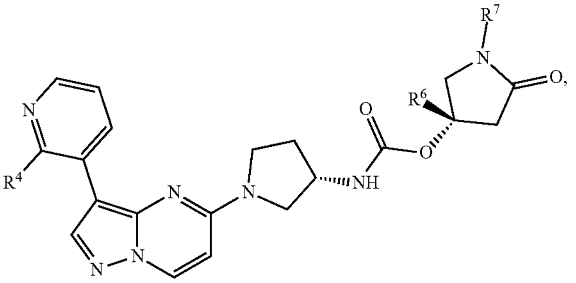

or a pharmaceutically acceptable salt thereof, wherein $R^4$, $R^6$, and $R^7$ are as defined herein.

In some embodiments, the present disclosure provides a compound of Formula (IC'):

(IC')

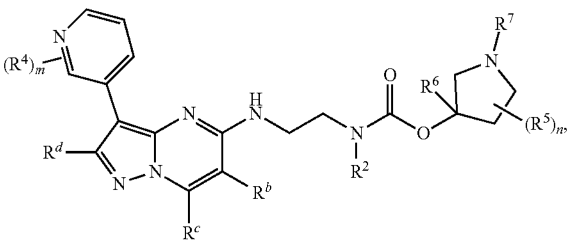

or pharmaceutically acceptable salt or deuterated form thereof, wherein:

- $R^b$, $R^c$, and $R^d$ are each independently H, halogen, $C_{1-6}$ alkyl, —OH, —O—($C_{1-6}$ alkyl), —$NH_2$, —NH—($C_{1-6}$ alkyl), or —NH—($C_{1-6}$ alkyl)$_2$
- $R^2$ is H or $C_{1-6}$ alkyl, or $R^1$ and $R^2$ taken together with the atoms to which they are attached form a 5- or 6-membered heterocyclyl;
- each $R^4$ is independently halogen, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), —NH-(heterocyclyl);
- each $R^5$ is independently H, halogen, $C_{1-6}$ alkyl, $C_{1-6}$ heteroalkyl, O—$C_{1-6}$ alkyl, $C_{1-5}$ alkylene-cycloalkyl, or $C_{1-5}$ alkylene-heterocyclyl, or two $R^5$ form an oxo;
- $R^6$ is H, $C_{1-6}$ alkyl, $C_{2-6}$ alkenyl, or $C_{2-6}$ alkynyl;
- $R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl;
- m is 0, 1, 2, or 3; and
- n is 0, 1, or 2

In some embodiments, the present disclosure provides a compound of Formula (IC):

(IC)

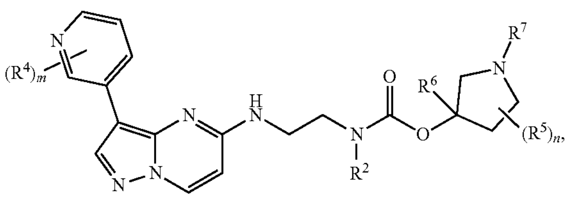

or pharmaceutically acceptable salt or deuterated form thereof, wherein:

- $R^2$ is H or $C_{1-6}$ alkyl, or $R^1$ and $R^2$ taken together with the atoms to which they are attached form a 5- or 6-membered heterocyclyl;
- each $R^4$ is independently halogen, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), —NH-(heterocyclyl);
- each $R^5$ is independently H, halogen, $C_{1-6}$ alkyl, $C_{1-6}$ heteroalkyl, O—$C_{1-6}$ alkyl, $C_{1-5}$ alkylene-cycloalkyl, or $C_{1-5}$ alkylene-heterocyclyl, or two $R^5$ form an oxo;
- $R^6$ is H, $C_{1-6}$ alkyl, $C_{2-6}$ alkenyl, or $C_{2-6}$ alkynyl;
- $R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl;
- m is 0, 1, 2, or 3; and
- n is 0, 1, or 2.

In some embodiments, the compound of Formula (IC) has the structure:

(IC-1)

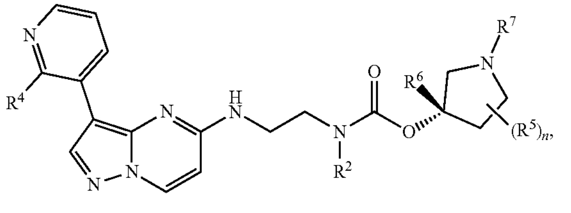

or a pharmaceutically acceptable salt thereof, wherein $R^4$, $R^5$, $R^6$, $R^7$, and n are as defined herein.

The present disclosure further provides a compound of Formula (ID'):

(ID')

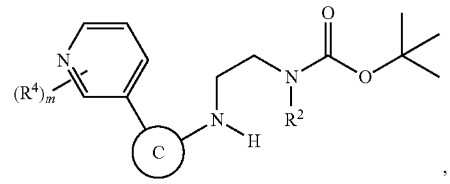

, or pharmaceutically acceptable salt, deuterated form, or stereoisomer thereof, wherein:

Ⓒ is

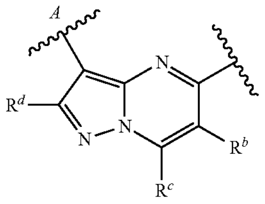

or

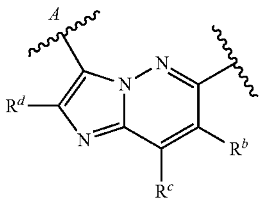

;

$R^2$ is H or $C_{1-6}$ alkyl;

each $R^4$ is independently halogen, —OH, —O—$C_{1-6}$ alkyl, —O—$C_{1-6}$ haloalkyl, —O-cycloalkyl, —O-heterocyclyl, —O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), —NH-(heterocyclyl);

$R^b$, $R^c$, and $R^d$ are each independently H, halogen, —$C_{1-6}$ alkyl, —OH, —O—($C_{1-6}$ alkyl), —$NH_2$, —NH—($C_{1-6}$ alkyl), or —NH—($C_{1-6}$ alkyl)$_2$; and m is 0, 1, 2, or 3.

In some embodiments, In some embodiments, the compound disclosed herein has the structure:

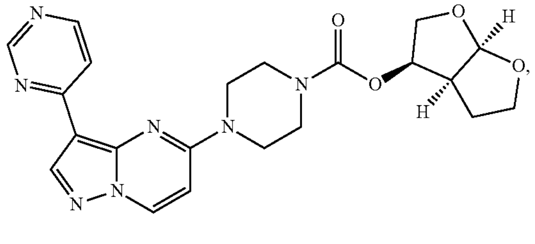

-continued

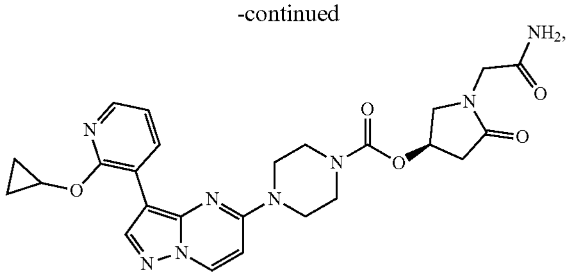

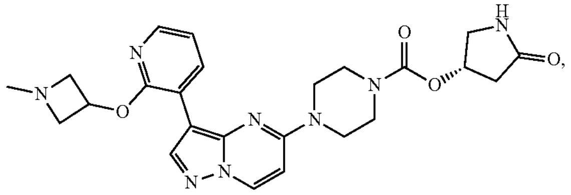

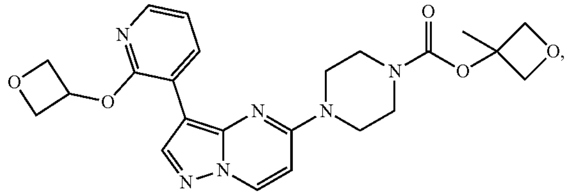

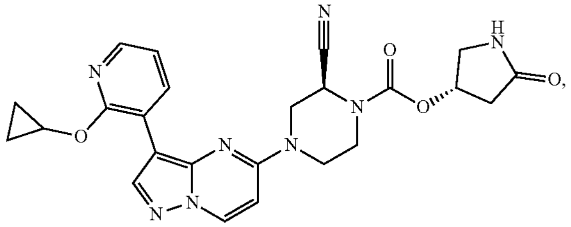

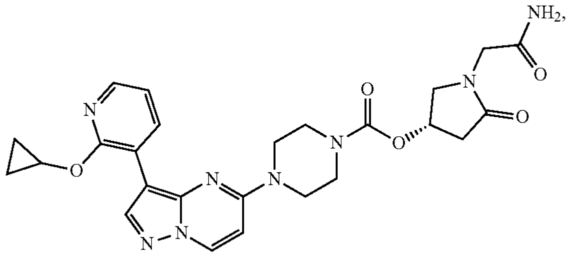

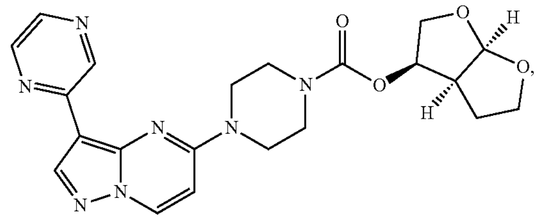

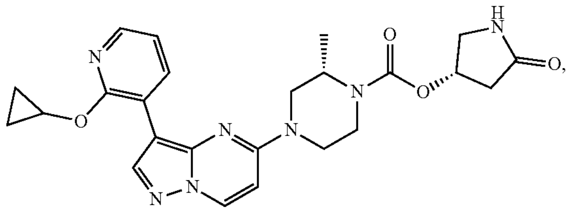

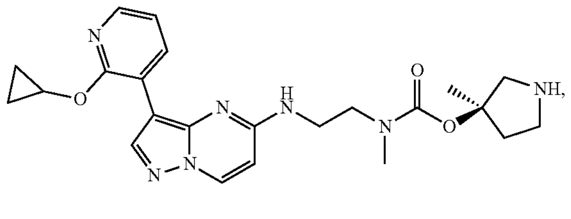

-continued
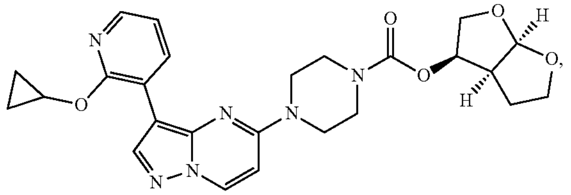
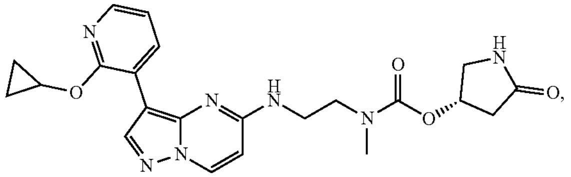
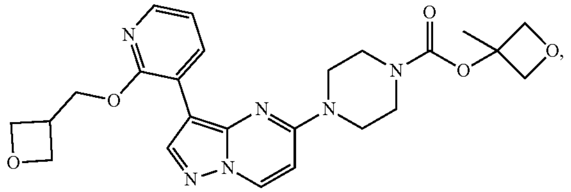
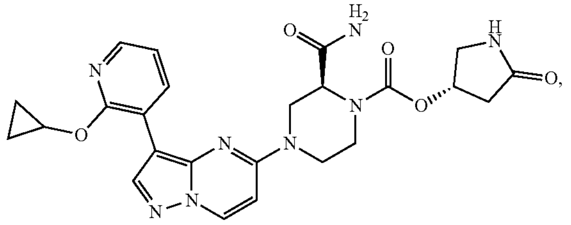
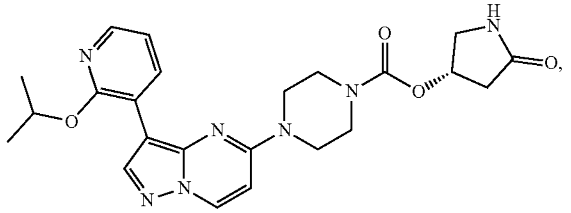
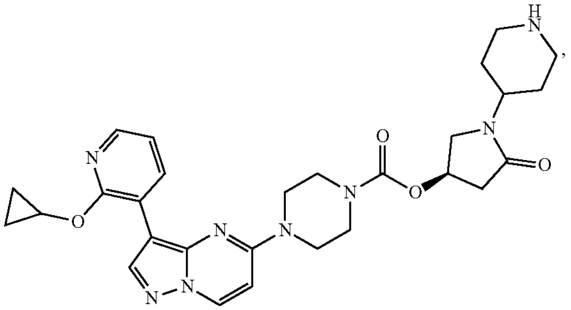
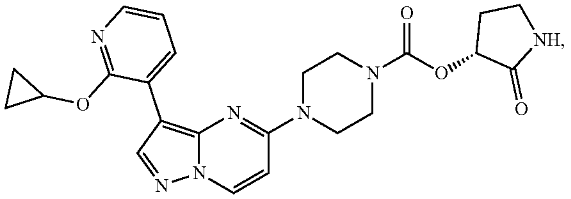
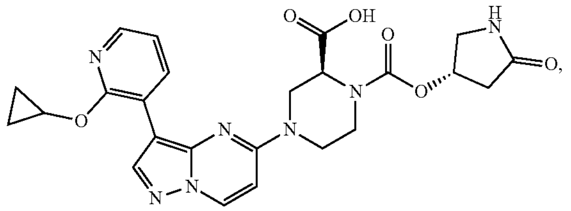
-continued
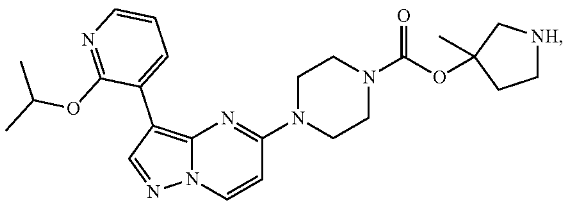
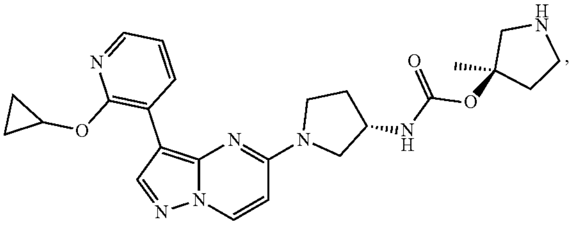
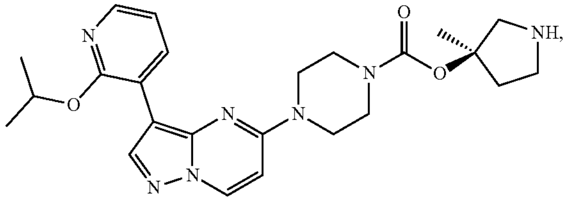
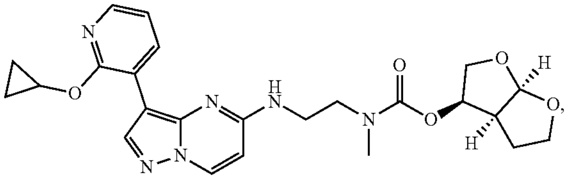
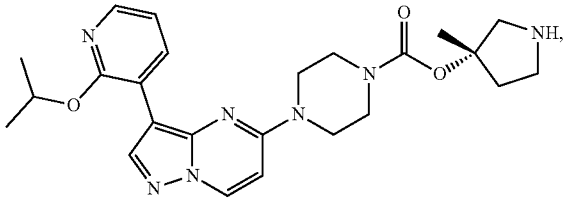
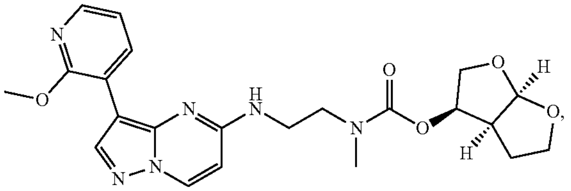
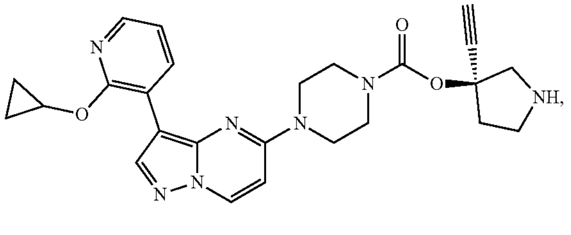
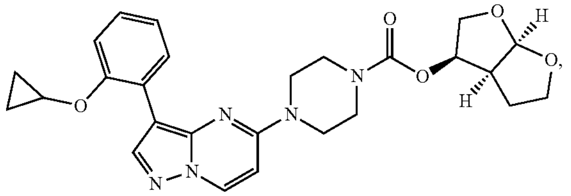

-continued
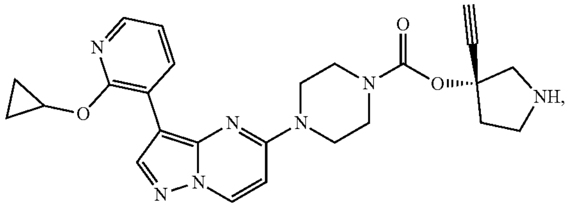,
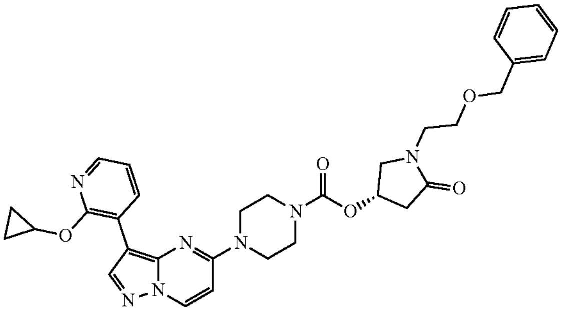,
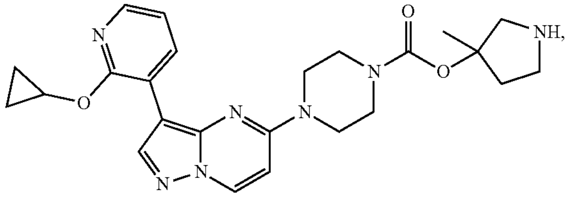,
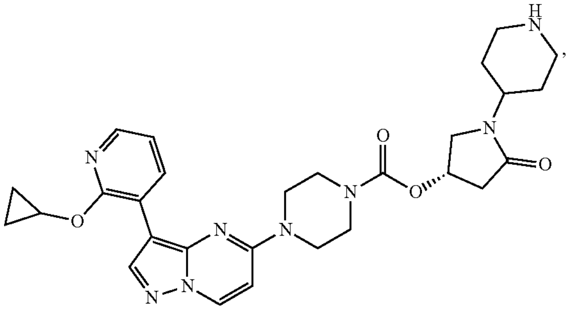,
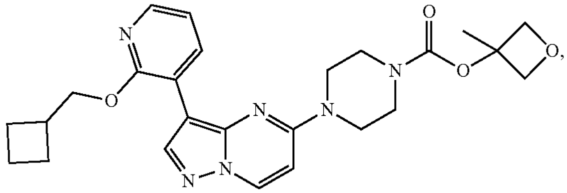,
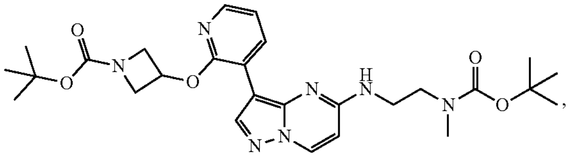,
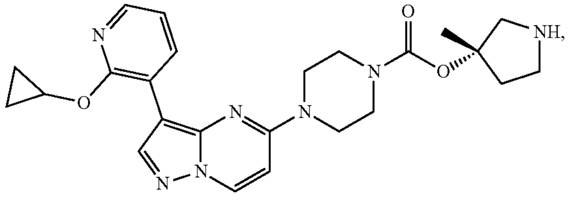,
-continued
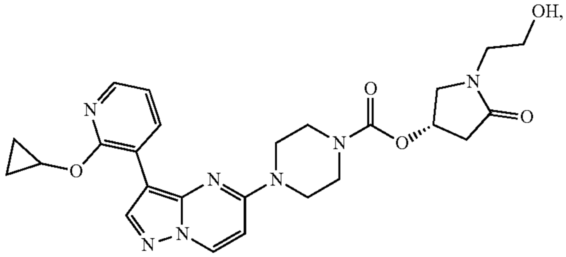,
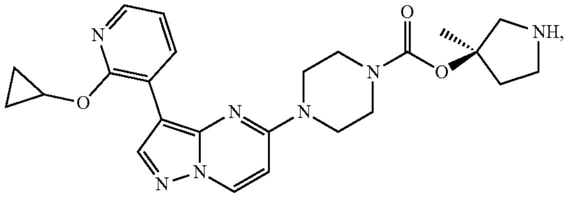,
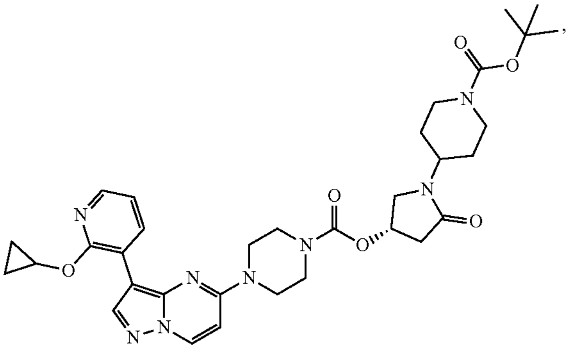,
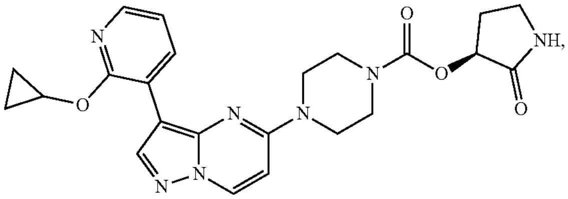,
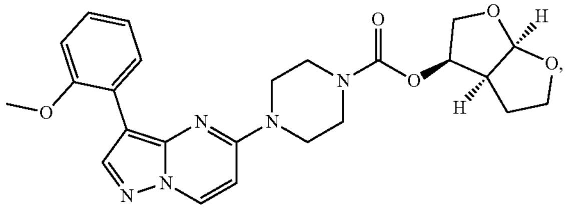,
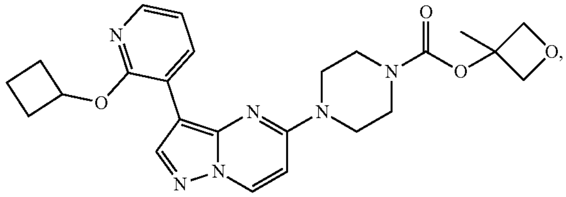,
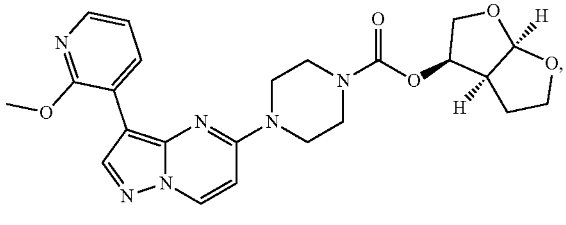, -continued
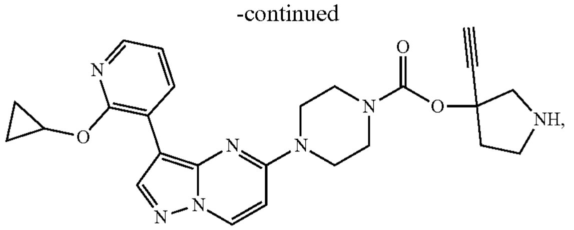
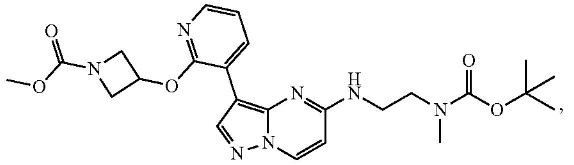
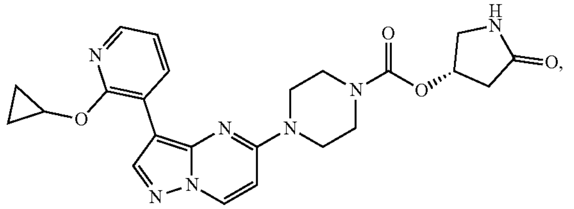
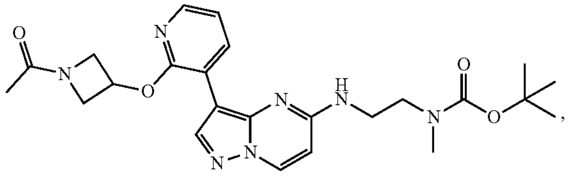
-continued
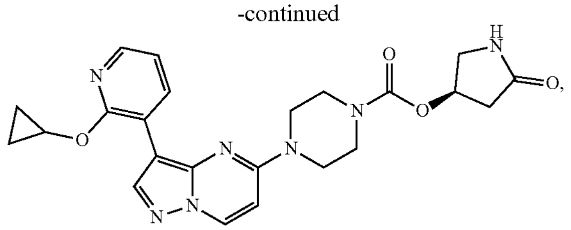
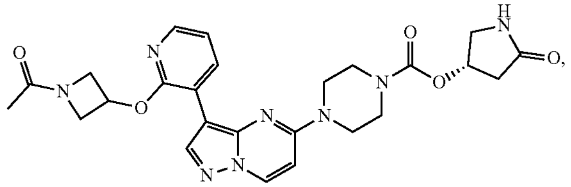
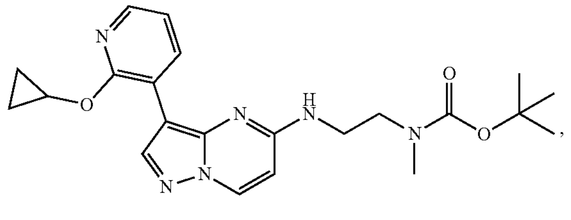
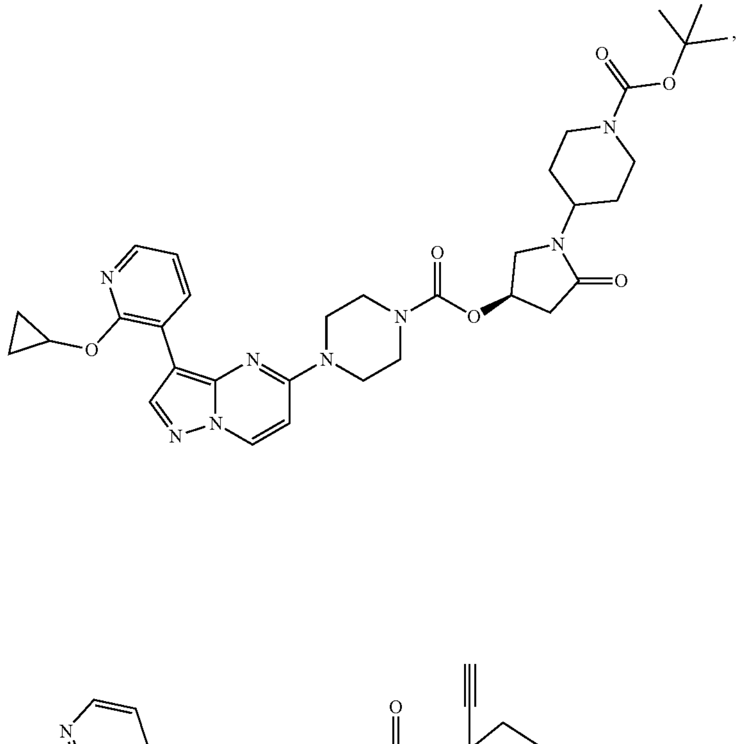
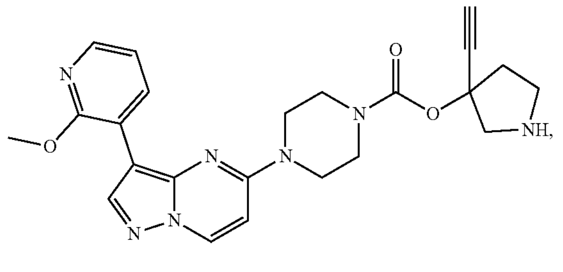

-continued
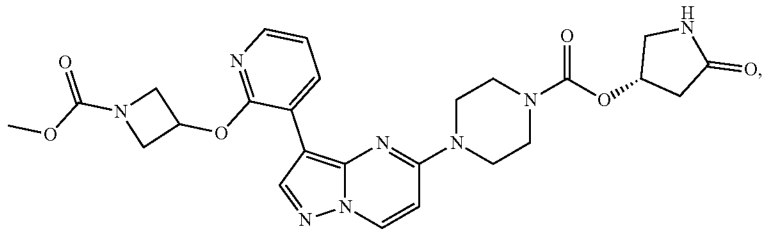
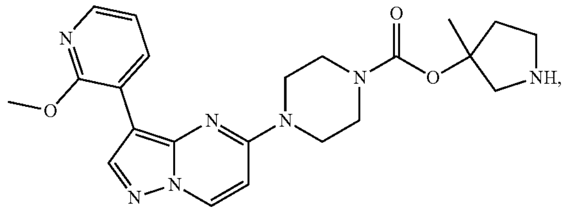
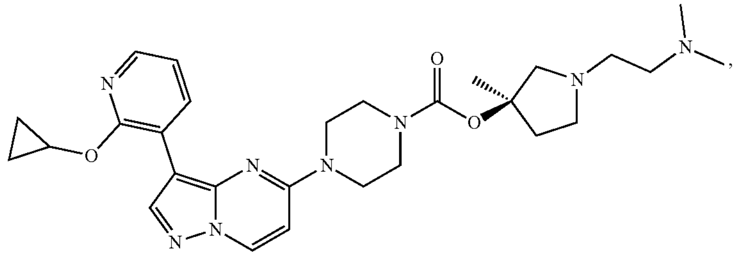
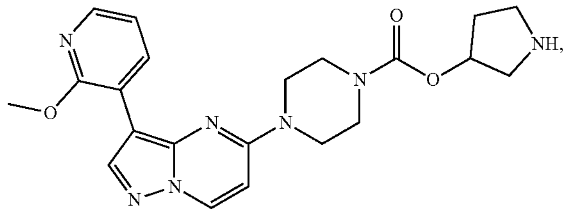
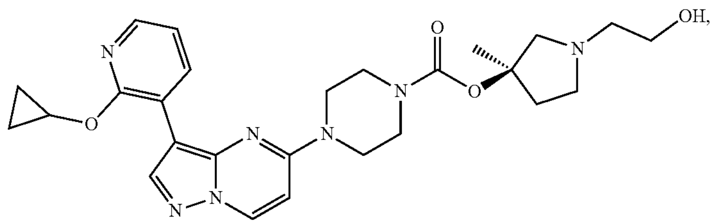
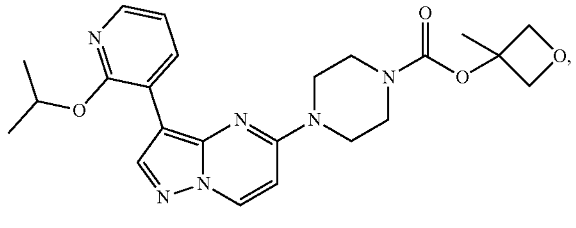
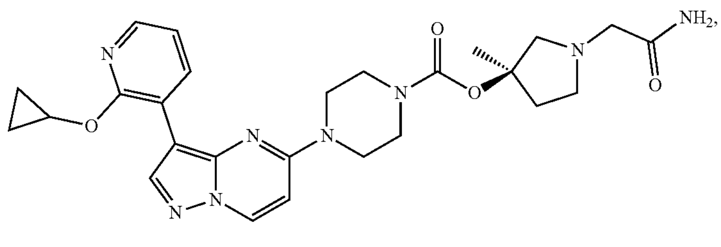

-continued
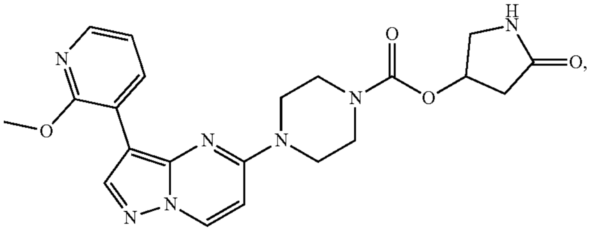
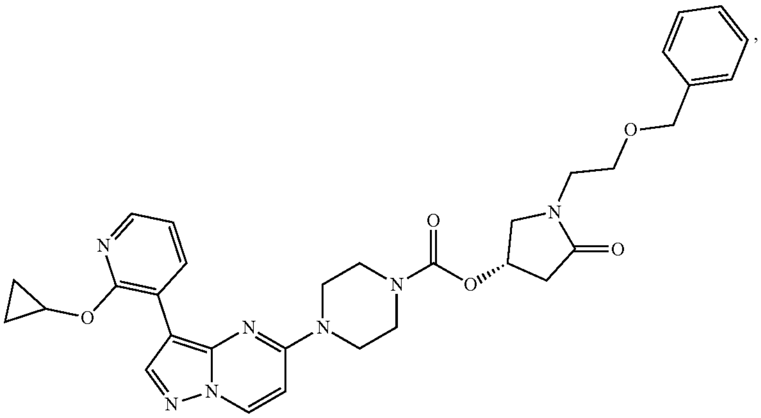
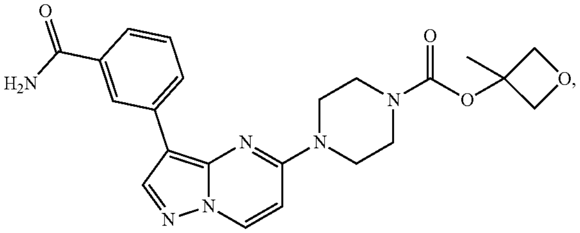
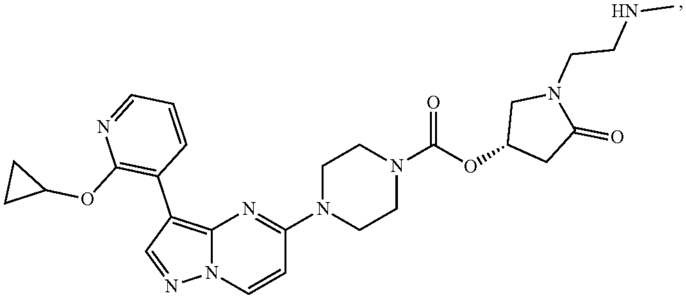
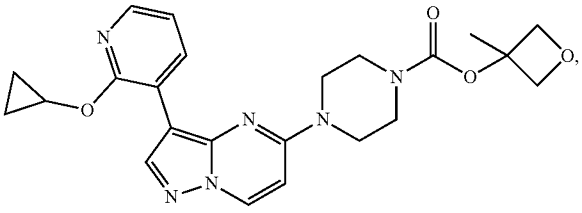
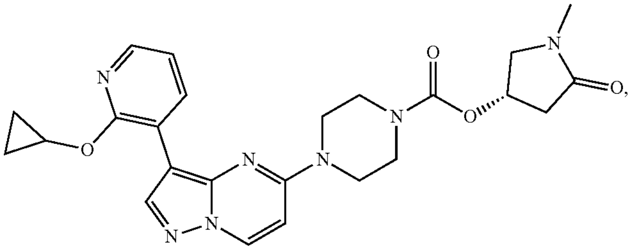

-continued
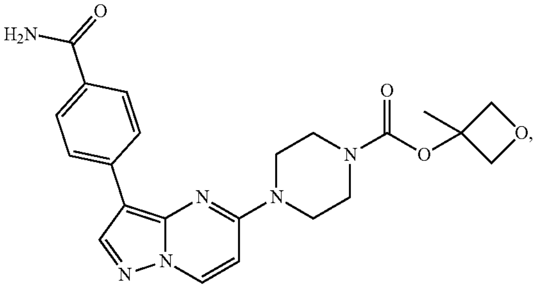
,
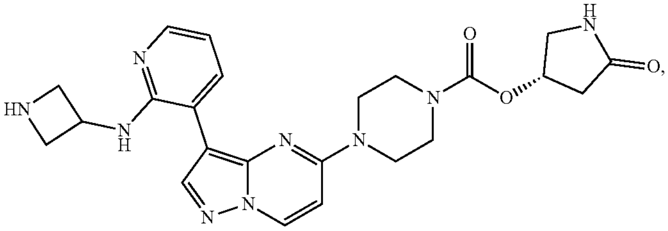
,
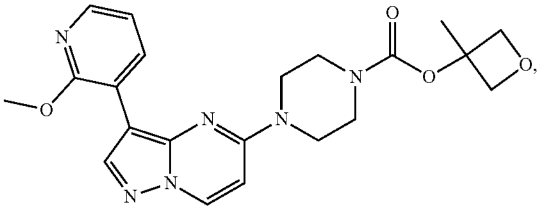
,
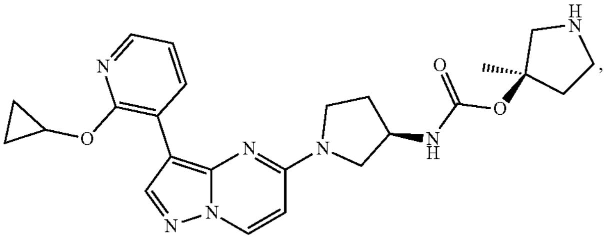
,
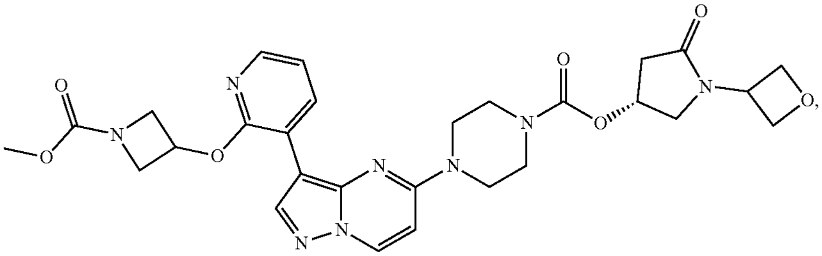
,
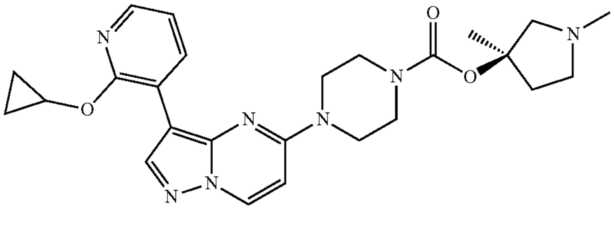
,
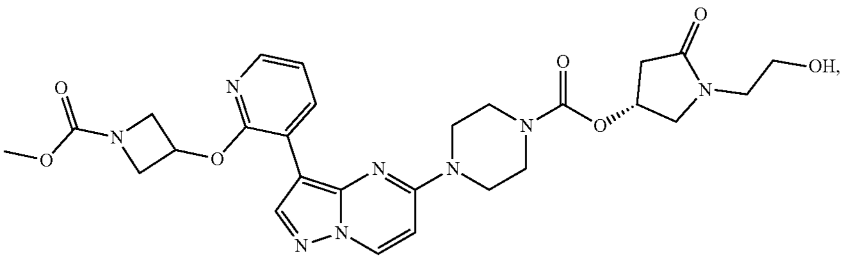
, -continued
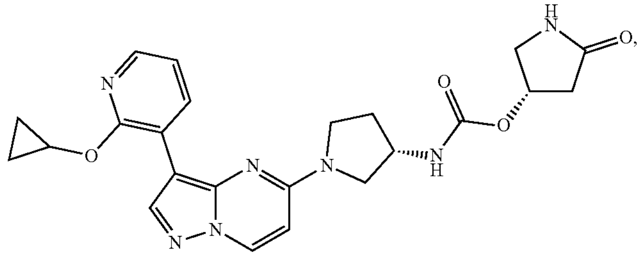
,
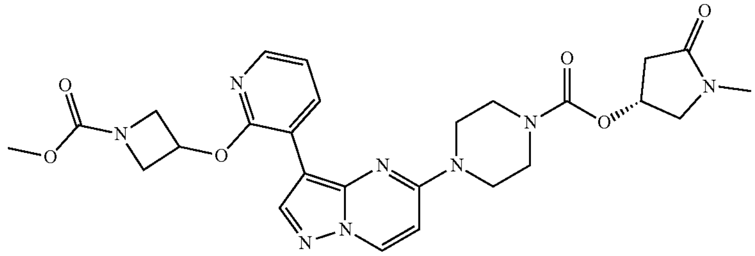
,
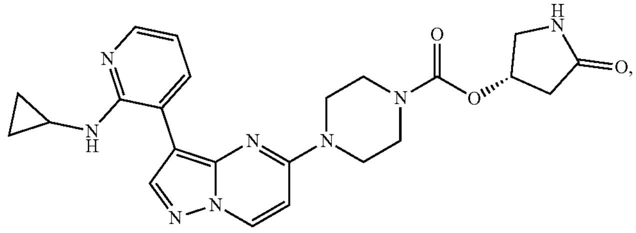
,
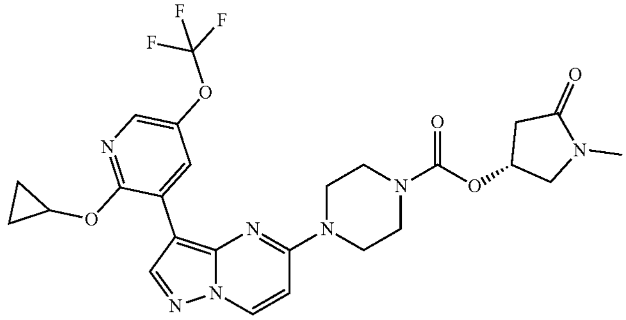
,
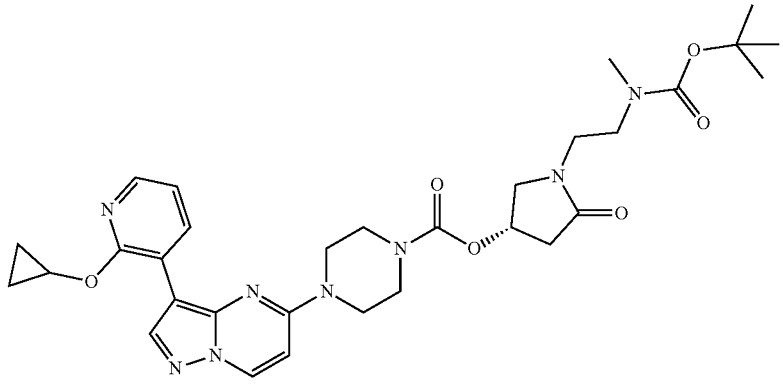
,
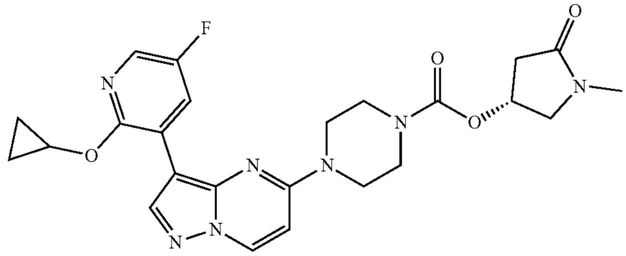
, -continued
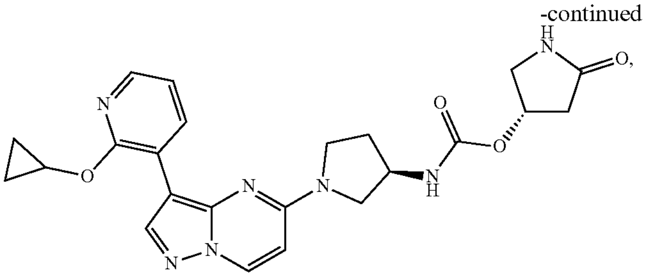
,
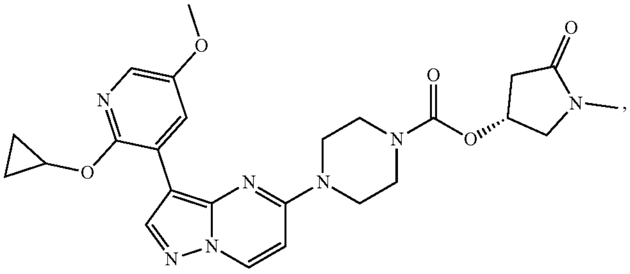
,
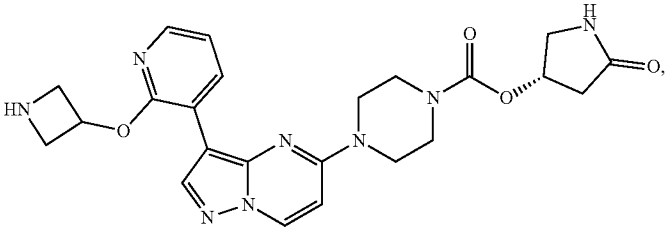
,
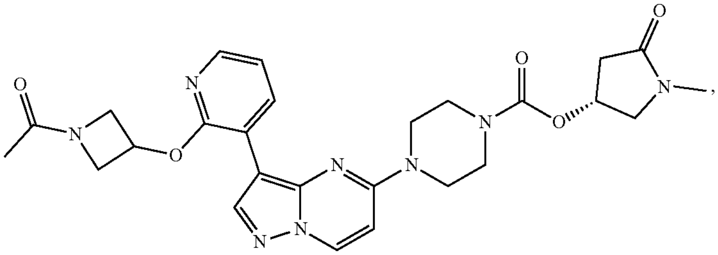
,
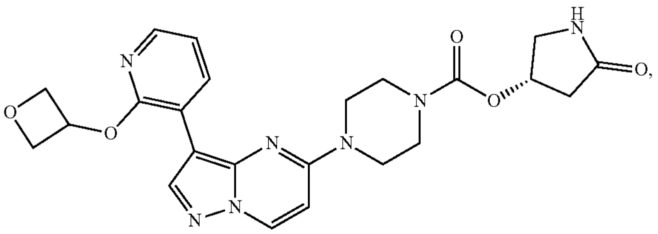
,
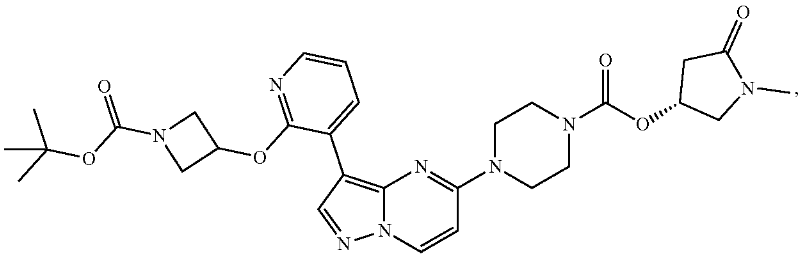
,
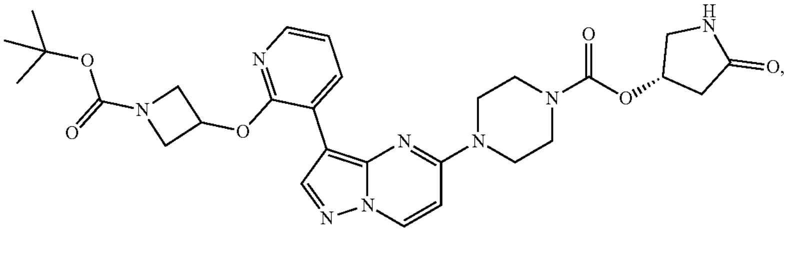
, -continued
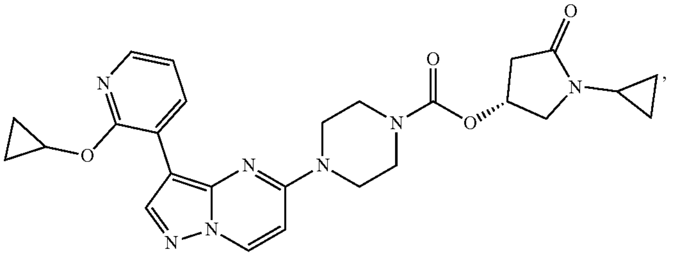
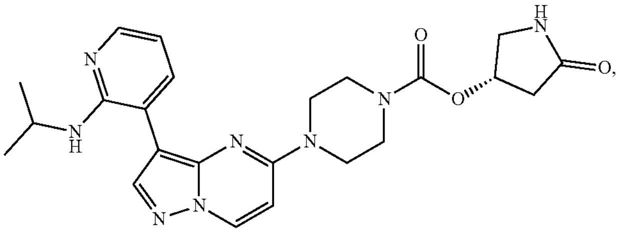
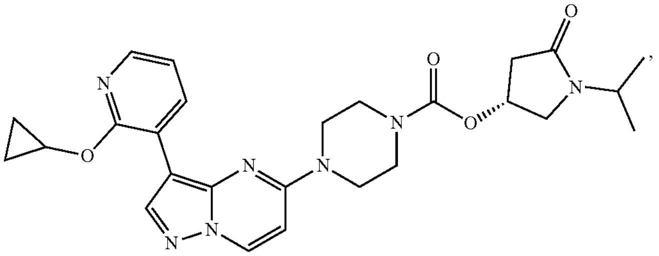
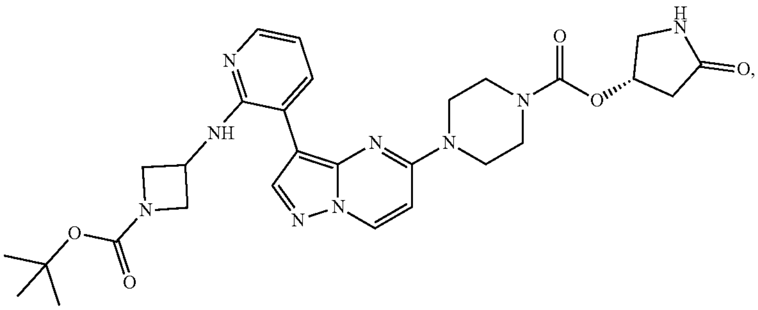
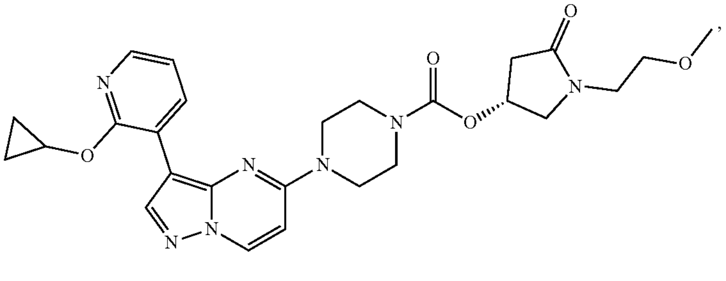
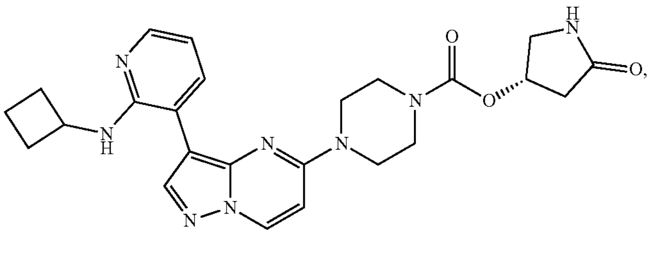

-continued
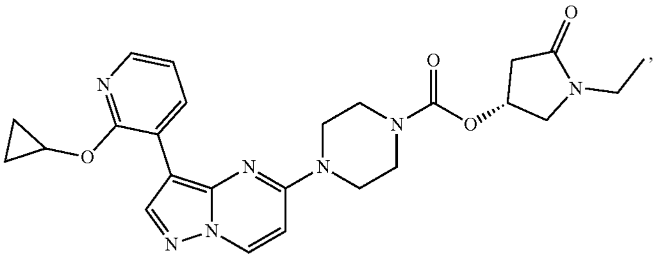
,
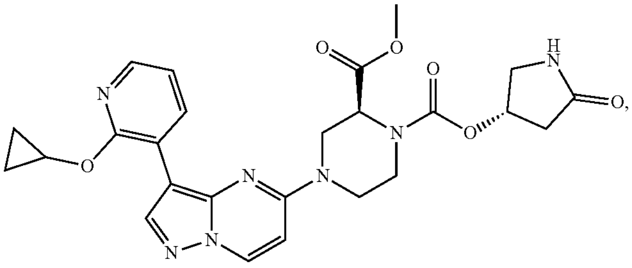
,
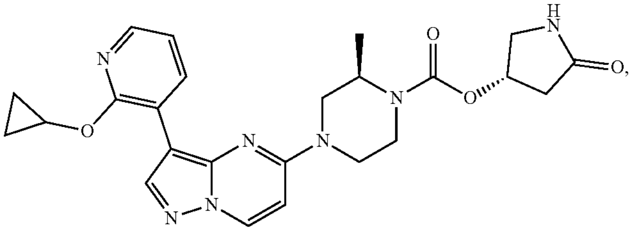
,
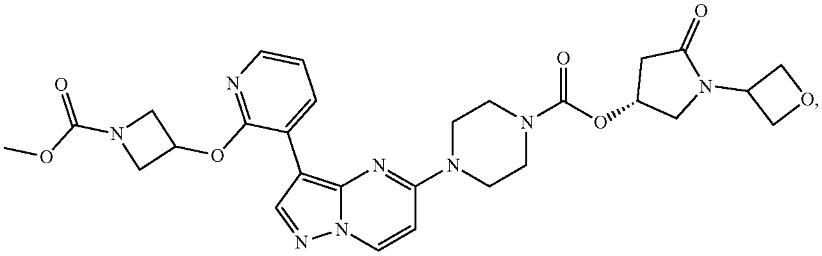
,
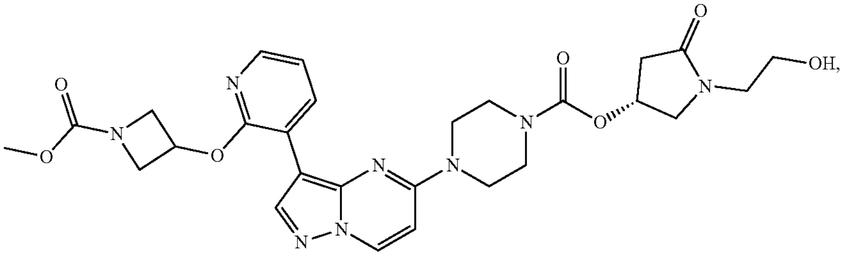
,
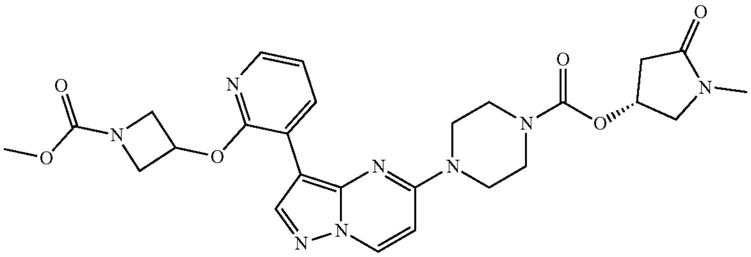
, -continued
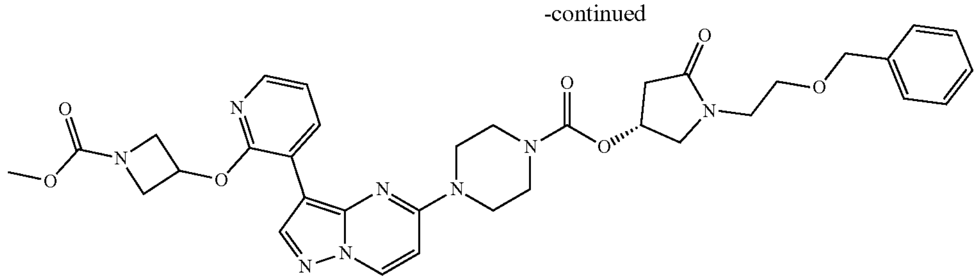
,
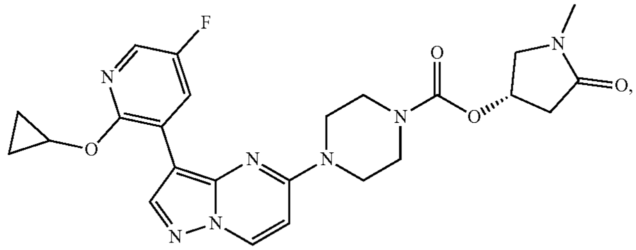
,
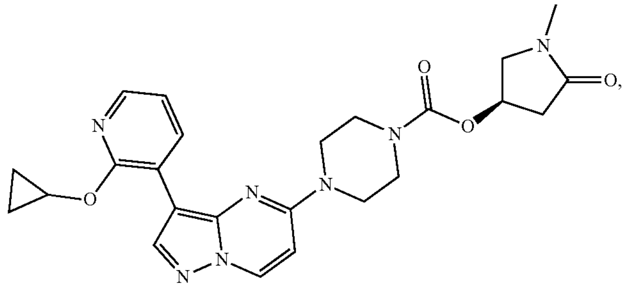
,
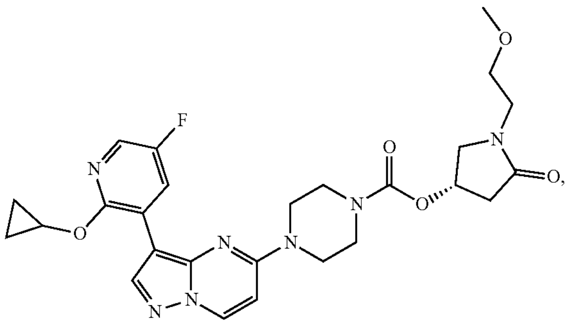
,
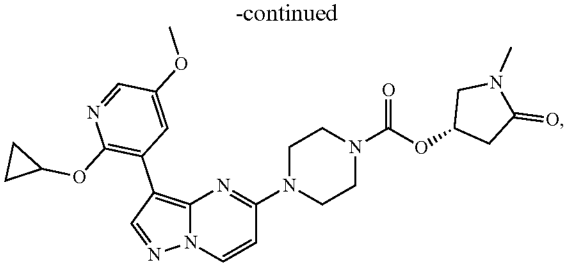
,
-continued
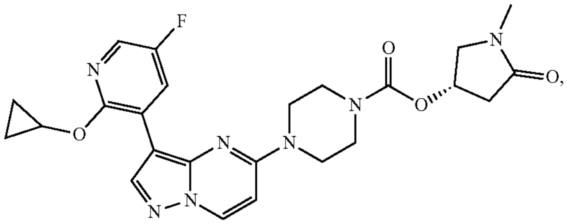
,
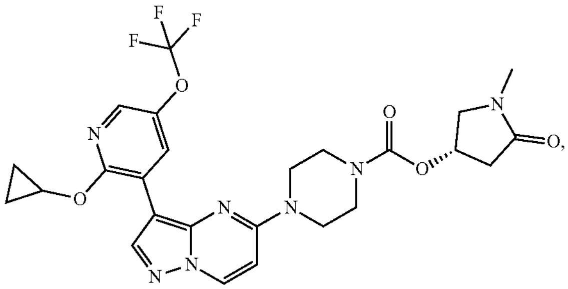
,
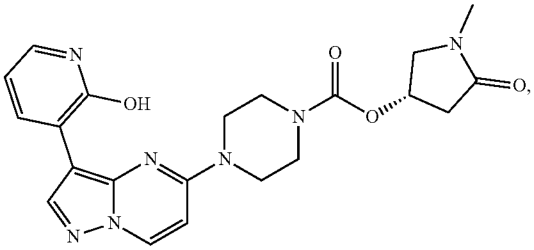
, -continued
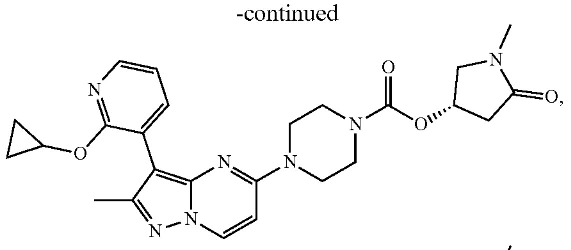
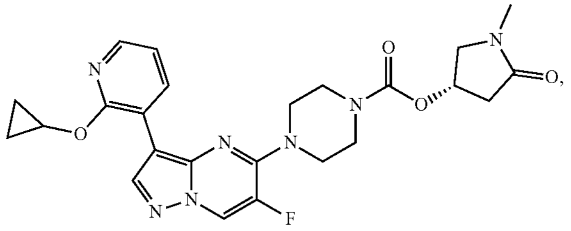
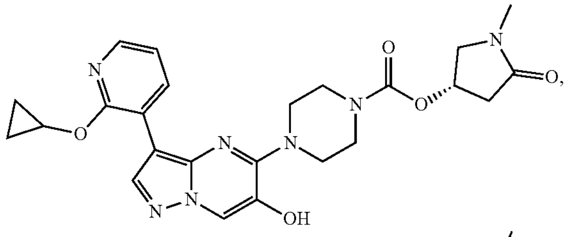
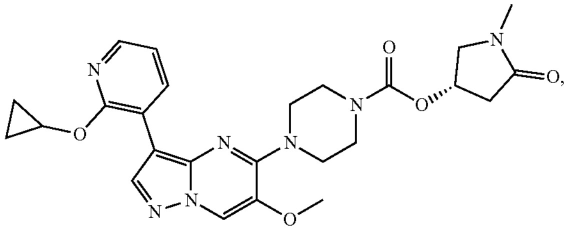
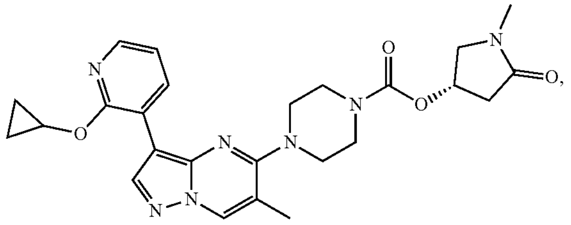
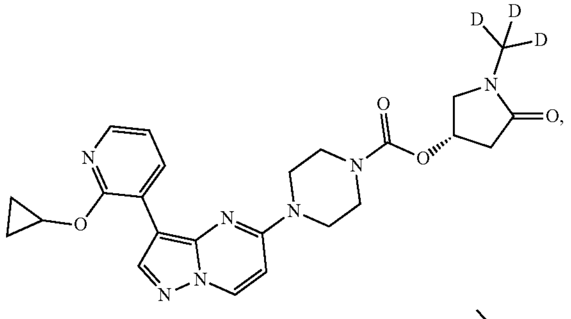
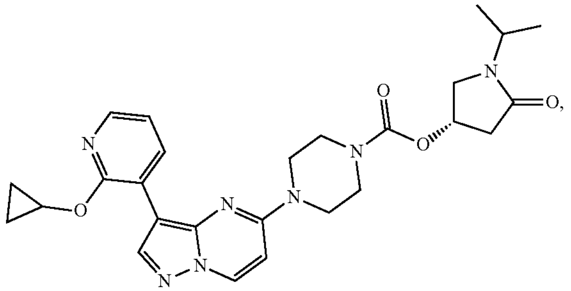
-continued
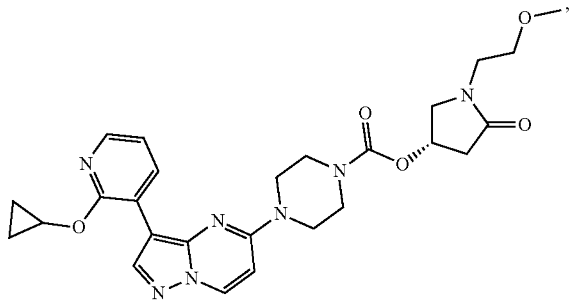
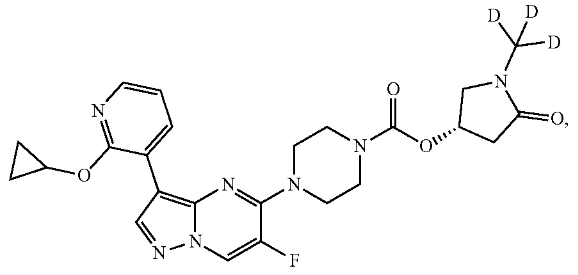
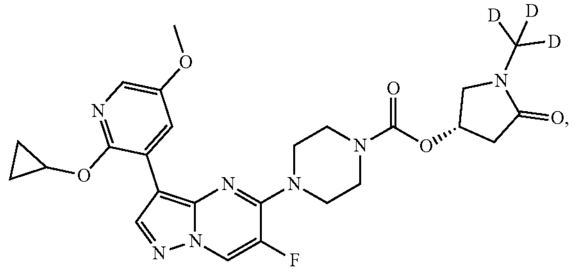
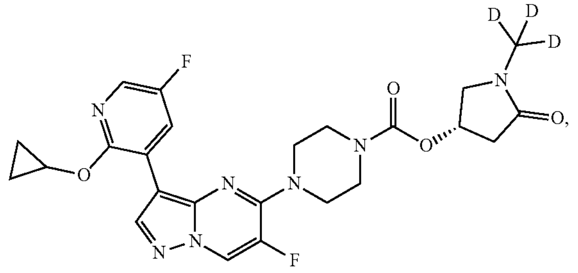
or a pharmaceutically acceptable salt thereof.
In some embodiments, the compound disclosed herein has the structure:
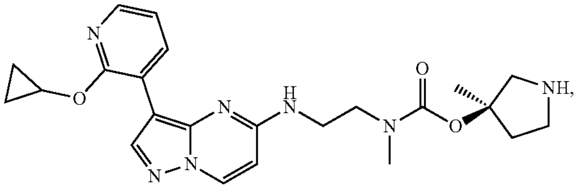
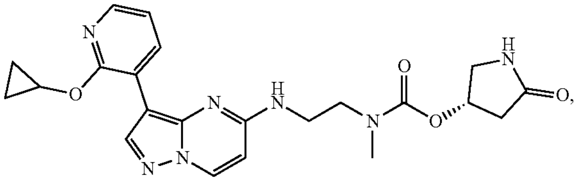

-continued
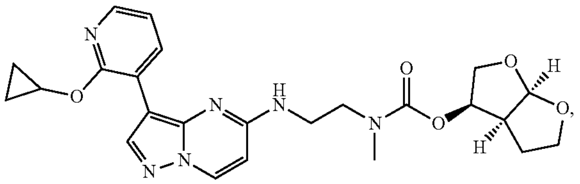
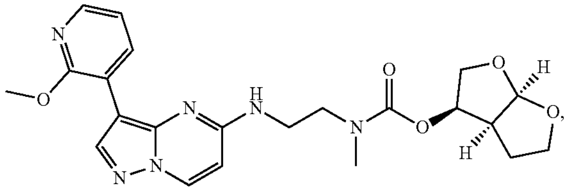
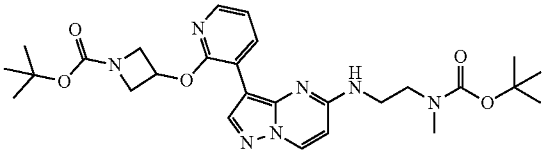
,
-continued
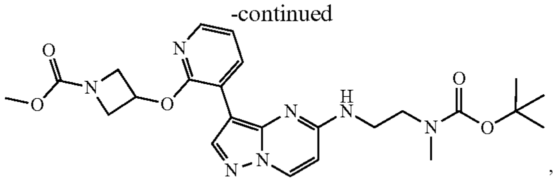
,
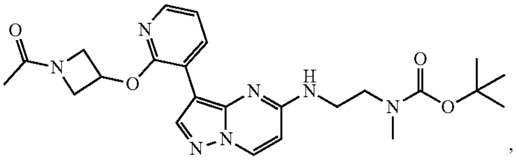
, or
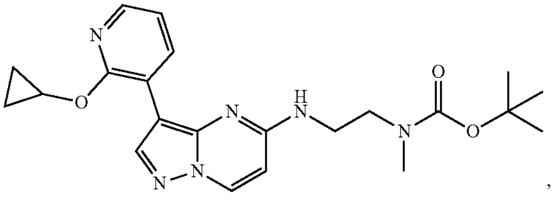
,
or a pharmaceutically acceptable salt thereof.
In some embodiments, the compound disclosed herein has the structure:
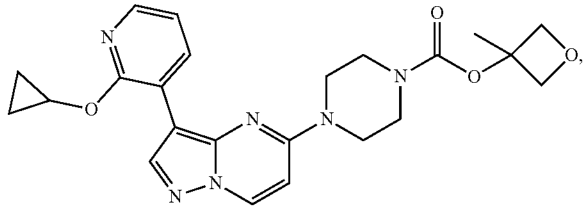
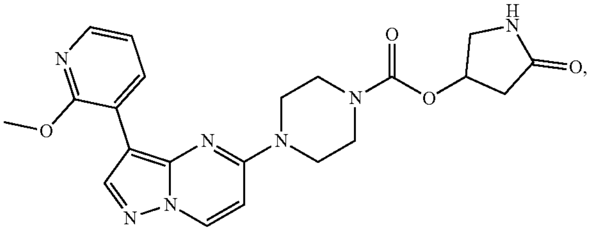
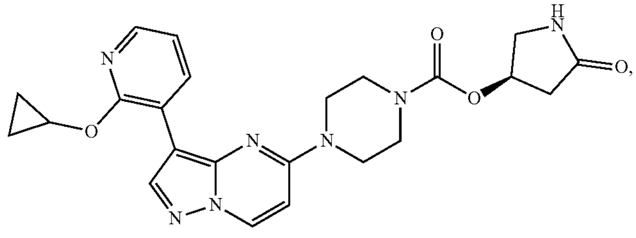
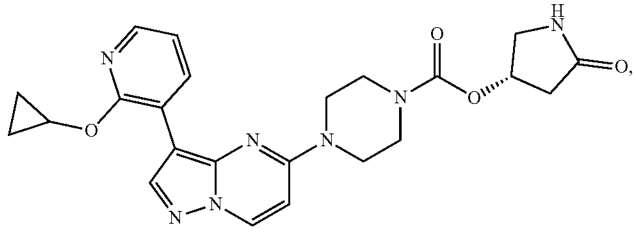
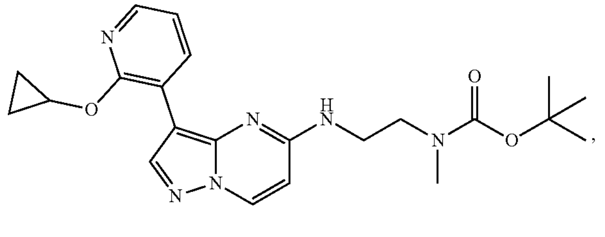

-continued
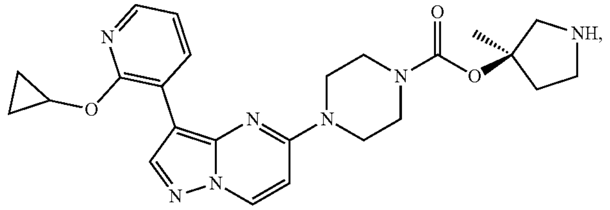
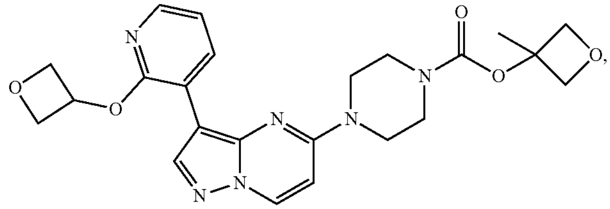
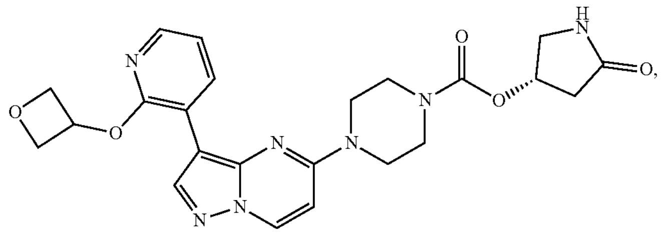
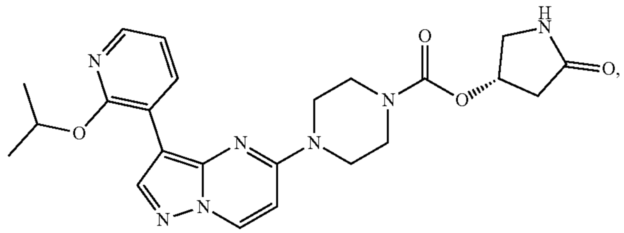
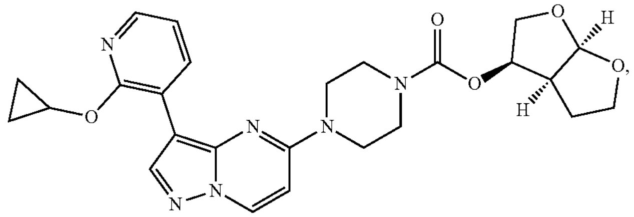
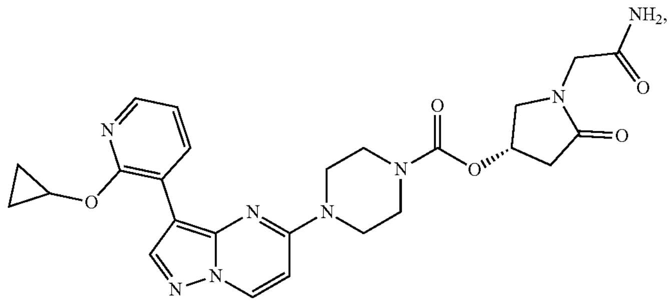

-continued
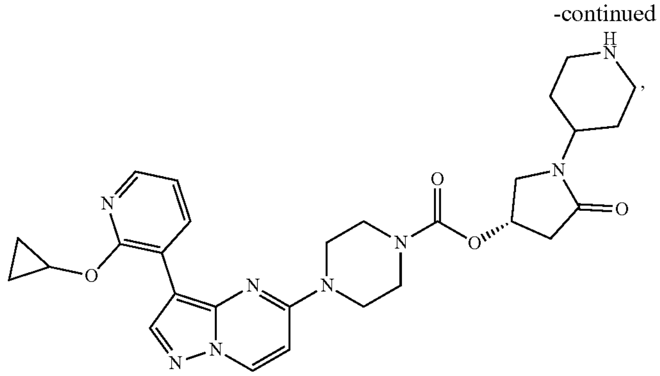
,
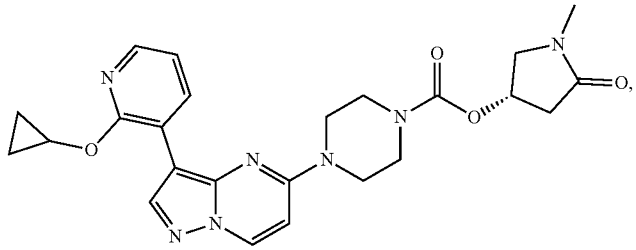
,
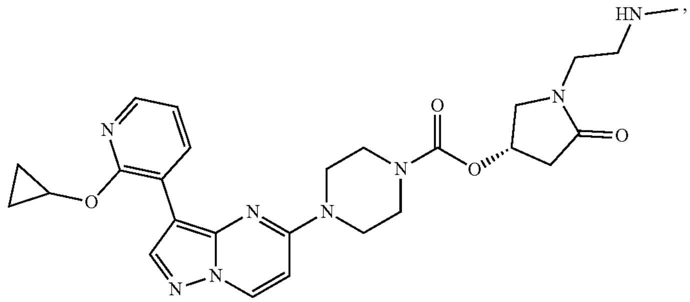
,
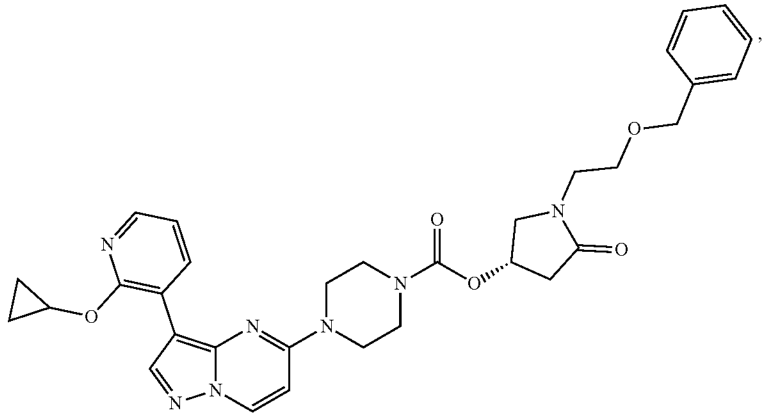
,
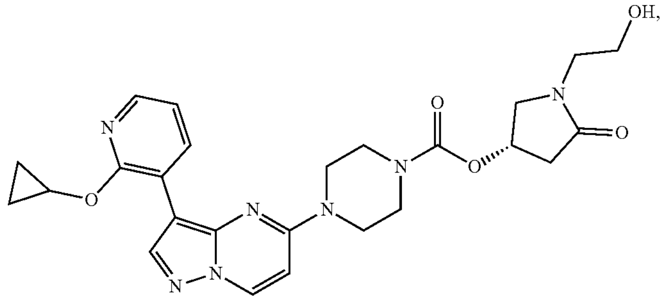
, -continued
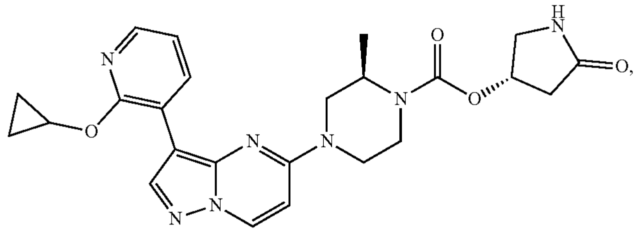
,
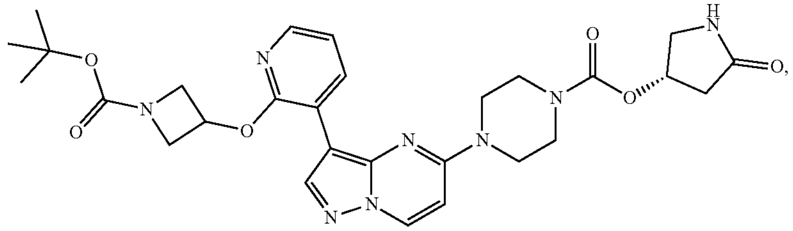
,
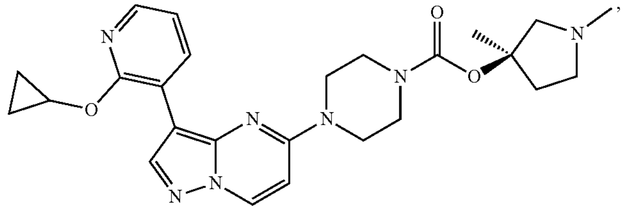
,
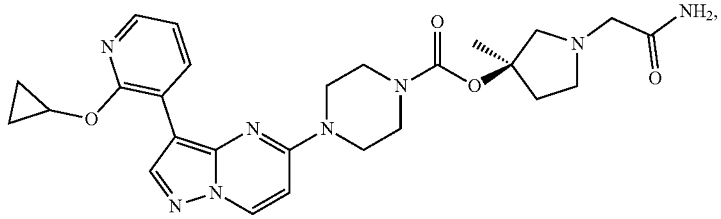
,
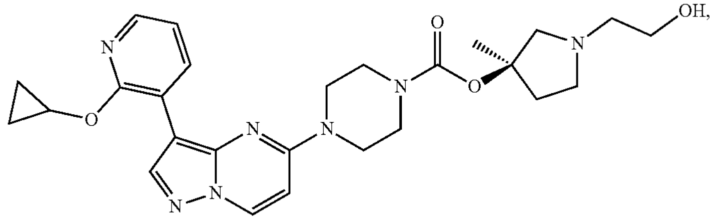
,
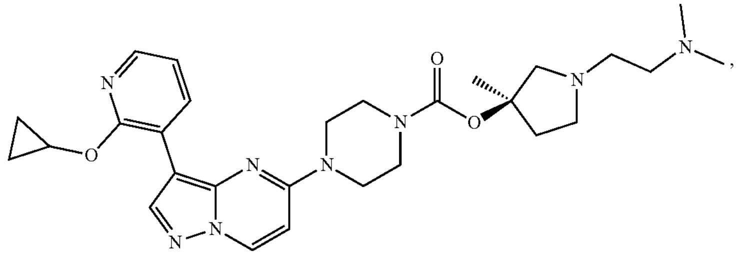
,
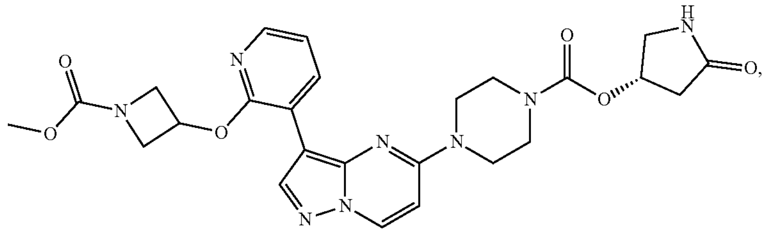
, -continued
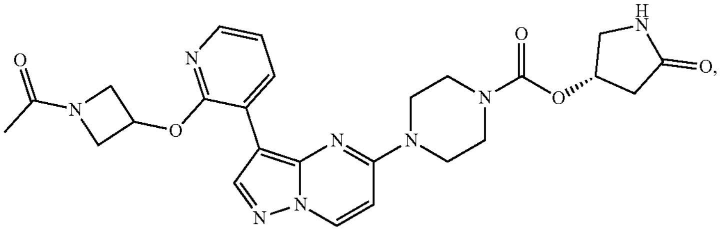
,
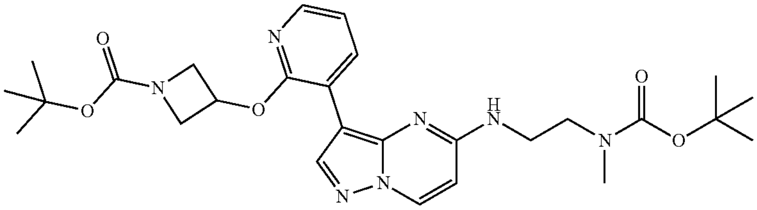
,
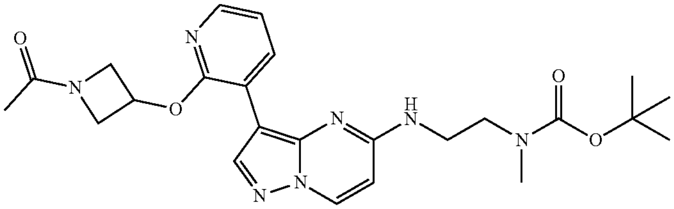
,
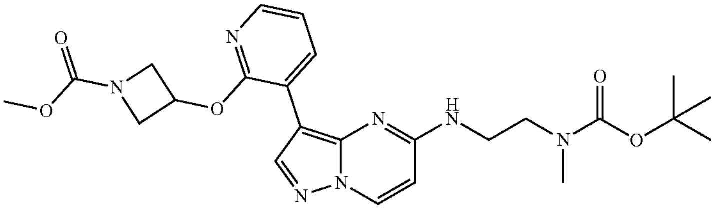
,
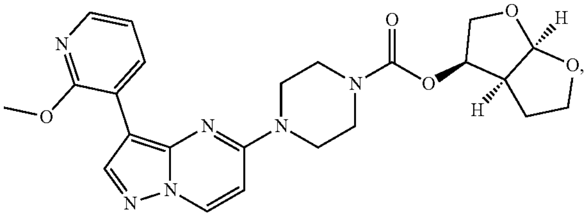
,
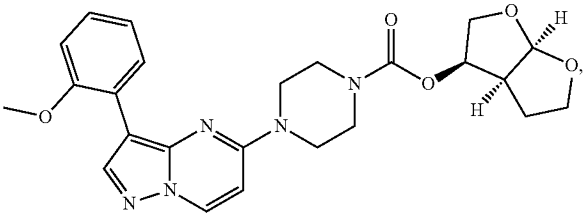
,
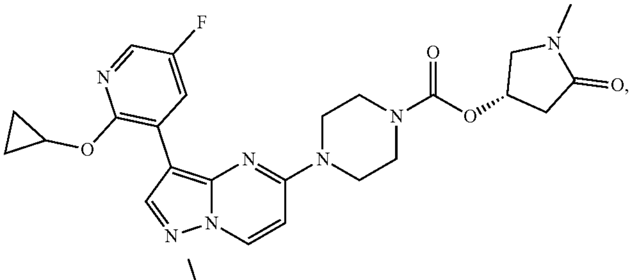
,
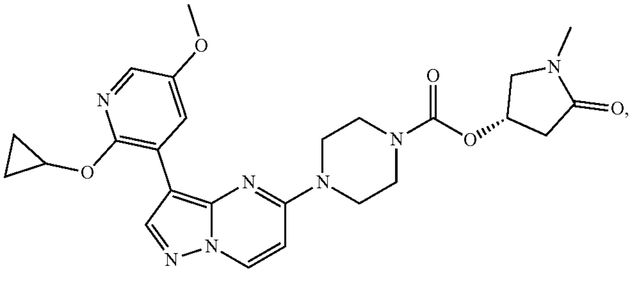
, -continued
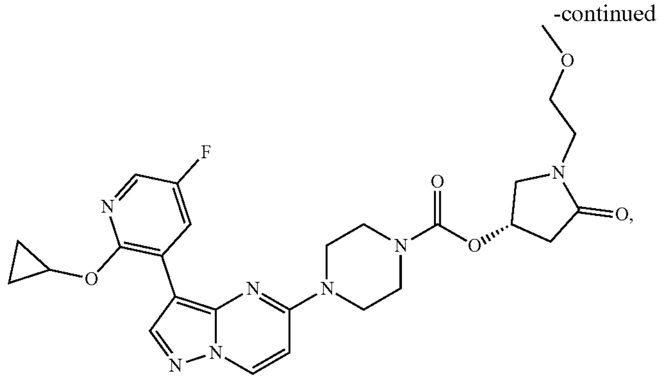
,
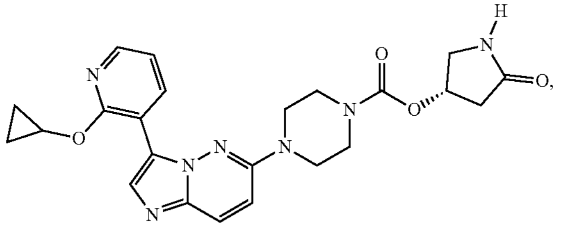
,
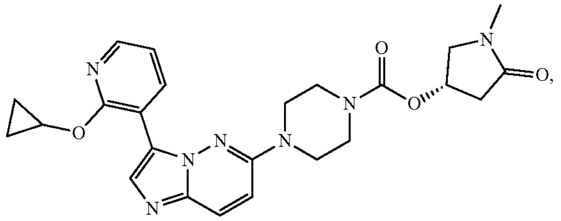
,
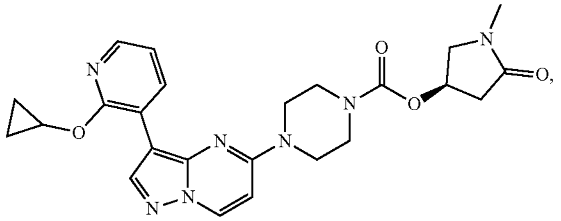
,
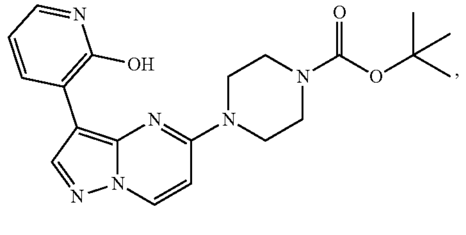
,
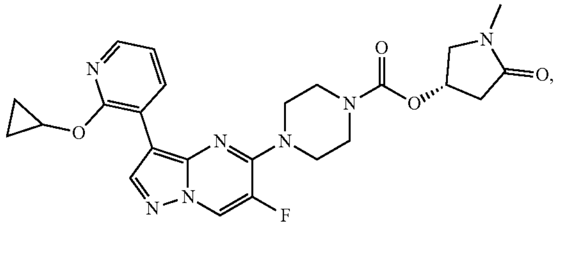
,
-continued
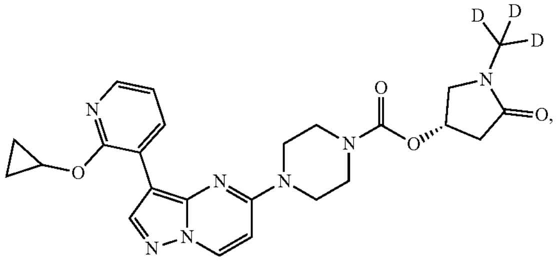
,
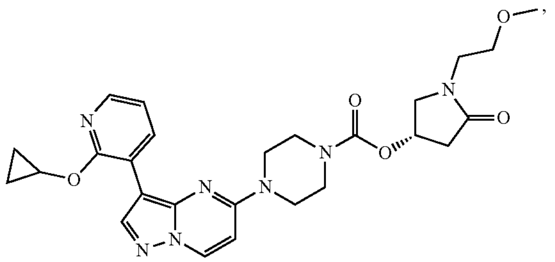
,
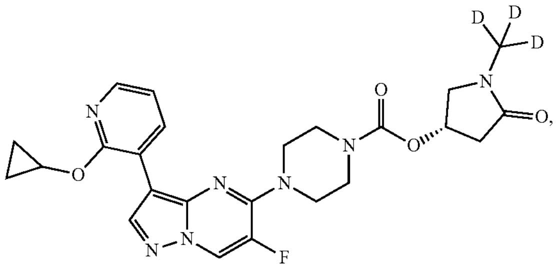
,
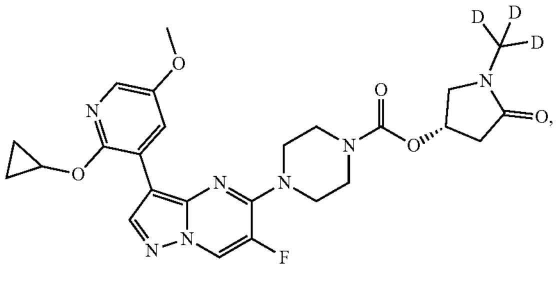
, -continued

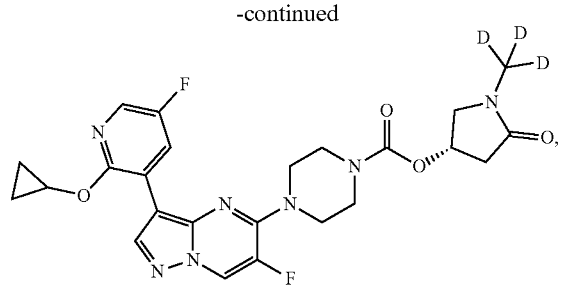

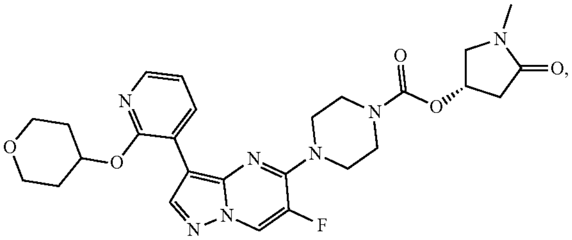

or a pharmaceutically acceptable salt thereof.

In some embodiments, the compound disclosed herein has the structure:

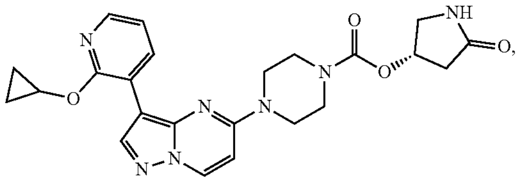

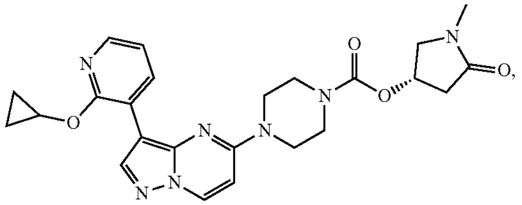

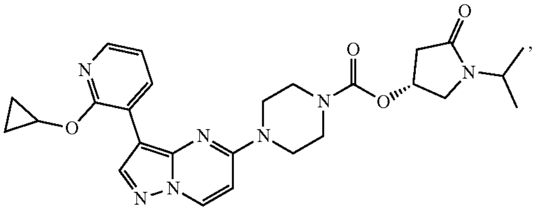

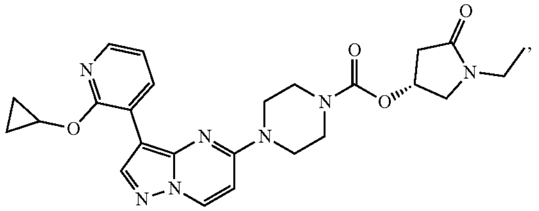

or

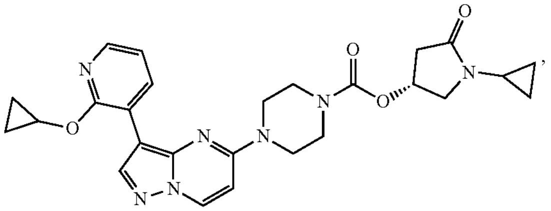

or a pharmaceutically acceptable salt thereof.

In some embodiments, the compound disclosed herein has the structure:

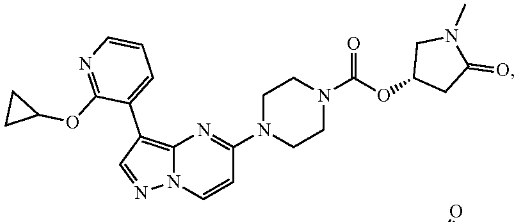

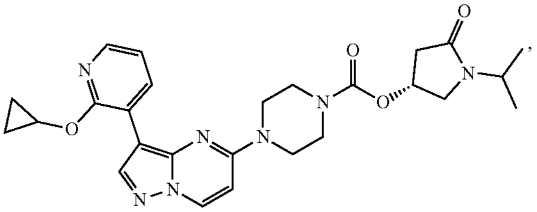

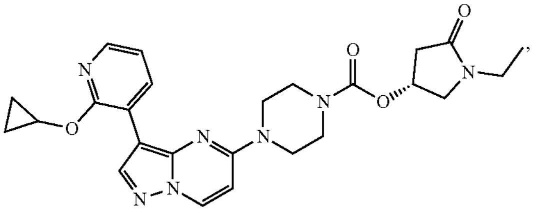

or

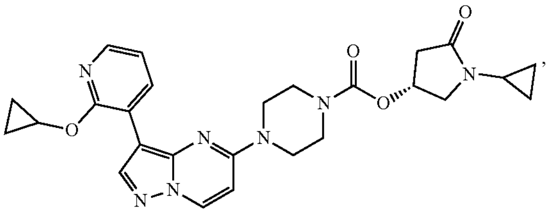

or a pharmaceutically acceptable salt thereof.

In some embodiments, the compound disclosed herein has the structure:

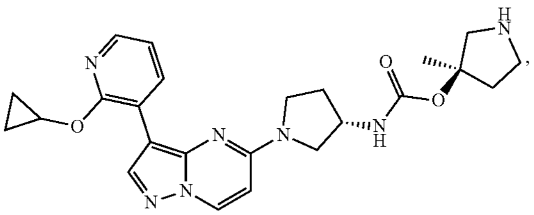

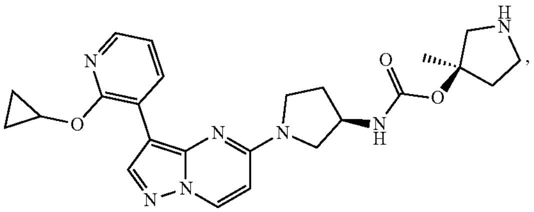

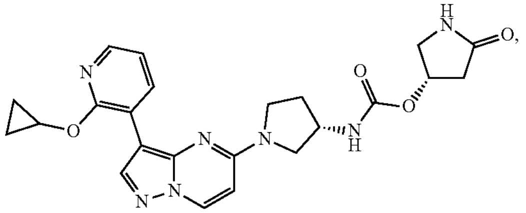

or

-continued
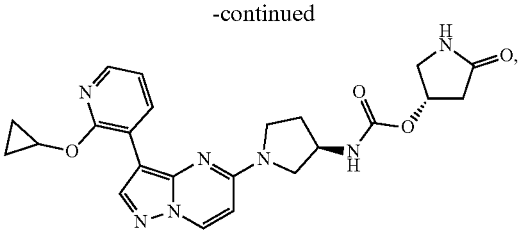
or a pharmaceutically acceptable salt thereof.
In some embodiments, the compound of the present disclosure is a compound of Table 1 or a pharmaceutically acceptable salt thereof.
TABLE 1
| Compounds of the Disclosure | |
|---|---|
| Compound ID | Structure |
| I-1 | 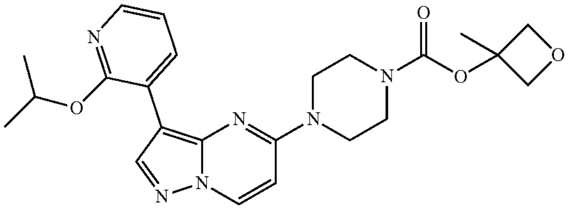 [SMILES: CC(C)Oc1ncccc1-c1cnn2ccc(N3CCN(C(=O)OC4(C)COC4)CC3)nc12] |
| I-2 | 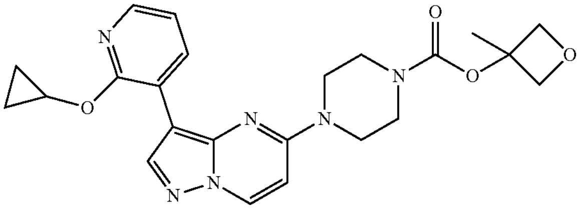 [SMILES: CC1(OC(=O)N2CCN(c3ccn4ncc(-c5cccnc5OC5CC5)c4n3)CC2)COC1] |
| I-3 | 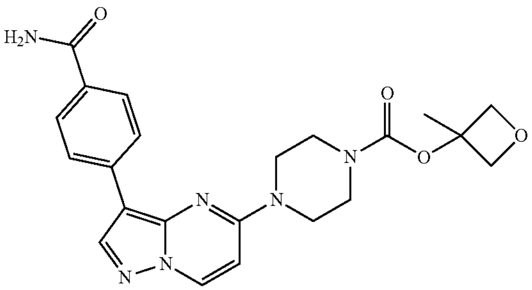 [SMILES: CC1(OC(=O)N2CCN(c3ccn4ncc(-c5ccc(C(N)=O)cc5)c4n3)CC2)COC1] |
| I-4 | 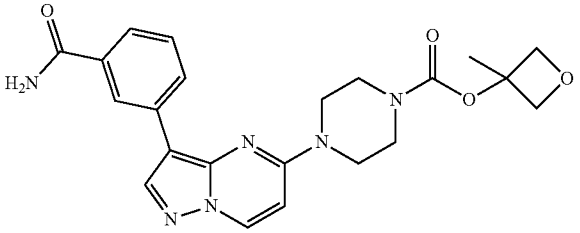 [SMILES: CC1(OC(=O)N2CCN(c3ccn4ncc(-c5cccc(C(N)=O)c5)c4n3)CC2)COC1] |

TABLE 1-continued
| Compound ID | Structure |
| --- | --- |
| I-5 | 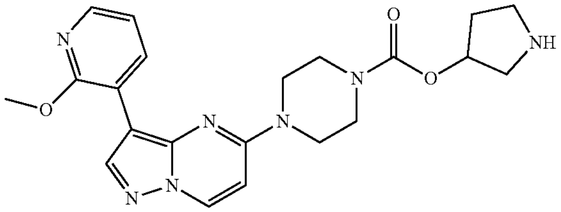 [SMILES: COc1ncccc1-c1cnn2ccc(N3CCN(C(=O)OC4CCNC4)CC3)nc12] |
| I-6 | 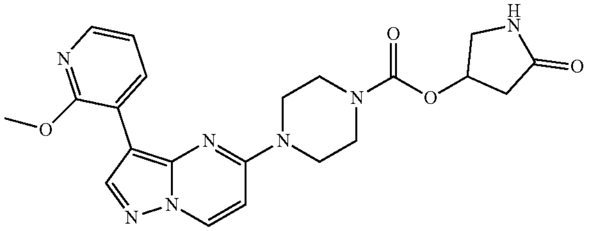 [SMILES: COc1ncccc1-c1cnn2ccc(N3CCN(C(=O)OC4CNC(=O)C4)CC3)nc12] |
| I-8 | 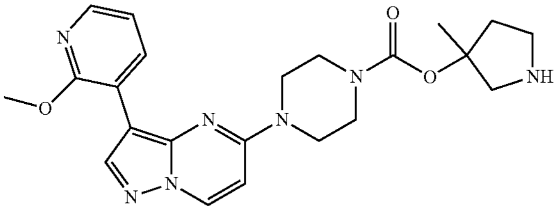 [SMILES: COc1ncccc1-c1cnn2ccc(N3CCN(C(=O)OC4(C)CCNC4)CC3)nc12] |
| I-9 | 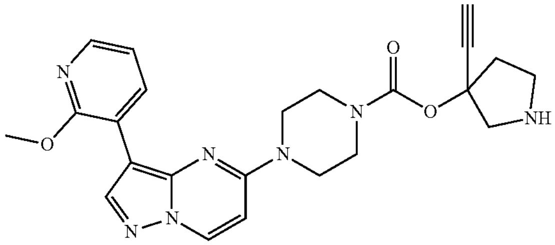 [SMILES: C#CC1(OC(=O)N2CCN(c3ccn4ncc(-c5cccnc5OC)c4n3)CC2)CCNC1] |
| I-10 | 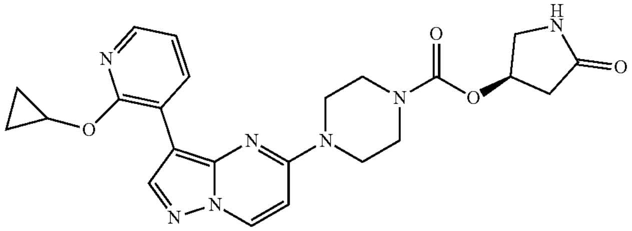 [SMILES: O=C1C[C@@H](OC(=O)N2CCN(c3ccn4ncc(-c5cccnc5OC5CC5)c4n3)CC2)CN1] |
| I-11 | 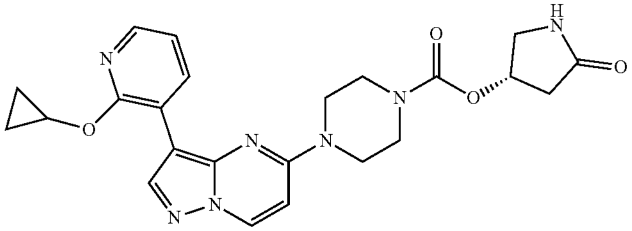 [SMILES: O=C1C[C@H](OC(=O)N2CCN(c3ccn4ncc(-c5cccnc5OC5CC5)c4n3)CC2)CN1] |
Compounds of the Disclosure TABLE 1-continued
| Compounds of the Disclosure | |
|---|---|
| Compound ID | Structure |
| I-12 | 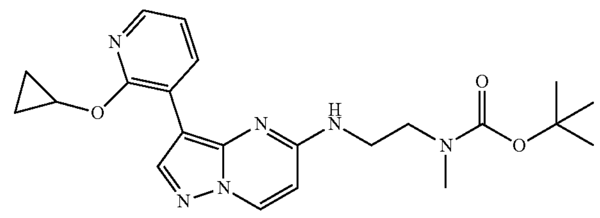 [SMILES: CN(CCNc1ccn2ncc(-c3cccnc3OC3CC3)c2n1)C(=O)OC(C)(C)C] |
| I-13 | 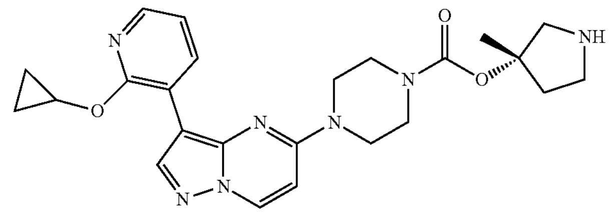 [SMILES: C[C@]1(OC(=O)N2CCN(c3ccn4ncc(-c5cccnc5OC5CC5)c4n3)CC2)CCNC1] |
| I-13-5 | 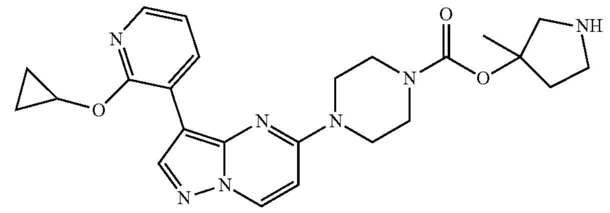 [SMILES: CC1(OC(=O)N2CCN(c3ccn4ncc(-c5cccnc5OC5CC5)c4n3)CC2)CCNC1] |
| I-14 | 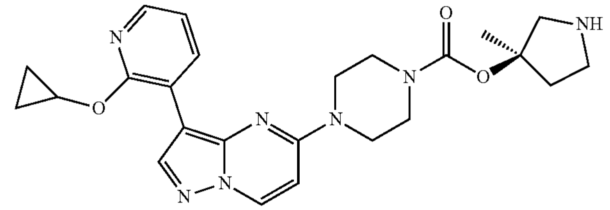 [SMILES: C[C@@]1(OC(=O)N2CCN(c3ccn4ncc(-c5cccnc5OC5CC5)c4n3)CC2)CCNC1] |
| I-15 | 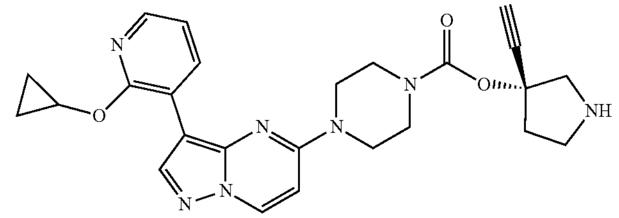 [SMILES: C#C[C@]1(OC(=O)N2CCN(c3ccn4ncc(-c5cccnc5OC5CC5)c4n3)CC2)CCNC1] |
| I-16 | 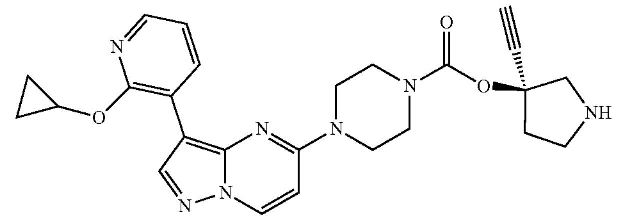 [SMILES: C#C[C@@]1(OC(=O)N2CCN(c3ccn4ncc(-c5cccnc5OC5CC5)c4n3)CC2)CCNC1] |

TABLE 1-continued
| Compounds of the Disclosure | |
|---|---|
| Compound ID | Structure |
| I-16-7 | 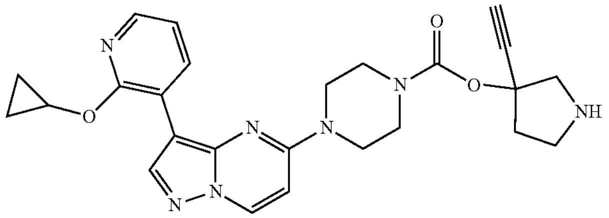 [SMILES: C#CC1(OC(=O)N2CCN(c3ccn4ncc(-c5cccnc5OC5CC5)c4n3)CC2)CCNC1] |
| I-17 | 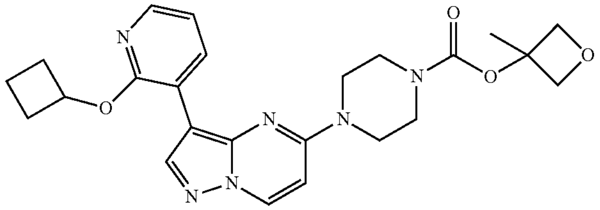 [SMILES: CC1(OC(=O)N2CCN(c3ccn4ncc(-c5cccnc5OC5CCC5)c4n3)CC2)COC1] |
| I-18 | 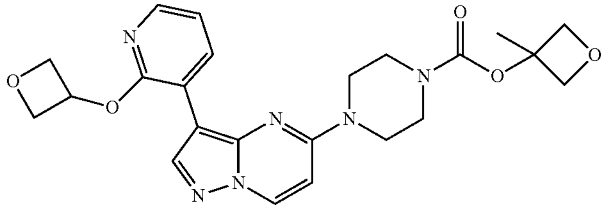 [SMILES: CC1(OC(=O)N2CCN(c3ccn4ncc(-c5cccnc5OC5COC5)c4n3)CC2)COC1] |
| I-19 | 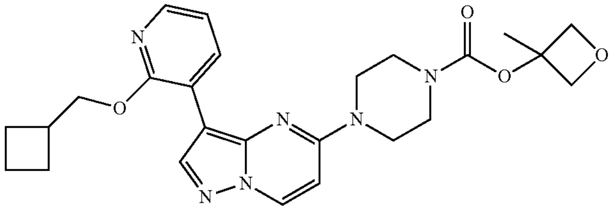 [SMILES: CC1(OC(=O)N2CCN(c3ccn4ncc(-c5cccnc5OCC5CCC5)c4n3)CC2)COC1] |
| I-20 | 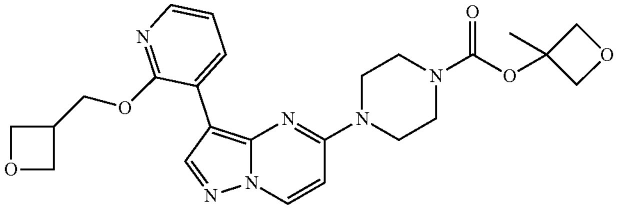 [SMILES: CC1(OC(=O)N2CCN(c3ccn4ncc(-c5cccnc5OCC5COC5)c4n3)CC2)COC1] |
| I-21 | 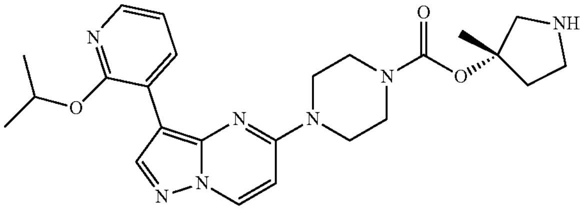 [SMILES: CC(C)Oc1ncccc1-c1cnn2ccc(N3CCN(C(=O)O[C@@]4(C)CCNC4)CC3)nc12] |
| I-21-5 | 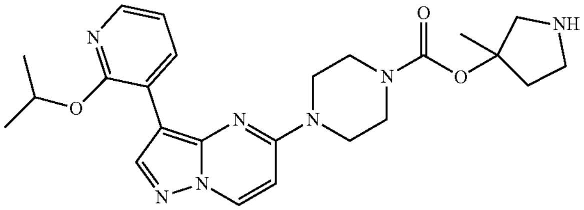 [SMILES: CC(C)Oc1ncccc1-c1cnn2ccc(N3CCN(C(=O)OC4(C)CCNC4)CC3)nc12] |

TABLE 1-continued
| Compounds of the Disclosure | |
|---|---|
| Compound ID | Structure |
| I-22 | 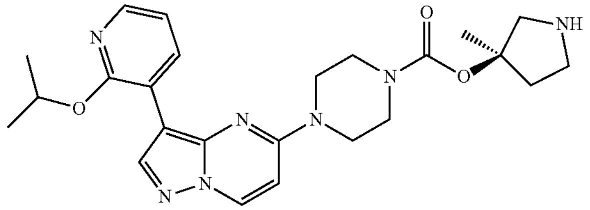 [SMILES: CC(C)Oc1ncccc1-c1cnn2ccc(N3CCN(C(=O)O[C@]4(C)CCNC4)CC3)nc12] |
| I-23 | 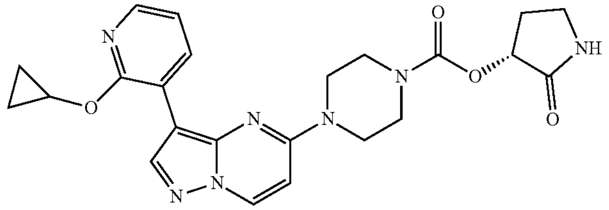 [SMILES: O=C1NCC[C@H]1OC(=O)N1CCN(c2ccn3ncc(-c4cccnc4OC4CC4)c3n2)CC1] |
| I-24 | 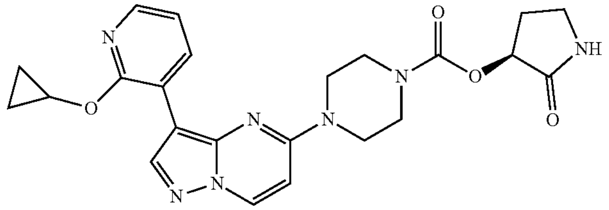 [SMILES: O=C1NCC[C@@H]1OC(=O)N1CCN(c2ccn3ncc(-c4cccnc4OC4CC4)c3n2)CC1] |
| I-25 | 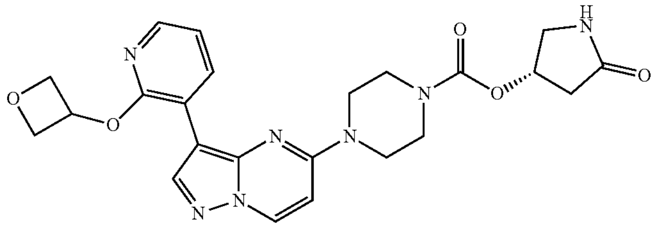 [SMILES: O=C1C[C@H](OC(=O)N2CCN(c3ccn4ncc(-c5cccnc5OC5COC5)c4n3)CC2)CN1] |
| I-26 | 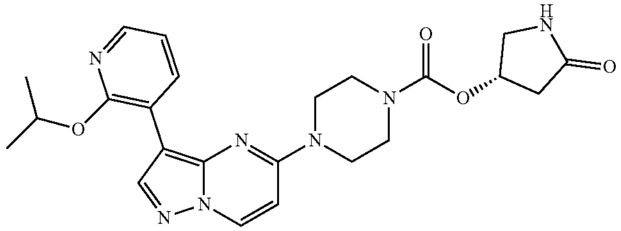 [SMILES: CC(C)Oc1ncccc1-c1cnn2ccc(N3CCN(C(=O)O[C@@H]4CNC(=O)C4)CC3)nc12] |
| I-27 | 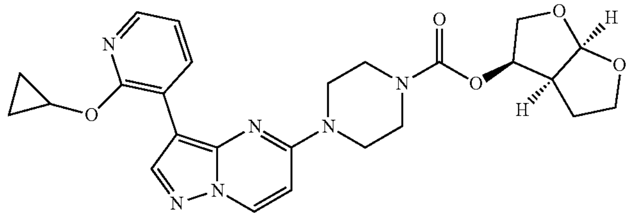 [SMILES: O=C(O[C@H]1CO[C@H]2OCC[C@H]21)N1CCN(c2ccn3ncc(-c4cccnc4OC4CC4)c3n2)CC1] |

TABLE 1-continued
| Compounds of the Disclosure | |
|---|---|
| Compound ID | Structure |
| I-28 | 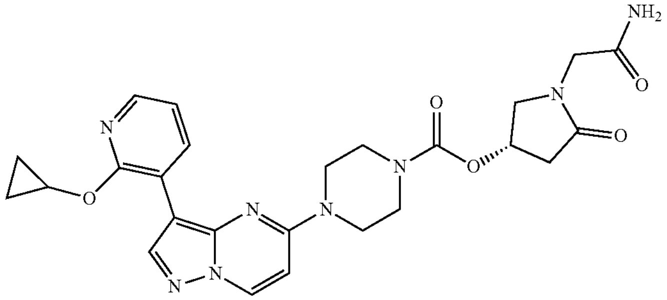 [SMILES: NC(=O)CN1C[C@@H](OC(=O)N2CCN(c3ccn4ncc(-c5cccnc5OC5CC5)c4n3)CC2)CC1=O] |
| I-29 | 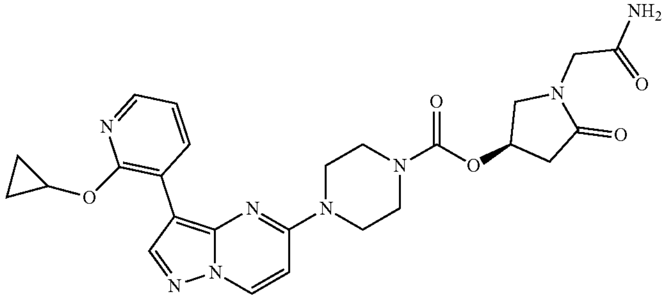 [SMILES: NC(=O)CN1C[C@H](OC(=O)N2CCN(c3ccn4ncc(-c5cccnc5OC5CC5)c4n3)CC2)CC1=O] |
| I-30 | 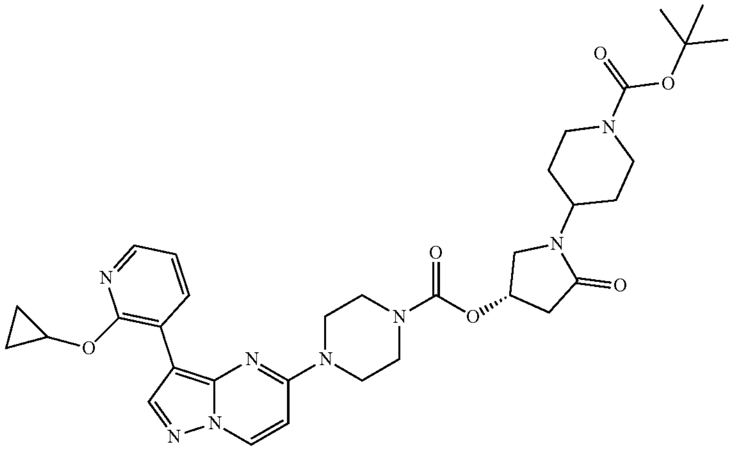 [SMILES: CC(C)(C)OC(=O)N1CCC(N2C[C@@H](OC(=O)N3CCN(c4ccn5ncc(-c6cccnc6OC6CC6)c5n4)CC3)CC2=O)CC1] |
| I-31 | 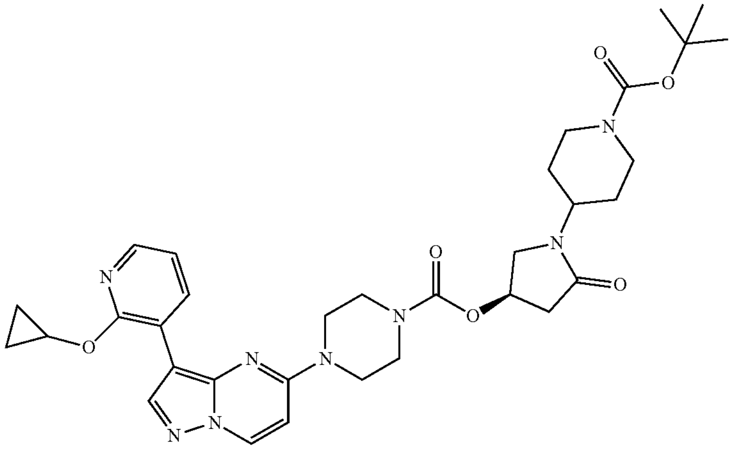 [SMILES: CC(C)(C)OC(=O)N1CCC(N2C[C@H](OC(=O)N3CCN(c4ccn5ncc(-c6cccnc6OC6CC6)c5n4)CC3)CC2=O)CC1] |

TABLE 1-continued
| Compounds of the Disclosure | |
|---|---|
| Compound ID | Structure |
| I-32 | 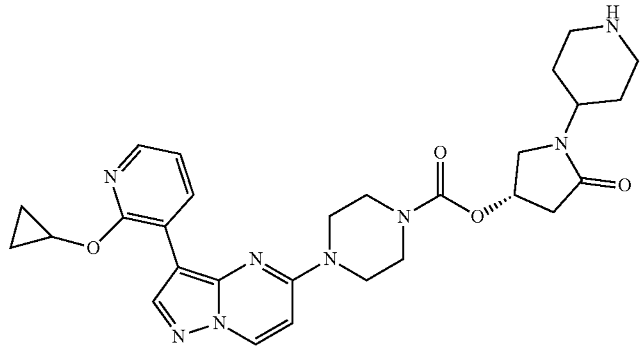 [SMILES: O=C(O[C@H]1CC(=O)N(C2CCNCC2)C1)N1CCN(c2ccn3ncc(-c4cccnc4OC4CC4)c3n2)CC1] |
| I-33 | 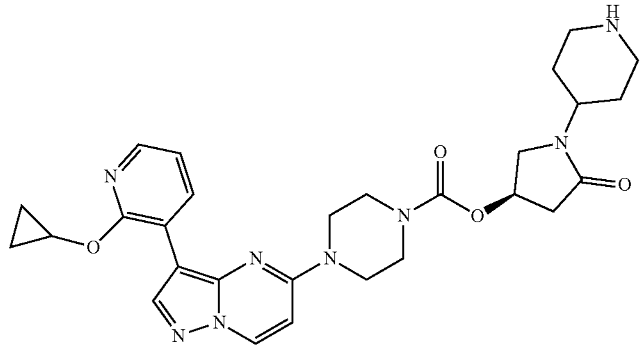 [SMILES: O=C(O[C@@H]1CC(=O)N(C2CCNCC2)C1)N1CCN(c2ccn3ncc(-c4cccnc4OC4CC4)c3n2)CC1] |
| I-34 | 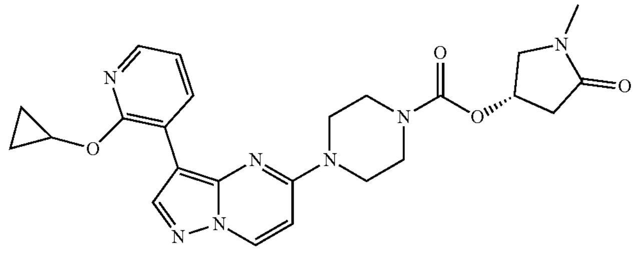 [SMILES: CN1C[C@@H](OC(=O)N2CCN(c3ccn4ncc(-c5cccnc5OC5CC5)c4n3)CC2)CC1=O] |
| I-35 | 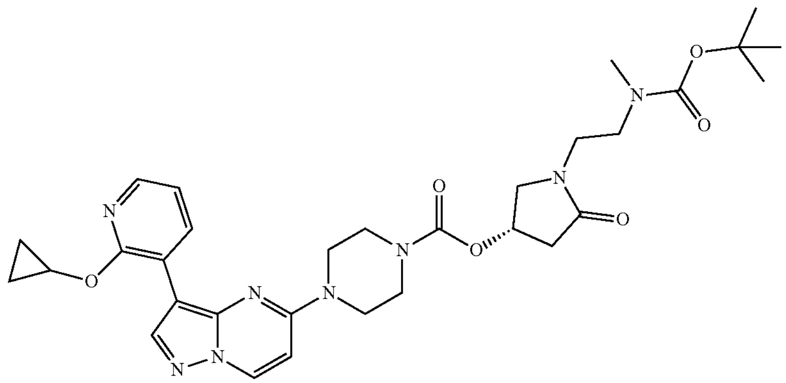 [SMILES: CN(CCN1C[C@@H](OC(=O)N2CCN(c3ccn4ncc(-c5cccnc5OC5CC5)c4n3)CC2)CC1=O)C(=O)OC(C)(C)C] |

TABLE 1-continued
| Compound ID | Structure |
|---|---|
| | Compounds of the Disclosure |
| I-36 | 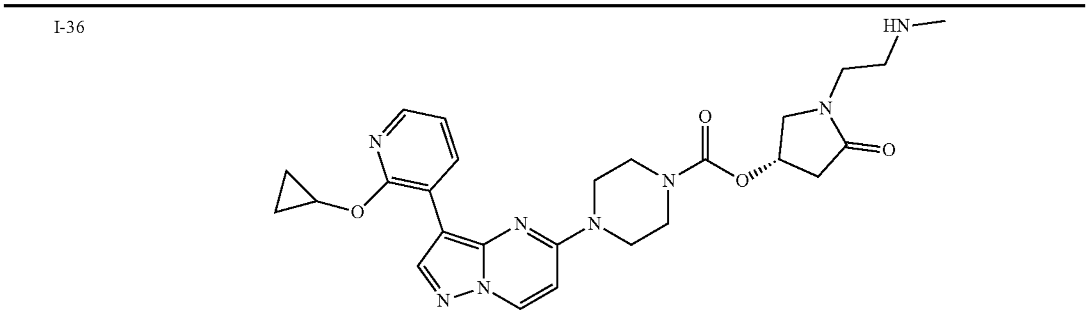 |
| I-37 | 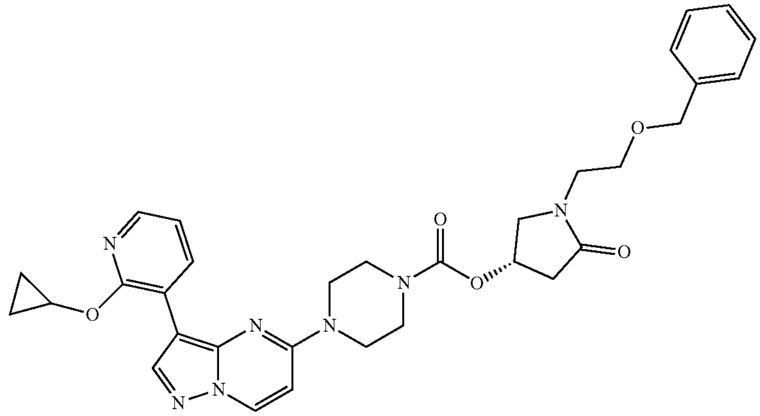 [SMILES: O=C1C[C@H](OC(=O)N2CCN(c3ccn4ncc(-c5cccnc5OC5CC5)c4n3)CC2)CN1CCOCc1ccccc1] |
| I-38 | 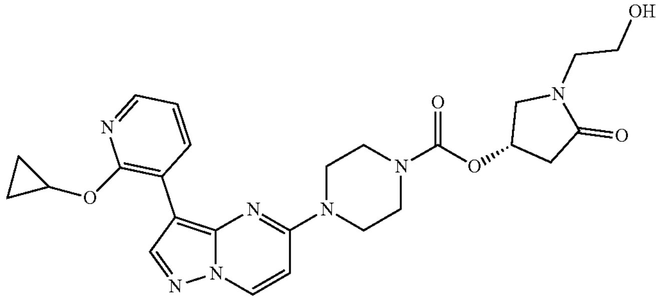 [SMILES: O=C1C[C@H](OC(=O)N2CCN(c3ccn4ncc(-c5cccnc5OC5CC5)c4n3)CC2)CN1CCO] |
| I-39 | 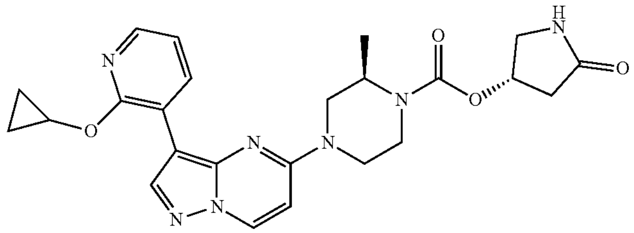 [SMILES: C[C@@H]1CN(c2ccn3ncc(-c4cccnc4OC4CC4)c3n2)CCN1C(=O)O[C@@H]1CNC(=O)C1] |
| I-40 | 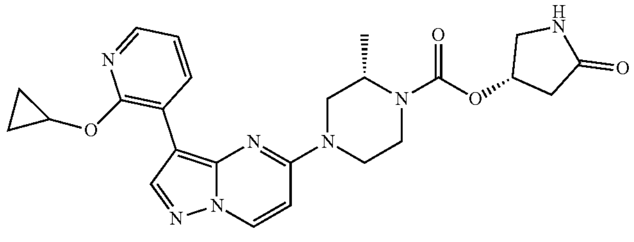 [SMILES: C[C@H]1CN(c2ccn3ncc(-c4cccnc4OC4CC4)c3n2)CCN1C(=O)O[C@@H]1CNC(=O)C1] |

TABLE 1-continued
| Compounds of the Disclosure | |
|---|---|
| Compound ID | Structure |
| I-41 | 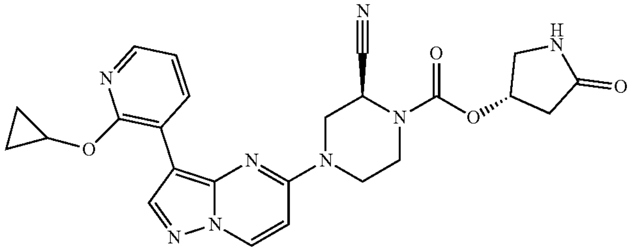 [SMILES: N#C[C@@H]1CN(c2ccn3ncc(-c4cccnc4OC4CC4)c3n2)CCN1C(=O)O[C@@H]1CNC(=O)C1] |
| I-41-4C | 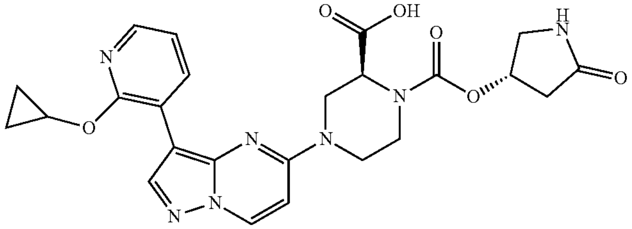 [SMILES: O=C1C[C@H](OC(=O)N2CCN(c3ccn4ncc(-c5cccnc5OC5CC5)c4n3)C[C@H]2C(=O)O)CN1] |
| I-41-5 | 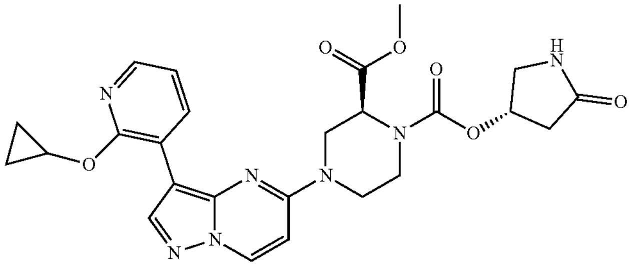 [SMILES: COC(=O)[C@@H]1CN(c2ccn3ncc(-c4cccnc4OC4CC4)c3n2)CCN1C(=O)O[C@@H]1CNC(=O)C1] |
| I-41-6 | 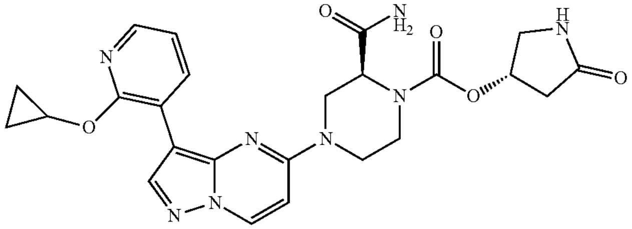 [SMILES: NC(=O)[C@@H]1CN(c2ccn3ncc(-c4cccnc4OC4CC4)c3n2)CCN1C(=O)O[C@@H]1CNC(=O)C1] |
| I-42 | 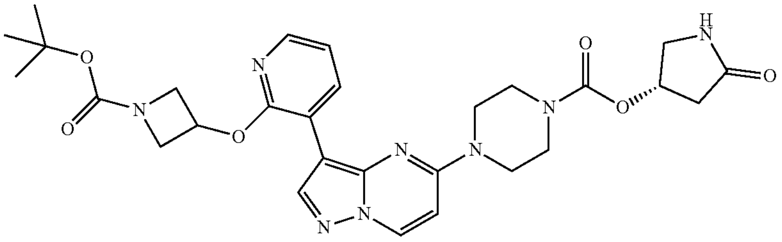 [SMILES: CC(C)(C)OC(=O)N1CC(Oc2ncccc2-c2cnn3ccc(N4CCN(C(=O)O[C@@H]5CNC(=O)C5)CC4)nc23)C1] |
| I-43 | 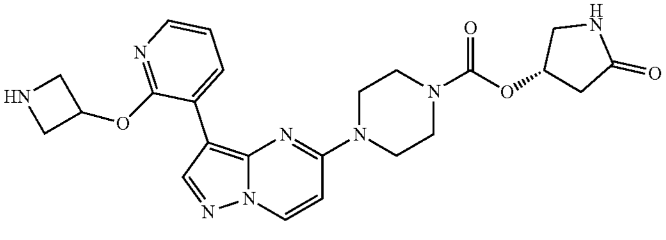 [SMILES: O=C1C[C@H](OC(=O)N2CCN(c3ccn4ncc(-c5cccnc5OC5CNC5)c4n3)CC2)CN1] |

TABLE 1-continued
| Compounds of the Disclosure | |
|---|---|
| Compound ID | Structure |
| I-44 | 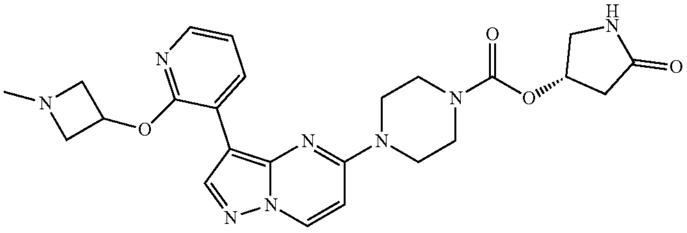 [SMILES: CN1CC(Oc2ncccc2-c2cnn3ccc(N4CCN(C(=O)O[C@@H]5CNC(=O)C5)CC4)nc23)C1] |
| I-45 | 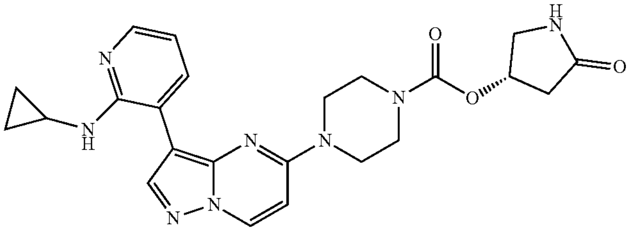 [SMILES: O=C1C[C@H](OC(=O)N2CCN(c3ccn4ncc(-c5cccnc5NC5CC5)c4n3)CC2)CN1] |
| I-46 | 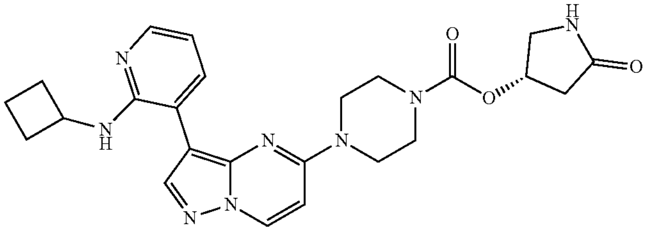 [SMILES: O=C1C[C@H](OC(=O)N2CCN(c3ccn4ncc(-c5cccnc5NC5CCC5)c4n3)CC2)CN1] |
| I-47 | 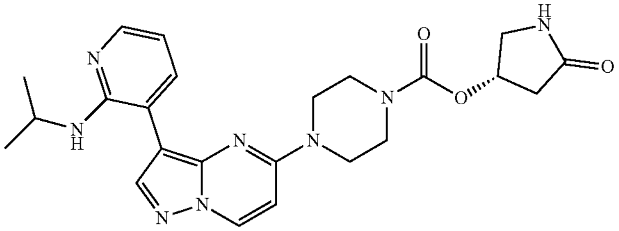 [SMILES: CC(C)Nc1ncccc1-c1cnn2ccc(N3CCN(C(=O)O[C@@H]4CNC(=O)C4)CC3)nc12] |
| I-48 | 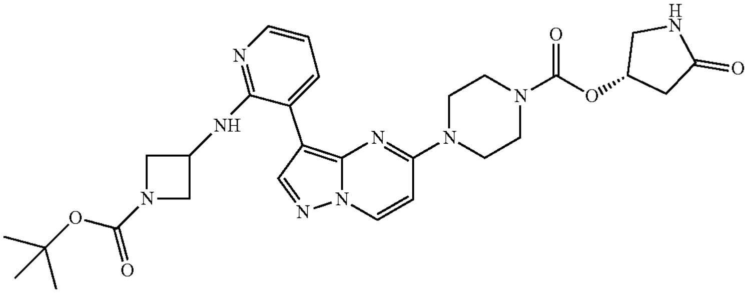 [SMILES: CC(C)(C)OC(=O)N1CC(Nc2ncccc2-c2cnn3ccc(N4CCN(C(=O)O[C@@H]5CNC(=O)C5)CC4)nc23)C1] |
| I-49 | 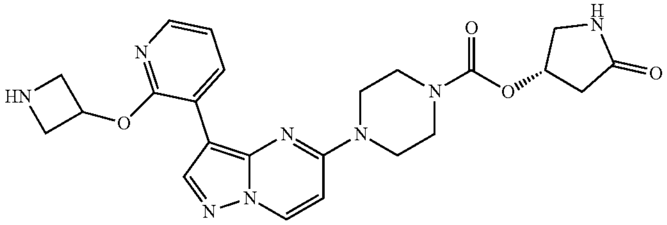 [SMILES: O=C1C[C@H](OC(=O)N2CCN(c3ccn4ncc(-c5cccnc5OC5CNC5)c4n3)CC2)CN1] |

TABLE 1-continued
| Compounds of the Disclosure | |
|---|---|
| Compound ID | Structure |
| I-50 | 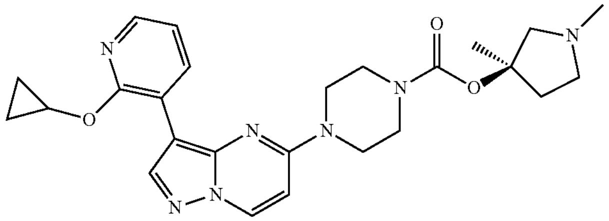 [SMILES: CN1CC[C@@](C)(OC(=O)N2CCN(c3ccn4ncc(-c5cccnc5OC5CC5)c4n3)CC2)C1] |
| I-51 | 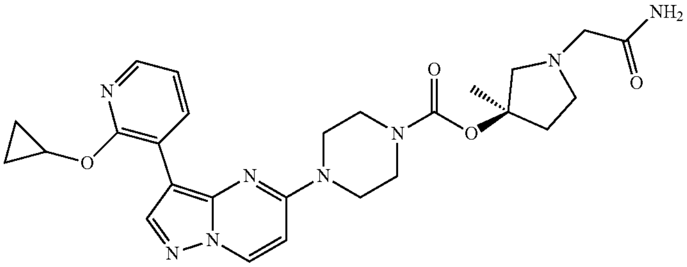 [SMILES: C[C@@]1(OC(=O)N2CCN(c3ccn4ncc(-c5cccnc5OC5CC5)c4n3)CC2)CCN(CC(N)=O)C1] |
| I-52 | 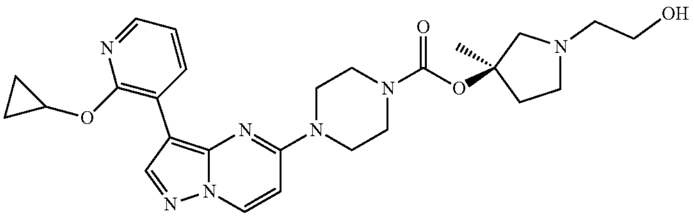 [SMILES: C[C@@]1(OC(=O)N2CCN(c3ccn4ncc(-c5cccnc5OC5CC5)c4n3)CC2)CCN(CCO)C1] |
| I-53 | 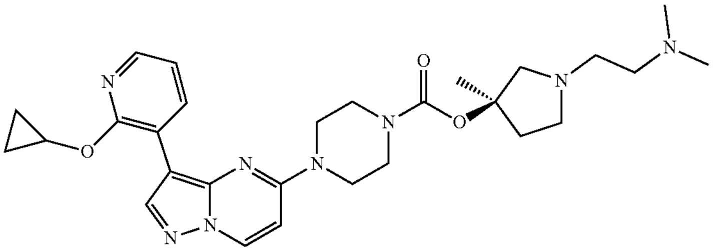 [SMILES: CN(C)CCN1CC[C@@](C)(OC(=O)N2CCN(c3ccn4ncc(-c5cccnc5OC5CC5)c4n3)CC2)C1] |
| I-54 | 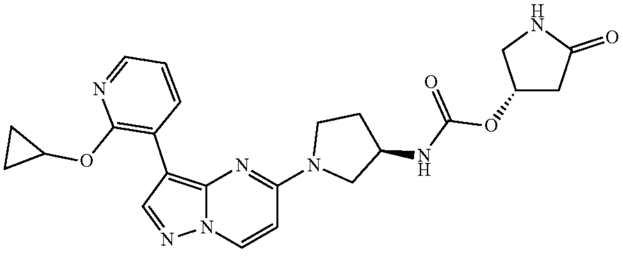 [SMILES: O=C1C[C@H](OC(=O)N[C@@H]2CCN(c3ccn4ncc(-c5cccnc5OC5CC5)c4n3)C2)CN1] |
| I-55 | 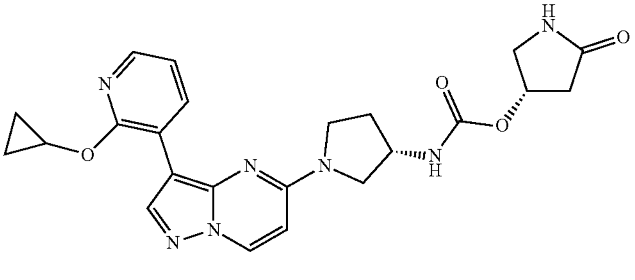 [SMILES: O=C1C[C@H](OC(=O)N[C@H]2CCN(c3ccn4ncc(-c5cccnc5OC5CC5)c4n3)C2)CN1] |

TABLE 1-continued
| Compounds of the Disclosure | |
|---|---|
| Compound ID | Structure |
| I-56 | 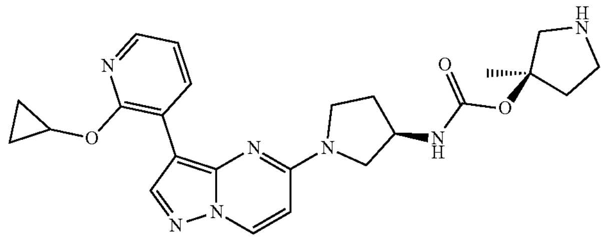 [SMILES: C[C@@]1(OC(=O)N[C@@H]2CCN(c3ccn4ncc(-c5cccnc5OC5CC5)c4n3)C2)CCNC1] |
| I-57 | 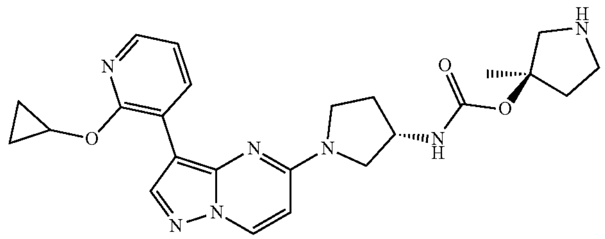 [SMILES: C[C@@]1(OC(=O)N[C@H]2CCN(c3ccn4ncc(-c5cccnc5OC5CC5)c4n3)C2)CCNC1] |
| I-58 | 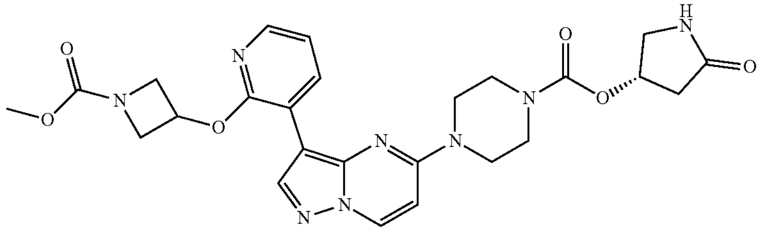 [SMILES: COC(=O)N1CC(Oc2ncccc2-c2cnn3ccc(N4CCN(C(=O)O[C@@H]5CNC(=O)C5)CC4)nc23)C1] |
| I-59 | 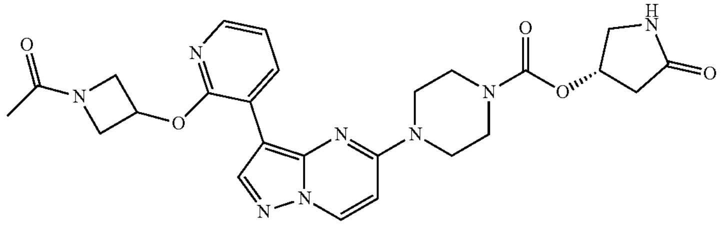 [SMILES: CC(=O)N1CC(Oc2ncccc2-c2cnn3ccc(N4CCN(C(=O)O[C@@H]5CNC(=O)C5)CC4)nc23)C1] |
| I-60 | 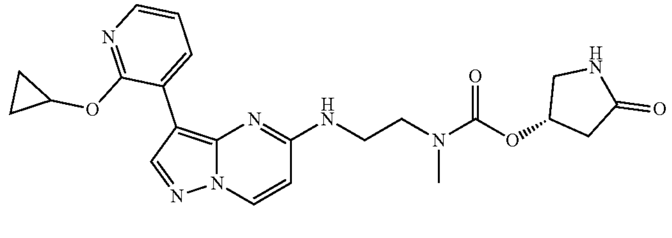 [SMILES: CN(CCNc1ccn2ncc(-c3cccnc3OC3CC3)c2n1)C(=O)O[C@@H]1CNC(=O)C1] |
| I-61 | 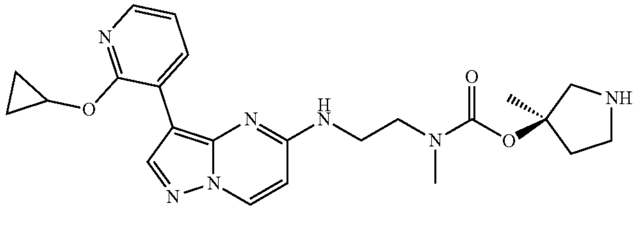 [SMILES: CN(CCNc1ccn2ncc(-c3cccnc3OC3CC3)c2n1)C(=O)O[C@]1(C)CCNC1] |

TABLE 1-continued
| Compounds of the Disclosure | |
|---|---|
| Compound ID | Structure |
| I-62 | 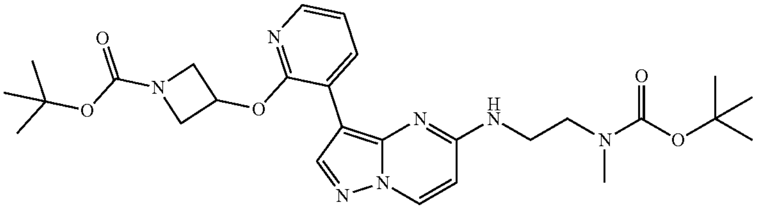 [SMILES: CN(CCNc1ccn2ncc(-c3cccnc3OC3CN(C(=O)OC(C)(C)C)C3)c2n1)C(=O)OC(C)(C)C] |
| I-63 | 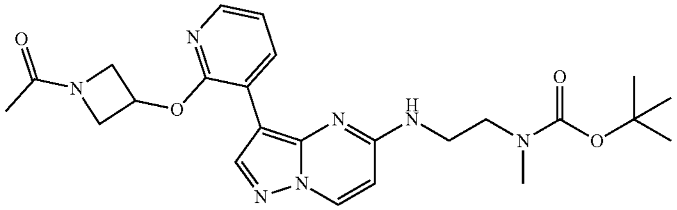 [SMILES: CC(=O)N1CC(Oc2ncccc2-c2cnn3ccc(NCCN(C)C(=O)OC(C)(C)C)nc23)C1] |
| I-64 | 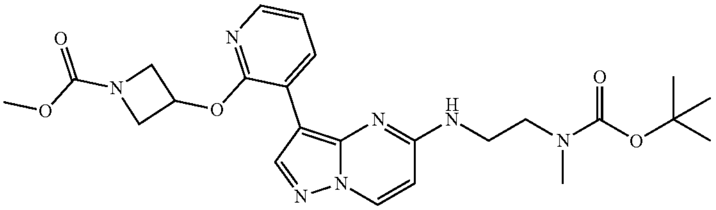 [SMILES: COC(=O)N1CC(Oc2ncccc2-c2cnn3ccc(NCCN(C)C(=O)OC(C)(C)C)nc23)C1] |
| I-65 | 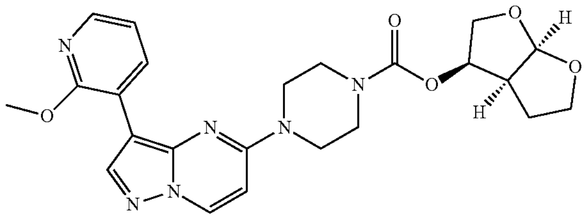 [SMILES: COc1ncccc1-c1cnn2ccc(N3CCN(C(=O)O[C@H]4CO[C@H]5OCC[C@H]54)CC3)nc12] |
| I-66 | 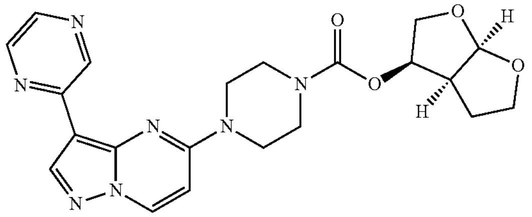 [SMILES: O=C(O[C@H]1CO[C@H]2OCC[C@H]21)N1CCN(c2ccn3ncc(-c4cnccn4)c3n2)CC1] |
| I-67 | 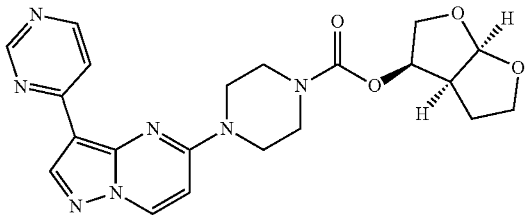 [SMILES: O=C(O[C@H]1CO[C@H]2OCC[C@H]21)N1CCN(c2ccn3ncc(-c4ccncn4)c3n2)CC1] |

TABLE 1-continued
| Compounds of the Disclosure | |
|---|---|
| Compound ID | Structure |
| I-68 | 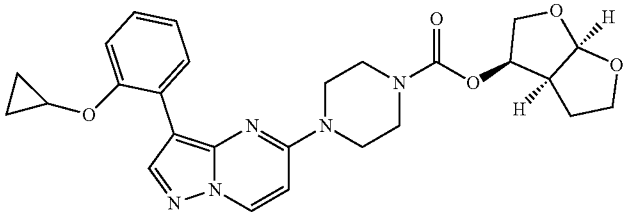 [SMILES: O=C(O[C@H]1CO[C@H]2OCC[C@H]21)N1CCN(c2ccn3ncc(-c4ccccc4OC4CC4)c3n2)CC1] |
| I-69 | 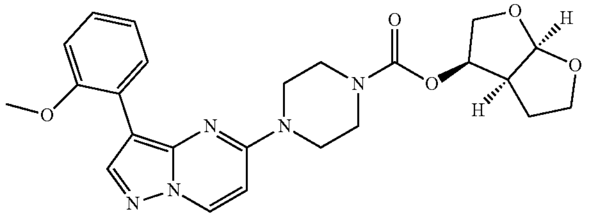 [SMILES: COc1ccccc1-c1cnn2ccc(N3CCN(C(=O)O[C@H]4CO[C@H]5OCC[C@H]54)CC3)nc12] |
| I-70 | 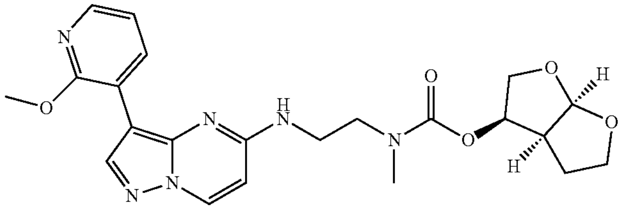 [SMILES: COc1ncccc1-c1cnn2ccc(NCCN(C)C(=O)O[C@H]3CO[C@H]4OCC[C@H]43)nc12] |
| I-71 | 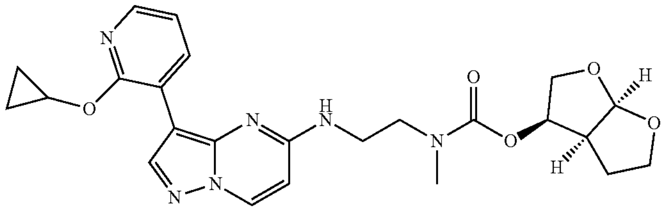 [SMILES: CN(CCNc1ccn2ncc(-c3cccnc3OC3CC3)c2n1)C(=O)O[C@H]1CO[C@H]2OCC[C@H]21] |
| I-72 | 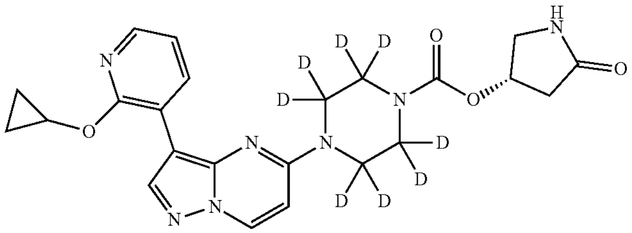 [SMILES: [2H]C1([2H])N(C(=O)O[C@@H]2CNC(=O)C2)C([2H])([2H])C([2H])([2H])N(c2ccn3ncc(-c4cccnc4OC4CC4)c3n2)C1([2H])[2H]] |
| I-73 | 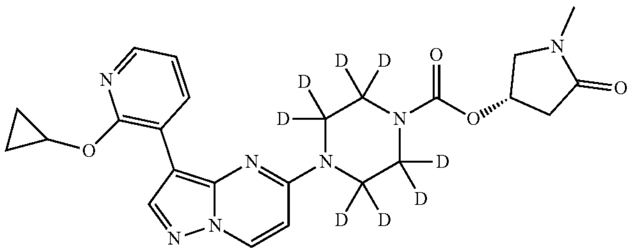 [SMILES: [2H]C1([2H])N(C(=O)O[C@H]2CC(=O)N(C)C2)C([2H])([2H])C([2H])([2H])N(c2ccn3ncc(-c4cccnc4OC4CC4)c3n2)C1([2H])[2H]] |

TABLE 1-continued
| Compounds of the Disclosure | |
|---|---|
| Compound ID | Structure |
| I-74 | 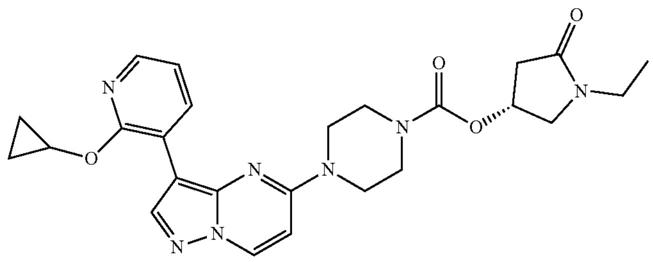 [SMILES: CCN1C[C@H](OC(=O)N2CCN(c3ccn4ncc(-c5cccnc5OC5CC5)c4n3)CC2)CC1=O] |
| I-75 | 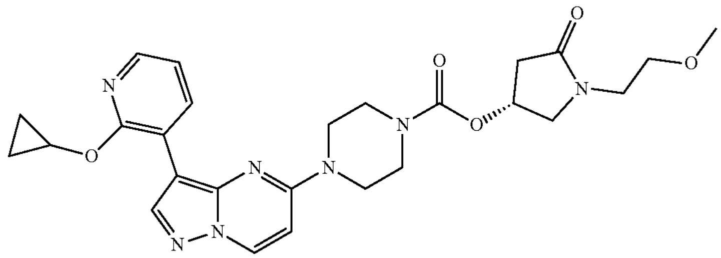 [SMILES: COCCN1C[C@H](OC(=O)N2CCN(c3ccn4ncc(-c5cccnc5OC5CC5)c4n3)CC2)CC1=O] |
| I-76 | 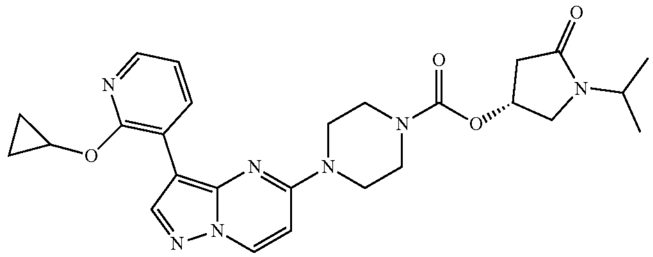 [SMILES: CC(C)N1C[C@H](OC(=O)N2CCN(c3ccn4ncc(-c5cccnc5OC5CC5)c4n3)CC2)CC1=O] |
| I-77-6 | 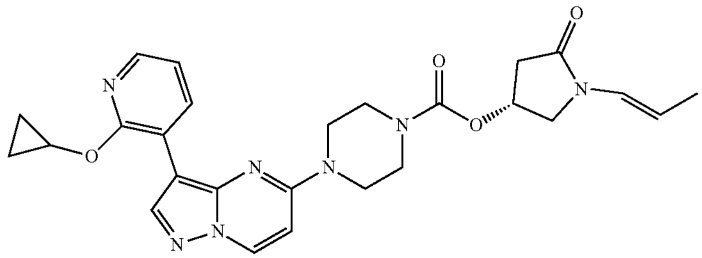 [SMILES: C/C=C/N1C[C@H](OC(=O)N2CCN(c3ccn4ncc(-c5cccnc5OC5CC5)c4n3)CC2)CC1=O] |
| I-78 | 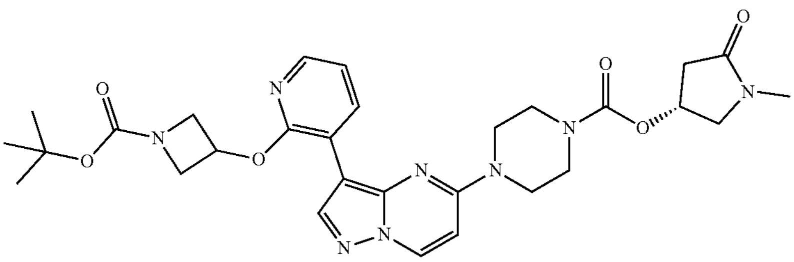 [SMILES: CN1C[C@H](OC(=O)N2CCN(c3ccn4ncc(-c5cccnc5OC5CN(C(=O)OC(C)(C)C)C5)c4n3)CC2)CC1=O] |

TABLE 1-continued
| Compounds of the Disclosure | |
|---|---|
| Compound ID | Structure |
| I-79 | 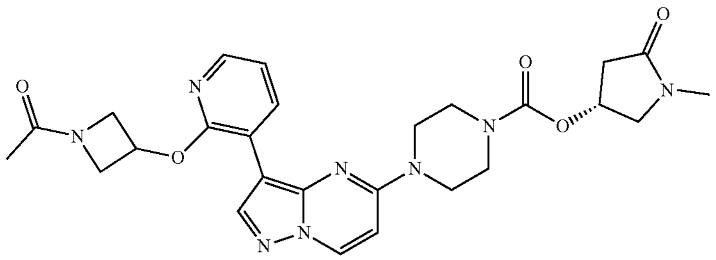 [SMILES: CC(=O)N1CC(Oc2ncccc2-c2cnn3ccc(N4CCN(C(=O)O[C@@H]5CC(=O)N(C)C5)CC4)nc23)C1] |
| I-80 | 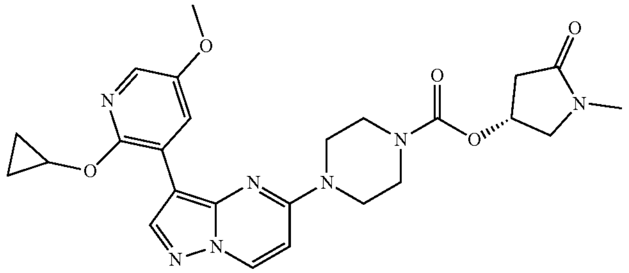 [SMILES: COc1cnc(OC2CC2)c(-c2cnn3ccc(N4CCN(C(=O)O[C@@H]5CC(=O)N(C)C5)CC4)nc23)c1] |
| I-81 | 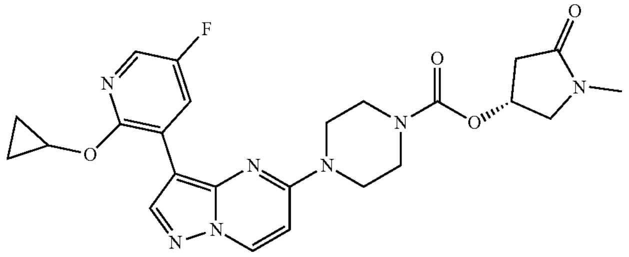 [SMILES: CN1C[C@H](OC(=O)N2CCN(c3ccn4ncc(-c5cc(F)cnc5OC5CC5)c4n3)CC2)CC1=O] |
| I-82 | 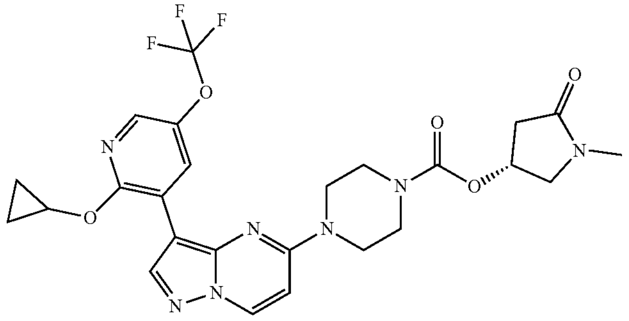 [SMILES: CN1C[C@H](OC(=O)N2CCN(c3ccn4ncc(-c5cc(OC(F)(F)F)cnc5OC5CC5)c4n3)CC2)CC1=O] |
| I-83 | 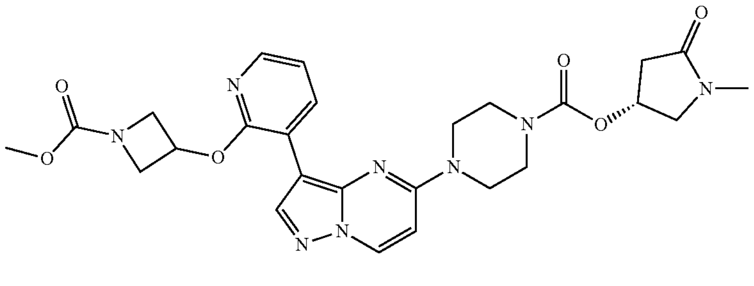 |

TABLE 1-continued
| Compounds of the Disclosure | |
|---|---|
| Compound ID | Structure |
| I-84 | 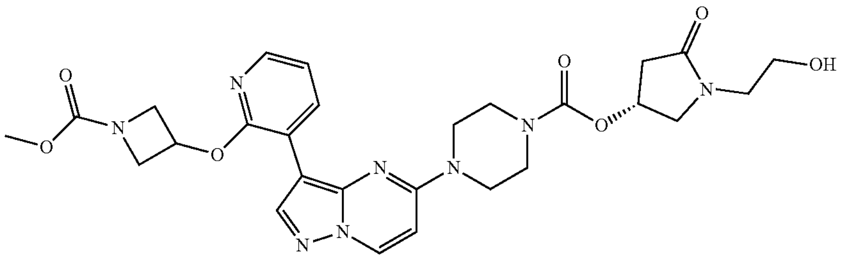 [SMILES: COC(=O)N1CC(Oc2ncccc2-c2cnn3ccc(N4CCN(C(=O)O[C@@H]5CC(=O)N(CCO)C5)CC4)nc23)C1] |
| I-84-6 | 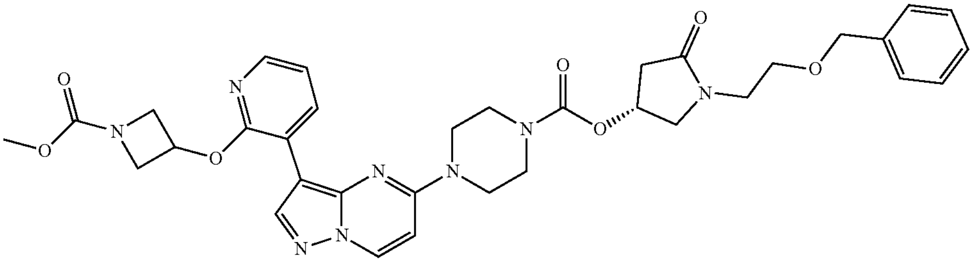 [SMILES: COC(=O)N1CC(Oc2ncccc2-c2cnn3ccc(N4CCN(C(=O)O[C@@H]5CC(=O)N(CCOCc6ccccc6)C5)CC4)nc23)C1] |
| I-85 | 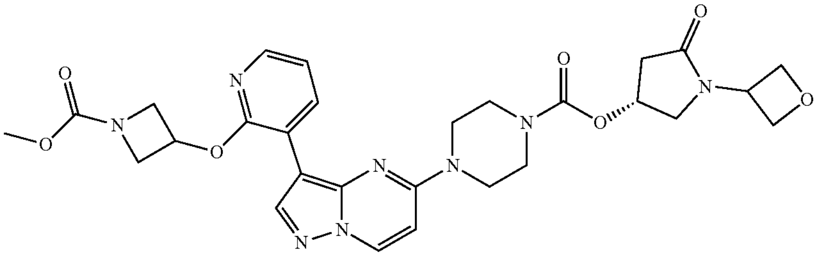 [SMILES: COC(=O)N1CC(Oc2ncccc2-c2cnn3ccc(N4CCN(C(=O)O[C@@H]5CC(=O)N(C6COC6)C5)CC4)nc23)C1] |
| I-86 | 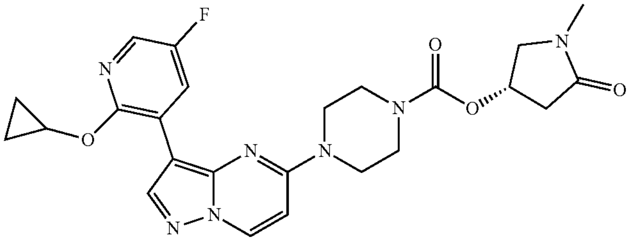 [SMILES: CN1C[C@@H](OC(=O)N2CCN(c3ccn4ncc(-c5cc(F)cnc5OC5CC5)c4n3)CC2)CC1=O] |
| I-87 | 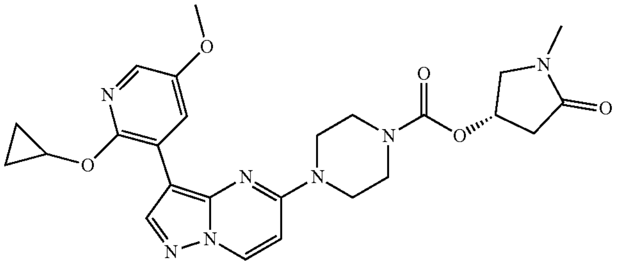 [SMILES: COc1cnc(OC2CC2)c(-c2cnn3ccc(N4CCN(C(=O)O[C@H]5CC(=O)N(C)C5)CC4)nc23)c1] |

TABLE 1-continued
| Compounds of the Disclosure | |
|---|---|
| Compound ID | Structure |
| I-88 | 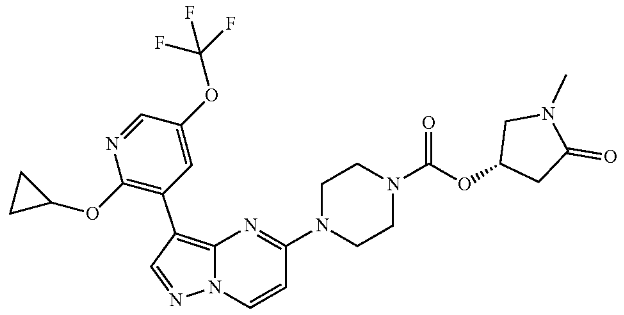 [SMILES: CN1C[C@@H](OC(=O)N2CCN(c3ccn4ncc(-c5cc(OC(F)(F)F)cnc5OC5CC5)c4n3)CC2)CC1=O] |
| I-89 | 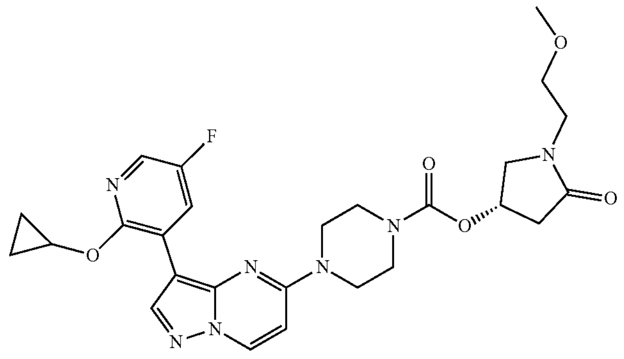 [SMILES: COCCN1C[C@@H](OC(=O)N2CCN(c3ccn4ncc(-c5cc(F)cnc5OC5CC5)c4n3)CC2)CC1=O] |
| I-94 | 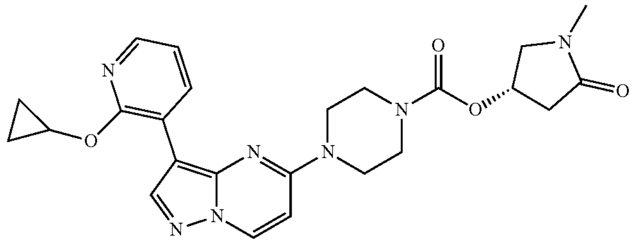 [SMILES: CN1C[C@@H](OC(=O)N2CCN(c3ccn4ncc(-c5cccnc5OC5CC5)c4n3)CC2)CC1=O] |
| I-98 | 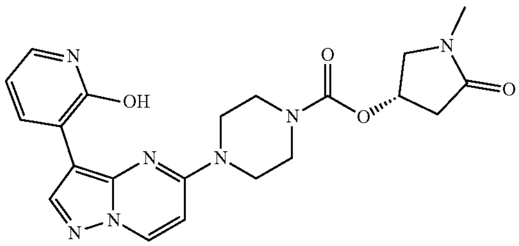 [SMILES: CN1C[C@@H](OC(=O)N2CCN(c3ccn4ncc(-c5cccnc5O)c4n3)CC2)CC1=O] |
| I-108 | 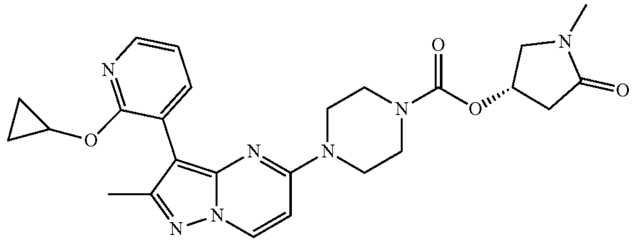 [SMILES: Cc1nn2ccc(N3CCN(C(=O)O[C@H]4CC(=O)N(C)C4)CC3)nc2c1-c1cccnc1OC1CC1] |

TABLE 1-continued
| Compounds of the Disclosure | |
|---|---|
| Compound ID | Structure |
| I-109 | 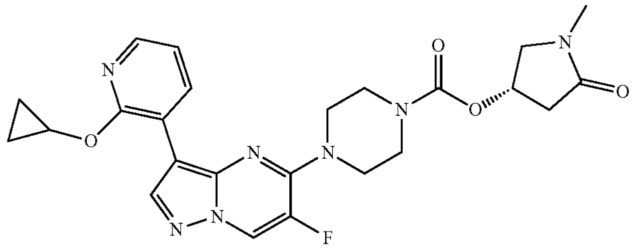 [SMILES: CN1C[C@@H](OC(=O)N2CCN(c3nc4c(-c5cccnc5OC5CC5)cnn4cc3F)CC2)CC1=O] |
| I-110 | 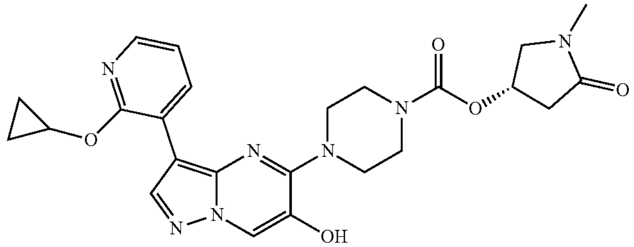 [SMILES: CN1C[C@@H](OC(=O)N2CCN(c3nc4c(-c5cccnc5OC5CC5)cnn4cc3O)CC2)CC1=O] |
| I-110-9 | 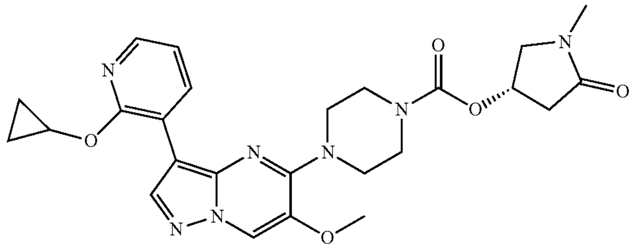 [SMILES: COc1cn2ncc(-c3cccnc3OC3CC3)c2nc1N1CCN(C(=O)O[C@H]2CC(=O)N(C)C2)CC1] |
| I-111 | 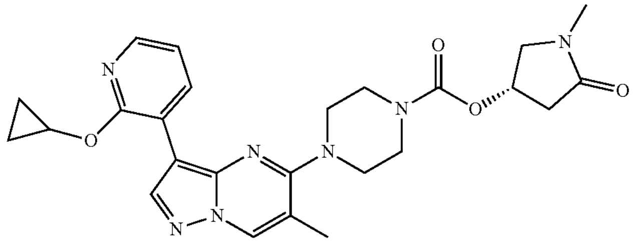 [SMILES: Cc1cn2ncc(-c3cccnc3OC3CC3)c2nc1N1CCN(C(=O)O[C@H]2CC(=O)N(C)C2)CC1] |
| I-113 | 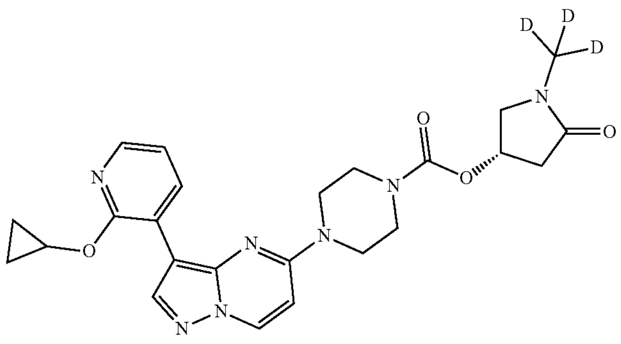 [SMILES: [2H]C([2H])([2H])N1C[C@@H](OC(=O)N2CCN(c3ccn4ncc(-c5cccnc5OC5CC5)c4n3)CC2)CC1=O] |

TABLE 1-continued
| Compound ID | Structure |
|---|---|
| I-114 | 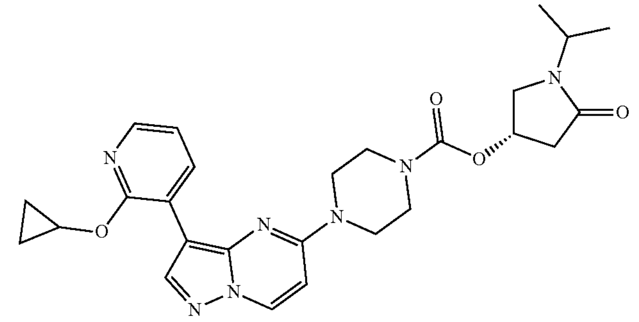 [SMILES: CC(C)N1C[C@@H](OC(=O)N2CCN(c3ccn4ncc(-c5cccnc5OC5CC5)c4n3)CC2)CC1=O] |
| I-115 | 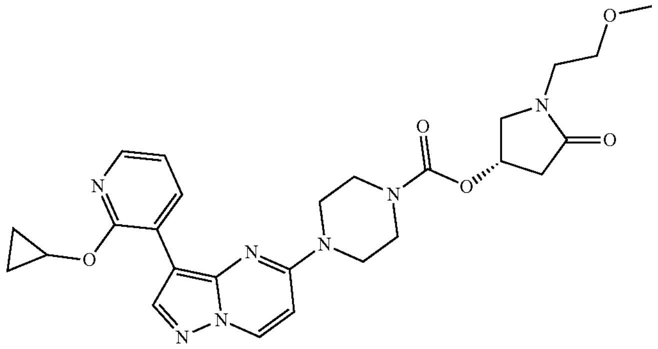 [SMILES: COCCN1C[C@@H](OC(=O)N2CCN(c3ccn4ncc(-c5cccnc5OC5CC5)c4n3)CC2)CC1=O] |
| I-116 | 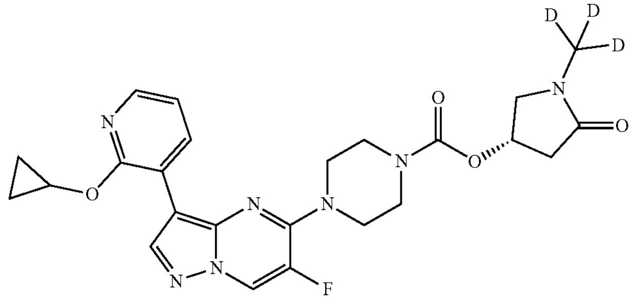 [SMILES: [2H]C([2H])([2H])N1C[C@@H](OC(=O)N2CCN(c3nc4c(-c5cccnc5OC5CC5)cnn4cc3F)CC2)CC1=O] |
| I-117 | 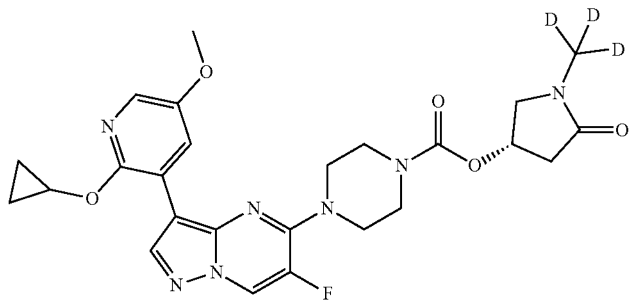 [SMILES: [2H]C([2H])([2H])N1C[C@@H](OC(=O)N2CCN(c3nc4c(-c5cc(OC)cnc5OC5CC5)cnn4cc3F)CC2)CC1=O] |
Compounds of the Disclosure TABLE 1-continued
| Compound ID | Structure |
|---|---|
| I-118 | 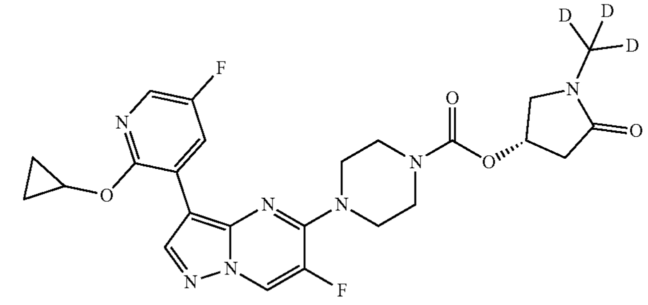 [SMILES: [2H]C([2H])([2H])N1C[C@@H](OC(=O)N2CCN(c3nc4c(-c5cc(F)cnc5OC5CC5)cnn4cc3F)CC2)CC1=O] |
| I-119 | 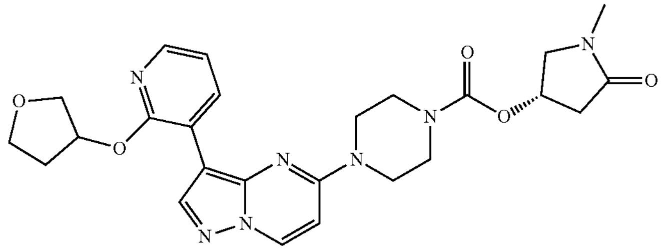 [SMILES: CN1C[C@@H](OC(=O)N2CCN(c3ccn4ncc(-c5cccnc5OC5CCOC5)c4n3)CC2)CC1=O] |
| I-120 | 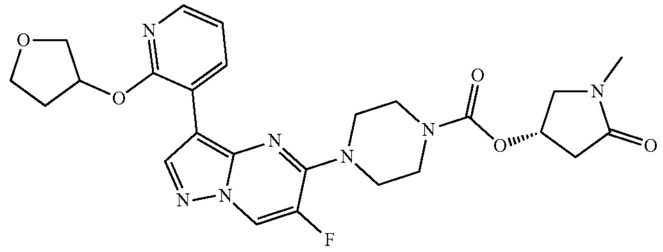 [SMILES: CN1C[C@@H](OC(=O)N2CCN(c3nc4c(-c5cccnc5OC5CCOC5)cnn4cc3F)CC2)CC1=O] |
| I-121 | 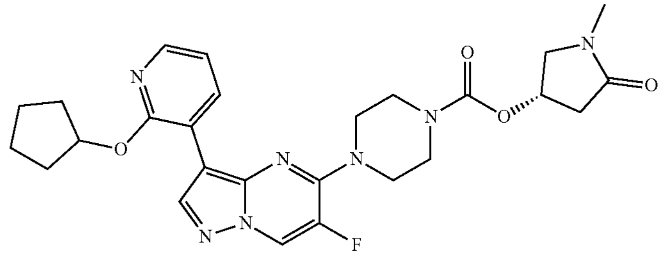 [SMILES: CN1C[C@@H](OC(=O)N2CCN(c3nc4c(-c5cccnc5OC5CCCC5)cnn4cc3F)CC2)CC1=O] |
| I-122 | 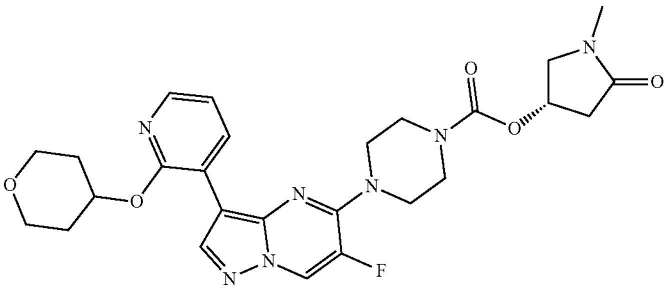 [SMILES: CN1C[C@@H](OC(=O)N2CCN(c3nc4c(-c5cccnc5OC5CCOCC5)cnn4cc3F)CC2)CC1=O] |
Compounds of the Disclosure TABLE 1-continued

| Compounds of the Disclosure | |
|---|---|
| Compound ID | Structure |
| I-123 | 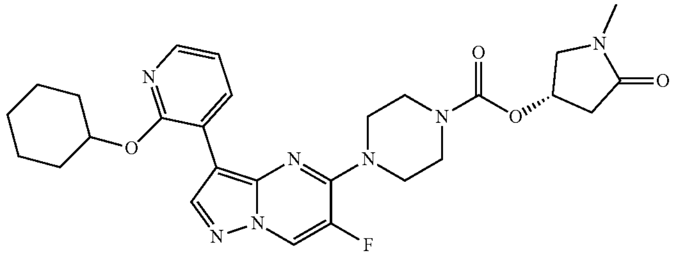 [SMILES: CN1C[C@@H](OC(=O)N2CCN(c3nc4c(-c5cccnc5OC5CCCCC5)cnn4cc3F)CC2)CC1=O] |
| I-124 | 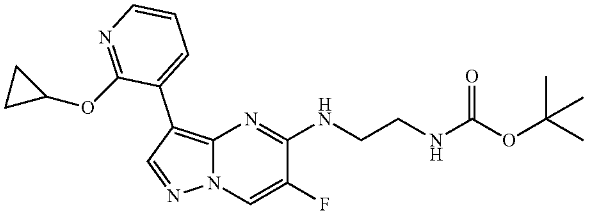 [SMILES: CC(C)(C)OC(=O)NCCNc1nc2c(-c3cccnc3OC3CC3)cnn2cc1F] |
| I-125 | 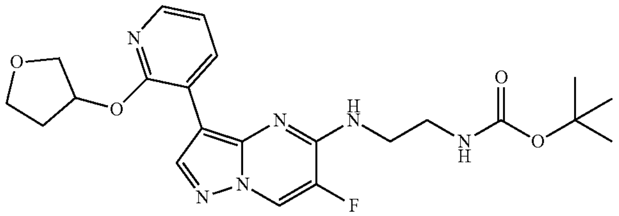 [SMILES: CC(C)(C)OC(=O)NCCNc1nc2c(-c3cccnc3OC3CCOC3)cnn2cc1F] |
| I-127 | 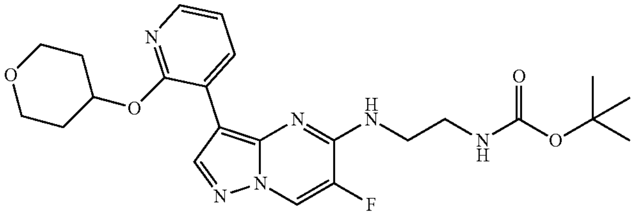 [SMILES: CC(C)(C)OC(=O)NCCNc1nc2c(-c3cccnc3OC3CCOCC3)cnn2cc1F] |
| I-129 | 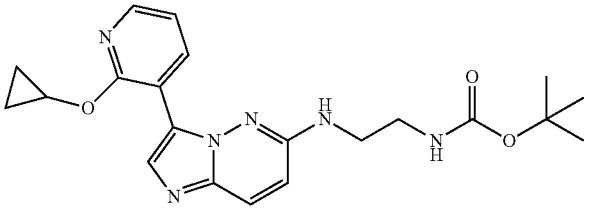 [SMILES: CC(C)(C)OC(=O)NCCNc1ccc2ncc(-c3cccnc3OC3CC3)n2n1] |

In some embodiments, the compound of the present disclosure is a compound of Table 2 having "A" activity in the AAK1 pSENs assay. In some embodiments, the compound of the present disclosure is a compound of Table 2 having "A" selectivity as measured by the ratio of AAK1 pSENs activity to GAK pSENs activity. In some embodiments, the compound of the present disclosure is a compound of Table 2 having "A" activity in the AAK1 pSENs assay and A" selectivity as measured by the ratio of AAK1 pSENs activity to GAK pSENs activity.

In some embodiments, the present disclosure provides a compound of Formula (II):

(II)

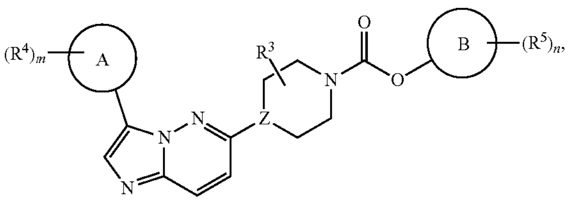

wherein Ⓐ, Ⓑ, Z, $R^3$, $R^4$, $R^5$, m, and n are as defined herein.

In some embodiments, the compound of Formula (II) disclosed herein has the structure:

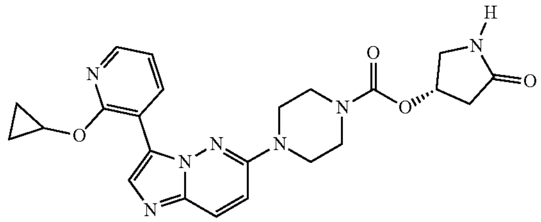

or

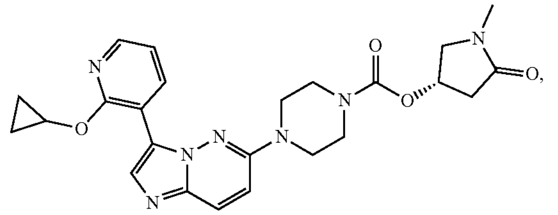

or a pharmaceutically acceptable salt thereof.

In some embodiments, the present disclosure provides a compound of Formula (III):

(III)

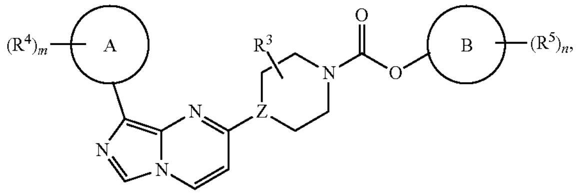

wherein Ⓐ, Ⓑ, Z, $R^3$, $R^4$, $R^5$, m, and n are as defined herein.

In some embodiments, the compound of Formula (III) disclosed herein has the structure:

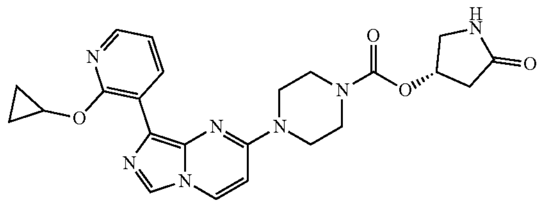

or

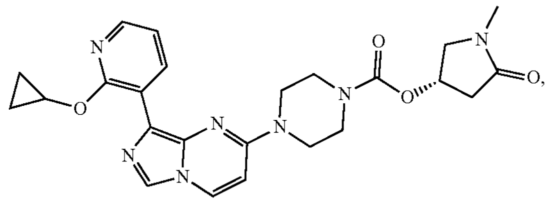

or a pharmaceutically acceptable salt thereof.

In some embodiments, the compounds disclosed herein or a pharmaceutically acceptable salts thereof bind AAK1. In some embodiments, the compounds or a pharmaceutically acceptable salts thereof are inhibitors of AAK1. In some embodiments, the compounds or a pharmaceutically acceptable salts thereof are selective inhibitors of AAK1. In some embodiments the compounds (e.g., compounds of Formulas (IA-4), (IA-5), and (IA-6)) or a pharmaceutically acceptable salt thereof are selective inhibitors of AAK1 over cyclin G-associated kinase (GAK) or BMP2 inducible kinase (BIKE). In some embodiments, the AAK1: GAK selectivity is greater than about 5:1, greater than about 10:1, greater than about 15:1, greater than about 20:1, greater than about 25:1, greater than about 50:1, greater than about 75:1, greater than about 100:1, greater than about 125:1, greater than about 150:1, greater than about 175:1, greater than about 200:1, greater than about 225:1, greater than about 250:1, greater than about 275:1, greater than about 300:1, greater than about 325:1, greater than about 350:1, greater than about 375:1, greater than about 400:1, greater than about 425:1, greater than about 450:1, greater than about 475:1, greater than 500:1, or greater than 1000:1, inclusive of all values and subranges therebetween. In some embodiments, the AAK1: GAK selectivity is from about 5:1 to about 500:1, from about 10:1 to about 500:1, from about 15:1 to about 500:1, from about 20:1 to about 500:1, from about 25:1 to about 500:1, from about 30:1 to about 500:1, from about 35:1 to about 500:1, from about 40:1 to about 500:1, from about 45:1 to about 500:1, from about 50:1 to about 55:1, from about 60:1 to about 500:1, from about 65:1 to about 500:1, from about 70:1 to about 500:1, from about 75:1 to about 500:1, from about 80:1 to about 500:1, from about 85:1 to about 500:1, from about 90:1 to about 500:1, from about 95:1 to about 500:1, or from about 100:1 to about 500:1, inclusive of all ranges and values therebetween. In some embodiments, the AAK1: BIKE selectivity is greater than about 5:1, greater than about 10:1, greater than about 15:1, greater than about 20:1, greater than about 25:1, greater than about 30:1, greater than about 35:1, greater than about 40:1, greater than about 45:1, greater than about 50:1, greater than about 55:1, greater than about 60:1, greater than about 65:1, greater than about 70:1, or greater than about 75:1, inclusive of all ranges and values therebetween.

Pharmaceutical Compositions

The present disclosure provides pharmaceutical compositions for use in the methods disclosed herein. In some embodiments, a pharmaceutical composition comprises one or more compounds disclosed herein or a pharmaceutically acceptable salt thereof.

In some embodiments of the present disclosure, a pharmaceutical compositions comprise a therapeutically effective amount of the one or more compounds disclosed herein or a pharmaceutically acceptable salt thereof.

In some embodiments, the present disclosure provides pharmaceutical compositions comprising a compound disclosed herein or a pharmaceutically acceptable salt thereof; and one or more pharmaceutically acceptable excipients and/or adjuvants.

The pharmaceutically acceptable excipients and adjuvants can be added to the composition or formulation for a variety of purposes. In some embodiments, the pharmaceutical compositions comprising a compound disclosed herein, or a pharmaceutically acceptable salt thereof, further comprise a pharmaceutically acceptable carrier. In some embodiments, a pharmaceutically acceptable carrier includes a pharmaceutically acceptable excipient, binder, and/or diluent. In some embodiments, suitable pharmaceutically acceptable carriers include, but are not limited to, inert solid fillers or diluents and sterile aqueous or organic solutions. In some embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, and the like.

A wide variety of administration methods may be used in conjunction with the pharmaceutical composition disclosed herein according to the methods disclosed herein. For example, compounds may be administered or co-administered topically, orally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, intrathecally, transmucosally, pulmonary, or parenterally, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly. In some embodiments, a pharmaceutical composition disclosed herein may be administered orally or parenterally, e.g., intravenously or subcutaneously. In some embodiments, the a pharmaceutical composition disclosed herein may be administered orally. In some embodiments, a pharmaceutical composition disclosed herein may be administered orally at a dosage of ≤15 mg/kg once per day.

The actual dosage employed may be varied depending upon the requirements of the subject and the severity of the condition being treated. The dosage regimen may be selected in accordance with a variety of factors including type, species, age, weight, sex and medical condition of the patient; the severity of the condition to be treated; the route of administration; the renal or hepatic function of the patient; and the particular compound employed. A physician or veterinarian of ordinary skill in the art can readily determine and prescribe the effective amount of the pharmaceutical composition disclosed herein required to prevent, counter or arrest the progress of the condition. For convenience, the total daily dosage may be divided and administered in portions during the day as required.

Methods of Treatment

The present disclosure further provides methods of treating or managing a disease or a disorder, e.g., a disease or disorder mediated by AAK1 activity, comprising administering to a subject in need thereof, a compound disclosed herein or a pharmaceutically acceptable salt thereof.

In some embodiments, the disease or a disorder mediated by AAK1 activity is a muscular dystrophy. Muscular dystrophies are genetic diseases characterized by progressive weakness and degeneration of the skeletal or voluntary muscles which control movement. The muscles of the heart and some other involuntary muscles are also affected in some forms of muscular dystrophy. In many cases, the histological picture shows variation in fiber size, muscle cell necrosis and regeneration, and often proliferation of connective and adipose tissue. In some embodiments, the muscular dystrophy is Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) or a congenital muscular dystrophy. In some embodiments, the muscular dystrophy is DMD.

In some embodiments, the disease or disorder mediated by AAK1 activity is a neurodegenerative disease. In some embodiments, the disease or disorder mediated by AAK1 activity is diabetic neuropathy.

The present disclosure also provides method for increasing skeletal muscle tissue growth or regeneration in a subject, comprising administering to the subject a compound disclosed herein or a pharmaceutically acceptable salt thereof.

In some embodiments, the subject has a muscular dystrophy. In some embodiments, the muscular dystrophy is Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) or a congenital muscular dystrophy. In some embodiments, the subject has DMD.

In specific embodiments, the present disclosure provides methods for treating or managing a muscular dystrophy, comprising administering to a subject in need thereof a compound disclosed herein or pharmaceutically acceptable salt thereof. In some embodiments, the muscular dystrophy is selected from the group consisting of: Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) and a congenital muscular dystrophy. In specific embodiments, the muscular dystrophy is DMD.

In some embodiments, the skeletal muscle tissue of the subject is damaged or injured as a result of physical injury or accident, disease, gene mutation, infection, over-use, loss of blood circulation, muscle atrophy, muscle wasting, dystrophic muscle, or ageing.

In some embodiments, the present disclosure provides methods for increasing asymmetric cell division of skeletal muscle stem cells, comprising contacting the skeletal muscle stem cells with a compound disclosed herein or pharmaceutically acceptable salt thereof. In particular embodiments, the stem cells are muscle stem cells, retinal stem cells, neural stem cells, hematopoietic stem cells, intestinal stem cells, epidermal stem cells, or cancer or tumor stem cells. In certain embodiments, the stem cells are muscle stem cells or satellite cells. In particular embodiments of any of the methods disclosed herein, the contacting between the inhibitor and the cells occurs in vitro, in vivo, ex vivo, or in situ. In some embodiments, the cells are mammalian cells. In specific embodiments, the cells are human cells.

In some embodiments, skeletal muscle stem cells within the skeletal muscle tissue of the subject have reduced asymmetric cell division as compared to normal, healthy skeletal muscle stem cells. In certain embodiments, the skeletal muscle stem cells are damaged or injured skeletal muscle stem cells or are present within damaged or injured skeletal muscle tissue. In some embodiments, the muscle tissue is damaged or injured as a result of: physical injury or accident, disease, gene mutation, infection, over-use, loss of blood circulation, muscle atrophy, muscle wasting, dystrophic muscle, or ageing. In some embodiments, the skeletal muscle stem cells are diseased skeletal muscle stem cells comprising a mutation associated with a muscular dystrophy, optionally Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) or a congenital muscular dystrophy.

In some embodiments, the compound or pharmaceutically acceptable salt thereof inhibits an activity of AAK1. In some embodiments, the compound or pharmaceutically acceptable salt thereof inhibits AAK1. In some embodiments of the present methods, the compound or pharmaceutically acceptable salt thereof is an AAK1 inhibitor, and the compound or pharmaceutically acceptable salt thereof does not substantially inhibit proliferation or cell cycle progression of the subject's skeletal muscle stem cells.

In some embodiments of the present methods, the compound or pharmaceutically acceptable salt thereof inhibits expression of AAK1, optionally by inhibiting transcription, translation, post-translational modification, or stability of the protein component, or the gene encoding the protein component.

In some embodiments of the present methods, the compound or pharmaceutically acceptable salt thereof binds to a polynucleotide sequence that regulates expression of AAK1. In some embodiments, the nucleotide sequence is present within the AAK1 gene.

In some embodiments of the present methods, the compound or pharmaceutically acceptable salt thereof binds to a polynucleotide sequence that regulates expression of AAK1. In some embodiments, the nucleotide sequence is present within the AAK1 gene. In some embodiments, the polynucleotide sequence is DNA or RNA.

In some embodiments of the present methods, the compound or pharmaceutically acceptable salt thereof is administered to the subject systemically or locally, optionally at a site of tissue damage or injury.

In some embodiments, the compound or pharmaceutically acceptable salt thereof is administered at a dose of about 0.01 mg/kg to about 300 mg/kg.

In some embodiments, the subject has a mutation of a dystrophin gene.

In some embodiments, the subject has damaged or injured skeletal muscle tissue.

In some embodiments, the subject is a mammal. In some embodiments, the subject is a human.

In some embodiments, the methods disclosed herein increase skeletal muscle tissue regeneration in the subject.

In some embodiments, not limited by mechanism, the methods disclosed herein relate to the preservation of, maintenance of, and/or regeneration of, muscle mass, connectivity, and/or function.

Numbered Embodiments

1. A compound of Formula (A):

(A)

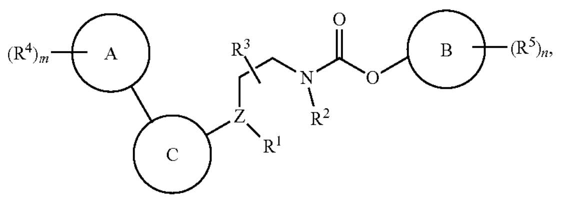

or pharmaceutically acceptable salt, deuterated form, or stereoisomer thereof, wherein:

(A) is phenyl or heteroaryl;

(B) is heterocyclyl;

(C) is

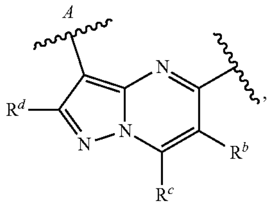,

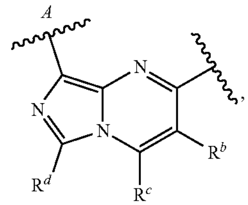, or

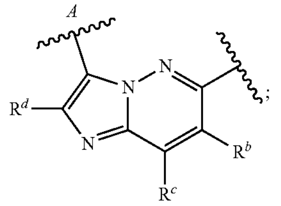;

Z is CH or N;

$R^1$ and $R^2$ are each independently H or —$C_{1-6}$ alkyl, or $R^1$ and $R^2$ taken together with the atoms to which they are attached form a 5- or 6-membered heterocyclyl;

$R^3$ is H, halogen, —$C_{1-6}$ alkyl, —CN, or —COR$^a$, or an $R^1$ and $R^3$ taken together with the atoms to which they are attached form a 5- or 6-membered heterocyclyl;

each $R^4$ is independently halogen, —OH, —O—$C_{1-6}$ alkyl, —O—$C_{1-6}$ haloalkyl, —O-cycloalkyl, —O-heterocyclyl, —O—($C_{1-5}$ alkylene)-cycloalkyl, —O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, —$C_{1-6}$ alkyl, $C_{1-6}$ heteroalkyl, —O—$C_{1-6}$ alkyl, heterocyclyl, —$C_{1-5}$ alkylene-cycloalkyl, or —$C_{1-5}$ alkylene-heterocyclyl, or two $R^5$ form an oxo;

$R^a$ is —OH, —O—($C_{1-6}$ alkyl), —NH$_2$, —NH—($C_{1-6}$ alkyl), or —NH—($C_{1-6}$ alkyl)$_2$; $R^b$, $R^c$, and $R^d$ are each independently H, halogen, $C_{1-6}$ alkyl, —OH, —O—($C_{1-6}$ alkyl), —NH$_2$, —NH—($C_{1-6}$ alkyl), or —NH—($C_{1-6}$ alkyl)$_2$;

m is 0, 1, 2, or 3; and n is 0, 1, or 2, provided that the compound is not:

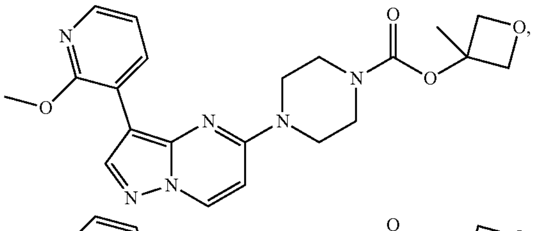

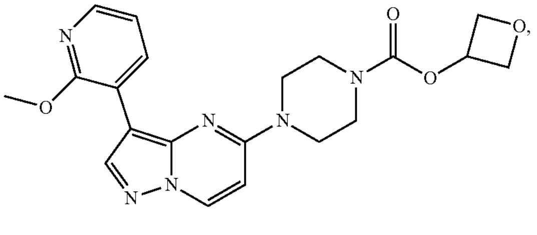

-continued

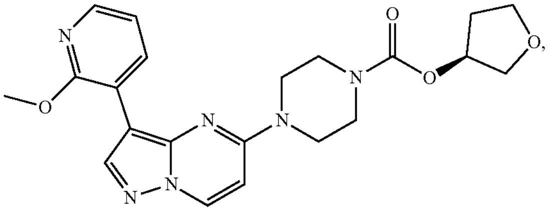

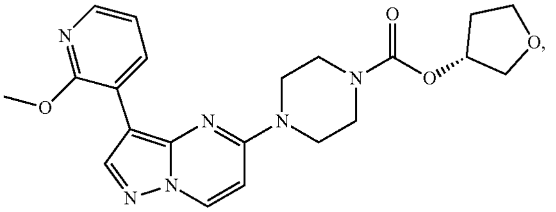

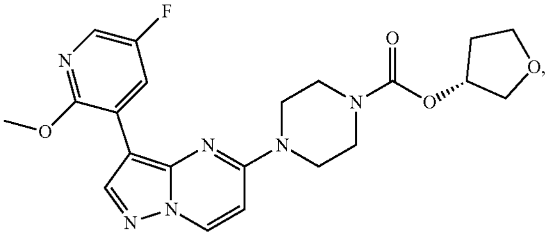

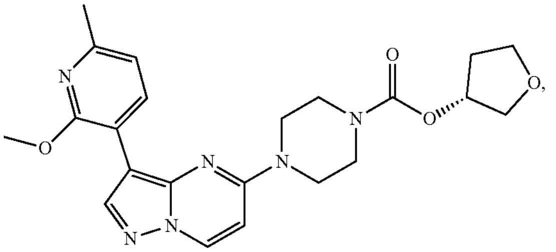

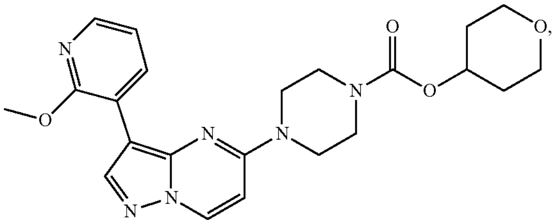

or

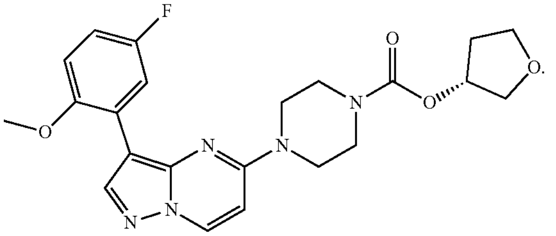

2. The compound of embodiment 1, wherein (C) is

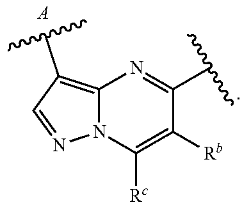

3. A compound of Formula (IA'):

(IA')

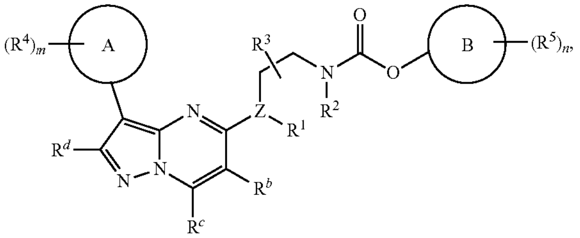

or pharmaceutically acceptable salt, deuterated form, or stereoisomer thereof, wherein:

(A) is phenyl or N-heteroaryl;

(B) is heterocyclyl;

Z is CH or N;

$R^1$ and $R^2$ are each independently H or $C_{1-6}$ alkyl, or an $R^1$ and $R^2$ taken together with the atoms to which they are attached for a 5- or 6-membered heterocyclyl;

$R^3$ is H, halogen, $C_{1-6}$ alkyl, CN, or $COR^a$;

each $R^4$ is independently halogen, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, $C_{1-6}$ alkyl, $C_{1-6}$ heteroalkyl, O—$C_{1-6}$ alkyl, heterocyclyl, $C_{1-5}$ alkylene-cycloalkyl, or $C_{1-5}$ alkylene-heterocyclyl, or two $R^5$ form an oxo;

$R^a$ is —OH, —O—$C_{1-6}$ alkyl, —$NH_2$, —NH—($C_{1-6}$ alkyl), or —N($C_{1-6}$ alkyl)$_2$;

$R^b$, $R^c$ and $R^d$ are each independently H, halogen, $C_{1-6}$ alkyl, —OH, —O—($C_{1-6}$ alkyl), —$NH_2$, —NH—($C_{1-6}$ alkyl), or —NH—($C_{1-6}$ alkyl)$_2$;

m is 0, 1, 2, or 3; and n is 0, 1, or 2, provided that the compound is not:

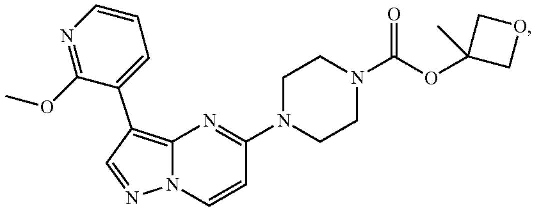

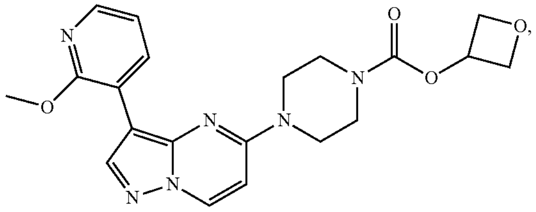

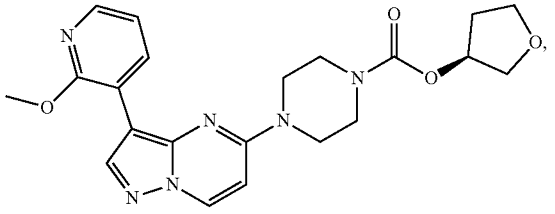

-continued

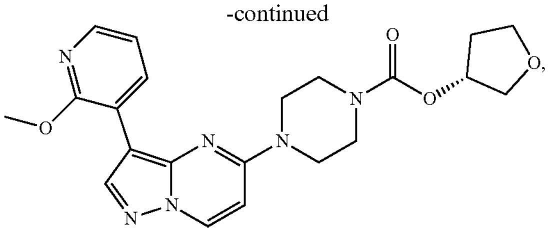

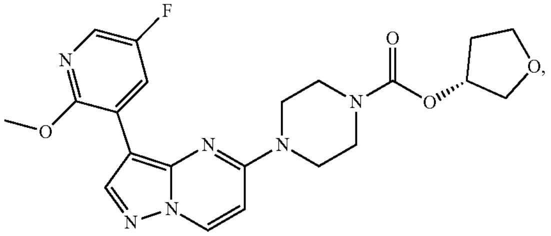

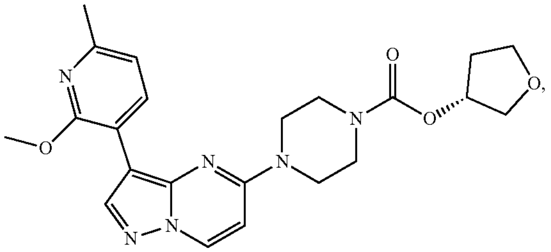

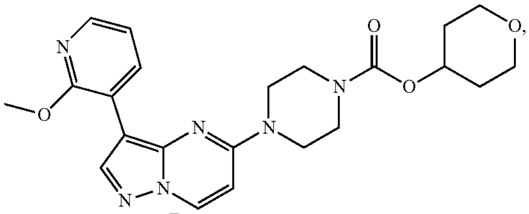

or

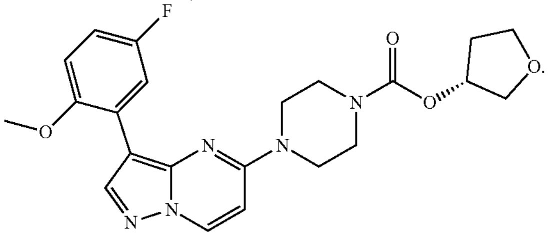

4. The compound of any one of embodiments 1-3, wherein $R^1$ and $R^3$ taken together with the atoms to which they are attached form a 5-membered heterocyclyl.

5. The compound of embodiment 4, wherein the 5-membered heterocyclyl is

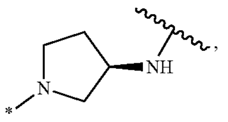

wherein * represents the point of attachment to Ⓒ.

6. The compound of any one of embodiments 1-3, wherein $R^1$ and $R^2$ taken together with the atoms to which they are attached form a 6-membered heterocyclyl.

7. The compound of embodiment 6, wherein the 6-membered heterocyclyl is

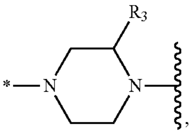

wherein * represents the point of attachment to Ⓒ.

8. The compound of any one of embodiments 1-3, wherein $R^1$ and $R^2$ are each independently H or Me.

9. A compound of Formula (IA'-1):

(IA'-1)

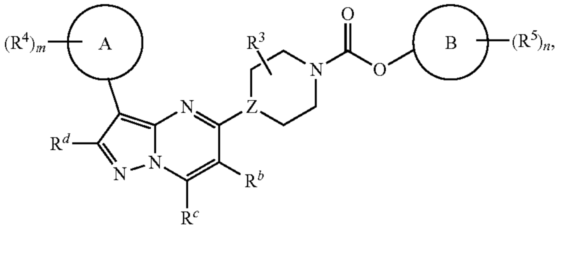

or pharmaceutically acceptable salt, deuterated form, or stereoisomer thereof, wherein:

Ⓐ is phenyl or N-heteroaryl;

Ⓑ is heterocyclyl;

Z is CH or N;

$R^3$ is H, halogen, —$C_{1-6}$ alkyl, —CN, or —$COR^a$;

each $R^4$ is independently halogen, —OH, —O—$C_{1-6}$ alkyl, —O—$C_{1-6}$ haloalkyl, —O-cycloalkyl, —O-heterocyclyl, —O—($C_{1-5}$ alkylene)-cycloalkyl, —O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, alkyl, —$C_{1-6}$ heteroalkyl, —O—$C_{1-6}$ alkyl, heterocyclyl, —$C_{1-5}$ alkylene-cycloalkyl, or —$C_{1-5}$ alkylene-heterocyclyl, or two $R^5$ form an oxo;

$R^a$ is —OH, —O—($C_{1-6}$ alkyl), —$NH_2$, —NH—($C_{1-6}$ alkyl), or —N($C_{1-6}$ alkyl)$_2$; $R^b$, $R^c$, and $R^d$ are each independently H, halogen, —$C_{1-6}$ alkyl, —OH, —O—($C_{1-6}$ alkyl), —$NH_2$, —NH—($C_{1-6}$ alkyl), or —NH—($C_{1-6}$ alkyl)$_2$;

m is 0, 1, 2, or 3; and n is 0, 1, or 2, provided that the compound is not:

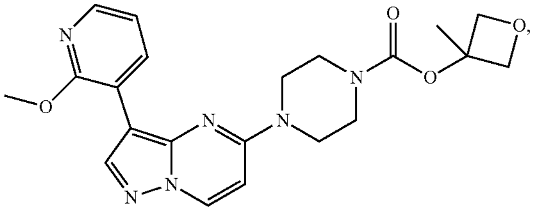

-continued

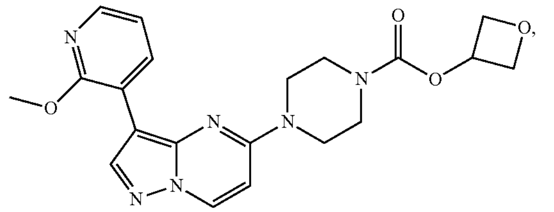

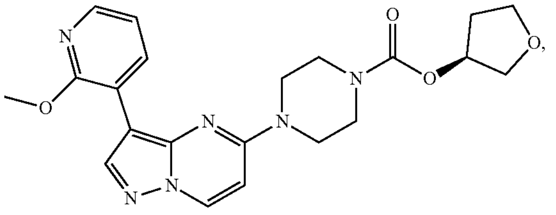

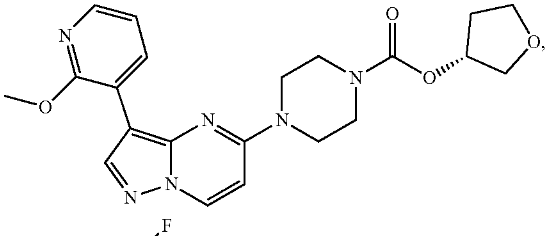

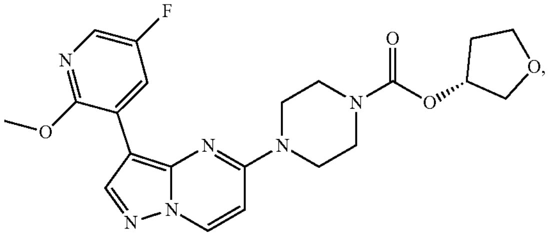

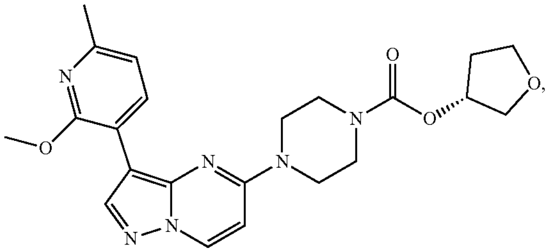

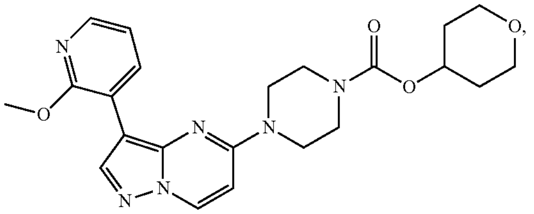

or

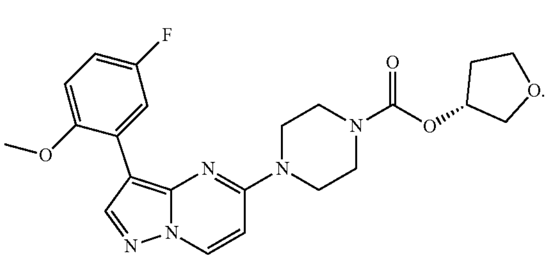

10. The compound of any one of embodiments 1-9, wherein Z is N.

11. A compound of Formula (IA'-2):

(IA'-2)

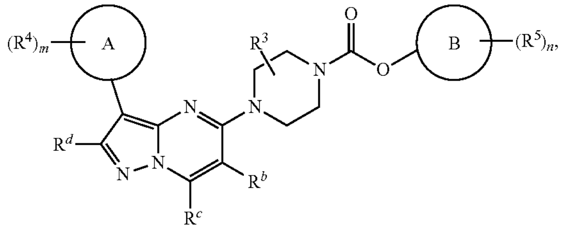

or pharmaceutically acceptable salt, deuterated form, or stereoisomer thereof, wherein:

Ⓐ is phenyl or N-heteroaryl;

Ⓑ is heterocyclyl;

$R^3$ is H, halogen, $C_{1-6}$ alkyl, CN, or $COR^a$;

each $R^4$ is independently halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently halogen, $C_{1-6}$ alkyl, $C_{1-6}$ heteroalkyl, O—$C_{1-6}$ alkyl, heterocyclyl, $C_{1-5}$ alkylene-cycloalkyl, or $C_{1-5}$ alkylene-heterocyclyl, or two $R^5$ form an oxo;

$R^a$ is —OH, —O—($C_{1-6}$ alkyl), —$NH_2$, —NH—($C_{1-6}$ alkyl), or —N($C_{1-6}$ alkyl)$_2$; $R^b$, $R^c$, and $R^d$ are each independently H, halogen, —$C_{1-6}$ alkyl, —OH, —O—($C_{1-6}$ alkyl), —$NH_2$, —NH—($C_{1-6}$ alkyl), or —NH—($C_{1-6}$ alkyl)$_2$;

m is 0, 1, 2, or 3; and n is 0, 1, or 2, provided that the compound is not:

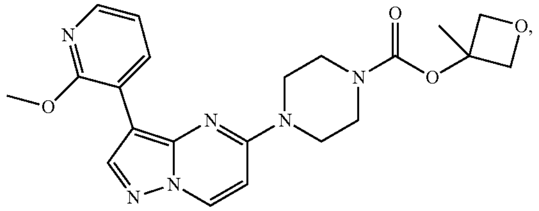

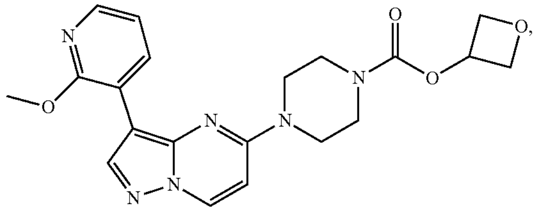

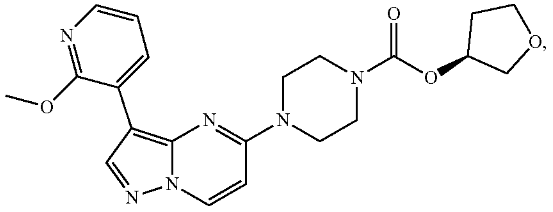

-continued

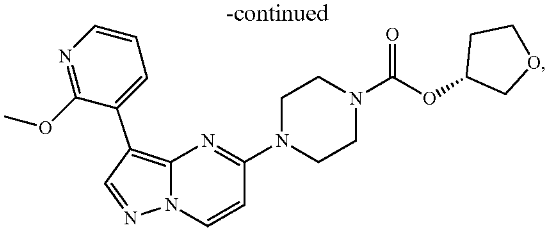

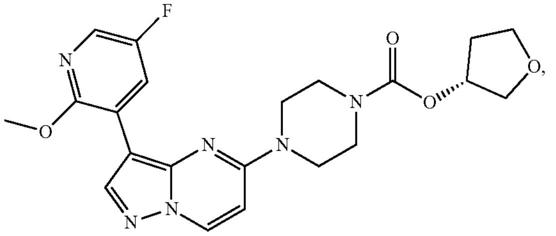

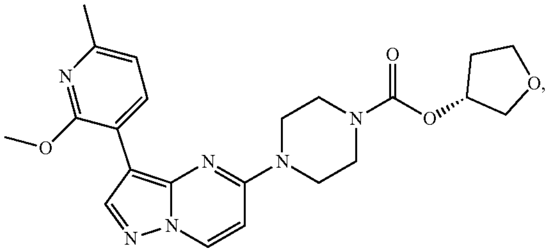

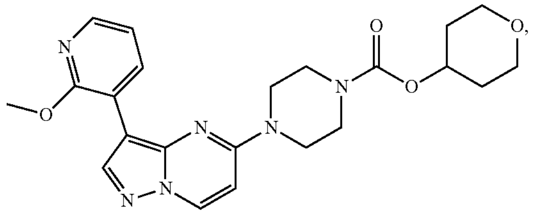

or

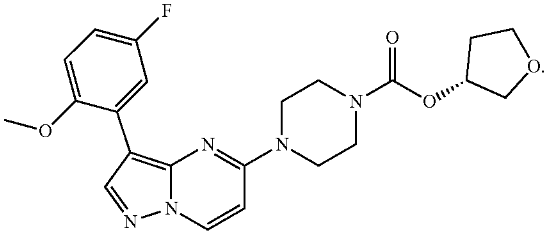

12. The compound of any one of embodiments 1-11, wherein Ⓐ is 6-membered N-heteroaryl.

13. The compound of embodiment 12, wherein the 6-membered heteroaryl is a pyridinyl, pyrazinyl, pyrimidinyl, or pyridazinyl.

14 The compound of embodiment 13, wherein the 6-membered heteroaryl is a pyridinyl, and the pyridinyl is a 3-pyridinyl.

15. The compound of any one of embodiments 1-12, wherein Ⓐ is:

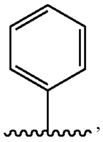,
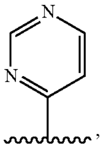,
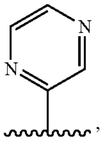, or
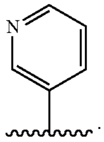.

16. The compound of any one of embodiments 1-15, wherein

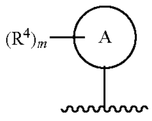

is:

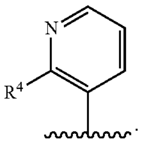

17. A compound of Formula (IA'-3):

(IA'-3)

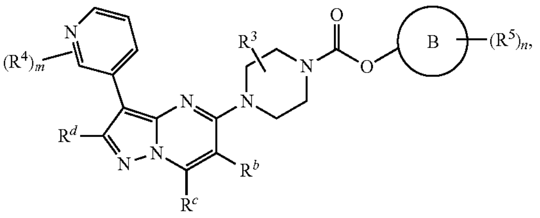

or pharmaceutically acceptable salt, deuterated form, or stereoisomer thereof, wherein: Ⓑ is heterocyclyl;

$R^3$ is H, halogen, —$C_{1-6}$ alkyl, —CN, or —$COR^a$;

each $R^4$ is independently halogen, —OH, —O—$C_{1-6}$ alkyl, —O—$C_{1-6}$ haloalkyl, —O-cycloalkyl, —O-heterocyclyl, —O—($C_{1-5}$ alkylene)-cycloalkyl, —O—($C_{1-5}$ alkylene)-heterocyclyl, —NH—($C_{1-6}$ alkyl), —N($C_{1-6}$ alkyl)$_2$, —NH-(cycloalkyl), —NH-(heterocyclyl);

each $R^5$ is independently halogen, —$C_{1-6}$ alkyl, —$C_{1-6}$ heteroalkyl, —O—$C_{1-6}$ alkyl, heterocyclyl, —$C_{1-5}$ alkylene-cycloalkyl, or —$C_{1-5}$ alkylene-heterocyclyl, or two $R^5$ form an oxo;

$R^a$ is —OH, —O—($C_{1-6}$ alkyl), —$NH_2$, —NH—($C_{1-6}$ alkyl), or —N($C_{1-6}$ alkyl)$_2$;

$R^b$, $R^c$, and $R^d$ are each independently H, halogen, $C_{1-6}$ alkyl, JOH, —O—($C_{1-6}$ alkyl), —$NH_2$, —NH—($C_{1-6}$ alkyl), or —NH—($C_{1-6}$ alkyl)$_2$;

m is 0, 1, 2, or 3; and n is 0, 1, or 2, provided that the compound is not:

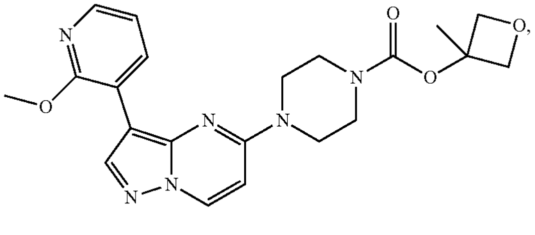

-continued

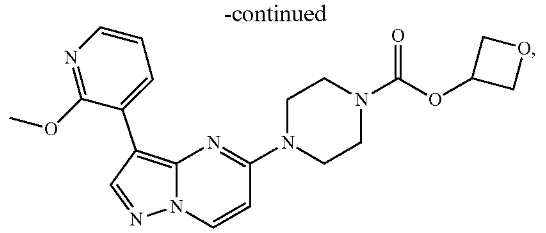

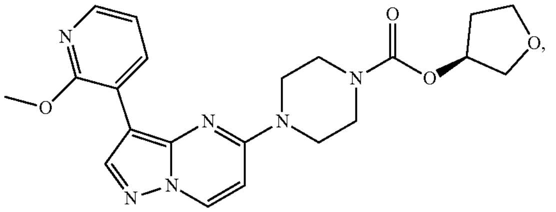

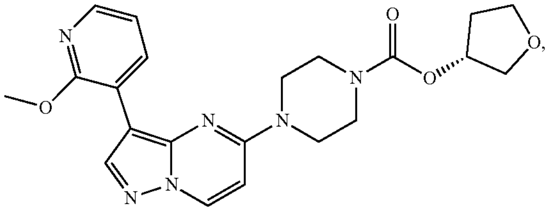

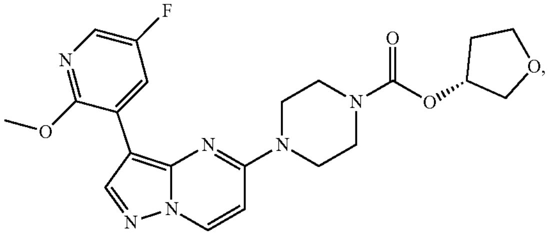

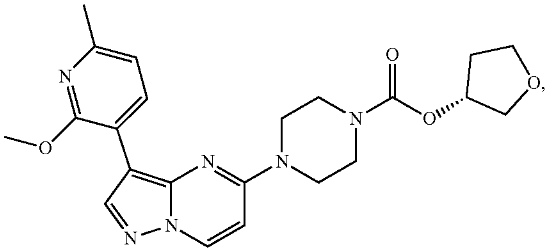

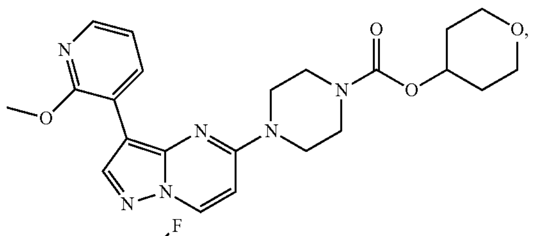

or

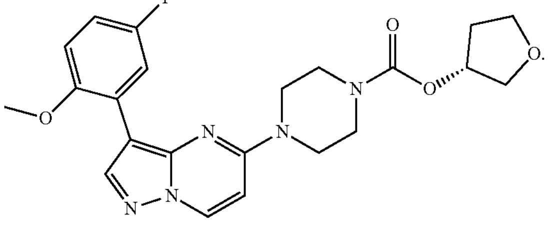

18. The compound of any one of embodiments 1-17, wherein Ⓑ is N-heterocyclyl or a bicyclic ether.

19. The compound of any one of embodiments 1-18, wherein Ⓑ is N-heterocyclyl.

20. The compound of any one of embodiments 1-18, wherein Ⓑ is 5-membered N-heterocyclyl.

21. The compound of any one of embodiments 1-20, wherein Ⓑ is

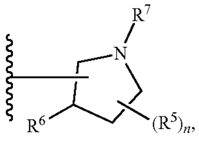

wherein each $R^5$ is independently halogen, $C_{1-6}$ alkyl, $C_{1-6}$ heteroalkyl, O—$C_{1-6}$ alkyl, $C_{1-5}$ alkylene-cycloalkyl, or $C_{1-5}$ alkylene-heterocyclyl, or two $R^5$ taken together form an oxo; $R^6$ is H, $C_{1-6}$ alkyl, $C_{2-6}$ alkenyl, or $C_{2-6}$ alkynyl; $R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, $C_{1-5}$ alkylene-C(O)—NH—($CH_2Ph$), or 4- to 8-membered heterocyclyl; and n is 0, 1, or 2.

22. The compound of any one of embodiments 1-21, wherein two $R^5$ taken together form an oxo.

23. The compound of any one of embodiments 1-22, wherein Ⓑ is

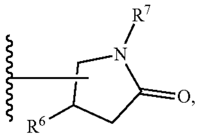

wherein $R^6$ is H, $C_{1-6}$ alkyl, $C_{2-6}$ alkenyl, or $C_{2-6}$ alkynyl; and $R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl.

24. The compound of any one of embodiments 1-23, wherein Ⓑ is

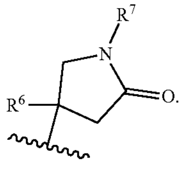

wherein Reis H, $C_{1-6}$ alkyl, $C_{2-6}$ alkenyl, or $C_{2-6}$ alkynyl; and $R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl.

25. The compound of any one of embodiments 1-18, wherein Ⓑ is

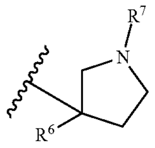,
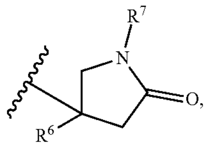,

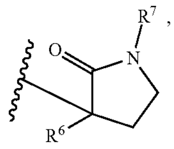, or
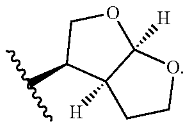

26. The compound of any one of embodiments 1-18, wherein (B) is

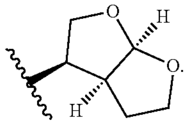 [SMILES: *[C@H]1CO[C@H]2OCC[C@H]21]

27. The compound of any one of embodiments 21-25, wherein $R^6$ is H, Me, or —C≡CH.

28. The compound of any one of embodiments 21-25, wherein $R^6$ is H or Me.

29. The compound of any one of embodiments 21-25, 27, and 28, wherein $R_7$ is H, $C_{1-6}$ alkyl, $C_{1-5}$ alkylene-OH, $C_{1-5}$ alkylene-O—($C_{1-3}$ alkyl), $C_{1-5}$ alkylene-O—$CH_2Ph$, $C_{1-5}$ alkylene-$NH_2$, $C_{1-5}$ alkylene-NH—($C_{1-3}$ alkyl), $C_{1-5}$ alkylene-N($C_{1-3}$ alkyl)$_2$, $C_{1-3}$ alkylene-C(O)—NH—($C_{1-3}$ alkyl), $C_{1-3}$ alkylene-C(O)—$NH_2$, or 4- to 6-membered heterocyclyl.

30. The compound of any one of embodiments 21-25 and 27-29, wherein $R_7$ is H, $CH_3$, $CH_2CH_3$, i-Pr,

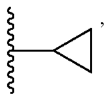 [SMILES: *C1CC1],

—$CH_2CH_2$—OH, —$CH_2CH_2$—$OCH_3$, —$CH_2CH_2$—Obn, —$CH_2CH_2$—$NH_2$, —$CH_2CH_2$—NH—($CH_3$), —$CH_2CH_2$—N($CH_3$)$_2$, —$CH_2C(O)$—$NH_2$, —$CH_2C$(O)—NH—($CH_3$), —$CH_2C(O)$—N($CH_3$)$_2$,

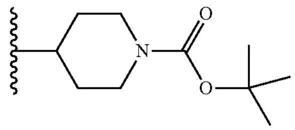,
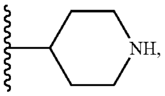

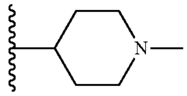,
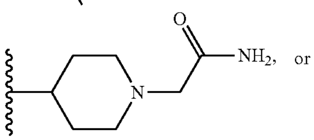 or

-continued

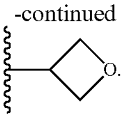

31. The compound of any one of embodiments 21-25 and 27-30, wherein $R^7$ is H or Me.

32. A compound of Formula (IA'-4):

(IA'-4)

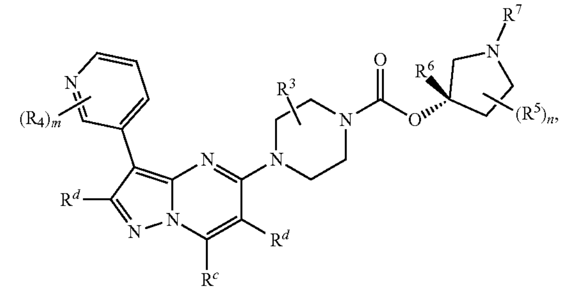

or pharmaceutically acceptable salt or deuterated form thereof, wherein:

$R^3$ is H, halogen, $C_{1-5}$ alkyl, —CN, or —COR$^a$;

each $R^4$ is independently halogen, —OH, —O—$C_{1-6}$ alkyl, —O—$C_{1-6}$ haloalkyl, —O-cycloalkyl, —O-heterocyclyl, —O—($C_{1-5}$ alkylene)-cycloalkyl, —O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently H, halogen, —$C_{1-6}$ alkyl, —$C_{1-6}$ heteroalkyl, —O—$C_{1-6}$ alkyl, —$C_{1-5}$ alkylene-cycloalkyl, or —$C_{1-5}$ alkylene-heterocyclyl, or two $R^5$ form an oxo;

$R^6$ is H, —$C_{1-6}$ alkyl, —$C_{2-6}$ alkenyl, or —$C_{2-6}$ alkynyl;

$R^7$ is H, —$C_{1-6}$ alkyl, —$C_{1-5}$ alkylene-OH, —$C_{1-5}$ alkylene-O—($C_{1-6}$ alkyl), —$C_{1-5}$ alkylene-O—$CH_2Ph$, —$C_{1-5}$ alkylene-$NH_2$, —$C_{1-5}$ alkylene-NH—($C_{1-6}$ alkyl), —$C_{1-5}$ alkylene-N($C_{1-6}$ alkyl)$_2$, —$C_{1-5}$ alkylene-NH—($CH_2Ph$), —$C_{1-5}$ alkylene-C(O)—$NH_2$, —$C_{1-5}$ alkylene-C(O)—NH—($C_{1-6}$ alkyl), —$C_{1-5}$ alkylene-C(O)—N($C_{1-6}$ alkyl)$_2$, or 4- to 8-membered heterocyclyl;

$R^a$ is —OH, —O—($C_{1-6}$ alkyl), —$NH_2$, —NH—($C_{1-6}$ alkyl), or —N($C_{1-6}$ alkyl)$_2$;

$R^b$, $R^c$, $R^d$ are each independently H, halogen, $C_{1-6}$ alkyl, —OH, —O—($C_{1-6}$ alkyl), —$NH_2$, —NH—($C_{1-6}$ alkyl), or —NH—($C_{1-6}$ alkyl)$_2$;

m is 0, 1, 2, or 3; and n is 0, 1, or 2.

33 The compound of any one of embodiments 1-32, wherein $R^3$ is H, Me, —C≡CH, —CN, or —C(O)OEt;

34. The compound of any one of embodiments 1-33, wherein $R^b$ is H, F, —OH, —OMe, or Me and $R^c$ is H.

35. A compound of Formula (IB):

(IB)

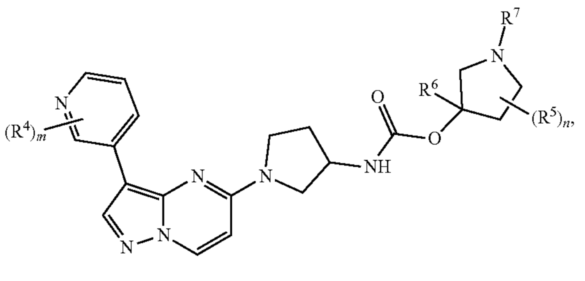

or pharmaceutically acceptable salt or deuterated form thereof, wherein:

each $R^4$ is independently halogen, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently H, halogen, $C_{1-6}$ alkyl, $C_{1-6}$ heteroalkyl, O—$C_{1-6}$ alkyl, $C_{1-5}$ alkylene-cycloalkyl, or $C_{1-5}$ alkylene-heterocyclyl, or two $R^5$ form an oxo;

$R^6$ is H, $C_{1-6}$ alkyl, $C_{2-6}$ alkenyl, or $C_{2-6}$ alkynyl;

$R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl;

m is 0, 1, or 2; and n is 0, 1, or 2.

36. The compound of embodiment 35, wherein the compound of Formula (IB) has the structure:

(IB-1)

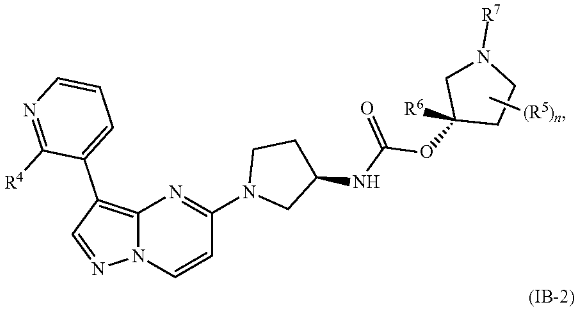

(IB-2)

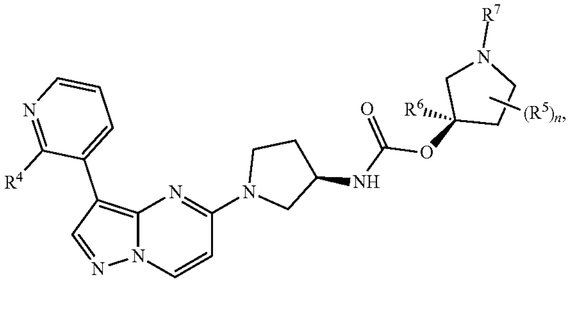

-continued (IB-3)

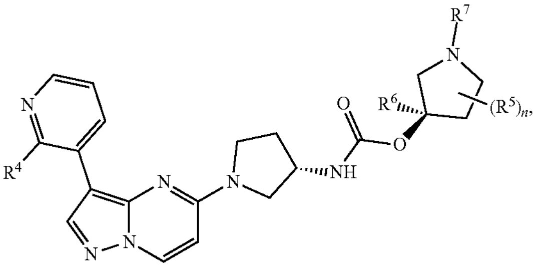

or (IB-4)

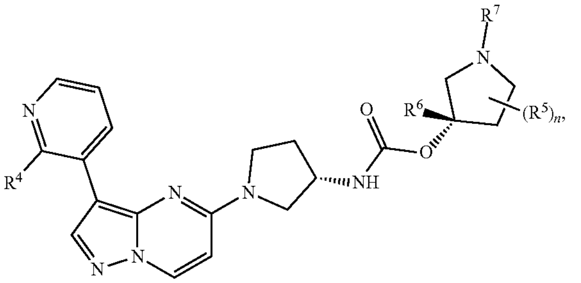

or a pharmaceutically acceptable salt thereof.

37. A compound of Formula (IC):

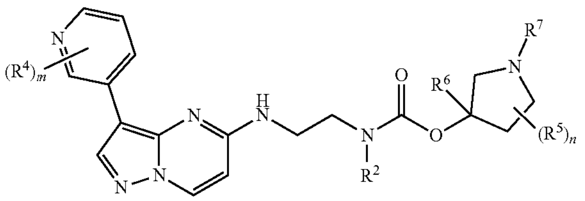

or pharmaceutically acceptable salt or deuterated form thereof, wherein:

$R^2$ is H or $C_{1-6}$ alkyl, or R' and $R^2$ taken together with the atoms to which they are attached form a 5- or 6-membered heterocyclyl;

each $R^4$ is independently halogen, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently H, halogen, $C_{1-6}$ alkyl, $C_{1-6}$ heteroalkyl, O—$C_{1-6}$ alkyl, $C_{1-5}$ alkylene-cycloalkyl, or $C_{1-5}$ alkylene-heterocyclyl, or two $R^5$ form an oxo;

$R^6$ is H, $C_{1-6}$ alkyl, $C_{2-6}$ alkenyl, or $C_{2-6}$ alkynyl;

$R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N(C)$_{1-6}$ alkyl)$_2$, or 4- to 8-membered heterocyclyl;

m is 0, 1, 2, or 3; and n is 0, 1, or 2.

38. The compound of 37, wherein the compound of Formula (IC) has the structure:

(IC-1)

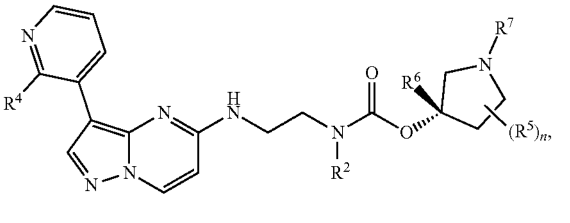

or a pharmaceutically acceptable salt thereof.

39. The compound of any one of embodiments 1-35 and 37, wherein $R^4$ is each independently halogen, —OH, —O—($C_{1-5}$ alkyl), —O—($C_{3-6}$ cycloalkyl), —O-(4- to 8-membered heterocyclyl), —NH—($C_{1-5}$ alkyl), —NH—($C_{3-6}$ cycloalkyl), or —NH-(4- to 8-membered heterocyclyl).

40. The compound of any one of embodiments 1-35, 37, and 39, wherein $R^4$ is each independently halogen, —O—($C_{1-5}$ alkyl), —O—($C_{3-6}$ cycloalkyl), or —O-(4- to 8-membered heterocyclyl).

41. The compound of any one of embodiments 1-35, 37, and 39, wherein $R^4$ is each independently:

F, 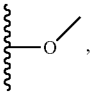, 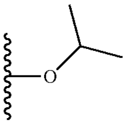, 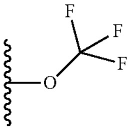,

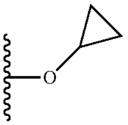, 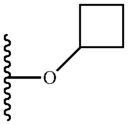, 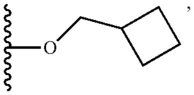,

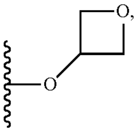 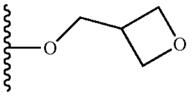, 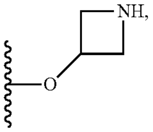

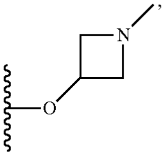 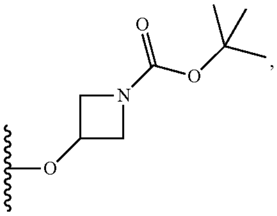,

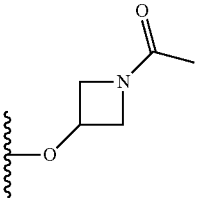, 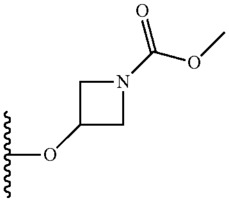,

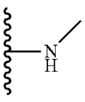, 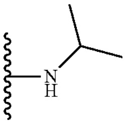, 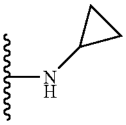, 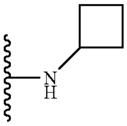,

-continued

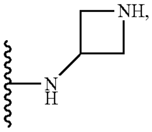 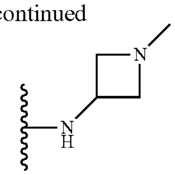, or

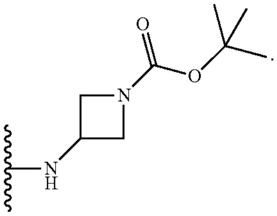.

42. The compound of any one of embodiments 1-35, 37, and 39-41, wherein $R^4$ is each independently:

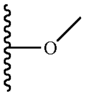, 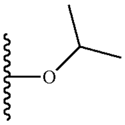, 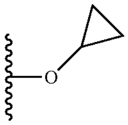, or

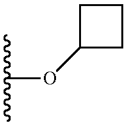.

43. The compound of any one of embodiments 32-42, wherein $R^5$ is H or two $R^5$ taken together form an oxo.

44. The compound of any one of embodiments 32-43, wherein two $R^5$ taken together form an oxo.

45. The compound of any one of embodiments 32-44, wherein $R^6$ is H, Me, or —C≡CH.

46. The compound of any one of embodiments 32-45, wherein $R^6$ is H or Me.

47. The compound of any one of embodiments 32-46, wherein $R_7$ is H, $C_{1-6}$ alkyl, $C_{1-5}$ alkylene-OH, $C_{1-5}$ alkylene-O—($C_{1-3}$ alkyl), $C_{1-5}$ alkylene-O—$CH_2Ph$, $C_{1-5}$ alkylene-$NH_2$, $C_{1-5}$ alkylene-NH—($C_{1-3}$ alkyl), $C_{1-5}$ alkylene-N($C_{1-3}$ alkyl)$_2$, $C_{1-3}$ alkylene-C(O)—NH—($C_{1-3}$ alkyl), $C_{1-3}$ alkylene-C(O)—$NH_2$, or 4- to 6-membered heterocyclyl.

48. The compound of any one of embodiments 32-47, wherein $R_7$ is H, $CH_3$, $CH_2CH_3$, i-Pr,

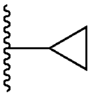,

—$CH_2CH_2$—OH, —$CH_2CH_2$—$OCH_3$, —$CH_2CH_2$—Obn, —$CH_2CH_2$—$NH_2$, —$CH_2CH_2$—NH—($CH_3$), —$CH_2CH_2$—N($CH_3$)$_2$, —$CH_2C$(O)—$NH_2$, —$CH_2C$(O)—NH—($CH_3$), —$CH_2C$(O)—N($CH_3$)$_2$,

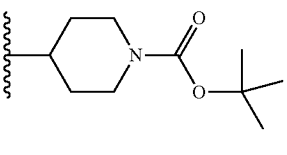, 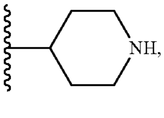

-continued

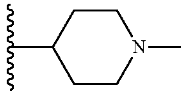
,
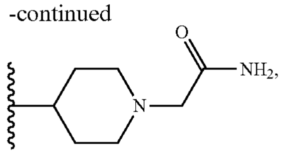
or
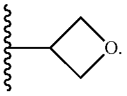

49. The compound of any one of embodiments 32-48, wherein $R_7$ is H or Me.

50. A compound of Formula (IA'-5):

(IA'-5)

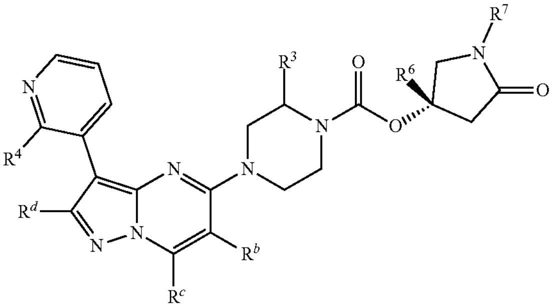

or pharmaceutically acceptable salt or deuterated form thereof, wherein:

$R^b$, $R^c$, and $R^d$ are each independently H, halogen, $C_{1-6}$ alkyl, —OH, —O—($C_{1-6}$ alkyl), —$NH_2$, —NH—($C_{1-6}$ alkyl), or —NH—($C_{1-6}$ alkyl)$_2$;

$R^3$ is H, halogen, $C_{1-6}$ alkyl, —CN, —C(O)$NH_2$, —C(O)OEt, or —C(O)OH;

$R^4$ is halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

$R^6$ is H, $C_{1-6}$ alkyl, $C_{2-6}$ alkenyl, or $C_{2-6}$ alkynyl; and $R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2$Ph, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-NH—($CH_2$Ph), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl.

51. The compound of embodiment 50, wherein $R^3$ is H, Me, —C≡CH, —CN, or —C(O)OEt;

52. The compound of embodiment 50 or 51, wherein $R^3$ is H.

53. The compound of any one of embodiments 50-52, wherein $R^6$ is H, Me, or —C≡CH.

54. The compound of any one of embodiments 50-53, wherein $R^6$ is H or Me.

55. The compound of embodiment 50, wherein the compound of Formula (IA'-5) has the structure:

(IA'-6)

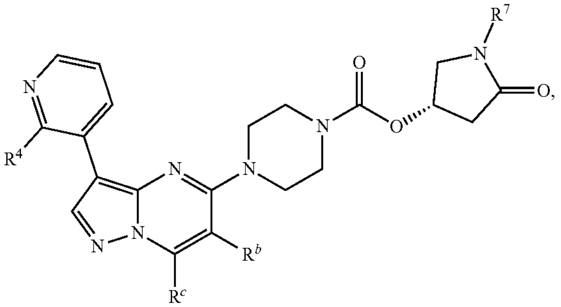

or pharmaceutically acceptable salt or deuterated form thereof.

56. The compound of any one of embodiments 50-55, wherein $R^4$ is —O—($C_{1-5}$ alkyl), —O—($C_{3-6}$ cycloalkyl), —O-(4- to 8-membered heterocyclyl), —NH—($C_{1-5}$ alkyl), NH—($C_{3-6}$ cycloalkyl), or —NH-(4- to 8-membered heterocyclyl).

57. The compound of any one of embodiments 50-56, wherein $R^4$ is —O—($C_{1-5}$ alkyl), —O—($C_{3-6}$ cycloalkyl), or —O-(4- to 8-membered heterocyclyl).

58. The compound of any one of embodiments 50-56, wherein $R^4$ is:

—OH,
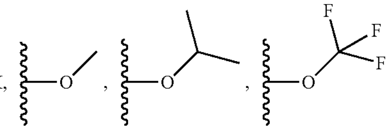
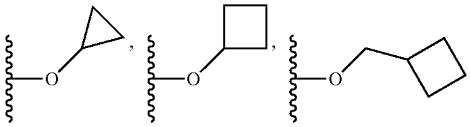
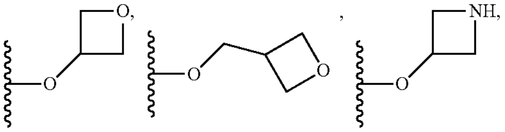
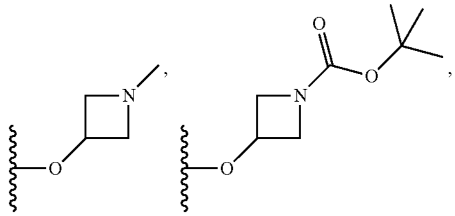
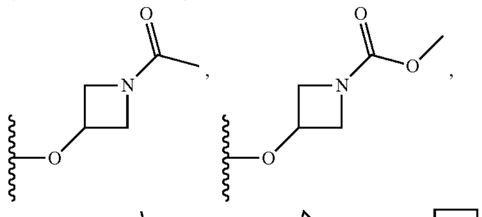
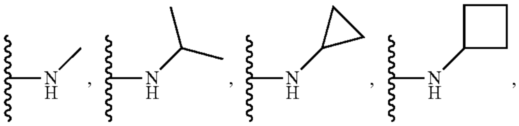

-continued

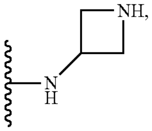, 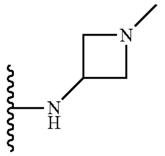, or

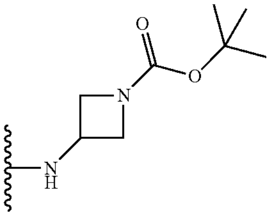.

59. The compound of any one of embodiments 50-58, wherein $R^4$ is:

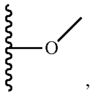, 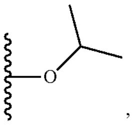, 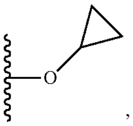, or

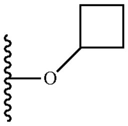.

60. The compound of any one of embodiments 50-59, wherein $R^7$ is H, $C_{1-6}$ alkyl, $C_{1-5}$ alkylene-OH, $C_{1-5}$ alkylene-O—($C_{1-5}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-5}$ alkylene-N($C_{1-6}$ alkyl)$_2$, $C_{1-5}$ alkylene-C(O)—NH—($C_{1-6}$ alkyl), $C_{1-5}$ alkylene-C(O)—$NH_2$, or 4- to 6-membered heterocyclyl.

61. The compound of any one of embodiments 50-60, wherein $R_7$ is H, $CH_3$, $CH_2CH_3$, i-Pr,

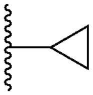,

—$CH_2CH_2$—OH, —$CH_2CH_2$—$OCH_3$, —$CH_2CH_2$—Obn, —$CH_2CH_2$—$NH_2$, —$CH_2CH_2$—NH—($CH_3$), —$CH_2CH_2$—N($CH_3$)$_2$, —$CH_2C$(O)—$NH_2$, —$CH_2C$(O)—NH—($CH_3$), $CH_2C$(O)—N($CH_3$)$_2$,

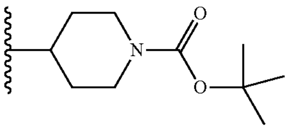,

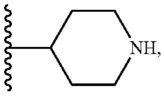, 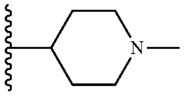,

-continued

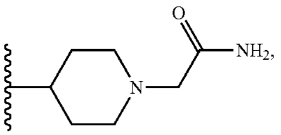 or 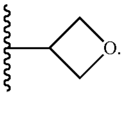.

62. The compound of any one of embodiments 50-61 wherein $R_7$ is H or Me.

63. The compound of any one of embodiments 1-15, 17-35, 37, and 39-49, wherein m is 1 or 2.

64. The compound of any one of embodiments 1-15, 17-35, 37, and 39-49, and 63, wherein m is 1.

65. The compound of any one of embodiments 1-22, and 27-49, wherein n is 0.

66. The compound of any one of embodiments 1-22, and 27-49, wherein n is 2.

67. The compound of embodiment 1, wherein the compound has the structure:

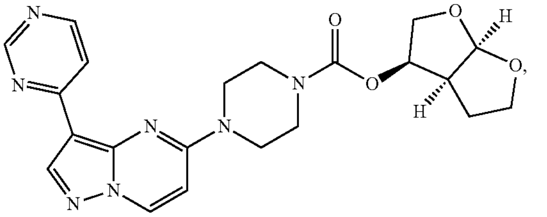

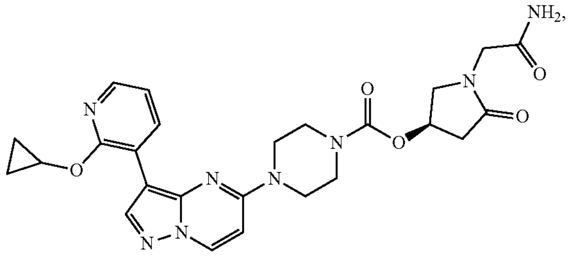

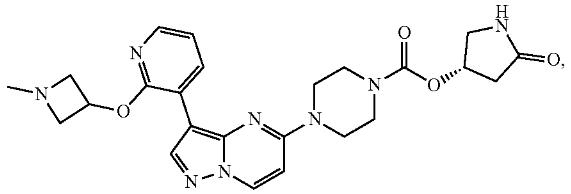

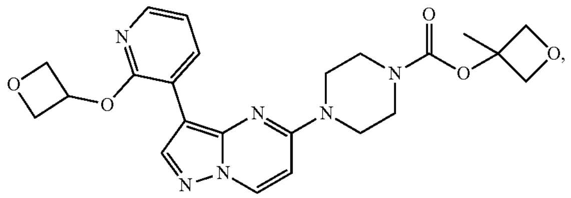

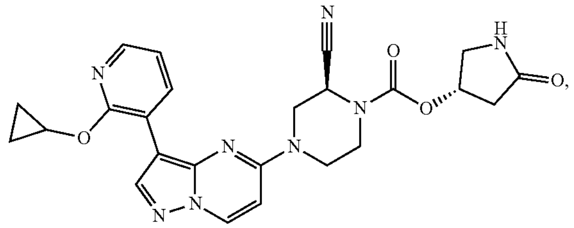

-continued
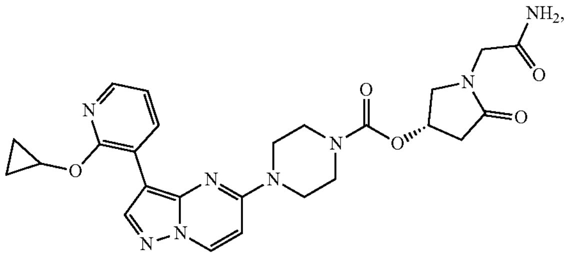
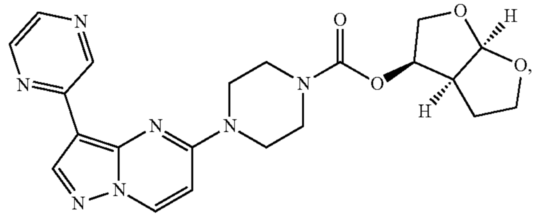
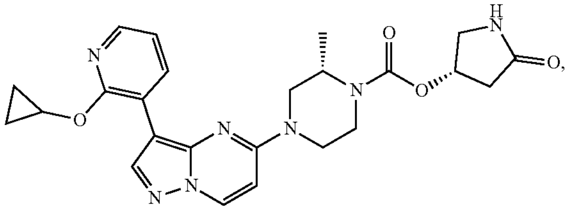
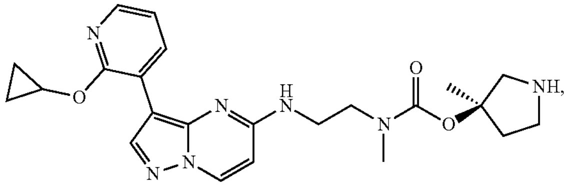
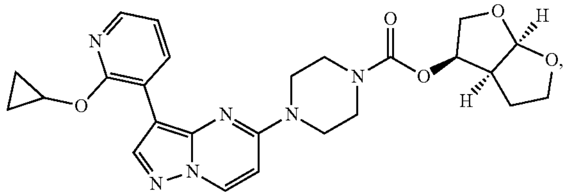
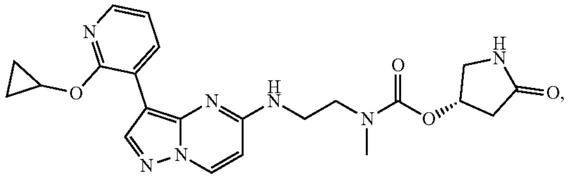
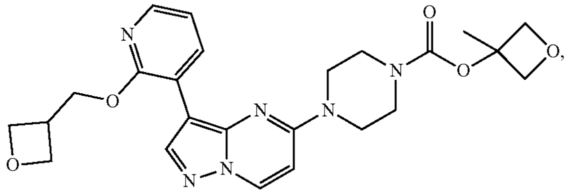
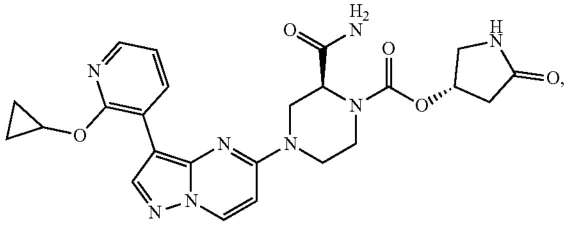
-continued
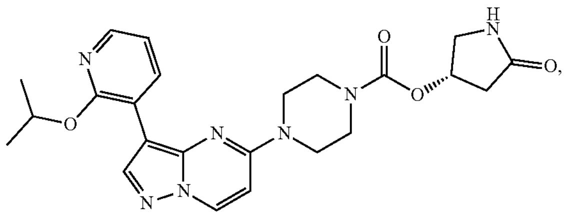
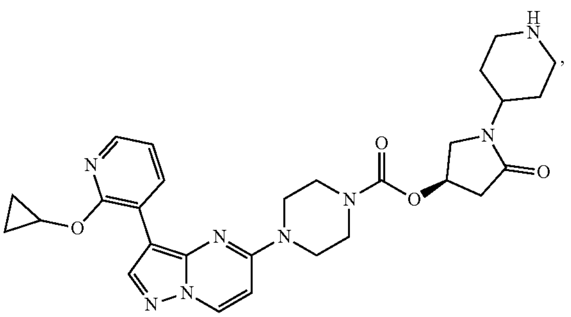
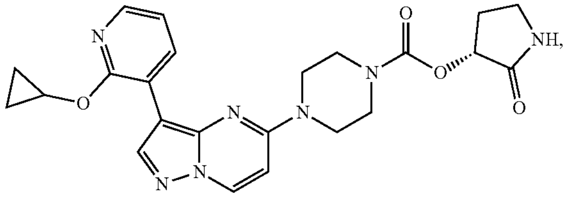
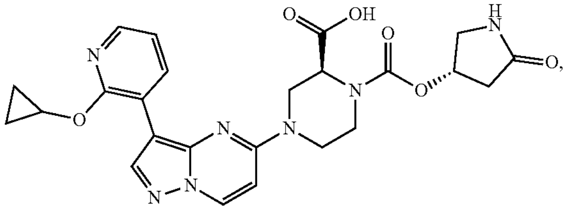
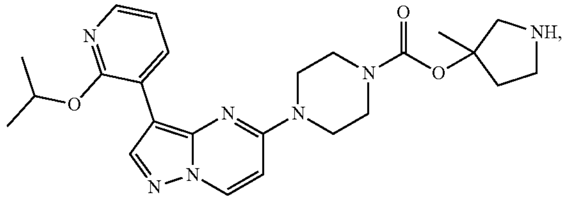
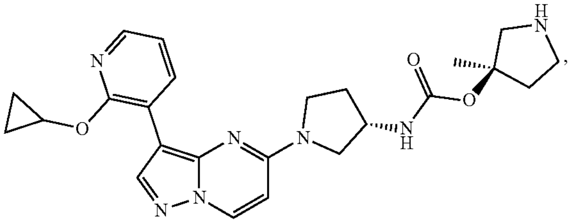
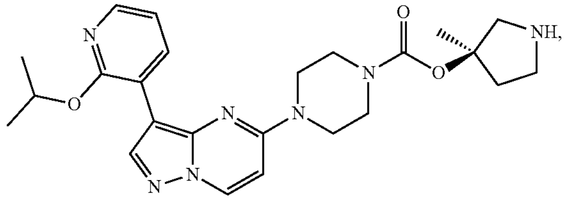

-continued
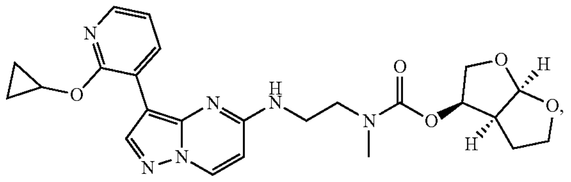
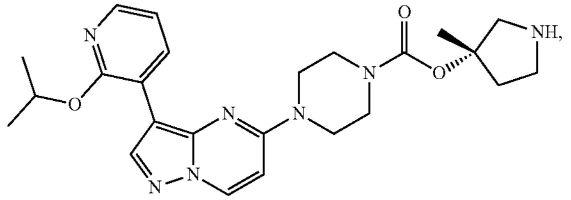
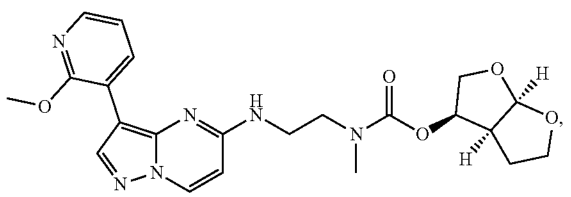
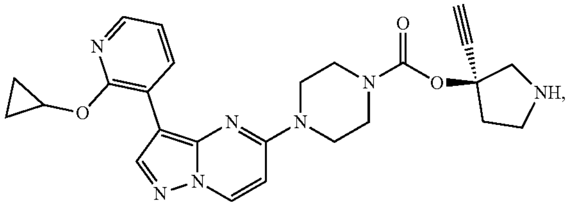
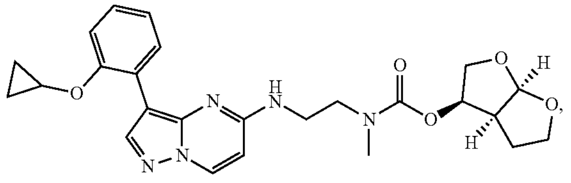
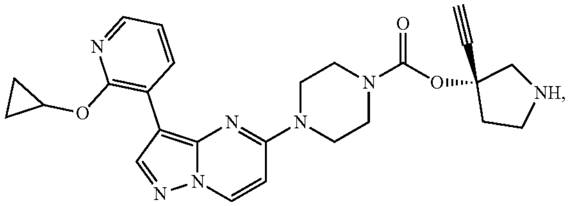
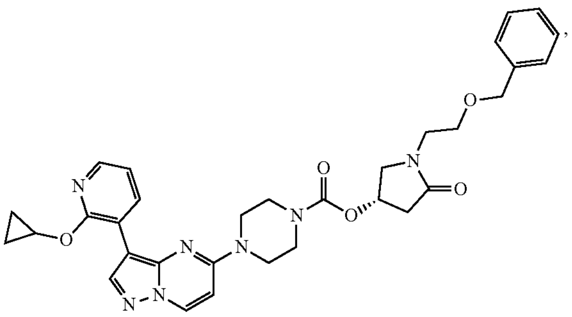
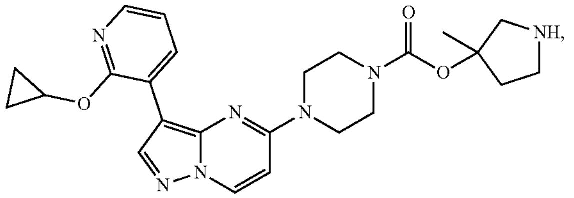
-continued
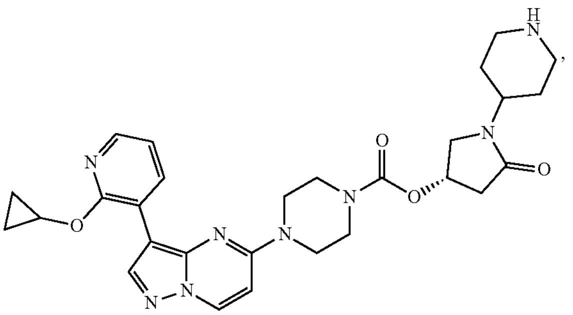
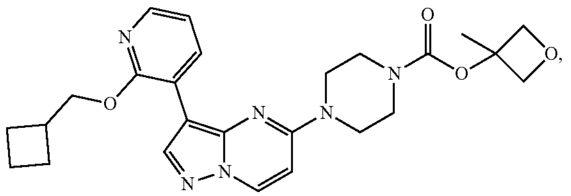
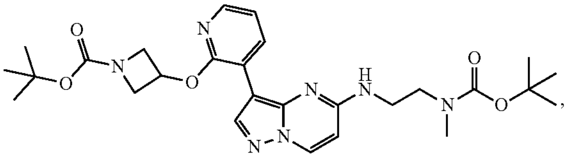
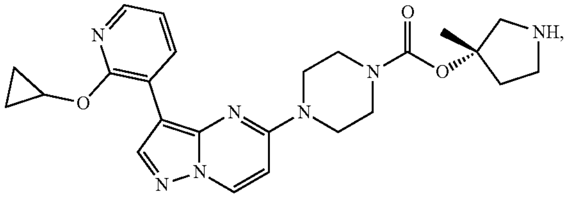
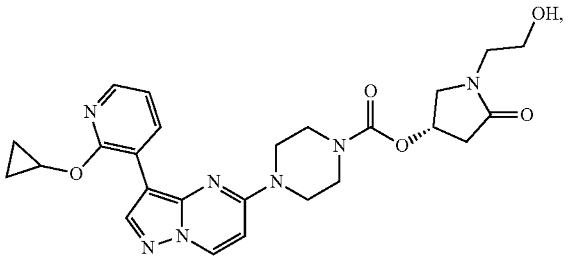
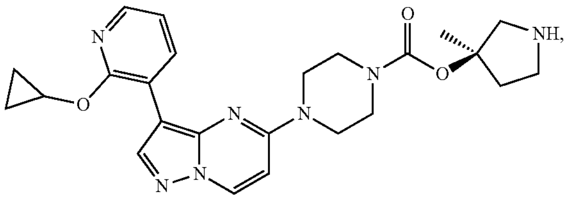
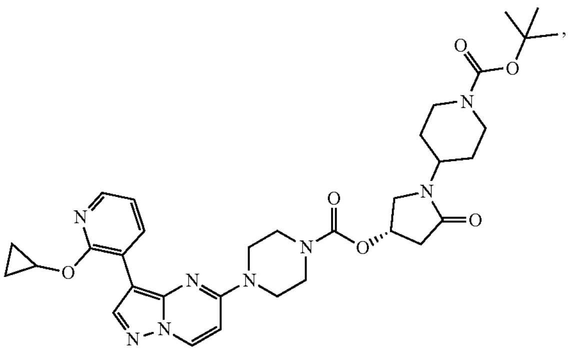

-continued
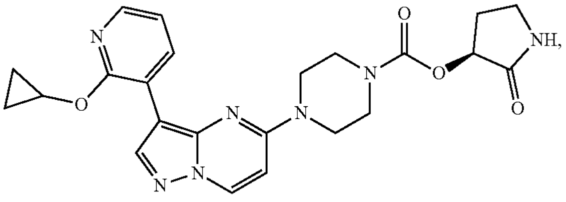
,
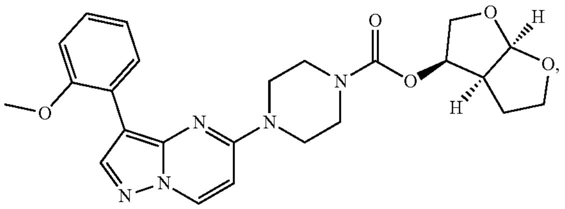
,
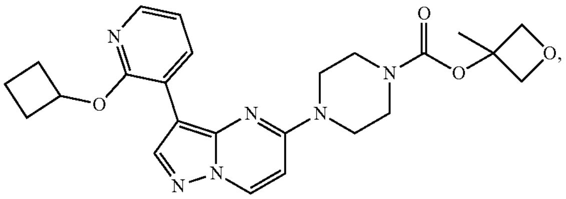
,
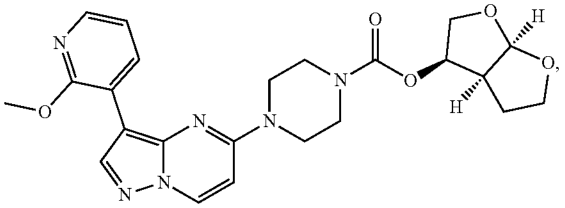
,
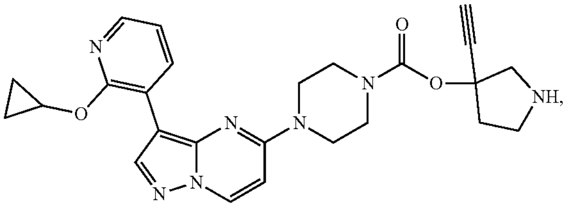
,
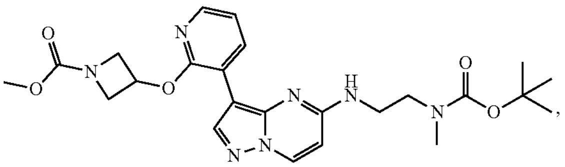
,
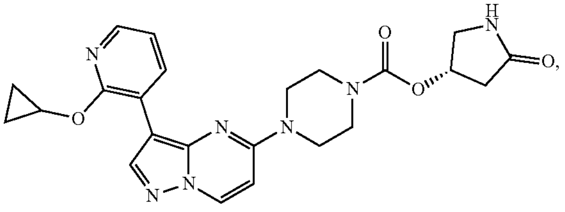
,
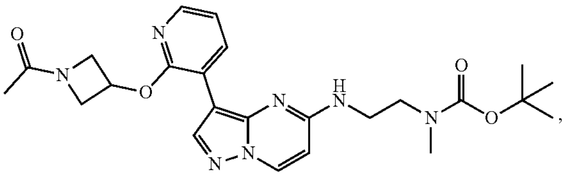
,
-continued
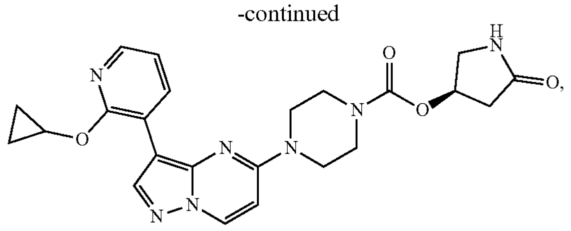
,
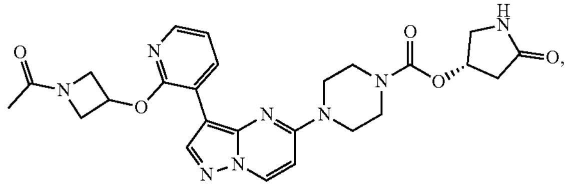
,
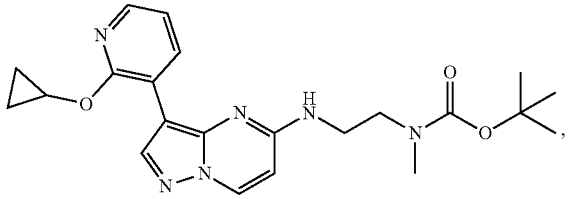
,
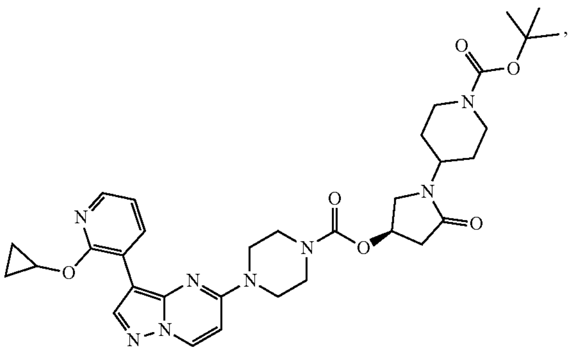
,
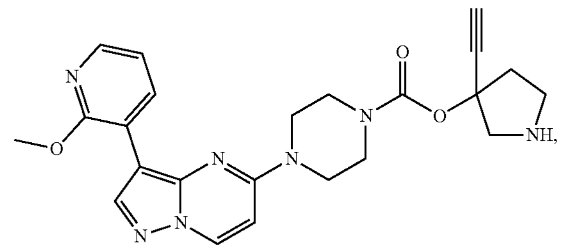
,
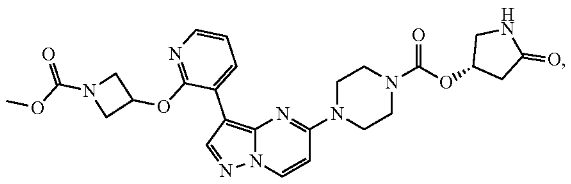
,
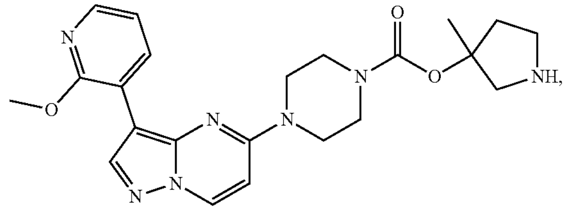
, -continued
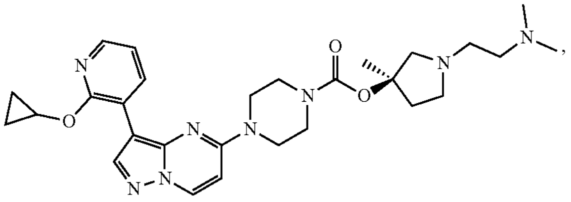
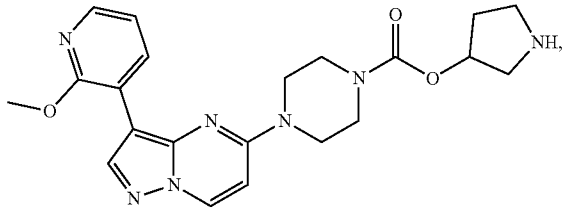
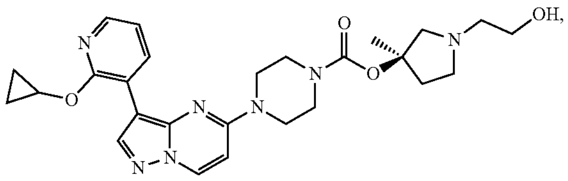
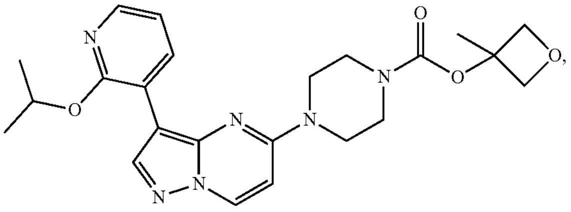
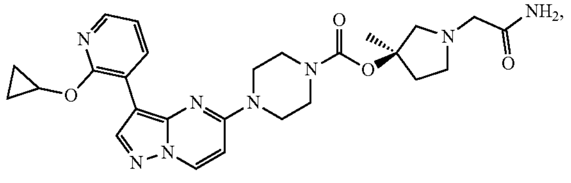
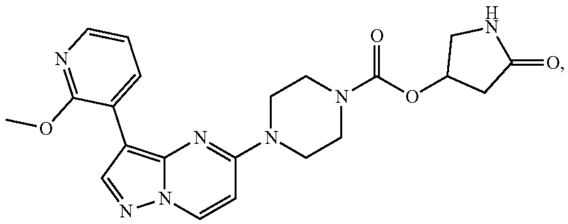
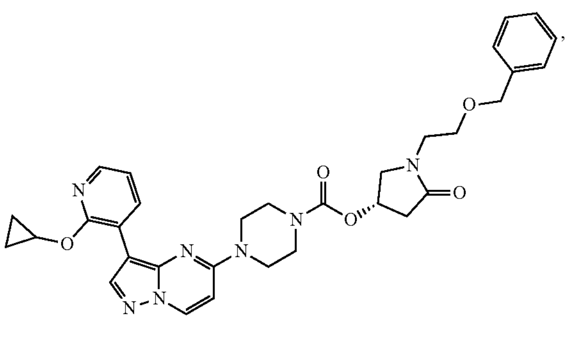
-continued
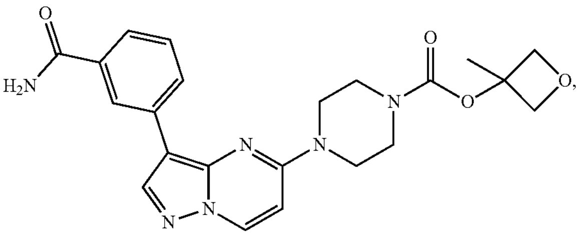
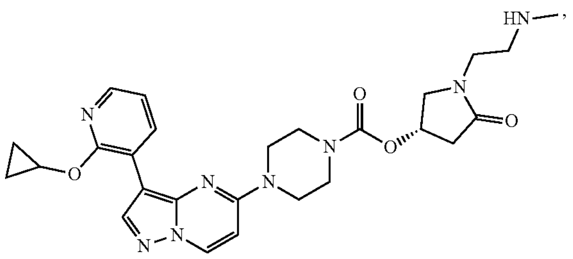
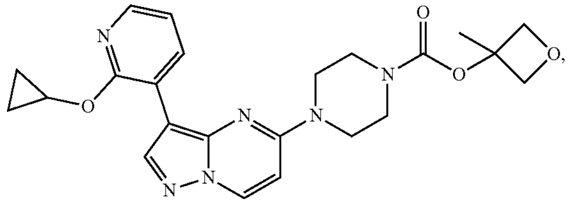
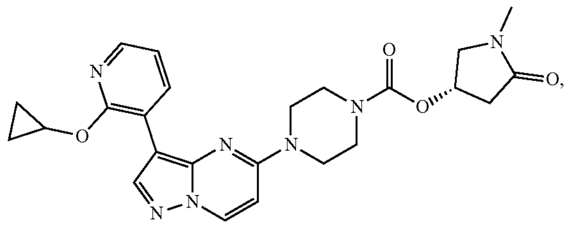
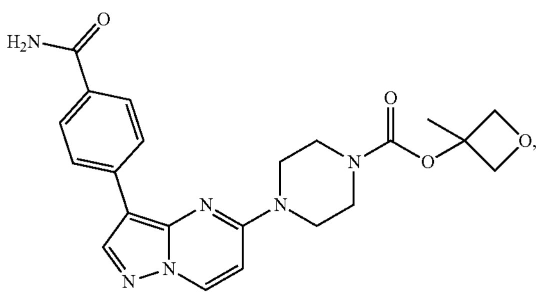

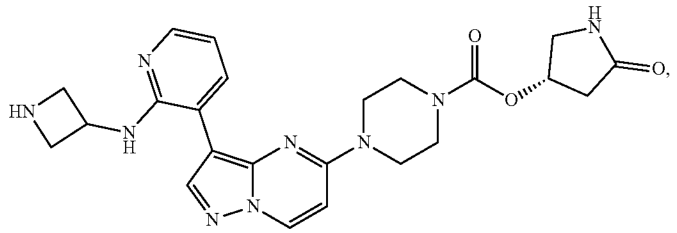
,
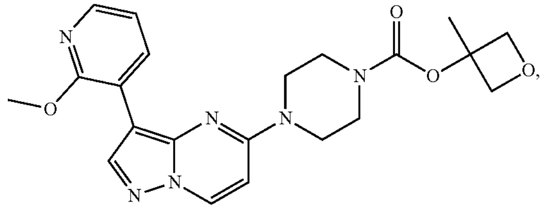
,
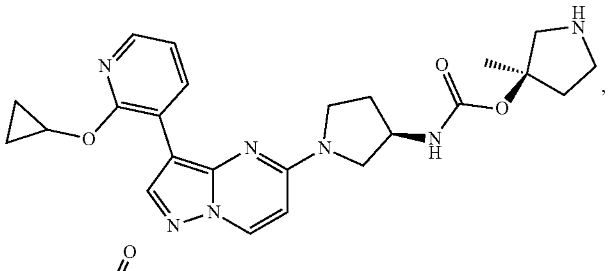
,
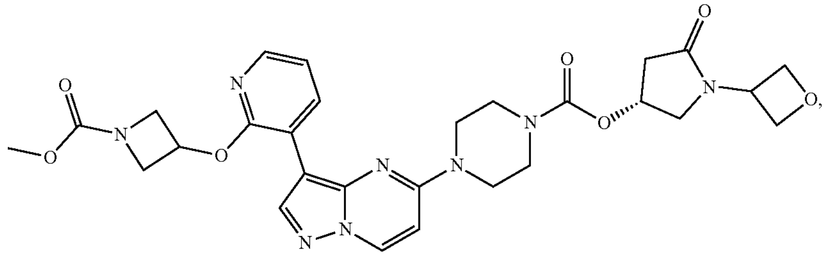
,
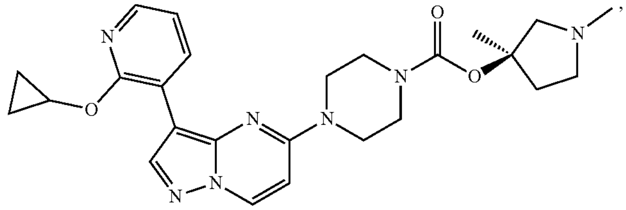
,
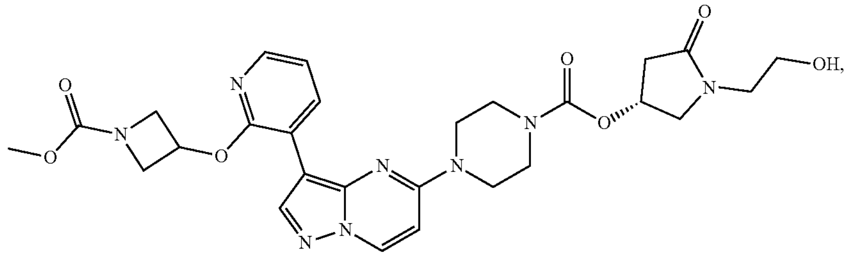
,
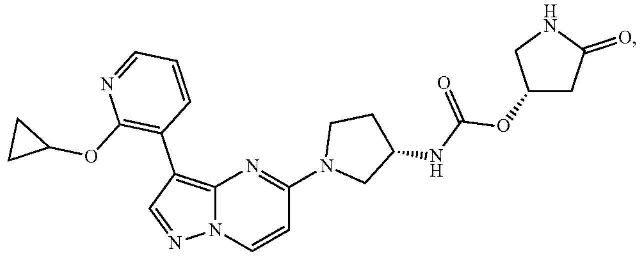
,
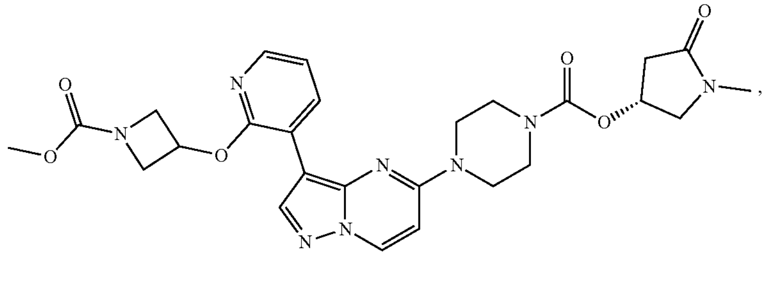
, -continued
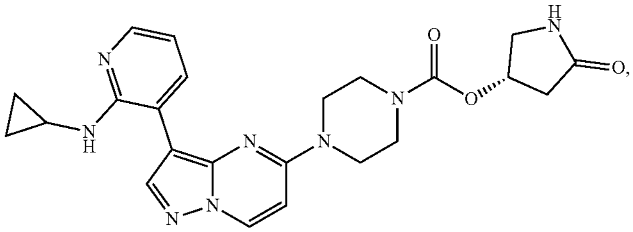
,
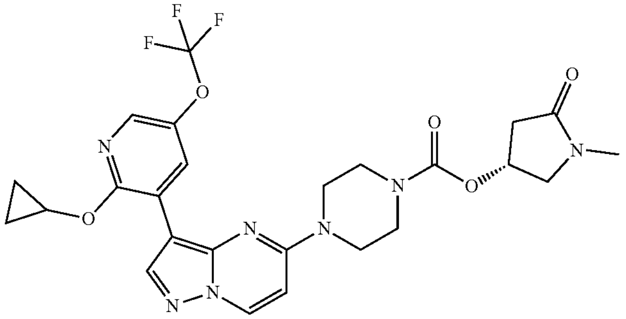
,
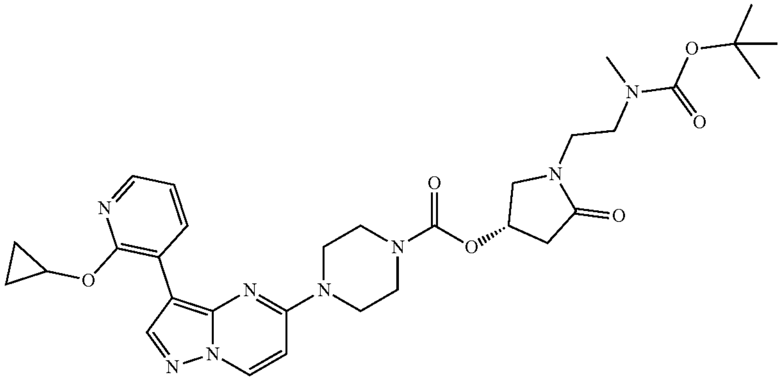
,
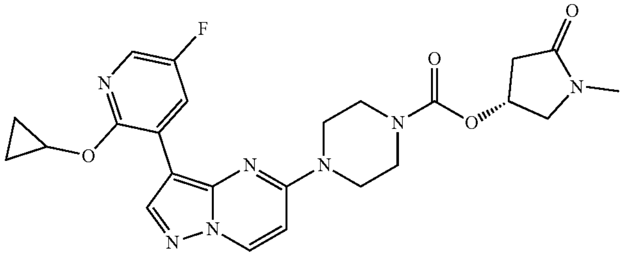
,
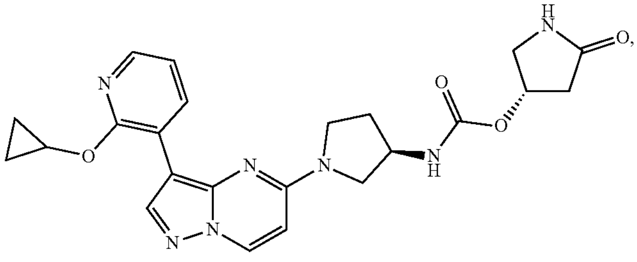
,
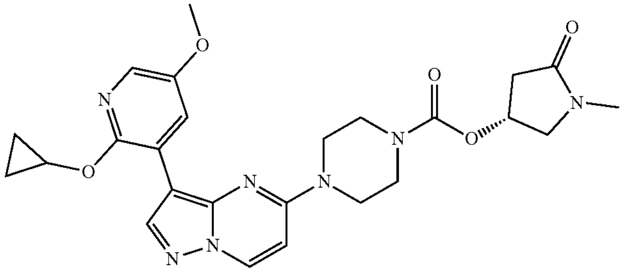
, -continued
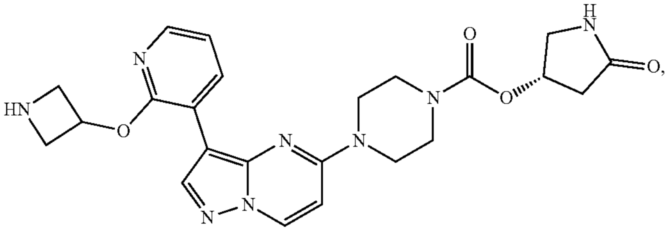
,
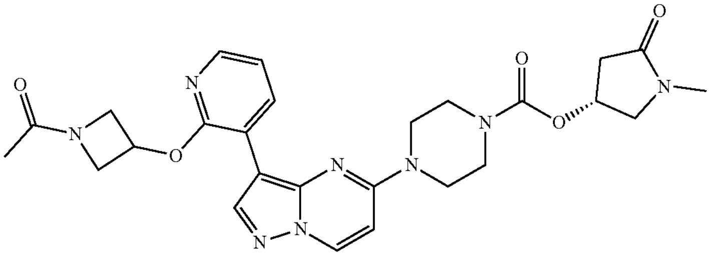
,
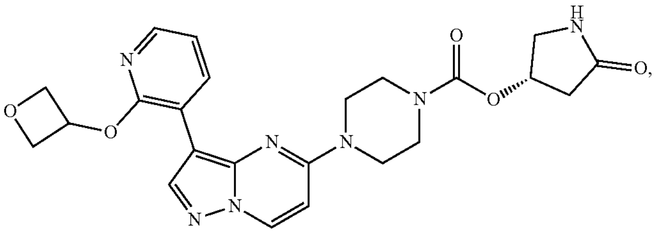
,
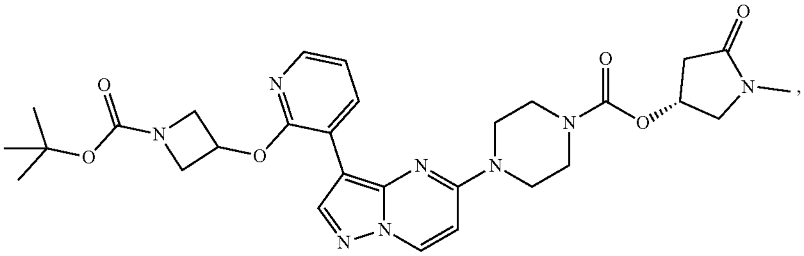
,
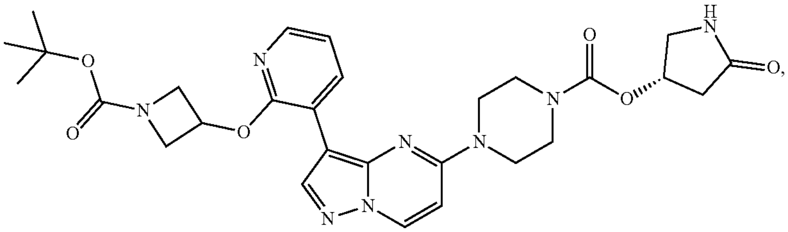
,
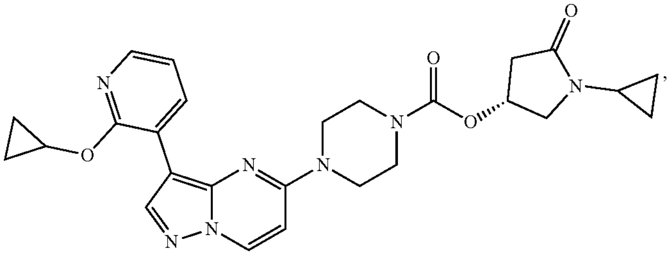
,
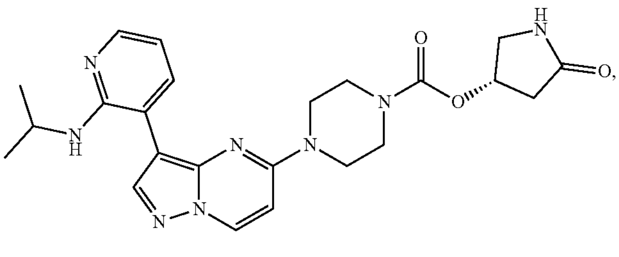
, -continued
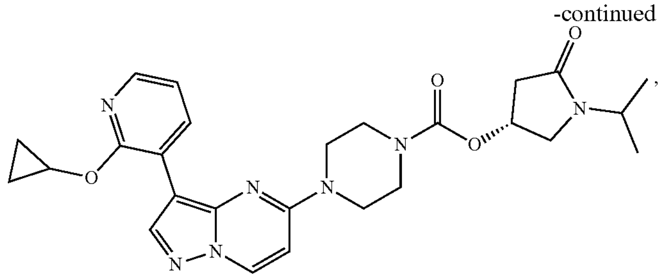
,
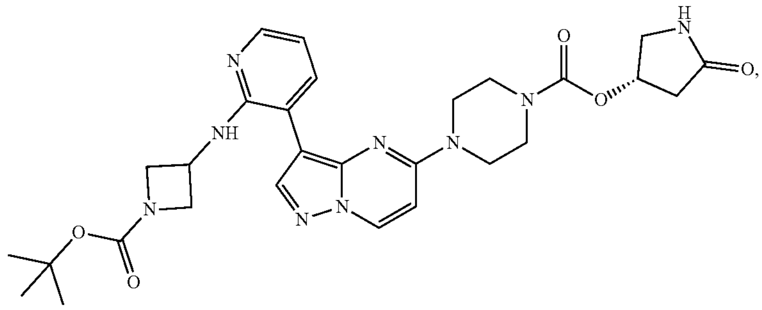
,
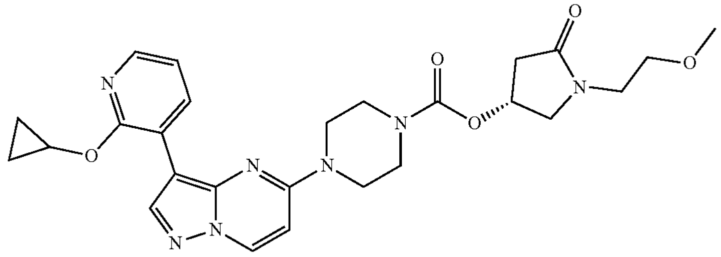
,
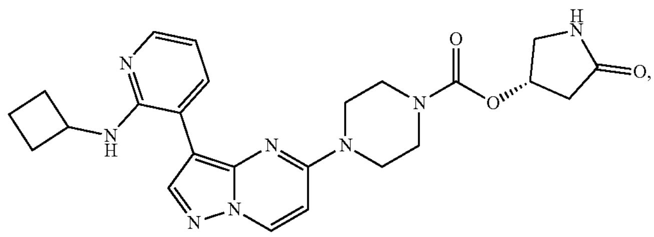
,
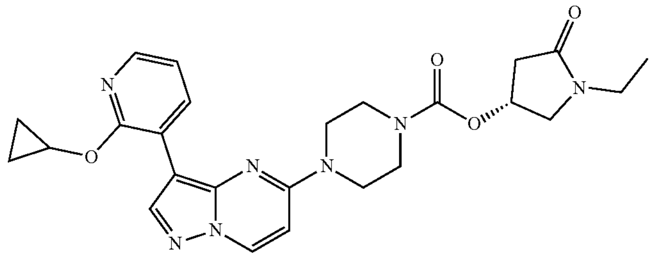
,
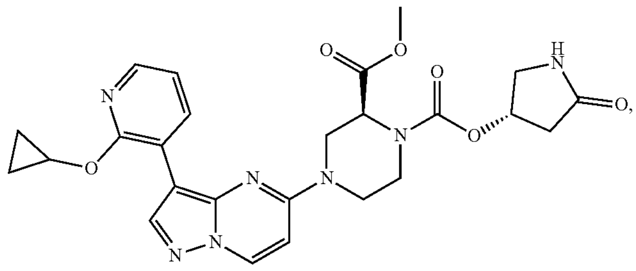
, -continued
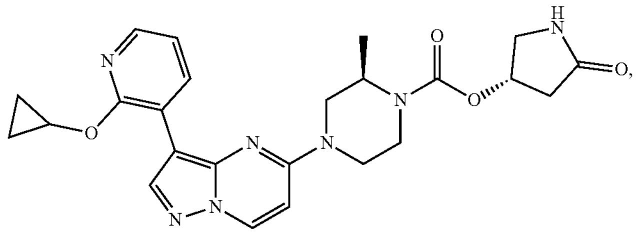
,
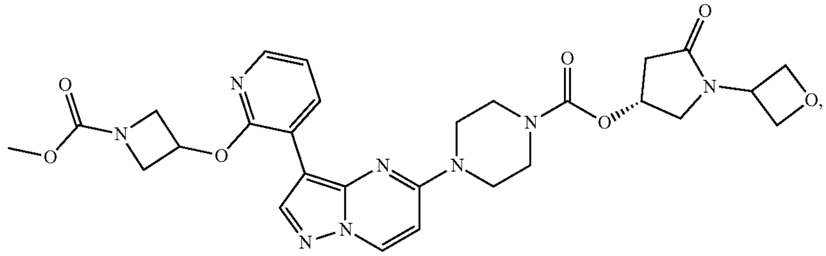
,
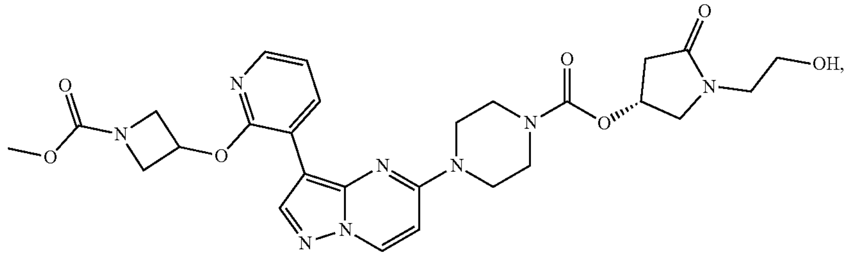
,
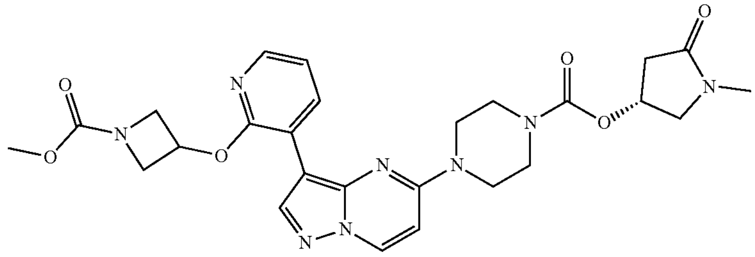
,
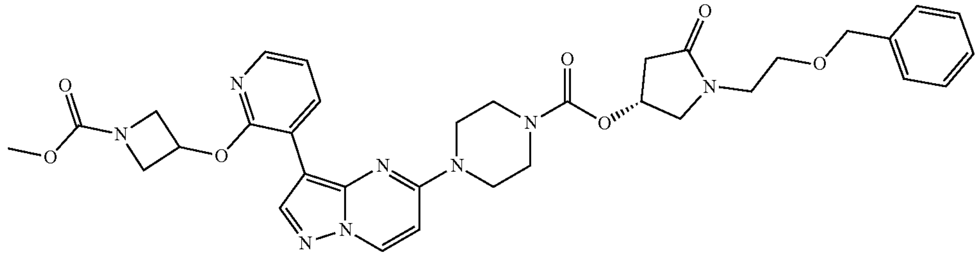
,
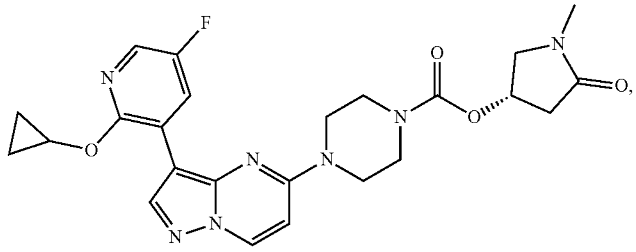
, -continued
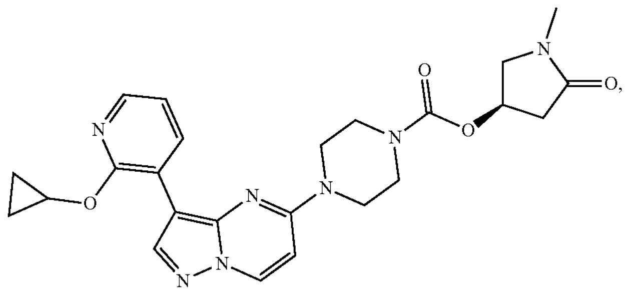
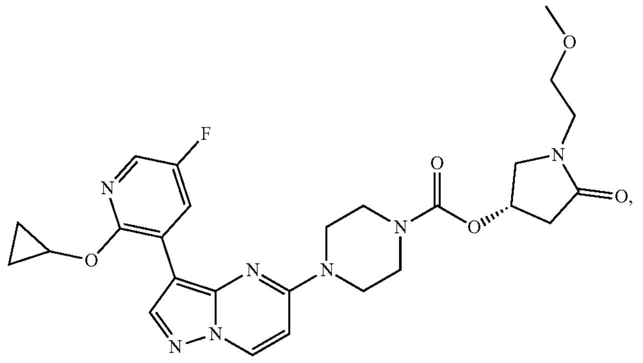
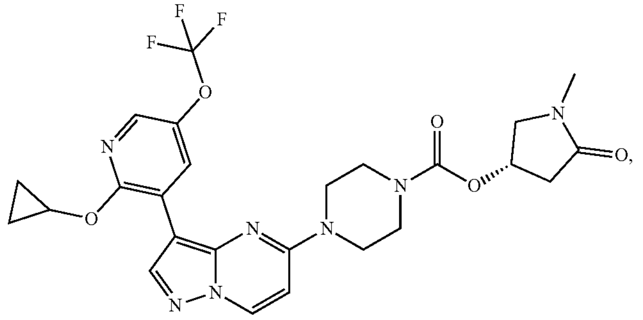
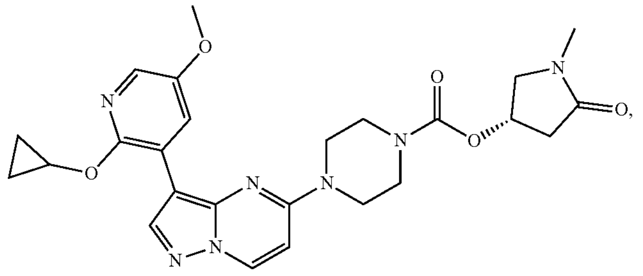
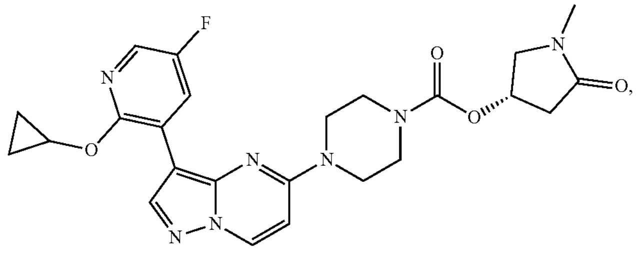
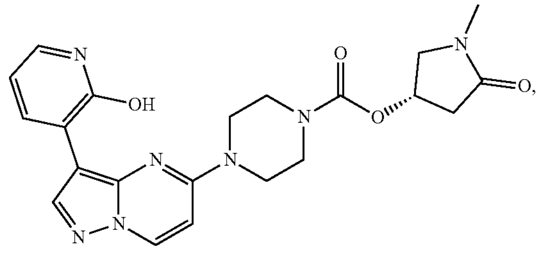

-continued
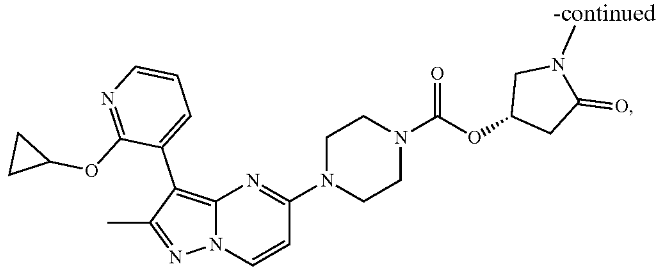
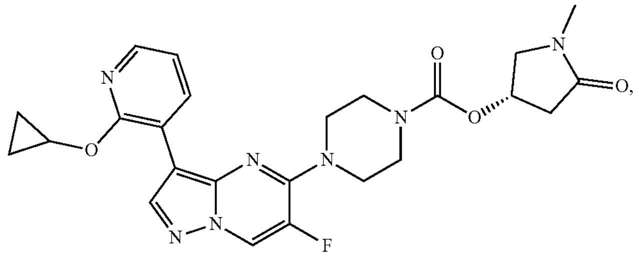
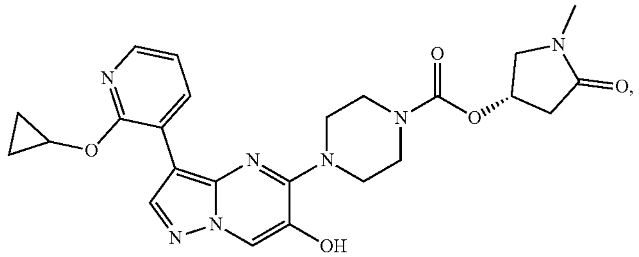
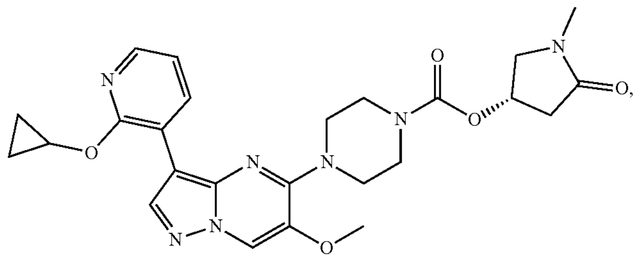
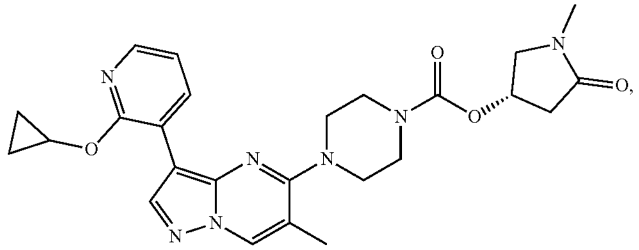
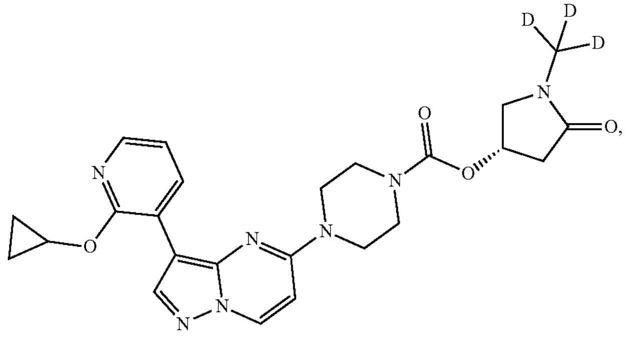

-continued
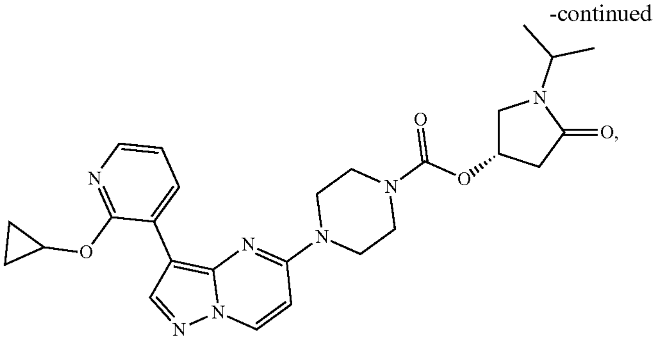
,
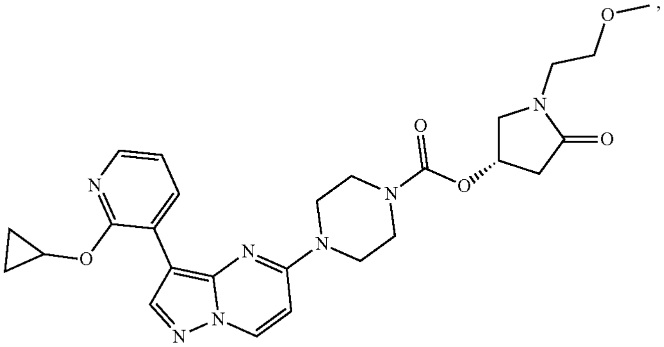
,
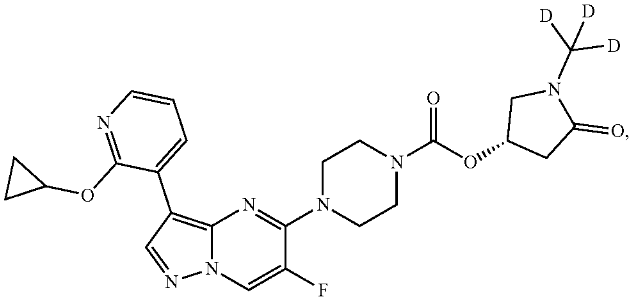
,
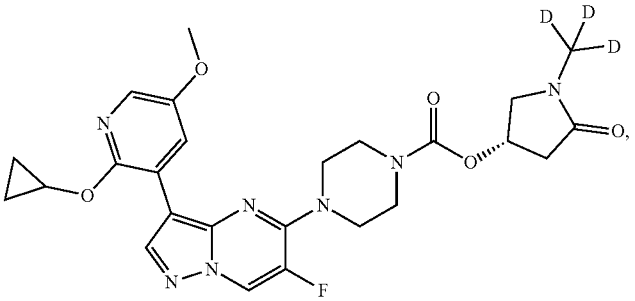
,
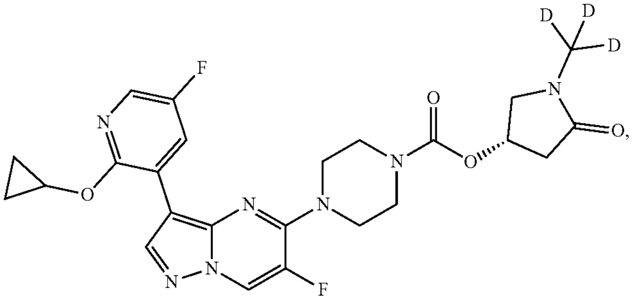
,
or a pharmaceutically acceptable salt thereof.

68. The compound of embodiment 1 or 67, wherein the compound has the structure:
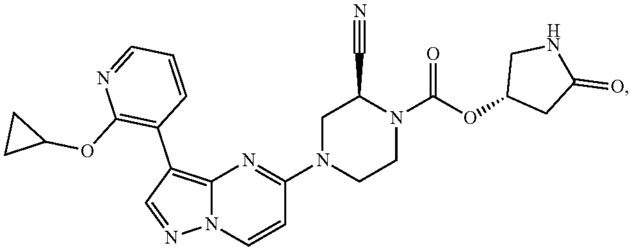
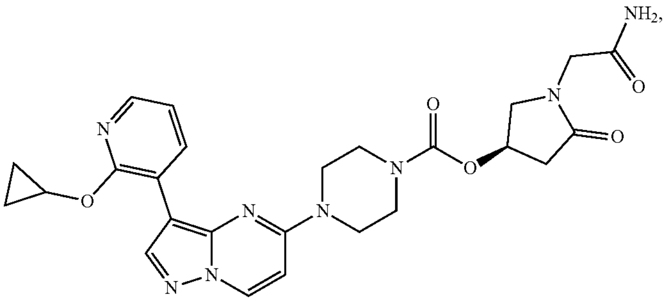
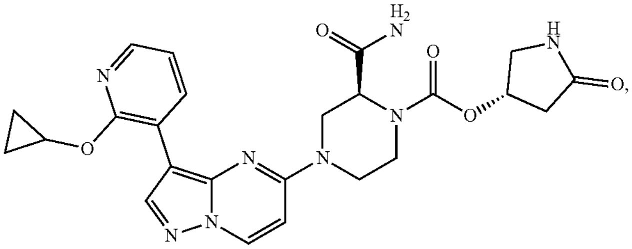
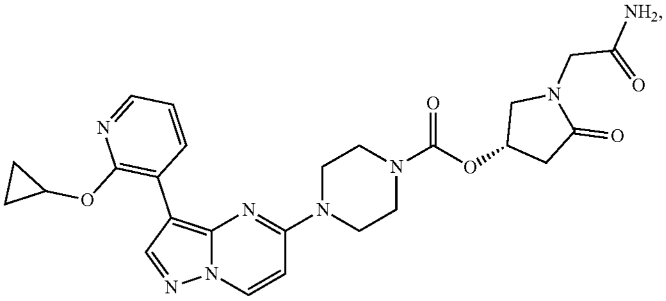
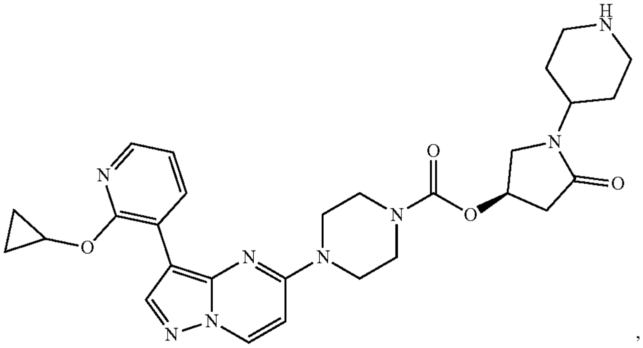
, -continued
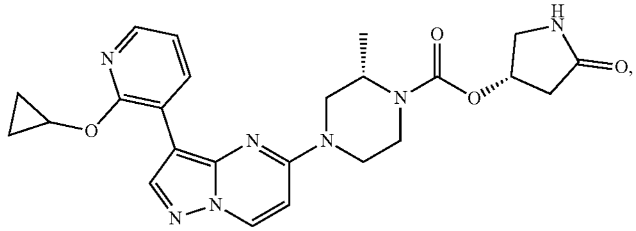
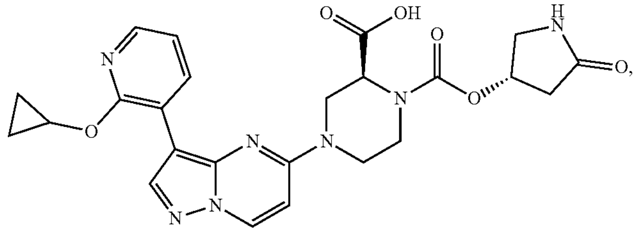
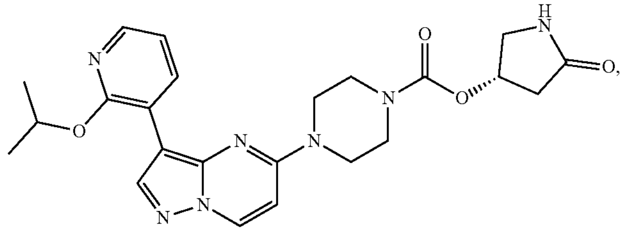
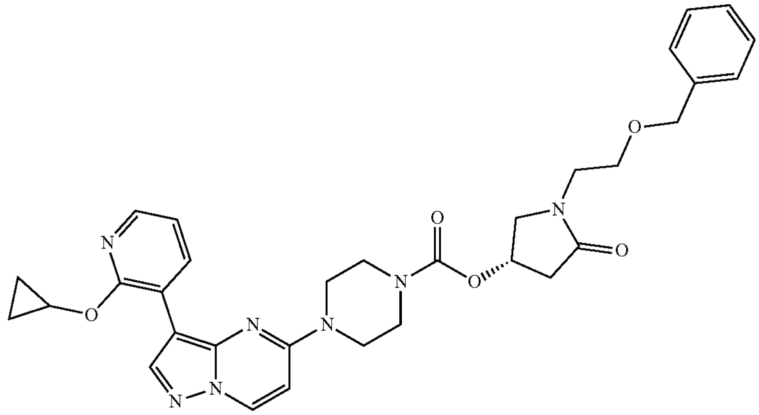
,
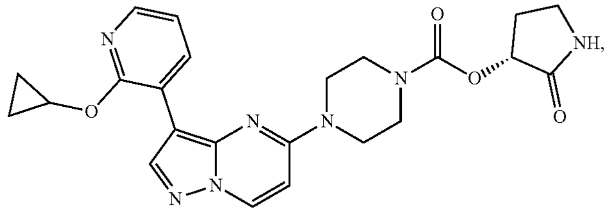
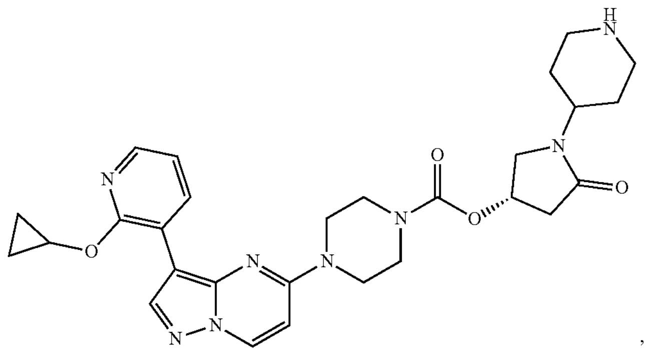
, -continued
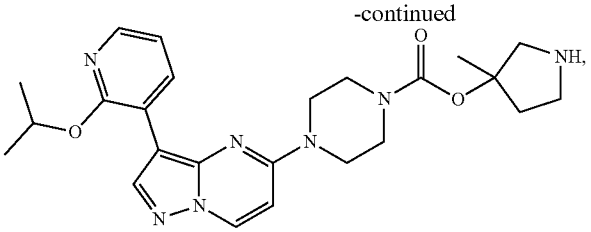
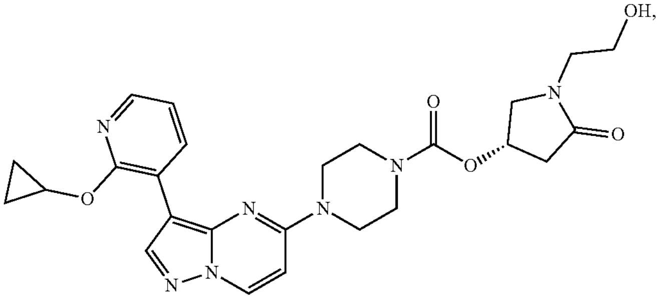
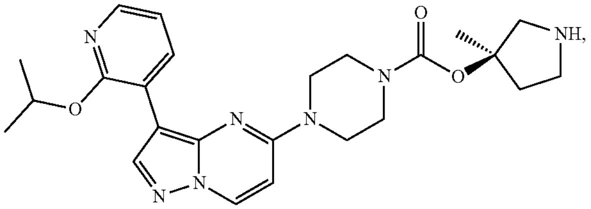
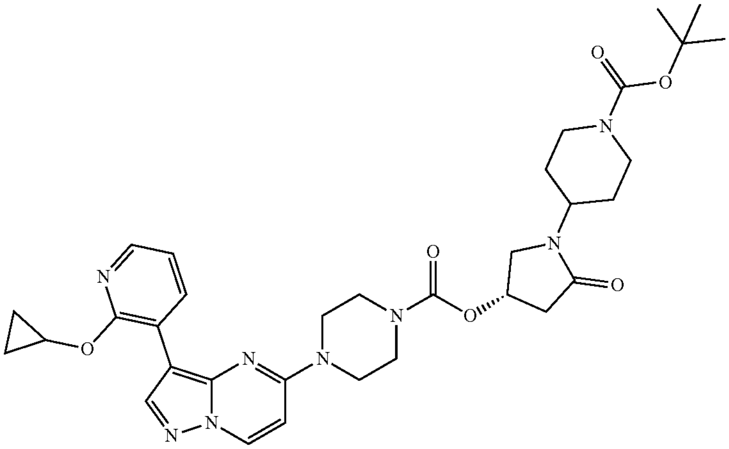
,
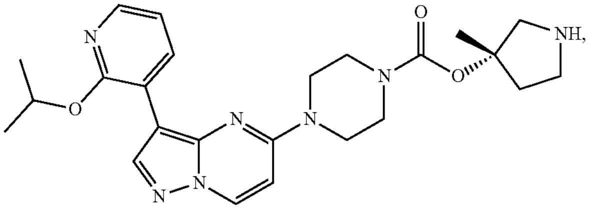

-continued
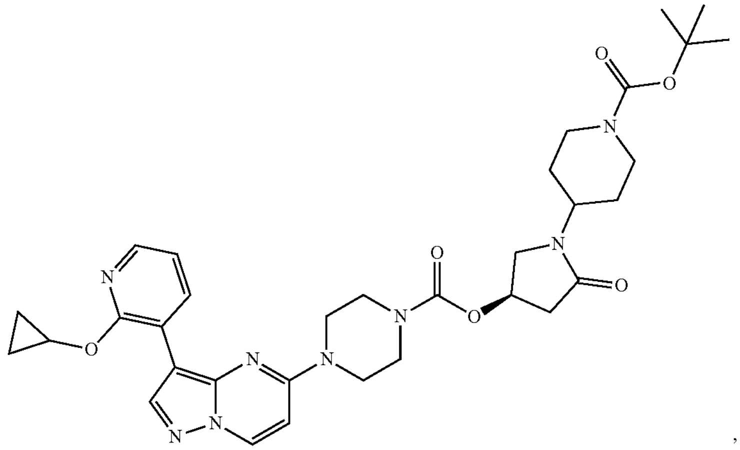
,
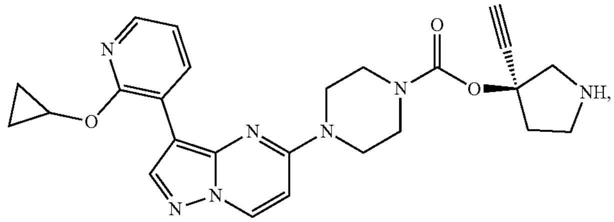
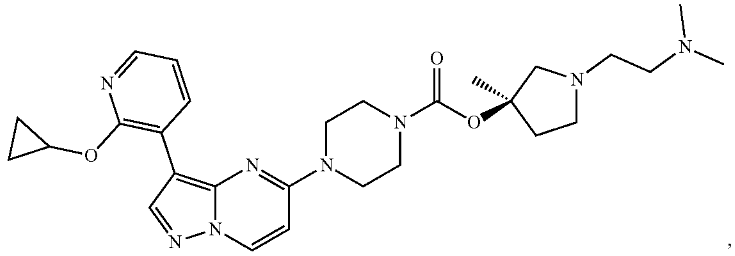
,
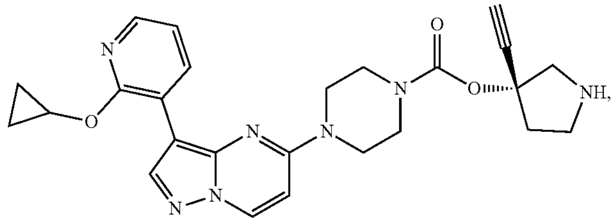
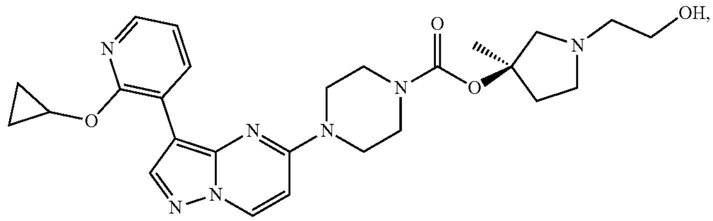
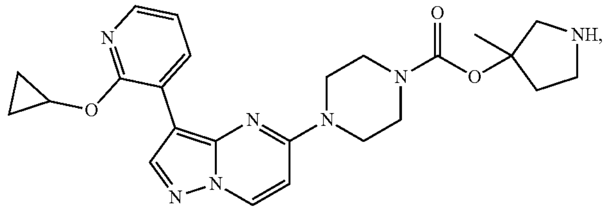

-continued
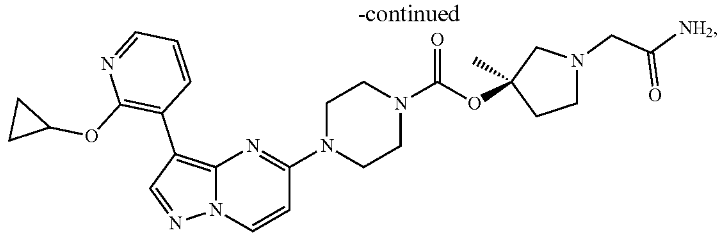
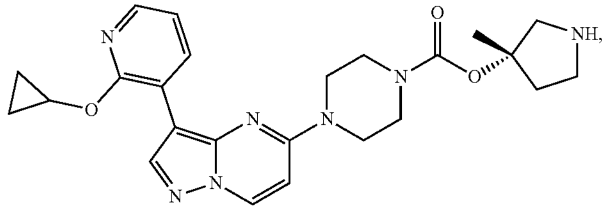
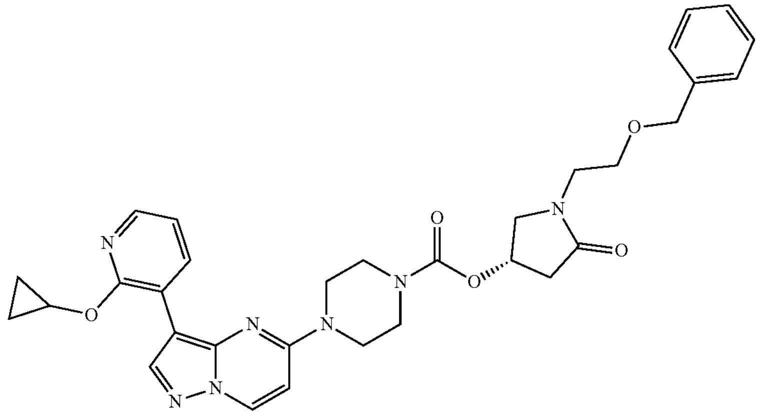
,
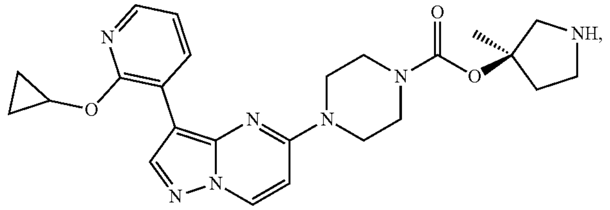
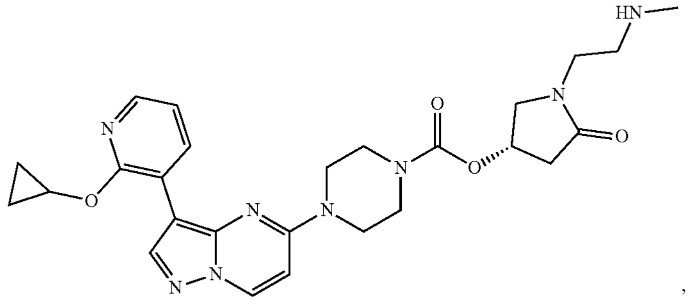
,
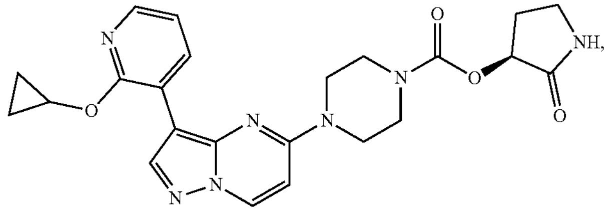

-continued
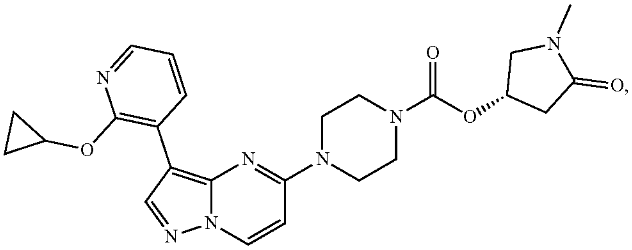
,
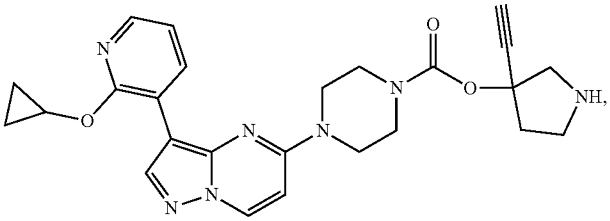
,
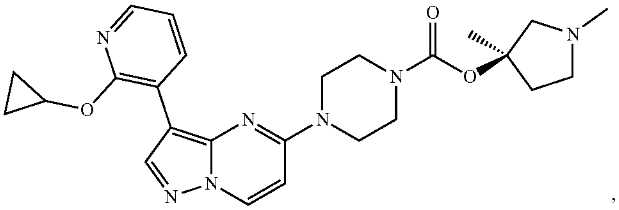
,
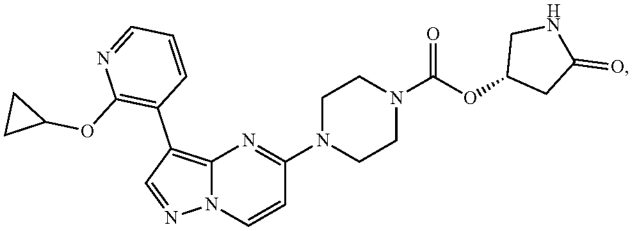
,
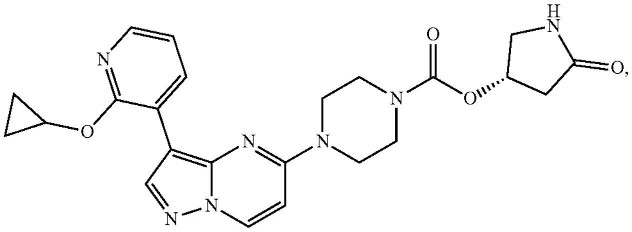
,
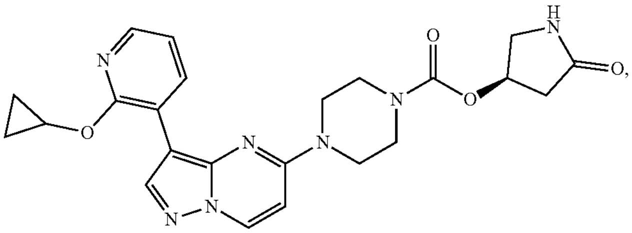
, -continued
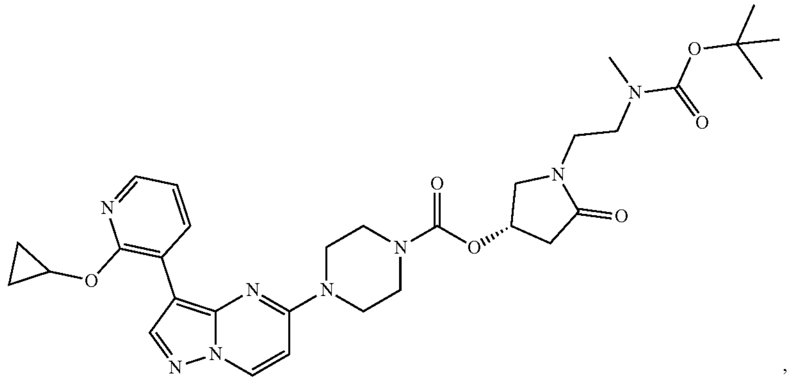
,
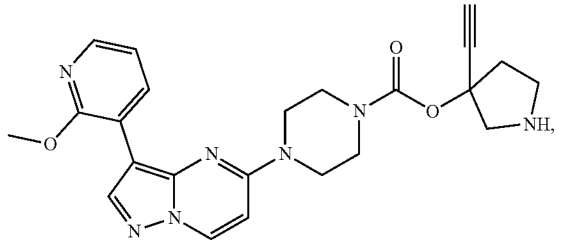
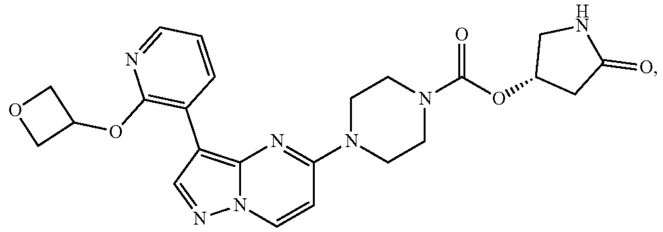
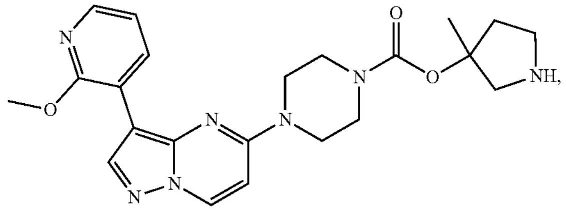
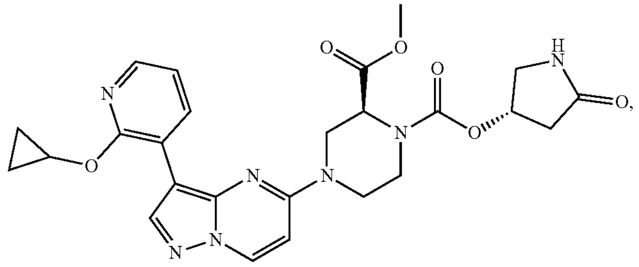
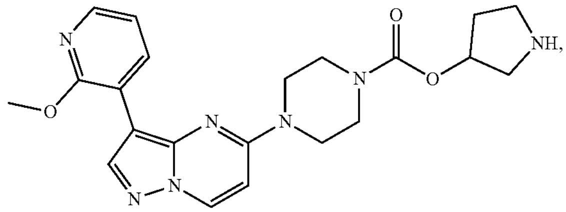

-continued
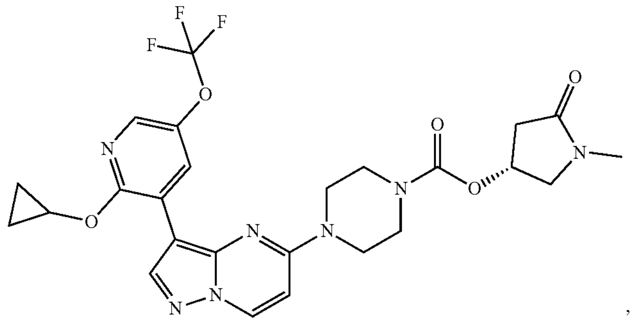
,
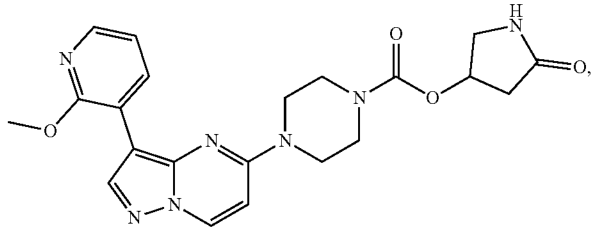
,
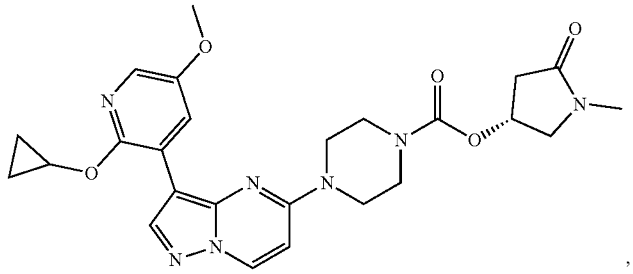
,
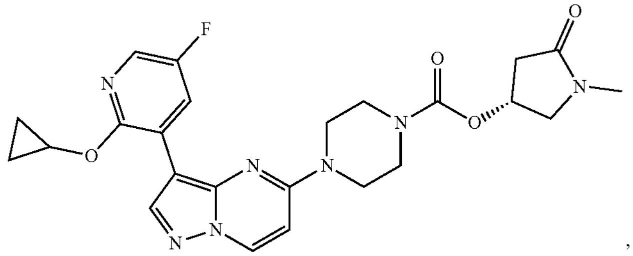
,
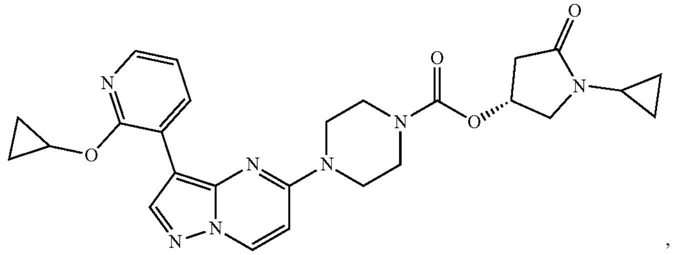
,
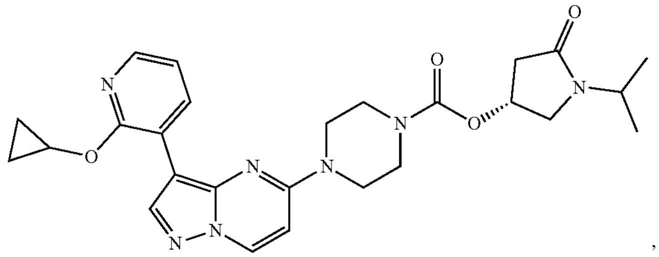
, -continued
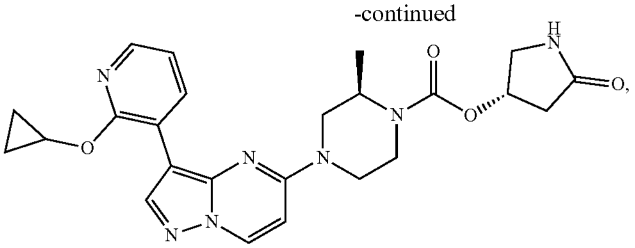
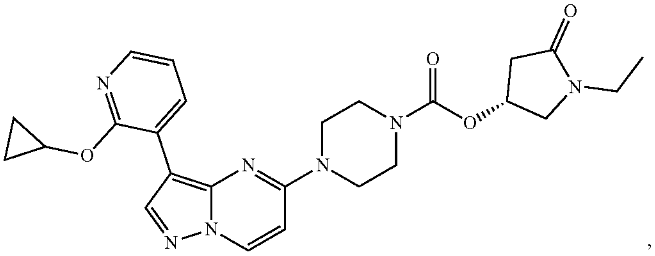
,
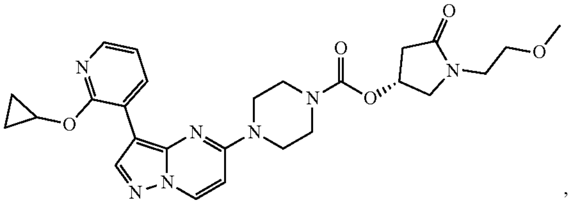
,
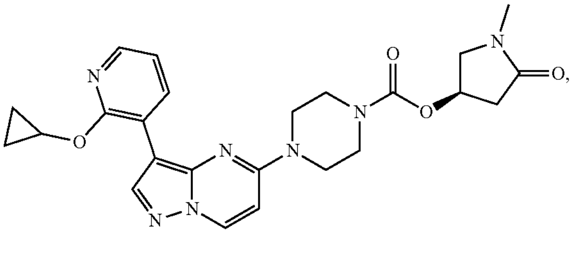
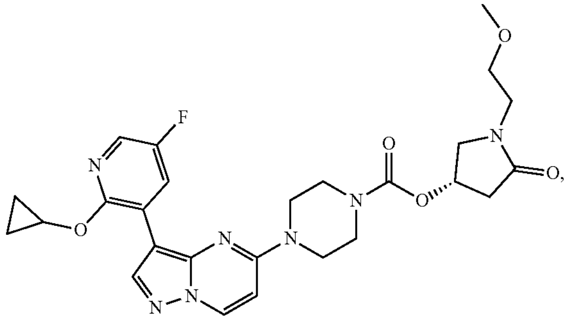
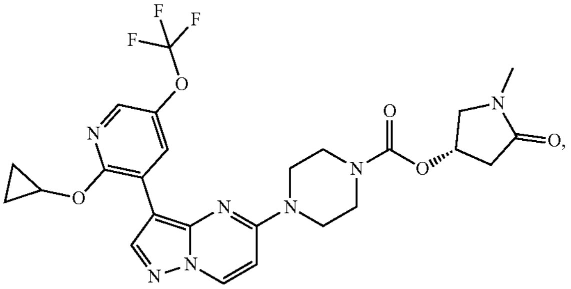
-continued
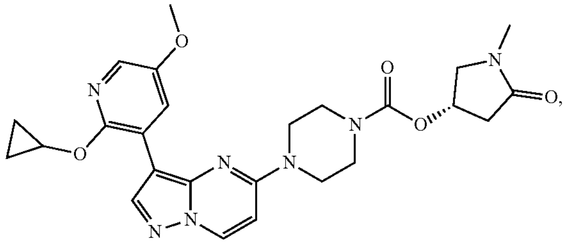
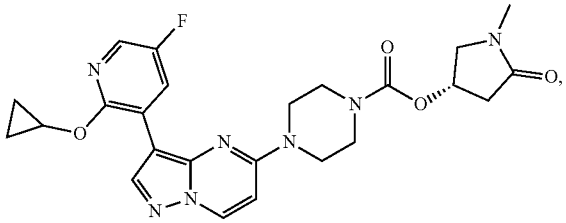
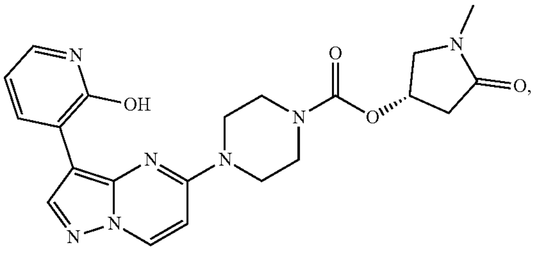
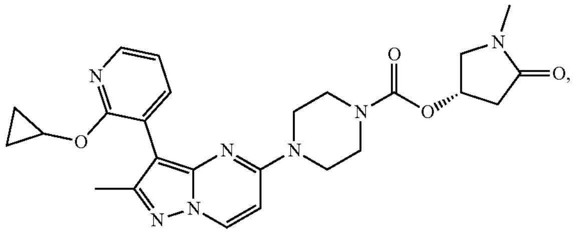

-continued

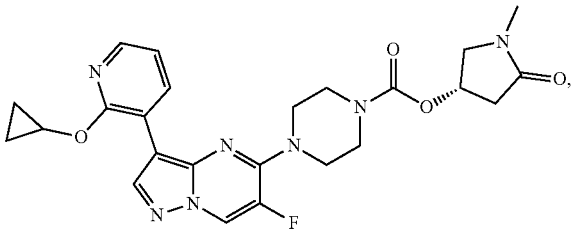

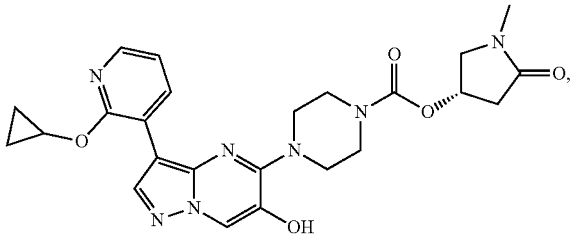

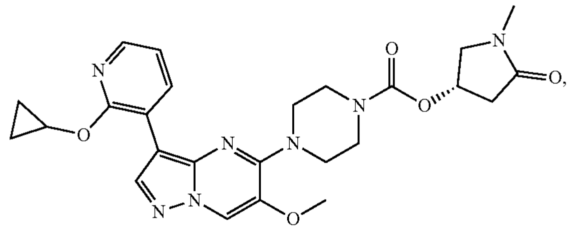

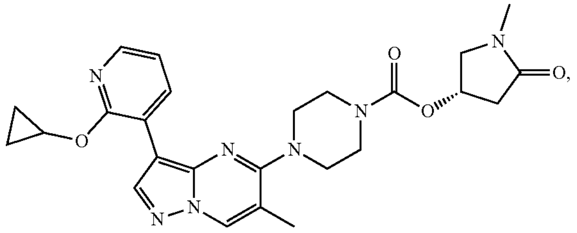

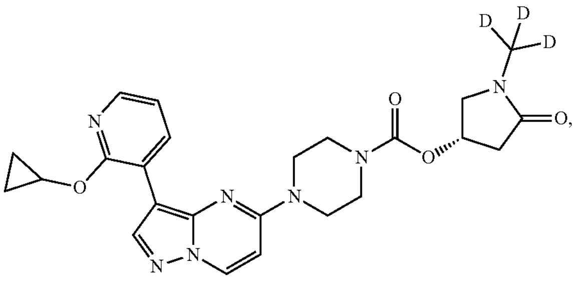

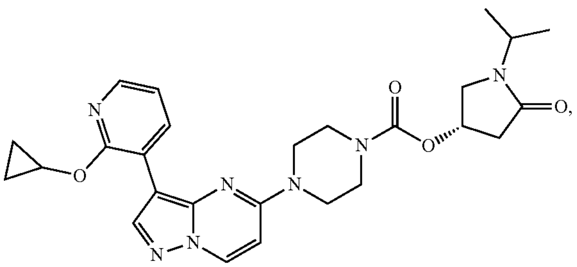

-continued

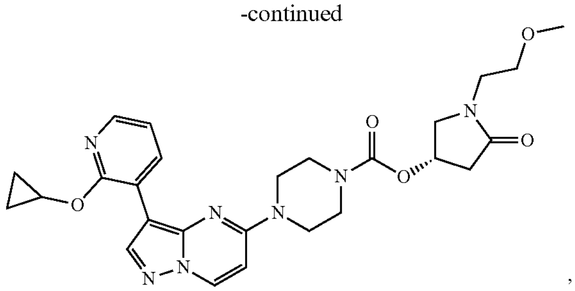

,

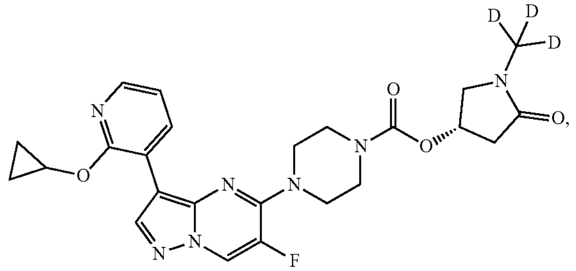

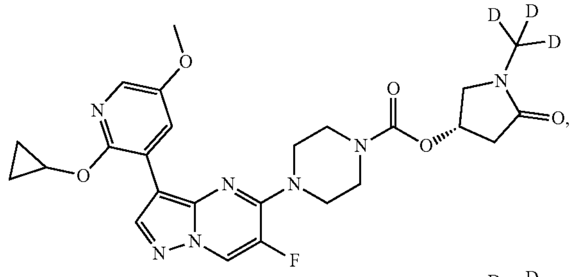

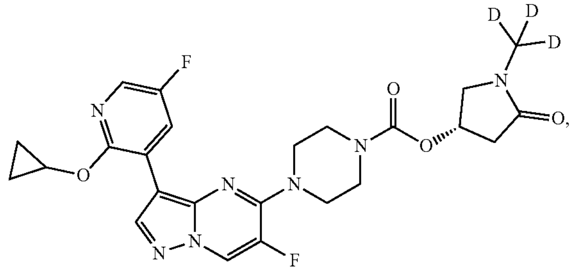

or a pharmaceutically acceptable salt thereof.

69. A method for treating or managing a disease or a disorder mediated by AAK1 activity, comprising administering to a subject in need thereof, a compound of any one of embodiments 1-69 or a pharmaceutically acceptable salt thereof.

70. The method of embodiment 69, wherein the disease or a disorder mediated by AAK1 activity is a muscular dystrophy.

71. The method of embodiment 69 or 70, wherein the muscular dystrophy is Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) or a congenital muscular dystrophy.

72. The method of any one of embodiments 69-71, wherein the subject has a mutation of a dystrophin gene.

73. A method for increasing skeletal muscle tissue growth or regeneration in a subject, comprising administering to the subject a compound of any one of embodiments 1-69 or a pharmaceutically acceptable salt thereof.

74. The method of embodiment 73, wherein the subject has damaged or injured skeletal muscle tissue.

75. The method of embodiment 74, wherein the skeletal muscle tissue is damaged or injured as a result of: physical injury or accident, disease, gene mutation, infection, over-use, loss of blood circulation, muscle atrophy, muscle wasting, dystrophic muscle, or ageing.

76. The method of embodiment 75, wherein the subject has a muscular dystrophy, optionally Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) or a congenital muscular dystrophy.

77. The method of any one of embodiments 73-76, wherein the subject has a mutation of a dystrophin gene.

78. The method of any one of embodiments 73-77, wherein skeletal muscle stem cells within the skeletal muscle tissue have reduced asymmetric cell division as compared to normal, healthy skeletal muscle stem cells.

79. The method of any one of embodiments 73-78, wherein the compound or pharmaceutically acceptable salt thereof in an AAK1 inhibitor, and the compound or pharmaceutically acceptable salt thereof does not substantially inhibit proliferation or cell cycle progression of the subject's skeletal muscle stem cells.

80. The method of any one of embodiments 73-79, wherein the method increases skeletal muscle tissue regeneration in the subject.

81. The method of any one of embodiments 73-80, wherein the subject is a mammal, optionally a human.

82. The method of any one of embodiments 73-81, wherein the compound or pharmaceutically acceptable salt thereof is administered to the subject systemically or locally, optionally at a site of tissue damage or injury.

83. The method of any one of embodiments 73-82, wherein the compound or pharmaceutically acceptable salt thereof inhibits expression of AAK1, optionally by inhibiting transcription, translation, post-translational modification, or stability of the protein component, or the gene encoding the protein component.

84. The method of embodiment 83, wherein the compound or pharmaceutically acceptable salt thereof binds to a polynucleotide sequence that regulates expression of AAK1.

85. The method of embodiment 84, wherein the nucleotide sequence is present within the AAK1 gene 86. The method of any embodiment 84 or embodiment 85, wherein the polynucleotide sequence is DNA or RNA.

87. A method for treating a muscular dystrophy, comprising administering to a subject in need thereof a compound of any one of embodiments 1-69 or pharmaceutically acceptable salt thereof.

88. The method of embodiment 87, wherein the subject has a muscular dystrophy selected from the group consisting of: Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) and a congenital muscular dystrophy.

89. The method of embodiment 87 OR 88, wherein the subject has a mutation of a dystrophin gene.

90. The method of any one of embodiments 87-91, wherein skeletal muscle stem cells within the skeletal muscle tissue have reduced asymmetric cell division as compared to normal, healthy skeletal muscle stem cells.

91. The method of any one of embodiments 87-92, wherein the compound or pharmaceutically acceptable salt thereof in an AAK1 inhibitor, and the compound or pharmaceutically acceptable salt thereof does not substantially inhibit proliferation or cell cycle progression of the subject's skeletal muscle stem cells.

92. The method of any one of embodiments 87-93, wherein the method increases skeletal muscle tissue regeneration in the subject.

93. The method of any one of embodiments 87-94, wherein the subject is a mammal, optionally a human.

94. The method of any one of embodiments 87-95, wherein the compound or pharmaceutically acceptable salt thereof is administered to the subject systemically or locally, optionally at a site of tissue damage or injury.

95. The method of any one of embodiments 87-96, wherein the compound or pharmaceutically acceptable salt thereof inhibits expression of AAK1, optionally by inhibiting transcription, translation, post-translational modification, or stability of the protein component, or the gene encoding the protein component.

96. The method of embodiment 97, wherein the compound or pharmaceutically acceptable salt thereof binds to a polynucleotide sequence that regulates expression of AAK1, optionally wherein the nucleotide sequence is present within the AAK1 gene.

97. The method of any embodiment 96, wherein the polynucleotide sequence is DNA or RNA.

98. The method of any one of embodiments 70-97, wherein the compound or pharmaceutically acceptable salt thereof inhibits AAK1.

99. The method of any one of embodiments 70-98, wherein the compound or pharmaceutically acceptable salt thereof is administered 1, 2, 3, 4, 5, 6, or 7 times per week.

100. The method of any one of embodiments 70-99, wherein the inhibitor is administered at a dose of about 0.01 mg/kg to about 300 mg/kg.

101. The method of any one of embodiments 70-100, wherein the inhibitor is administered at a dose of about 0.1 mg/kg to about 20 mg/kg.

EXAMPLES

Example 1: Synthesis of Reference Compound I (RC-1)

(3-methyloxetan-3-yl)-4-[3-(2-methoxy-3-pyridyl)pyrazolo[1,5-a]pyrimidin-5-yl]piperazine-1-carboxylate

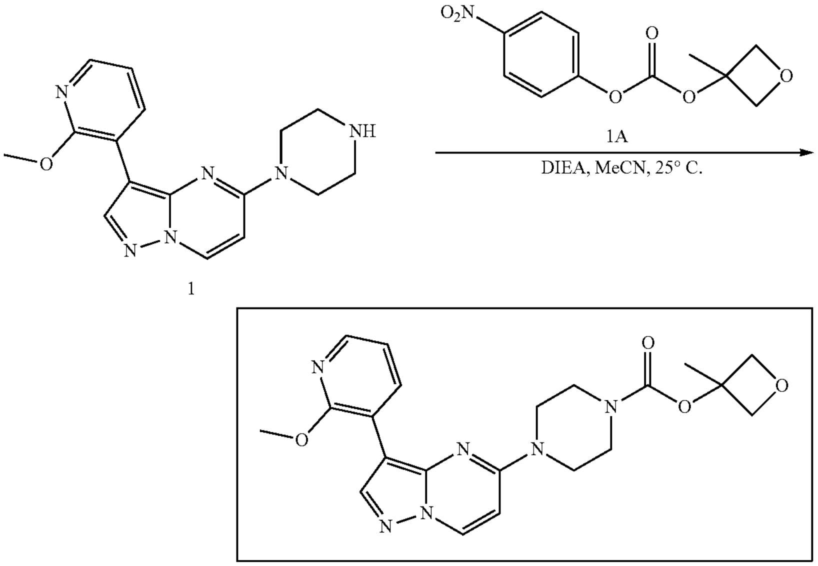

1

RC-1

To a solution of (3-methyloxetan-3-yl) (4-nitrophenyl) carbonate (300 mg, 1.18 mmol, 1 eq) 3-(2-methoxy-3-pyridyl)-5-piperazin-1-yl-pyrazolo[1,5-a]pyrimidine (367.71 mg, 1.18 mmol, 1 eq) in MeCN (6 mL) was added DIEA (612.51 mg, 4.74 mmol, 825.48 uL, 4 eq). The mixture was stirred at 25° C. for 6 hr. The reaction mixture was concentrated under reduced pressure to give a residue. The crude was purified by preparative HPLC. The pure fractions were collected and the volatiles were removed under vacuum. The residue was partitioned between acetonitrile (20 mL) and water (100 mL). The solution was lyophilized to dryness to give (3-methyloxetan-3-yl)-4-[3-(2-methoxy-3-pyridyl)pyrazolo[1,5-a]pyrimidin-5-yl]piperazine-1-carboxylate (200.26 mg, 462.30 umol, 39.02% yield, 97.985% purity) as a solid.

LCMS m/z=425.2 $[M+H]^+$.

$^1H$ NMR (400 MHz, DMSO-$d_6$) δ=8.86-8.69 (m, 2H), 8.54-8.46 (m, 1H), 8.01-7.92 (m, 1H), 7.12-7.00 (m, 1H), 6.85-6.76 (m, 1H), 4.71-4.60 (m, 2H), 4.46-4.35 (m, 2H), 3.99 (s, 3H), 3.83-3.71 (m, 4H), 3.61-3.53 (m, 2H), 3.53-3.46 (m, 2H), 1.66 (s, 3H).

Example 2: Synthesis of Compound I-1

(3-methyloxetan-3-yl)-4-[3-(2-isopropoxy-3-pyridyl)pyrazolo[1,5-a]pyrimidin-5-yl]piperazine-1-carboxylate

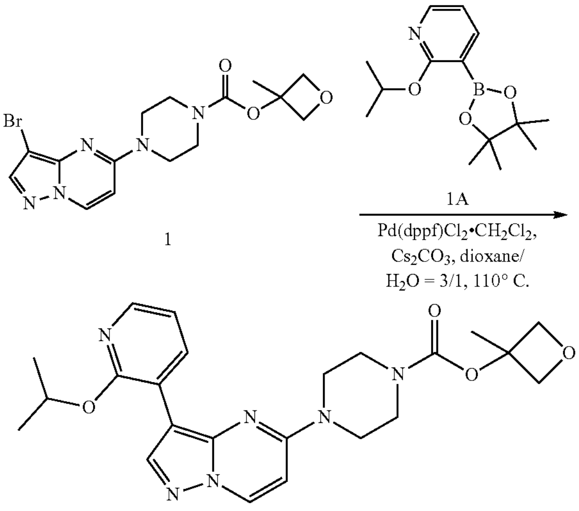

1

I-1

A mixture of (3-methyloxetan-3-yl) 4-(3-bromopyrazolo[1,5-a]pyrimidin-5-yl)piperazine-1-carboxylate (100 mg, 252.37 umol, 1 eq), 2-isopropoxy-3-(4,4,5,5-tetramethyl-1, 3,2-dioxaborolan-2-yl)pyridine (66.41 mg, 252.37 umol, 1 eq), $Cs_2CO_3$ (164.46 mg, 504.75 umol, 2 eq) in dioxane (0.75 mL) and $H_2O$ (0.25 mL) was degassed and purged with $N_2$ for 3 times, then added $Pd(dppf)Cl_2 \cdot CH_2Cl_2$ (41.22 mg, 50.47 umol, 0.2 eq) and then the mixture was stirred at 110° C. for 1 hr under $N_2$ atmosphere. The reaction mixture was concentrated under reduced pressure to give a residue. The crude was purified by preparative HPLC. Pure fractions were collected and the volatiles were removed under vacuum. The residue was partitioned between acetonitrile (5 mL) and water (30 mL). The solution was lyophilized to dryness to give (3-methyloxetan-3-yl) 4-[3-(2-isopropoxy-3-pyridyl)pyrazolo[1,5-a]pyrimidin-5-yl]piperazine-1-carboxylate (11.36 mg, 24.17 umol, 10.94% yield, 96.27% purity) as a grey solid.

LCMS m/z=453.2 $[M+H]^+$.

$^1H$ NMR (400 MHz, DMSO-$d_6$) δ=8.77 (m, 2H), 8.53 (s, 1H), 7.96 (s, 1H), 7.03 (s, 1H), 6.81 (d, J=6.9 Hz, 1H), 5.55-5.25 (m, 1H), 4.67 (d, J=5.8 Hz, 2H), 4.43 (d, J=5.9 Hz, 2H), 3.78 (s, 4H), 3.54 (s, 4H), 1.66 (s, 3H), 1.40 (d, J=5.0 Hz, 6H).

Example 3: Synthesis of Compound I-2

(3-methyloxetan-3-yl) (4-nitrophenyl) carbonate

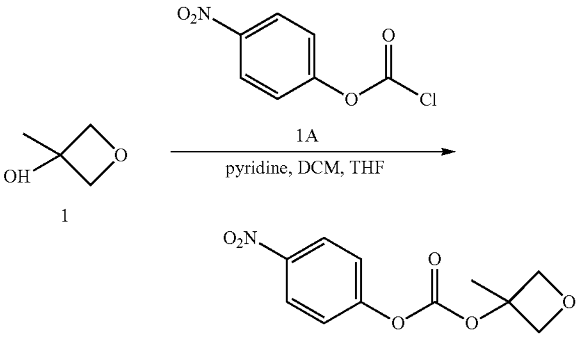

2

A mixture of 3-methyloxetan-3-ol (1 g, 11.35 mmol, 1 eq) and (2.69 g, 34.05 mmol, 2.75 mL, 3 eq) in DCM (10 mL) and THF (2 mL) was cooled to 0° C. and added pyridine, (4-nitrophenyl) carbonochloridate (2.29 g, 11.35 mmol, 1 eq) under a nitrogen atmosphere. The mixture was degassed and purged with $N_2$ for 3 times, and then the mixture was stirred at 25° C. for 1 hr under $N_2$ atmosphere. The reaction mixture was diluted with water and extracted with DCM (50 mL×3). The combined organic layers were washed with brine, dried over sodium sulphate, and concentrated under reduced pressure to give a residue. The residue was purified by flash silica gel chromatography to give (3-methyloxetan-3-yl)-(4-nitrophenyl) carbonate (2.2 g, 4.90 mmol, 43.16% yield, 56.387% purity) as a liquid.

LCMS m/z=254.0 $[M+H]^+$.

$^1H$ NMR (400 MHz, $CDCl_3$) δ=8.42-8.25 (m, 2H), 7.48-7.34 (m, 2H), 4.92 (d, J=7.5 Hz, 2H), 4.59 (d, J=8.1 Hz, 2H), 2.01-1.79 (m, 3H).

(3-methyloxetan-3-yl)-4-(3-bromopyrazolo[1,5-a]pyrimidin-5-yl)piperazine-1-carboxylate

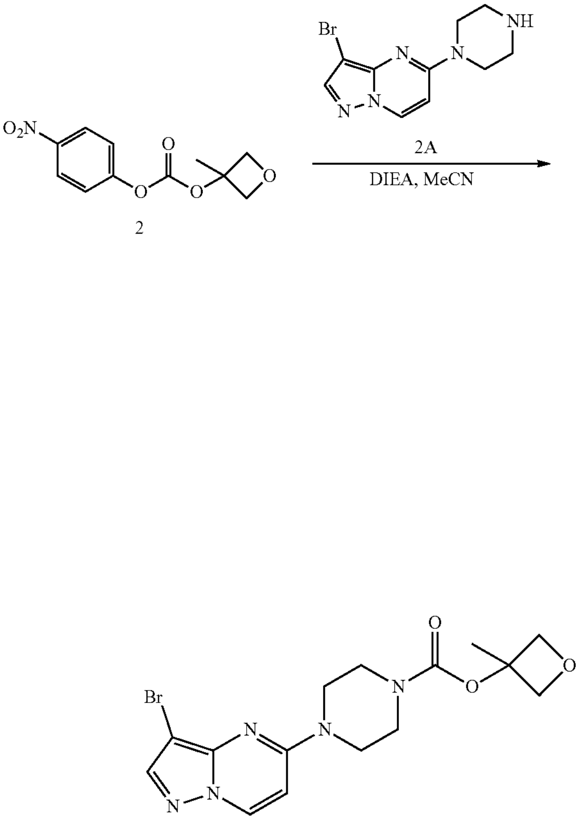

3

To a solution of (3-methyloxetan-3-yl) (4-nitrophenyl) carbonate (1.1 g, 4.34 mmol, 1 eq), 3-bromo-5-piperazin-1-yl-pyrazolo[1,5-a]pyrimidine (1.23 g, 4.34 mmol, 1 eq) in MeCN (15 mL) was added DIEA (1.68 g, 13.03 mmol, 2.27 mL, 3 eq). The mixture was stirred at 25° C. for 6 hr. The reaction mixture was concentrated under reduced pressure to remove solvent. The residue was purified by flash silica gel chromatography to give (3-methyloxetan-3-yl)-4-(3-bromopyrazolo[1,5-a]pyrimidin-5-yl)piperazine-1-carboxylate (1.01 g, 2.49 mmol, 57.24% yield, 97.55% purity) as a solid.

LCMS m/z=395.9$^+$$[M+H]^+$.

$^1H$ NMR (400 MHz, DMSO-$d_6$) δ=8.70 (d, J=7.9 Hz, 1H), 7.98 (s, 1H), 6.80 (d, J=7.9 Hz, 1H), 4.66 (d, J=7.0 Hz, 2H), 4.42 (d, J=7.5 Hz, 2H), 3.85-3.66 (m, 4H), 3.51 (br s, 4H), 1.66 (s, 3H).

(3-methyloxetan-3-yl)-4-[3-[2-(cyclopropoxy)-3-pyridyl]pyrazolo[1,5-a]pyrimidin-5-yl]piperazine-1-carboxylate (Compound I-2)

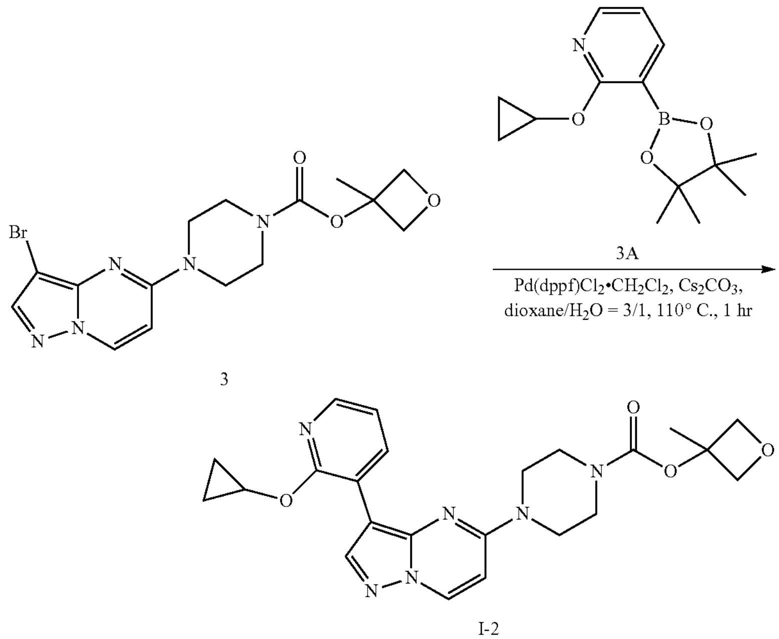

3

I-2

A mixture of 2-(cyclopropoxy)-3-(4,4,5,5-tetramethyl-1,3,2-dioxaborolan-2-yl)pyridine (75 mg, 287.22 umol, 1 eq), (3-methyloxetan-3-yl) 4-(3-bromopyrazolo[1,5-a]pyrimidin-5-yl)piperazine-1-carboxylate (113.81 mg, 287.22 umol, 1 eq), $Cs_2CO_3$ (280.75 mg, 861.66 umol, 3 eq), Pd(dppf)$Cl_2$·$CH_2Cl_2$ (46.91 mg, 57.44 umol, 0.2 eq) in dioxane (1.5 mL) and $H_2O$ (0.5 mL) was degassed and purged with $N_2$ for 3 times, and then the mixture was stirred at 110° C. for 1 hr under $N_2$ atmosphere. The reaction mixture was filtered and concentrated under reduced pressure to give a residue. The residue was purified by preparative HPLC. The pure fractions were collected and the volatiles were removed under vacuum. The residue was partitioned between acetonitrile (2 mL) and water (10 mL). The solution was lyophilized to dryness to give (3-methyloxetan-3-yl)-4-[3-[2-(cyclopropoxy)-3-pyridyl]pyrazolo[1,5-a]pyrimidin-5-yl]piperazine-1-carboxylate (8.32 mg, 17.70 umol, 6.16% yield, 95.835% purity) as an oil.

LCMS m/z=451.2 $[M+H]^+$.

$^1$H NMR (400 MHz, methanol-$d_4$) δ=8.87-8.76 (m, 1H), 8.46-8.41 (m, 1H), 8.40-8.33 (m, 1H), 8.00-7.91 (m, 1H), 7.10-7.02 (m, 1H), 6.74-6.63 (m, 1H), 4.80 (d, J=7.1 Hz, 2H), 4.53-4.48 (m, 2H), 4.37-4.30 (m, 1H), 3.82-3.74 (m, 4H), 3.68-3.54 (m, 4H), 1.77-1.70 (m, 3H), 0.90-0.76 (m, 4H).

Example 4: Synthesis of Compound I-3

(3-methyloxetan-3-yl)-4-[3-(4-carbamoylphenyl)pyrazolo[1,5-a]pyrimidin-5-yl]piperazine-1-carboxylate

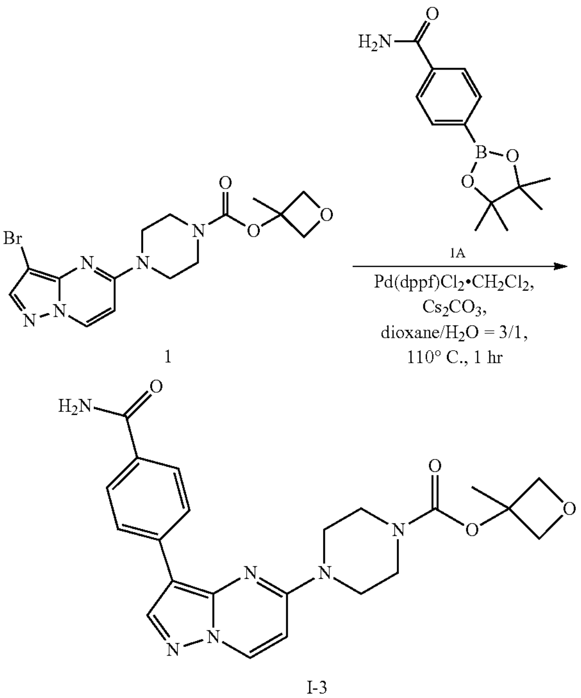

1

I-3

A mixture of (3-methyloxetan-3-yl)-4-(3-bromopyrazolo[1,5-a]pyrimidin-5-yl)piperazine-1-carboxylate (100 mg, 252.37 umol, 1 eq), 4-(4,4,5,5-tetramethyl-1,3,2-dioxaborolan-2-yl)benzamide (62.36 mg, 252.37 umol, 1 eq), $Cs_2CO_3$ (164:46 mg, 504.75 umol, 2 eq) in dioxane (0.75 mL) and $H_2O$ (0.25 mL) was degassed and purged with $N_2$ for 3 times, then the mixture was added $Pd(dppf)Cl_2 \cdot CH_2Cl_2$ (41.22 mg, 50.47 umol, 0.2 eq) and stirred at 110° C. for 1 hr under $N_2$ atmosphere. The reaction mixture was filtered and concentrated under reduced pressure to give a residue. The residue was purified by flash silica gel chromatography to afford the crude compound. Then the crude was further purified by preparative HPLC to give (3-methyloxetan-3-yl)-4-[3-(4-carbamoylphenyl)pyrazolo[1,5-a]pyrimidin-5-yl]piperazine-1-carboxylate (12.15 mg, 27.68 umol, 10.97% yield, 99.42% purity) as an oil.

LCMS m/z=437.0 $[M+H]^+$.

$^1$H NMR (400 MHz, DMSO-$d_6$) δ=8.86-8.63 (m, 1H), 8.60-8.35 (m, 1H), 8.14 (d, J=1.0 Hz, 2H), 7.90 (d, J=1.0 Hz, 3H), 7.23 (s, 1H), 6.86 (d, J=1.0 Hz, 1H), 4.65 (d, J=1.0 Hz, 2H), 4.37 (d, J=1.0 Hz, 2H), 3.89-3.76 (m, 4H), 3.61-3.52 (m, 4H), 1.66 (s, 3H).

Example 5: Synthesis of Compound I-4

(3-methyloxetan-3-yl)-4-[3-(3-carbamoylphenyl)pyrazolo[1,5-a]pyrimidin-5-yl]piperazine-1-carboxylate

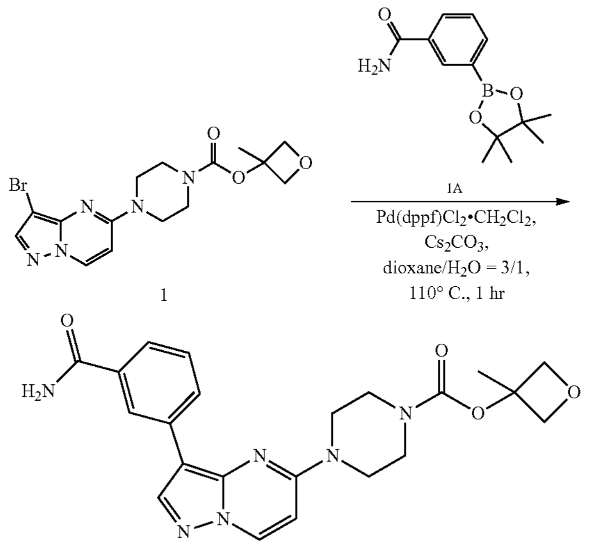

I-4

A mixture of (3-methyloxetan-3-yl)-4-(3-bromopyrazolo[1,5-a]pyrimidin-5-yl)piperazine-1-carboxylate (100 mg, 252.37 umol, 1 eq), 3-(4,4,5,5-tetramethyl-1,3,2-dioxaborolan-2-yl)benzamide (74.83 mg, 302.85 umol, 1.2 eq), $Pd(dppf)Cl_2 \cdot CH_2Cl_2$ (41.22 mg, 50.47 umol, 0.2 eq), $Cs_2CO_3$ (164.46 mg, 504.75 umol, 2 eq) in dioxane (1.5 mL), $H_2O$ (0.5 mL) was degassed and purged with $N_2$ for 3 times, and then the mixture was stirred at 110° C. for 1 hr under $N_2$ atmosphere. The reaction mixture was concentrated under reduced pressure to remove solvent. The crude was purified by flash silica gel chromatography to give crude product. Then the crude was further purified by preparative HPLC. The pure fractions were collected and the volatiles were removed under vacuum. The residue was partitioned between acetonitrile (2 mL) and water (10 mL). The solution was lyophilized to dryness to give (3-methyloxetan-3-yl)-4-[3-(3-carbamoylphenyl)pyrazolo[1,5-a]pyrimidin-5-yl]piperazine-1-carboxylate (25.25 mg, 55.55 umol, 22.01% yield, 96.019% purity) as a solid.

LCMS m/z=437.1 $[M+H]^+$.

$^1$H NMR (400 MHz, DMSO-$d_6$) δ=8.73 (d, J=7.9 Hz, 1H), 8.56 (s, 1H), 8.49 (s, 1H), 8.25 (d, J=7.8 Hz, 1H), 7.97 (s, 1H), 7.63 (d, J=7.6 Hz, 1H), 7.50-7.41 (m, J=7.8, 7.8 Hz, 1H), 7.33 (s, 1H), 6.80 (d, J=7.9 Hz, 1H), 4.67 (d, J=7.0 Hz, 2H), 4.42 (d, J=7.1 Hz, 2H), 3.81 (s, 4H), 3.53 (s, 4H), 1.66 (s, 3H).

Example 6: Synthesis of Compound I-5

3-bromo-5-(piperazin-1-yl)pyrazolo[1,5-a]pyrimidine

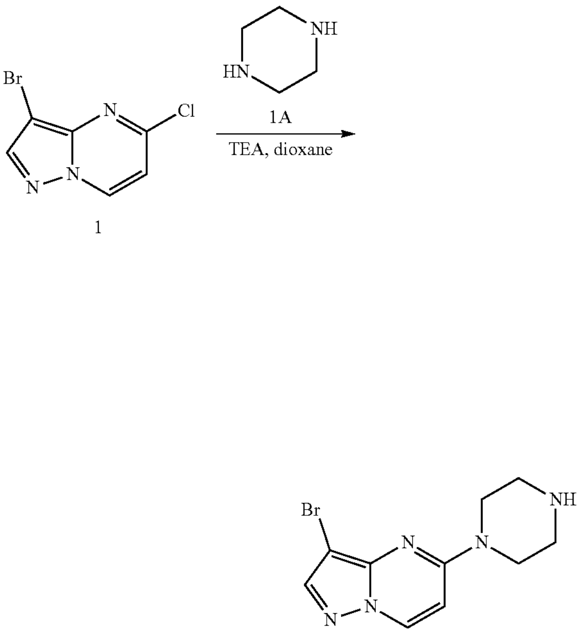

2

To a solution of 3-bromo-5-chloro-pyrazolo[1,5-a]pyrimidine (5 g, 21.51 mmol, 1 eq) and piperazine (5.56 g, 64.53 mmol, 3 eq) in dioxane (50 mL) was added TEA (6.53 g, 64.53 mmol, 8.98 mL, 3 eq). The mixture was stirred at 90° C. for 1 hr. LCMS (EC9655-1-P1A1) showed that desired MS was found. The mixture was filtered and the filtrate was concentrated to afford a residue. The residue was purified by silica gel chromatography (column height: 250 mm, diameter: 100 mm, 100-200 mesh silica gel, DCM/MeOH=9:1, $R_f$=0.30) to afford 3-bromo-5-piperazin-1-yl-pyrazolo[1,5-a]pyrimidine (6.63 g, crude) an oil.

LCMS m/z=284.0 $[C_{10}H_{12}{}^{81}BrN_5+H]^+$.

$^1$H NMR (DMSO-$d_6$, 400 MHz) 8.61 (d, J=7.9 Hz, 1H), 7.93 (s, 1H), 6.74 (d, J=7.9 Hz, 1H), 3.6-3.6 (m, 3H), 3.56 (s, 2H), 2.7-2.8 (m, 4H).

3-(2-methoxy-3-pyridyl)-5-piperazin-1-yl-pyrazolo [1,5-a]pyrimidine

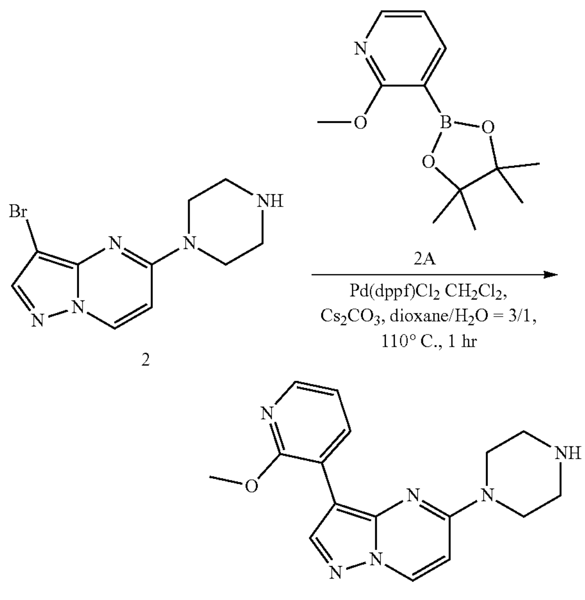

2 2A 3

A mixture of 3-bromo-5-piperazin-1-yl-pyrazolo[1,5-a] pyrimidine (2 g, 7.09 mmol, 1 eq), 2-methoxy-3-(4,4,5,5-tetramethyl-1,3,2-dioxaborolan-2-yl)pyridine (1.67 g, 7.09 mmol, 1 eq), $Cs_2CO_3$ (4.62 g, 14.18 mmol, 2 eq) in dioxane (15 mL) and $H_2O$ (5 mL) was degassed and purged with $N_2$ for 3 times, then added Pd(dppf)$Cl_2$·$CH_2Cl_2$ (1.16 g, 1.42 mmol, 0.2 eq) and then the mixture was stirred at 110° C. for 1 hr under $N_2$ atmosphere. The reaction mixture was concentrated under reduced pressure to give a residue. The residue was purified by flash silica gel chromatography to afford 3-(2-methoxy-3-pyridyl)-5-piperazin-1-yl-pyrazolo [1,5-a]pyrimidine (1.69 g, 4.47 mmol, 62.99% yield, 82% purity).

LCMS m/z=311.0 $[M+H]^+$.

$^1$H NMR (400 MHz, DMSO-$d_6$) δ 8.88-8.58 (m, 2H), 8.54-8.45 (m, 1H), 8.03-7.80 (m, 1H), 7.11-6.66 (m, 2H), 4.06-3.96 (m, 3H), 3.73-3.62 (m, 4H), 2.89-2.77 (m, 5H).

(4-nitrophenyl)-4-[3-(2-methoxy-3-pyridyl)pyrazolo [1,5-a]pyrimidin-5-yl]piperazine-1-carboxylate

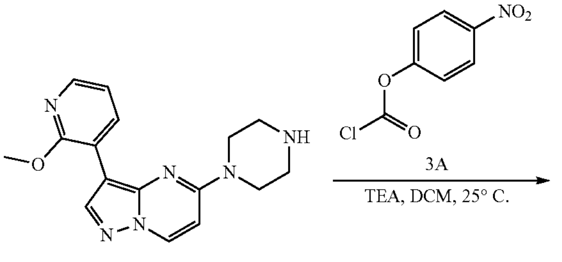

3 3A

-continued

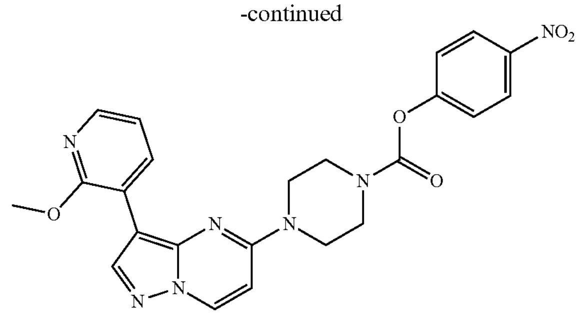

4

A mixture of 3-(2-methoxy-3-pyridyl)-5-piperazin-1-yl-pyrazolo[1,5-a]pyrimidine (400 mg, 1.29 mmol, 1 eq) in DCM (4 mL), was added TEA (391.25 mg, 3.87 mmol, 538.18 uL, 3 eq) and (4-nitrophenyl) carbonochloridate (311.74 mg, 1.55 mmol, 1.2 eq) under 0° C., and then the mixture was stirred at 25° C. for 0.5 hr. The mixture was filtered and the filtrate was concentrated to afford the crude. The residue was purified by silica gel chromatography (column height: 250 mm, diameter: 100 mm, 100-200 mesh silica gel, PE/EA=1:1, $R_f$=0.20) to afford (4-nitrophenyl) 4-[3-(2-methoxy-3-pyridyl)pyrazolo[1,5-a]pyrimidin-5-yl] piperazine-1-carboxylate (416 mg, 438.61 umol, 34.03% yield, 50.13% purity) as a solid.

LCMS m/z=476.1 $[M+H]^+$.

$^1$H NMR (DMSO-$d_6$, 400 MHz) δ=8.83 (dd, J=1.9, 7.5 Hz, 1H), 8.79 (d, J=7.9 Hz, 1H), 8.52 (s, 1H), 8.3-8.3 (m, 1H), 8.3-8.3 (m, 1H), 7.98 (dd, J=1.9, 4.9 Hz, 1H), 7.5-7.5 (m, 1H), 7.5-7.5 (m, 1H), 7.08 (dd, J=4.8, 7.5 Hz, 1H), 6.86 (d, J=7.9 Hz, 1H), 4.00 (s, 3H), 3.89 (br s, 4H), 3.80 (br s, 2H), 3.64 (br s, 2H).

(1-tert-butoxycarbonylpyrrolidin-3-yl)-4-[3-(2-methoxy-3-pyridyl)pyrazolo[1,5-a]pyrimidin-5-yl] piperazine-1-carboxylate

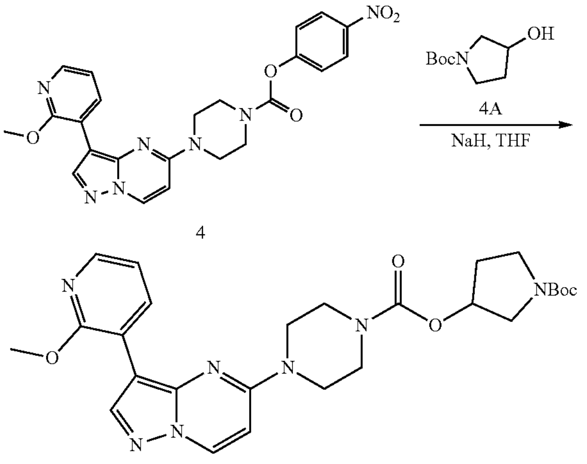

4 4A 5

To a solution of NaH (20.19 mg, 504.78 umol, 60% purity, 3 eq) in THF (0.5 mL) was added tert-butyl 3-hydroxypyrrolidine-1-carboxylate (315.04 mg, 1.68 mmol, 10 eq) and (4-nitrophenyl) 4-[3-(2-methoxy-3-pyridyl)pyrazolo[1,5-a] pyrimidin-5-yl]piperazine-1-carboxylate (80 mg, 168.26 umol, 1 eq) in one portion at 0° C. under $N_2$. The mixture was stirred at 25° C. for 1 hr. The mixture was poured into sat. $NH_4Cl$ (aq.) (50 mL) and extracted with DCM (20 mL×3), the combined organic layers were concentrated to afford the crude. The residue was purified by preparative HPLC. The pure fractions were collected and the volatiles were removed under vacuum. The residue was partitioned between acetonitrile (2 mL) and water (10 mL). The solution was lyophilized to dryness to give the product (1-tert-butoxycarbonylpyrrolidin-3-yl)-4-[3-(2-methoxy-3-pyridyl)pyrazolo[1,5-a]pyrimidin-5-yl]piperazine-1-carboxylate (45 mg, 85.95 umol, 51.08% yield) as a solid.

LCMS m/z=524.2 $[M+H]^+$.

Pyrrolidin-3-yl4-[3-(2-methoxy-3-pyridyl)pyrazolo[1,5-a]pyrimidin-5-yl]piperazine-1-carboxylate

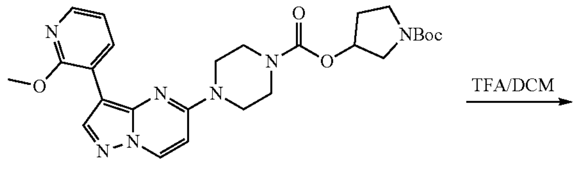

5

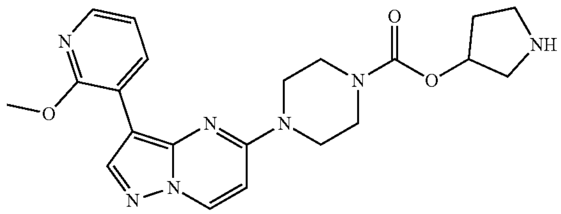

I-5

To a solution of (1-tert-butoxycarbonylpyrrolidin-3-yl), 4-[3-(2-methoxy-3-pyridyl)pyrazolo[1,5-a]pyrimidin-5-yl]piperazine-1-carboxylate (45 mg, 85.95 umol, 1 eq) in DCM (1 mL) was added TFA (29.40 mg, 257.84 umol, 19.09 uL, 3 eq). The mixture was stirred at 25° C. for 0.5 hr. The mixture was filtered and the filtrate was concentrated to afford the crude. The residue was purified by preparative HPLC. The pure fractions were collected and the volatiles were removed under vacuum. The residue was partitioned between acetonitrile (2 mL) and water (10 mL). The solution was lyophilized to dryness to give the product. pyrrolidin-3-yl 4-[3-(2-methoxy-3-pyridyl)pyrazolo[1,5-a]pyrimidin-5-yl]piperazine-1-carboxylate (20.93 mg, 49.43 umol, 57.51% yield, 100% purity) was obtained as an oil.

LCMS m/z=424.0 $[M+H]^+$.

SFC $t_R$=0.651 min, 1.544 min; 49.24%, 50.76%.

$^1H$ NMR (methanol-$d_4$, 400 MHz) δ=8.8-8.9 (m, 1H), 8.53 (s, 1H), 8.49 (d, J=7.9 Hz, 1H), 7.9-8.0 (m, 1H), 7.0-7.1 (m, 1H), 6.75 (d, J=7.9 Hz, 1H), 5.3-5.4 (m, 1H), 4.06 (s, 3H), 3.8-3.9 (m, 4H), 3.66 (s, 4H), 3.50 (d, J=2.8 Hz, 2H), 3.4-3.5 (m, 2H), 2.2-2.3 (m, 2H).

Example 7: Synthesis of Compound I-6

3-bromo-5-(piperazin-1-yl)pyrazolo[1,5-a]pyrimidine

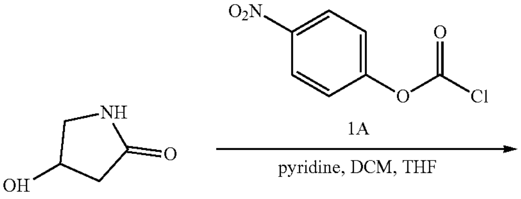

1A

1

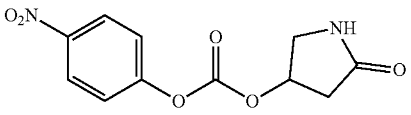

2

A mixture of 4-hydroxypyrrolidin-2-one (500 mg, 4.95 mmol, 1 eq), (4-nitrophenyl) carbonochloridate (996.82 mg, 4.95 mmol, 1 eq), pyridine (1.17 g, 14.84 mmol, 1.20 mL, 3 eq), in DCM (5 mL) and THF (1 mL) was degassed and purged with $N_2$ for 3 times, and then the mixture was stirred at 25° C. for 1 hr under $N_2$ atmosphere. The reaction mixture was filtered and concentrated under reduced pressure to give 4-nitrophenyl) (5-oxopyrrolidin-3-yl) carbonate (1.1 g, 4.13 mmol, 83.55% yield) as a solid.

LCMS m/z=266.9 $[M+H]^+$.

(5-Oxopyrrolidin-3-yl) 4-[3-(2-methoxy-3-pyridyl)pyrazolo[1,5-a]pyrimidin-5-yl]piperazine-1-carboxylate

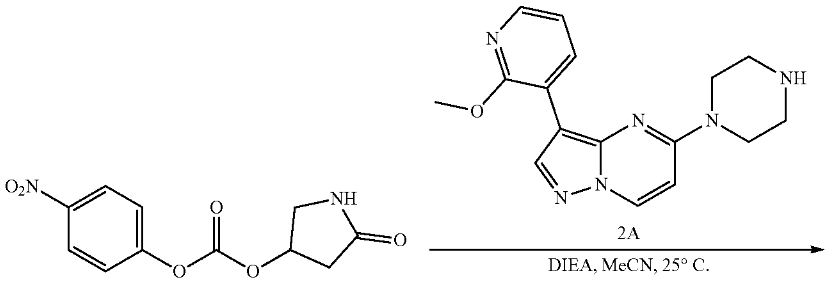

2A

2

-continued

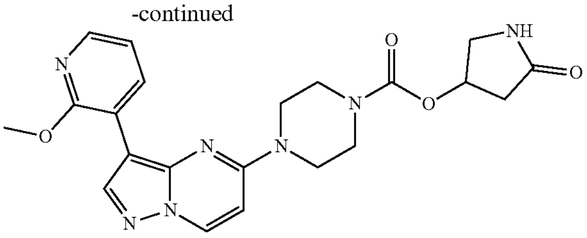

I-6

To a solution of (4-nitrophenyl) (5-oxopyrrolidin-3-yl) carbonate (300 mg, 1.13 mmol, 1 eq) and 3-(2-methoxy-3-pyridyl)-5-piperazin-1-yl-pyrazolo[1,5-a]pyrimidine (349.75 mg, 1.13 mmol, 1 eq) in MeCN (3 mL) was added DIEA (436.94 mg, 3.38 mmol, 588.87 uL, 3 eq). The mixture was stirred at 25° C. for 1 hr. The reaction mixture was filtered and concentrated under reduced pressure to give a residue. The crude was purified by preparative HPLC. The pure fractions were collected and the volatiles were removed under vacuum. The residue was partitioned between acetonitrile (20 mL) and water (100 mL). The solution was lyophilized to dryness to give (5-oxopyrrolidin-3-yl)-4-[3-(2-methoxy-3-pyridyl)pyrazolo[1,5-a]pyrimidin-5-yl] piperazine-1-carboxylate (215.48 mg, 474.75 μmol, 42.13% yield, 96.38% purity) as a solid.

LCMS m/z=438.1 $[M+H]^+$.

SFC $t_R$=1.163, 2.400 min; 50.367%, 49.633%).

$^1$H NMR (400 MHz, DMSO-$d_6$) δ=8.85-8.80 (m, 1H), 8.79-8.74 (m, 1H), 8.54-8.49 (m, 1H), 8.00-7.95 (m, 1H), 7.77-7.71 (m, 1H), 7.12-7.05 (m, 1H), 6.85-6.79 (m, 1H), 5.25-5.16 (m, 1H), 3.99 (s, 3H), 3.80-3.74 (m, 4H), 3.64-3.59 (m, 1H), 3.56-3.50 (m, 4H), 3.25 (d, J=11.4 Hz, 1H), 2.66-2.61 (m, 1H), 2.21-2.12 (m, 1H).

Example 8: Synthesis of Compound I-8 tert-butyl 3-methyl-3-(4-nitrophenoxy)carbonyloxy-pyrrolidine-1-carboxylate

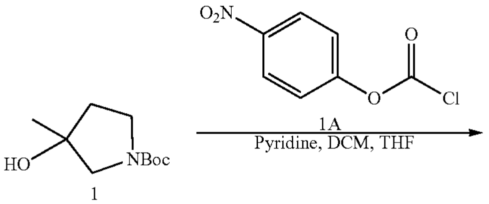

1

-continued

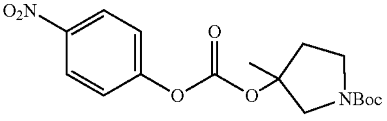

2

A mixture of tert-butyl 3-hydroxy-3-methyl-pyrrolidine-1-carboxylate (400 mg, 1.99 mmol, 1 eq), (4-nitrophenyl) carbonochloridate (400.60 mg, 1.99 mmol, 1 eq), pyridine (471.62 mg, 5.96 mmol, 481.25 uL, 3 eq) in DCM (4 mL) and THF (0.8 mL) was stirred at 25° C. for 2 hr. The reaction mixture was diluted with water (15 mL) and DCM (10 mL*3). The combined organic layers were washed with brine solution, dried over sodium sulphate, concentrated under reduced pressure. The crude was purified by flash silica gel chromatography to give tert-butyl 3-methyl-3-(4-nitrophenoxy)carbonyloxy-pyrrolidine-1-carboxylate (227 mg, 257.25 μmol, 12.94% yield, 41.518% purity) as an oil.

LCMS m/z=266.9 $[M-100+H]^+$.

$^1$H NMR (400 MHz, DMSO-$d_6$) δ=8.32 (d, J=9.1 Hz, 2H), 8.13 (d, J=9.1 Hz, 2H), 7.57 (d, J=9.1 Hz, 2H), 6.94 (d, J=9.3 Hz, 2H), 3.74 (br d, J=12:3 Hz, 1H), 2.11-1.98 (m, 1H), 1.66 (s, 3H), 1.41 (br d, J=2.9 Hz, 9H).

(1-tert-Butoxycarbonyl-3-methyl-pyrrolidin-3-yl)-4-[3-(2-methoxy-3-pyridyl)pyrazolo[1,5-a]pyrimidin-5-yl]piperazine-1-carboxylate

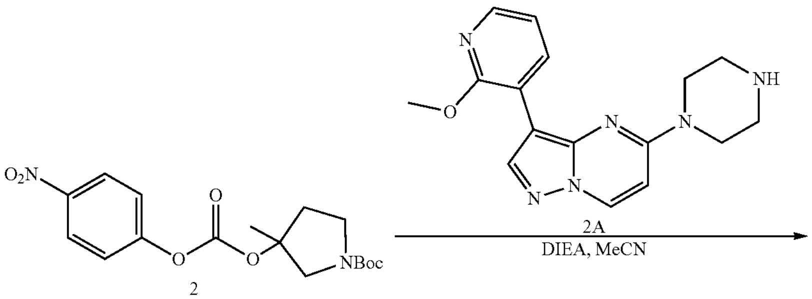

2

-continued

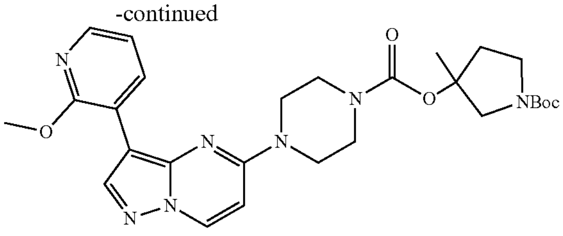

3

To a solution of tert-butyl 3-methyl-3-(4-nitrophenoxy)carbonyloxy-pyrrolidine-1-carboxylate (120 mg, 327.54 umol, 1 eq), 3-(2-methoxy-3-pyridyl)-5-piperazin-1-yl-pyrazolo[1,5-a]pyrimidine (101.65 mg, 327.54 umol, 1 eq) in MeCN (2 mL) was added DIEA (127.00 mg, 982.63 umol, 171.16 uL, 3 eq). The mixture was stirred at 25° C. for 1 hr. The reaction mixture was concentrated under reduced pressure to remove solvent. The crude was purified by flash silica gel chromatography to give (1-tert-butoxycarbonyl-3-methyl-pyrrolidin-3-yl)-4-[3-(2-methoxy-3-pyridyl)pyrazolo[1,5-a]pyrimidin-5-yl]piperazine-1-carboxylate (100 mg, 142.57 umol, 43.53% yield, 76.647% purity) as a solid.

LCMS m/z=538.2 $[M+H]^+$.

$^1$H NMR (400 MHz, DMSO-$d_6$) δ=8.81 (d, J=6.9 Hz, 1H), 8.76 (d, J=8.0 Hz, 1H), 8.51 (s, 1H), 7.99 (d, J=4.9 Hz, 1H), 7.08 (dd, J=4.7, 7.3 Hz, 1H), 6.82 (d, J=7.9 Hz, 1H), 4.00 (s, 3H), 3.75 (br s, 4H), 3.50 (br d, J=3.4 Hz, 4H), 3.18 (br d, J=4.4 Hz, 2H), 2.33. (br s, 3H), 1.99 (s, 1H), 1.58 (br s, 3H), 1.39 (s, 9H).

(3-Methylpyrrolidin-3-yl)-4-[3-(2-methoxy-3-pyridyl)pyrazolo[1,5-a]pyrimidin-5-yl]piperazine-1-carboxylate

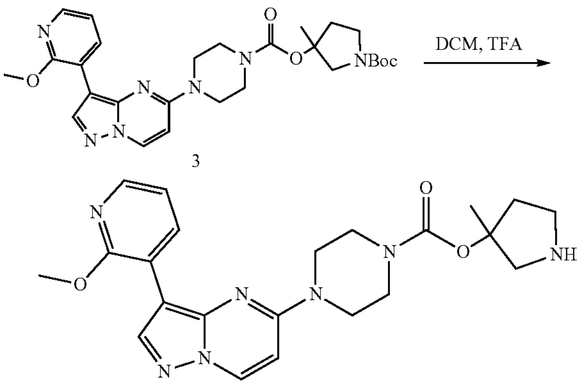

3

I-8

To a solution of (1-tert-butoxycarbonyl-3-methyl-pyrrolidin-3-yl) 4-[3-(2-methoxy-3-pyridyl)pyrazolo[1,5-a]pyrimidin-5-yl]piperazine-1-carboxylate (100.0 mg, 186.0 umol, 1 eq) in DCM (1 mL) was added TFA (4.34 g, 38.03 mmol, 2.82 mL, 204.45 eq). The mixture was stirred at 25° C. for 1 hr. The reaction mixture was concentrated under reduced pressure. The crude was purified by preparative HPLC. The pure fractions were collected and the volatiles were removed under vacuum. The residue was partitioned between acetonitrile (20 mL) and water (100 mL). The solution was lyophilized to dryness to (3-methylpyrrolidin-3-yl) 4-[3-(2-methoxy-3-pyridyl)pyrazolo[1,5-a]pyrimidin-5-yl]piperazine-1-carboxylate (43.52 mg, 98.18 umol, 52.78% yield, 98.699% purity) as an oil.

LCMS m/z=438.1 $[M+H]^+$.

SFC $t_R$=1.518, 1.578 min; 38.159%, 61.841%.

$^1$H NMR (400 MHz, methanol-$d_4$) δ=7.17 (d, J=1.0 Hz, 1H), 6.83 (s, 1H), 6.75 (d, J=7.1 Hz, 1H), 6.29 (d, J=1.0 Hz, 1H), 5.43-5.33 (m, 1H), 4.98 (d, J=1.0 Hz, 1H), 2.45 (s, 3H), 2.35 (d, J=1.0 Hz, 1H), 2.12-1.88 (m, 9H), 1.82-1.57 (m, 2H), 1.10-0.96 (m, 1H), 0.63-0.47 (m, 1H), 0.13 (s, 3H).

Example 9: Synthesis of Compound I-9

(1-tert-Butoxycarbonyl-3-ethynyl-pyrrolidin-3-yl)-4-[3-(2-methoxy-3-pyridyl)pyrazolo[1,5-a]pyrimidin-5-yl]piperazine-1-carboxylate

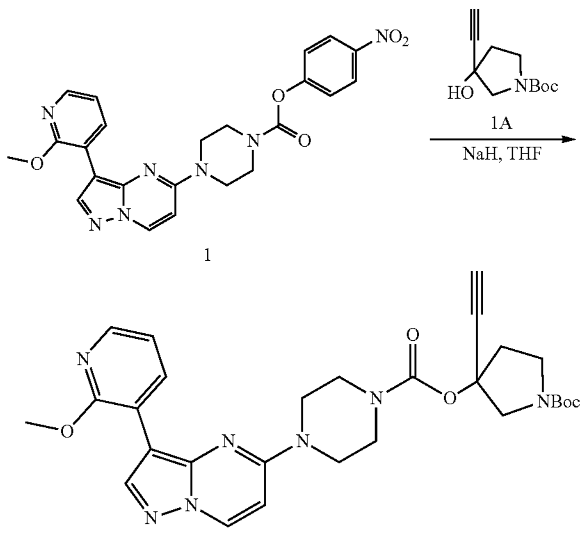

1

2

To a solution of NaH (37.85 mg, 946.46 umol, 60% purity, 3 eq) in THF (2 mL) was added tert-butyl 3-ethynyl-3-hydroxy-pyrrolidine-1-carboxylate (199.95 mg, 946.46 umol, 3 eq) and (4-nitrophenyl) 4-[3-(2-methoxy-3-pyridyl)pyrazolo[1,5-a]pyrimidin-5-yl]piperazine-1-carboxylate (150 mg, 315.49 umol, 1 eq) at 0° C. under $N_2$ atmosphere. The mixture was stirred at 25° C. for 1 hr. The mixture was poured into sat. $NH_4Cl$ (aq.) (20 mL) and extracted with DCM (20 mL*3), the combined organic layers were concentrated to afford the crude. The residue was purified by preparative HPLC. The pure fractions were collected and the volatiles were removed under vacuum. The residue was partitioned between acetonitrile (2 mL) and water (10 mL).

The solution was lyophilized to dryness to give (1-tert-butoxycarbonyl-3-ethynyl-pyrrolidin-3-yl)-4-[3-(2-methoxy-3-pyridyl)pyrazolo[1,5-a]pyrimidin-5-yl]piperazine-1-carboxylate (85 mg, 86.15 umol, 27.31% yield, 55.50% purity) as a solid.

LCMS m/z=548.3 $[M+H]^+$.

$^1H$ NMR (400 MHz, methanol-$d_4$) δ=8.84 (dd, J=1.6, 7.5 Hz, 1H), 8.52 (s, 1H), 8.46 (d, J=7.9 Hz, 1H), 7.94 (dd, J=1.8, 4.9 Hz, 1H), 7.03 (dd, J=5.0, 7.5 Hz, 1H), 6.71 (d, J=7.9 Hz, 1H), 4.57 (s, 1H), 4.06 (s, 3H), 3.93 (d, J=12.1 Hz, 1H), 3.80 (br d, J=3.3 Hz, 4H), 3.77 (br s, 1H), 3.64 (br d, J=4.9 Hz, 4H), 3.4-3.6 (m, 2H), 2.5-2.6 (m, 1H), 2.4-2.5 (m, 1H), 1.46 (s, 9H).

(3-Ethynylpyrrolidin-3-yl) 4-[3-(2-methoxy-3-pyridyl)pyrazolo[1,5-a]pyrimidin-5-yl]piperazine-1-carboxylate

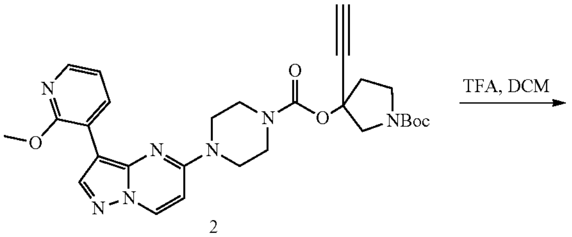

2

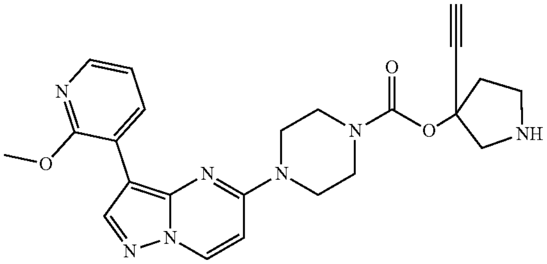

I-9

To a solution of (1-tert-butoxycarbonyl-3-ethynyl-pyrrolidin-3-yl)-4-[3-(2-methoxy-3-pyridyl)pyrazolo[1,5-a]pyrimidin-5-yl]piperazine-1-carboxylate (40 mg, 73.05 umol, 1 eq) in DCM (0.5 mL) was added TFA (24.99 mg, 219.14 umol, 16.23 uL, 3 eq). The mixture was stirred at 25° C. for 0.5 hr. The mixture was filtered and the filtrate was concentrated to afford the crude. The residue was purified by preparative HPLC. The pure fractions were collected and the volatiles were removed under vacuum. The residue was partitioned between acetonitrile (2 mL) and water (10 mL). The solution was lyophilized to dryness to give (3-ethynylpyrrolidin-3-yl)-4-[3-(2-methoxy-3-pyridyl)pyrazolo[1,5-a]pyrimidin-5-yl]piperazine-1-carboxylate (5.84 mg, 12.98 umol, 17.77% yield, 99.46% purity) as a solid.

LCMS m/z=448.1 $[M+H]^+$.

SFC $t_R$=0.973, 1.181 min; 97.0%, 3.02%.

$^1H$ NMR (400 MHz, methanol-$d_4$) δ=8.8-8.9 (m, J=1.8, 7.6 Hz, 1H), 8.52 (s, 1H), 8.47 (d, J=7.9 Hz, 1H), 7.9-8.0 (m, J=1.8, 4.9 Hz, 1H), 7.0-7.1 (m, 1H), 6.72 (d, J=7.9 Hz, 1H), 4.06 (s, 3H), 3.94 (d, J=12.8 Hz, 1H), 3.83 (d, J=1.0 Hz, 4H), 3.65 (d, J=6.3 Hz, 4H), 3.59 (d, J=13.0 Hz, 1H), 3.4-3.5 (m, 2H), 3.34 (s, 1H), 2.7-2.8 (m, 1H), 2.4-2.6 (m, 1H).

Example 10: Synthesis of Compound I-10

(4-Nitrophenyl) [(3R)-5-oxopyrrolidin-3-yl] carbonate

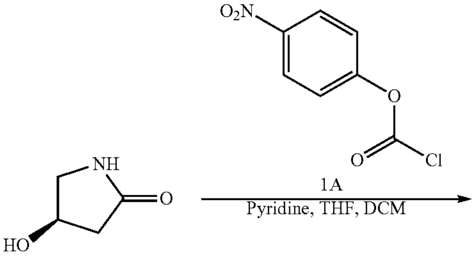

1

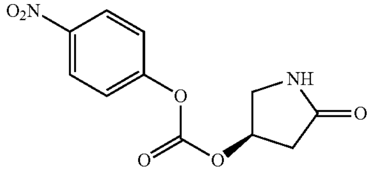

2

A mixture of (4R)-4-hydroxypyrrolidin-2-one (3 g, 29.67 mmol, 1 eq), (4-nitrophenyl) carbonochloridate (5.98 g, 29.67 mmol, 1 eq), pyridine (7.04 g, 89.02 mmol, 7.18 mL, 3 eq) in DCM (30 mL) and THF (7.5 mL) was degassed and purged with $N_2$ for 3 times, and then the mixture was stirred at 25° C. for 1 hour under $N_2$ atmosphere. The reaction mixture was filtered and concentrated under reduced pressure to give (4-nitrophenyl) [(3R)-5-oxopyrrolidin-3-yl] carbonate (10.99 g, crude) as a black oil.

LCMS m/z=267.1 $[M+H]^+$.

[(3R)-5-Oxopyrrolidin-3-yl]-4-[3-[2-(cyclopropoxy)-3-pyridyl]pyrazolo[1,5-a]pyrimidin-5-yl]piperazine-1-carboxylate

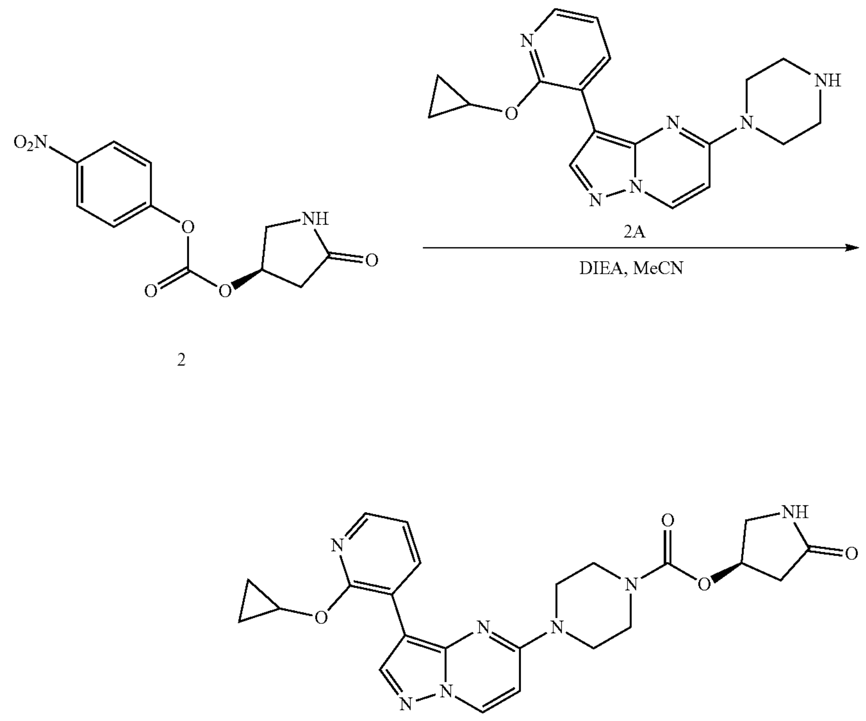

I-10

To a solution of (4-nitrophenyl) [(3R)-5-oxopyrrolidin-3-yl] carbonate (3.17 g, 11.89 mmol, 4 eq) and 3-[2-(cyclopropoxy)-3-pyridyl]-5-piperazin-1-yl-pyrazolo[1,5-a]pyrimidine (1 g, 2.97 mmol, 1 eq) in MeCN (31 mL) was added DIEA (1.34 g, 10.40 mmol, 1.81 mL, 3.5 eq). The mixture was stirred at 25° C. for 1 hour. The reaction mixture was filtered and concentrated under reduced pressure to give a residue. The crude was purified by preparative HPLC. The pure fractions were collected and the volatiles were removed under vacuum. The residue was partitioned between acetonitrile (10 mL) and water (30 mL). The solution was lyophilized to dryness to give [(3R)-5-oxopyrrolidin-3-yl] 4-[3-[2-(cyclopropoxy)-3-pyridyl]pyrazolo[1,5-a]pyrimidin-5-yl]piperazine-1-carboxylate (660 mg, 1.36 mmol, 45.63% yield, 95.25% purity) as a solid.

LCMS m/z=464.1 $[M+H]^+$.

SFC $t_R$=2.802, 2.934 min; 99.61%, 0.39%.

$^1H$ NMR (400 MHz, DMSO-$d_6$) δ=8.82-8.77 (m, 1H), 8.75 (d, J=7.9 Hz, 1H), 8.34 (s, 1H), 8.03-7.95 (m, 1H), 7.74 (s, 1H), 7.16-7.07 (m, 1H), 6.81 (d, J=7.9 Hz, 1H), 5.24-5.16 (m, 1H), 4.44-4.35 (m, 1H), 3.80-3.72 (m, 4H), 3.64-3.58 (m, 1H), 3.57-3.46 (m, 4H), 3.28-3.21 (m, 1H), 2.69-2.59 (m, 1H), 2.21-2.12 (m, 1H), 0.84-0.74 (m, 4H).

Example 11: Synthesis of Compound I-11

3-Bromo-2-(cyclopropoxy)pyridine

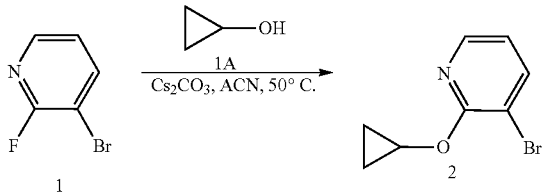

1 2

To a solution of 3-bromo-2-fluoro-pyridine (50 g, 284.11 mmol, 1 eq), cyclopropanol (21.45 g, 369.35 mmol, 1.3 eq) in MeCN (300 mL) was added $Cs_2CO_3$ (138.85 g, 426.17 mmol, 1.5 eq). The mixture was stirred at 70° C. for 2 hr. The reaction mixture was concentrated under reduced pressure to give the crude product. The other reaction (50 g scale) was performed by same procedures to afford the other batch crude product. The two crude batches were combined and purified by FCC to obtain 3-bromo-2-(cyclopropoxy)pyridine (53 g, 239.42 mmol, 42.14% yield, 96.7% purity) as an oil.

LCMS m/z=214.2 $[M+H]^+$.

$^1H$ NMR (400 MHz, DMSO-$d_6$) δ=8.21 (br d, J=4.8 Hz, 1H), 8.02 (d, J=7.6 Hz, 1H), 6.99 (dd, J=5.5, 6.9 Hz, 1H), 4.38-4.18 (m, 1H), 0.83-0.77 (m, 2H), 0.70 (br s, 2H).

2-(Cyclopropoxy)-3-(4,4,5,5-tetramethyl-1,3,2-dioxaborolan-2-yl)pyridine

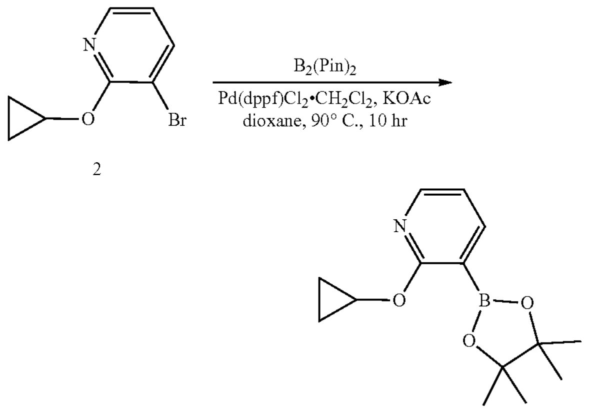

2

3

A mixture of 3-bromo-2-(cyclopropoxy)pyridine (25 g, 116.79 mmol, 1 eq), 4,4,5,5-tetramethyl-2-(4,4,5,5-tetramethyl-1,3,2-dioxaborolan-2-yl)-1,3,2-dioxaborolane (35.59 g, 140.15 mmol, 1.2 eq), KOAc (22.92 g, 233.58 mmol, 2 eq) and $Pd(dppf)Cl_2{\cdot}CH_2Cl_2$ (9.54 g, 11.68 mmol, 0.1 eq) in dioxane (400 mL) was degassed and purged with $N_2$ for 3 times, and then the mixture was stirred at 90° C. for 10 hr under $N_2$ atmosphere. The reaction mixture was concentrated under reduced pressure. The crude was purified by FCC to obtain 2-(cyclopropoxy)-3-(4,4,5,5-tetramethyl-1,3,2-dioxaborolan-2-yl)pyridine (15.6 g, 18.98 mmol, 16.25% yield, 31.768% purity) as a liquid.

LCMS m/z=262.1 $[M+H]^+$.

$^1H$ NMR (400 MHz, DMSO-$d_6$) δ=8.26 (dd, J=2.1, 5.0 Hz, 1H), 7.84 (dd, J=2.1, 7.1 Hz, 1H), 6.97 (dd, J=4.9, 7.1 Hz, 1H), 4.22 (tt, J=3.0, 6.2 Hz, 1H), 1.25 (s, 12H), 0.74-0.68 (m, 2H), 0.61-0.55 (m, 2H).

3-bromo-5-piperazin-1-yl-pyrazolo[1,5-a]pyrimidine

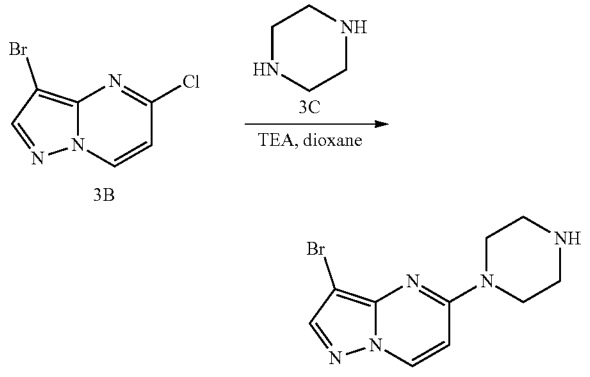

3B

3A

To a solution of 3-bromo-5-chloro-pyrazolo[1,5-a]pyrimidine (50 g, 215.09 mmol, 1 eq) and TEA (65.29 g, 645.26 mmol, 89.81 mL, 3 eq) in dioxane (100 mL) was added piperazine (55.58 g, 645.26 mmol, 3 eq). The mixture was stirred at 90° C. for 10 hr. The reaction mixture was diluted with water and extracted with EA (200 mL*3). The combined organic layers were washed with brine solution, dried over sodium sulphate, concentrated under reduced pressure. The residue was used into the next step without further purification. The product 3-bromo-5-piperazin-1-yl-pyrazolo[1,5-a]pyrimidine (56.6 g, 197.54 mmol, 91.84% yield, 98.469% purity) was obtained as a solid.

LCMS m/z=282.0 $[M+H]^+$.

$^1H$ NMR (400 MHz, DMSO-$d_6$) δ=8.61 (d, J=7.9 Hz, 1H), 7.94 (s, 1H), 6.74 (d, J=7.9 Hz, 1H), 3.69-3.58 (m, 4H), 3.17 (s, 1H), 2.83-2.70 (m, 4H).

3-[2-(Cyclopropoxy)-3-pyridyl]-5-piperazin-1-yl-pyrazolo[1,5-a]pyrimidine

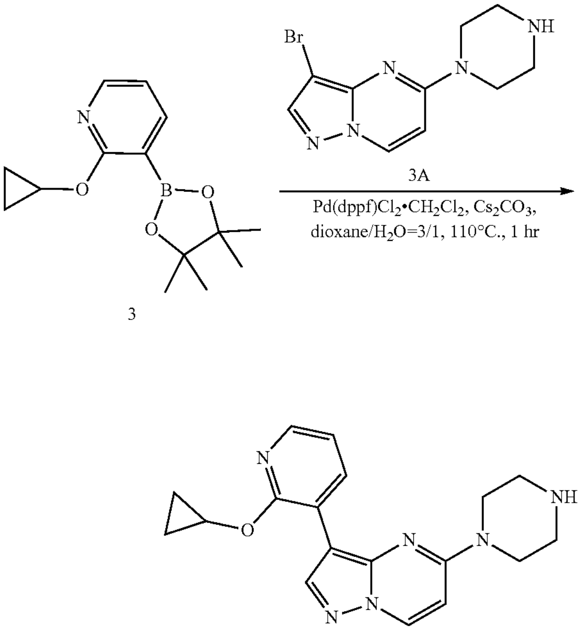

3

4

A mixture of 2-(cyclopropoxy)-3-(4,4,5,5-tetramethyl-1,3,2-dioxaborolan-2-yl)pyridine (28.8 g, 110.29 mmol, 1 eq), 3-bromo-5-piperazin-1-yl-pyrazolo[1,5-a]pyrimidine (31.12 g, 110.29 mmol, 1 eq), $Pd(dppf)Cl_2{\cdot}CH_2Cl_2$ (9.01 g, 11.03 mmol, 0.1 eq), $Cs_2CO_3$ (71.87 g, 220.59 mmol, 2 eq) and in dioxane (300 mL) and $H_2O$ (100 mL) was degassed and purged with $N_2$ for 3 times, and then the mixture was stirred at 110° C. for 1 hr under $N_2$ atmosphere. The reaction mixture was concentrated under reduced pressure. The crude was purified by FCC (ISCO®; 12 g SepaFlash®Silica Flash Column, eluent of 0~12% MeOH/DCM gradient @ 80 mL/min) to give 3-[2-(cyclopropoxy)-3-pyridyl]-5-piperazin-1-yl-pyrazolo[1,5-a]pyrimidine (19.2 g, 55.58 mmol, 50.39% yield, 97.376% purity) as a liquid.

LCMS m/z=337.2 $[M+H]^+$.

$^1H$ NMR (400 MHz, DMSO-$d_6$) δ=8.78 (br d, J=7.1 Hz, 1H), 8.67 (br d, J=7.6 Hz, 1H), 8.32 (s, 1H), 7.99 (br s, 1H), 7.10 (br t, J=5.0 Hz, 1H), 6.78 (br d, J=7.6 Hz, 1H), 5.75 (s, 1H), 4.40 (br s, 1H), 3.65 (br s, 4H), 2.80 (br s, 4H), 0.78 (br s, 4H).

(4-Nitrophenyl) [(3S)-5-oxopyrrolidin-3-yl] carbonate

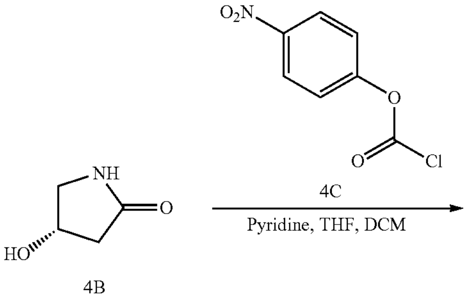

-continued

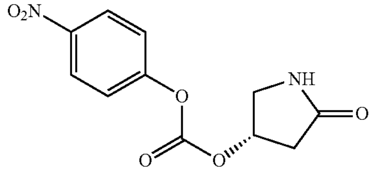

4A

A mixture of (4S)-4-hydroxypyrrolidin-2-one (30 g, 296.73 mmol, 1 eq), (4-nitrophenyl) carbonochloridate (59.81 g, 296.73 mmol, 1 eq), Pyridine (46.94 g, 593.45 mmol, 47.90 mL, 2 eq) in DCM (150 mL) and THF (30 mL) was degassed and purged with $N_2$ for 3 times, and then the mixture was stirred at 25° C. for 10 hr under $N_2$ atmosphere. The reaction mixture was diluted with water, and extracted with DCM (2000 mL×3). The combined organic layers were washed with brine solution, dried over sodium sulphate, concentrated under reduced pressure. The residue was used into the next step without further purification. The product (4-nitrophenyl) [(3S)-5-oxopyrrolidin-3-yl] carbonate (44.4 g, 135.21 mmol, 45.57% yield, 81.065% purity) was obtained as a solid.

LCMS m/z=267.1 $[M+H]^+$.

$^1H$ NMR (400 MHz, DMSO-$d_6$) δ=8.32 (br d, J=9.0 Hz, 2H), 7.85 (br s, 1H), 7.60 (br d, J=9.0 Hz, 2H), 5.34 (br t, J=5.6 Hz, 1H), 3.73-3.63 (m, 2H), 3.45 (br d, J=11.9 Hz, 1H), 2.35 (br d, J=17.6 Hz, 1H).

[(3S)-5-Oxopyrrolidin-3-yl]-4-[3-[2-(cyclopropoxy)-3-pyridyl]pyrazolo[1,5-a]pyrimidin-5-yl]piperazine-1-carboxylate hydrochloric acid

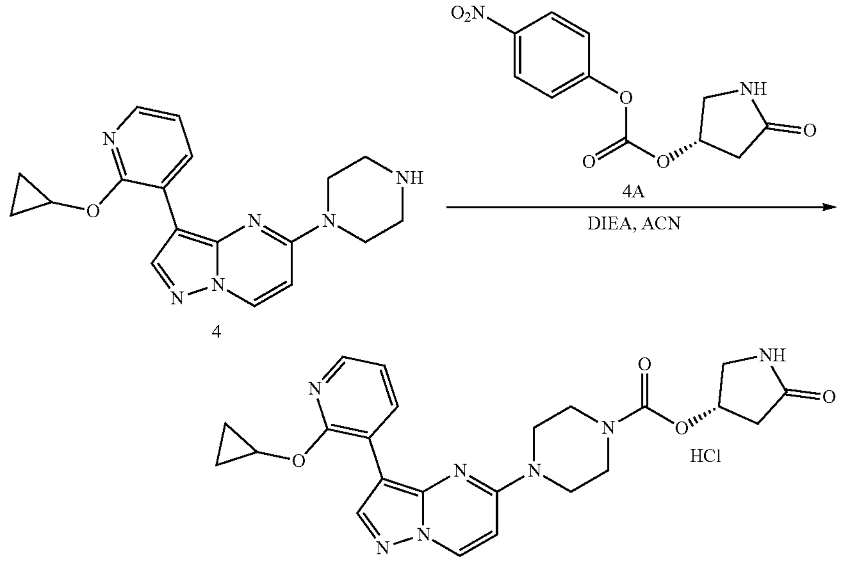

To a solution of 3-[2-(cyclopropoxy)-3-pyridyl]-5-piperazin-1-yl-pyrazolo[1,5-a]pyrimidine (10 g, 29.73 mmol, 1 eq), (4-nitrophenyl) [(3S)-5-oxopyrrolidin-3-yl] carbonate (11.87 g, 44.59 mmol, 1.5 eq) in MeCN (150 mL) was added DIEA (7.68 g, 59.45 mmol, 10.36 mL, 2 eq) and 4-pyrrolidin-1-ylpyridine (440.57 mg, 2.97 mmol, 0.1 eq). The mixture was stirred at 25° C. for 1 hr. The mixture was concentrated under reduced pressure. The residue was diluted with water and extracted with DCM (300 mL×3). The combined organic layers were washed with brine solution, dried over sodium sulphate, and concentrated under reduced pressure. The crude was purified by preparative HPLC and converted to the HCl salt to provide [(3S)-5-oxopyrrolidin-3-yl] 4-[3-[2-(cyclopropoxy)-3-pyridyl]pyrazolo[1,5-a]pyrimidin-5-yl]piperazine-1-carboxylate hydrochloric acid (7.50 g, 15.59 mmol, 26.2% yield) as the desired product.

LCMS m/z=464.2 $[M+H]^+$.

SFC $t_R$=1.720 min; 100%.

$^1H$ NMR (400 MHz, DMSO-$d_6$) δ=8.80 (dd, J=1.8, 7.6 Hz, 1H), 8.75 (br d, J=7.9 Hz, 1H), 8.35 (s, 1H), 8.01 (br dd,

J=1.9, 4.8 Hz, 1H), 7.75 (s, 1H), 7.12 (dd, J=4.8, 7.6 Hz, 1H), 6.82 (br d, J=7.9 Hz, 1H), 5.21 (br s, 1H), 4.48-4.35 (m, 1H), 3.77 (br s, 4H), 3.64-3.60 (m, 1H), 3.53 (br s, 4H), 3.24 (br s, 1H), 2.64 (br dd, J=6.9, 17.5 Hz, 1H), 2.17 (br dd, J=1.6, 17.4 Hz, 1H), 0.82-0.75 (m, 4H).

LCMS m/z=464.1 $[M+H]^+$.

SFC $t_R$=1.709 min; 100%).

$^1$H NMR (400 MHz, DMSO-$d_6$) δ=8.81 (dd, J=1.6, 7.4 Hz, 1H), 8.76 (br d, J=7.9 Hz, 1H), 8.35 (s, 1H), 8.02 (br dd, J=1.6, 4.7 Hz, 1H), 7.75 (s, 1H), 7.13 (dd, J=4.9, 7.4 Hz, 1H), 6.82 (br d, J=7.9 Hz, 1H), 5.27-5.24 (m, 1H), 4.53-4.30 (m, 1H), 3.77 (br s, 4H), 3.62 (br dd, J=5.6, 11.4 Hz, 1H), 3.53 (brs, 4H), 3.25 (br d, J=11.6 Hz, 1H), 2.64 (br d, J=10.6 Hz, 1H), 2.17 (br d, J=17.3 Hz, 1H), 0.83-0.75 (m, 4H).

LCMS m/z=464.1 $[M+H]^+$.

SFC $t_R$=1.728 min; 100%.

$^1$H NMR (400 MHz, DMSO-$d_6$) δ=8.80 (br d, J=7.4 Hz, 1H), 8.76 (d, J=7.9 Hz, 1H), 8.35 (s, 1H), 8.05-7.96 (m, 1H), 7.74 (s, 1H), 7.12 (dd, J=4.9, 7.4 Hz, 1H), 6.82 (d, J=7.9 Hz, 1H), 5.21 (br t, J=5.9 Hz, 1H), 4.45-4.33 (m, 1H), 3.77 (br s, 4H), 3.64 (br s, 1H), 3.53 (br s, 4H), 3.25 (br d, J=11.5 Hz, 1H), 2.64 (dd, J=6.9, 17.6 Hz, 1H), 2.17 (br d, J=17.1 Hz, 1H), 0.83-0.77 (m, 4H).

The other reaction (5.2 g scale) was performed by same procedures to afford the fourth batch pure product (3S)-5-oxopyrrolidin-3-yl] 4-[3-[2-(cyclopropoxy)-3-pyridyl]pyrazolo[1,5-a]pyrimidin-5-yl]piperazine-1-carboxylate hydrochloric acid (3.0 g, 5.79 mmol, 70.98 yield, 96.43% purity).

LCMS m/z=464.1 $[M+H]^+$.

SFC $t_R$=1.951 min; 100%.

$^1$H NMR (400 MHz, DMSO-$d_6$) δ=8.81 (dd, J=1.6, 7.4 Hz, 1H), 8.76 (d, J=7.9 Hz, 1H), 8.35 (s, 1H), 8.05-7.97 (m, 1H), 7.74 (s, 1H), 7.13 (dd, J=4.9, 7.4 Hz, 1H), 6.82 (d, J=7.9 Hz, 1H), 5.21 (br t, J=5.7 Hz, 1H), 4.48-4.34 (m, 1H), 3.97 (br s, 4H), 3.63 (br s, 1H), 3.53 (br s, 4H), 3.25 (br d, J=11.4 Hz, 1H), 2.67 (br d, J=6.9 Hz, 1H), 2.17 (br d, J=17.5 Hz, 1H), 0.85-0.75 (m, 4H).

$^{13}$C NMR (100 MHz, DMSO-$d_6$) δ=174.30, 159.07, 155.49, 154.01, 144.75, 144.37, 142.02, 136.46, 134.95, 117.68, 116.50, 98.80, 97.31, 70.95, 49.98, 48.19, 44.02, 42.82, 37.07, 5.68.

Example 12: Synthesis of Compound I-12 tert-Butyl N-[2-[(3-bromopyrazolo[1,5-a]pyrimidin-5-yl)amino]ethyl]-N-methyl-carbamate

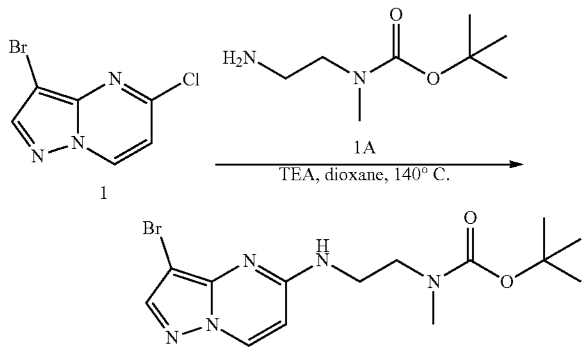

1

2

To a solution of 3-bromo-5-chloro-pyrazolo[1,5-a]pyrimidine (200 mg, 860.34 umol, 1 eq) and tert-butyl N(2-aminoethyl)-N-methyl-carbamate (224.86 mg, 1.29 mmol, 230.63 uL, 1.5 eq) in dioxane (2 mL) was added TEA (174.11 mg, 1.72 mmol, 239.50 uL, 2 eq). The mixture was stirred at 140° C. for 0.5 hr. The reaction mixture was filtered and concentrated under reduced pressure to give crude product tert-butyl N-[2-[(3-bromopyrazolo[1,5-a]pyrimidin-5-yl)amino]ethyl]-N-methyl-carbamate (390 mg, crude) as a solid. The crude was used into the next step without further purification.

LCMS m/z=372.0 $[M+H]^+$.

tert-butyl N-[2-[[3-[2-(Cyclopropoxy)-3-pyridyl]pyrazolo[1,5-a]pyrimidin-5-yl]amino]ethyl]-N-methyl-carbamate

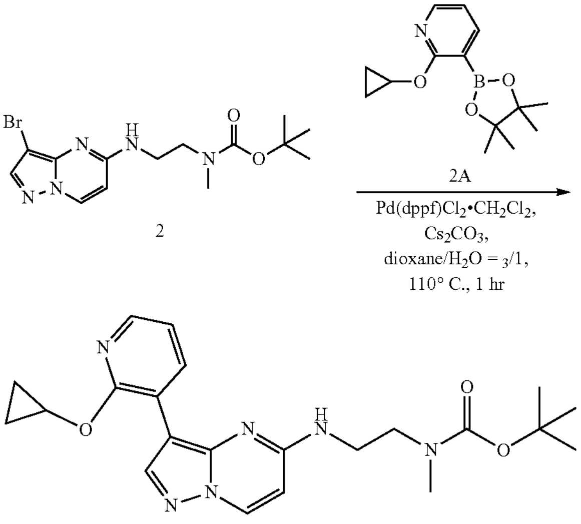

2

I-12

To a solution of tert-butyl N-[2-[(3-bromopyrazolo[1,5-a]pyrimidin-5-yl)amino]ethyl]-N-methyl-carbamate (60 mg, 162.06 umol, 1 eq) and 2-(cyclopropoxy)-3-(4,4,5,5-tetramethyl-1,3,2-dioxaborolan-2-yl)pyridine (46.55 umol, mg, 178.26 umol, 1.1 eq) in dioxane (1 mL) and $H_2O$ (0.3 mL) was added Pd(dppf)$Cl_2$·$CH_2Cl_2$ (26.47 mg, 32.41 umol, 0.2 eq) and $CS_2CO_3$ (158.40 mg, 486.17 umol, 3 eq). The mixture was stirred at 110° C. for 1 hr. The reaction mixture was filtered and concentrated under reduced pressure to give a residue. Then the product was further purified by preparative HPLC. The pure fractions were collected and the volatiles were removed under vacuum. The residue was partitioned between acetonitrile (2 mL) and water (10 mL). The solution was lyophilized to dryness to give the product. Compound tert-butyl N-[2-[[3-[2-(cyclopropoxy)-3-pyridyl]pyrazolo[1,5-a]pyrimidin-5-yl]amino]ethyl]-N-methyl-carbamate (12.54 mg, 29.39 umol, 18.14% yield, 99.5% purity) was obtained as a solid.

LCMS m/z=425.2 $[M+H]^+$.

$^1$H NMR (400 MHz, DMSO-$d_6$) δ=8.85 (dd, J=1.6, 7.6 Hz, 1H), 8.45 (d, J=7.5 Hz, 1H), 8.25 (s, 1H), 7.99 (dd, J=1.9, 4.9 Hz, 1H), 7.55 (br s, 1H), 7.03 (dd, J=4.8, 7.6 Hz, 1H), 6.32 (d, J=7.5 Hz, 1H), 4.53-4.40 (m, 1H), 3.61-3.42 (m, 4H), 2.87 (s, 3H), 1.33 (s, 9H), 0.86-0.73 (m, 4H).

Example 13: Synthesis of Compound I-13-5, Compound I-13, Compound I-14

(1-tert-Butoxycarbonyl-3-methyl-pyrrolidin-3-yl) 4-[3-[2-(cyclopropoxy)-3-pyridyl]pyrazolo[1,5-a] pyrimidin-5-yl]piperazine-1-carboxylate

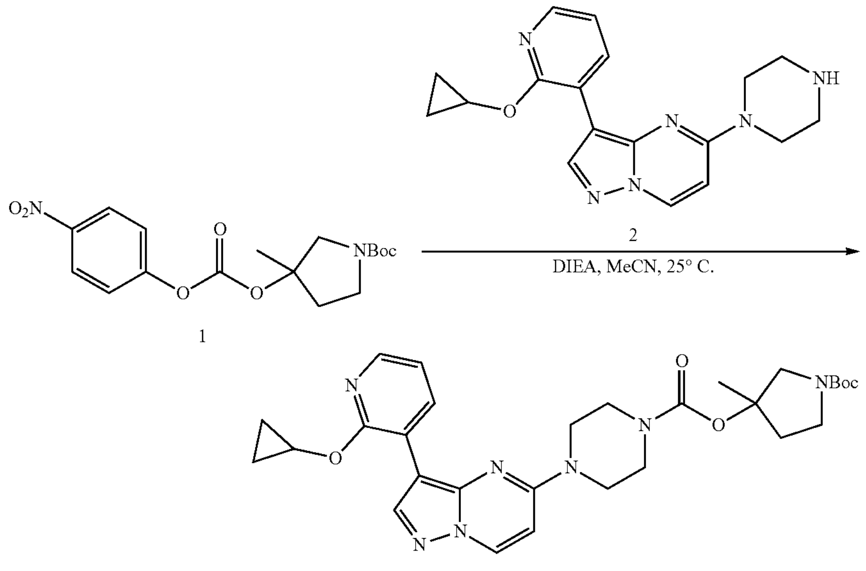

1

3

To a solution of 3-[2-(cyclopropoxy)-3-pyridyl]-5-piperazin-1-yl-pyrazolo[1,5-a]pyrimidine (456.52 mg, 1.36 mmol, 1.1 eq), tert-butyl 3-methyl-3-(4-nitrophenoxy)carbonyloxy-pyrrolidine-1-carboxylate (452 mg, 1.23 mmol, 1 eq) in MeCN (7 mL) was added DIEA (318.91 mg, 2.47 mmol, 429.79 μL, 2 eq). The mixture was stirred at 25° C. for 1 hr. The reaction mixture was concentrated under reduced pressure. Then the product was further purified by preparative HPLC. The pure fractions were collected and the volatiles were removed under vacuum. The solution was lyophilized to dryness to give (1-tert-butoxycarbonyl-3-methyl-pyrrolidin-3-yl)-4-[3-[2-(cyclopropoxy)-3-pyridyl] pyrazolo[1,5-a]pyrimidin-5-yl]piperazine-1-carboxylate (50.0 mg, 95.33% purity.

LCMS m/z=564.5 [M+H]$^+$.

The impure fractions were collected and the volatiles were removed under vacuum. The solution was lyophilized to dryness to give (1-tert-butoxycarbonyl-3-methyl-pyrrolidin-3-yl) 4-[3-[2-(cyclopropoxy)-3-pyridyl]pyrazolo[1,5-a] pyrimidin-5-yl]piperazine-1-carboxylate (70 mg, 49.68 umol, 4.03% yield, 40% purity) as an oil.

LCMS m/z=564.3 [M+H]$^+$.

[(3R)-1-tert-Butoxycarbonyl-3-methyl-pyrrolidin-3-yl] 4-[3-[2-(cyclopropoxy)-3-pyridyl]pyrazolo[1,5-a]pyrimidin-5-yl]piperazine-1-carboxylate & (3S)-1-tert-butoxycarbonyl-3-methyl-pyrrolidin-3-yl] 4-[3-[2-(cyclopropoxy)-3-pyridyl]pyrazolo[1,5-a] pyrimidin-5-yl]piperazine-1-carboxylate

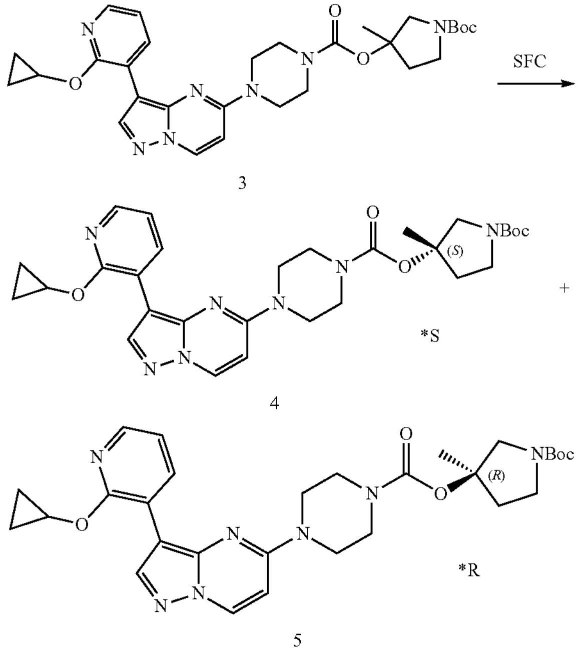

3

4

5

The pure batch product 3 was further separated by SFC. The pure fractions were collected and the volatiles were removed under vacuum, to give [(3R)-1-tert-butoxycarbonyl-3-methyl-pyrrolidin-3-yl]-4-[3-[2-(cyclopropoxy)-3-pyridyl]pyrazolo[1,5-a]pyrimidin-5-yl]piperazine-1-carboxylate (20.0 mg, 35.13 μmol, 2.85% yield, 99% purity) as an oil and (3S)-1-tert-butoxycarbonyl-3-methyl-pyrrolidin-3-yl]-4-[3-[2-(cyclopropoxy)-3-pyridyl]pyrazolo[1,5-a]pyrimidin-5-yl]piperazine-1-carboxylate (23 mg, 39.17 μmol, 3.18% yield, 96% purity) as an oil

[(3R)-1-tert-butoxycarbonyl-3-methyl-pyrrolidin-3-yl] 4-[3-[2-(cyclopropoxy)-3-pyridyl]pyrazolo[1,5-a]pyrimidin-5-yl]piperazine-1-carboxylate LCMS m/z=564.6 $[M+H]^+$.

SFC, $t_R$=1.655, 2.306 min; 99.891%, 0.109%.

(3S)-1-tert-Butoxycarbonyl-3-methyl-pyrrolidin-3-yl] 4-[3-[2-(cyclopropoxy)-3-pyridyl]pyrazolo[1,5-a]pyrimidin-5-yl]piperazine-1-carboxylate LCMS m/z=564.3 $[M+H]^+$.

SFC $t_R$=1.677, 2.301 min; 0.262, 99.738%.

(3-Methylpyrrolidin-3-yl) 4-[3-[2-(cyclopropoxy)-3-pyridyl]pyrazolo[1,5-a] pyrimidin-5-yl]piperazine-1-carboxylate

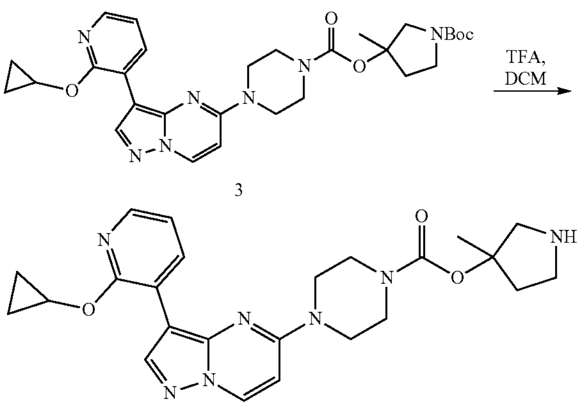

3

I-13-5

To a solution of (1-tert-butoxycarbonyl-3-methyl-pyrrolidin-3-yl)-4-[3-[2-(cyclopropoxy)-3-pyridyl]pyrazolo[1,5-a]pyrimidin-5-yl]piperazine-1-carboxylate (70.0 mg, 124.19 μmol, 40% purity, 1 eq) in DCM (0.6 mL) was added TFA (307.00 mg, 2.69 mmol, 0.2 mL, 21.68 eq). The mixture was stirred at 25° C. for 0.5 hr. The reaction mixture was concentrated under reduced pressure. The product was further purified by preparative HPLC. The pure fractions were collected and the volatiles were removed under vacuum. The solution was lyophilized to dryness to give the crude product. Then the crude was further purified by preparative HPLC. The pure fractions were collected and the volatiles were removed under vacuum. The solution was lyophilized to dryness to give (3-methylpyrrolidin-3-yl)-4-[3-[2-(cyclopropoxy)-3-pyridyl]pyrazolo[1,5-a]pyrimidin-5-yl]piperazine-1-carboxylate (1.03 mg, 2.20 μmol, 14.92% yield, 98.810% purity) as a solid.

LCMS m/z=464.2 $[M+H]^+$.

SFC $t_R$=1.139, 1.461 min; 47.86%, 52.14%.

$^1$H NMR (400 MHz, DMSO-$d_6$) δ=8.79 (d, J=7.5 Hz, 1H), 8.75 (d, J=7.9 Hz, 1H), 8.35 (s, 1H), 8.01 (d, J=4.9 Hz, 1H), 7.14-7.09 (m, 1H), 6.81 (d, J=8.0 Hz, 1H), 4.47-4.36 (m, 1H), 3.77-3.72 (m, 4H), 3.53-3.48 (m, 4H), 3.17-3.05 (m, 2H), 2.92-2.85 (m, 1H), 2.83-2.77 (m, 1H), 2.73-2.65 (m, 1H), 2.16-2.08 (m, 1H), 1.81-1.67 (m, 1H), 1.55 (s, 3H), 0.82-0.76 (m, 4H).

[(3S)-3-Methylpyrrolidin-3-yl]-4-[3-[2-(cyclopropoxy)-3-pyridyl]pyrazolo[1,5-a]pyrimidin-5-yl] piperazine-1-carboxylate

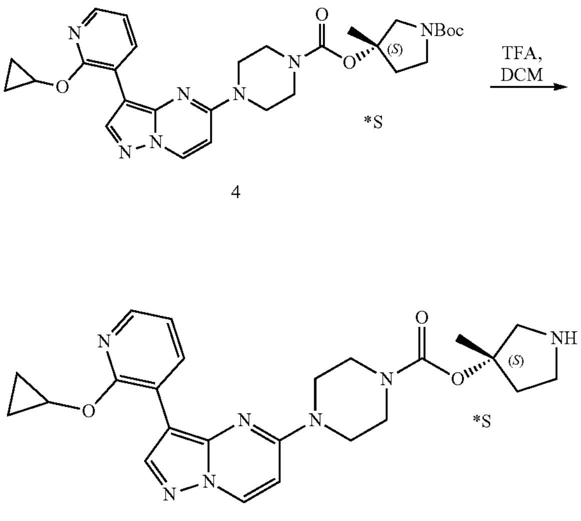

4

I-13

To a solution of [(3S)-1-tert-butoxycarbonyl-3-methyl-pyrrolidin-3-yl] 4-[3-[2-(cyclopropoxy)-3-pyridyl]pyrazolo[1,5-a]pyrimidin-5-yl]piperazine-1-carboxylate (23.00 mg, 40.81 μmol, 1 eq) in DCM (0.6 mL) was added TFA (4.65 mg, 40.81 μmol, 3.03 μL, 1 eq). The mixture was stirred at 25° C. for 1 hr. The reaction mixture was concentrated under reduced pressure to remove solvent. Then the product was further purified by prep. HPLC (column: Waters Xbridge C18 150*25 mm*10 μm; mobile phase: [water ($NH_4HCO_3$)-MeCN]; gradient: 17%-47% B over 10 min). The pure fractions were collected and the volatiles were removed under vacuum. The residue was partitioned between acetonitrile (2 mL) and water (10 mL). The solution was lyophilized to dryness to give [(3S)-3-methylpyrrolidin-3-yl]-4-[3-[2-(cyclopropoxy)-3-pyridyl]pyrazolo[1,5-a]pyrimidin-5-yl] piperazine-1-carboxylate (11.68 mg, 24.35 umol, 59.68% yield, 96.650% purity) as a solid.

LCMS m/z=464.3 $[M+H]^+$.

SFC $t_R$=1.418 min; 100%.

$^1$H NMR (400 MHz, DMSO-$d_6$) δ=8.80-8.77 (m, 1H), 8.76-8.71 (m, 1H), 8.37-8.31 (m, 1H), 8.03-7.99 (m, 1H), 7.13-7.07 (m, 1H), 6.80 (d, J=7.9 Hz, 1H), 4.46-4.32 (m, 1H), 3.77-3.71 (m, 4H), 3.52-3.48 (m, 4H), 3.26-3.08 (m, 2H), 2.96-2.69 (m, 3H), 2.24-2.08 (m, 1H), 1.85-1.66 (m, 1H), 1.55 (s, 3H), 0.83-0.77 (m, 4H).

[(3R)-3-Methylpyrrolidin-3-yl]-4-[3-[2-(cyclopropoxy)-3-pyridyl]pyrazolo[1,5-a]pyrimidin-5-yl]piperazine-1-carboxylate

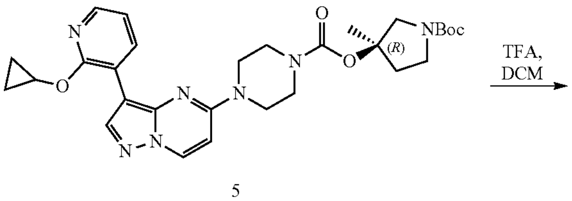

5

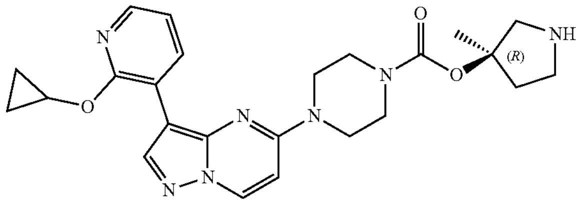

I-14

To a solution of [(3R)-1-tert-butoxycarbonyl-3-methyl-pyrrolidin-3-yl] 4-[3-[2-(cyclopropoxy)-3-pyridyl]pyrazolo[1,5-a]pyrimidin-5-yl]piperazine-1-carboxylate (20.00 mg, 35.48 μmol, 1 eq) in DCM (0.6 mL) was added TFA (307.00 mg, 2.69 mmol, 0.2 mL, 75.88 eq). The mixture was stirred at 25° C. for 1 hr. The reaction mixture was concentrated under reduced pressure to remove solvent. Then the product was further purified by preparative HPLC. The pure fractions were collected and the volatiles were removed under vacuum. The residue was partitioned between acetonitrile (2 mL) and water (10 mL). The solution was lyophilized to dryness to give [(3R)-3-methylpyrrolidin-3-yl]-4-[3-[2-(cyclopropoxy)-3-pyridyl]pyrazolo[1,5-a]pyrimidin-5-yl]piperazine-1-carboxylate (14.50 mg, 31.22 μmol, 87.99% yield, 99.813% purity) as a solid.

LCM m/z=464.2 $[M+H]^+$.

SFC $t_R$=1.476, 1.620 min; 99.206%, 0.794%.

$^1H$ NMR (400 MHz, DMSO-$d_6$) δ=8.81-8.77 (m, 1H), 8.76-8.72 (m, 1H), 8.35 (s, 1H), 8.05-8.00 (m, 1H), 7.14-7.10 (m, 1H), 6.81 (d, J=7.9 Hz, 1H), 4.45-4.37 (m, 1H), 3.77-3.72 (m, 4H), 3.53-3.48 (m, 4H), 3.12-3.07 (m, 1H), 2.92-2.85 (m, 1H), 2.83-2.71 (m, 2H), 2.46-2.27 (m, 1H), 2.18-2.05 (m, 1H), 1.82-1.67 (m, 1H), 1.55 (s, 3H), 0.82-0.78 (m, 4H).

Example 14: Synthesis of Compound I-15 and Compound I-16 and Compound I-16-7 tert-Butyl 3-ethynyl-3-(4-nitrophenoxy)carbonyloxy-pyrrolidine-1-carboxylate

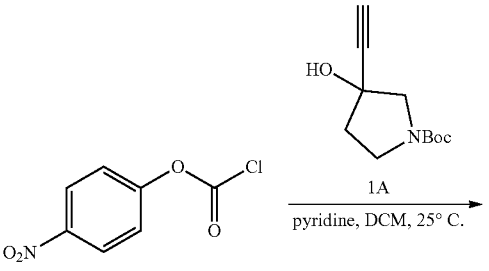

1

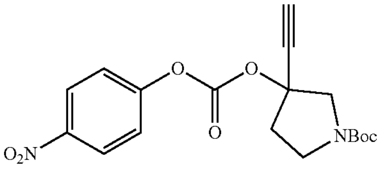

2

A mixture of tert-butyl 3-ethynyl-3-hydroxy-pyrrolidine-1-carboxylate (200 mg, 946.71 μmol, 1 eq) in DCM (2 mL) was added pyridine (224.66 mg, 2.84 mmol, 229.24 μL, 3 eq) and (4-nitrophenyl) carbonochloridate (286.24 mg, 1.42 mmol, 1.5 eq). The mixture was stirred at 25° C. for 1 hr. The reaction mixture was filtered and concentrated under reduced pressure to give crude product tert-butyl 3-ethynyl-3-(4-nitrophenoxy)carbonyloxy-pyrrolidine-1-carboxylate (370.0 mg, 542.28 μmol, 57.28% yield, 55.16% purity) as a solid. The crude was used in next step without any purification.

LCMS m/z=399.2 $[M+Na]^+$.

(1-tert-Butoxycarbonyl-3-ethynyl-pyrrolidin-3-yl) 4-[3-[2-(cyclopropoxy)-3-pyridyl]pyrazolo[1,5-a]pyrimidin-5-yl]piperazine-1-carboxylate

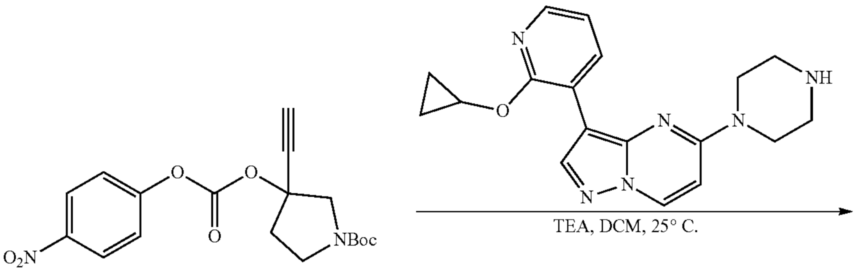

2

-continued

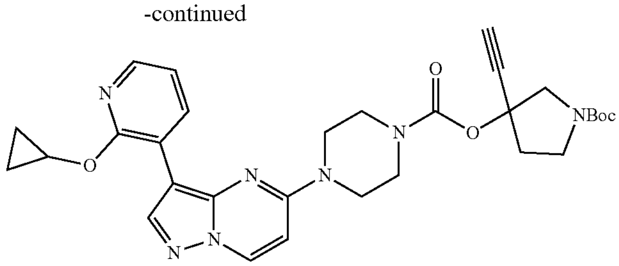

3

A mixture of 3-[2-(cyclopropoxy)-3-pyridyl]-5-piperazin-1-yl-pyrazolo[1,5-a]pyrimidine (300 mg, 891.82 μmol, 1 eq) in DCM (1 mL) was added TEA (270.73 mg, 2.68 mmol, 372.39 μL, 3 eq) and tert-butyl 3-ethynyl-3-(4-nitrophenoxy)carbonyloxy-pyrrolidine-1-carboxylate (335.65 mg, 891.82 μmol, 1 eq). The mixture was stirred at 25° C. for 1 hr. The reaction mixture was concentrated under reduced pressure to give a residue. The crude was purified by preparative HPLC. The residue was partitioned between acetonitrile (20 mL) and water (100 mL). The solution was lyophilized to dryness to give (1-tert-butoxycarbonyl-3-ethynyl-pyrrolidin-3-yl)-4-[3-[2-(cyclopropoxy)-3-pyridyl]pyrazolo[1,5-a]pyrimidin-5-yl]piperazine-1-carboxylate (590 mg, 871.46 μmol, 78.17% yield, 84.73% purity) as a solid.

LCMS m/z=574.2 $[M+H]^+$.

3-ethynylpyrrolidin-3-yl-4-(3-(2-cyclopropoxypyridin-3-yl)pyrazolo[1,5-a]pyrimidin-5-yl)piperazine-1-carboxylate

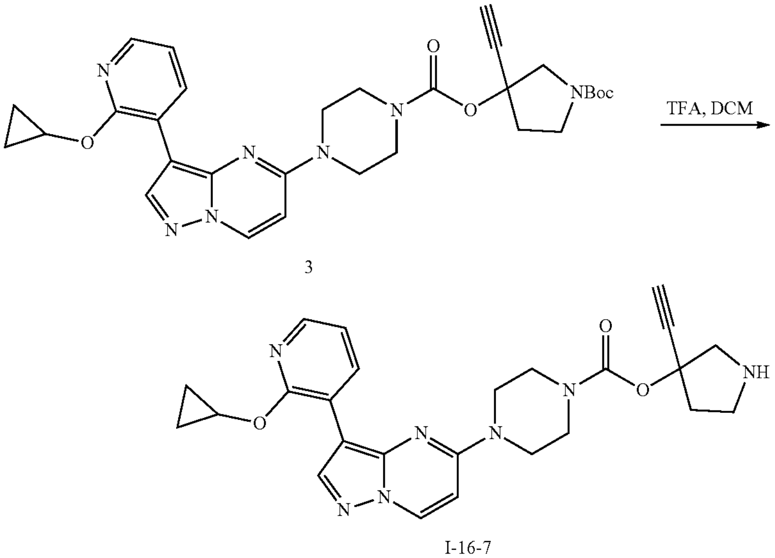

3

I-16-7

A mixture of (1-tert-butoxycarbonyl-3-ethynyl-pyrrolidin-3-yl)-4-[3-[2-(cyclopropoxy)-3-pyridyl]pyrazolo[1,5-a]pyrimidin-5-yl]piperazine-1-carboxylate (24 mg, 41.84 μmol, 1 eq) in DCM (1 mL) was added TFA (4.77 mg, 41.84 μmol, 3.11 μL, 1 eq). The mixture was stirred at 25° C. for 1 hr. The reaction mixture was concentrated under reduced pressure to give a residue. The crude was purified by preparative HPLC. The pure fractions were collected and the volatiles were removed under vacuum. The residue was partitioned between acetonitrile (5 mL) and water 30 mL). The solution was lyophilized to dryness to give (3-ethynylpyrrolidin-3-yl)-4-[3-[2-(cyclopropoxy)-3-pyridyl]pyrazolo[1,5-a]pyrimidin-5-yl]piperazine-1-carboxylate (11.18 mg, 23.34 μmol, 55.78% yield, 98.84% purity) as an oil.

LCMS m/z=474.2 $[M+H]^+$.

SFC $t_R$=2.041, 2.703 min; 51.044%, 48.956%.

$^1H$ NMR (400 MHz, $CDCl_3$) δ=8.86 (d, J=7.6 Hz, 1H), 8.49-8.27 (m, 2H), 8.08 (d, J=5.3 Hz, 1H), 7.10 (d, J=7.5 Hz,

1H), 6.34 (d, J=7.9 Hz, 1H), 4.54-4.34 (m, 1H), 3.96 (d, J=12.6 Hz, 1H), 3.86-3.55 (m, 8H), 3.54-3.35 (m, 4H), 2.91-2.75 (m, 1H), 2.71 (s, 1H), 2.54-2.35 (m, 1H), 0.96-0.87 (m, 2H), 0.87-0.82 (m, 2H).

[(3R)-1-tert-Butoxycarbonyl-3-ethynyl-pyrrolidin-3-yl]-4-[3-[2-(cyclopropoxy)-3-pyridyl]pyrazolo[1,5-a]pyrimidin-5-yl]piperazine-1-carboxylate

[(3S)-1-tert-Butoxycarbonyl-3-ethynyl-pyrrolidin-3-yl]-4-[3-[2-(cyclopropoxy)-3-pyridyl]pyrazolo[1,5-a]pyrimidin-5-yl]piperazine-1-carboxylate

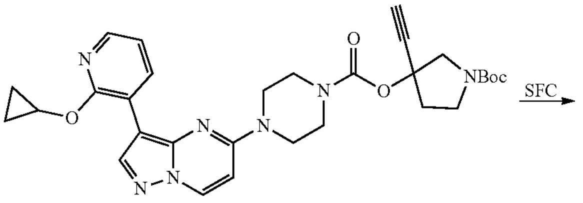

3

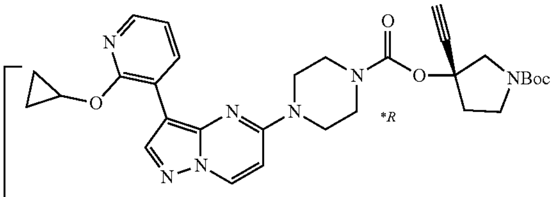

4

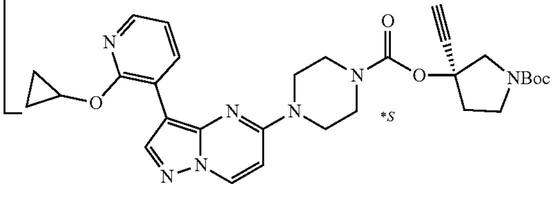

5

The compound 3 (1-tert-butoxycarbonyl-3-ethynyl-pyrrolidin-3-yl)-4-[3-[2-(cyclopropoxy)-3-pyridyl]pyrazolo[1,5-a]pyrimidin-5-yl]piperazine-1-carboxylate (90 mg, 156.89 umol) was further purified by SFC. The residue was partitioned between acetonitrile (20 mL) and water (100 mL). The solution was lyophilized to dryness to give the products.

The compound 4 [(3R)-1-tert-butoxycarbonyl-3-ethynyl-pyrrolidin-3-yl—4-[3-[2-(cyclopropoxy)-3-pyridyl]pyrazolo[1,5-a]pyrimidin-5-yl]piperazine-1-carboxylate (43 mg, 74.96 μmol, 47.78% yield, 100% purity) was obtained as an oil. The product 5 [(3S)-1-tert-butoxycarbonyl-3-ethynyl-pyrrolidin-3-yl]-4-[3-[2-(cyclopropoxy)-3-pyridyl]pyrazolo[1,5-a]pyrimidin-5-yl]piperazine-1-carboxylate (47 mg, 81.33 μmol, 51.84% yield, 99.27% purity) was obtained as an oil.

[(3R)-1-tert-butoxycarbonyl-3-ethynyl-pyrrolidin-3-yl]-4-[3-[2-(cyclopropoxy)-3-pyridyl]pyrazolo[1,5-a]pyrimidin-5-yl]piperazine-1-carboxylate LCMS m/z=574.4 $[M+H]^+$.

SFC $t_R$=0.853 min; 100%.

[(3S)-1-tert-butoxycarbonyl-3-ethynyl-pyrrolidin-3-yl]-4-[3-[2-(cyclopropoxy)-3-pyridyl]pyrazolo[1,5-a]pyrimidin-5-yl]piperazine-1-carboxylate LCMS m/z=574.3 $[M+H]^+$.

SFC $t_R$=0.888, 1.467 min; 0.173%, 99.827%.

[(3R)-3-Ethynylpyrrolidin-3-yl]-4-[3-[2-(cyclopropoxy)-3-pyridyl]pyrazolo[1,5-a]pyrimidin-5-yl]piperazine-1-carboxylate

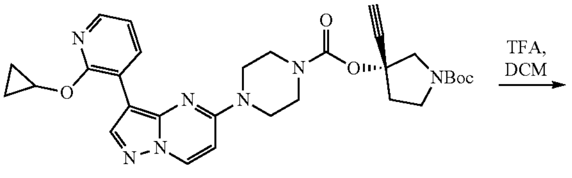

4

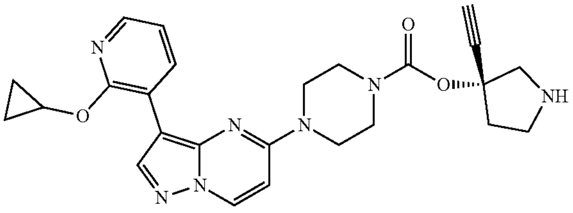

I-15

A mixture of [(3R)-1-tert-butoxycarbonyl-3-ethynyl-pyrrolidin-3-yl] 4-[3-[2-(cyclopropoxy)-3-pyridyl]pyrazolo[1,5-a]pyrimidin-5-yl]piperazine-1-carboxylate (40.00 mg, 69.73 μmol, 1 eq) in DCM (1 mL) was added TFA (279.09 mg, 2.45 mmol, 181.82 μL, 35.10 eq). The mixture was stirred at 25° C. for 0.5 hr. The reaction mixture was filtered and concentrated under reduced pressure to give a residue. The crude was purified by preparative HPLC. The solution was lyophilized to dryness to give [(3R)-3-ethynylpyrrolidin-3-yl]-4-[3-[2-(cyclopropoxy)-3-pyridyl]pyrazolo[1,5-a]pyrimidin-5-yl]piperazine-1-carboxylate (12.98 mg, 27.27 μmol, 39.10% yield, 99.470% purity) as a solid.

LCMS m/z=474.2 $[M+H]^+$.

SFC $t_R$=2.092 min; 100%.

$^1$H NMR (400 MHz, DMSO-$d_6$) δ=8.82-8.70 (m, 2H), 8.35 (s, 1H), 8.01 (d, J=4.9 Hz, 1H), 7.12 (d, J=7.5 Hz, 1H), 6.82 (d, J=7.9 Hz, 1H), 4.45-4.37 (m, 1H), 3.76 (s, 4H), 3.56-3.49 (m, 5H), 3.32-3.31 (m, 1H), 3.00 (d, J=12.5 Hz, 1H), 2.93-2.82 (m, 2H), 2.34-2.27 (m, 1H), 2.18-2.07 (m, 1H), 0.82-0.77 (m, 4H).

[(3S)-3-Ethynylpyrrolidin-3-yl]-4-[3-[2-(cyclopropoxy)-3-pyridyl]pyrazolo[1,5-a]pyrimidin-5-yl]piperazine-1-carboxylate

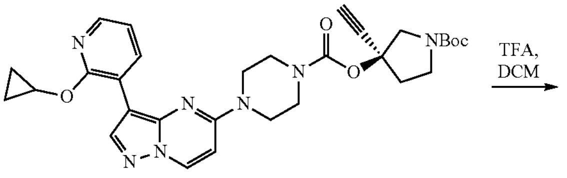

5

-continued

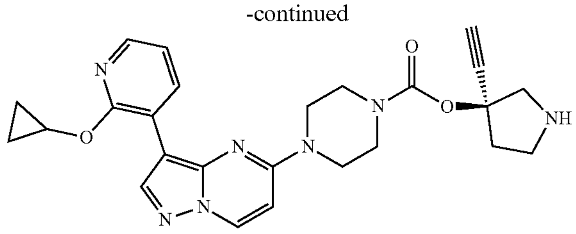

I-16

A mixture of [(3S)-1-tert-butoxycarbonyl-3-ethynyl-pyrrolidin-3-yl]-4-[3-[2-(cyclopropoxy)-3-pyridyl]pyrazolo[1,5-a]pyrimidin-5-yl]piperazine-1-carboxylate (40 mg, 69.73 μmol, 1 eq) in DCM (1 mL) was added TFA (263.14 mg, 2.31 mmol, 171.43 μL, 33.10 eq). The mixture was stirred at 25° C. for 0.5 hr. The reaction mixture was filtered and concentrated under reduced pressure to give a residue. The crude was purified by preparative HPLC. The solution was lyophilized to dryness to give [(3S)-3-ethynylpyrrolidin-3-yl]-4-[3-[2-(cyclopropoxy)-3-pyridyl]pyrazolo[1,5-a]pyrimidin-5-yl]piperazine-1-carboxylate (21.02 mg, 44.04 μmol, 63.15% yield, 99.201% purity) as a solid.

LCMS m/z=474.2 $[M+H]^+$.

SFC $t_R$=2.708 min; 100%.

$^1H$ NMR (400 MHz, DMSO-$d_6$) δ=8.81-8.73 (m, 2H), 8.35 (s, 1H), 8.02 (d, J=4.8 Hz, 1H), 7.12 (d, J=7.5 Hz, 1H), 6.82 (d, J=8.0 Hz, 1H), 4.46-4.34 (m, 1H), 3.77 (s, 4H), 3.57-3.48 (m, 5H), 3.31 (s, 1H), 3.00 (d, J=12.5 Hz, 1H), 2.94-2.82 (m, 2H), 2.34-2.29 (m, 1H), 2.16-2.08 (m, 1H), 0.82-0.76 (m, 4H).

Example 15: Synthesis of Compound I-17

3-Bromo-2-(cyclobutoxy)pyridine

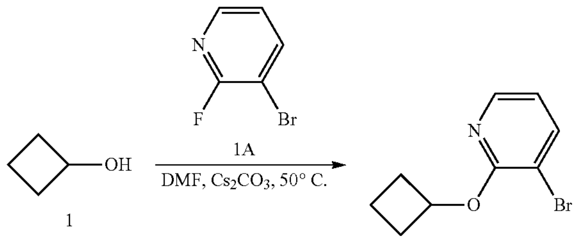

1 2

To a solution of 3-bromo-2-fluoro-pyridine (5.00 g, 28.41 mmol, 1 eq) in DMF (15 mL) was added $Cs_2CO_3$ (55.54 g, 170.47 mmol, 6 eq) and cyclobutanol (2.05 g, 28.41 mmol, 1 eq). The mixture was stirred at 50° C. for 1 hr. The reaction mixture was filtered and concentrated under reduced pressure to give a crude product. The crude was purified by flash silica gel chromatography to give 3-bromo-2-(cyclobutoxy)pyridine (6.28 g, 27.53 mmol, 96.91% yield) as a colorless liquid.

$^1H$ NMR (400 MHz, $CDCl_3$) δ=7.97 (dd, J=1.5, 4.9 Hz, 1H), 7.70 (dd, J=1.6, 7.6 Hz, 1H), 6.66 (dd, J=4.9, 7.6 Hz, 1H), 5.15 (quin, J=7.4 Hz, 1H), 2.50-2.31 (m, 2H), 2.22-2.01 (m, 2H), 1.88-1.73 (m, 1H), 1.69-1.47 (m, 1H).

2-(Cyclobutoxy)-3-(4,4,5,5-tetramethyl-1,3,2-dioxaborolan-2-yl)pyridine

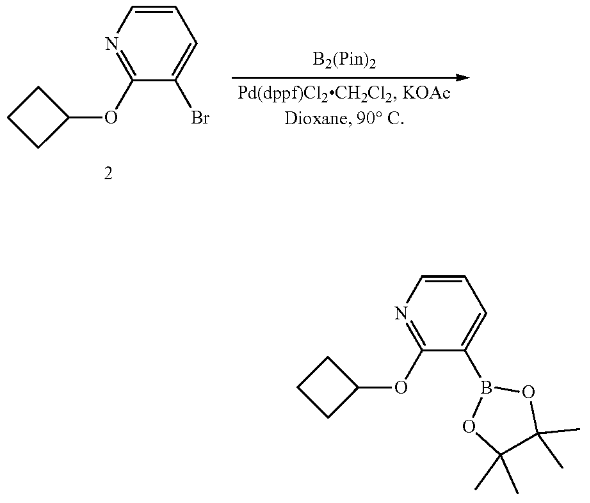

2

3

A mixture of 3-bromo-2-(cyclobutoxy)pyridine (500 mg, 2.19 mmol, 1 eq), 4,4,5,5-tetramethyl-2-(4,4,5,5-tetramethyl-1,3,2-dioxaborolan-2-yl)-1,3,2-dioxaborolane (835.01 mg, 3.29 mmol, 1.5 eq), KOAc (645.42 mg, 6.58 mmol, 3 eq), Pd(dppf)$Cl_2$·$CH_2Cl_2$ (358.04 mg, 438.43 μmol, 0.2 eq) in dioxane (15 mL) was degassed and purged with $N_2$ for 3 times, and then the mixture was stirred at 90° C. for 3 hr under $N_2$ atmosphere. The reaction mixture was filtered and concentrated under reduced pressure to give a crude product. The crude was purified by flash silica gel chromatography to give 2-(cyclobutoxy)-3-(4,4,5,5-tetramethyl-1,3,2-dioxaborolan-2-yl)pyridine (300 mg, 1.09 mmol, 49.74% yield) as an oil.

LCMS m/z=276.3 $[M+H]^+$.

$^1H$ NMR (400 MHz, $CDCl_3$) δ=8.10 (dd, J=2.1, 4.9 Hz, 1H), 7.81 (dd, J=2.0, 7.0 Hz, 1H), 6.74 (dd, J=5.0, 7.0 Hz, 1H), 5.3-5.1 (m, 1H), 2.43-2.35 (m, 2H), 2.15-2.00 (m, 2H), 1.65-1.51 (m, 2H), 1.29 (s, 12H).

(3-Methyloxetan-3-yl) 4-[3-[2-(cyclobutoxy)-3-pyridyl]pyrazolo[1,5-a]pyrimidin-5—yl]piperazine-1-carboxylate (I-17)

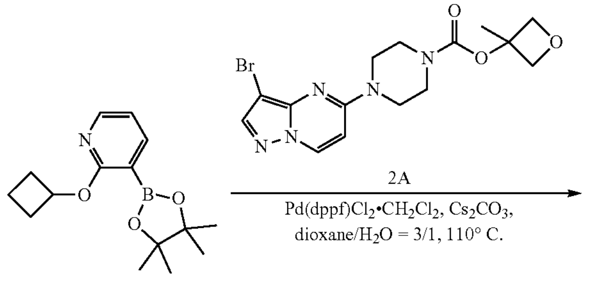

3

-continued

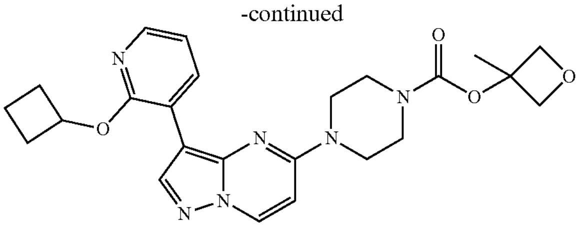

I-17

A mixture of 2-(cyclobutoxy)-3-(4,4,5,5-tetramethyl-l1,3,2-dioxaborolan-2-yl)pyridine (150 mg, 545.16 μmol, 1.5 eq), (3-methyloxetan-3-yl) 4-(3-bromopyrazolo[1,5-a]pyrimidin-5-yl)piperazine-1-carboxylate (144.01 mg, 363.44 μmol, 1 eq), $Pd(dppf)Cl_2 \cdot CH_2Cl_2$ (296.80 mg, 363.44 μmol, 0.2 eq), $Cs_2CO_3$ (355.25 mg, 1.09 mmol, 3 eq) in dioxane (3 mL) and $H_2O$ (1 mL) was degassed and purged with $N_2$ for 3 times, and then the mixture was stirred at 110° C. for 1 hr under $N_2$ atmosphere. The reaction mixture was filtered- and concentrated under reduced pressure to give a residue. The crude was purified by preparative HPLC. The pure fractions were collected and the volatiles were removed under vacuum. The residue was partitioned between acetonitrile (5 mL) and water (30 mL). The solution was lyophilized to dryness to give (3-methyloxetan-3-yl) 4-[3-[2-(cyclobutoxy)-3-pyridyl]pyrazolo[1,5-a]pyrimidin-5-yl]piperazine-1-carboxylate (37.44 mg, 79.84 umol, 21.97% yield, 99.06% purity) as a solid.

LCMS m/z=465.3 $[M+H]^+$ $^1H$ NMR (400 MHz, DMSO-$d_6$) δ=8.84-8.73 (m, 2H), 8.56 (s, 1H), 7.93 (d, J=4.8 Hz, 1H), 7.06 (d, J=7.5 Hz, 1H), 6.84 (d, J=7.9 Hz, 1H), 5.34-5.25 (m, 1H), 4.67 (d, J=7.3 Hz, 2H), 4.42 (d, J=7.4 Hz, 2H), 3.78 (d, J=5.3 Hz, 4H), 3.62-3.48 (m, 4H), 2.46-2.43 (m, 2H), 2.20-2.13 (m, 2H), 1.88-1.80 (m, 1H), 1.76-1.68 (m, 1H), 1.66 (s, 3H).

Example 16: Synthesis of Compound I-18

2-Fluoro-3-(4,4,5,5-tetramethyl-1,3,2-dioxaborolan-2-yl)pyridine

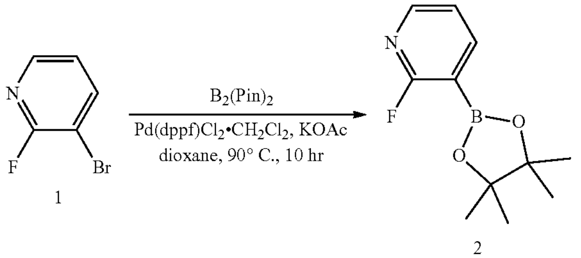 [SMILES: Fc1ncccc1Br ; CC1(C)OB(c2cccnc2F)OC1(C)C]

1 2

A mixture of 3-bromo-2-fluoro-pyridine (4.00 g, 22.73 mmol, 1 eq), 4,4,5,5-tetramethyl-2-(4,4,5,5-tetramethyl-1,3,2-dioxaborolan-2-yl)-1,3,2-dioxaborolane (8.66 g, 34.09 mmol, 1.5 eq), $Pd(dppf)Cl_2 \cdot CH_2Cl_2$ (1.86 g, 2.27 mmol, 0.1 eq), KOAc (6.69 g, 68.19 mmol, 3 eq) in dioxane (20 mL) was degassed and purged with $N_2$ for 3 times, and then the mixture was stirred at 90° C. for 10 hr under $N_2$ atmosphere. The reaction mixture was filtered with diatomite and concentrated under reduced pressure to give a crude product, the crude was purified by FCC to give 2-fluoro-3-(4,4,5,5-tetramethyl-1,3,2-dioxaborolan-2-yl)pyridine (4.45 g, 15.35 mmol, 67.54% yield, 76.946% purity) as an oil.

LCMS m/z=223.8 $[M+H]^+$ $^1H$ NMR (400 MHz, $CDCl_3$) δ=8.22 (dd, J=1.9, 4.7 Hz, 1H), 8.15-8.04 (m, 1H), 7.11 (ddd, J=2.6, 4.8, 7.2 Hz, 1H), 1.29 (s, 12H).

(3-methyloxetan-3-yl)-4-[3-(2-fluoro-3-pyridyl)pyrazolo[1,5-a]pyrimidin-5-yl]piperazine-1-carboxylate

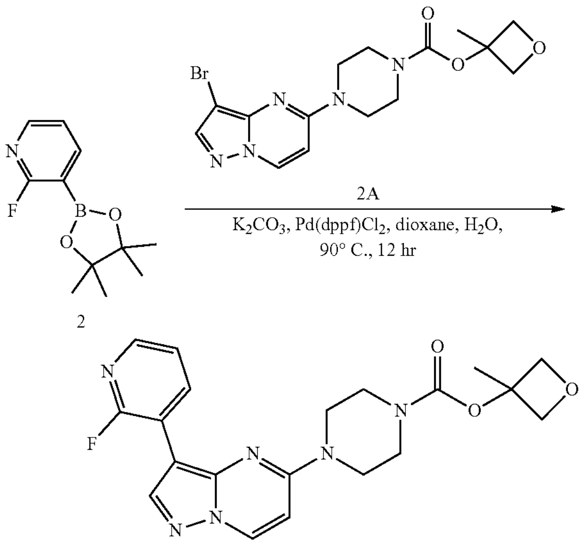

2

3

A mixture of 2-fluoro-3-(4,4,5,5-tetramethyl-1,3,2-dioxaborolan-2-yl)pyridine (337.75 mg, 1.51 mmol, 1.5 eq), (3-methyloxetan-3-yl) 4-(3-bromopyrazolo[1,5-a]pyrimidin-5-yl)piperazine-1-carboxylate (400 mg, 1.01 mmol, 1 eq), $K_2CO_3$ (418.57 mg, 3.03 mmol, 3 eq), Pd(dppf)$Cl_2 \cdot CH_2Cl_2$ (82.44 mg, 100.95 μmol, 0.1 eq) in DMF (10 mL) and $H_2O$ (1 mL) was degassed and purged with $N_2$ for 3 times, and then the mixture was stirred at 90° C. for 12 hr under $N_2$ atmosphere. The reaction mixture was concentrated under reduced pressure to give a residue. The residue was purified by column chromatography ($SiO_2$, DCM: MeOH=1/0 to 10/1) and the crude product was purified by reversed-phase HPLC (0.1% $NH_3 \cdot H_2O$) to give (3-methyloxetan-3-yl)-4-[3-(2-fluoro-3-pyridyl)pyrazolo[1,5-a]pyrimidin-5-yl]piperazine-1-carboxylate (100 mg, 237.41 μmol, 23.52% yield, 97.91% purity) as an oil.

LCMS m/z=413.2 $[M+H]^+$

(3-Methyloxetan-3-yl)-4-[3-[2-(oxetan-3-yloxy)-3-pyridyl]pyrazolo[1,5-a]pyrimidin-5-yl]piperazine-1-carboxylate (I-18)

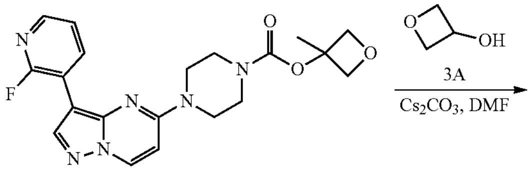

3

-continued

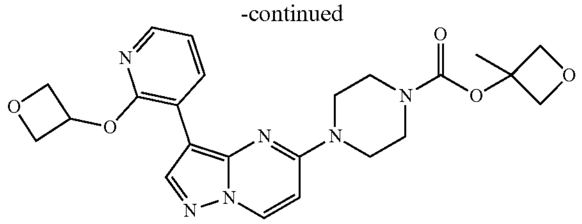

I-18

A mixture of (3-methyloxetan-3-yl) 4-[3-(2-fluoro-3-pyridyl)pyrazolo[1,5-a]pyrimidin-5-yl]piperazine-1-carboxylate (40 mg, 96.99 μmol, 1 eq), oxetan-3-ol (14.37 mg, 193.98 μmol, 2 eq), $Cs_2CO_3$ (94.80 mg, 290.97 μmol, 3 eq) in DMF (2 mL) was degassed and purged with $N_2$ for 3 times, and then the mixture was stirred at 80° C. for 1 hr under $N_2$ atmosphere. The reaction mixture was concentrated under reduced pressure to give a residue, the residue was purified by preparative HPLC. The product (3-methyloxetan-3-yl)-4-[3-[2-(oxetan-3-yloxy)-3-pyridyl]pyrazolo[1,5-a]pyrimidin-5-yl]piperazine-1-carboxylate (1.6 mg, 3.32 μmol, 3.43% yield, 96.93% purity) was obtained as a solid.

LCMS m/z=467.3 $[M+H]^+$.

$^1$H NMR (400 MHz, DMSO-$d_6$): 8.87-8.82 (m, 1H), 8.78 (d, J=7.8 Hz, 1H), 8.58 (s, 1H), 7.94-7.88 (m, 1H), 7.15-7.09 (m, 1H), 6.84 (d, J=8.0 Hz, 1H), 5.73-5.59 (m, 1H), 4.95 (t, J=6.8 Hz, 2H), 4.74-4.62 (m, 4H), 4.42 (d, J=7.2 Hz, 2H), 3.82-3.73 (m, 4H), 3.60-3.46 (m, 4H), 1.66 (s, 3H).

Example 17: Synthesis of Compound I-19

3-[2-(Cyclopropoxy)-3-pyridyl]-5-piperazin-1-yl-pyrazolo[1,5-a]pyrimidine

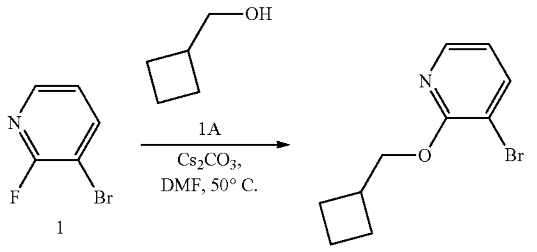

1

2

To a solution of 3-bromo-2-fluoro-pyridine (500 mg, 2.84 mmol, 1 eq) and cyclobutylmethanol (293.65 mg, 3.41 mmol, 321.64 μL, 1.2 eq) in DMF (5 mL) was added $Cs_2CO_3$ (1.85 g, 5.68 mmol, 2 eq). The mixture was stirred at 50° C. for 1 hr. TLC (PE/EA=3/1, $R_f$=0.7) showed that the reaction was completed. The reaction mixture was diluted with water (30 mL) and extracted with EA (30 mL×3). The combined organic layers were washed with brine solution, dried over sodium sulphate, concentrated under reduced pressure to give a crude product. The crude was purified by FCC to give 3-[2-(cyclopropoxy)-3-pyridyl]-5-piperazin-1-yl-pyrazolo[1,5-a]pyrimidine (3.35 g, 9.96 mmol, 51.22% yield) as a liquid.

$^1$H NMR (400 MHz, DMSO-$d_6$) δ=8.14 (dd, J=1.6, 4.9 Hz, 1H), 8.02 (dd, J=1.6, 7.6 Hz, 1H), 6.93 (dd, J=4.9, 7.6 Hz, 1H), 4.29 (d, J=6.5 Hz, 2H), 2.86-2.65 (m, 1H), 2.11-2.01 (m, 2H), 1.93-1.83 (m, 4H).

2-(cyclobutylmethoxy)-3-(4,4,5,5-tetramethyl-1,3,2-dioxaborolan-2-yl)pyridine

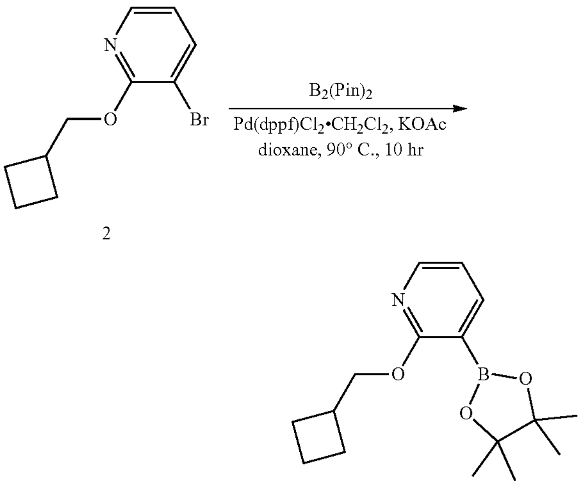

2

3

A mixture of 3-bromo-2-(cyclobutylmethoxy)pyridine (350 mg, 1.45 mmol, 1 eq), 4,4,5,5-tetramethyl-2-(4,4,5,5-tetramethyl-1,3,2-dioxaborolan-2-yl)-1,3,2-dioxaborolane (440.51 mg, 1.73 mmol, 1.2 eq), KOAc (283.75 mg, 2.89 mmol, 2 eq) and $Pd(dppf)Cl_2{\cdot}CH_2Cl_2$ (236.11 mg, 289.12 μmol, 0.2 eq) in dioxane (3 mL) was degassed and purged with $N_2$ for 3 times, and then the mixture was stirred at 90° C. for 10 hr under $N_2$ atmosphere. The reaction mixture was filtered and concentrated under reduced pressure to give a residue. The crude was purified by FCC to give 2-(cyclobutylmethoxy)-3-(4,4,5,5-tetramethyl-1,3,2-dioxaborolan-2-yl)pyridine (250 mg, 297.34 μmol, 20.57% yield, 34.393% purity) as a liquid.

LCMS m/z=290.3 $[M+H]^+$.

$^1$H NMR (400 MHz, DMSO-$d_6$) δ=8.20 (dd, J=2.1, 5.0 Hz, 1H), 7.85 (dd, J=2.1, 7.1 Hz, 1H), 6.92 (dd, J=5.0, 7.0 Hz, 1H), 4.16 (d, J=5.4 Hz, 2H), 2.73-2.66 (m, 1H), 2.07-1.99 (m, 2H), 1.93-1.77 (m, 4H), 1.16 (s, 12H).

3-Methyloxetan-3-yl 4-(3-(2-(cyclobutylmethoxy)pyridin-3-yl)pyrazolo[1,5-a]pyrimidin-5-yl)piperazine-1-carboxylate

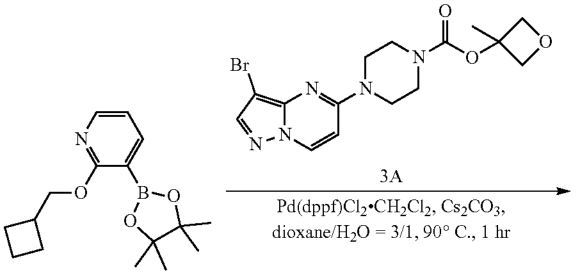

3

-continued

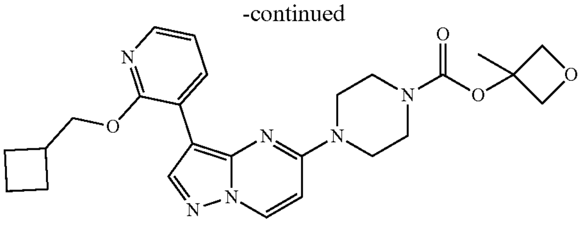

I-19

A mixture of (3-methyloxetan-3-yl)-4-(3-bromopyrazolo[1,5-a]pyrimidin-5-yl)piperazine-1-carboxylate (80 mg, 201.90 μmol, 1 eq), 2-(cyclobutylmethoxy)-3-(4,4,5,5-tetramethyl-1,3,2-dioxaborolan-2-yl)pyridine (134.28 mg, 464.37 μmol, 2.3 eq), $Cs_2CO_3$ (197.35 mg, 605.70 μmol, 3 eq), and Pd(dppf)$Cl_2$·$CH_2Cl_2$ (32.98 mg, 40.38 μmol, 0.2 eq) in dioxane (0:9 mL) and $H_2O$ (0.3 mL) was degassed and purged with $N_2$ for 3 times, and then the mixture was stirred at 90° C. for 1 hr under $N_2$ atmosphere. The reaction mixture was filtered and concentrated under reduced pressure to give a residue. The crude was purified by FCC to give a crude product. The crude was further purified by preparative HPLC. The pure fractions were collected and the volatiles were removed under vacuum. The residue was partitioned between acetonitrile (20 mL) and water (100 mL). The solution was lyophilized to dryness to give (3-methyloxetan-3-yl)-4-[3-[2-(cyclobutylmethoxy)-3-pyridyl]pyrazolo[1,5-a]pyrimidin-5-yl]piperazine-1-carboxylate (10.99 mg, 22.91 μmol, 11.35% yield, 99.773% purity) as a solid.

LCMS m/z=479.2 $[M+H]^+$.

$^1$H NMR (400 MHz, DMSO-$d_6$) δ=8.85-8.79 (m, 1H), 8.75 (d, J=7.9 Hz, 1H), 8.47 (s, 1H), 7.97-7.90 (m, 1H), 7.12-7.01 (m, 1H), 6.83 (d, J=7.9 Hz, 1H), 4.66 (d, J=7.0 Hz, 2H), 4.42 (d, J=7.3 Hz, 2H), 4.37 (d, J=6.9 Hz, 2H), 3.84-3.71 (m, 4H), 3.64-3.43 (m, 4H), 2.93-2.79 (m, 1H), 2.17-2.05 (m, 2H), 2.01-1.84 (m, 4H), 1.66 (s, 3H).

Example 18: Synthesis of Compound I-20

3-bromo-2-(oxetan-3-ylmethoxy)pyridine

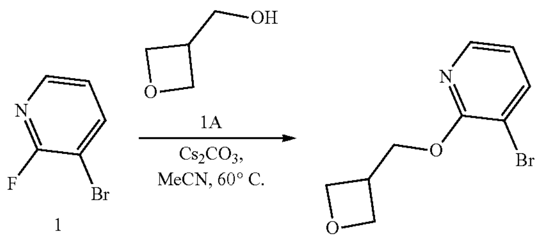

1 2

A mixture of 3-bromo-2-fluoro-pyridine (2 g, 11.36 mmol, 1 eq) in MeCN (10 mL) was added $Cs_2CO_3$ (11.11 g, 34.09 mmol, 3 eq) and oxetan-3-ylmethanol (1.00 g, 11.36 mmol, 1 eq). The mixture was stirred at 60° C. for 1 hr. The reaction mixture was filtered and concentrated under reduced pressure to give a crude product. The crude was purified by flash silica gel chromatography to give 3-bromo-2-(oxetan-3-ylmethoxy)pyridine (2.12 g, 8.47 mmol, 74.53% yield, 97.514% purity) as an oil.

LCMS m/z=244.2 $[M+H]^+$.

$^1$H NMR (400 MHz, $CDCl_3$) δ=8.00 (dd, J=1.6, 4.8 Hz, 1H), 7.73 (dd, J=1.6, 7.6 Hz, 1H), 6.71 (dd, J=4.9, 7.6 Hz, 1H), 4.79 (dd, J=6.2, 7.8 Hz, 2H), 4.57-4.51 (m, 4H), 3.47-3.36 (m, 1H).

3-methyloxetan-3-yl)-4-[3-[2-(oxetan-3-ylmethoxy)-3-pyridyl]pyrazolo[1,5-a]pyrimidin-5-yl]piperazine-1-carboxylate (I-20)

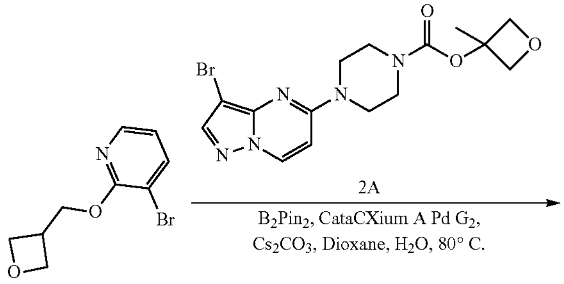

2

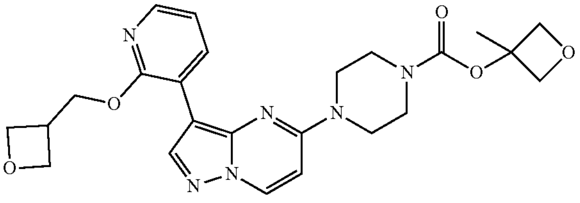

I-20

A mixture of (3-methyloxetan-3-yl) 4-(3-bromopyrazolo[1,5-a]pyrimidin-5-yl)piperazine-1-carboxylate (500 mg, 1.26 mmol, 1 eq), 3-bromo-2-(oxetan-3-ylmethoxy)pyridine (924.01 mg, 3.79 mmol, 3 eq), 4,4,5,5-tetramethyl-2-(4,4,5,5-tetramethyl-1,3,2-dioxaborolan-2-yl)-1,3,2-dioxaborolane (640.87 mg, 2.52 mmol, 2 eq), [2-(2-aminophenyl)phenyl]-chloro-palladium; bis(1-adamantyl)-butyl-phosphane (84.37 mg, 126.19 μmol, 0.1 eq) and $CS_2CO_3$ (1.23 g, 3.79 mmol, 3 eq) in dioxane (0.5 mL) and $H_2O$ (0.05 mL) was degassed and purged with $N_2$ for 3 times, and then the mixture was stirred at 80° C. for 1 hr under $N_2$ atmosphere. The reaction mixture was filtered and concentrated under reduced pressure to give a crude product. The crude was purified by preparative HPLC. The solution was lyophilized to dryness to give 3-methyloxetan-3-yl)-4-[3-[2-(oxetan-3-ylmethoxy)-3-pyridyl]pyrazolo[1,5-a]pyrimidin-5-yl]piperazine-1-carboxylate (I-20, 18.64 mg, 36.99 μmol, 7.11% yield, 95.362% purity) as a solid.

LCMS m/z=481.0 $[M+H]^+$.

$^1$H NMR (400 MHz, DMSO-$d_6$) δ=8.90-8.83 (m, 1H), 8.76 (d, J=7.9 Hz, 1H), 8.52 (s, 1H), 8.01-7.92 (m, 1H), 7.13-7.07 (m, 1H), 6.84 (d, J=8.0 Hz, 1H), 4.82-4.75 (m, 2H), 4.67 (d, J=7.1 Hz, 2H), 4.60 (d, J=6.1 Hz, 2H), 4.54 (t, J=5.9 Hz, 2H), 4.43 (d, J=7.3 Hz, 2H), 3.83-3.76 (m, 4H), 3.61-3.57 (m, 1H), 3.56-3.44 (m, 4H), 1.67 (s, 3H).

Example 19: Synthesis of Compound I-21-5, Compound I-21, and Compound I-22 tert-Butyl 3-methyl-3-(4-nitrophenoxy)carbonyloxy-pyrrolidine-1-carboxylate

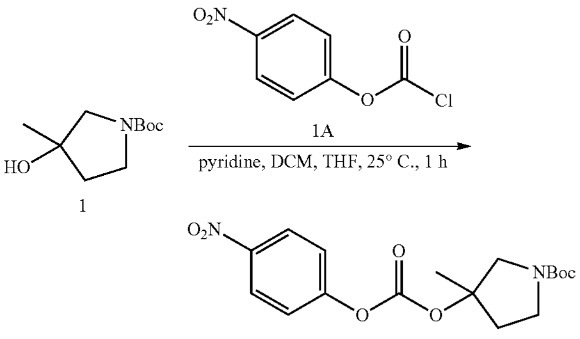

2

To a solution of tert-butyl 3-hydroxy-3-methyl-pyrrolidine-1-carboxylate (1 g, 4.97 mmol, 1 eq) in DCM (10 mL) was added pyridine (1.18 g, 14.91 mmol, 1.20 mL, 3 eq) and (4-nitrophenyl) carbonochloridate (1.00 g, 4.97 mmol, 1 eq) in THF (2 mL) at 0° C. The mixture was stirred at 25° C. for 2 hr. TLC (PE:EA=0:1, $R_f$=0.53) showed a new spot was formed. The reaction mixture was concentrated under reduced pressure to give crude product tert-butyl 3-methyl-3-(4-nitrophenoxy)carbonyloxy-pyrrolidine-1-carboxylate (2 g, crude) as a solid.

(1-tert-butoxycarbonyl-3-methyl-pyrrolidin-3-yl)-4-(3-bromopyrazolo[1,5-a]pyrimidin-5-yl)piperazine-1-carboxylate

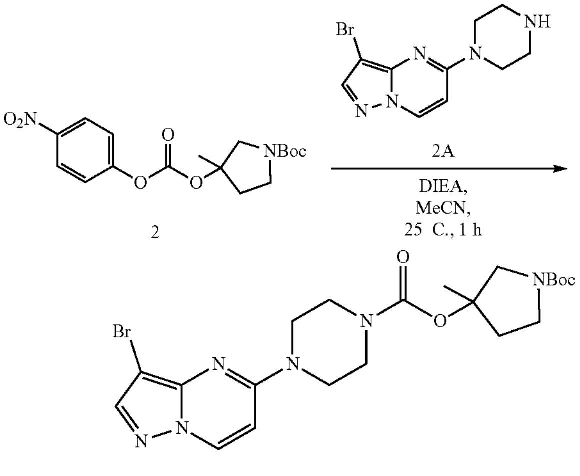

3

A mixture of tert-butyl 3-methyl-3-(4-nitrophenoxy)carbonyloxy-pyrrolidine-1-carboxylate (1.82 g, 4.96 mmol, 2 eq), 3-bromo-5-piperazin-1-yl-pyrazolo[1,5-a]pyrimidine (0.7 g, 2.48 mmol, 1 eq), DIEA (1.12 g, 8.68 mmol, 1.51 mL, 3.5 eq) in MeCN (20 mL) was degassed and purged with $N_2$ for 3 times, and then the mixture was stirred at 25° C. for 1 hr under $N_2$ atmosphere. LCMS showed reactant 2 was consumed completely and one main peak with desired mass was detected. The reaction mixture was filtered and concentrated under reduced pressure to give a residue. The residue was purified by flash silica gel chromatography (ISCO®; 20 g SepaFlash® Silica Flash Column, Eluent of 54% EA/PE gradient @ 80 mL/min) to give (1-tert-butoxycarbonyl-3-methyl-pyrrolidin-3-yl)-4-(3-bromopyrazolo[1,5-a]pyrimidin-5-yl)piperazine-1-carboxylate (1.26 g, 2.47 mmol, 100.00% yield) as a solid.

LCMS m/z=411.0 $[M+H]^+$.

SFC $t_R$=1.789, 1.843 min; 50.50%, 49.50%.

$^1H$ NMR (400 MHz, DMSO-$d_6$) δ=8.69 (d, J=7.9 Hz, 1H), 8.00-7.94 (m, 1H), 6.81-6.73 (m, 1H), 3.79-3.64 (m, 5H), 3.45 (br s, 4H), 3.32-3.22 (m, 2H), 2.33-2.21 (m, 1H), 1.97-1.88 (m, 1H), 1.56 (s, 3H), 1.38 (s, 9H).

tert-Butoxycarbonyl-3-methyl-pyrrolidin-3-yl) 4-[3-(2-isopropoxy-3-pyridyl)pyrazolo[1,5-a]pyrimidin-5-yl]piperazine-1-carboxylate

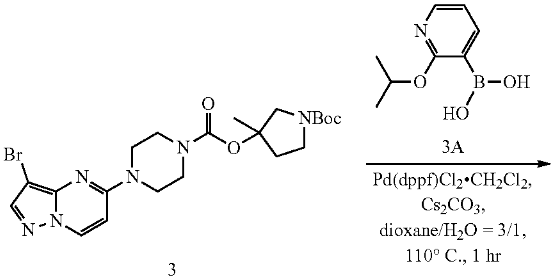

3

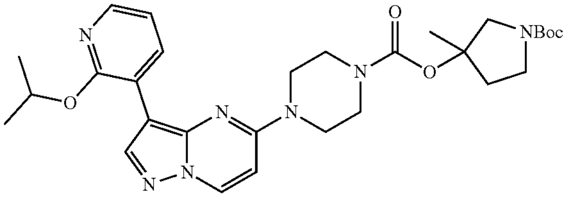

4

A mixture of (1-tert-butoxycarbonyl-3-methyl-pyrrolidin-3-yl) 4-(3-bromopyrazolo[1,5-a]pyrimidin-5-yl)piperazine-1-carboxylate (1.26 g, 2.47 mmol, 1 eq), (2-isopropoxy-3-pyridyl) boronic acid (447.70 mg, 2.47 mmol, 1 eq), $Pd(dppf)Cl_2 \cdot CH_2Cl_2$ (403.99 mg, 494.70 μmol, 0.2 eq), $Cs_2CO_3$ (2.42 g, 7.42 mmol, 3 eq) in dioxane (10.5 mL) and $H_2O$ (3.5 mL) was degassed and purged with $N_2$ for 3 times, and then the mixture was stirred at 110° C. for 1 hr under $N_2$ atmosphere, showed 15% of reactant 3 was remained, and one major new spot with larger polarity was detected. The reaction mixture was filtered and concentrated under reduced pressure to give a residue. The residue was purified by flash silica gel chromatography to give (1-tert-butoxycarbonyl-3-methyl-pyrrolidin-3-yl) 4-[3-(2-isopropoxy-3-pyridyl)pyrazolo[1,5-a]pyrimidin-5-yl]piperazine-1-carboxylate (795 mg, 1.41 mmol, 56.82% yield) as a solid.

LCMS m/z=566.4 $[M+H]^+$.

(3-Methylpyrrolidin-3-yl)-4-[3-(2-isopropoxy-3-pyridyl)pyrazolo[1,5-a]pyrimidin-5-yl]piperazine-1-carboxylate (I-21-6)

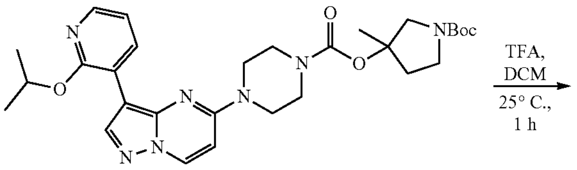

4

-continued

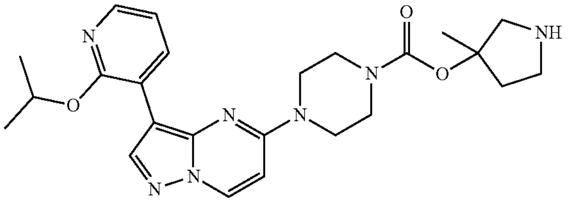

1-21-5

To a solution of (1-tert-butoxycarbonyl-3-methyl-pyrrolidin-3-yl) 4-[3-(2-isopropoxy-3-pyridyl)pyrazolo[1,5-a]pyrimidin-5-yl]piperazine-1-carboxylate (795 mg, 1.41 mmol, 1 eq) in DCM (7.9 mL) was added TFA (3.99 g, 35.00 mmol, 2.6 mL, 24.90 eq). The mixture was stirred at 25° C. for 1 hour. The crude was purified by preparative HPLC. The pure fractions were collected and the volatiles were removed under vacuum. The residue was partitioned between acetonitrile (5 mL) and water (15 mL). The solution was lyophilized to dryness to give (3-methylpyrrolidin-3-yl)-4-[3-(2-isopropoxy-3-pyridyl)pyrazolo[1,5-a]pyrimidin-5-yl]piperazine-1-carboxylate (I-21-5, 260 mg, 545.75 μmol, 38.83% yield, 97.72% purity) as a solid.

LCMS m/z=466.4 $[M+H]^+$.

SFC $t_R$=1.697, 1.824 min; 41.39%, 58.61%.

$^1$H NMR (400 MHz, methanol-$d_4$) δ=8.96-8.78 (m, 1H), 8.60 (s, 1H), 8.50 (d, J=7.9 Hz, 1H), 7.98-7.85 (m, 1H), 7.12-6.89 (m, 1H), 6.76 (d, J=7.9 Hz, 1H), 5.59-5.28 (m, 1H), 4.01-3.91 (m, 1H), 3.89-3.77 (m, 4H), 3.71-3.56 (m, 4H), 3.53-3.40 (m, 2H), 3.27-3.24 (m, 1H), 2.72-2.52 (m, 1H), 2.24-2.02 (m, 1H), 1.72 (s, 3H), 1.44 (d, J=6.1 Hz, 6H).

[(3S)-3-Methylpyrrolidin-3-yl] 4-[3-(2-isopropoxy-3-pyridyl)pyrazolo[1,5-a]pyrimidin-5-yl]piperazine-1-carboxylate (I-21, 120 mg, 244.85 μmol, 94.99% yield, 94.99% purity) & [(3R)-3-methylpyrrolidin-3-yl] 4-[3-(2-isopropoxy-3-pyridyl)pyrazolo[1,5-a]pyrimidin-5-yl]piperazine-1-carboxylate (I-22)

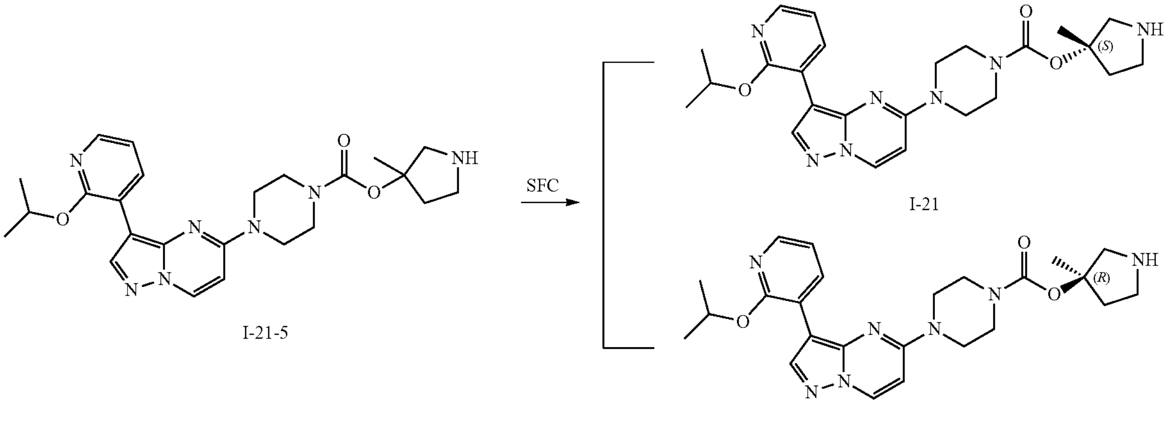

I-21-5 I-21 I-22

(3-methylpyrrolidin-3-yl) 4-[3-(2-isopropoxy-3-pyridyl)pyrazolo[1,5-a]pyrimidin-5-yl]piperazine-1-carboxylate was further separated by SFC. The pure fractions were collected and the volatiles were removed under vacuum. The residue was partitioned between acetonitrile (20 mL) and water (25 mL). The solution was lyophilized to dryness to give two compounds. [(3S)-3-methylpyrrolidin-3-yl]-4-[3-(2-isopropoxy-3-pyridyl)pyrazolo[1,5-a]pyrimidin-5-yl]piperazine-1-carboxylate (123 mg, 264.21 μmol, 47.31% yield) was obtained as a solid and [(3R)-3-methylpyrrolidin-3-yl]-4-[3-(2-isopropoxy-3-pyridyl)pyrazolo[1,5-a]pyrimidin-5-yl]piperazine-1-carboxylate (120 mg, 250.70 μmol, 94.89% yield, 97.26% purity) was obtained as a solid.

Compound I-21

LCMS m/z=466.4 $[M+H]^+$.

SFC $t_R$=4.306, 7.285 min; 0.138%, 99.862%.

$^1$H NMR (400 MHz, DMSO-$d_6$) δ=8.82-8.69 (m, 2H), 8.52 (s, 1H), 8.00-7.88 (m, 1H), 7.09-6.97 (m, 1H), 6.81 (d, J=8.0 Hz, 1H), 5.46-5.33 (m, 1H), 3.81-3.67 (m, 4H), 3.56-3.45 (m, 4H), 3.09 (d, J=12.0 Hz, 1H), 2.92-2.76 (m, 2H), 2.73 (d, J=12.0 Hz, 1H), 2.55-2.52 (m, 1H), 2.16-2.05 (m, 1H), 1.79-1.69 (m, 1H), 1.54 (s, 3H), 1.39 (d, J=6.1 Hz, 6H).

Compound I-22

LCMS m/z=466.5 $[M+H]^+$.

SFC $t_R$=4.282, 7.310 min; 99.578%, 0.422%.

$^1$H NMR (400 MHz, DMSO-$d_6$) δ=8.81-8.70 (m, 2H), 8.52 (s, 1H), 7.99-7.88 (m, 1H), 7.07-6.98 (m, 1H), 6.81 (d, J=7.9 Hz, 1H), 5.44-5.33 (m, 1H), 3.78-3.69 (m, 4H), 3.54-3.44 (m, 4H), 3.24-3.15 (m, 1H), 2.98-2.84 (m, 2H), 2.81 (d, J=12.1 Hz, 1H), 2.54-2.51 (m, 1H), 2.24-2.12 (m, 1H), 1.85-1.70 (m, 1H), 1.56 (s, 3H), 1.39 (d, J=6.1 Hz, 6H).

Example 20: Synthesis of Compound I-23

(4-nitrophenyl) [(3R)-2-oxopyrrolidin-3-yl] carbonate

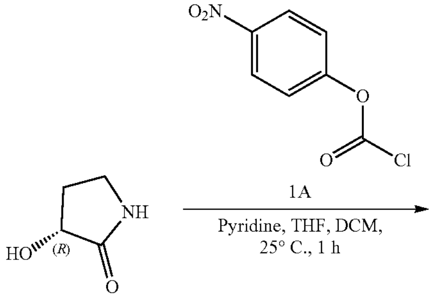

1

-continued

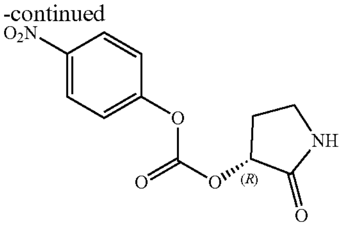

2

A mixture of (3R)-3-hydroxypyrrolidin-2-one (200 mg, 1.98 mmol, 1 eq), (4-nitrophenyl) carbonochloridate (398.73 mg, 1.98 mmol, 1 eq), pyridine (469.42 mg, 5.93 mmol, 479.00 μL, 3 eq) in DCM (2 mL) and THF (0.5 mL) was degassed and purged with $N_2$ for 3 times, and then the mixture was stirred at 25° C. for 1 hour under $N_2$ atmosphere. The reaction mixture was filtered and concentrated under reduced pressure to give a crude product (4-nitrophenyl) [(3R)-2-oxopyrrolidin-3-yl] carbonate (500 mg, 1.88 mmol, 94.95% yield) as a black oil. The crude product was used into the next step without further purification.

LCMS m/z=267.0 $[M+H]^+$.

[(3R)-2-oxopyrrolidin-3-yl]-4-[3-[2-(cyclopropoxy)-3-pyridyl]pyrazolo[1,5-a]pyrimidin-5-yl]piperazine-1-carboxylate 1

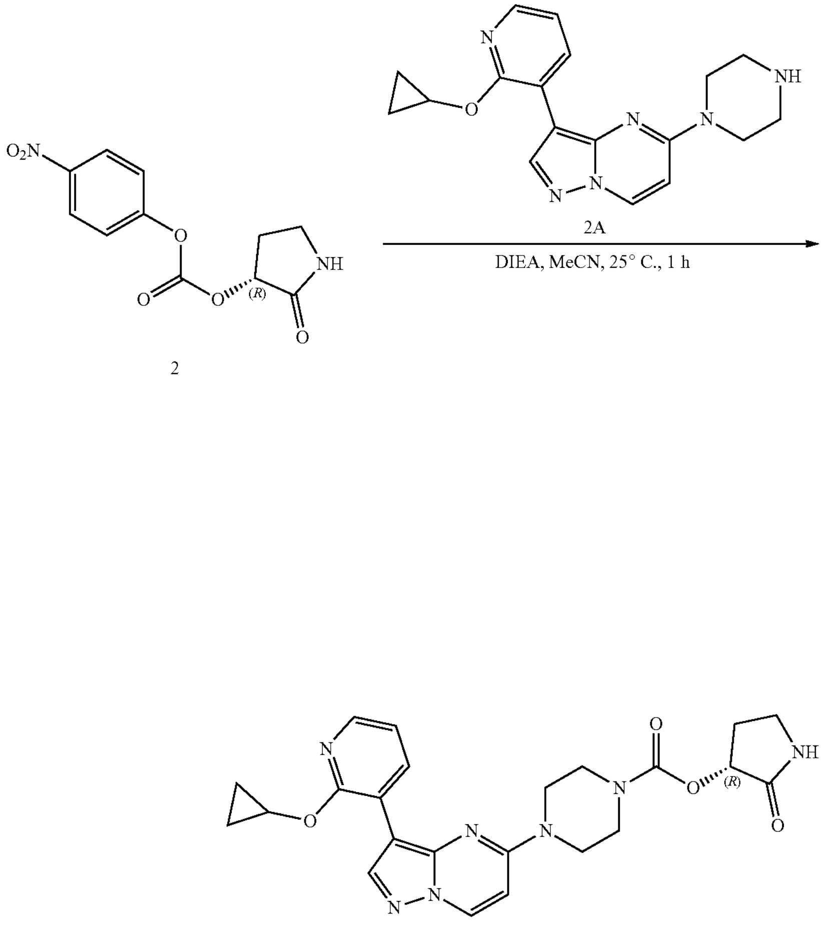

2

I-23

To a solution of (4-nitrophenyl) [(3R)-2-oxopyrrolidin-3-yl] carbonate (356.11 mg, 1.34 mmol, 3 eq) and 3-[2-(cyclopropoxy)-3-pyridyl]-5-piperazin-1-yl-pyrazolo[1,5-a]pyrimidine (150 mg, 445.91 umol, 1 eq) in MeCN (3.5 mL) was added DIEA (201.71 mg, 1.56 mmol, 271.84 μL, 3.5 eq). The mixture was stirred at 25° C. for 1 hour. The reaction mixture was filtered and concentrated under reduced pressure to give a residue. The crude was purified by preparative. HPLC. The pure fractions were collected and the volatiles were removed under vacuum. The residue was partitioned between acetonitrile (20 mL) and water (25 mL). The solution was lyophilized to dryness to give the crude product. The crude was purified again by preparative. HPLC. The pure fractions were collected and the volatiles were removed under vacuum. The residue was partitioned between acetonitrile (5 mL) and water (15 mL). The solution was lyophilized to dryness to give [(3R)-2-oxopyrrolidin-3-yl]-4-[3-[2-(cyclopropoxy)-3-pyridyl]pyrazolo[1,5-a]pyrimidin-5-yl]piperazine-1-carboxylate (I-23, 65 mg, 136.92 umol, 30.71% yield, 97.63% purity) as a solid.

LCMS m/z=463.9 $[M+H]^+$.

SFC $t_R$=1.625 min; 100%.

$^1$H NMR (400 MHz, methanol-$d_4$) δ=8.90-8.83 (m, 1H), 8.47 (d, J=7.9 Hz, 1H), 8.40 (s, 1H), 8.00-7.94 (m, 1H), 7.11-7.03 (m, 1H), 6.73 (d, J=1.0 Hz, 1H), 5.34-5.26 (m, 1H), 4.93-4.90 (m, 1H), 4.39-4.31 (m, 1H), 3.89-3.78 (m, 4H), 3.75-3.58 (m, 4H), 3.46-3.34 (m, 2H), 2.66-2.54 (m, 1H), 2.19-2.06 (m, 1H), 0.91-0.78 (m, 4H).

Example 21: Synthesis of Compound I-24

(4-Nitrophenyl) [(3S)-2-oxopyrrolidin-3-yl] carbonate

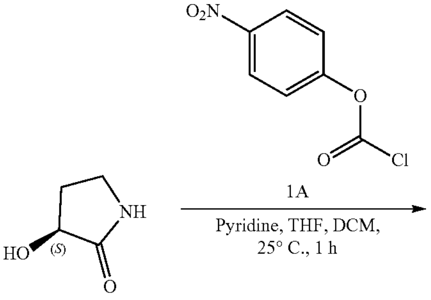

1

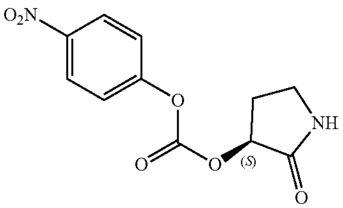

2

A mixture of (3S)-3-hydroxypyrrolidin-2-one (200 mg, 1.98 mmol, 1 eq), (4-nitrophenyl) carbonochloridate (398.73 mg, 1.98 mmol, 1 eq), pyridine (469.42 mg, 5.93 mmol, 479.00 uL, 3 eq) in DCM (2 mL) and THF (0.5 mL) was degassed and purged with $N_2$ for 3 times, and then the mixture was stirred at 25° C. for 1 hour under $N_2$ atmosphere. The reaction mixture was filtered and concentrated under reduced pressure to give (4-nitrophenyl) [(3S)-2-oxopyrrolidin-3-yl] carbonate (400 mg, 1.50 mmol, 75.96% yield) as a black oil. The crude was used into the next step without further purification.

LCMS m/z=267.0 $[M+H]^+$.

[(3S)-2-Oxopyrrolidin-3-yl]-4-[3-[2-(cyclopropoxy)-3-pyridyl]pyrazolo[1,5-a]pyrimidin-5-yl]piperazine-1-carboxylate

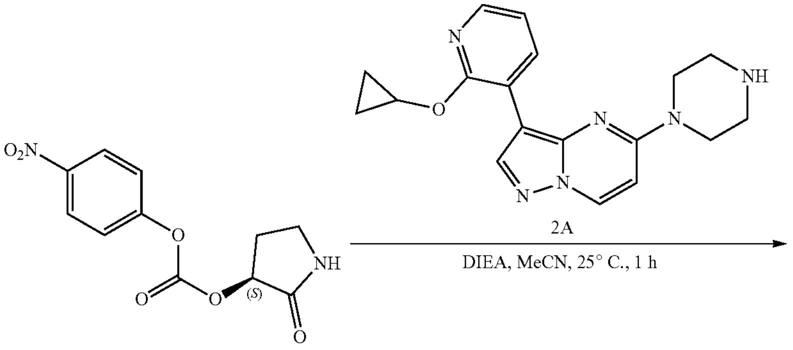

2

-continued

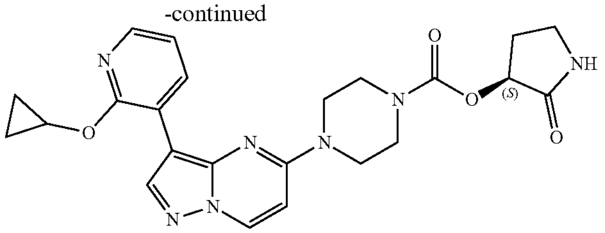

I-24

To a solution of (4-nitrophenyl) [(3S)-2-oxopyrrolidin-3-yl] carbonate (356.11 mg, 1.34 mmol, 3 eq) and 3-[2-(cyclopropoxy)-3-pyridyl]-5-piperazin-1-yl-pyrazolo[1,5a] pyrimidine (150 mg, 445.91 μmol, 1 eq) in MeCN (3.5 mL) was added DIEA (201.71 mg, 1.56 mmol, 271.84 μL, 3.5 eq). The mixture was stirred at 25° C. for 1 hour. The reaction mixture was filtered and concentrated under reduced pressure to give a residue. The crude was purified by preparative HPLC. The pure fractions were collected and the volatiles were removed under vacuum. The residue was partitioned between acetonitrile (5 mL) and water (15 mL). The solution was lyophilized to dryness to give [(3S)-2-oxopyrrolidin-3-yl]-4-[3-[2-(cyclopropoxy)-3-pyridyl]pyrazolo[1,5-a]pyrimidin-5-yl]piperazine-1-carboxylate (105.7 mg, 221.25 μmol, 49.02% yield, 95.84% purity) as a solid.

LCMS m/z=464.0 $[M+H]^+$.

SFC $t_R$=1.655 min; 100%.

$^1$H NMR (400 MHz, methanol-$d_4$) δ=8.90-8.85 (m, 1H), 8.48 (d, J=7.9 Hz, 1H), 8.40 (s, 1H), 8.00-7.96 (m, 1H), 7.13-7.06 (m, 1H), 6.78-6.71 (m, 1H), 5.34-5.27 (m, 1H), 4.39-4.32 (m, 1H), 3.92-3.79 (m, 4H), 3.76-3.58 (m, 4H), 3.46-3.36 (m, 2H), 2.66-2.56 (m, 1H), 2.17-2.03 (m, 1H), 0.91-0.77 (m, 4H).

Example 22: Synthesis of Compound I-25

(3S)-5-Oxopyrrolidin-3-yl]-4-(3-bromopyrazolo[1,5-a]pyrimidin-5-yl)piperazine-1-carboxylate

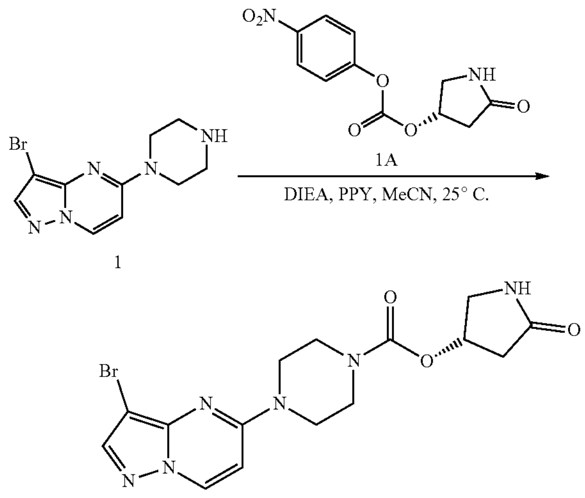

1

2

To a solution of 3-bromo-5-piperazin-1-yl-pyrazolo[1,5-a]pyrimidine (2 g, 7.09 mmol, 1 eq) and (4-nitrophenyl) [(3S)-5-oxopyrrolidin-3-yl]carbonate (2.83 g, 10.63 mmol, 1.5 eq) in MeCN (20 mL) was added DIEA (2.75 g, 21.27 mmol, 3.70 mL, 3 eq) and 4-pyrrolidin-1-yl-pyridine (105.06 mg, 708.87 μmol, 0.1 eq). The mixture was stirred at 25° C. for 1 hr. The reaction mixture was concentrated under reduced pressure to give a residue. The crude was purified by flash silica gel chromatography to give [(3S)-5-oxopyrrolidin-3-yl] 4-(3-bromopyrazolo[1,5-a]pyrimidin-5-yl)piperazine-1-carboxylate (2.8 g, 6.84 mmol, 60.87% yield, 100% purity) as an oil.

LCMS m/z=409.0 $[M+H]^+$.

$^1$H NMR (400 MHz, DMSO-$d_6$) δ=8.69 (d, J=7.9 Hz, 1H), 7.97 (s, 1H), 7.71 (s, 1H), 6.77 (d, J=8.0 Hz, 1H), 5.25-5.15 (m, 1H), 3.73 (br s, 4H), 3.61 (dd, J=5.7, 11.4 Hz, 1H), 3.50 (br d, J=4.9 Hz, 4H), 3.24 (br d, J=11.5 Hz, 1H), 2.66-2.60 (m, 1H), 2.16 (dd, J=2.0, 17.5 Hz, 1H).

3-Bromo-2-(oxetan-3-yloxy)pyridine

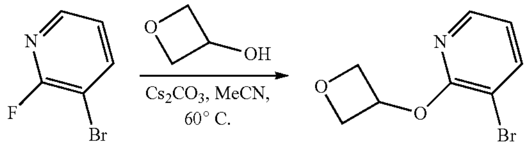

3A

To a solution of 3-bromo-2-fluoro-pyridine (1.2 g, 6.82 mmol, 1 eq) in MeCN (2 mL) was added $Cs_2CO_3$ (6.67 g, 20.46 mmol, 3 eq) and oxetan-3-ol (505.12 mg, 6.82 mmol, 1 eq). The mixture was stirred at 60° C. for 1 hr. The reaction mixture was filtered with diatomite and concentrated under reduced pressure to give a residue. The residue was purified by flash silica gel chromatography to give 3-bromo-2-(oxetan-3-yloxy)pyridine (1.30 g, 5.65 mmol, 82.87% yield, 100% purity) as a colorless oil.

LCMS m/z=230.1 $[M+H]^+$.

$^1$H NMR (400 MHz, $CDCl_3$) δ=7.93 (dd, J=1.6, 4.9 Hz, 1H), 7.76 (dd, J=1.6, 7.6 Hz, 1H), 6.73 (dd, J=4.9, 7.6 Hz, 1H), 5.55 (quin, J=5.9 Hz, 1H), 4.93 (t, J=7.1 Hz, 2H), 4.72 (dd, J=5.7, 7.4 Hz, 2H).

[(3S)-5-Oxopyrrolidin-3-yl] 4-[3-[2-(oxetan-3-yloxy)-3-pyridyl]pyrazolo[1,5-a]pyrimidin-5-yl] piperazine-1-carboxylate (I-25)

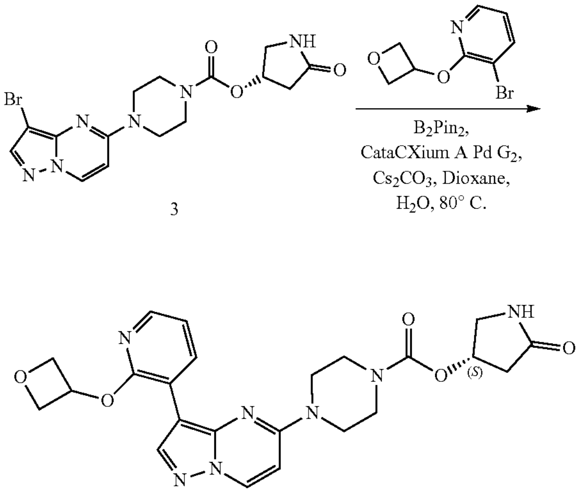

3

I-25

A mixture of 3-bromo-2-(oxetan-3-yloxy)pyridine (505.95 mg, 2.20 mmol, 3 eq), (S)-5-oxopyrrolidin-3-yl 4-(3-bromopyrazolo[1,5-a]pyrimidin-5-yl)piperazine-1-carboxylate (300 mg, 733.07 μmol, 1 eq), 4,4,5,5-tetramethyl-2-(4,4,5,5-tetramethyl-1,3,2-dioxaborolan-2-yl)-1,3,2-dioxaborolane (372.31 mg, 1.47 mmol, 2 eq), [2-(2-aminophenyl)phenyl]-chloro-palladium; bis(1-adamantyl)-butyl-phosphane (98.03 mg, 146.61 μmol, 0.2 eq) and $Cs_2CO_3$ (716.55 mg, 2.20 mmol, 3 eq) in dioxane (3 mL) and $H_2O$ (0.3 mL) was degassed and purged with $N_2$ for 3 times, and then the mixture was stirred at 80° C. for 1 hr under $N_2$ atmosphere. The reaction mixture was filtered and concentrated under reduced pressure to give a crude product. The crude was purified by preparative HPLC. The solution was lyophilized to dryness to give [(3S)-5-oxopyrrolidin-3-yl]-4-[3-[2-(oxetan-3-yloxy)-3-pyridyl]pyrazolo[1,5-a]pyrimidin-5-yl]piperazine-1-carboxylate (17.64 mg, 36.35 μmol, 4.96% yield, 98.80% purity) as a solid.

LCMS m/z=480.2 $[M+H]^+$.

SFC $t_R$=1.769 min; 100%.

$^1H$ NMR (400 MHz, DMSO-$d_6$) δ=8.85-8.82 (m, 1H), 8.77 (d, J=7.9 Hz, 1H), 8.58 (s, 1H), 7.92-7.89 (m, 1H), 7.71 (s, 1H), 7.14-7.10 (m, 1H), 6.83 (d, J=7.9 Hz, 1H), 5.69-5.63 (m, 1H), 5.20 (t, J=6.0 Hz, 1H), 4.94 (t, J=6.9 Hz, 2H), 4.70-4.67 (m, 2H), 3.79-3.75 (m, 4H), 3.63-3.59 (m, 1H), 3.55-3.51 (m, 4H), 3.24 (d, J=11.0 Hz, 1H), 2.61 (d, J=6.9 Hz, 1H), 2.19-2.13 (m, 1H).

Example 23: Synthesis of Compound I-26

3-(2-Isopropoxy-3-pyridyl)-5-piperazin-1-yl-pyrazolo[1,5-a]pyrimidine

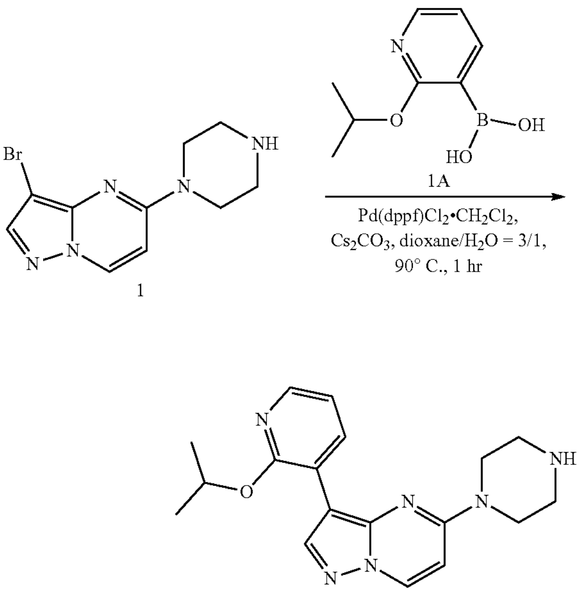

1

1A

2

A mixture of 3-bromo-5-piperazin-1-yl-pyrazolo[1,5-a]pyrimidine (400 mg, 1.42 mmol, 1 eq), (2-isopropoxy-3-pyridyl) boronic acid (333.59 mg, 1.84 mmol, 1.3 eq), $Pd(dppf)Cl_2 \cdot CH_2Cl_2$ (231.56 mg, 283.55 μmol, 0.2 eq), $Cs_2CO_3$ (1.39 g, 4.25 mmol, 3 eq) in dioxane (3 mL) and $H_2O$ (1 mL) was degassed and purged with $N_2$ for 3 times, and then the mixture was stirred at 90° C. for 1 hour under $N_2$ atmosphere. The reaction mixture was filtered and concentrated under reduced pressure to give a residue. The residue was purified by flash silica gel chromatography to give 3-(2-isopropoxy-3-pyridyl)-5-piperazin-1-yl-pyrazolo[1,5-a]pyrimidine (470 mg, 1.39 mmol, 97.96% yield) as a solid.

LCMS m/z=339.1 $[M+H]^+$.

[(3S)-5-Oxopyrrolidin-3-yl]-4-[3-(2-isopropoxy-3-pyridyl)pyrazolo[1,5-a]pyrimidin-5-yl]piperazine-1-carboxylate

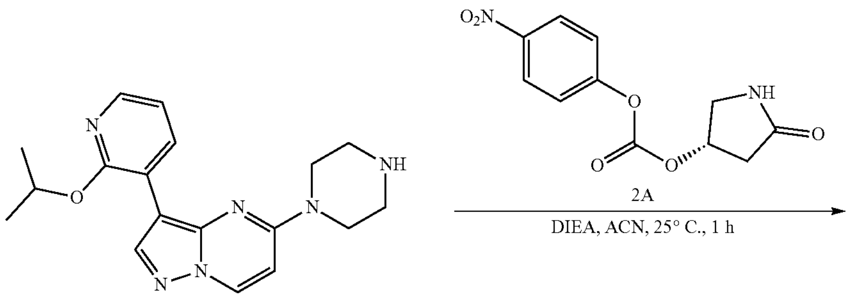

2

2A

-continued

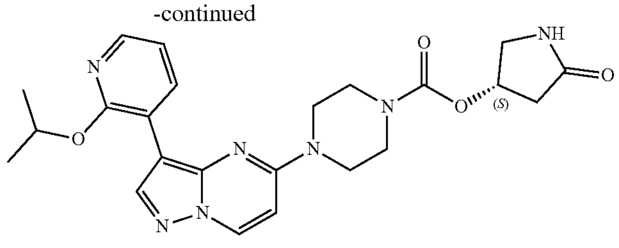

I-26

A mixture of 3-(2-isopropoxy-3-pyridyl)-5-piperazin-1-yl-pyrazolo[1,5-a]pyrimidine (470.0 mg, 1.39 mmol, 1 eq), (4-nitrophenyl) [(3S)-5-oxopyrrolidin-3-yl] carbonate (1.11 g, 4.17 mmol, 3 eq), DIEA (628.25 mg, 4.86 mmol, 846.70 μL, 3.5 eq) in MeCN (12 mL) was degassed and purged with $N_2$ for 3 times, and then the mixture was stirred at 25° C. for 1 hour under $N_2$ atmosphere. The reaction mixture was filtered and concentrated under reduced pressure to give a residue. The crude was purified by preparative HPLC. The pure fractions were collected and the volatiles were removed under vacuum. The residue was partitioned between acetonitrile (5 mL) and water (15 mL). The solution was lyophilized to dryness to give [(3S)-5-oxopyrrolidin-3-yl]-4-[3-(2-isopropoxy-3-pyridyl)pyrazolo[1,5-a]pyrimidin-5-yl]piperazine-1-carboxylate (319 mg, 675.68 μmol, 48.65% yield, 98.60% purity) as a solid.

LCMS m/z=466.0 $[M+H]^+$.

SFC $t_R$=2.497 min; 100%.

$^1H$ NMR (400 MHz, DMSO-$d_6$) δ=8.82-8.71 (m, 2H), 8.50 (s, 1H), 7.98-7.90 (m, 1H), 7.74 (s, 1H), 7.08-6.98 (m, 1H), 6.81 (d, J=8.0 Hz, 1H), 5.45-5.33 (m, 1H), 5.25-5.15 (m, 1H), 3.80-3.70 (m, 4H), 3.65-3.58 (m, 1H), 3.55-3.47 (m, 4H), 3.25 (d, J=11.5 Hz, 1H), 2.69-2.59 (m, 1H), 2.23-2.11 (m, 1H), 1.39 (d, J=6.1 Hz, 6H).

Example 24: Synthesis of Compound I-27

[(3aS,4R,6aR)-2,3,3a,4,5,6a-Hexahydrofuro[2,3-b]furan-4-yl](4-nitrophenyl) carbonate

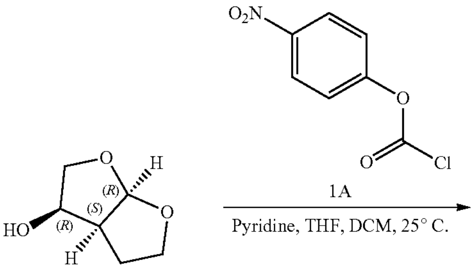

1

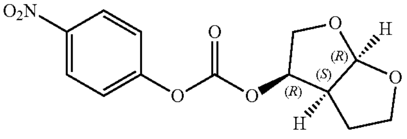

2

A mixture of (3aS, 4R, 6aR)-2,3,3a,4,5,6a-hexahydrofuro[2,3-b]furan-4-ol (1.0 g, 7.68 mmol, 1 eq) in DCM (10 mL) and THF (2 mL) was cooled to 0° C., then the mixture was added pyridine (1.22 g, 15.37 mmol, 1.24 mL, 2 eq) and (4-nitrophenyl) carbonochloridate (1.63 g, 8.07 mmol, 1.05 eq). The reaction was allowed to stirred at 25° C. for 1 hr. The mixture was concentrated to the crude product. The crude was purified by FCC to give [(3aS,4R,6aR)-2,3,3a,4,5,6a-hexahydrofuro[2,3-b]furan-4-yl](4-nitrophenyl) carbonate (1.4 g, 4.74 mmol, 61.71% yield) as a solid.

LCMS m/z=295.3 [M]).

$^1H$ NMR (400 MHz, DMSO-$d_6$): 8.32 (br d, J=9.0 Hz, 2H), 7.60 (br d, J=9.0 Hz, 2H), 5.64 (d, J=5.1 Hz, 1H), 5.22 (td, J=5.4, 7.9 Hz, 1H), 4.01-3.95 (m, 1H), 3.90-3.87 (m, 1H), 3.83-3.63 (m, 2H), 3.20-3.05 (m, 1H), 2.05-1.97 (m, 1H), 1.93-1.79 (m, 1H).

[(3aS,4R,6aR)-2,3,3a,4,5,6a-hexahydrofuro[2,3-b]furan-4-yl]-4-[3-[2-(cyclopropoxy)-3-pyridyl]pyrazolo[1,5-a]pyrimidin-5-yl]piperazine-1-carboxylate

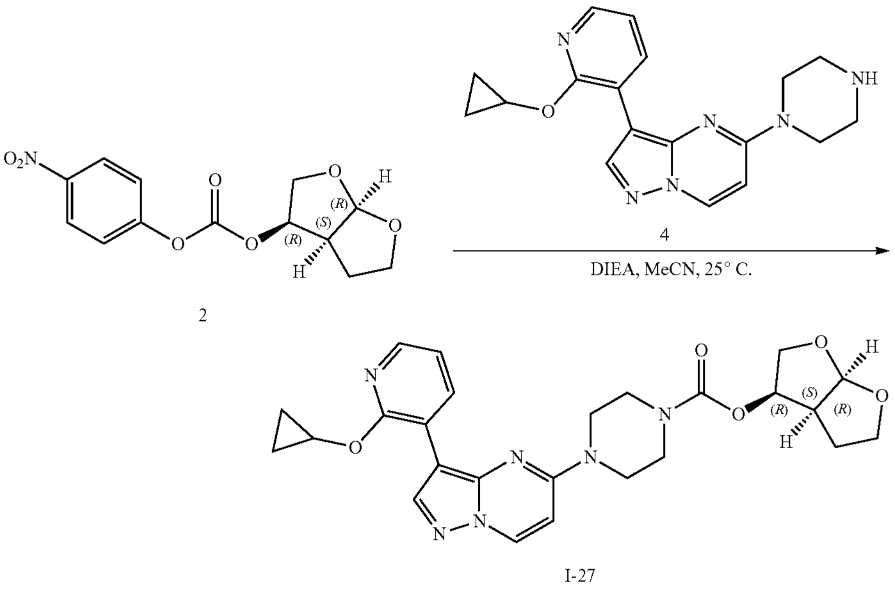

To a solution of 3-[2-(cyclopropoxy)-3-pyridyl]-5-piperazin-1-yl-pyrazolo[1,5-a]pyrimidine (100 mg, 297.27 μmol, 1 eq) and DIEA (76.84 mg, 594.55 μmol, 103.56 μL, 2 eq) in MeCN (0.6 mL) was added [(3aS,4R,6aR)-2,3,3a,4,5,6a-hexahydrofuro[2,3-b]furan-4-yl] (4-nitrophenyl) carbonate (96.55 mg, 327.00 μmol, 1.1 eq). The mixture was stirred at 25° C. for 1 hr. The mixture was concentrated to give the crude product. The residue was purified by preparative HPLC to give [(3aS,4R,6aR)-2,3,3a,4,5,6a-hexahydrofuro[2,3-b]furan-4-yl]-4-[3-[2-(cyclopropoxy)-3-pyridyl]pyrazolo[1,5-a]pyrimidin-5-yl]piperazine-1-carboxylate (35.77 mg, 71.67 μmol, 24.11% yield, 98.689% purity) as a powder.

LCMS m/z=493.2 $[M+H]^+$.

SFC $t_R$=1.051 min; 100%.

$^1$H NMR (400 MHz, DMSO-$d_6$): 8.83-8.70 (m, 2H), 8.34 (s, 1H), 8.05-7.95 (m, 1H), 7.18-7.06 (m, 1H), 6.80 (d, J=7.8 Hz, 1H), 5.62 (d, J=5.2 Hz, 1H), 5.14-5.04 (m, 1H), 4.45-4.35 (m, 1H), 3.99-3.93 (m, 1H), 3.92-3.84 (m, 1H), 3.83-3.72 (m, 5H), 3.71-3.65 (m, 1H), 3.61-3.48 (m, 4H), 3.09-2.98 (m, 1H), 2.02-1.92 (m, 1H), 1.89-1.74 (m, 1H), 0.86-0.71 (m, 4H).

Example 25: Synthesis of Compound I-28

[(3S)-1-(2-Amino-2-oxo-ethyl)-5-oxo-pyrrolidin-3-yl] 4-[3-[2-(cyclopropoxy)-3-pyridyl]pyrazolo[1,5-a]pyrimidin-5-yl]piperazine-1-carboxylate

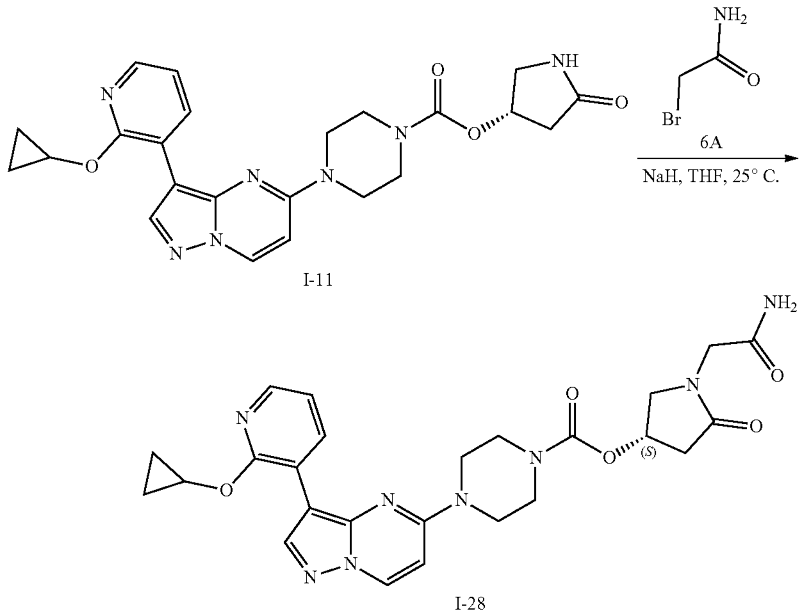

To a mixture of [(3S)-5-oxopyrrolidin-3-yl]-4-[3-[2-(cyclopropoxy)-3-pyridyl]pyrazolo[1,5-a]pyrimidin-5-yl]piperazine-1-carboxylate (40 mg, 86.30 μmol, 1 eq) in dry THF (1 mL) was added NaH (5.18 mg, 129.45 μmol, 60% purity, 1.5 eq) at 0° C. under $N_2$ atmosphere. The mixture was stirred at this temperature for 10 min. Then 2-bromoacetamide (17.86 mg, 129.45 μmol, 1.5 eq) was added at 0° C. The mixture was warmed to 25° C. and stirred for 1 hr under $N_2$ atmosphere. The mixture was added to the sat. $NH_4Cl$ (aq.) (10 mL), then extracted with EA (15 mL*3), the organic phase was concentrated to give the crude product. Then the product was further purified by preparative HPLC to give [(3S)-1-(2-amino-2-oxo-ethyl)-5-oxo-pyrolidin-3-yl] 4-[3-[2-(cyclopropoxy)-3-pyridyl]pyrazolo[1,5-a]pyrimidin-5-yl]piperazine-1-carboxylate (10.16 mg, 19.07 μmol, 22.10% yield, 97.712% purity) as a powder.

LCMS m/z=521.2 $[M+H]^+$.

SFC $t_R$=0.943 min; 100%.

$^{1}$H NMR (400 MHz, DMSO-$d_6$): 8.85-8.67 (m, 2H), 8.40-8.27 (m, 1H), 8.07-7.92 (m, 1H), 7.47-7.33 (m, 1H), 7.17-7.03 (m, 2H), 6.81 (d, J=7.8 Hz, 1H), 5.25-5.11 (m, 1H), 4.50-4.29 (m, 1H), 3.87-3.70 (m, 6H), 3.61-3.48 (m, 4H), 3.45-3.37 (m, 2H), 2.84-2.74 (m, 1H), 2.37-2.31 (m, 1H), 0.87-0.69 (m, 4H).

Example 26: Synthesis of Compound I-29

[(3R)-1-(2-Amino-2-oxo-ethyl)-5-oxo-pyrrolidin-3-yl] 4-[3-[2-(cyclopropoxy)-3-pyridyl]pyrazolo[1,5-a]pyrimidin-5-yl]piperazine-1-carboxylate

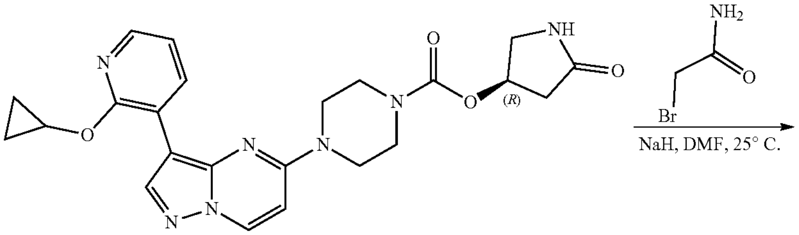

I-10

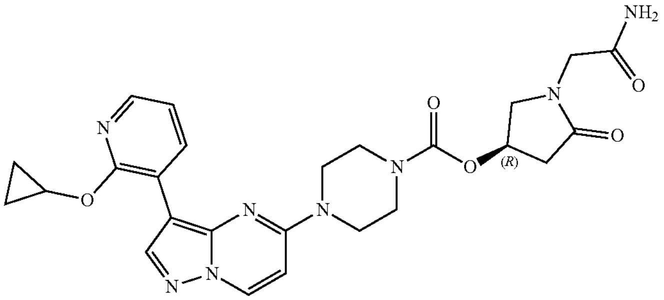

I-29

A mixture of [(3R)-5-oxopyrrolidin-3-yl] 4-[3-[2-(cyclopropoxy)-3-pyridyl]pyrazolo-[1,5-a]pyrimidin-5-yl]piperazine-1-carboxylate (100 mg, 215.76 μmol, 1 eq) in THF (1 mL) was added NaH slowly (10.36 mg, 258.91 μmol, 60% purity, 1.2 eq) at 0° C. over 10 min, and then 2-bromoacetamide (29.77 mg, 215.76 μmol, 1 eq) was added slowly at 0° C. The resulting mixture was stirred at 25° C. for 16 hr. Sat. $NH_4Cl$ (aq.) (5 mL) was slowly added to quench the reaction at 0° C., then extracted with EA (5 mL×3), the organic phase was concentrated to give the crude product. The residue was purified by preparative HPLC. The residue was partitioned between acetonitrile (2 mL) and water (10 mL). The solution was lyophilized to dryness to give the product. Compound [(3R)-1-(2-amino-2-oxo-ethyl)-5-oxo-pyrrolidin-3-yl] 4-[3-[2-(cyclopropoxy)-3-pyridyl]pyrazolo[1,5-a]pyrimidin-5-yl]piperazine-1-carboxylate (4 mg, 7.60 μmol, 3.52% yield, 98.94% purity) was obtained as a powder.

LCMS m/z=521.1 $[M+H]^+$.

SFC $t_R$=2.129 min; 100%.

$^{1}$H NMR (400 MHz, methanol-$d_4$) δ=8.95-8.83 (m, 1H), 8.54-8.45 (m, 1H), 8.41 (s, 1H), 8.04-7.94 (m, 1H), 7.16-7.02 (m, 1H), 6.82-6.70 (m, 1H), 5.36-5.26 (m, 1H), 4.42-4.30 (m, 1H), 4.02 (s, 2H), 3.98-3.89 (m, 1H), 3.87-3.80 (m, 4H), 3.70-3.61 (m, 4H), 3.60-3.53 (m, 1H), 3.00-2.88 (m, 1H), 2.60-2.46 (m, 1H), 0.91-0.80 (m, 4H).

Example 27: Synthesis of Compound I-30 and Compound I-32

Trimethyl-(1-methyl-1-phenyl-ethyl) peroxy-silane

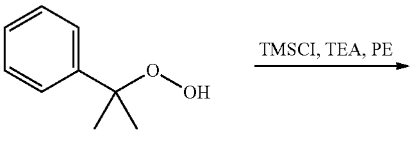

1C

-continued

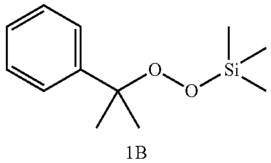

1B

To a solution of (1-hydroperoxy-1-methyl-ethyl)benzene (6 g, 39.42 mmol, 5.78 mL, 1 eq) in PE (50 mL) was added TEA (5.98 g, 59.14 mmol, 8.23 mL, 1.5 eq) and TMSCl (5.14 g, 47.31 mmol, 6.00 mL, 1.2 eq) slowly. The mixture was stirred at 10° C. for 1 hr. Then the reaction mixture was washed with water 150 mL (50 mL×3) and aqueous NaCl 50 mL, dried over $Na_2SO_4$, filtered and concentrated under reduced pressure to give trimethyl-(1-methyl-1-phenyl-ethyl) peroxy-silane (8.69 g, 38.73 mmol, 98.24% yield) as an oil.

$^1$H NMR (400 MHz, $CDCl_3$) δ=7.30-7.24 (m, 2H), 7.18-7.11 (m, 2H), 7.09-7.02 (m, 1H), 1.40 (s, 6H), 0.00 (s, 9H).

Tert-Butyl 4-[(4S)-4-[tert-butyl(diphenyl)silyl]oxy-2-oxo-pyrrolidin-1-yl]piperidine-1-carboxylate

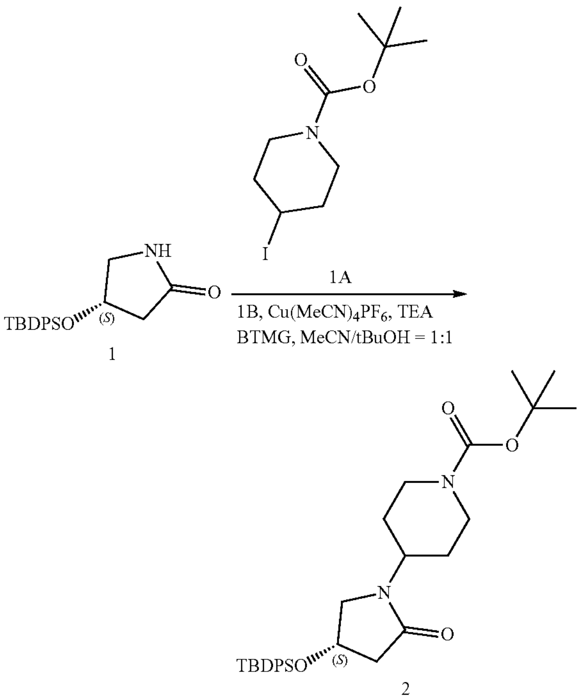

1

2

A mixture of (4S)-4-[tert-butyl(diphenyl)silyl]oxypyrrolidin-2-one (3.5 g, 10.31 mmol, 1.5 eq), tert-butyl 4-iodopiperidine-1-carboxylate (2.14 g, 6.87 mmol, 1 eq), TEA (3.48 g, 34.36 mmol, 4.78 mL, 5 eq) was purged with $N_2$ for 3 times, then the mixture was added 2-tert-butyl-1,1,3,3-tetramethyl-guanidine (2.35 g, 13.75 mmol, 2.76 mL, 2 eq) and trimethyl((2-phenylpropan-2-yl) peroxy) silane (7.71 g, 34.36 mmol, 8.20 mL, 5 eq) which was dissolved in MeCN (1 mL) and t-BuOH (1 mL) under $N_2$ atmosphere. Finally cuprous; acetonitrile; hexafluorophosphate (256.16 mg, 687.28 μmol, 0.1 eq) was added into the mixture under $N_2$ atmosphere, and then the mixture was stirred at 25° C. for 1 hr under $N_2$ atmosphere. The reaction mixture was concentrated under reduced pressure to give a residue. The residue was diluted with ethyl acetate (30 mL). The organic layer was washed with water 90 mL (30 mL×3), dried over $Na_2SO_4$, filtered and concentrated under reduced pressure to give a crude. The crude was purified by FCC to give tert-butyl 4-[(4S)-4-[tert-butyl(diphenyl)silyl]oxy-2-oxo-pyrrolidin-1-yl]piperidine-1-carboxylate (2 g, 3.25 mmol, 47.32% yield, 85.005% purity) as a gum.

LCMS m/z=467.2 [M+H−56]$^+$.

$^1$H NMR (400 MHz, DMSO-$d_6$) δ=7.63-7.52 (m, 4H), 7.49-7.41 (m, 6H), 4.45-4.36 (m, 1H), 4.08-3.92 (m, 4H), 3.44-3.34 (m, 1H), 3.30-3.19 (m, 2H), 3.19-3.12 (m, 1H), 2.81-2.66 (m, 2H), 2.48-2.42 (m, 2H), 2.17-2.09 (m, 1H), 1.41-1.37 (m, 9H), 1.00 (s, 9H).

tert-Butyl 4-[(4S)-4-hydroxy-2-oxo-pyrrolidin-1-yl]piperidine-1-carboxylate

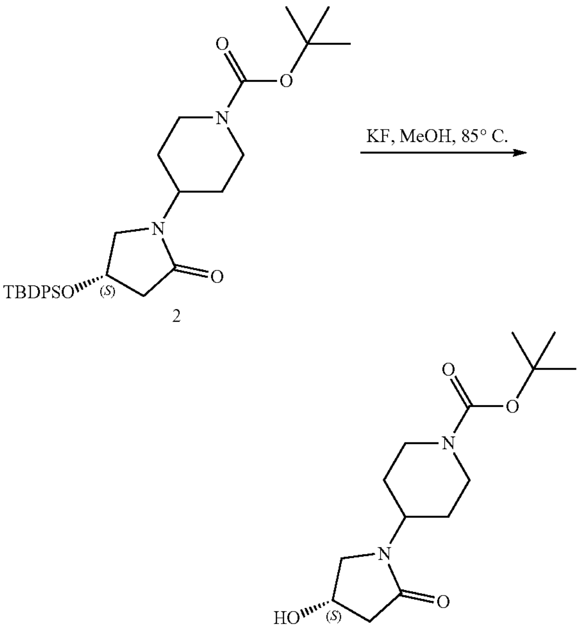

2

3

To a solution of tert-butyl 4-[(4S)-4-[tert-butyl(diphenyl)silyl]oxy-2-oxo-pyrrolidin-1-yl]piperidine-1-carboxylate (1 g, 1.91 mmol, 1 eq) in MeOH (4 mL) was added KF (555.68 mg, 9.56 mmol, 224.07 μL, 5 eq). The mixture was stirred at 85° C. for 1 hr. LCMS showed that desired MS was found. The reaction mixture was concentrated under reduced pressure to give a residue. The crude was purified by FCC to give tert-butyl 4-[(4S)-4-hydroxy-2-oxo-pyrrolidin-1-yl]piperidine-1-carboxylate (500 mg, 1.50 mmol, 78.47% yield, 85.363% purity) as a gum.

LCMS m/z=285.2 [M+H]$^+$.

$^1$H NMR (400 MHz, DMSO-$d_6$) δ=5.12 (d, J=4.0 Hz, 1H), 4.29-4.20 (m, 1H), 4.05-3.96 (m, 2H), 3.94-3.85 (m, 1H), 3.48-3.40 (m, 1H), 3.10-3.02 (m, 1H), 2.84-2.65 (m, 2H), 2.11-1.96 (m, 2H), 1.55-1.45 (m, 3H), 1.45-1.42 (m, 1H), 1.39 (s, 9H).

Tert-butyl 4-[(4S)-4-(4-nitrophenoxy)carbonyloxy-2-oxo-pyrrolidin-1-yl]piperidine-1-carboxylate

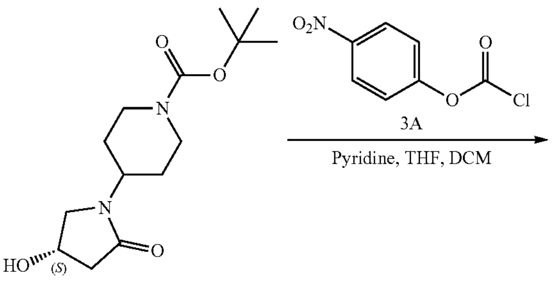

3

-continued

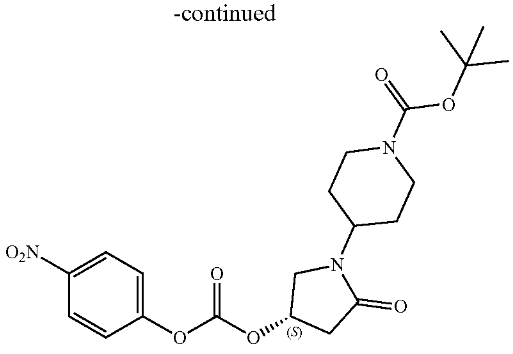

4

To a solution of tert-butyl 4-[(4S)-4-hydroxy-2-oxo-pyrrolidin-1-yl]piperidine-1-carboxylate (250 mg, 879.20

μmol, 1 eq) in THF (0.5 mL) and DCM (2.5 mL) was added pyridine (347.72 mg, 4.40 mmol, 354.82 μL, 5 eq) and (4-nitrophenyl) carbonochloridate (212.66 mg, 1.06 mmol, 1.2 eq). The mixture was stirred at 25° C. for 0.5 hr. LCMS showed that desired MS was found. The reaction mixture was concentrated under reduced pressure to give a residue. The crude was purified by FCC (ISCO®; 5 g SepaFlash® Silica Flash Column, eluent of 0~10% Methanol/Dichloromethane gradient @ 30 mL/min) to give tert-butyl 4-[(4S)-4-(4-nitrophenoxy)carbonyloxy-2-oxo-pyrrolidin-1-yl]piperidine-1-carboxylate (400 mg, 889.97 μmol, 88.02% yield) as red gum.

LCMS m/z=394.3 $[M+H-56]^+$.

[(3S)-1-(1-tert-Butoxycarbonyl-4-piperidyl)-5-oxo-pyrrolidin-3-yl] 4-[3-[2-(cyclopropoxy)-3-pyridyl]pyrazolo[1,5-a]pyrimidin-5-yl]piperazine-1-carboxylate

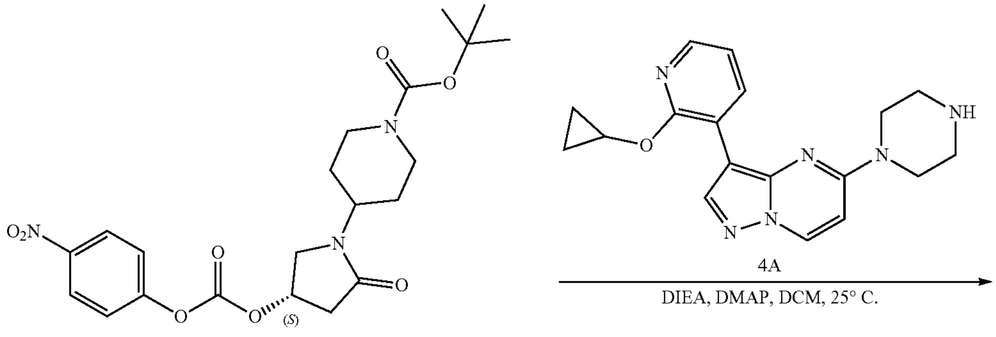

4

4A

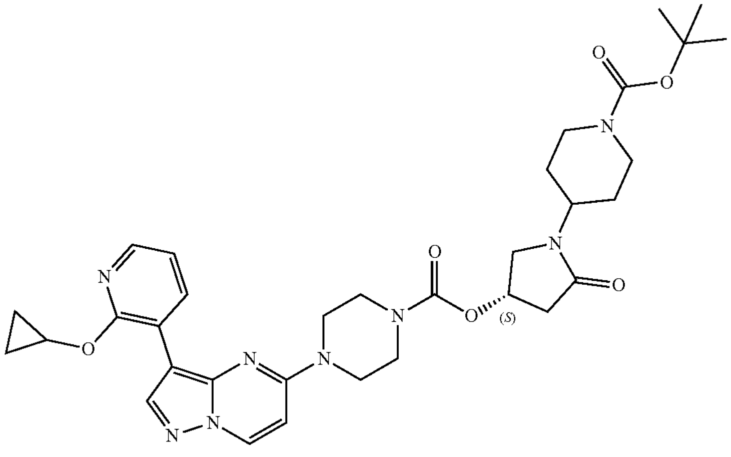

I-30

To a solution of tert-butyl 4-[(4S)-4-(4-nitrophenoxy)carbonyloxy-2-oxo-pyrrolidin-1-yl]piperidine-1-carboxylate (30 mg, 66.75 μmol, 1 eq) in DCM (1 mL) was added DIEA (17.25 mg, 133.50 μmol, 23.25 μL, 2 eq), 3-[2-(cyclopropoxy)-3-pyridyl]-5-piperazin-1-yl-pyrazolo[1,5-a]pyrimidine (26.94 mg, 80.10 μmol, 1.2 eq) and DMAP (1.63 mg, 13.35 μmol, 0.2 eq). The mixture was stirred at 25° C. for 1 hr. The reaction mixture was concentrated under reduced pressure to give a residue. The crude was purified by preparative HPLC. The pure fractions were collected and the volatiles were removed under vacuum. The residue was partitioned between acetonitrile (20 mL) and water (100 mL). The solution was lyophilized to dryness to give [(3S)-1-(1-tert-butoxycarbonyl-4-piperidyl)-5-oxo-pyrrolidin-3-yl]-4-[3-[2-(cyclopropoxy)-3-pyridyl]pyrazolo-[1,5-a]pyrimidin-5-yl]piperazine-1-carboxylate (7.48 mg, 11.50 μmol, 17.23% yield, 99.441% purity) as a powder.

LCMS m/z=647.4 $[M+H]^+$.

SFC $t_R$=1.635 min; 100%.

$^1$H NMR (400 MHz, DMSO-$d_6$) δ=8.82-8.70 (m, 2H), 8.34 (s, 1H), 8.04-7.94 (m, 1H), 7.15-7.06 (m, J=4.9, 7.4 Hz, 1H), 6.81 (d, J=7.9 Hz, 1H), 5.23-5.09 (m, J=5.5, 5.5 Hz, 1H), 4.45-4.36 (m, 1H), 4.10-3.89 (m, 3H), 3.82-3.70 (m, 4H), 3.69-3.61 (m, 1H), 3.57-3.48 (m, J=4.3 Hz, 4H), 2.86-2.61 (m, 4H), 2.34-2.24 (m, 1H), 1.60-1.44 (m, J=4.1, 12.3 Hz, 4H), 1.39 (s, 9H), 0.84-0.74 (m, 4H).

[(3S)-5-Oxo-1-(4-piperidyl)pyrrolidin-3-yl] 4-[3-[2-(cyclopropoxy)-3-pyridyl]pyrazolo[1,5-a]pyrimidin-5-yl]piperazine-1-carboxylate To a solution of [(3S)-1-(1-tert-butoxycarbonyl-4-piperidyl)-5-oxo-pyrrolidin-3-yl] 4-[3-[2-(cyclopropoxy)-3-pyridyl]pyrazolo[1,5-a]pyrimidin-5-yl]piperazine-1-carboxylate (200 mg, 309.25 μmol, 1 eq) in DCM (1.5 mL) was added TFA (767.50 mg, 6.73 mmol, 0.5 mL, 21.77 eq). The mixture was stirred at 25° C. for 1 hr. The reaction mixture was concentrated under reduced pressure to give a residue. The crude was purified by preparative HPLC. The pure fractions were collected and the volatiles were removed under vacuum. The residue was partitioned between acetonitrile (20 mL) and water (100 mL). The solution was lyophilized to dryness to give the product. The product [(3S)-5-oxo-1-(4-piperidyl)pyrrolidin-3-yl]-4-[3-[2-(cyclopropoxy)-3-pyridyl]pyrazolo[1,5-a]pyrimidin-5-yl]piperazine-1-carboxylate (24.83 mg, 41.22 μmol, 13.33% yield, 98.377% purity, FA) was obtained as a solid.

LCMS m/z=547.5 $[M+H]^+$.

SFC, $t_R$=1.280 min; 100%.

$^1$H NMR (400 MHz, $CDCl_3$) δ=8.75-8.67 (m, 1H), 8.52 (s, 1H), 8.50-8.40 (m, 1H), 8.40-8.35 (m, 1H), 8.12-8.03 (m, 1H), 7.06-6.99 (m, 1H), 6.42-6.34 (m, 1H), 5.39-5.23 (m, 1H), 4.50-4.37 (m, 1H), 4.32-4.15 (m, 1H), 3.79-3.73 (m, 5H), 3.68-3.58 (m, 5H), 3.48-3.40 (m, 4H), 2.98-2.87 (m, 2H), 2.87-2.80 (m, 1H), 2.61-2.52 (m, 1H), 2.11-1.92 (m, 2H), 1.91-1.79 (m, 2H), 0.90-0.81 (m, 4H).

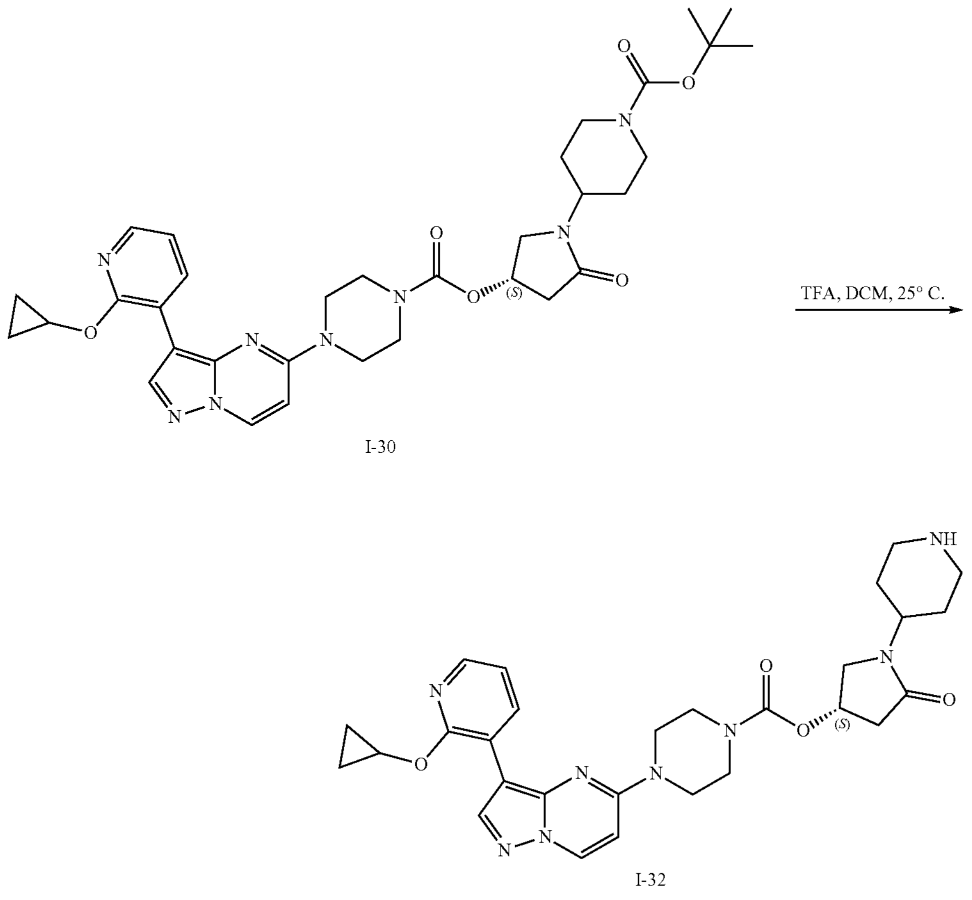

I-30

I-32

Example 28: Synthesis of Compound I-31 and Compound I-33

(4R)-4-[tert-Butyl(diphenyl)silyl]oxypyrrolidin-2-one

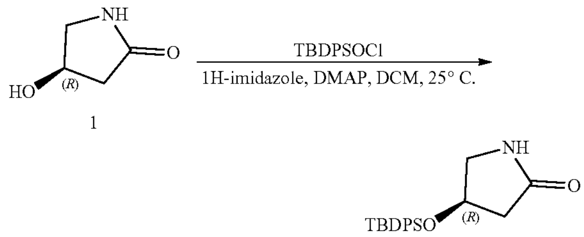

1

2

To a solution of (4R)-4-hydroxypyrrolidin-2-one (3 g, 29.67 mmol, 1 eq) and tert-butyl-chloro-diphenyl-silane (9.79 g, 35.61 mmol, 9.11 mL, 1.2 eq) in DCM (10 mL) was added 1H-imidazole (4.04 g, 59.35 mmol, 2 eq) and DMAP (725.02 mg, 5.93 mmol, 0.2 eq). The mixture was stirred at 25° C. for 1 hr. The reaction mixture was filtered with diatomite and concentrated under reduced pressure to give the crude product. The crude was purified by flash silica gel chromatography to give (4R)-4-[tert-butyl(diphenyl)silyl]oxypyrrolidin-2-one (9.5 g, 25.47 mmol, 85.85% yield, 91.04% purity) as a colorless oil.

LCMS m/z=340.3 $[M+H]^+$.

$^1H$ NMR (400 MHz, methanol-$d_4$) δ=7.61 (dd, J=1.4, 7.8 Hz, 4H), 7.47-7.33 (m, 6H), 4.58-4.50 (m, 1H), 3.38 (dd, J=5.5, 10.6 Hz, 1H), 3.28-3.18 (m, 2H), 2.40 (dd, J=6.4, 17.0 Hz, 1H), 2.20 (dd, J=3.0, 17.0 Hz, 1H), 1.02 (s, 9H).

tert-Butyl (R)-4-(4-((tert-butyldiphenylsilyl)oxy)-2-oxopyrrolidin-1-yl)piperidine-1-carboxylate

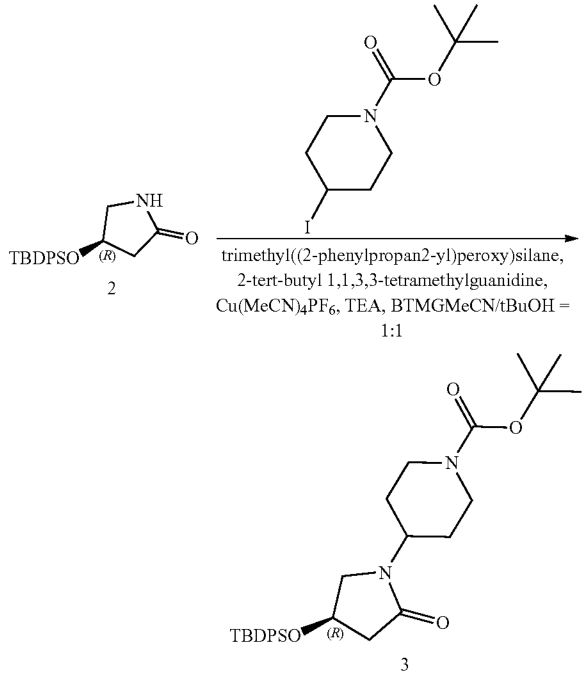

2

3

A mixture of (4R)-4-[tert-butyl(diphenyl)silyl]oxypyrrolidin-2-one (500 mg, 1.47 mmol, 1.5 eq), tert-butyl 4-iodopiperidine-1-carboxylate (305.50 mg, 981.83 μmol, 1 eq), $Cu(MeCN)_4PF_6$ (36.59 mg, 98.18 μmol, 0.1 eq) was degassed and purged with $N_2$ for 3 times, then trimethyl((2-phenylpropan2-yl) peroxy) silane (1.10 g, 4.91 mmol, 5 eq) and 2-tert-butyl1,1,3,3-tetramethylguanidine (336.34 mg, 1.96 mmol, 394.30 μL, 2 eq) in MeCN (1 mL) and t-BuOH (1 mL) were added, finally was added TEA (496.76 mg, 4.91 mmol, 683.30 μL, 5 eq). The mixture was stirred at 25° C. for 1 hr under $N_2$ atmosphere. The reaction mixture was filtered with diatomite and concentrated under reduced pressure to give a crude product. The crude was purified by flash silica gel chromatography to give tert-butyl (R)-4-(4-((tert-butyldiphenylsilyl)oxy)-2-oxopyrrolidin-1-yl)piperidine-1-carboxylate (160 mg, 266.28 μmol, 27.12% yield, 87% purity) as an oil.

LCMS m/z=467.4 $[M+H]^+$.

Tert-butyl (R)-4-(4-hydroxy-2-oxopyrrolidin-1-yl) piperidine-1-carboxylate

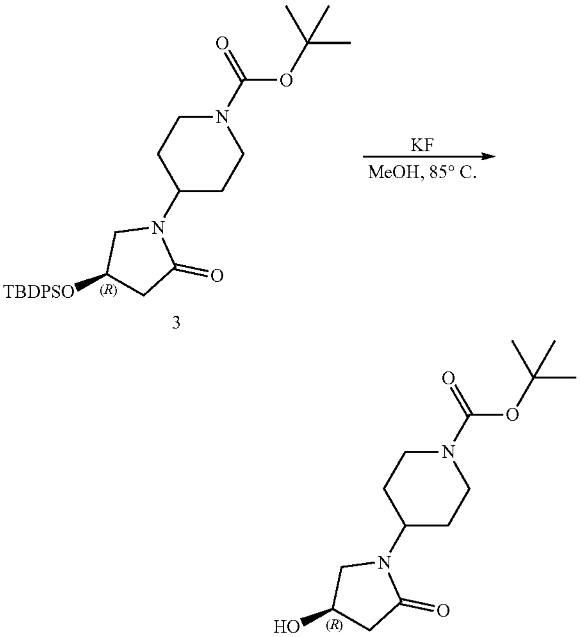

3

4

To a solution of tert-butyl (R)-4-(4-((tert-butyldiphenylsilyl)oxy)-2-oxopyrrolidin-1-yl)piperidine-1-carboxylate (160.00 mg, 306.07 μmol, 1 eq) in MeOH (2 mL) was added KF (88.91 mg, 1.53 mmol, 35.85 μL, 5 eq). The mixture was stirred at 85° C. for 12 hr. The reaction mixture was filtered with diatomite and concentrated under reduced pressure to give a crude product. The crude was purified by flash silica gel chromatography to give tert-butyl (R)-4-(4-hydroxy-2-oxopyrrolidin-1-yl)piperidine-1-carboxylate (40 mg, 140.52 μmol, 45.91% yield, 99.89% purity) as an oil.

LCMS m/z=229.2 $[M+H]^+$.

$^1H$ NMR (400 MHz, $CDCl_3$) δ=4.52 (br s, 1H), 4.20-4.12 (m, 2H), 3.56 (br dd, J=5.5, 10.5 Hz, 1H), 3.26 (br d, J=10.5 Hz, 1H), 2.84-2.66 (m, 3H), 2.40 (br d, J=17.3 Hz, 1H), 1.83-1.49 (m, 6H), 1.46 (s, 9H).

Tert-butyl(S)-4-(4-(((4-Nitrophenoxy)carbonyl)oxy)-2-oxopyrrolidin-1-yl)piperidine-1-carboxylate

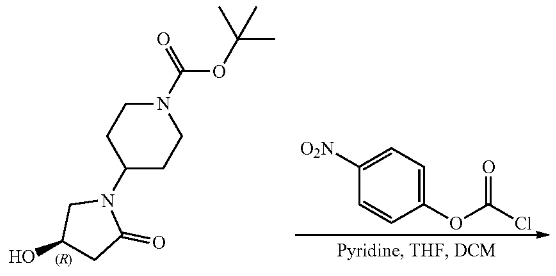

4

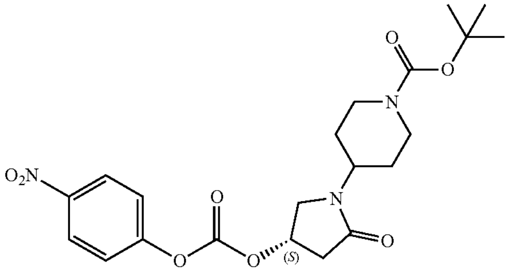

5

To a solution of tert-butyl (R)-4-(4-hydroxy-2-oxopyrrolidin-1-yl)piperidine-1-carboxylate (20 mg, 70.34 μmol, 1 eq) in THF (0.1 mL) and DCM (0.5 mL) was added pyridine (27.82 mg, 351.68 μmol, 28.39 μL, 5 eq) and 4-nitrophenyl carbonochloridate (17.01 mg, 84.40 μmol, 1.2 eq). The mixture was stirred at 25° C. for 0.5 hr. The reaction mixture was filtered with diatomite and concentrated under reduced pressure to give tert-butyl(S)-4-(4-(((4-nitrophenoxy)carbonyl)oxy)-2-oxopyrrolidin-1-yl)piperidine-1-carboxylate (50 mg, crude) as a solid.

LCMS m/z=394.2 [M+H]$^+$.

(R)-1-(1-(tert-Butoxycarbonyl)piperidin-4-yl)-5-oxopyrrolidin-3-yl 4-(3-(2-cyclopropoxypyridin-3-yl)pyrazolo[1,5-a]pyrimidin-5-yl)piperazine-1-carboxylate

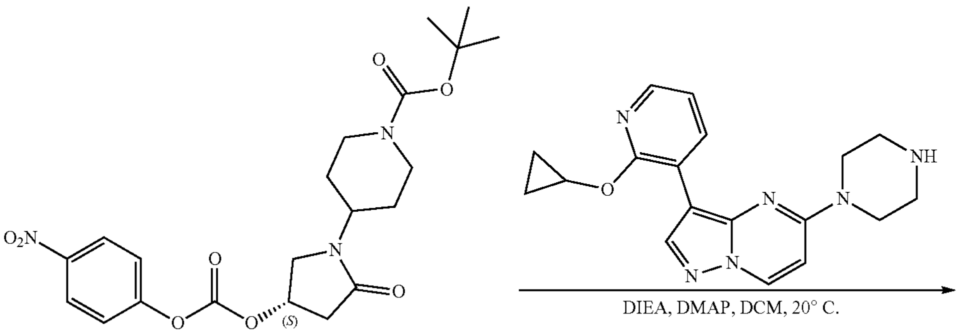

5

-continued

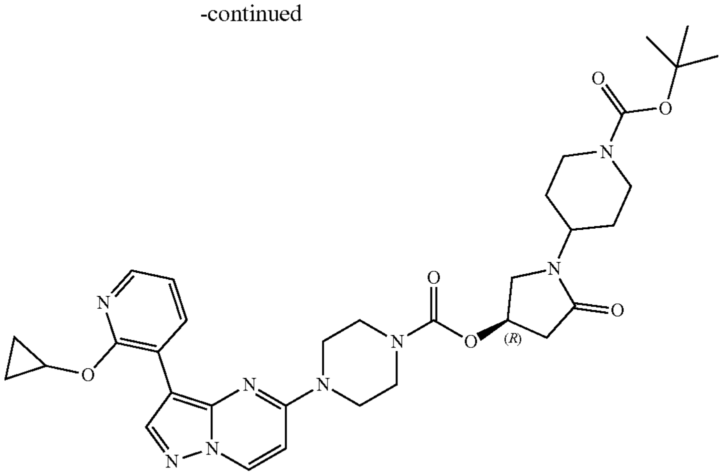

I-31

To a solution of tert-butyl(S)-4-(4-(((4-nitrophenoxy)carbonyl)oxy)-2-oxopyrrolidin-1-yl)piperidine-1-carboxylate (30 mg, 66.75 μmol, 1 eq) and 3-[2-(cyclopropoxy)-3-pyridyl]-5-piperazin-1-yl-pyrazolo[1,5-a]pyrimidine (22.45 mg, 66.75 μmol, 1 eq) in DCM (0.5 mL) was added DMAP (1.63 mg, 13.35 μmol, 0.2 eq) and DIEA (25.88 mg, 200.24 μmol, 34.88 μL, 3 eq). The mixture was stirred at 25° C. for 0.5 hr. The reaction mixture was filtered and concentrated under reduced pressure to give a crude product. The crude was purified by preparative HPLC. The solution was lyophilized to dryness to give (R)-1-(1-(tert-butoxycarbonyl)piperidin-4-yl)-5-oxopyrrolidin-3-yl-4-(3-(2-cyclopropoxypyridin-3-yl)pyrazolo[1,5-a]pyrimidin-5-yl)piperazine-1-carboxylate (6.67 mg, 10.23 μmol, 15.32% yield, 99.175% purity) as a powder.

LCMS m/z=647.5 $[M+H]^+$.

SFC $t_R$=1.673 min; 100%.

$^1H$ NMR (400 MHz, $CDCl_3$) δ=8.71 (d, J=7.4 Hz, 1H), 8.52 (s, 1H), 8.37 (d, J=7.8 Hz, 1H), 8.09 (d, J=4.3 Hz, 1H), 7.08-6.98 (m, 1H), 6.38 (d, J=7.8 Hz, 1H), 5.37-5.24 (m, 1H), 4.51-4.36 (m, 1H), 4.29-4.09 (m, 3H), 3.79-3.72 (m, 4H), 3.70 (d, J=5.6 Hz, 1H), 3.68-3.56 (m, 4H), 3.38 (d, J=11.3 Hz, 1H), 2.87-2.73 (m, 3H), 2.56 (d, J=17.8 Hz, 1H), 1.68-1.62 (m, 2H), 1.61-1.52 (m, 2H), 1.46 (s, 9H), 0.89-0.81 (m, 4H).

(R)-5-Oxo-1-(piperidin-4-yl)pyrrolidin-3-yl 4-(3-(2-cyclopropoxypyridin-3-yl)pyrazolo[1,5-a]pyrimidin-5-yl)piperazine-1-carboxylate

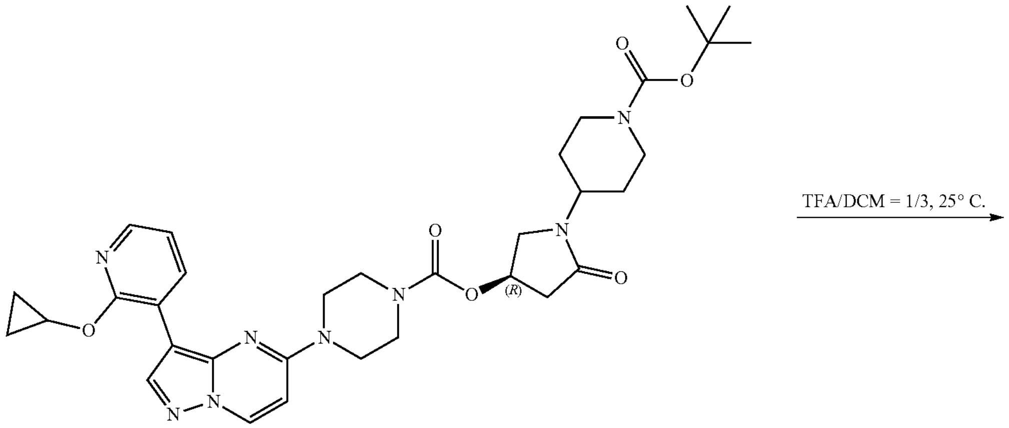

I-31

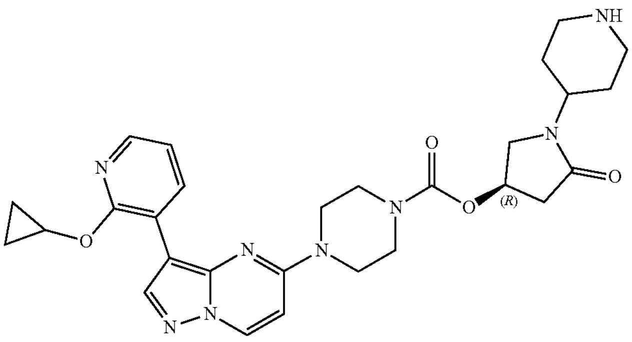

I-33

To a solution of (R)-1-(1-(tert-butoxycarbonyl)piperidin-4-yl)-5-oxopyrrolidin-3-yl 4-(3-(2-cyclopropoxypyridin-3-yl)pyrazolo[1,5-a]pyrimidin-5-yl)piperazine-1-carboxylate (90 mg, 139.16 μmol, 1 eq) in DCM (1 mL) was added TFA (460.50 mg, 4.04 mmol, 0.3 mL, 29.02 eq). The mixture was stirred at 25° C. for 1 hr. The reaction mixture was filtered and concentrated under reduced pressure to give a crude product. The crude was purified by preparative HPLC. The solution was lyophilized to dryness to give (R)-5-oxo-1-(piperidin-4-yl)pyrrolidin-3-yl 4-(3-(2-cyclopropoxypyridin-3-yl)pyrazolo[1,5-a]pyrimidin-5-yl)piperazine-1-carboxylate (5.40 mg, 9.51 μmol, 37.14% yield, 96.29% purity) as a solid.

LCMS m/z=547.3 $[M+H]^+$.

SFC $t_R$=1.470 min; 100%.

$^1H$ NMR (400 MHz, $CDCl_3$) δ=8.75-8.67 (m, 1H), 8.52 (s, 1H), 8.37 (d, J=7.9 Hz, 1H), 8.12-8.06 (m, 1H), 7.08-6.99 (m, 1H), 6.39 (d, J=7.9 Hz, 1H), 5.32 (t, J=6.3 Hz, 1H), 4.49-4.38 (m, 1H), 4.18-4.07 (m, 1H), 3.82-3.74 (m, 4H), 3.74-3.71 (m, 1H), 3.69-3.57 (m, 4H), 3.47-3.40 (m, 1H), 3.18 (d, J=11.3 Hz, 2H), 2.86-2.79 (m, 1H), 2.79-2.68 (m, 2H), 2.59-2.52 (m, 1H), 1.76-1.66 (m, 3H), 1.66-1.57 (m, 2H), 0.88-0.83 (m, 4H).

Example 29: Synthesis of Compound I-34

(4S)-4-[tert-Butyl(diphenyl)silyl]oxy-1-methyl-pyrrolidin-2-one

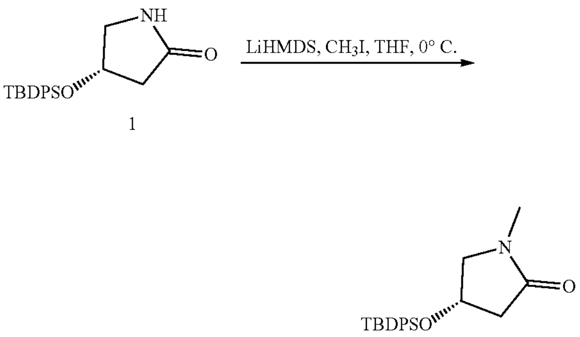

1

2

A mixture of (4S)-4-[tert-butyl(diphenyl)silyl]oxypyrrolidin-2-one (5 g, 14.73 mmol, 1 eq), $CH_3I$ (6.27 g, 44.18 mmol, 2.75 mL, 3 eq), LiHMDS (1 M, 29.45 mL, 2 eq) in THF (20 mL) was degassed and purged with $N_2$ for 3 times, and then the mixture was stirred at 0° C. for 1 hr under $N_2$ atmosphere. The reaction mixture was concentrated under reduced pressure to give a residue. The residue was purified by column chromatography ($SiO_2$, DCM:MeOH=1/0 to 10/1) to give (4S)-4-[tert-butyl(diphenyl)silyl]oxy-1-methyl-pyrrolidin-2-one (3.7 g, 9.84 mmol, 66.81% yield, 94.01% purity) as an oil.

LCMS m/z=354.2 $[M+H]^+$.

$^1H$ NMR (400 MHz, DMSO-$d_6$) δ=7.63-7.56 (m, 4H), 7.52-7.40 (m, 6H), 4.45 (dt, J=2.9, 6.0 Hz, 1H), 3.45 (dd, J=5.8, 10.4 Hz, 1H), 3.20 (dd, J=2.4, 10.5 Hz, 1H), 2.68 (s, 3H), 2.44 (dd, J=6.8, 16.8 Hz, 1H), 2.14 (dd, J=2.6, 16.8 Hz, 1H), 1.00 (s, 9H).

(4S)-4-Hydroxy-1-methyl-pyrrolidin-2-one

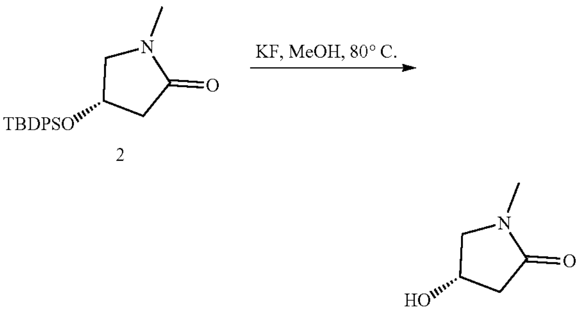

2

3

The product 3 was prepared according to the synthesis method of I-35.

Compound (4S)-4-hydroxy-1-methyl-pyrrolidin-2-one (100 mg, crude) was obtained as an oil.

$^1H$ NMR (400 MHz, DMSO-$d_6$) δ=5.15 (d, J=4.0 Hz, 1H), 4.25 (dtd, J=2.4, 4.0, 6.0 Hz, 1H), 3.52 (dd, J=5.6, 10.4 Hz, 1H), 3.09 (dd, J=2.0, 10.4 Hz, 1H), 2.69 (s, 3H), 2.49-2.41 (m, 1H), 2.00 (dd, J=2.4, 16.8 Hz, 1H).

[(3S)-1-Methyl-5-oxo-pyrrolidin-3-yl](4-nitrophenyl)carbonate

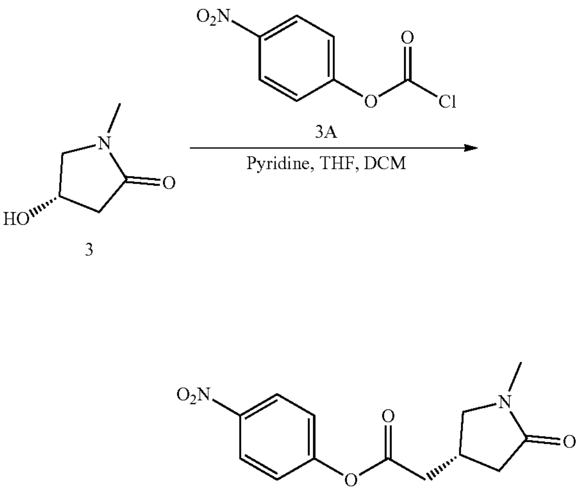

3

4

The product 4 was prepared according to the synthesis method of Compound I-35. Compound [(3S)-1-methyl-5-oxo-pyrrolidin-3-yl](4-nitrophenyl) carbonate (100 mg, 344.14 μmol, 39.62% yield, 96.44% purity) was obtained as a colorless oil.

LCMS m/z=281.0 $[M+H]^+$.

$^1H$ NMR (400 MHz, DMSO-$d_6$) δ=8.32 (d, J=9.3 Hz, 2H), 7.59 (d, J=9.1 Hz, 2H), 5.29 (t, J=6.1 Hz, 1H), 3.78 (dd, J=5.6, 11.9 Hz, 1H), 3.56 (d, J=11.9 Hz, 1H), 2.85-2.78 (m, 1H), 2.78-2.75 (m, 1H), 2.76 (s, 3H), 2.75-2.73 (m, 1H).

[(3S)-1-methyl-5-oxo-pyrrolidin-3-yl] 4-[3-[2-(cyclopropoxy)-3-pyridyl]pyrazolo[1,5-a]pyrimidin-5-yl]piperazine-1-carboxylate

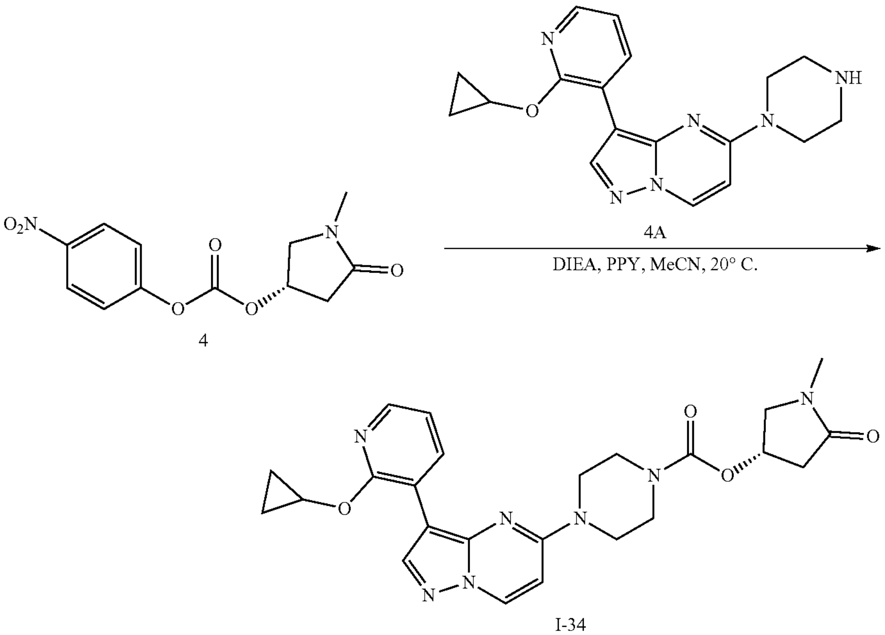

A mixture of [(3S)-1-methyl-5-oxo-pyrrolidin-3-yl](4-nitrophenyl) carbonate (80.00 mg, 285.48 μmol, 2 eq), 3-[2-(cyclopropoxy)-3-pyridyl]-5-piperazin-1-yl-pyrazolo[1,5-a]pyrimidine (48.02 mg, 142.74 μmol, 1 eq), DIEA (36.90 mg, 285.48 μmol, 49.72 μL, 2 eq), 4-pyrrolidin-1-ylpyridine (4.23 mg, 28.55 μmol, 0.2 eq) in MeCN (5 mL) was stirred at 20° C. for 2 hr. The reaction mixture was concentrated under reduced pressure to give a residue. The residue was purified to give [(3S)-1-methyl-5-oxo-pyrrolidin-3-yl]-4-[3-[2-(cyclopropoxy)-3-pyridyl]pyrazolo[1,5-a]pyrimidin-5-yl]piperazine-1-carboxylate (I-34, 12.5 mg, 25.62 μmol, 17.95% yield) as the product.

LCMS m/z=478.2 $[M+H]^+$.

Compound I-34

LCMS m/z=478.2 $[M+H]^+$.

SFC $t_R$=1.068 min; 100%.

$^1$H NMR (400 MHz, DMSO-$d_6$) δ=8.81-8.77 (m, 1H), 8.75 (d, J=8.0 Hz, 1H), 8.35 (s, 1H), 8.03-7.99 (m, 1H), 7.13-7.09 (m, 1H), 6.81 (d, J=8.0 Hz, 1H), 5.21-5.12 (m, 1H), 4.45-4.36 (m, 1H), 3.79-3.74 (m, 4H), 3.74-3.70 (m, 1H), 3.56-3.50 (m, 4H), 3.39-3.35 (m, 1H), 2.74 (s, 3H), 2.73-2.66 (m, 1H), 2.32-2.26 (m, 1H), 0.82-0.76 (m, 4H).

Example 30: Synthesis of Compound I-35 and Compound I-36

(S)-4-((tert-butyldiphenylsilyl)oxy)pyrrolidin-2-one

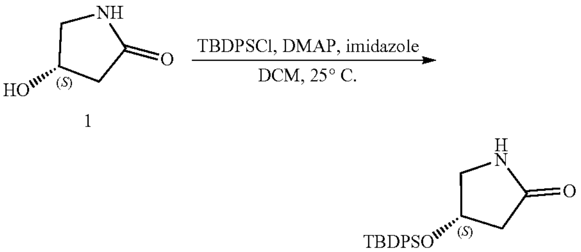

To a solution of (4S)-4-hydroxypyrrolidin-2-one (3 g, 29.67 mmol, 1 eq), tert-butyl-chloro-diphenyl-silane (9.79 g, 35.61 mmol, 9.11 mL, 1.2 eq) in DCM (10 mL) was added 1H-imidazole (4.04 g, 59.35 mmol, 2 eq) and DMAP (725.01 mg, 5.93 mmol, 0.2 eq). The mixture was stirred at 25° C. for 12 hr. LCMS showed that desired mass was found. The reaction mixture was concentrated under reduced pressure to remove solvent. The residue was purified by flash silica gel chromatography to give(S)-4-((tert-butyldiphenylsilyl)oxy)pyrrolidin-2-one (10.53 g, 28.13 mmol, 94.81% yield) as colorless oil.

LCMS m/z=340.1 $[M+H]^+$.

$^1$H NMR (400 MHz, $CDCl_3$) δ=7.70-7.61 (m, 4H), 7.50-7.36 (m, 6H), 6.17 (br s, 1H), 4.56-4.50 (m, 1H), 3.40-3.34 (m, 1H), 3.31-3.26 (m, 1H), 2.40-2.35 (m, 2H), 1.11-1.06 (m, 9H).

Tert-butyl (S)-(2-(4-(tert-butyldiphenylsilyl)oxy)-2-oxopyrrolidin-1-yl)ethyl)(methyl)carbamate

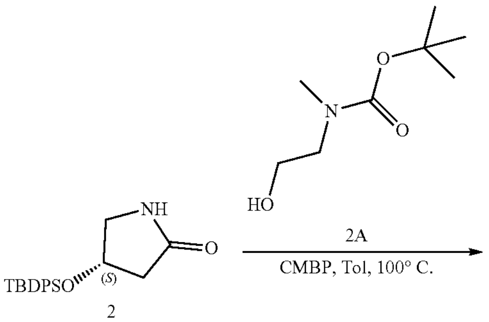

2

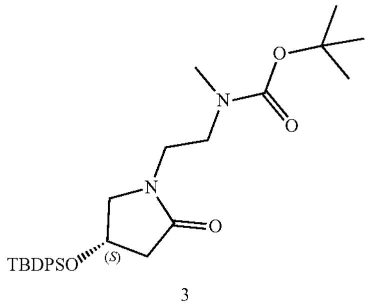

3

A mixture of(S)-4-((tert-butyldiphenylsilyl)oxy)pyrrolidin-2-one (3 g, 8.84 mmol, 1 eq), tert-butyl N(2-hydroxyethyl)-N-methyl-carbamate (2.32 g, 13.25 mmol, 1.5 eq), 2-(tributyl-phosphanylidene) acetonitrile (3.20 g, 13.25 mmol, 1.5 eq) in Tol. (10 mL) was degassed and purged with $N_2$ for 3 times, and then the mixture was stirred at 110° C. for 12 hr under $N_2$ atmosphere. LCMS showed that desired mass was found. The reaction mixture was concentrated under reduced pressure to remove solvent. The residue was purified by flash silica gel chromatography. Then the product was further purified by preparative HPLC. The pure fractions were collected and the volatiles were removed under vacuum. The residue was partitioned between acetonitrile (2 mL) and water (10 mL). The solution was lyophilized to dryness to give tert-butyl(S)-(2-(4-((tert-butyldiphenylsilyl)oxy)-2-oxopyrrolidin-1-yl)ethyl)(methyl)-carbamate (668 mg, 883.56 μmol, 10.0% yield) as an oil.

LCMS m/z=497.3 $[M+H]^+$.

$^1$H NMR (400 MHz, $CDCl_3$) δ=7.65-7.60 (m, 4H), 7.48-7.36 (m, 6H), 4.43 (br d, J=4.3 Hz, 1H), 3.70-3.51 (m, 2H), 3.45-3.12 (m, 4H), 2.86 (s, 3H), 2.45-2.34 (m, 2H), 1.41 (br s, 9H), 1.06 (s, 9H).

Tert-butyl(S)-(2-(4-hydroxy-2-oxopyrrolidin-1-yl)ethyl)(methyl)carbamate

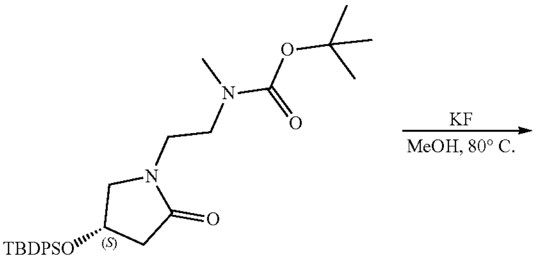

3

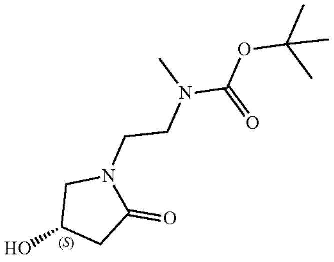

4

To a solution of tert-butyl(S)-(2-(4-((tert-butyldiphenylsilyl)oxy)-2-oxopyrrolidin-1-yl)ethyl)(methyl)carbamate (0.6 g, 1.21 mmol, 1 eq) in MeOH (3 mL) was added KF (350.89 mg, 6.04 mmol, 141.49 μL, 5 eq). The mixture was stirred at 80° C. for 12 hr. LC-MS showed that desired mass was found. The reaction mixture was concentrated under reduced pressure to remove solvent. The residue was purified by flash silica gel chromatography to give tert-butyl (S)-(2-(4-hydroxy-2-oxopyrrolidin-1-yl)ethyl)(methyl)carbamate (237 mg, 917.49 μmol, 75.95% yield) as an oil.

LCMS m/z=259.1 $[M+H]^+$.

$^1$H NMR (400 MHz, $CDCl_3$) δ=4.32 (br d, J=1.4 Hz, 1H), 4.16-3.91 (m, 2H), 3.72-3.53 (m, 2H), 2.94 (s, 3H), 2.84 (dt, J=3.3, 7.3 Hz, 2H), 2.63 (br dd, J=6.0, 17.6 Hz, 1H), 2.32 (br d, J=17.5 Hz, 1H), 1.47-1.39 (m, 9H).

Tert-butyl(S)-methyl (2-(4-(((4-nitrophenoxy)carbonyl)oxy)-2-oxopyrrolidin-1-yl)ethyl)carbamate

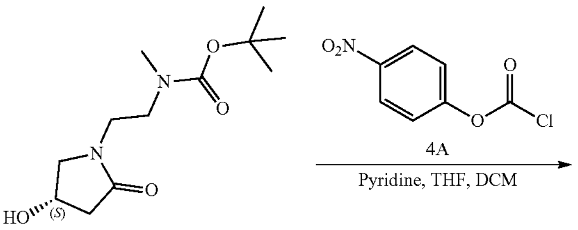

4

-continued

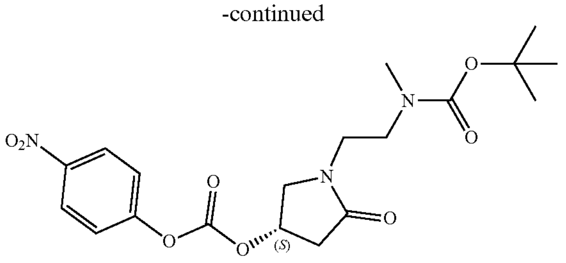

5

To a solution of tert-butyl(S)-(2-(4-hydroxy-2-oxopyrrolidin-1-yl)ethyl)(methyl)carbamate (180 mg, 696.83 μmol, 1 eq) in THF (1 mL) and DCM (5 mL) was added pyridine (110.24 mg, 1.39 mmol, 112.49 μL, 2 eq) and (4-nitrophenyl) carbonochloridate (421.37 mg, 2.09 mmol, 3 eq). The mixture was stirred at 25° C. for 3 hr. LCMS showed that desired mass was found. The reaction mixture was concentrated under reduced pressure to remove solvent. The residue was purified by prep. TLC ($SiO_2$, ethyl acetate/petroleum ether=100:0). to give tert-butyl(S)-methyl (2-(4-(((4-nitrophenoxy)carbonyl)oxy)-2-oxopyrrolidin-1-yl)ethyl)carbamate (0.264 g, 390.93 umol, 56.10% yield) as an oil LCMS m/z=324.1 $[M+H]^+$.

Procedure for preparation of Compound I-35

(S)-1-(2-((tert-butoxycarbonyl)(methyl)amino)ethyl)-5-oxopyrrolidin-3-yl-4-(3-(2-cyclopropoxypyridin-3-yl)pyrazolo[1,5-a]pyrimidin-5-yl)piperazine-1-carboxylate To a solution of tert-butyl(S)-methyl (2-(4-(((4-nitrophenoxy)carbonyl)oxy)-2-oxopyrrolidin-1-yl)ethyl)carbamate (264 mg, 623.50 μmol, 1 eq) in DCM (1 mL) was added DIEA (161.17 mg, 1.25 mmol, 217.20 μL, 2 eq), DMAP (15.23 mg, 124.70 μmol, 0.2 eq) and 3-[2-(cyclopropoxy)-3-pyridyl]-5-piperazin-1-yl-pyrazolo[1,5-a]pyrimidine (209.74 mg, 623.50 μmol, 1 eq). The mixture was stirred at 25° C. for 12 hr. LCMS showed that desired mass was found. The reaction mixture was concentrated under reduced pressure to remove solvent. Then the product was further purified by preparative HPLC. The pure fractions were collected and the volatiles were removed under vacuum. The residue was partitioned between acetonitrile (2 mL) and water (10 mL). The solution was lyophilized to dryness to give(S)-1-(2-((tert-butoxycarbonyl)(methyl)amino)ethyl)-5-oxopyrrolidin-3-yl-4-(3-(2-cyclopropoxypyridin-3-yl)pyrazolo[1,5-a]pyrimidin-5-yl)piperazine-1-carboxylate (0.195 g, 306.15 μmol, 49.10% yield, 97.45% purity) as a solid.

LCMS m/z=621.5 $[M+H]^+$.

Compound I-35

SFC $t_R$=1.369 min; 100%.

$^1H$ NMR (400 MHz, DMSO-$d_6$) δ=8.90-8.65 (m, 2H), 8.34 (s, 1H), 8.07-7.85 (m, 1H), 7.10 (d, J=7.4 Hz, 1H), 6.82 (d, J=7.9 Hz, 1H), 5.28-5.06 (m, 1H), 4.47-4.35 (m, 1H), 3.76 (s, 5H), 3.52 (s, 4H), 3.46-3.33 (m, 3H), 3.31-3.18 (m, 2H), 2.77 (s, 3H), 2.72-2.57 (m, 1H), 2.37-2.23 (m, 1H), 1.39 (s, 9H), 0.84-0.73 (m, 4H).

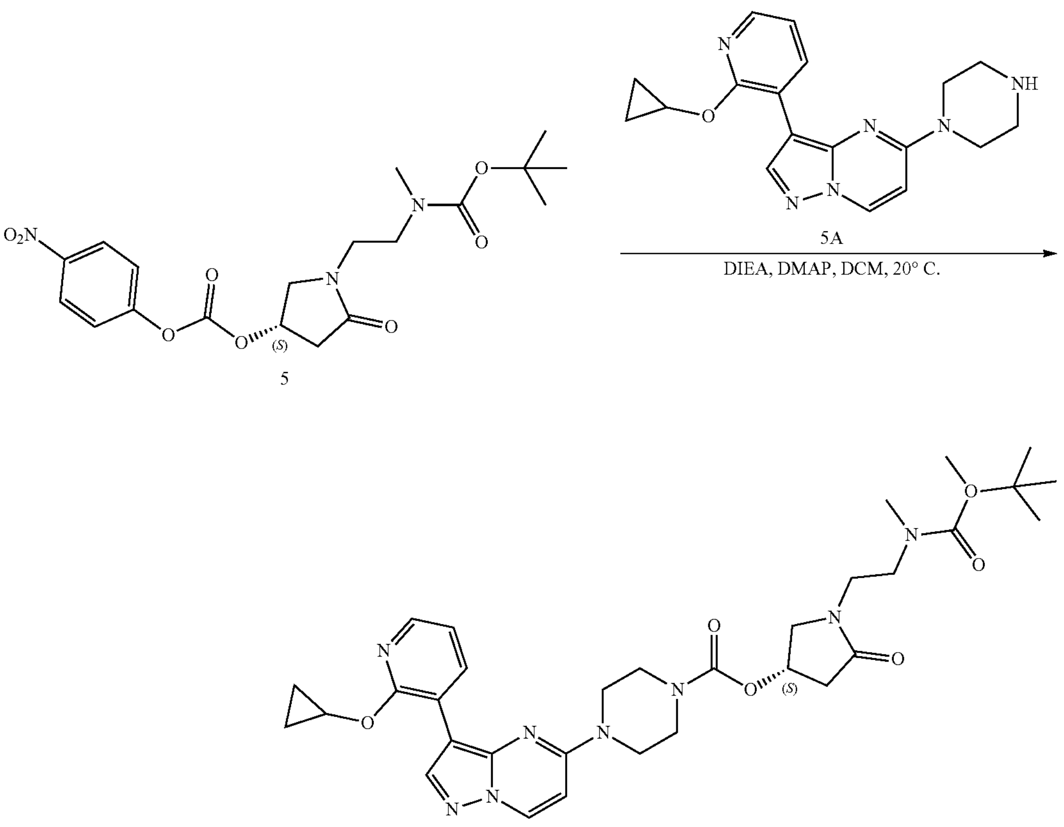

I-35

Procedure for Preparation of Compound I-36

(S)-1-(2-(methylamino)ethyl)-5-(oxopyrrolidin-3-yl)-4-(3-(2-cyclopropoxypyridin-3-yl)pyrazolo[1,5-a]pyrimidin-5-yl)piperazine-1-carboxylate

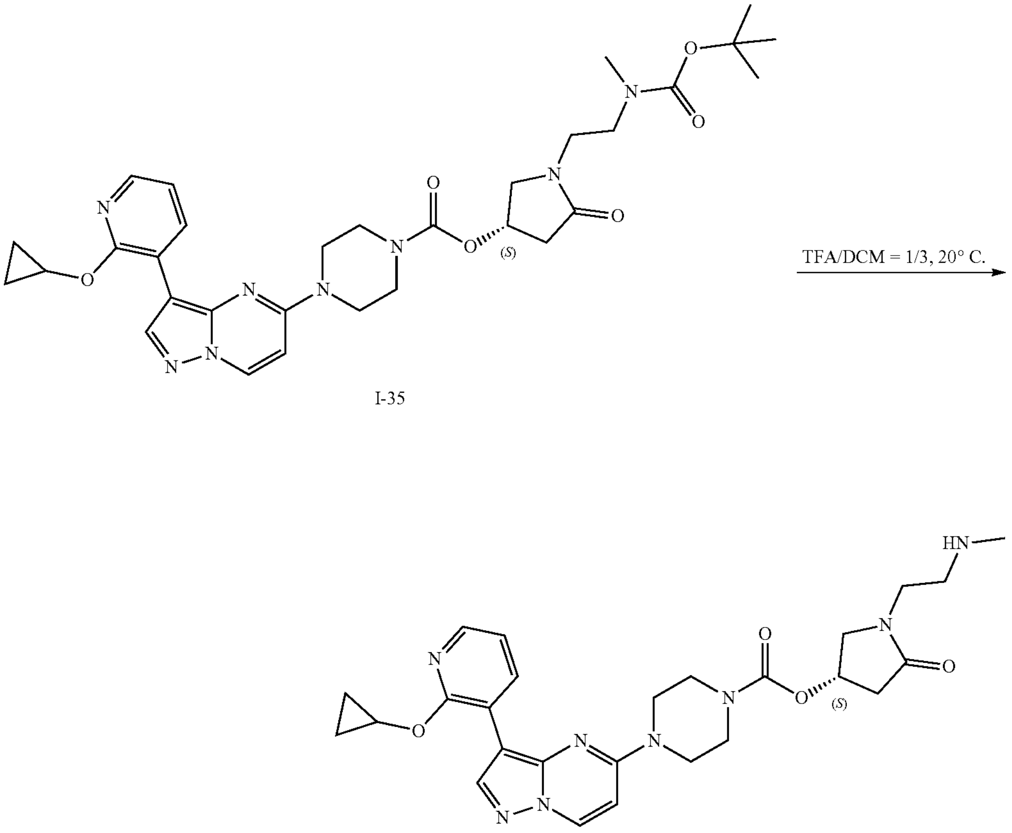

I-35

I-36

To a solution of(S)-1-(2-((tert-butoxycarbonyl)(methyl)amino)ethyl)-5-oxopyrrolidin-3-yl 4-(3-(2-cyclopropoxy-pyridin-3-yl)pyrazolo[1,5-a]pyrimidin-5-yl)piperazine-1-carboxylate (0.145 g, 233.61 μmol, 1 eq) in DCM (5 mL) was added TFA (1.07 g, 9.34 mmol, 694.10 μL, 40 eq). The mixture was stirred at 25° C. for 1 hr. LCMS showed that desired mass was found. Then the product was further purified by prep. HPLC (column: Phenomenex luna C18 150*25 mm*10 μm; mobile phase: [water (HCOOH)-MeCN]; gradient: 11%-41% B over 15 min). The pure fractions were collected and the volatiles were removed under vacuum. The residue was partitioned between acetonitrile (2 mL) and water (10 mL). The solution was lyophilized to dryness to give(S)-1-(2-(methylamino)ethyl)-5-(oxopyrrolidin-3-yl)-4-(3-(2-cyclopropoxypyridin-3-yl)pyrazolo[1,5-a]pyrimidin-5-yl)piperazine-1-carboxylate (89.61 mg, 170.96 μmol, 73.18% yield, 99.32% purity) as a solid.

LCMS m/z=521.2 $[M+H]^+$.

SFC $t_R$=1.455 min; 100%.

$^1H$ NMR (400 MHz, DMSO-$d_6$) δ=8.80-8.73 (m, 2H), 8.36-8.32 (m, 1H), 8.02-7.99 (m, J=1.8, 4.8 Hz, 1H), 7.14-7.07 (m, J=4.8, 7.6 Hz, 1H), 6.82 (d, J=8.0 Hz, 1H), 5.25-5.11 (m, 1H), 4.43-4.33 (m, 1H), 3.84-3.73 (m, 5H), 3.63-3.53 (m, 4H), 3.42-3.31 (m, 3H), 3.16-2.90 (m, 3H), 2.81-2.68 (m, J=7.4, 17.4 Hz, 1H), 2.55-2.51 (m, 3H), 2.39-2.32 (m, J=2.6, 17.4 Hz, 1H), 0.82-0.74 (m, 4H).

Example 31: Synthesis of Compound I-37 and Compound I-38

(4S)-1-(2-benzyloxyethyl)-4-[tert-butyl(diphenyl)silyl]oxy-pyrrolidin-2-one

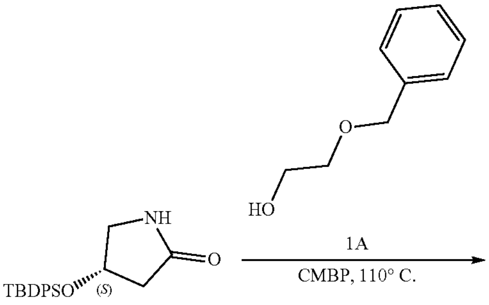

1

-continued

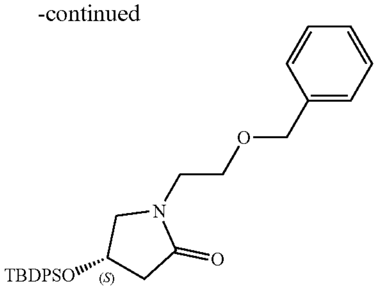

2

The product 2 was prepared according to the synthesis method of I-35. The product (4S)-1-(2-benzyloxyethyl)-4-[tert-butyl(diphenyl)silyl]oxy-pyrrolidin-2-one (2 g, 2.83 mmol, 32.06% yield, 67.093% purity) was obtained as a gum.

LCMS m/z=474.4 $[M+H]^+$.

$^1$H NMR (400 MHz, DMSO-$d_6$) δ=7.61-7.54 (m, 5H), 7.48-7.42 (m, 5H), 7.34-7.26 (m, 5H), 4.57-4.32 (m, 4H), 4.14-4.04 (m, 1H), 3.57-3.45 (m, 2H), 3.17 (d, J=5.3 Hz, 4H), 0.99 (s, 9H).

(4S)-1-(2-benzyloxyethyl)-4-hydroxy-pyrrolidin-2-one

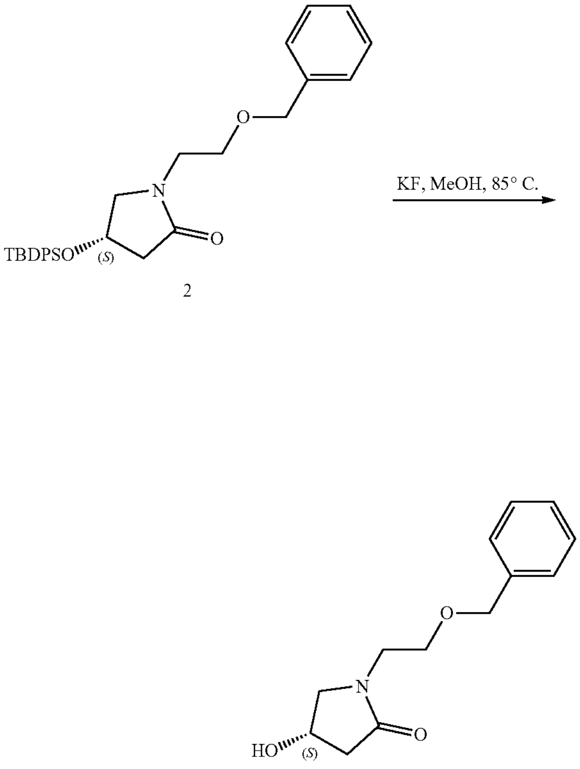

2

3

The product 3 was prepared according to the synthesis method of I-35. The product (4S)-1-(2-benzyloxyethyl)-4-hydroxy-pyrrolidin-2-one (264 mg, 1.10 mmol, 28.99% yield, 97.839% purity) was obtained as a gum.

LCMS m/z=257.9 $[M+Na]^+$.

$^1$H NMR (400 MHz, DMSO-$d_6$) δ=7.39-7.21 (m, 5H), 5.15 (d, J=3.9 Hz, 1H), 4.52-4.42 (m, 2H), 4.31-4.21 (m, 1H), 3.62-3.49 (m, 3H), 3.47-3.39 (m, 1H), 3.30 (s, 1H), 3.23-3.17 (m, 1H), 2.13-1.91 (m, 2H).

[(3S)-1-(2-benzyloxyethyl)-5-oxo-pyrrolidin-3-yl](4-nitrophenyl)carbonate

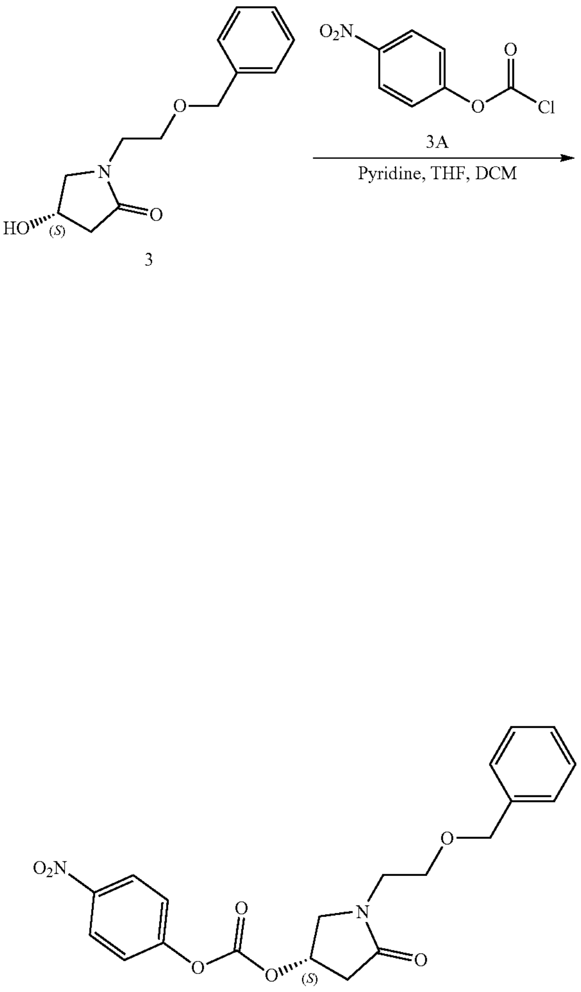

3

3A

4

The product 4 was prepared according to the synthesis method of I-35. The product [(3S)-1-(2-benzyloxyethyl)-5-oxo-pyrrolidin-3-yl](4-nitrophenyl) carbonate (50 mg, 102.20 μmol, 20.04% yield, 81.835% purity) was obtained as a gum.

LCMS m/z=400.9 $[M+H]^+$.

$^1$H NMR (400 MHz, DMSO-$d_6$) δ=8.38-8.25 (m, 2H), 7.64-7.53 (m, 2H), 7.35-7.31 (m, 5H), 5.36-5.27 (m, 1H), 4.49 (s, 2H), 3.90-3.80 (m, 1H), 3.70-3.61 (m, 1H), 3.59-3.50 (m, 3H), 3.49-3.41 (m, 3H).

Procedure for preparation of I-37

[(3S)-1-(2-benzyloxyethyl)-5-oxo-pyrrolidin-3-yl]-4-[3-[2-(cyclopropoxy)-3-pyridyl]pyrazolo[1,5-a]pyrimidin-5-yl]piperazine-1-carboxylate

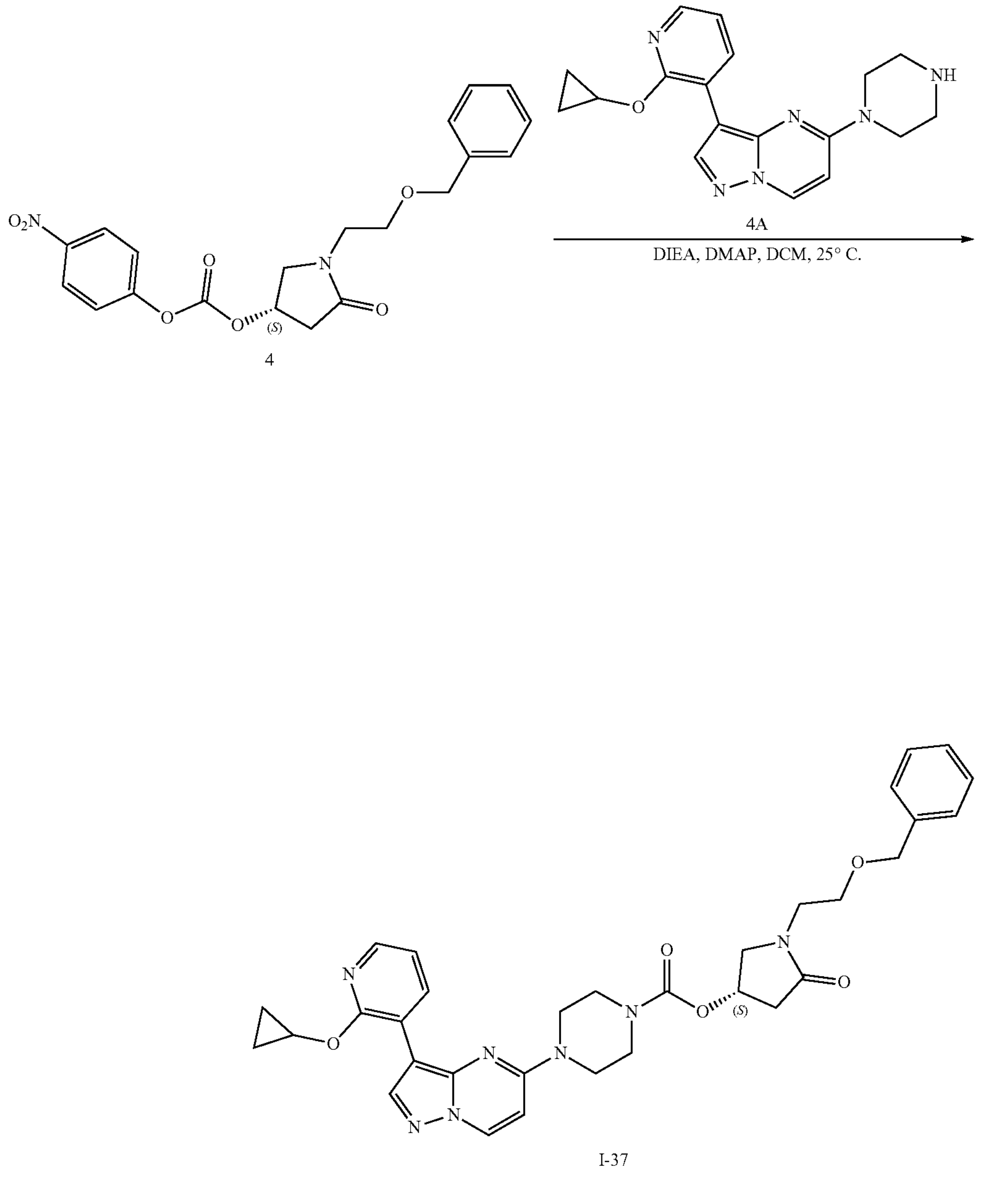

To a solution of [(3S)-1-(2-benzyloxyethyl)-5-oxo-pyrrolidin-3-yl](4-nitrophenyl) carbonate (50 mg, 124.88 μmol, 1 eq) in DCM (1 mL) was added DIEA (32.28 mg, 249.76 μmol, 43.50 μL, 2 eq), 3-[2-(cyclopropoxy)-3-pyridyl]-5-piperazin-1-yl-pyrazolo[1,5-a]pyrimidine (42.01 mg, 124.88 μmol, 1 eq) and DMAP (1.53 mg, 12.49 μmol, 0.1 eq). The mixture was stirred at 25° C. for 1 hr. The reaction mixture was concentrated under reduced pressure to give a residue. The crude was purified by preparative HPLC. The pure fractions were collected and the volatiles were removed under vacuum. The residue was partitioned between acetonitrile (20 mL) and water (100 mL). The solution was lyophilized to dryness to give the product. The product [(3S)-1-(2-benzyloxyethyl)-5-oxo-pyrrolidin-3-yl]-4-[3-[2-(cyclopropoxy)-3-pyridyl]pyrazolo[1,5-a]pyrimidin-5-yl] piperazine-1-carboxylate (2.51 mg, 4.07 μmol, 6.08% yield, 96.921% purity) was obtained as a powder.

LCMS m/z=598.5 $[M+H]^+$.

SFC $t_R$=2.227 min; 100%.

$^1H$ NMR (400 MHz, DMSO-$d_6$) δ=8.99-8.53 (m, 2H), 8.51-8.22 (m, 1H), 8.15-7.90 (m, 1H), 7.68-7.14 (m, 5H), 7.13-6.98 (m, 1H), 6.89-6.69 (m, 1H), 5.28-5.06 (m, 1H), 4.65-4.21 (m, 3H), 3.91-3.60 (m, 6H), 3.58-3.43 (m, 8H), 2.82-2.69 (m, 1H), 2.35-2.24 (m, J=16.3 Hz, 1H), 1.00-0.63 (m, 4H).

Procedure for Preparation of I-38

[(3S)-1-(2-Hydroxyethyl)-5-oxo-pyrrolidin-3-yl]-4-[3-[2-(cyclopropoxy)-3-pyridyl]pyrazolo[1,5-a]pyrimidin-5-yl]piperazine-1-carboxylate

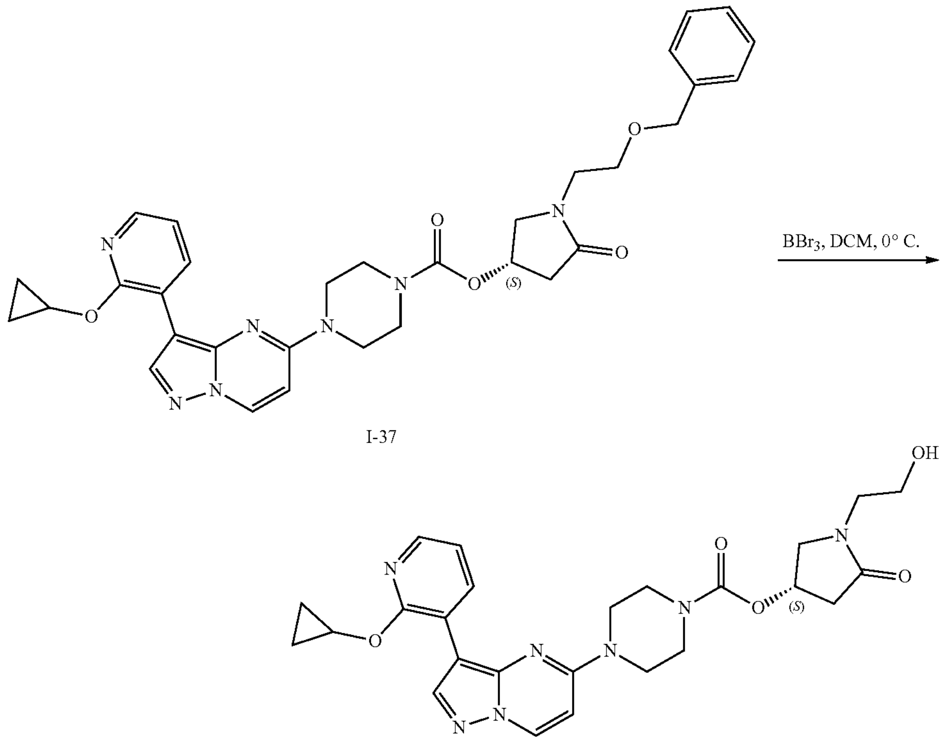

I-37

I-38

To a solution of [(3S)-1-(2-benzyloxyethyl)-5-oxo-pyrrolidin-3-yl] 4-[3-[2-(cyclopropoxy)-3-pyridyl]pyrazolo[1,5-a]pyrimidin-5-yl]piperazine-1-carboxylate (40 mg, 66.93 μmol, 1 eq) in DCM (1 mL) was added $BBr_3$ (83.83 mg, 334.64 μmol, 32.24 μL, 5 eq). The mixture was stirred at 0° C. for 0.5 hr. The reaction was quenched with water (1 mL) at 0° C. and concentrated under reduced pressure to give a residue. The crude was purified by preparative HPLC. The pure fractions were collected and the volatiles were removed under vacuum. The residue was partitioned between acetonitrile (20 mL) and water (100 mL). The solution was lyophilized to dryness to give the product. The product [(3S)-1-(2-hydroxyethyl)-5-oxo-pyrrolidin-3-yl]-4-[3-[2-(cyclopropoxy)-3-pyridyl]pyrazolo[1,5-a]pyrimidin-5-yl]piperazine-1-carboxylate (11.68 mg, 22.75 μmol, 33.99% yield, 98.84% purity) was obtained as a gum.

LCMS m/z=508.2 $[M+H]^+$.

SFC $t_R$=1.261 min; 100%).

$^1H$ NMR (400 MHz, CHLOROFORM-d) δ=8.77-8.68 (m, 1H), 8.54-8.48 (m, 1H), 8.37 (d, J=7.8 Hz, 1H), 8.11-8.05 (m, 1H), 7.08-6.98 (m, 1H), 6.38 (d, J=7.8 Hz, 1H), 5.37-5.28 (m, 1H), 4.53-4.37 (m, 1H), 3.98-3.89 (m, J=5.9, 11.6 Hz, 1H), 3.89-3.71 (m, 6H), 3.70-3.59 (m, 4H), 3.58-3.44 (m, 3H), 2.91-2.81 (m, J=17.9 Hz, 1H), 2.79-2.63 (m, 1H), 2.58 (d, J=17.9 Hz, 1H), 0.91-0.83 (m, 4H).

Example 32: Synthesis of Compound I-39 tert-Butyl(2R)-4-(3-bromopyrazolo[1,5-a]pyrimidin-5-yl)-2-methyl-piperazine-1-carboxylate

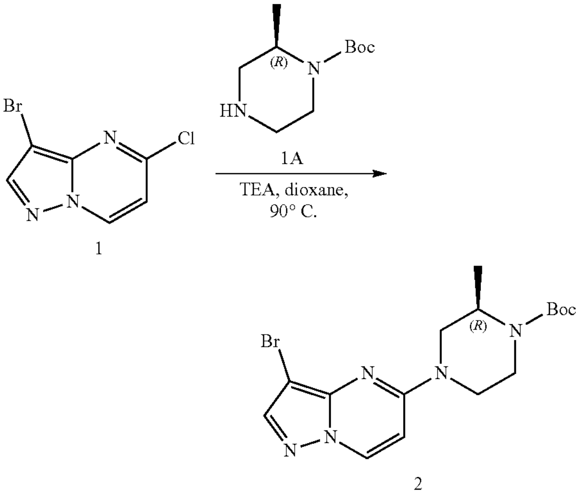

1 1A 2

To a solution of 3-bromo-5-chloro-pyrazolo[1,5-a]pyrimidine (100 mg, 430.17 μmol, 1 eq) in dioxane (1 mL) was added TEA (130.59 mg, 1.29 mmol, 179.62 µL, 3 eq). The mixture was stirred at 90° C. for 1 hr. The reaction mixture was concentrated under reduced pressure to give a residue. The residue was purified by flash silica gel chromatography to give tert-butyl (2R)-4-(3-bromopyrazolo[1,5-a]pyrimidin-5-yl)-2-methyl-piperazine-1-carboxylate (120 mg, 302.82 µmol, 70.39% yield) as an oil.

LCMS m/z=398.1 $[M+H]^+$.

$^1$H NMR (400 MHz, DMSO-$d_6$) δ=8.67 (d, J=7.9 Hz, 1H), 7.96 (s, 1H), 6.76 (d, J=8.0 Hz, 1H), 4.36 (br d, J=10.1 Hz, 1H), 4.22 (br s, 2H), 4.02 (q, J=7.1 Hz, 1H), 3.81 (br d, J=12.8 Hz, 1H), 3.32-3.26 (m, 1H), 3.22-2.99 (m, 2H), 1.42 (s, 9H), 1.07 (d, J=6.6 Hz, 3H)

tert-Butyl(2R)-4-[3-[2-(cyclopropoxy)-3-pyridyl]pyrazolo[1,5-a]pyrimidin-5-yl]-2-methyl-piperazine-1-carboxylate

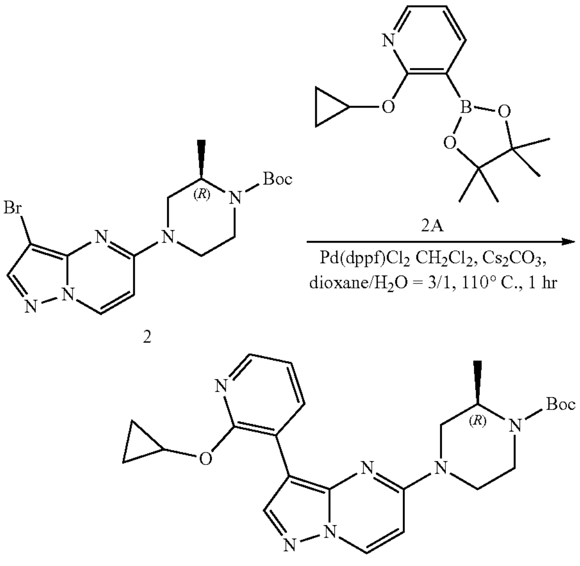

2

2A

3

A mixture of tert-butyl (2R)-4-(3-bromopyrazolo[1,5-a]pyrimidin-5-yl)-2-methyl-piperazine-1-carboxylate (120 mg, 302.82 µmol, 1 eq), 2-(cyclopropoxy)-3-(4,4,5,5-tetramethyl-1,3,2-dioxaborolan-2-yl)pyridine (79.07 mg, 302.82 µmol, 1 eq), Pd(dppf)$Cl_2$·$CH_2Cl_2$ (49.46 mg, 60.56 µmol, 0.2 eq), $Cs_2CO_3$ (295.99 mg, 908.45 µmol, 3 eq) in dioxane/$H_2O$=3/1 (1 mL) was degassed and purged with $N_2$ for 3 times, and then the mixture was stirred at 110° C. for 1 hr under $N_2$ atmosphere. The reaction mixture was concentrated under reduced pressure to give a residue. The residue was purified by flash silica gel chromatography to give tert-butyl (2R)-4-[3-[2-(cyclopropoxy)-3-pyridyl]pyrazolo[1,5-a]pyrimidin-5-yl]-2-methyl-piperazine-1-carboxylate (60 mg, 133.18 µmol, 43.98% yield) as a solid.

LCMS m/z=451.3 $[M+H]^+$.

$^1$H NMR (400 MHz, DMSO-$d_6$) δ=8.80 (dd, J=1.9, 7.5 Hz, 1H), 8.73 (d, J=8.0 Hz, 1H), 8.34 (s, 1H), 8.01 (dd, J=1.8, 4.8 Hz, 1H), 7.13 (dd, J=4.9, 7.5 Hz, 1H), 6.81 (d, J=8.0 Hz, 1H), 4.42-4.39 (m, 1H), 4.34-4.20 (m, 3H), 4.19-4.13 (m, 1H), 3.90-3.75 (m, 2H), 3.16 (br t, J=10.3 Hz, 2H), 1.43 (s, 9H), 1.11-1.07 (m, 2H), 0.86-0.74 (m, 4H).

3-[2-(Cyclopropoxy)-3-pyridyl]-5-[(3R)-3-methylpiperazin-1-yl]pyrazolo[1,5-a]pyrimidine

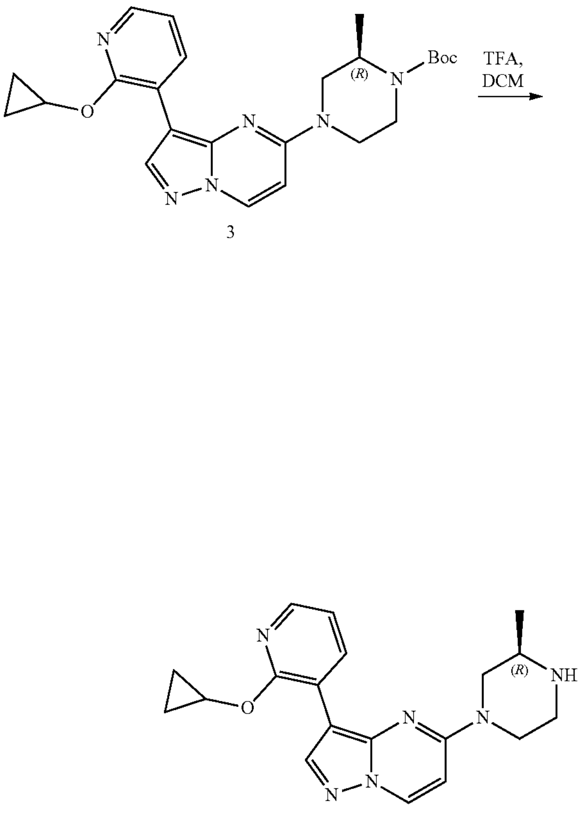

3

4

To a solution of tert-butyl (2R)-4-[3-[2-(cyclopropoxy)-3-pyridyl]pyrazolo[1,5-a]pyrimidin-5-yl]-2-methyl-piperazine-1-carboxylate (1 g, 2.22 mmol, 1 eq) in TFA/DCM=1/3 (10 mL). The mixture was stirred at 25° C. for 1 hr. The reaction mixture was filtered and concentrated under reduced pressure to give a residue. The residue was purified by preparative HPLC. The residue was partitioned between acetonitrile (2 mL) and water (10 mL). The solution was lyophilized to dryness to give the product 3-[2-(cyclopropoxy)-3-pyridyl]-5-[(3R)-3-methylpiperazin-1-yl]pyrazolo[1,5-a]pyrimidine (200 mg, 570.75 umol, 25.71% yield) as a solid.

LCMS m/z=351.2 $[M+H]^+$.

Procedure for Preparation of I-39

[(3S)-5-oxopyrrolidin-3-yl]-(2R)-4-[3-[2-(cyclopropoxy)-3-pyridyl]pyrazolo[1,5-a]pyrimidin-5-yl]-2-methyl-piperazine-1-carboxylate

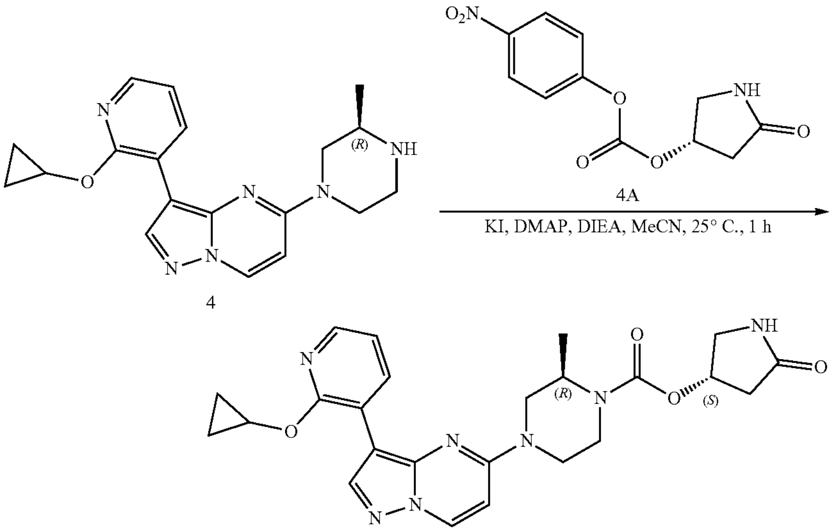

4

I-39

To a solution of 3-[2-(cyclopropoxy)-3-pyridyl]-5-[(3R)-3-methylpiperazin-1-yl]pyrazolo[1,5-a]pyrimidine (40 mg, 114.15 μmol, 1 eq) and (4-nitrophenyl) [(3S)-5-oxopyrrolidin-3-yl] carbonate (33.43 mg, 125.56 μmol, 1.1 eq) in MeCN (0.5 mL) was added DIEA (44.26 mg, 342.45 μmol, 59.65 μL, 3 eq) and KI (3.79 mg, 22.83 μmol, 0.2 eq), DMAP (2.79 mg, 22.83 μmol, 0.2 eq). The mixture was stirred at 90° C. for 1 hr. The reaction mixture was concentrated under reduced pressure to give a residue. The crude product was purified by preparative HPLC. The pure fractions were collected and the volatiles were removed under vacuum. The residue was partitioned between acetonitrile (2 mL) and water (10 mL). The solution was lyophilized to dryness to give the product [(3S)-5-oxopyrrolidin-3-yl]-(2R)-4-[3-[2-(cyclopropoxy)-3-pyridyl]pyrazolo[1,5-a]pyrimidin-5-yl]-2-methyl-piperazine-1-carboxylate (25.7 mg, 51.74 μmol, 45.32% yield, 96.13% purity) as a solid.

LCMS m/z=478.3 $[M+H]^+$.

SFC $t_R$=2.444 min; 100%.

$^1H$ NMR (400 MHz, methanol-$d_4$) δ=8.94-8.82 (m, 1H), 8.54-8.34 (m, 2H), 8.01-7.93 (m, 1H), 7.13-7.04 (m, 1H), 6.78-6.66 (m, 1H), 5.42-5.25 (m, 1H), 4.49-4.26 (m, 4H), 4.07-3.94 (m, 1H), 3.83-3.72 (m, 1H), 3.49-3.41 (m, 2H), 3.40-3.33 (m, 1H), 3.27-3.20 (m, 1H), 2.88-2.74 (m, 1H), 2.45-2.33 (m, 1H), 1.23 (d, J=6.6 Hz, 3H), 0.90-0.77 (m, 4H).

Example 33: Synthesis of Compound I-40 tert-butyl (2S)-4-(3-bromopyrazolo[1,5-a]pyrimidin-5-yl)-2-methyl-piperazine-1-carboxylate

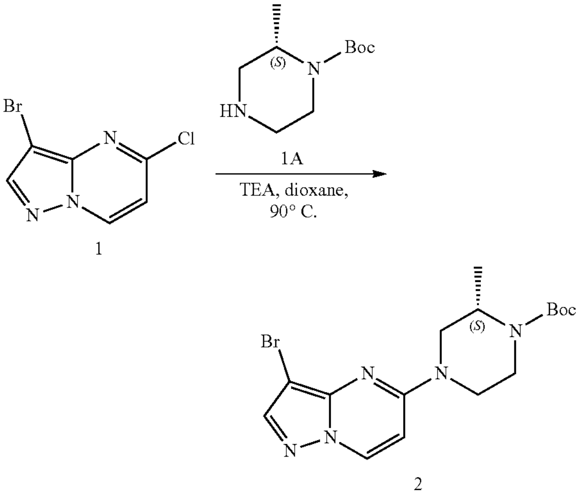

1

2

To a solution of 3-bromo-5-chloro-pyrazolo[1,5-a]pyrimidine (300 mg, 1.29 mmol, 1 eq) in dioxane (5 mL) was added TEA (261.17 mg, 2.58 mmol, 359.25 μL, 2 eq) and tert-butyl (2S)-2-methylpiperazine-1-carboxylate (258.46 mg, 1.29 mmol, 1 eq). The mixture was stirred at 90° C. for 0.5 hr. The reaction mixture was concentrated under reduced pressure to remove dioxane. The residue was purified by FCC to give tert-butyl (2S)-4-(3-bromopyrazolo[1,5-a]pyrimidin-5-yl)-2-methyl-piperazine-1-carboxylate (320 mg, 807.51 μmol, 62.57% yield, 100.000% purity) as a gum.

LCMS m/z=396.1 $[M+H]^+$.

$^1$H NMR (400 MHz, DMSO-$d_6$) δ=8.68 (br d, J=7.9 Hz, 1H), 7.96 (s, 1H), 6.77 (br d, J=7.8 Hz, 1H), 4.41-4.31 (m, 1H), 4.21 (br d, J=4.1 Hz, 2H), 4.15 (br s, 1H), 4.06-3.97 (m, 1H), 3.85-3.75 (m, 1H), 3.17-3.05 (m, 2H), 1.42 (s, 9H), 1.10-1.05 (m, 3H).

tert-Butyl (2S)-4-[3-[2-(cyclopropoxy)-3-pyridyl] pyrazolo[1,5-a]pyrimidin-5-yl]-2-methyl-piperazine-1-carboxylate

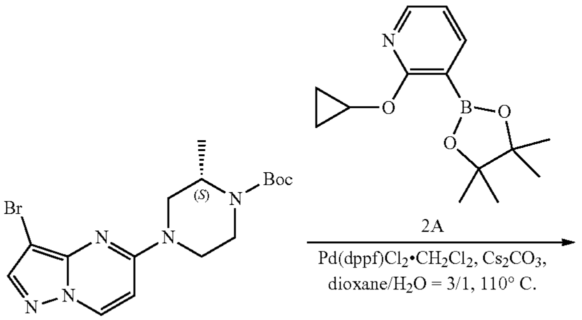

2

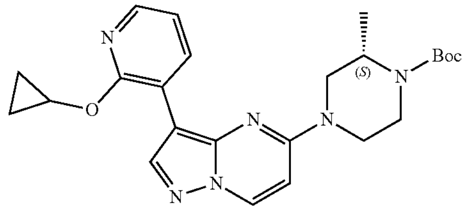

3

A mixture of tert-butyl (2S)-4-(3-bromopyrazolo[1,5-a]pyrimidin-5-yl)-2-methyl-piperazine-1-carboxylate (100 mg, 252.35 μmol, 1 eq), 2-(cyclopropoxy)-3-(4,4,5,5-tetramethyl-1,3,2-dioxaborolan-2-yl)pyridine (131.79 mg, 504.69 μmol, 2 eq), Pd(dppf)$Cl_2$·$CH_2Cl_2$ (41.22 mg, 50.47 μmol, 0.2 eq), $Cs_2CO_3$ (246.66 mg, 757.04 μmol, 3 eq) in dioxane (1.5 mL) and $H_2O$ (0.5 mL) was degassed and purged with $N_2$ for 3 times, and then the mixture was stirred at 110° C. for 1 hr under $N_2$ atmosphere. The reaction mixture was concentrated under reduced pressure to remove dioxane. The residue was diluted with ethyl acetate (10 mL). The organic layers were washed with $H_2O$ (10 mL×3), dried over $Na_2SO_4$, filtered and concentrated under reduced pressure to give a residue. The crude was purified by FCC to give tert-butyl (2S)-4-[3-[2-(cyclopropoxy)-3-pyridyl]pyrazolo[1,5-a]pyrimidin-5-yl]-2-methyl-piperazine-1-carboxylate (100 mg, 158.28 umol, 62.72% yield, 71.31% purity) as a solid.

LCMS m/z=451.3 [M+H]+.

3-[2-(Cyclopropoxy)-3-pyridyl]-5-[(3S)-3-methylpiperazin-1-yl]pyrazolo[1,5-a]pyrimidine

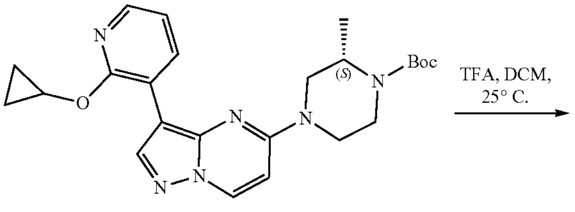

3

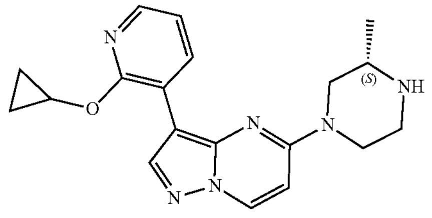

4

To a solution of tert-butyl (2S)-4-[3-[2-(cyclopropoxy)-3-pyridyl]pyrazolo[1,5-a]pyrimidin-5-yl]-2-methyl-piperazine-1-carboxylate (100 mg, 221.96 μmol, 1 eq) in DCM (1 mL) was added TFA (460.50 mg, 4.04 mmol, 0.3 mL, 18.20 eq). The mixture was stirred at 25° C. for 0.5 hr. The reaction mixture was concentrated under reduced pressure to give 3-[2-(cyclopropoxy)-3-pyridyl]-5-[(3S)-3-methylpiperazin-1-yl]pyrazolo[1,5-a]pyrimidine (100 mg, 197.86 μmol, 89.14% yield, 69.334% purity) as a solid. The crude was used into the next step without further purification.

LCMS m/z=351.1 [M+H]+.

Procedure for Preparation of I-40

[(3S)-5-Oxopyrrolidin-3-yl](2S)-4-[3-[2-(cyclopropoxy)-3-pyridyl]pyrazolo[1,5-a]pyrimidin-5-yl]-2-methyl-piperazine-1-carboxylate

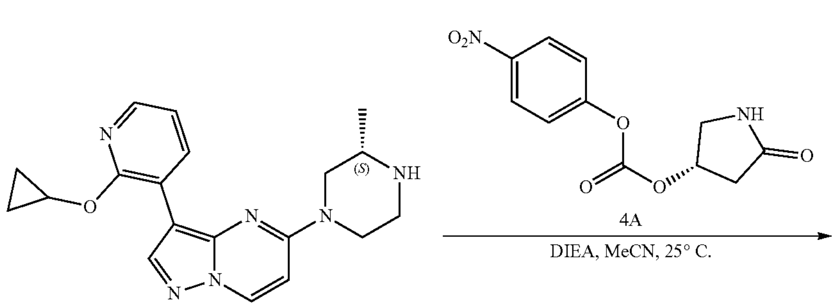

4

-continued

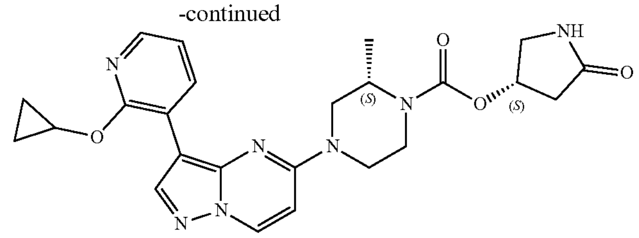

I-40

To a solution of 3-[2-(cyclopropoxy)-3-pyridyl]-5-[(3S)-3-methylpiperazin-1-yl]pyrazolo[1,5-a]pyrimidine (100 mg, 285.37 μmol, 1 eq) in MeCN (2 mL) was added DIEA (73.77 mg, 570.75 μmol, 99.41μ, 2 eq) and (4-nitrophenyl) [(3S)-5-oxopyrrolidin-3-yl] carbonate (75.97 mg, 285.37 μmol, 1 eq). The mixture was stirred at 25° C. for 45 min. The reaction mixture was concentrated under reduced pressure to give a residue. The crude was purified by preparative HPLC. The solution was lyophilized to dryness to give [(3S)-5-oxopyrrolidin-3-yl](2S)-4-[3-[2-(cyclopropoxy)-3-pyridyl] pyrazolo[1,5-a]pyrimidin-5-yl]-2-methyl-piperazine-1-carboxylate (8.01 mg, 16.75 μmol, 26.65% yield, 99.825% purity) as a solid.

LCMS m/z=478.3 $[M+H]^+$.

SFC $t_R$=1.019 min; 100%.

$^1H$ NMR (400 MHz, DMSO-$d_6$) δ=8.80 (d, J=7.5 Hz, 1H), 8.73 (d, J=7.8 Hz, 1H), 8.34 (s, 1H), 8.01 (d, J=4.5 Hz, 1H), 7.73 (s, 1H), 7.16-7.08 (m, 1H), 6.81 (d, J=8.0 Hz, 1H), 5.22 (s, 1H), 4.45-4.36 (m, 2H), 4.33-4.25 (m, 2H), 3.88 (d, J=12.8 Hz, 1H), 3.65-3.59 (m, 1H), 3.29-3.11 (m, 4H), 2.68-2.61 (m, 1H), 2.15 (d, J=17.3 Hz, 1H), 1.12 (d, J=6.5 Hz, 3H), 0.82-0.76 (m, 4H).

Example 34: Synthesis of Compound I-41, Compound I-41-4C, and Compound I-41-6

(S)-4-(3-(2-Cyclopropoxypyridin-3-yl)pyrazolo[1,5-a]pyrimidin-5-yl)piperazine-2-carboxylic acid

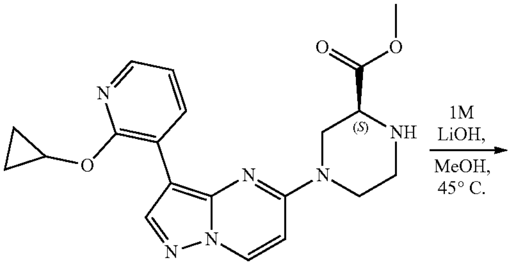

1

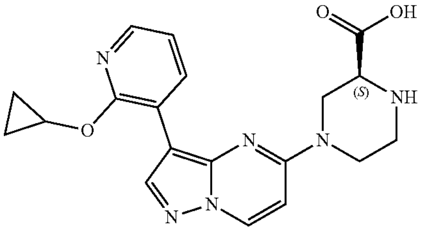

2

To a solution of methyl(S)-4-(3-(2-cyclopropoxypyridin-3-yl)pyrazolo[1,5-a]pyrimidin-5-yl)piperazine-2-carboxylate (1.3 g, 3.30 mmol, 1 eq) in MeOH (5 mL) was added LiOH (1 M, 4.94 mL, 1.5 eq). The mixture was stirred at 45° C. for 2 hr. The reaction mixture was concentrated under reduced pressure to give(S)-4-(3-(2-cyclopropoxypyridin-3-yl)pyrazolo[1,5-a]pyrimidin-5-yl)piperazine-2-carboxylic acid (1.21 g, 1.94 mmol, 58.87% yield, 61% purity) as a solid.

LCMS m/z=381.1 $[M+H]^+$.

(S)-4-(3-(2-Cyclopropoxypyridin-3-yl)pyrazolo[1,5-a]pyrimidin-5-yl)-1-((((S)-5-oxopyrrolidin-3-yl)oxy)carbonyl)piperazine-2-carboxylic acid

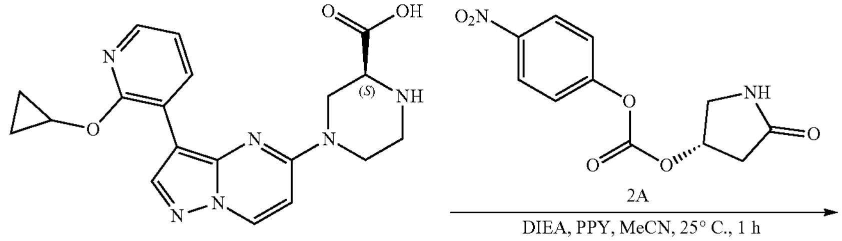

2

-continued

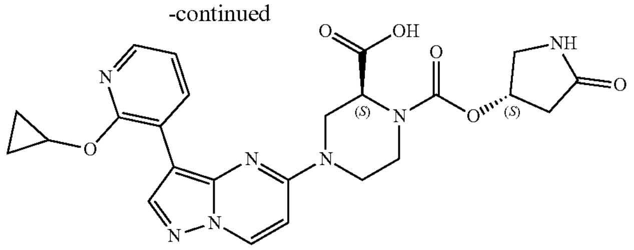

1-41-4C

To a solution of(S)-4-(3-(2-cyclopropoxypyridin-3-yl) pyrazolo[1,5-a]pyrimidin-5-yl)piperazine-2-carboxylic acid (600 mg, 1.58 mmol, 1 eq), (4-nitrophenyl) [(3S)-5-oxopyrrolidin-3-yl] carbonate (587.84 mg, 2.21 mmol, 1.4 eq) in MeCN (6 mL) was added DIEA (611.55 mg, 4.73 mmol, 824.19 µL, 3 eq) and 4-pyrrolidin-1-ylpyridine (46.75 mg, 315.46 µmol, 0.2 eq). The mixture was stirred at 45° C. for 1 hr The reaction mixture was concentrated under reduced pressure. The crude was purified by preparative HPLC. The pure fractions were collected and the volatiles were removed under vacuum. The residue was partitioned between acetonitrile (2 mL) and water (10 mL). The solution was lyophilized to dryness to give(S)-4-(3-(2-cyclopropoxypyridin-3-yl) pyrazolo[1,5-a]pyrimidin-5-yl)-1-((((S)-5-oxopyrrolidin-3-yl)oxy)carbonyl)piperazine-2-carboxylic acid (11.75 mg, 22.78 µmol, 1.44% yield, 98.37% purity) as a solid.

LCMS m/z=508.1 $[M+H]^+$.

SFC $t_R$=1.805 min; 100%.

$^1$H NMR (400 MHz, DMSO-$d_6$) δ=8.81 (d, J=7.0 Hz, 1H), 8.74 (d, J=7.4 Hz, 1H), 8.35 (s, 1H), 8.02 (d, J=4.5 Hz, 1H), 7.80-7.65 (m, 1H), 7.09 (t, J=5.0 Hz, 1H), 6.78 (d, J=7.6 Hz, 1H), 5.26-5.18 (m, 1H), 5.03-4.80 (m, 1H), 4.78-4.66 (m, 1H), 4.48-4.29 (m, 2H), 3.89 (d, J=13.3 Hz, 1H), 3.65-3.57 (m, 1H), 3.47-3.42 (m, 1H), 3.23-3.19 (m, 1H), 3.11 (d, J=11.0 Hz, 1H), 2.78-2.55 (m, 2H), 2.22-2.11 (m, 1H), 0.82-0.77 (m, 4H).

(S)-5-Oxopyrrolidin-3-yl-(S)-2-carbamoyl-4-(3-(2-cyclopropoxypyridin-3-yl)pyrazolo[1,5-a]pyrimidin-5-yl)piperazine-1-carboxylate

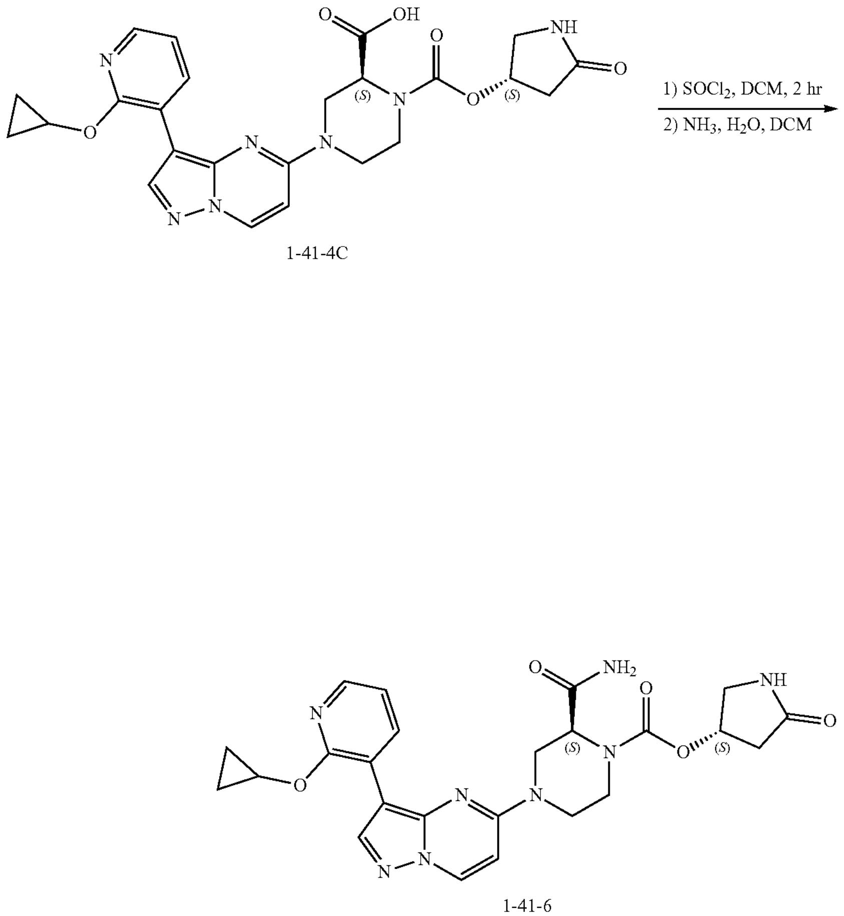

1-41-4C 1-41-6

To a solution of(S)-4-(3-(2-cyclopropoxypyridin-3-yl)pyrazolo[1,5-a]pyrimidin-5-yl)-1-((((S)-5-oxopyrrolidin-3-yl)oxy)carbonyl)piperazine-2-carboxylic acid (50 mg, 98.52 μmol, 1 eq) in DCM (4 mL) was added dropwise $SOCl_2$ (351.64 mg, 2.96 mmol, 214.67 μL, 30 eq) at 0° C. After addition, the mixture was stirred at this temperature for 0.5 hr, and then $NH_3 \cdot H_2O$ (369.94 mg, 2.96 mmol, 406.53 μL, 28% purity, 30 eq) in DCM (4 mL) was added dropwise at 25° C. The resulting mixture was stirred at 25° C. for 3 hr. The reaction mixture was concentrated under reduced pressure. The crude was purified by preparative HPLC. The pure fractions were collected and the volatiles were removed under vacuum. The residue was partitioned between acetonitrile (2 mL) and water (10 mL). The solution was lyophilized to dryness to give(S)-5-oxopyrrolidin-3-yl(S)-2-carbamoyl-4-(3-(2-cyclopropoxypyridin-3-yl)pyrazolo[1,5-a]pyrimidin-5-yl)piperazine-1-carboxylate (39 mg, 76.14 μmol, 77.28% yield, 98.885% purity) as a solid.

LCMS m/z=507.2 $[M+H]^+$.

SFC $t_R$=2.180 min; 100%).

$^1$H NMR (400 MHz, DMSO-$d_6$) δ=8.83 (d, J=7.6 Hz, 1H), 8.74 (d, J=7.9 Hz, 1H), 8.34 (s, 1H), 8.06-7.98 (m, 1H), 7.76-7.68 (m, 2H), 7.25-7.17 (m, 1H), 7.13-7.08 (m, 1H), 6.73 (d, J=7.9 Hz, 1H), 5.21 (d, J=5.1 Hz, 1H), 5.02-4.62 (m, 1H), 4.59-4.54 (m, 1H), 4.43-4.38 (m, 1H), 4.36-4.10 (m, 1H), 3.92-3.83 (m, 1H), 3.69-3.59 (m, 1H), 3.54-3.47 (m, 2H), 3.15 (d, J=11.1 Hz, 1H), 2.71-2.58 (m, 2H), 2.25-2.14 (m, 1H), 0.82-0.78 (m, 4H).

(S)-5-Oxopyrrolidin-3-yl(S)-2-cyano-4-(3-(2-cyclopropoxypyridin-3-yl)pyrazolo[1,5-a]pyrimidin-5-yl)piperazine-1-carboxylate To a solution of(S)-5-oxopyrrolidin-3-yl(S)-2-carbamoyl-4-(3-(2-cyclopropoxypyridin-3-yl)pyrazolo[1,5-a]pyrimidin-5-yl)piperazine-1-carboxylate (40 mg, 78.97 μmol, 1 eq), TEA (15.98 mg, 157.94 μmol, 21.98μ, 2 eq) in DCM (2 mL) was added TFAA (132.69 mg, 631.77 μmol, 87.82 μL, 8 eq). The mixture was stirred at 25° C. for 3 hr. The reaction mixture was concentrated under reduced pressure. The crude was purified by preparative HPLC. The pure fractions were collected and the volatiles were removed under vacuum. The residue was partitioned between acetonitrile (2 mL) and water (10 mL). The solution was lyophilized to dryness to give(S)-5-oxopyrrolidin-3-yl(S)-2-cyano-4-(3-(2-cyclopropoxypyridin-3-yl)pyrazolo[1,5-a]pyrimidin-5-yl)piperazine-1-carboxylate (1.03 mg, 2.06 μmol, 2.60% yield, 97.50% purity) as a solid.

LCMS m/z=489.1 $[M+H]^+$.

SFC $t_R$=1.132 min; 84.3%.

$^1$H NMR (400 MHz, methanol-$d_4$) δ=8.95-8.86 (m, J=7.6 Hz, 1H), 8.58 (d, J=7.9 Hz, 1H), 8.45 (s, 1H), 8.02 (d, J=6.9 Hz, 1H), 7.18-7.12 (m, 1H), 6.86 (d, J=8.0 Hz, 1H), 5.49-5.38 (m, 2H), 5.03-4.95 (m, 2H), 4.63-4.53 (m, 1H), 4.43-4.35 (m, 1H), 4.18 (d, J=12.6 Hz, 1H), 3.87-3.78 (m, 1H), 3.52-3.49 (m, 1H), 3.48-3.42 (m, 1H), 3.29-3.21 (m, J=10.6 Hz, 1H), 2.91-2.80 (m, J=6.9, 17.9 Hz, 1H), 2.52-2.40 (m, 1H), 0.92-0.83 (m, 4H).

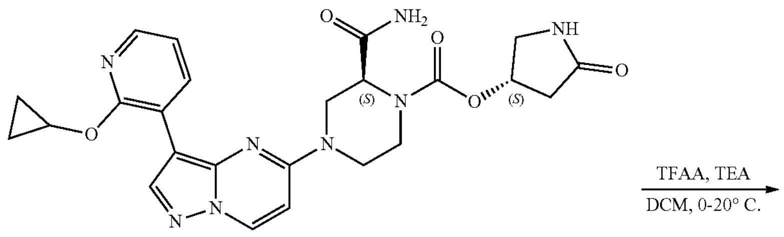

I-41-6

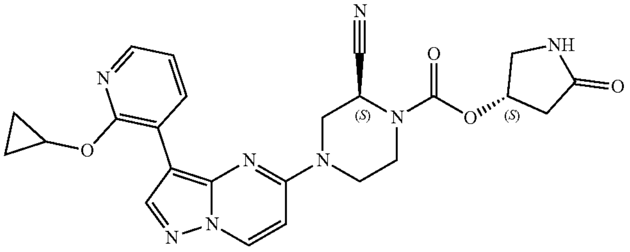

I-41

Example 35: Synthesis of Compound I-41-5

1-(tert-Butyl) 2-methyl(S)-4-(3-bromopyrazolo[1,5-a]pyrimidin-5-yl)piperazine-1,2-dicarboxylate

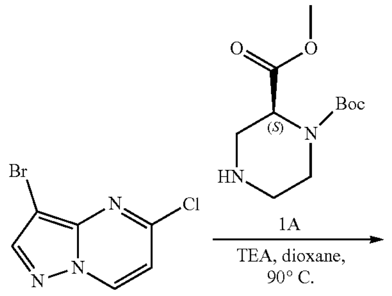

1

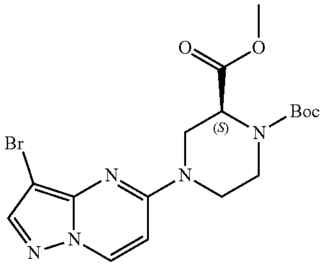

2

A mixture of 3-bromo-5-chloro-pyrazolo[1,5-a]pyrimidine (200 mg, 860.34 μmol, 1 eq), 1-(tert-butyl) 2-methyl (S)-piperazine-1,2-dicarboxylate (231.19 mg, 946.38 μmol, 1.1 eq), TEA (261.17 mg, 2.58 mmol, 359.25 μL, 3 eq) in dioxane (2 mL) was degassed and purged with $N_2$ for 3 times, and then the mixture was stirred at 90° C. for 4 hr under $N_2$ atmosphere. The reaction mixture was filtered and concentrated under reduced pressure to give a residue. The residue was purified by flash silica gel chromatography to give 1-(tert-butyl) 2-methyl(S)-4-(3-bromopyrazolo[1,5-a]pyrimidin-5-yl)piperazine-1,2-dicarboxylate (230 mg, 522.4 μmol, 60.72% yield) as an oil.

LCMS m/z=440.0 $[M+H]^+$.

$^1$H NMR (400 MHz, methanol-$d_4$) δ=8.37 (d, J=7.9 Hz, 1H), 7.82 (s, 1H), 6.69-6.53 (m, 1H), 5.04-4.88 (m, 1H), 4.82-4.70 (m, 1H), 4.39 (br s, 1H), 3.95-3.85 (m, 1H), 3.67 (d, J=2.5 Hz, 3H), 3.51-3.33 (m, 2H), 3.25-3.08 (m, 1H), 1.46 (br d, J=19.8 Hz, 9H).

1-(tert-Butyl) 2-methyl(S)-4-(3-(2-cyclopropoxypyridin-3-yl)pyrazolo[1,5-a]pyrimidin-5-yl)piperazine-1,2-dicarboxylate

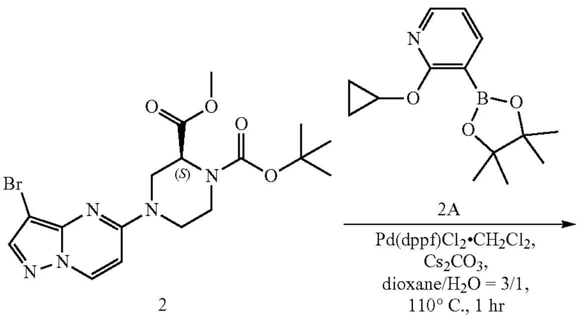

2

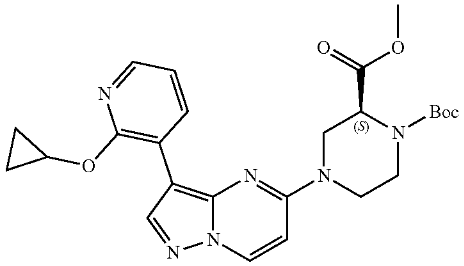

3

A mixture of 1-(tert-butyl) 2-methyl(S)-4-(3-bromopyrazolo[1,5-a]pyrimidin-5-yl)piperazine-1,2-dicarboxylate (200 mg, 454.25 μmol, 1 eq), 2-(cyclopropoxy)-3-(4,4,5,5-tetramethyl-1,3,2-dioxaborolan-2-yl)pyridine (118.61 mg, 454.25 μmol, 1 eq), $Cs_2CO_3$ (444.01 mg, 1.36 mmol, 3 eq) in dioxane/$H_2O$=3/1 (2 mL) was degassed and purged with $N_2$ for 3 times, and the Pd(dppf)$Cl_2$·$CH_2Cl_2$ (74.19 mg, 90.85 μmol, 0.2 eq) was added in the mixture under $N_2$ atmosphere. Then the mixture was stirred at 110° C. for 1 hr. under $N_2$ atmosphere. The reaction mixture was filtered and concentrated under reduced pressure to give a residue. The residue was purified by flash silica gel chromatography to give 1-(tert-butyl) 2-methyl(S)-4-(3-(2-cyclopropoxypyridin-3-yl)pyrazolo[1,5-a]pyrimidin-5-yl)piperazine-1,2-dicarboxylate (130 mg, 262.87 μmol, 57.87% yield) as a solid.

LCMS m/z=495.3 $[M+H]^+$.

$^1$H NMR (400 MHz, DMSO-$d_6$) δ=8.83-8.73 (m, 2H), 8.35 (s, 1H), 8.03 (dd, J=1.8, 4.9 Hz, 1H), 7.13 (dd, J=5.0, 7.1 Hz, 1H), 6.77 (d, J=7.9 Hz, 1H), 5.03-4.88 (m, 1H), 4.81-4.71 (m, 1H), 4.40 (dt, J=2.9, 6.0 Hz, 1H), 3.89-3.75 (m, 1H), 3.60 (br d, J=6.4 Hz, 1H), 3.48 (br d, J=5.5 Hz, 3H), 1.45-1.36 (m, 12H), 0.84-0.74 (m, 4H).

Methyl(S)-4-(3-(2-cyclopropoxypyridin-3-yl)pyrazolo[1,5-a]pyrimidin-5-yl)piperazine-2-carboxylate

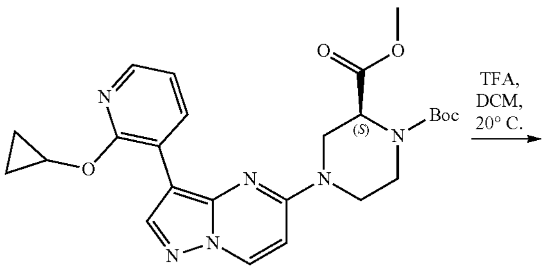

3

-continued

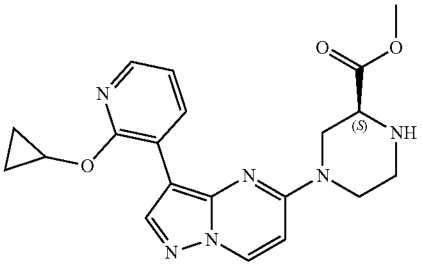

4

A solution of 1-(tert-butyl) 2-methyl(S)-4-(3-(2-cyclopropoxypyridin-3-yl)pyrazolo[1,5-a]pyrimidin-5-yl)piperazine-1,2-dicarboxylate (0.6 g, 1.21 mmol, 1 eq) in DCM/TFA=3/1 (6 mL) was stirred at 20° C. for 1 hr. The reaction mixture was filtered and concentrated under reduced pressure to give a residue. Then the residue was further purified by preparative HPLC. The pure fractions were collected and the volatiles were removed under vacuum. The residue was partitioned between acetonitrile (2 mL) and water (10 mL). The solution was lyophilized to dryness to give methyl(S)-4-(3-(2-cyclopropoxypyridin-3-yl)pyrazolo[1,5-a]pyrimidin-5-yl)piperazine-2-carboxylate (350 mg, 887.36 μmol, 73.14% yield) as a solid.

LCMS m/z=395.0 $[M+H]^+$.

2-Methyl 1-((S)-5-oxopyrrolidin-3-yl) (S)-4-(3-(2-cyclopropoxypyridin-3-yl)pyrazolo[1,5-a]pyrimidin-5-yl)piperazine-1,2-dicarboxylate

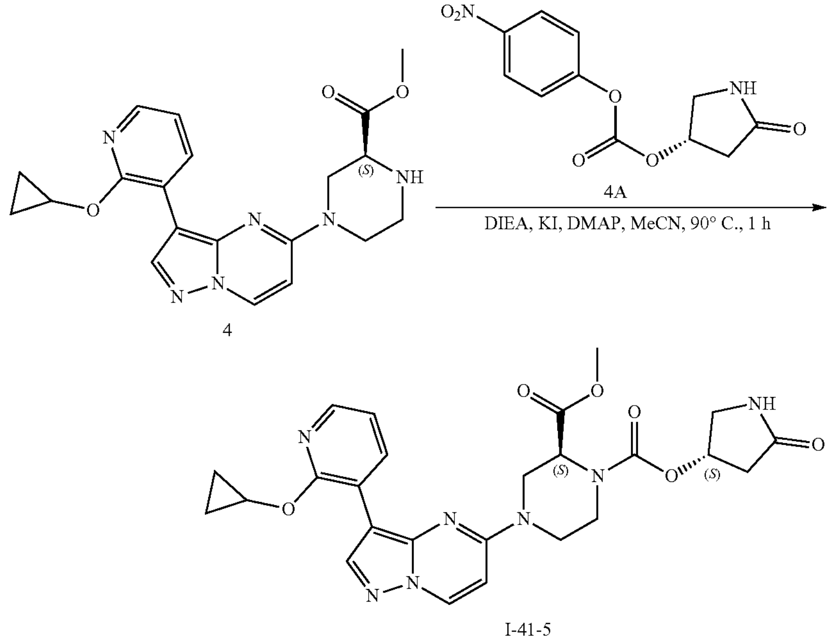

I-41-5

To a solution of methyl(S)-4-(3-(2-cyclopropoxypyridin-3-yl)pyrazolo[1,5-a]pyrimidin-5-yl)piperazine-2-carboxylate (100 mg, 253.53 μmol, 1 eq) and (4-nitrophenyl) [(3S)-5-oxopyrrolidin-3-yl] carbonate (74.24 mg, 278.89 μmol, 1.1 eq) in $CH_3CN$ (1 mL) was added DIEA (98.30 mg, 760.60 μmol, 132.48 μL, 3 eq), DMAP (6.19 mg, 50.71 μmol, 0.2 eq) and KI (8.42 mg, 50.71 μmol, 0.2 eq). The mixture was stirred at 90° C. for 1 hr. The reaction mixture was filtered and concentrated under reduced pressure to give a residue. Then the product was further purified by preparative HPLC. The pure fractions were collected and the volatiles were removed under vacuum. The residue was partitioned between acetonitrile (2 mL) and water (10 mL). The solution was lyophilized to dryness to give 2-methyl 1-((S)-5-oxopyrrolidin-3-yl) (S)-4-(3-(2-cyclopropoxypyridin-3-yl)pyrazolo[1,5-a]pyrimidin-5-yl)piperazine-1,2-dicarboxylate (7.35 mg, 13.91 μmol, 5.49% yield, 98.73% purity) as a solid.

LCMS m/z=522.0 $[M+H]^+$.

SFC $t_R$=2.773 min; 100%.

$^1$H NMR (400 MHz, DMSO-$d_6$): δ=8.84-8.68 (m, 2H), 8.35 (s, 1H), 8.02 (d, J=4.8 Hz, 1H), 7.82-7.63 (m, 1H), 7.15-7.08 (m, 1H), 6.77 (d, J=7.9 Hz, 1H), 5.28-5.17 (m, 1H), 5.02-4.91 (m, 1H), 4.85 (d, J=15.4 Hz, 1H), 4.43-4.30 (m, 2H), 3.88 (s, 1H), 3.67-3.55 (m, 2H), 3.49 (s, 3H), 3.26 (s, 1H), 3.06 (d, J=11.0 Hz, 1H), 2.75-2.57 (m, 2H), 2.22-2.08 (m, 1H), 0.83-0.74 (m, 4H).

Example 36: Synthesis of Compound I-42 and Compound I-43 tert-Butyl 3-[(3-bromo-2-pyridyl)oxy]azetidine-1-carboxylate

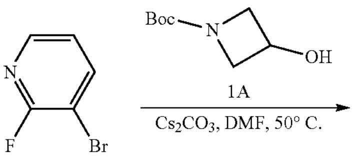

1

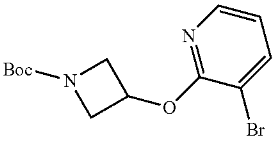

2

To a solution of 3-bromo-2-fluoro-pyridine (2.0 g, 11.36 mmol, 1 eq) in DMF (20 mL) was added $Cs_2CO_3$ (7.41 g, 22.73 mmol, 2 eq) and tert-butyl 3-hydroxyazetidine-1-carboxylate (1.97 g, 11.36 mmol, 1 eq). The mixture was stirred at 50° C. for 1 hr. The reaction mixture was concentrated under reduced pressure to remove DMF (20 mL). The residue was purified by FCC to give tert-butyl 3-[(3-bromo-2-pyridyl)oxy]azetidine-1-carboxylate (3 g, 9.11 mmol, 80.19% yield, 100.000% purity) as a gum.

LCMS m/z=273.1 [M+H]$^+$.

$^1$H NMR (400 MHz, DMSO-$d_6$) δ=8.13 (dd, J=1.6, 4.9 Hz, 1H), 8.07 (dd, J=1.5, 7.8 Hz, 1H), 7.04-6.96 (m, 1H), 5.36-5.26 (m, 1H), 4.33-4.22 (m, 2H), 3.82 (br dd, J=3.2, 9.4 Hz, 2H), 1.38 (s, 9H).

tert-Butyl 3-[3-(4,4,5,5-tetramethyl-1,3,2-dioxaborolan-2-yl)-2-pyridyl]oxy]azetidine-1-carboxylate

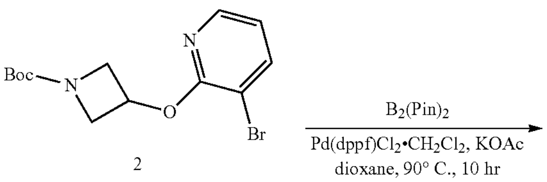

2

-continued

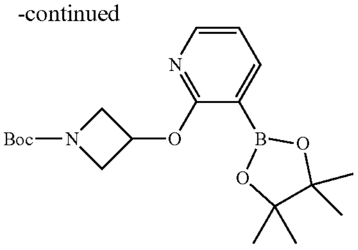

3

A mixture of tert-butyl 3-[(3-bromo-2-pyridyl)oxy]azetidine-1-carboxylate (3 g, 9.11 mmol, 1 eq), 4,4,5,5-tetramethyl-2-(4,4,5,5-tetramethyl-1,3,2-dioxaborolan-2-yl)-1,3,2-dioxaborolane (4.63 g, 18.23 mmol, 2 eq), KOAc (1.79 g, 18.23 mmol, 2 eq), $Pd(dppf)Cl_2 \cdot CH_2Cl_2$ (744.23 mg, 911.33 μmol, 0.1 eq) in dioxane (20 mL) was degassed and purged with $N_2$ for 3 times, and then the mixture was stirred at 90° C. for 10 hr under $N_2$ atmosphere. The reaction mixture was concentrated under reduced pressure to give a residue. The crude was purified by FCC to give tert-butyl 3-[[3-(4,4,5,5-tetramethyl-1,3,2-dioxaborolan-2-yl)-2-pyridyl]oxy]azetidine-1-carboxylate (2.5 g, 6.64 mmol, 72.91% yield) as a gum.

LCMS m/z=477.1 [M+H]$^+$.

$^1$H NMR (400 MHz, DMSO-$d_6$) δ=8.30-8.07 (m, 1H), 8.00-7.65 (m, 1H), 7.07-6.82 (m, 1H), 5.31-5.18 (m, 1H), 4.25 (br t, J=7.6 Hz, 2H), 3.85-3.71 (m, 2H), 1.40-1.37 (m, 9H), 1.36-1.04 (m, 12H).

tert-Butyl 3-[[3-(5-piperazin-1-ylpyrazolo[1,5-a]pyrimidin-3-yl)-2-pyridyl]oxy]azetidine-1-carboxylate

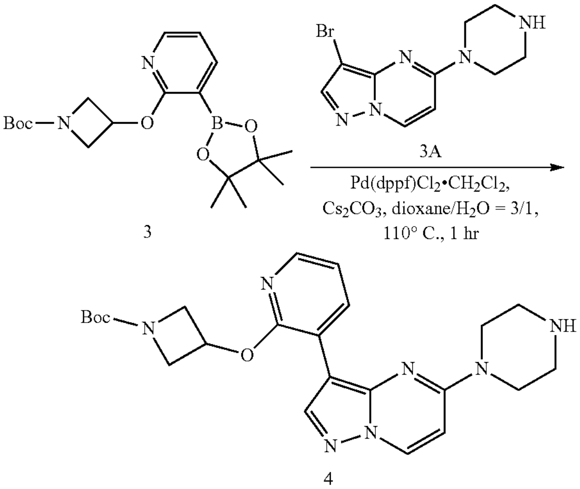

4

A mixture of tert-butyl 3-[[3-(4,4,5,5-tetramethyl-1,3,2-dioxaborolan-2-yl)-2-pyridyl]oxy]azetidine-1-carboxylate (2 g, 5.32 mmol, 1 eq), 3-bromo-5-piperazin-1-yl-pyrazolo[1,5-a]pyrimidine (1.50 g, 5.32 mmol, 1 eq), Pd(dppf)$Cl_2 \cdot CH_2Cl_2$ (868.18 mg, 1.06 mmol, 0.2 eq), $Cs_2CO_3$ (5.20 g, 15.95 mmol, 3 eq) in dioxane (15 mL) and $H_2O$ (5 mL) was degassed and purged with $N_2$ for 3 times, and then the mixture was stirred at 110° C. for 1 hr under $N_2$ atmosphere. The reaction mixture was concentrated under reduced pressure to remove dioxane. The residue was purified by FCC to give tert-butyl 3-[[3-(5-piperazin-1-ylpyrazolo[1,5-a]pyrimidin-3-yl)-2-pyridyl]oxy]azetidine-1-carboxylate (1.90 g, 3.98 mmol, 59.97% yield, 94.691% purity) as a gum.

LCMS m/z=452.1 $[M+H]^+$.

$^1$H NMR (400 MHz, DMSO-$d_6$) δ=8.87-8.78 (m, 1H), 8.70 (d, J=7.9 Hz, 1H), 8.52 (s, 1H), 7.92 (br d, J=4.5 Hz, 1H), 7.17-7.08 (m, 1H), 6.80 (d, J=8.0 Hz, 1H), 5.45-5.36 (m, 1H), 4.37-4.24 (m, 2H), 3.94 (br d, J=6.5 Hz, 2H), 3.65 (br d, J=4.4 Hz, 4H), 3.19-3.13 (m, 1H), 2.84-2.77 (m, 4H), 1.39 (s, 9H).

[(3S)-5-Oxopyrrolidin-3-yl] 4-[3-[2-(1-tert-butoxycarbonylazetidin-3-yl)oxy-3-pyridyl]pyrazolo[1,5-a]pyrimidin-5-yl]piperazine-1-carboxylate

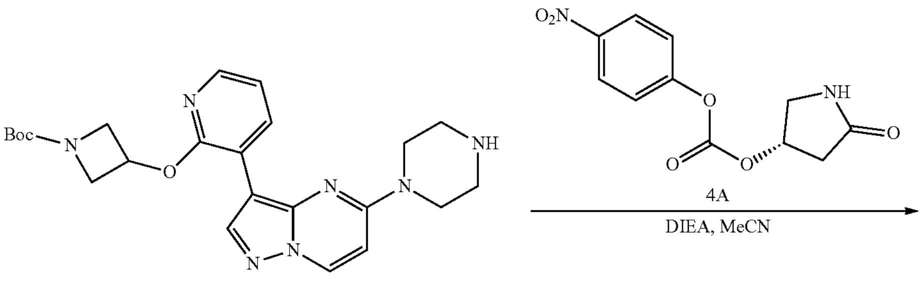

4

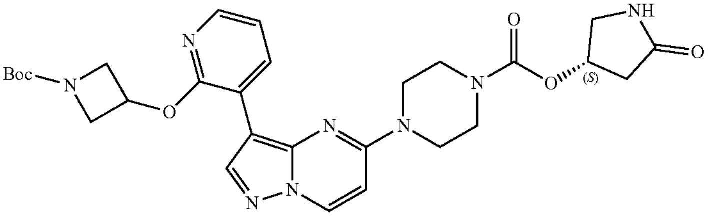

I-42

To a solution of tert-butyl 3-[[3-(5-piperazin-1-ylpyrazolo[1,5-a]pyrimidin-3-yl)-2-pyridyl]oxy]azetidine-1-carboxylate (0.50 g, 1.11 mmol, 1 eq) in MeCN (8 mL) was added DIEA (286.24 mg, 2.21 mmol, 385.77 μL, 2 eq) and (4-nitrophenyl) [(3S)-5-oxopyrrolidin-3-yl] carbonate (589.58 mg, 2.21 mmol, 2 eq). The mixture was stirred at 25° C. for 1 hr. The reaction mixture was concentrated under reduced pressure to give a residue. The crude was purified by preparative HPLC. The solution was lyophilized to dryness to give [(3S)-5-oxopyrrolidin-3-yl] 4-[3-[2-(1-tert-butoxycarbonylazetidin-3-yl)oxy-3-pyridyl]pyrazolo[1,5-a]pyrimidin-5-yl]piperazine-1-carboxylate (13.23 mg, 22.61 μmol, 93.45% yield, 98.89% purity).

LCMS m/z=579.2 $[M+H]^+$.

SFC $t_R$=1.523 min; 100%.

$^1$H NMR (400 MHz, DMSO-$d_6$) δ=8.85-8.81 (m, 1H), 8.77 (d, J=7.9 Hz, 1H), 8.54 (s, 1H), 7.96-7.91 (m, 1H), 7.74-7.70 (m, 1H), 7.16-7.10 (m, 1H), 6.83 (d, J=8.0 Hz, 1H), 5.45-5.38 (m, 1H), 5.24-5.18 (m, 1H), 4.31 (t, J=7.9 Hz, 2H), 3.97-3.91 (m, 2H), 3.80-3.75 (m, 4H), 3.63-3.59 (m, 1H), 3.56-3.51 (m, 4H), 3.26 (d, J=11.4 Hz, 1H), 2.69-2.58 (m, 2H), 2.20-2.12 (m, 1H), 1.39 (s, 9H).

[(3S)-5-Oxopyrrolidin-3-yl] 4-[3-[2-(azetidin-3-yloxy)-3-pyridyl]pyrazolo[1,5-a]pyrimidin-5-yl]piperazine-1-carboxylate

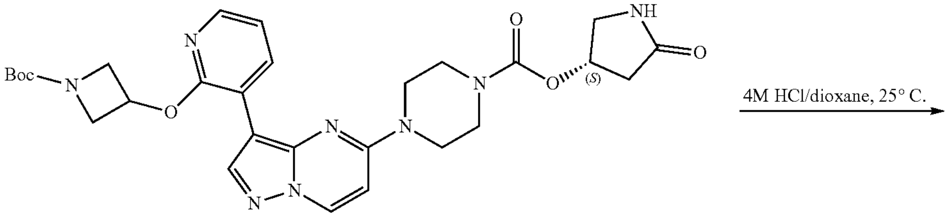

I-42

-continued

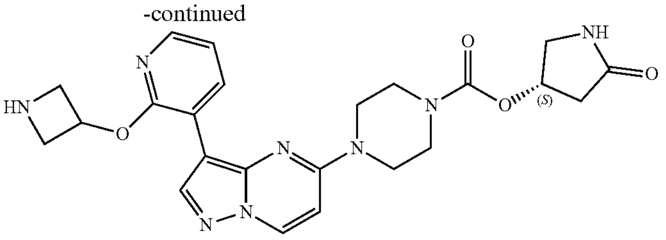

I-43

To a solution of [(3S)-5-oxopyrrolidin-3-yl] 4-[3-[2-(1-tert-butoxycarbonylazetidin-3-yl)oxy-3-pyridyl]pyrazolo[1,5-a]pyrimidin-5-yl]piperazine-1-carboxylate (62 mg, 107.15 μmol, 1 eq) was added HCl/dioxane (4 M, 1.5 mL, 56.00 eq). The mixture was stirred at 25° C. for 1 hr. The reaction mixture was filtered with diatomite and concentrated under reduced pressure to give a crude product. The crude was purified by prep. HPLC (column: Phenomenex luna C18 250*50 mm*15 um; mobile phase: [water (HCl)-MeCN]; gradient: 0%-20% B over 10 min). The solution was lyophilized to dryness to give [(3S)-5-oxopyrrolidin-3-yl] 4-[3-[2-(azetidin-3-yloxy)-3-pyridyl]pyrazolo[1,5-a]pyrimidin-5-yl]piperazine-1-carboxylate (24.39 mg, 49.34 μmol, 46.05% yield, 96.80% purity) as a solid.

LCMS m/z=479.2 $[M+H]^+$.

SFC $t_R$=0.551 min; 100%.

$^1$H NMR (400 MHz, DMSO-$d_6$) δ=9.34 (d, J=7.9 Hz, 1H), 8.86 (d, J=7.9 Hz, 1H), 8.84-8.81 (m, 1H), 8.78 (s, 1H), 8.47 (d, J=6.1 Hz, 1H), 7.74 (s, 1H), 7.69-7.59 (m, 1H), 6.93 (d, J=8.0 Hz, 1H), 5.88-5.72 (m, 1H), 5.21 (t, J=6.0 Hz, 1H), 5.18-5.07 (m, 1H), 4.92-4.78 (m, 1H), 3.91-3.79 (m, 4H), 3.63 (d, J=5.6 Hz, 1H), 3.61-3.58 (m, 2H), 3.57-3.51 (m, 4H), 3.24 (d, J=11.4 Hz, 1H), 2.65-2.61 (m, 1H), 2.19-2.10 (m, 1H).

Example 37: Synthesis of Compound I-44

(S)-5-Oxopyrrolidin-3-yl 4-(3-(2-((1-methylazetidin-3-yl)oxy)pyridin-3-yl)pyrazolo[1,5-a]pyrimidin-5-yl)piperazine-1-carboxylate

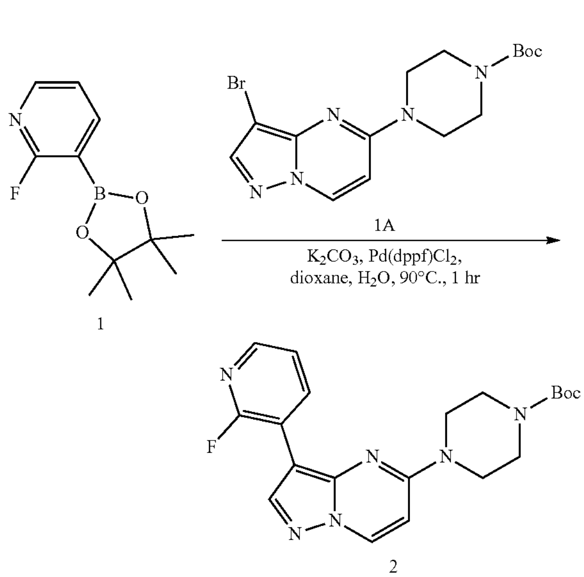

A mixture of 2-fluoro-3-(4,4,5,5-tetramethyl-1,3,2-dioxaborolan-2-yl)pyridine (2.63 g, 11.77 mmol, 1.5 eq), tert-butyl 4-(3-bromopyrazolo[1,5-a]pyrimidin-5-yl)piperazine-1-carboxylate (3 g, 7.85 mmol, 1 eq), Pd(dppf)$Cl_2$·$CH_2Cl_2$ (640.91 mg, 784.82 μmol, 0.1 eq), $Cs_2CO_3$ (7.67 g, 23.54 mmol, 3 eq) in dioxane (15 mL) and $H_2O$ (5 mL) was degassed and purged with $N_2$ for 3 times, and then the mixture was stirred at 90° C. for 1 hr under $N_2$ atmosphere. The reaction mixture was concentrated under reduced pressure to remove solvent. The residue was purified by flash silica gel chromatography to give(S)-5-(oxopyrrolidin-3-yl)-4-(3-(2-((1-methylazetidin-3-yl)oxy)pyridin-3-yl)pyrazolo[1,5-a]pyrimidin-5-yl)piperazine-1-carboxylate (2 g, 4.28 mmol, 54.47% yield, 85.17% purity) as a solid.

LCMS m/z=399.4 $[M+H]^+$.

$^1$H NMR (400 MHz, $CDCl_3$) δ=8.83 (ddd, J=1.9, 7.7, 9.8 Hz, 1H), 8.36 (d, J=4.0 Hz, 1H), 8.29 (d, J=7.9 Hz, 1H), 7.96-7.87 (m, 1H), 7.22-7.18 (m, 1H), 6.35 (d, J=7.9 Hz, 1H), 3.71-3.65 (m, 4H), 3.57-3.52 (m, 4H), 1.43 (s, 9H).

tert-Butyl 4-(3-(2-((1-methylazetidin-3-yl)oxy)pyridin-3-yl)pyrazolo[1,5-a]pyrimidin-5-yl)piperazine-1-carboxylate

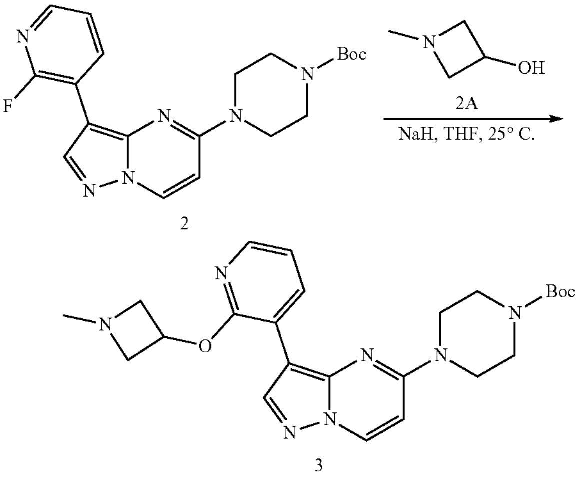

To a solution of NaH (301.15 mg, 7.53 mmol, 60% purity, 3 eq) in THF (2 mL) was added tert-butyl(S)-5-oxopyrrolidin-3-yl 4-(3-(2-((1-methylazetidin-3-yl)oxy)pyridin-3-yl)pyrazolo[1,5-a]pyrimidin-5-yl)piperazine-1-carboxylate (1.0 g, 2.51 mmol, 1 eq) and 1-methylazetidin-3-ol (437.31 mg, 5.02 mmol, 2 eq) in one portion at 0° C. under $N_2$ atmosphere. The mixture was stirred at 25° C. for 1 hr. The mixture was poured into $NH_4Cl$ aq (10 mL) and extracted with DCM (100 mL*3), the combined organic layers were concentrated to afford the crude. The residue was purified by flash silica gel chromatography to give tert-butyl 4-(3-(2-((1-methylazetidin-3-yl)oxy)pyridin-3-yl)pyrazolo[1,5-a]pyrimidin-5-yl)piperazine-1-carboxylate (510 mg, 813.99 μmol, 32.43% yield, 74.30% purity) as a solid.

LCMS m/z=466.2 $[M+H]^+$.

$^1H$ NMR (400 MHz, $CDCl_3$) δ=8.68 (br d, J=7.4 Hz, 1H), 8.59 (s, 1H), 8.30 (d, J=7.9 Hz, 1H), 7.87 (br d, J=4.6 Hz, 1H), 6.93 (dd, J=4.9, 7.3 Hz, 1H), 6.32 (d, J=7.8 Hz, 1H), 5.30 (t, J=5.9 Hz, 1H), 3.93 (br t, J=7.0 Hz, 2H), 3.66 (br d, J=4.1 Hz, 4H), 3.53 (br d, J=5.0 Hz, 4H), 3.17 (br t, J=6.9 Hz, 2H), 2.39 (s, 3H), 1.43 (s, 9H).

3-(2-((1-Methylazetidin-3-yl)oxy)pyridin-3-yl)-5-(piperazin-1-yl)pyrazolo[1,5-a]pyrimidine

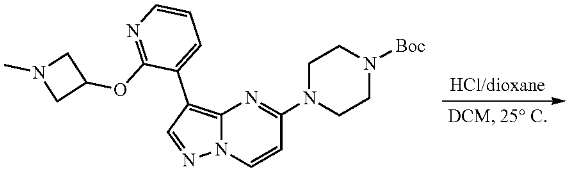

3

-continued

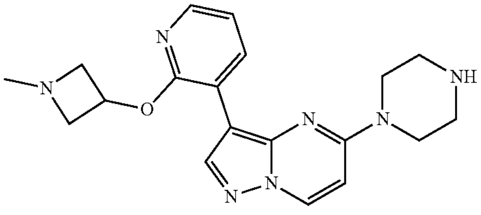

4

To a solution of tert-butyl 4-(3-(2-((1-methylazetidin-3-yl)oxy)pyridin-3-yl)pyrazolo[1,5-a]pyrimidin-5-yl)piperazine-1-carboxylate (460 mg, 793.69 μmol, 1 eq) in DCM (1 mL) was added HCl/dioxane (4 M, 6 mL). The mixture was stirred at 25° C. for 0.2 hr. The reaction mixture was concentrated under reduced pressure to give 3-(2-((1-methylazetidin-3-yl)oxy)pyridin-3-yl)-5-(piperazin-1-yl)pyrazolo[1,5-a]pyrimidine (440 mg, crude, HCl) as an oil.

LCMS m/z=266.3 $[M+H]^+$.

$^1H$ NMR (400 MHz, $D_2O$) δ=9.26 (d, J=7.8 Hz, 1H), 8.65-8.46 (m, 2H), 8.17 (br d, J=6.1 Hz, 1H), 7.53 (t, J=7.1 Hz, 1H), 6.78 (d, J=8.0 Hz, 1H), 5.96-5.85 (m, 1H), 5.30-5.23 (m, 1H), 4.85 (br dd, J=8.5, 12.5 Hz, 2H), 4.04 (br t, J=4.6 Hz, 4H), 3.75-3.68 (m, 2H), 3.38-3.34 (m, 4H), 2.85 (s, 3H).

(S)-5-Oxopyrrolidin-3-yl 4-(3-(2-((1-methylazetidin-3-yl)oxy)pyridin-3-yl)pyrazolo[1,5-a]pyrimidin-5-yl)piperazine-1-carboxylate

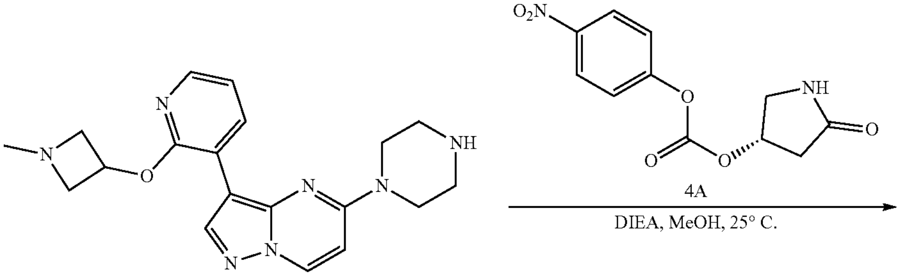

4

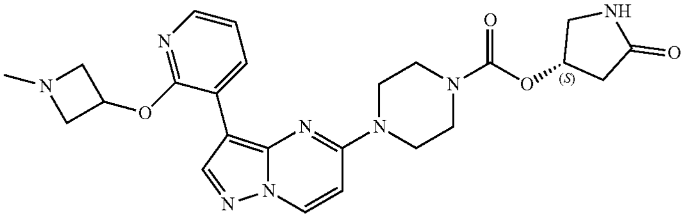

I-44

A mixture of 3-(2-((1-methylazetidin-3-yl)oxy)pyridin-3-yl)-5-(piperazin-1-yl)pyrazolo[1,5-a]pyrimidine (49 mg, 121.92 μmol, 1 eq, HCl), (4-nitrophenyl) [(3S)-5-oxopyrrolidin-3-yl] carbonate (32.46 mg, 121.92 μmol, 1 eq), DIEA (47.27 mg, 365.77 μmol, 63.71 μL, 3 eq) in MeOH (1 mL) was degassed and purged with $N_2$ for 3 times, and then the mixture was stirred at 25° C. for 0.1 hr under $N_2$ atmosphere. The reaction mixture was concentrated under reduced pressure to remove solvent. Then the product was further purified by preparative HPLC. The pure fractions were collected and the volatiles were removed under vacuum. The residue was partitioned between acetonitrile (2 mL) and water (10 mL). The solution was lyophilized to dryness to give(S)-5-oxopyrrolidin-3-yl 4-(3-(2-((1-methylazetidin-3-yl)oxy)

pyridin-3-yl)pyrazolo[1,5-a]pyrimidin-5-yl)piperazine-1-carboxylate (5.00 mg, 9.82 μmol, 8.05% yield, 96.74% purity) as an oil.

LCMS m/z=493.2 $[M+H]^+$.

SFC $t_R$=0.758 min; 100%.

$^1$H NMR (400 MHz, DMSO-$d_6$) δ=9.36 (d, J=7.6 Hz, 1H), 9.31-9.11 (m, 2H), 8.87 (d, J=7.8 Hz, 1H), 8.73 (s, 1H), 8.45 (d, J=5.9 Hz, 1H), 7.75 (s, 1H), 7.68 (t, J=6.9 Hz, 1H), 6.93 (d, J=7.9 Hz, 1H), 5.87-5.75 (m, 1H), 5.26-5.09 (m, 2H), 4.84-4.74 (m, 1H), 3.91-3.77 (m, 4H), 3.77-3.68 (m, 1H), 3.66-3.59 (m, 2H), 3.58-3.50 (m, 4H), 3.24 (d, J=11.4 Hz, 1H), 2.75 (s, 3H), 2.69-2.62 (m, 1H), 2.15 (d, J=17.1 Hz, 1H).

Example 38: Synthesis of Compound I-45

3-Bromo-N-cyclopropyl-pyridin-2-amine

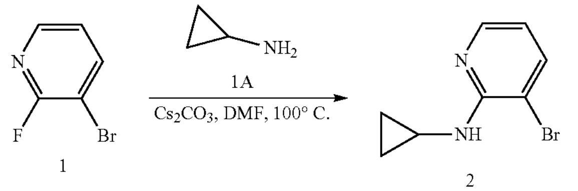

1 2

A mixture of 3-bromo-2-fluoro-pyridine (1 g, 5.68 mmol, 1 eq), cyclopropanamine (486.64 mg, 8.52 mmol, 590.58 μL, 1.5 eq), $Cs_2CO_3$ (3.70 g, 11.36 mmol, 2 eq) in DMF (20 mL) was degassed and purged with $N_2$ for 3 times, and then the mixture was stirred at 100° C. for 12 hr under $N_2$ atmosphere. The reaction mixture was filtered and concentrated under reduced pressure to give a residue. The residue was purified by column chromatography to give 3-bromo-N-cyclopropyl-pyridin-2-amine (500 mg, 2.33 mmol, 41.03% yield, 99.36% purity) as an oil.

LCMS m/z=212.9 $[M+H]^+$.

N-cyclopropyl-3-(4,4,5,5-tetramethyl-1,3,2-dioxaborolan-2-yl)pyridin-2-amine

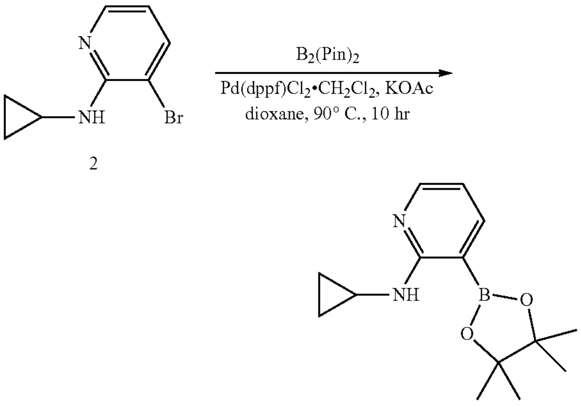

2

3

A mixture of 3-bromo-N-cyclopropyl-pyridin-2-amine (400 mg, 1.88 mmol, 1 eq), $B_2Pin_2$ (715.07 mg, 2.82 mmol, 1.5 eq), KOAc (552.72 mg, 5.63 mmol, 3 eq) and Pd(dppf) $Cl_2·CH_2Cl_2$ (153.31 mg, 187.73 μmol, 0.1 eq) in dioxane (10 mL) was degassed and purged with $N_2$ for 3 times, and then the mixture was stirred at 90° C. for 5 hr under $N_2$ atmosphere. The reaction mixture was concentrated under reduced pressure to give N-cyclopropyl-3-(4,4,5,5-tetramethyl-1,3,2-dioxaborolan-2-yl)pyridin-2-amine (450 mg, crude) as a black oil.

LCMS m/z=261.2 $[M+H]^+$.

N-Cyclopropyl-3-(5-piperazin-1-ylpyrazolo[1,5-a]pyrimidin-3-yl)pyridin-2-amine

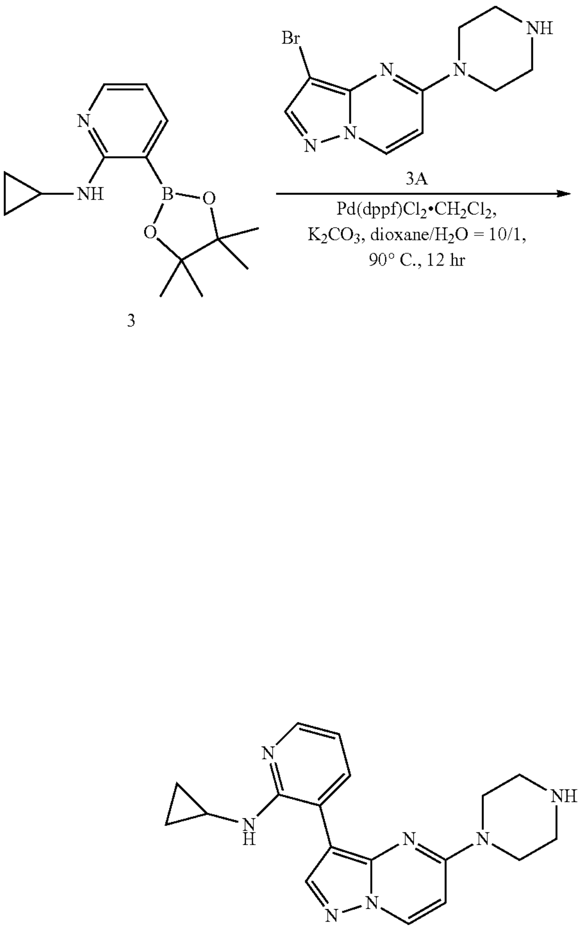

3

4

A mixture of N-cyclopropyl-3-(4,4,5,5-tetramethyl-1,3,2-dioxaborolan-2-yl)pyridin-2-amine (442.57 mg, 1.70 mmol, 1.2 eq), 3-bromo-5-piperazin-1-yl-pyrazolo[1,5-a]pyrimidine (400 mg, 1.42 mmol, 1 eq), $K_2CO_3$ (587.82 mg, 4.25 mmol, 3 eq), $Pd(dppf)Cl_2·CH_2Cl_2$ (115.78 mg, 141.77 μmol, 0.1 eq) in dioxane (10 mL) and $H_2O$ (1 mL) was degassed and purged with $N_2$ for 3 times, and then the mixture was stirred at 90° C. for 12 hr under $N_2$ atmosphere, TLC indicated Reactant 1 was consumed completely, the reaction mixture was concentrated under reduced pressure to give a residue. The residue was purified by column chromatography to give N-cyclopropyl-3-(5-piperazin-1-ylpyrazolo[1,5-a]pyrimidin-3-yl)pyridin-2-amine (400 mg, 632.07 μmol, 44.58% yield, 53% purity) as an oil.

LCMS m/z=336.2 $[M+H]^+$.

[(3S)-5-Oxopyrrolidin-3-yl] 4-[3-[2-(cyclopropylamino)-3-pyridyl]pyrazolo[1,5-a]pyrimidin-5-yl] piperazine-1-carboxylate

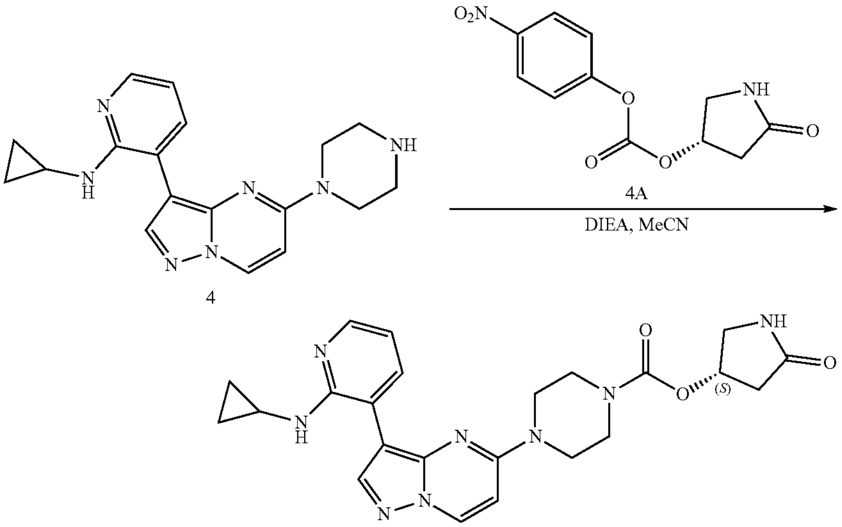

I-45

A mixture of N-cyclopropyl-3-(5-piperazin-1-ylpyrazolo[1,5-a]pyrimidin-3-yl)pyridin-2-amine (375 mg, 1.12 mmol, 1 eq), (4-nitrophenyl) [(3S)-5-oxopyrrolidin-3-yl] carbonate (297.63 mg, 1.12 mmol, 1 eq), DIEA (433.50 mg, 3.35 mmol, 584.23 μL, 3 eq) in MeCN (10 mL) was degassed and purged with $N_2$ for 3 times, and then the mixture was stirred at 25° C. for 2 hr under $N_2$ atmosphere. The reaction mixture was concentrated under reduced pressure to give a residue. The residue was purified by preparative HPLC. Compound [(3S)-5-oxopyrrolidin-3-yl] 4-[3-[2-(cyclopropylamino)-3-pyridyl]pyrazolo[1,5-a]pyrimidin-5-yl]piperazine-1-carboxylate (5.1 mg, 10.52 μmol, 40.54% yield, 95.4% purity) was obtained as a solid.

LCMS m/z=463.2 $[M+H]^+$.

SFC $t_R$=2.401, 100%.

$^1$H NMR (400 MHz, DMSO-$d_6$) δ=8.74 (d, J=8.0 Hz, 1H), 8.09 (s, 1H), 8.06-8.02 (m, 1H), 7.72 (s, 1H), 7.58-7.54 (m, 1H), 7.01-6.96 (m, 1H), 6.79 (d, J=8.0 Hz, 1H), 6.70-6.64 (m, 1H), 5.23-5.17 (m, 1H), 3.77-3.70 (m, 4H), 3.63-3.59 (m, 1H), 3.55-3.49 (m, 4H), 3.26-3.22 (m, 1H), 2.84-2.78 (m, 1H), 2.66-2.60 (m, 1H), 2.20-2.13 (m, 1H), 0.69-0.63 (m, 2H), 0.36-0.31 (m, 2H).

Example 39: Synthesis of Compound I-46

3-Bromo-N-cyclobutylpyridin-2-amine

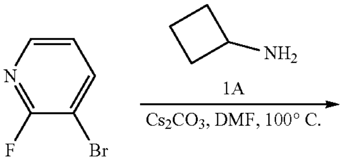

1

-continued

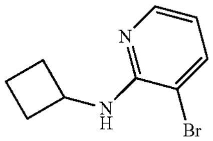
2

To a solution of 3-bromo-2-fluoro-pyridine (1.0 g, 5.68 mmol, 1 eq) in DMF (5 mL) was added $Cs_2CO_3$ (3.70 g, 11.36 mmol, 2 eq) and cyclobutanamine (606.19 mg, 8.52 mmol, 730.35 μL, 1.5 eq). The mixture was stirred at 100° C. for 12 hr. The reaction mixture was concentrated under reduced pressure to remove solvent. The residue was purified by flash silica gel chromatography to give 3-bromo-N-cyclobutyl-pyridin-2-amine (1.08 g, 4.76 mmol, 83.69% yield) as an oil.

LCMS m/z=227.0 $[M+H]^+$.

$^1$H NMR (400 MHz, $CDCl_3$) δ=8.04 (br d, J=4.4 Hz, 1H), 7.58 (br d, J=7.6 Hz, 1H), 6.43 (dd, J=4.9, 7.2 Hz, 1H), 5.13 (br s, 1H), 4.52 (sxt, J=7.9 Hz, 1H), 2.54-2.35 (m, 2H), 1.97-1.84 (m, 2H), 1.83-1.69 (m, 2H).

N-cyclobutyl-3-(4,4,5,5-tetramethyl-1,3,2-dioxaborolan-2-yl)pyridin-2-amine

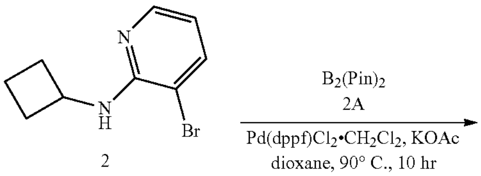

2

-continued

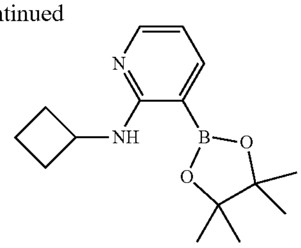

3

A mixture of 3-bromo-N-cyclobutyl-pyridin-2-amine (0.5 g, 2.20 mmol, 1 eq), 4,4,5,5-tetramethyl-2-(4,4,5,5-tetramethyl-1,3,2-dioxaborolan-2-yl)-1,3,2-dioxaborolane (838.63 mg, 3.30 mmol, 1.5 eq), $Pd(dppf)Cl_2 \cdot CH_2Cl_2$ (359.59 mg, 440.33 μmol, 0.2 eq), KOAc (648.23 mg, 6.61 mmol, 3 eq) and in dioxane (5 mL) was degassed and purged with $N_2$ for 3 times, and then the mixture was stirred at 90° C. for 10 hr under $N_2$ atmosphere. LCMS showed Reactant 2 was consumed completely and desired mass was detected. The reaction mixture was concentrated under reduced pressure to remove solvent. The residue was purified by flash silica gel chromatography (ISCO®; 5 g SepaFlash® Silica Flash Column, Eluent of 0~30% Ethyl acetate/Petroleum ether gradient @18 mL/min) to give N-cyclobutyl-3-(4,4,5,5-tetramethyl-1,3,2-dioxaborolan-2-yl)pyridin-2-amine (0.1 g, 364.74 μmol, 16.57% yield) as a solid.

LCMS m/z=193.2 $[M+H]^+$.

$^1$H NMR (400 MHz, $CDCl_3$) δ=8.13-8.05 (m, 1H), 7.72 (dd, J=2.1, 7.1 Hz, 1H), 6.39 (dd, J=5.0, 7.1 Hz, 1H), 6.34-6.29 (m, 1H), 4.50-4.40 (m, 1H), 2.39-2.33 (m, 2H), 1.83-1.74 (m, 2H), 1.71-1.64 (m, 2H), 1.27 (s, 12H).

N-cyclobutyl-3-(5-(piperazin-1-yl)pyrazolo[1,5-a]pyrimidin-3-yl)pyridin-2-amine

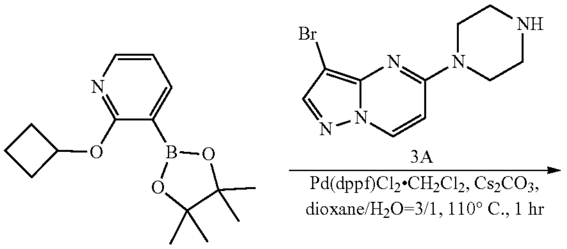

3

-continued

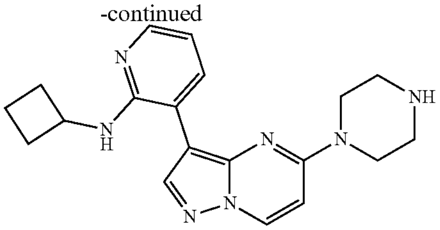

4

To a solution of N-cyclobutyl-3-(4,4,5,5-tetramethyl-1,3,2-dioxaborolan-2-yl)pyridin-2-amine (0.1 g, 364.74 μmol, 1 eq), 3-bromo-5-piperazin-1-yl-pyrazolo[1,5-a]pyrimidine (102.91 mg, 364.74 μmol, 1 eq) in dioxane (3 mL), $H_2O$ (1 mL) was added $Pd(dppf)Cl_2 \cdot CH_2Cl_2$ (59.57 mg, 72.95 μmol, 0.2 eq) and $Cs_2CO_3$ (356.52 mg, 1.09 mmol, 3 eq). The mixture was stirred at 110° C. for 1 hr. d. The reaction mixture was concentrated under reduced pressure to remove solvent. The residue was purified by flash silica gel chromatography to give N-cyclobutyl-3-(5-piperazin-1-ylpyrazolo[1,5-a]pyrimidin-3-yl)pyridin-2-amine (81 mg, 231.80 μmol, 63.55% yield) as a solid.

LCMS m/z=350.3 $[M+H]^+$.

$^1$H NMR (400 MHz, $CDCl_3$) δ=8.33 (d, J=7.9 Hz, 1H), 8.11 (dd, J=1.6, 5.0 Hz, 1H), 7.99 (s, 1H), 7.51 (dd, J=1.7, 7.3 Hz, 1H), 6.64 (dd, J=5.1, 7.3 Hz, 1H), 6.39 (d, J=7.9 Hz, 1H), 6.34 (dd, J=5.8, 7.9 Hz, 1H), 6.22 (br d, J=7.1 Hz, 1H), 4.63-4.52 (m, 1H), 3.74-3.71 (m, 4H), 3.00 (br s, 4H), 2.52-2.42 (m, 2H), 1.83-1.71 (m, 4H).

[(3S)-5-oxopyrrolidin-3-yl] 4-[3-[2-(cyclobutylamino)-3-pyridyl]pyrazolo[1,5-a]pyrimidin-5-yl]piperazine-1-carboxylate

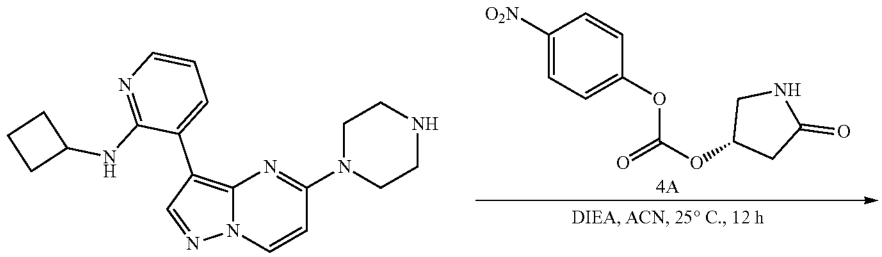

4

-continued

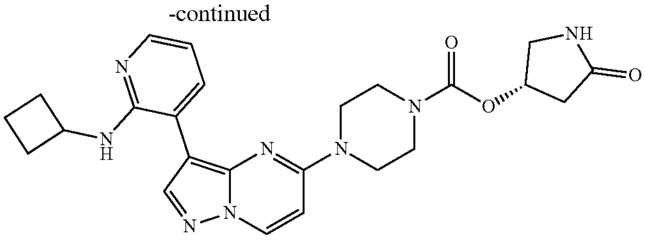

I-46

To a solution of N-cyclobutyl-3-(5-piperazin-1-ylpyrazolo[1,5-a]pyrimidin-3-yl)pyridin-2-amine (0.08 g, 228.94 μmol, 1 eq) in MeCN (3 mL) was added DIEA (88.77 mg, 686.83 μmol, 119.63 μL, 3 eq) and (4-nitrophenyl) [(3S)-5-oxopyrrolidin-3-yl] carbonate (73.14 mg, 274.73 μmol, 1.2 eq). The mixture was stirred at 25° C. for 12 hr. LCMS showed Reactant 4 was consumed completely and desired mass was detected. The reaction mixture was concentrated under reduced pressure to remove solvent. Then the product was further purified by prep. HPLC (column: Waters Xbridge C18 150*50 mm*10 μm; mobile phase: [water ($NH_3H_2O$)-MeCN]; gradient: 17%-47% B over 10 min). The pure fractions were collected and the volatiles were removed under vacuum. The residue was partitioned between acetonitrile (2 mL) and water (10 mL). The solution was lyophilized to dryness to give [(3S)-5-oxopyrrolidin-3-yl] 4-[3-[2-(cyclobutylamino)-3-pyridyl]pyrazolo[1,5-a]pyrimidin-5-yl]piperazine-1-carboxylate (22.71 mg, 46.61 μmol, 20.36% yield, 97.81% purity) as a solid.

LCMS m/z=477.2 $[M+H]^+$.

SFC $t_R$=2.257 min; 100%.

$^1$H NMR (400 MHz, DMSO-$d_6$) δ=8.76 (d, J=7.9 Hz, 1H), 8.06 (s, 1H), 7.99-7.92 (m, 1H), 7.72 (s, 1H), 7.52 (dd, J=1.4, 7.5 Hz, 1H), 6.80 (d, J=7.9 Hz, 1H), 6.61 (dd, J=4.9, 7.2 Hz, 1H), 6.43 (br d, J=7.0 Hz, 1H), 5.19 (br t, J=5.8 Hz, 1H), 4.53-4.41 (m, 1H), 3.74 (br s, 4H), 3.60 (dd, J=5.6, 11.4 Hz, 1H), 3.51 (br s, 4H), 3.23 (br d, J=11.4 Hz, 1H), 2.69-2.58 (m, 1H), 2.31 (br d, J=7.9 Hz, 2H), 2.15 (br d, J=17.5 Hz, 1H), 1.87-1.74 (m, 2H), 1.74-1.61 (m, 2H).

Example 40: Synthesis of Compound I-47

N-isopropyl-3-(4,4,5,5-tetramethyl-1,3,2-dioxaborolan-2-yl)pyridin-2-amine

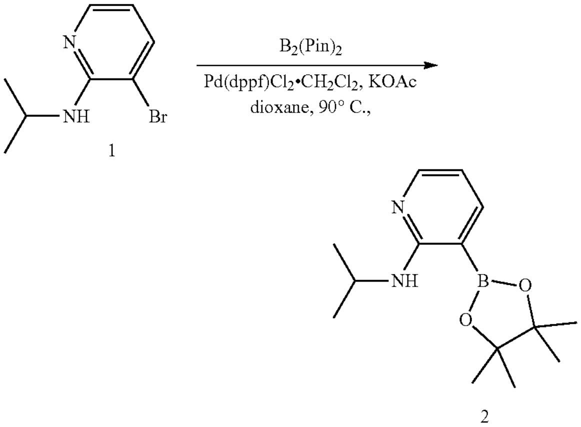

A mixture of 3-bromo-N-isopropyl-pyridin-2-amine (660 mg, 3.07 mmol, 1 eq), 4,4,5,5-tetramethyl-2-(4,4,5,5-tetramethyl-1,3,2-dioxaborolan-2-yl)-1,3,2-dioxaborolane (1.56 g, 6.14 mmol, 2 eq), $Pd(dppf)Cl_2 \cdot CH_2Cl_2$ (250.58 mg, 306.85 μmol, 0.1 eq), KOAc (602.30 mg, 6.14 mmol, 2 eq) in dioxane (8 mL) was degassed and purged with $N_2$ for 3 times, and then the mixture was stirred at 90° C. for 10 hr under $N_2$ atmosphere. The reaction mixture was concentrated under reduced pressure to give a residue. The crude was purified by FCC to give N-isopropyl-3-(4,4,5,5-tetramethyl-1,3,2-dioxaborolan-2-yl)pyridin-2-amine (600 mg, 2.29 mmol, 74.59% yield) as a gum.

LCMS m/z=263.2 $[M+H]^+$.

$^1$H NMR (400 MHz, DMSO-$d_6$) δ=8.18-7.85 (m, 1H), 7.73-7.22 (m, 1H), 6.51-6.33 (m, 1H), 6.32-6.01 (m, 1H), 4.06-3.87 (m, 1H), 1.29 (s, 6H), 1.23-1.04 (m, 12H).

N-isopropyl-3-(5-piperazin-1-ylpyrazolo[1,5-a]pyrimidin-3-yl)pyridin-2-amine

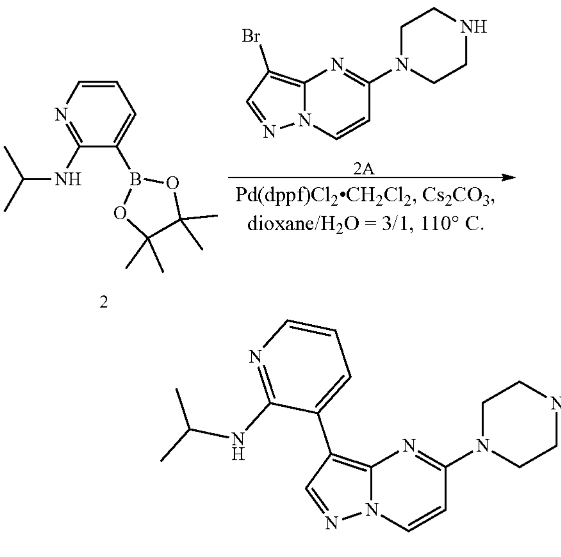

3

A mixture of N-isopropyl-3-(4,4,5,5-tetramethyl-1,3,2-dioxaborolan-2-yl)pyridin-2-amine (500 mg, 1.91 mmol, 1 eq), 3-bromo-5-piperazin-1-yl-pyrazolo[1,5-a]pyrimidine (538.12 mg, 1.91 mmol, 1 eq), $Pd(dppf)Cl_2 \cdot CH_2Cl_2$ (311.51 mg, 381.45 μmol, 0.2 eq), $Cs_2CO_3$ (1.86 g, 5.72 mmol, 3 eq) in dioxane (9 mL) and $H_2O$ (3 mL) was degassed and purged with $N_2$ for 3 times, and then the mixture was stirred at 110° C. for 1 hr under $N_2$ atmosphere. The reaction mixture was concentrated under reduced pressure to give a residue. The crude was purified by FCC to give N-isopropyl-3-(5-piperazin-1-yl)pyrazolo[1,5-a]pyrimidin-3-yl)pyridin-2-amine (260 mg, 622.56 μmol, 27.20% yield, 80.794% purity) as a gum.

LCMS m/z=338.2 $[M+H]^+$.

$^1$H NMR (400 MHz, DMSO-$d_6$) δ=8.72-8.65 (m, 1H), 8.06-7.96 (m, 2H), 7.49 (dd, J=1.8, 7.3 Hz, 1H), 6.81-6.72 (m, 1H), 6.59 (dd, J=5.0, 7.3 Hz, 1H), 5.98 (br d, J=7.4 Hz, 1H), 4.24-4.14 (m, 1H), 3.63 (br s, 4H), 3.16 (s, 1H), 2.77 (br d, J=4.8 Hz, 4H), 1.16 (d, J=6.4 Hz, 6H).

[(3S)-5-oxopyrrolidin-3-yl] 4-[3-[2-(isopropylamino)-3-pyridyl]pyrazolo[1,5-a]pyrimidin-5-yl] piperazine-1-carboxylate

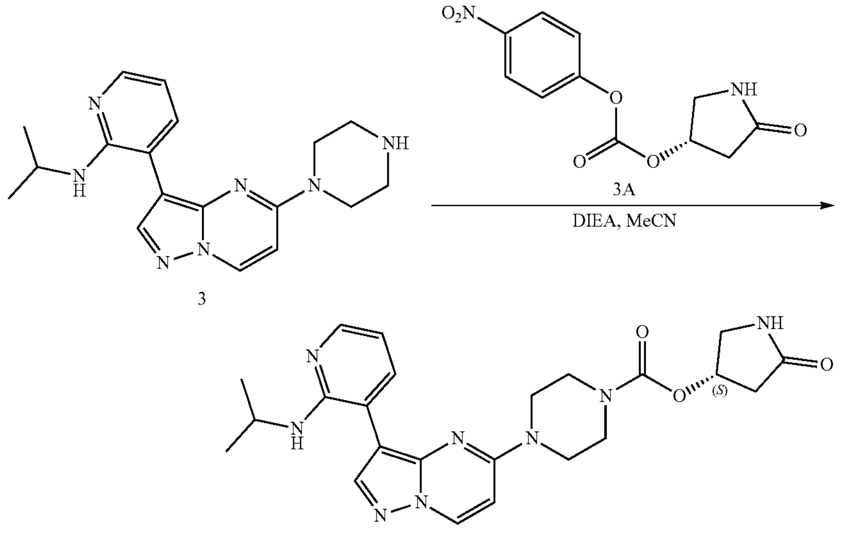

3

I-47

To a solution of N-isopropyl-3-(5-piperazin-1-ylpyrazolo[1,5-a]pyrimidin-3-yl)pyridin-2-amine (100 mg, 296.37 μmol, 1 eq) in MeCN (2 mL) was added DIEA (76.61 mg, 592.73 μmol, 103.24 μL, 2 eq) and (4-nitrophenyl) [(3S)-5-oxopyrrolidin-3-yl] carbonate (78.89 mg, 296.37 μmol, 1 eq). The mixture was stirred at 25° C. for 1 hr. The reaction mixture was concentrated under reduced pressure to give a residue. The crude was purified by prep. HPLC (column: Waters Xbridge C18 150*50 mm*10 um; mobile phase: [water ($NH_3H_2O$)-MeCN]; gradient: 23%-53% B over 10 min). The solution was lyophilized to dryness to give [(3S)-5-oxopyrrolidin-3-yl]-4-[3-[2-(isopropylamino)-3-pyridyl]pyrazolo[1,5-a]pyrimidin-5-yl]piperazine-1-carboxylate (26.28 mg, 60.27 μmol, 28.00% yield, 98.926% purity) as a solid.

LCMS m/z=465.2 $[M+H]^+$.

SFC $t_R$=1.558 min 100%.

$^1$H NMR (400 MHz, $CDCl_3$) δ=8.39 (d, J=7.8 Hz, 1H), 8.13 (d, J=5.0 Hz, 1H), 8.03 (s, 1H), 7.52 (d, J=6.6 Hz, 1H), 6.63 (t, J=5.9 Hz, 1H), 6.40 (d, J=7.9 Hz, 1H), 5.64-5.54 (m, 1H), 5.42-5.37 (m, 1H), 5.37-4.86 (m, 1H), 4.49-4.22 (m, 1H), 3.83-3.78 (m, 1H), 3.77-3.70 (m, 4H), 3.65-3.56 (m, 4H), 3.48 (d, J=11.5 Hz, 1H), 2.79-2.71 (m, 1H), 2.50-2.42 (m, 1H), 1.24 (d, J=6.4 Hz, 6H).

Example 41: Synthesis of Compound I-48 tert-butyl3-((3-bromopyridin-2-yl)amino)azetidine-1-carboxylate

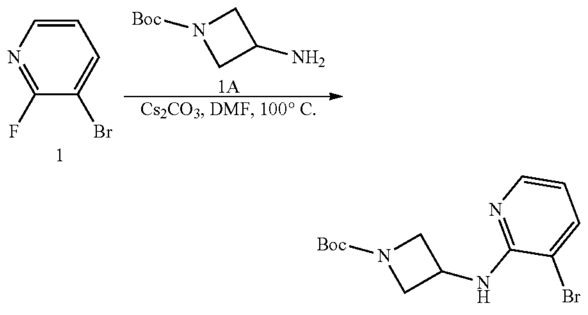

1

2

To a solution of 3-bromo-2-fluoro-pyridine (1 g, 5.68 mmol, 1 eq) in DMF (10 mL) was added $Cs_2CO_3$ (3.70 g, 11.36 mmol, 2 eq) and tert-butyl 3-aminoazetidine-1-carboxylate (1.17 g, 6.82 mmol, 1.2 eq). The mixture was stirred at 100° C. for 12 hr. The mixture was concentrated to give the crude product. The crude was purified by FCC to give tert-butyl 3-[(3-bromo-2-pyridyl)amino]azetidine-1-carboxylate (650 mg, 1.83 mmol, 32.18% yield, 92.332% purity) as an oil.

LCMS m/z=329.9 [M+H]$^+$.

$^1$H NMR (400 MHz, DMSO-$d_6$) δ=8.01 (dd, J=1.4, 4.8 Hz, 1H), 7.77 (dd, J=1.5, 7.6 Hz, 1H), 6.78 (b rd, J=5.9 Hz, 1H), 6.56 (dd, J=4.9, 7.6 Hz, 1H), 4.65-4.52 (m, 1H), 4.07 (br s, 2H), 3.85 (br s, 2H), 1.38 (s, 9H).

tert-butyl 3-[[3-(4,4,5,5-tetramethyl-1,3,2-dioxaborolan-2-yl)-2-pyridyl]amino]azetidine-1-carboxylate

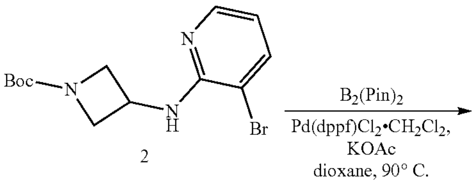

2

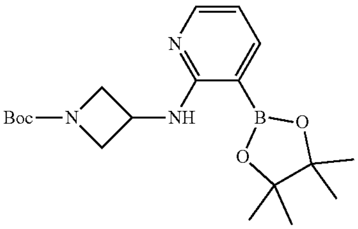

3

To a mixture of tert-butyl 3-[(3-bromo-2-pyridyl)amino]azetidine-1-carboxylate (650 mg, 1.98 mmol, 1 eq) and 4,4,5,5-tetramethyl-2-(4,4,5,5-tetramethyl-1,3,2-dioxaborolan-2-yl)-1,3,2-dioxaborolane (603.50 mg, 2.38 mmol, 1.2 eq) in dioxane (10 mL) was added KOAc (485.92 mg, 4.95 mmol, 2.5 eq), and Pd(dppf)$Cl_2$·$CH_2Cl_2$ (323.47 mg, 396.09 μmol, 0.2 eq), then the mixture was degassed and purged with $N_2$ for 3 times. The mixture was stirred at 90° C. for 3 hr under $N_2$ atmosphere. The mixture was concentrated to give the crude product. The crude was purified by FCC to give tert-butyl 3-[[3-(4,4,5,5-tetramethyl-1,3,2-dioxaborolan-2-yl)-2-pyridyl]amino]azetidine-1-carboxylate (340 mg, 728.26 μmol, 36.77% yield, 80.38% purity).

LCMS m/z=376.2 [M+H]$^+$.

$^1$H NMR (400 MHz, DMSO-$d_6$): 8.12 (br d, J=3.9 Hz, 1H), 7.72 (br d, J=7.1 Hz, 1H), 6.62-6.56 (m, 1H), 6.50 (br d, J=5.5 Hz, 1H), 4.56-4.48 (m, 1H), 4.16 (br t, J=7.9 Hz, 2H), 3.66 (br d, J=4.4 Hz, 2H), 1.39 (s, 9H), 1.31 (s, 12H).

tert-butyl 3-[[3-(5-piperazin-1-ylpyrazolo[1,5-a]pyrimidin-3-yl)-2-pyridyl]amino]azetidine-1-carboxylate

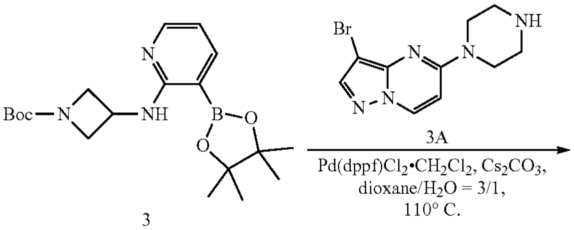

3

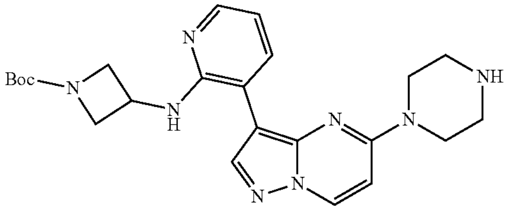

4

To a mixture of tert-butyl 3-[[3-(4,4,5,5-tetramethyl-1,3,2-dioxaborolan-2-yl)-2-pyridyl]amino]azetidine-1-carboxylate (340 mg, 728.26 μmol, 1 eq) and 3-bromo-5-piperazin-1-yl-pyrazolo[1,5-a]pyrimidine (205.47 mg, 728.26 μmol, 1 eq) in dioxane (4.5 mL) and $H_2O$ (1.5 mL) was added $Cs_2CO_3$ (711.84 mg, 2.18 mmol, 3 eq), then added Pd(dppf)$Cl_2$·$CH_2Cl_2$ (118.94 mg, 145.65 μmol, 0.2 eq). The mixture was degassed and purged with $N_2$ 3 times and then was stirred at 110° C. for 3 hr under $N_2$ atmosphere. The mixture was concentrated to the crude product. The crude was purified by FCC to give tert-butyl 3-[[3-(5-piperazin-1-ylpyrazolo[1,5-a]pyrimidin-3-yl)-2-pyridyl]amino]azetidine-1-carboxylate (290 mg, 643.68 μmol, 88.39% yield) as black solid.

LCMS m/z=451.4 [M+H]$^+$.

[(3S)-5-oxopyrrolidin-3-yl] 4-[3-[2-[(1-tert-butoxycarbonylazetidin-3-yl)amino]-3-pyridyl]pyrazolo[1,5-a]pyrimidin-5-yl]piperazine-1-carboxylate

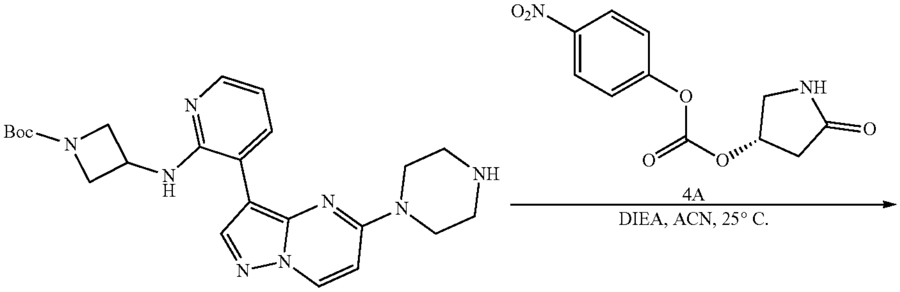

4

-continued

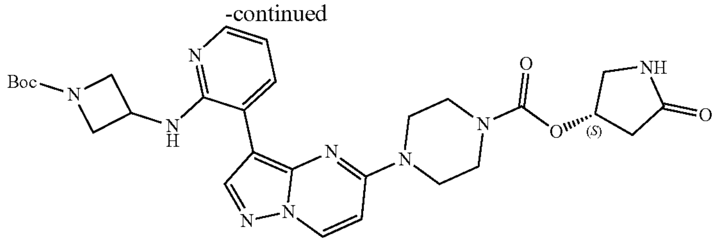

I-48

To a mixture of tert-butyl 3-[[3-(5-piperazin-1-ylpyrazolo[1,5-a]pyrimidin-3-yl)-2-pyridyl]amino]azetidine-1-carboxylate (100 mg, 221.96 μmol, 1 eq) and (4-nitrophenyl) [(3S)-5-oxopyrrolidin-3-yl]carbonate (59.09 mg, 221.96 μmol, 1 eq) in MeCN (0.8 mL) was added DIEA (57.37 mg, 443.92 μmol, 77.32 μL, 2 eq). The mixture was stirred at 25° C. for 2 hr. LCMS showed that desired MS was found. The mixture was concentrated to the crude product. The product was purified by prep. HPLC (column: Waters xbridge 150*25 mm 10 um; mobile phase: [water ($NH_4HCO_3$)-MeCN]; gradient: 25%-55% B over 10 min). The pure fractions were collected and the volatiles were removed under vacuum. The residue was partitioned between acetonitrile (2 mL) and water (10 mL). The solution was lyophilized to dryness to give [(3S)-5-oxopyrrolidin-3-yl] 4-[3-[2-[(1-tert-butoxycarbonylazetidin-3-yl)amino]-3-pyridyl]pyrazolo[1,5-a]pyrimidin-5-yl]piperazine-1-carboxylate (15.89 mg, 27.22 μmol, 12.26% yield, 98.956% purity) as a powder.

LCMS m/z=578.3 $[M+H]^+$.

SFC $t_R$=1.935 min; 99.784%.

$^1$H NMR (400 MHz, DMSO-$d_6$) δ=8.80-8.72 (m, 1H), 8.12 (s, 1H), 8.02-7.95 (m, 1H), 7.70 (s, 1H), 7.64-7.58 (m, 1H), 6.88-6.77 (m, 2H), 6.73-6.67 (m, 1H), 5.22-5.13 (m, 1H), 4.66-4.54 (m, 1H), 4.22-4.08 (m, 2H), 3.75-3.57 (m, 7H), 3.54-3.42 (m, 4H), 3.25-3.18 (m, 1H), 2.69-2.57 (m, 1H), 2.20-2.09 (m, 1H), 1.36 (s, 9H).

Example 42: Synthesis of Compound I-49

(S)-5-oxopyrrolidin-3-yl 4-(3-(2-(azetidin-3-ylamino)pyridin-3-yl)pyrazolo[1,5-a]pyrimidin-5-yl) piperazine-1-carboxylate

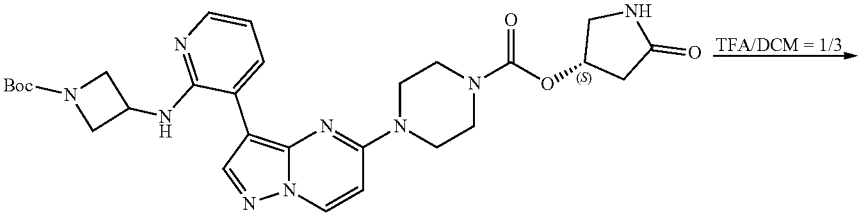

I-48

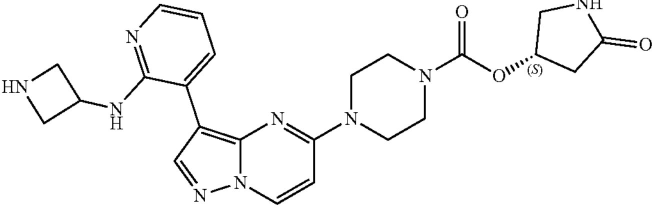

I-49

To a mixture of(S)-5-oxopyrrolidin-3-yl 4-(3-(2-((1-(tert-butoxycarbonyl) azetidin-3-yl)amino)pyridin-3-yl)pyrazolo[1,5-a]pyrimidin-5-yl)piperazine-1-carboxylate (330 mg, 571.30 μmol, 1 eq) in DCM (3 mL) was added TFA (1 mL). The mixture was stirred at 25° C. for 20 min. LCMS showed that desired MS was found. The mixture was concentrated to the crude product. The crude was purified by preparative HPLC to give(S)-5-oxopyrrolidin-3-yl 4-(3-(2-(azetidin-3-ylamino)pyridin-3-yl)pyrazolo[1,5-a]pyrimidin-5-yl)piperazine-1-carboxylate (37.03 mg, 61.83 μmol, 10.82% yield, 98.778% purity, TFA) as solid.

LCMS m/z=478.2 $[M+H]^+$.

SFC $t_R$=0.607 min; 100%.

$^1$H NMR (400 MHz, DMSO-$d_6$): δ=9.00 (s, 1H), 8.84 (d, J=7.8 Hz, 1H), 8.49-8.44 (m, 2H), 8.27-8.22 (m, 2H), 8.20 (d, J=6.4 Hz, 1H), 7.75 (s, 1H), 7.20-7.11 (m, 1H), 6.90 (d, J=7.8 Hz, 1H), 5.27-5.14 (m, 1H), 5.03-4.91 (m, 1H), 4.77-4.56 (m, 2H), 3.82-3.71 (m, 4H), 3.66-3.59 (m, 1H), 3.58-3.47 (m, 4H), 3.31-3.20 (m, 3H), 2.71-2.59 (m, 1H), 2.21-2.08 (m, 1H).

Example 43: Synthesis of Compound I-50

Tert-butyl (3R)-3-hydroxy-3-methyl-pyrrolidine-1-carboxylate

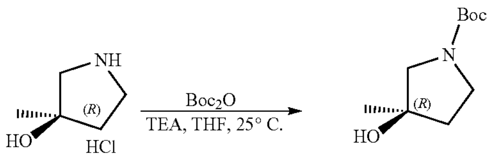

1 2

To a solution of (3R)-3-methylpyrrolidin-3-ol (2 g, 14.53 mmol, 1 eq, HCl) in THF (20 mL) was added TEA (2.94 g, 29.07 mmol, 4.05 mL, 2 eq) and BoczO (3.49 g, 15.99 mmol, 3.67 mL, 1.1 eq). The mixture was stirred at 25° C. for 12 hr. TLC (PE:EA=1:1, $R_f$=0.1) indicated (3R)-3-methylpyrrolidin-3-ol was consumed completely and one new spot formed. The reaction was clean according to TLC. The reaction mixture was concentrated under reduced pressure to remove solvent. The crude product was purified by re-crystallization from PE (20 mL) at 25° C. to give tert-butyl (3R)-3-hydroxy-3-methyl-pyrrolidine-1-carboxylate (2.70 g, 13.42 mmol, 92.30% yield) as a solid.

$^1$H NMR (400 MHz, DMSO-$d_6$) δ=4.71 (s, 1H), 3.32-3.25 (m, 2H), 3.21-3.14 (m, 1H), 3.09-2.99 (m, 1H), 1.77-1.66 (m, 2H), 1.39 (s, 9H), 1.25 (d, J=2.1 Hz, 3H).

Tert-butyl (R)-3-methyl-3-(((4-nitrophenoxy)carbonyl)oxy)pyrrolidine-1-carboxylate

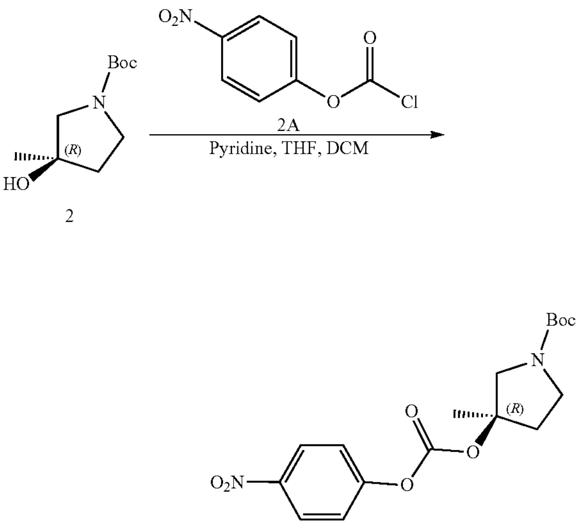

2

3

To a solution of tert-butyl (3R)-3-hydroxy-3-methyl-pyrrolidine-1-carboxylate (1.5 g, 7.45 mmol, 1 eq) in THF (1 mL), DCM (5 mL) was added pyridine (1.18 g, 14.91 mmol, 1.20 mL, 2 eq) and (4-nitrophenyl) carbonochloridate (1.65 g, 8.20 mmol, 1.1 eq). The mixture was stirred at 25° C. for 2 hr. The reaction mixture was concentrated under reduced pressure to remove solvent. The residue was purified by column chromatography ($SiO_2$, Petroleum ether/Ethyl acetate=5/1 to 3/1) to give tert-butyl (R)-3-methyl-3-(((4-nitrophenoxy)carbonyl)oxy)pyrrolidine-1-carboxylate (1.4 g, 3.82 mmol, 51.27% yield) as an oil.

LCMS m/z=389.1 $[M+Na]^+$.

$^1$H NMR (400 MHz, $CDCl_3$) δ=8.35-8.24 (m, 2H), 7.45-7.31 (m, 2H), 3.53-3.49 (m, 2H), 3.38 (br d, J=11.9 Hz, 1H), 3.24 (d, J=11.5 Hz, 1H), 1.91-1.82 (m, 2H), 1.46 (s, 9H), 1.42 (s, 3H).

[(3R)-1-tert-butoxycarbonyl-3-methyl-pyrrolidin-3-yl]-4-[3-[2-(cyclopropoxy)-3-pyridyl]pyrazolo[1,5-a]pyrimidin-5-yl]piperazine-1-carboxylate

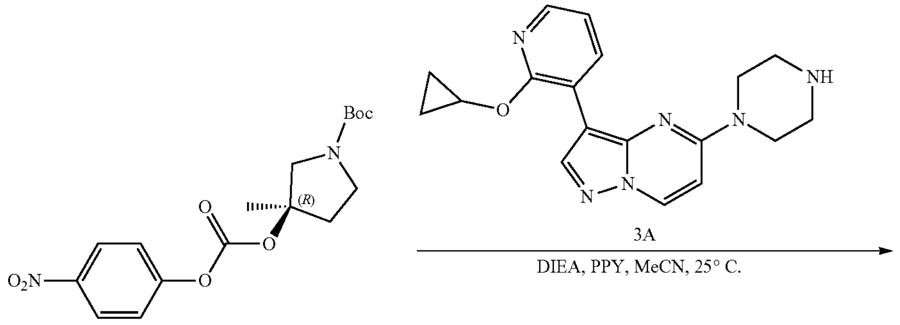

3

-continued

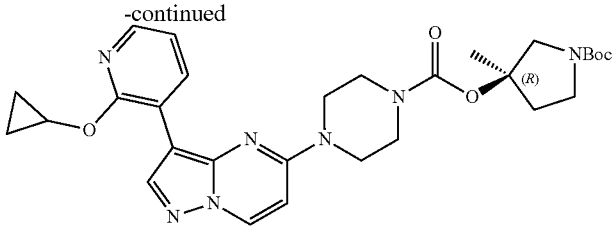

4

To a solution of tert-butyl (3R)-3-methyl-3-(4-nitrophenoxy)carbonyloxy-pyrrolidine-1-carboxylate (200 mg, 545.90 μmol, 1 eq), 3-[2-(cyclopropoxy)-3-pyridyl]-5-piperazin-1-yl-pyrazolo[1,5-a]pyrimidine (183.64 mg, 545.90 μmol, 1 eq) in MeCN (2 mL) was added DIEA (141.11 mg, 1.09 mmol, 190.17 μL, 2 eq) and 4-pyrrolidin-1-ylpyridine (8.09 mg, 54.59 μmol, 0.1 eq). The mixture was stirred at 25° C. for 1 hr. The reaction mixture was filtered with diatomite and concentrated under reduced pressure to give crude product. The crude was purified by FCC (ISCO®; 4 g SepaFlash® Silica Flash Column, eluent of 0~6% Methanol/Dichloromethane gradient @ 25 mL/min) to give [(3R)-1-tert-butoxycarbonyl-3-methyl-pyrrolidin-3-yl]-4-[3-[2-(cyclopropoxy)-3-pyridyl]pyrazolo[1,5-a]pyrimidin-5-yl] piperazine-1-carboxylate (300 mg, 429.42 μmol, 78.66% yield, 80.680% purity) as an oil.

LCMS m/z=564.3 $[M+H]^+$.

$^1$H NMR (400 MHz, DMSO-$d_6$) δ=8.76 (dd, J=7.6, 13.9 Hz, 2H), 8.34 (s, 1H), 8.01 (br d, J=4.8 Hz, 1H), 7.10 (dd, J=4.9, 7.4 Hz, 1H), 6.81 (d, J=7.9 Hz, 1H), 4.41 (br d, J=3.3 Hz, 1H), 3.80-3.67 (m, 4H), 3.49 (br s, 4H), 3.16 (br d, J=11.0 Hz, 2H), 3.09-2.97 (m, 2H), 1.72 (br s, 2H), 1.57 (s, 3H), 1.24 (s, 9H), 0.86-0.72 (m, 4H).

[(3R)-3-methylpyrrolidin-3-yl]-4-[3-[2-(cyclopropoxy)-3-pyridyl]pyrazolo[1,5-a]pyrimidin-5-yl] piperazine-1-carboxylate

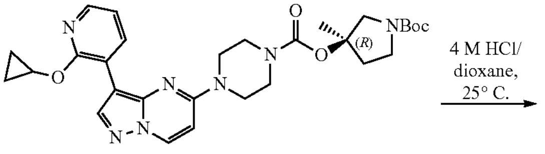

4

-continued

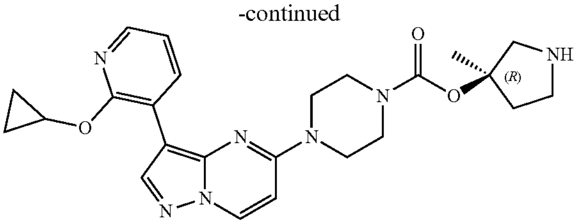

5

A mixture of [(3R)-1-tert-butoxycarbonyl-3-methyl-pyrrolidin-3-yl] 4-[3-[2-(cyclopropoxy)-3-pyridyl]pyrazolo[1,5-a]pyrimidin-5-yl]piperazine-1-carboxylate (300 mg, 532.25 μmol, 1 eq) in HCl/dioxane (4 M, 4 mL, 30.06 eq), the mixture was stirred at 25° C. for 20 min. The reaction mixture was filtered with diatomite and concentrated under reduced pressure to give [(3R)-3-methylpyrrolidin-3-yl]-4-[3-[2-(cyclopropoxy)-3-pyridyl]pyrazolo[1,5-a]pyrimidin-5-yl]piperazine-1-carboxylate (260 mg, 388.81 μmol, 73.05% yield, 74.770% purity, HCl) as an oil.

LCMS m/z=464.3 $[M+H]^+$.

[(3R)-1,3-dimethylpyrrolidin-3-yl]-4-[3-[2-(cyclopropoxy)-3-pyridyl]pyrazolo[1,5-a]pyrimidin-5-yl] piperazine-1-carboxylate

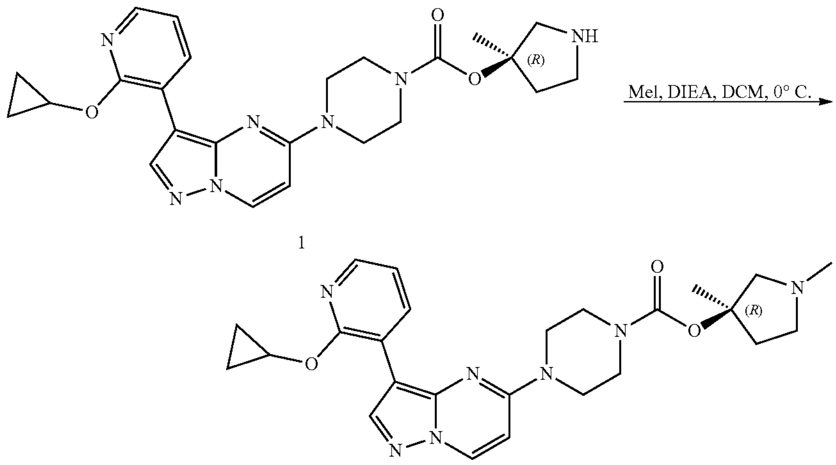

1

I-50

To [(3R)-3-methylpyrrolidin-3-yl]-4-[3-[2-(cyclopropoxy)-3-pyridyl]pyrazolo[1,5-a]pyrimidin-5-yl]piperazine-1-carboxylate (50 mg, 100.00 μmol, 1 eq, HCl) in DCM (1 mL) was added DIEA (25.85 mg, 200.00 μmol, 34.84 μL, 2 eq) and iodomethane (14.19 mg, 100.00 μmol, 6.23 μL, 1 eq). The mixture was stirred at 0° C. for 1 hr. The reaction mixture was filtered with diatomite and concentrated under reduced pressure to give crude product. The product was purified by preparative HPLC. The pure fractions were collected and the volatiles were removed under vacuum. The residue was partitioned between acetonitrile (20 mL) and water (100 mL). The solution was lyophilized to dryness to give [(3R)-1,3-dimethylpyrrolidin-3-yl]-4-[3-[2-(cyclopropoxy)-3-pyridyl]pyrazolo[1,5-a]pyrimidin-5-yl]piperazine-1-carboxylate (7.19 mg, 14.31 μmol, 7.16% yield, 95.061% purity) as a solid.

LCMS m/z=478.3 $[M+H]^+$.

SFC $t_R$=1.417; 100%.

$^1H$ NMR (400 MHz, DMSO-$d_6$) δ=8.79 (d, J=7.6 Hz, 1H), 8.74 (d, J=7.8 Hz, 1H), 8.34 (s, 1H), 8.01 (d, J=4.6 Hz, 1H), 7.14-7.05 (m, 1H), 6.80 (d, J=7.9 Hz, 1H), 4.46-4.32 (m, 1H), 3.74 (s, 4H), 3.49 (s, 4H), 2.78-2.69 (m, 1H), 2.67-2.55 (m, 1H), 2.49-2.42 (m, 2H), 2.21 (s, 3H), 2.18-2.08 (m, 1H), 1.97-1.81 (m, 1H), 1.54 (s, 3H), 0.85-0.70 (m, 4H).

Example 44: Synthesis of Compound I-51

(R)-1-(2-amino-2-oxoethyl)-3-(methylpyrrolidin-3-yl)-4-(3-(2-cyclopropoxypyridin-3-yl)pyrazolo[1,5-a]pyrimidin-5-yl)piperazine-1-carboxylate

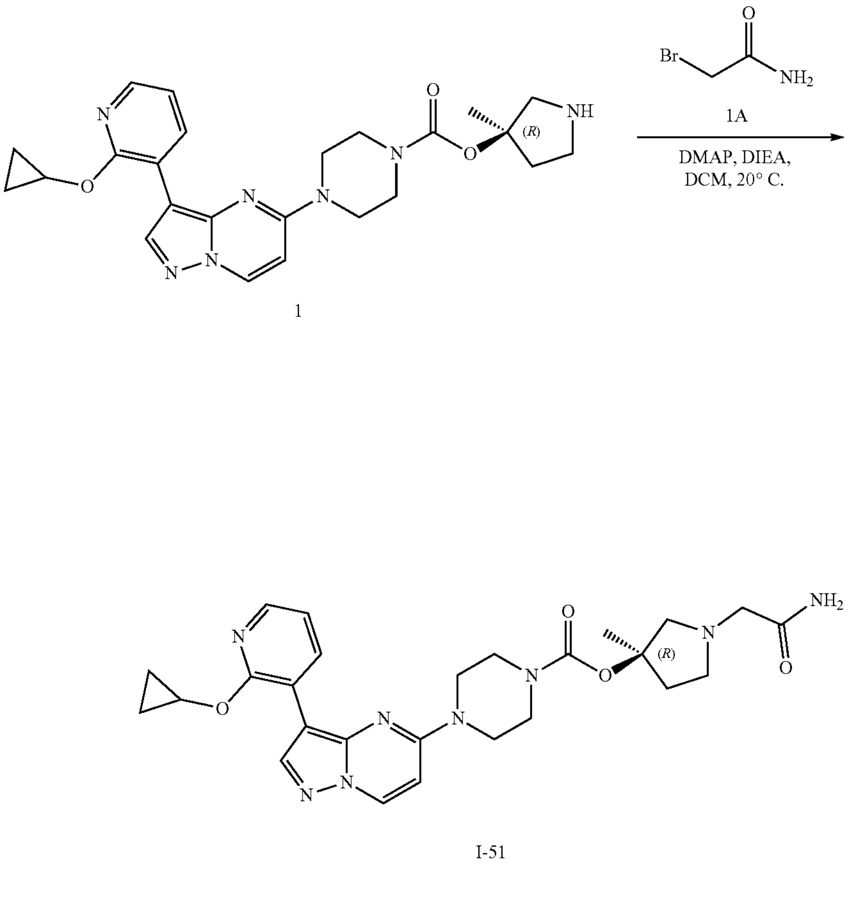

To a solution of (R)-3-(methylpyrrolidin-3-yl)-4-(3-(2-cyclopropoxypyridin-3-yl)pyrazolo[1,5-a]pyrimidin-5-yl) piperazine-1-carboxylate (29.76 mg, 215.74 μmol, 1 eq) in DCM (0.5 mL) was added DMAP (5.27 mg, 43.15 μmol, 0.2 eq) and DIEA (83.65 mg, 647.21 μmol, 112.73 μL, 3 eq). The mixture was stirred at 25° C. for 1 hr. The reaction mixture was concentrated under reduced pressure. The crude was purified by preparative. HPLC. The pure fractions were collected and the volatiles were removed under vacuum. The residue was partitioned between acetonitrile (2 mL) and water (10 mL). The solution was lyophilized to dryness to give (R)-1-(2-amino-2-oxoethyl)-3-(methylpyrrolidin-3-yl)-4-(3-(2-cyclopropoxypyridin-3-yl)pyrazolo[1,5-a]pyrimidin-5-yl)piperazine-1-carboxylate (8.29 mg, 15.87 μmol, 7.36% yield, 99.68% purity) as a solid.

LCMS m/z=521.2 $[M+H]^+$.

SFC $t_R$=1.132 min; 100%.

$^1H$ NMR (400 MHz, DMSO-$d_6$) δ=8.79 (d, J=5.5 Hz, 1H), 8.74 (d, J=6.0 Hz, 1H), 8.35 (s, 1H), 8.01 (s, 1H), 7.20-7.01 (m, 3H), 6.81 (d, J=6.6 Hz, 1H), 4.51-4.29 (m, 1H), 3.82-3.69 (m, 4H), 3.55-3.45 (m, 4H), 3.05-2.96 (m, 2H), 2.92-2.81 (m, 2H), 2.74-2.66 (m, 1H), 2.61 (d, J=6.6 Hz, 1H), 2.24-2.12 (m, 1H), 1.98-1.85 (m, J=5.5 Hz, 1H), 1.57 (s, 3H), 0.85-0.73 (m, 4H).

I-51

Example 45: Synthesis of Compound I-52

[(3R)-1-(2-benzyloxyethyl)-3-methyl-pyrrolidin-3-yl]-4-[3-[2-(cyclopropoxy)-3-pyridyl]pyrazolo[1,5-a]pyrimidin-5-yl]piperazine-1-carboxylate

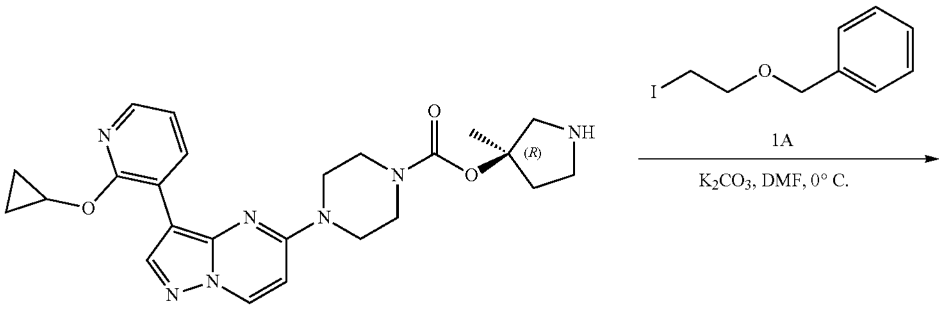

1

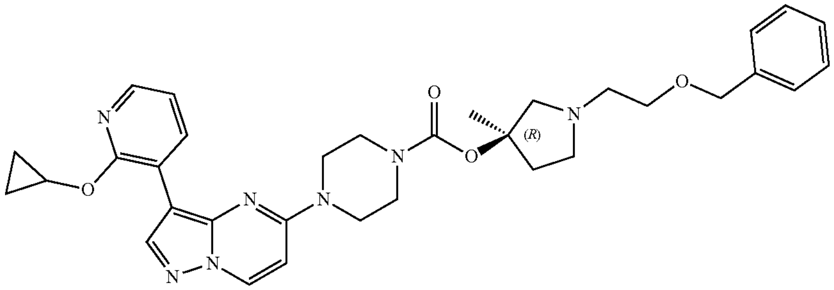

2

To a solution of [(3R)-3-methylpyrrolidin-3-yl]-4-[3-[2-(cyclopropoxy)-3-pyridyl]pyrazolo[1,5-a]pyrimidin-5-yl] piperazine-1-carboxylate (200 mg, 431.47 μmol, 1 eq) in DMF (1 mL) was added $K_2CO_3$ (178.90 mg, 1.29 mmol, 3 eq) and 2-iodoethoxymethylbenzene (113.08 mg, 431.47 μmol, 1 eq). Then the mixture was stirred at 0° C. for 6 hr. The reaction mixture was concentrated under reduced pressure. The crude was purified by FCC to give [(3R)-1-(2-benzyloxyethyl)-3-methyl-pyrrolidin-3-yl]-4-[3-[2-(cyclopropoxy)-3-pyridyl]pyrazolo[1,5-a]pyrimidin-5-yl] piperazine-1-carboxylate (180 mg, 234.90 μmol, 54.44% yield, 78% purity) as a solid.

LCMS m/z=598.4 $[M+H]^+$.

[(3R)-1-(2-hydroxyethyl)-3-methyl-pyrrolidin-3-yl]-4-[3-[2-(cyclopropoxy)-3-pyridyl]pyrazolo[1,5-a] pyrimidin-5-yl]piperazine-1-carboxylate

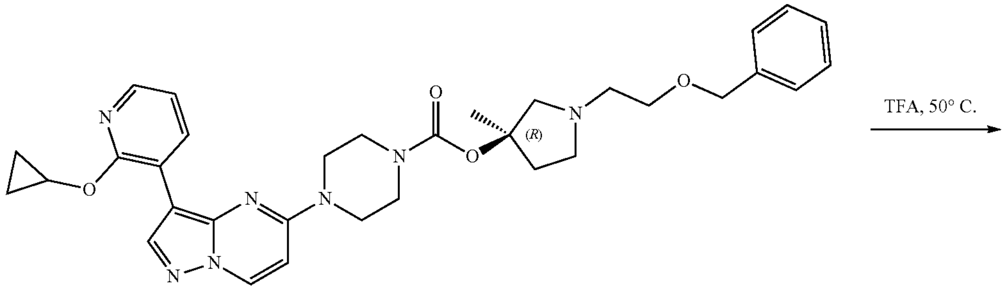

2

-continued

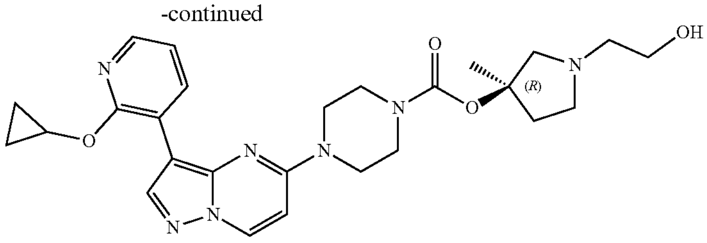

I-52

To a solution of [(3R)-1-(2-benzyloxyethyl)-3-methyl-pyrrolidin-3-yl]-4-[3-[2-(cyclopropoxy)-3-pyridyl]pyrazolo[1,5-a]pyrimidin-5-yl]piperazine-1-carboxylate (80 mg, 133.85 μmol, 1 eq) in TFA (0.5 mL). The mixture was stirred at 50° C. for 8 hr. The reaction mixture was concentrated under reduced pressure. The crude was purified by preparative HPLC. The pure fractions were collected and the volatiles were removed under vacuum. The residue was partitioned between acetonitrile (20 mL) and water (100 mL). The solution was lyophilized to dryness to give the product. [(3R)-1-(2-hydroxyethyl)-3-methyl-pyrrolidin-3-yl]-4-[3-[2-(cyclopropoxy)-3-pyridyl]pyrazolo[1,5-a]pyrimidin-5-yl]piperazine-1-carboxylate (7.39 mg, 13.98 μmol, 10.45% yield, 96.049% purity) was obtained as a solid.

LCMS m/z=508.3 $[M+H]^+$.

SFC $t_R$=0.604 min; 100%.

$^1$H NMR (400 MHz, DMSO-$d_6$) δ=7.97 (d, J=7.5 Hz, 1H), 7.65 (d, J=7.5 Hz, 1H), 7.59 (s, 1H), 7.33-7.11 (m, 1H), 6.36-6.15 (m, 1H), 5.88 (d, J=7.3 Hz, 1H), 3.63-3.61 (m, 1H), 3.44-3.34 (m, 1H), 3.15-2.96 (m, 8H), 2.89-2.84 (m, 4H), 2.77-2.63 (m, 2H), 2.60-2.56 (m, 2H), 1.95-1.82 (m, 1H), 1.62-1.41 (m, 1H), 0.93 (s, 3H), 0.08-0.02 (m, 4H).

Example 46: Synthesis of Compound I-53

(R)-1-(2-(dimethylamino)ethyl)-3-(methylpyrrolidin-3-yl)-4-(3-(2-cyclopropoxypyridin-3-yl)pyrazolo[1,5-a]pyrimidin-5-yl)piperazine-1-carboxylate

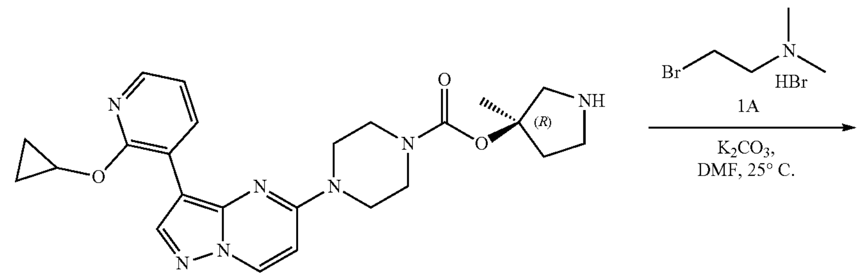

1

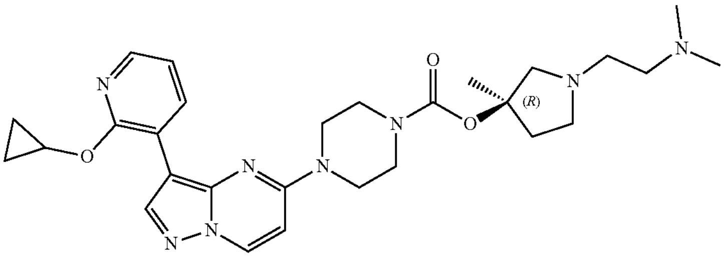

I-53

To a mixture of (R)-3-methylpyrrolidin-3-yl 4-(3-(2-cyclopropoxypyridin-3-yl)pyrazolo[1,5-a]pyrimidin-5-yl)piperazine-1-carboxylate in DMF (1 mL) was added $K_2CO_3$ (119.65 mg, 865.72 μmol, 5eq). The mixture was stirred at 25° C. for 2 hr. The mixture was filtered and the filter was purified by preparative HPLC to give (R)-1-(2-(dimethylamino)ethyl)-3-(methylpyrrolidin-3-yl)-4-(3-(2-cyclopropoxypyridin-3-yl)pyrazolo[1,5-a]pyrimidin-5-yl)piperazine-1-carboxylate (2.54 mg, 4.49 μmol, 2.59% yield, 94.49%, purity) as a powder.

LCMS m/z=535.3 $[M+H]^+$.

SFC $t_R$=0.414 min; 100%).

$^1$H NMR (400 MHz, $CDCl_3$): δ=8.78-8.67 (m, 1H), 8.51 (s, 1H), 8.40-8.30 (m, 1H), 8.12-8.05 (m, 1H), 7.06-6.99 (m, 1H), 6.41-6.34 (m, 1H), 4.46-4.41 (m, 1H), 3.76-3.72 (m, 4H), 3.63-3.59 (m, 4H), 3.03-2.99 (m, 1H), 2.80-2.75 (m, 1H), 2.72-2.67 (m, 1H), 2.63-2.57 (m, 2H), 2.46-2.40 (m, 2H), 2.30-2.25 (m, 1H), 2.25 (s, 6H), 2.04-1.98 (m, 2H), 1.64 (s, 3H), 0.88-0.84 (m, 4H).

Example 47: Synthesis of Compound I-54

Tert-butyl N-[(3R)-1-(3-bromopyrazolo[1,5-a]pyrimidin-5-yl)pyrrolidin-3-yl]carbamate

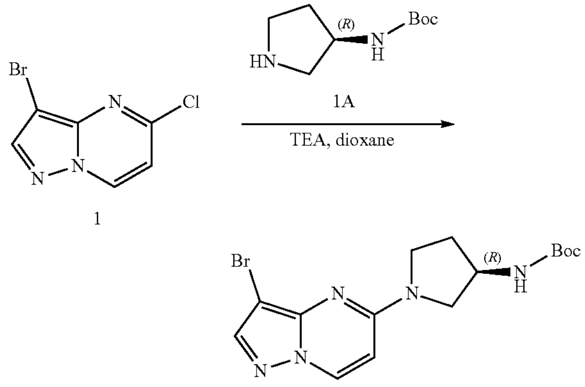

1

2

To a solution of 3-bromo-5-chloro-pyrazolo[1,5-a]pyrimidine (500 mg, 2.15 mmol, 1 eq) in dioxane (8 mL) was added TEA (435.29 mg, 4.30 mmol, 598.74 μL, 2 eq) and tert-butyl N-[(3R)-pyrrolidin-3-yl]carbamate (400.60 mg, 2.15 mmol, 1 eq). The mixture was stirred at 90° C. for 0.5 hr. The reaction mixture was concentrated under reduced pressure to remove dioxane. The residue was diluted with water 30 mL. The mixture were washed with ethyl acetate 90 mL (30 mL*3), dried over $Na_2SO_4$, filtered and concentrated under reduced pressure to give a residue. The crude was purified by FCC to give tert-butyl N-[(3R)-1-(3-bromopyrazolo[1,5-a]pyrimidin-5-yl)pyrrolidin-3-yl]carbamate (800 mg, 1.99 mmol, 92.44% yield, 95.004% purity) as a solid.

LCMS m/z=382.0 $[M+H]^+$.

$^1$H NMR (400 MHz, DMSO-$d_6$) δ=7.89-7.75 (m, 1H), 6.85-6.62 (m, 1H), 4.05 (br s, 1H), 3.89 (br d, J=5.8 Hz, 1H), 3.20-3.14 (m, 1H), 2.92-2.77 (m, 2H), 2.75-2.64 (m, 1H), 1.91-1.78 (m, 1H), 1.62-1.49 (m, 1H), 1.48-1.39 (m, 2H), 1.37 (s, 9H), 1.33-1.12 (m, 2H), 0.89-0.81 (m, 6H).

Tert-butyl N-[(3R)-1-[3-[2-(cyclopropoxy)-3-pyridyl]pyrazolo[1,5-a]pyrimidin-5-yl]pyrrolidin-3-yl]carbamate

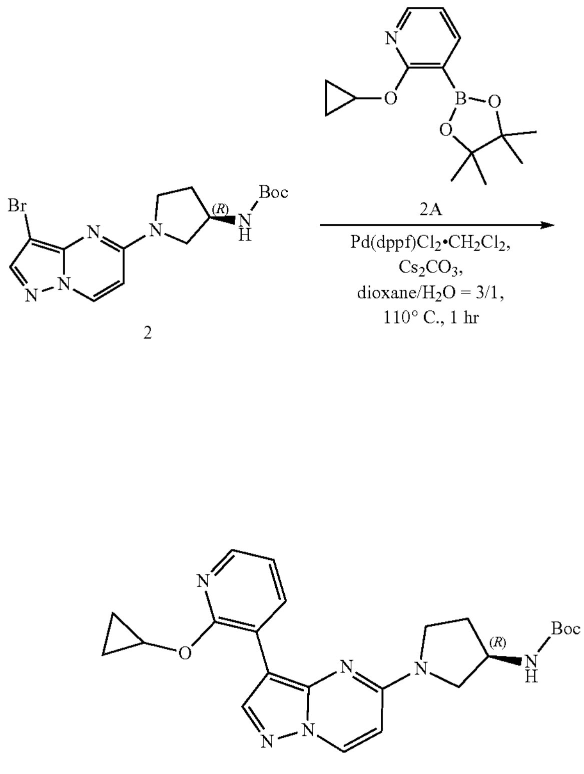

2

3

A mixture of tert-butyl N-[(3R)-1-(3-bromopyrazolo[1,5-a]pyrimidin-5-yl)pyrrolidin-3-yl]carbamate (300 mg, 784.82 μmol, 1 eq), 2-(cyclopropoxy)-3-(4,4,5,5-tetramethyl-1,3,2-dioxaborolan-2-yl)pyridine (307.40 mg, 1.18 mmol, 1.5 eq), Pd(dppf)$Cl_2$·$CH_2Cl_2$ (128.18 mg, 156.96 μmol, 0.2 eq), $Cs_2CO_3$ (767.12 mg, 2.35 mmol, 3 eq) in dioxane (4.5 mL) and $H_2O$ (1.5 mL) was degassed and purged with $N_2$ for 3 times, and then the mixture was stirred at 110° C. for 1 hr under $N_2$ atmosphere. The reaction mixture was concentrated under reduced pressure to remove dioxane. The residue was diluted with water 30 mL. The combined organic layers were washed with ethyl acetate 90 mL (30 mL×3), dried over $Na_2SO_4$, filtered and concentrated under reduced pressure to give a residue. The crude was purified by FCC (ISCO®; 5 SepaFlash® Silica Flash Column, eluent of 0~10% Methanol/Dichloromethane gradient @ 40 mL/min) to give tert-butyl N-[(3R)-1-[3-[2-(cyclopropoxy)-3-pyridyl]pyrazolo[1,5-a]pyrimidin-5-yl]pyrrolidin-3-yl]carbamate (400 mg, 613.11 μmol, 78.12% yield, 66.907% purity) as a gum.

LCMS m/z=437.3 $[M+H]^+$.

$^1$H NMR (400 MHz, DMSO-$d_6$) δ=9.02-8.47 (m, 1H), 8.40-8.14 (m, 1H), 8.03-7.72 (m, 1H), 7.71-7.41 (m, 1H), 7.38-6.89 (m, 2H), 6.57-6.28 (m, 1H), 4.45-4.31 (m, 1H), 4.27-4.15 (m, 1H), 4.13-4.07 (m, 1H), 3.50 (br s, 3H), 2.20-2.09 (m, 1H), 1.99-1.81 (m, 1H), 1.54-1.29 (m, 9H), 0.84-0.49 (m, 4H).

(3R)-1-[3-[2-(cyclopropoxy)-3-pyridyl]pyrazolo[1,5-a]pyrimidin-5-yl]pyrrolidin-3-amine

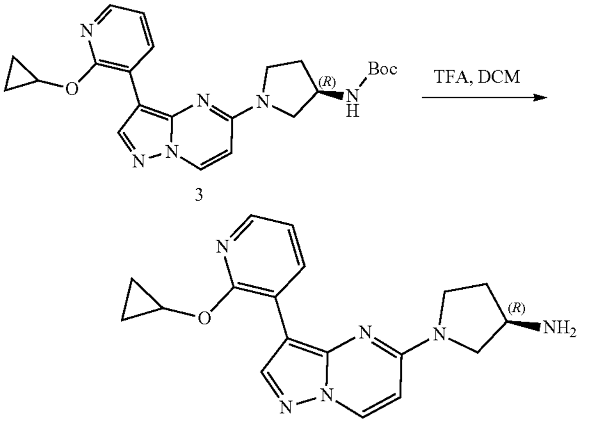

3

4

To a solution of tert-butyl N-[(3R)-1-[3-[2-(cyclopropoxy)-3-pyridyl]pyrazolo[1,5-a]pyrimidin-5-yl]pyrrolidin-3-yl]carbamate (400 mg, 916.37 μmol, 1 eq) in DCM (3 mL) was added TFA (767.50 mg, 6.73 mmol, 0.5 mL, 7.35 eq). The mixture was stirred at 25° C. for 1 hr. LCMS showed that desired MS was found. The reaction mixture was concentrated under reduced pressure to give (3R)-1-[3-[2-(cyclopropoxy)-3-pyridyl]pyrazolo[1,5-a]pyrimidin-5-yl]pyrrolidin-3-amine (300 mg, 553.69 μmol, 60.42% yield, 62.085% purity) as a gum.

LCMS m/z=336.8 $[M+H]^+$.

[(3S)-5-oxopyrrolidin-3-yl] N-[(3R)-1-[3-[2-(cyclopropoxy)-3-pyridyl]pyrazolo[1,5-a]pyrimidin-5-yl]pyrrolidin-3-yl]carbamate To a solution of (3R)-1-[3-[2-(cyclopropoxy)-3-pyridyl]pyrazolo[1,5-a]pyrimidin-5-yl]pyrrolidin-3-amine (300 mg, 891.82 μmol, 1 eq) in MeCN (5 mL) was added DIEA (230.52 mg, 1.78 mmol, 310.68 μL, 2 eq), (4-nitrophenyl) [(3S)-5-oxopyrrolidin-3-yl]carbonate (237.41 mg, 891.82 μmol, 1 eq) and DMAP (10.90 mg, 89.18 μmol, 0.1 eq). The mixture was stirred at 25° C. for 1 hr. The reaction mixture was concentrated under reduced pressure to give a residue. The crude was purified by preparative HPLC. The pure fractions were collected and the volatiles were removed under vacuum. The residue was partitioned between acetonitrile (20 mL) and water (100 mL). The solution was lyophilized to dryness to give the product. The product [(3S)-5-oxopyrrolidin-3-yl] N-[(3R)-1-[3-[2-(cyclopropoxy)-3-pyridyl]pyrazolo[1,5-a]pyrimidin-5-yl]pyrrolidin-3-yl] carbamate (37.97 mg, 83.95 μmol, 9.41% yield, 99.844% purity) was obtained as a solid.

LCMS m/z=464.2 $[M+H]^+$.

SFC $t_R$=1.755; 100%.

$^1$H NMR (400 MHz, DMSO-$d_6$) δ=8.99-8.83 (m, 1H), 8.72-8.60 (m, J=7.6 Hz, 1H), 8.33 (s, 1H), 8.03-7.92 (m, 1H), 7.82-7.64 (m, 2H), 7.17 (s, 1H), 6.53-6.35 (m, J=7.5 Hz, 1H), 5.24-5.08 (m, 1H), 4.48-4.35 (m, 1H), 4.31-4.15 (m, 1H), 3.80-3.54 (m, 4H), 3.19-3.12 (m, 1H), 2.61 (br dd, J=6.6, 17.4 Hz, 2H), 2.25-2.16 (m, 1H), 2.10-2.01 (m, 1H), 2.01-1.91 (m, 1H), 0.83-0.76 (m, 4H).

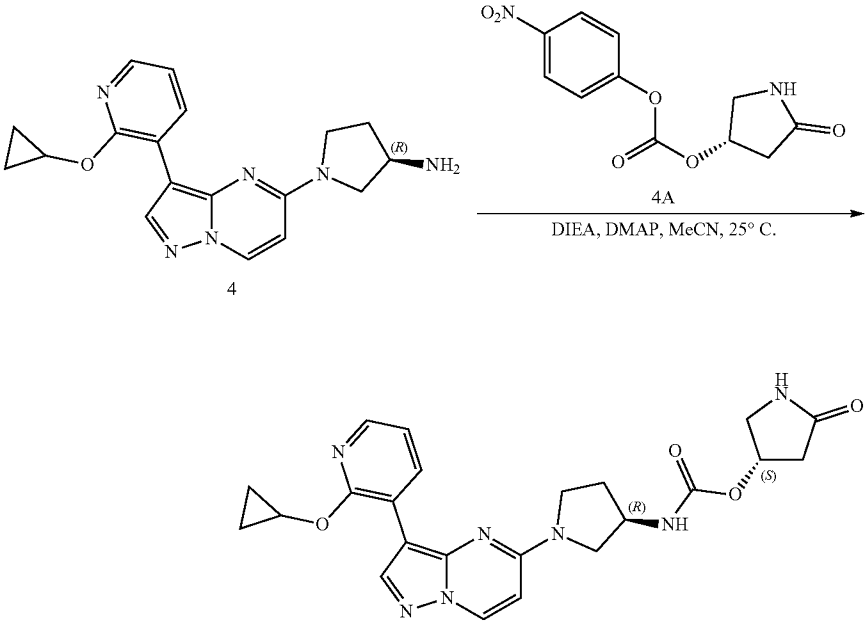

4

4A

I-54

Example 48: Synthesis of Compound I-55

Tert-butyl(S)-(1-(3-bromopyrazolo[1,5-a]pyrimidin-5-yl)pyrrolidin-3-yl)carbamate

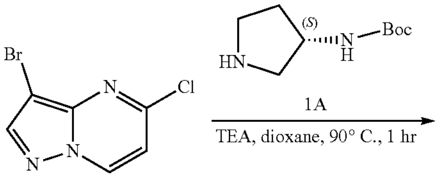

1

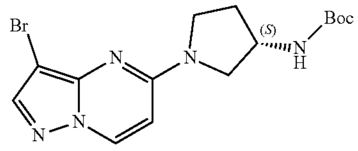

2

The product 2 was prepared according to the synthesis method of Compound I-54 (1.1 procedure for preparation of compound 2). The product tert-butyl(S)-(1-(3-bromopyrazolo[1,5-a]pyrimidin-5-yl)pyrrolidin-3-yl)carbamate (4.2 g, 10.99 mmol, 85.14% yield) was obtained as a solid.

LCMS m/z=383.9 $[M+H]^+$.

Tert-butyl(S)-(1-(3-(2-cyclopropoxypyridin-3-yl)pyrazolo[1,5-a]pyrimidin-5-yl)pyrrolidin-3-yl)carbamate

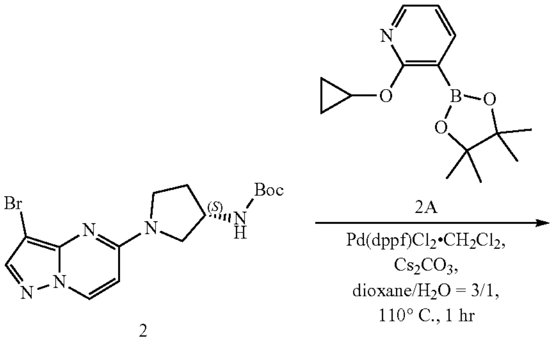

2

-continued

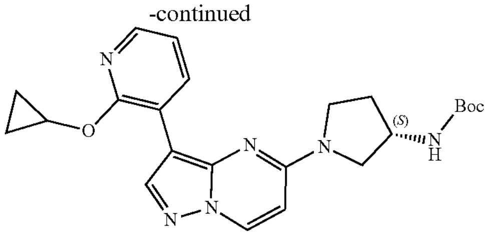

3

The product 3 was prepared according to the synthesis method of I-54. The product tert-butyl(S)-(1-(3-(2-cyclopropoxypyridin-3-yl)pyrazolo[1,5-a]pyrimidin-5-yl)pyrrolidin-3-yl)carbamate (3.2 g, 7.33 mmol, 66.72% yield) was obtained as a solid.

LCMS m/z=437.2 $[M+H]^+$.

(S)-1-(3-(2-cyclopropoxypyridin-3-yl)pyrazolo[1,5-a]pyrimidin-5-yl)pyrrolidin-3-amine

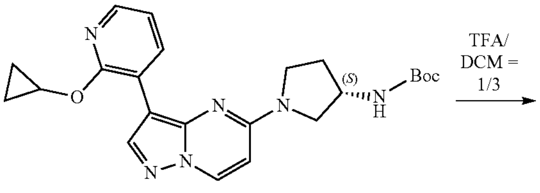

3

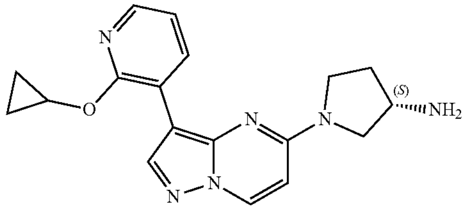

4

The product 3 was prepared according to the synthesis method of I-54. The product. (S)-1-(3-(2-cyclopropoxypyridin-3-yl)pyrazolo[1,5-a]pyrimidin-5-yl)pyrrolidin-3-amine was obtained as a solid.

LCMS m/z=337.1 $[M+H]^+$.

(S)-5-oxopyrrolidin-3-yl ((S)-1-(3-(2-cyclopropoxypyridin-3-yl)pyrazolo[1,5-a]pyrimidin-5-yl)pyrrolidin-3-yl)carbamate

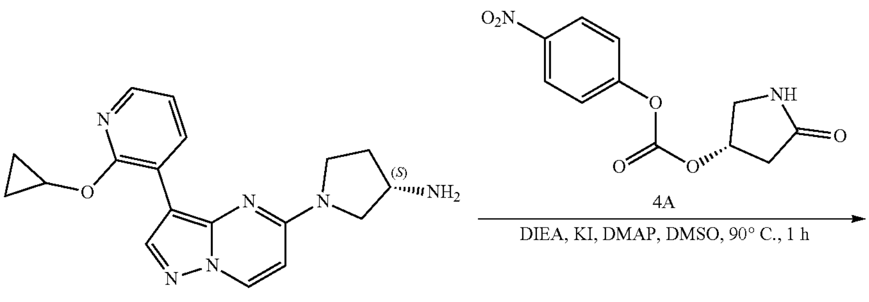

4

-continued

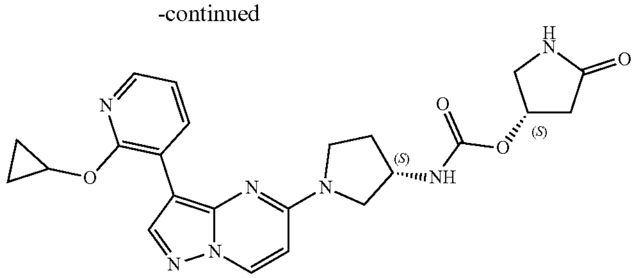

I-55

The product I-55 was prepared according to the synthesis method of I-54. The product. (S)-5-oxopyrrolidin-3-yl ((S)-1-(3-(2-cyclopropoxypyridin-3-yl)pyrazolo[1,5-a]pyrimidin-5-yl)pyrrolidin-3-yl)carbamate was obtained as a solid.

LCMS m/z=464.4 $[M+H]^+$.

SFC $t_R$=5.128 min, 100%.

$^1$H NMR (400 MHz, DMSO-$d_6$) δ=8.91 (s, 1H), 8.67 (d, J=7.0 Hz, 1H), 8.34 (s, 1H), 8.04-7.93 (m, 1H), 7.80-7.68 (m, 2H), 7.15-7.05 (m, 1H), 6.47 (d, J=7.1 Hz, 1H), 5.24-5.10 (m, 1H), 4.46-4.36 (m, 1H), 4.27-4.14 (m, 1H), 3.87-3.48 (m, 5H), 3.18 (d, J=11.4 Hz, 1H), 2.69-2.56 (m, 1H), 2.20 (s, 1H), 2.09-1.92 (m, 2H), 0.84-0.77 (m, 4H).

Example 49: Synthesis of Compound I-56

Tert-butyl (3R)-3-[[(3R)-1-[3-[2-(cyclopropoxy)-3-pyridyl]pyrazolo[1,5-a]pyrimidin-5-yl]pyrrolidin-3-yl]carbamoyloxy]-3-methyl-pyrrolidine-1-carboxylate

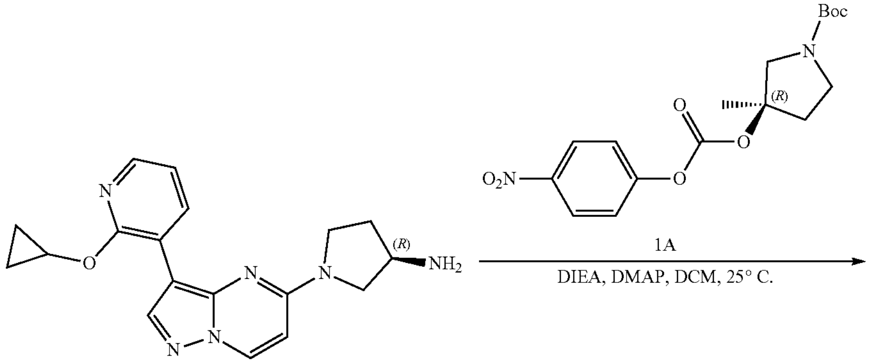

1

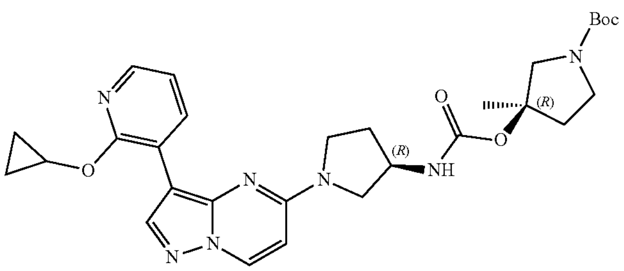

2

To a solution of tert-butyl (3R)-3-methyl-3-(4-nitrophenoxy)carbonyloxy-pyrrolidine-1-carboxylate (0.1 g, 272.95 μmol, 1 eq) in DCM (1 mL) was added DIEA (70.55 mg, 545.90 μmol, 95.09 μL, 2 eq), (3R)-1-[3-[2-(cyclopropoxy)-3-pyridyl]pyrazolo[1,5-a]pyrimidin-5-yl]pyrrolidin-3-amine (91.82 mg, 272.95 μmol, 1 eq) and DMAP (6.67 mg, 54.59 μmol, 0.2 eq). The mixture was stirred at 25° C. for 1 h. The reaction mixture was concentrated under reduced pressure to afford tert-butyl (3R)-3-[[(3R)-1-[3-[2-(cyclopropoxy)-3-pyridyl]pyrazolo[1,5-a]pyrimidin-5-yl]pyrrolidin-3-yl]carbamoyloxy]-3-methyl-pyrrolidine-1-carboxylate (0.15 g, crude).

LCMS m/z=564.4 $[M+H]^+$.

(R)-3-methylpyrrolidin-3-yl ((R)-1-(3-(2-cyclopropoxypyridin-3-yl)pyrazolo[1,5-a]pyrimidin-5-yl)pyrrolidin-3-yl)carbamate

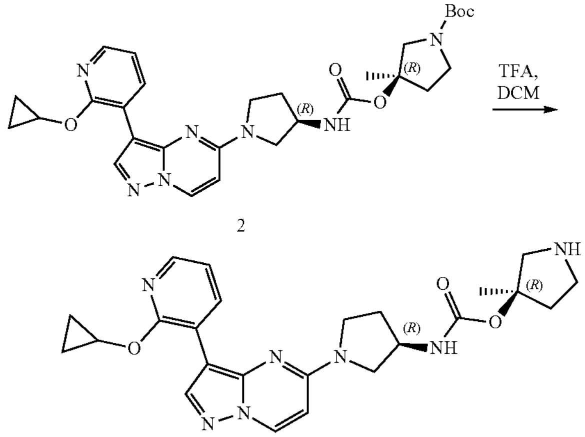

2

I-56

To a solution of tert-butyl (3R)-3-[[(3R)-1-[3-[2-(cyclopropoxy)-3-pyridyl]pyrazolo[1,5-a]pyrimidin-5-yl]pyrrolidin-3-yl]carbamoyloxy]-3-methyl-pyrrolidine-1-carboxylate (0.15 g, 266.12 μmol, 1 eq) in DCM (1 mL) was added TFA (910.33 mg, 7.98 mmol, 593.05 μL, 30 eq). The mixture was stirred at 25° C. for 2 hr. The reaction mixture was concentrated under reduced pressure to remove solvent. Then the product was further purified by prep. HPLC The pure fractions were collected and the volatiles were removed under vacuum. The residue was partitioned between acetonitrile (2 mL) and water (10 mL). The solution was lyophilized to dryness to give (R)-3-methylpyrrolidin-3-yl ((R)-1-(3-(2-cyclopropoxypyridin-3-yl)pyrazolo[1,5-a]pyrimidin-5-yl)pyrrolidin-3-yl)carbamate (10.11 mg, 21.48 μmol, 8.07% yield, 98.49% purity) as a solid.

LCMS m/z=464.1 $[M+H]^+$.

SFC $t_R$=1.863 min; 100%.

$^1$H NMR (400 MHz, DMSO-$d_6$) δ=8.92 (s, 1H), 8.67 (d, J=7.6 Hz, 1H), 8.34 (s, 1H), 8.02-7.96 (m, J=1.8, 4.8 Hz, 1H), 7.43-7.35 (m, 1H), 7.16-7.06 (m, J=5.1, 7.3 Hz, 1H), 6.48 (d, J=7.8 Hz, 1H), 4.47-4.37 (m, 1H), 4.26-4.17 (m, 1H), 3.82-3.56 (m, 4H), 3.01 (d, J=11.9 Hz, 1H), 2.86-2.71 (m, 3H), 2.24-2.15 (m, 1H), 2.08-2.01 (m, 1H), 1.98-1.91 (m, 1H), 1.78-1.68 (m, 1H), 1.55 (s, 1H), 1.51 (s, 3H), 0.82-0.78 (m, 4H).

Example 50: Synthesis of Compound I-57

Tert-butyl (R)-3-((((S)-1-(3-(2-cyclopropoxypyridin-3-yl)pyrazolo[1,5-a]pyrimidin-5-yl)pyrrolidin-3-yl)carbamoyl)oxy)-3-methylpyrrolidine-1-carboxylate

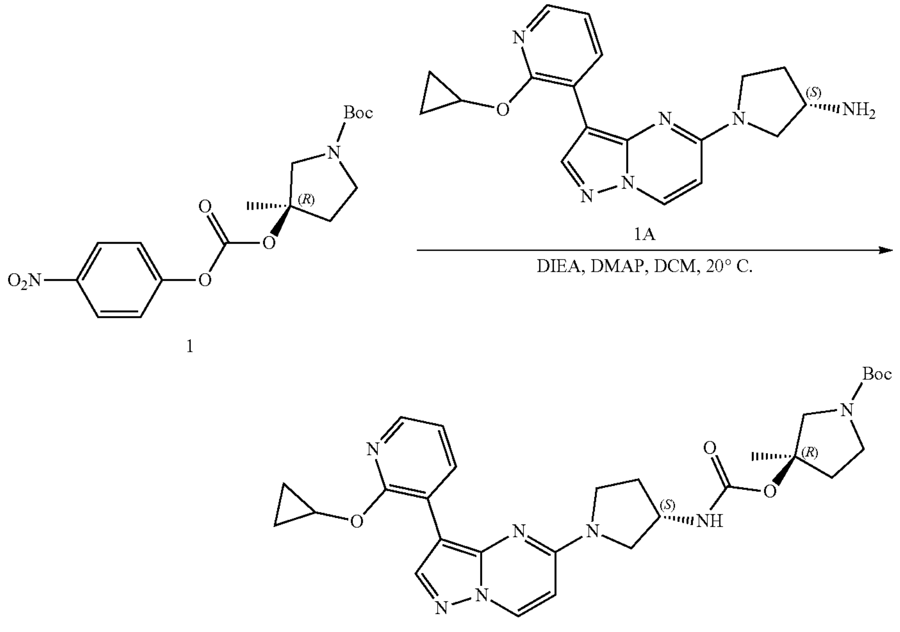

1A

1

2

The product 2 was prepared according to the synthesis method of I-56. Compound tert-butyl (R)-3-((((S)-1-(3-(2-cyclopropoxypyridin-3-yl)pyrazolo[1,5-a]pyrimidin-5-yl)pyrrolidin-3-yl)carbamoyl)oxy)-3-methylpyrrolidine-1-carboxylate (300 mg, 532.25 μmol, 65.00% yield) was obtained as a solid.

LCMS m/z=564.4 $[M+H]^+$.

(R)-3-methylpyrrolidin-3-yl ((S)-1-(3-(2-cyclopropoxypyridin-3-yl)pyrazolo[1,5-a]pyrimidin-5-yl)pyrrolidin-3-yl)carbamate

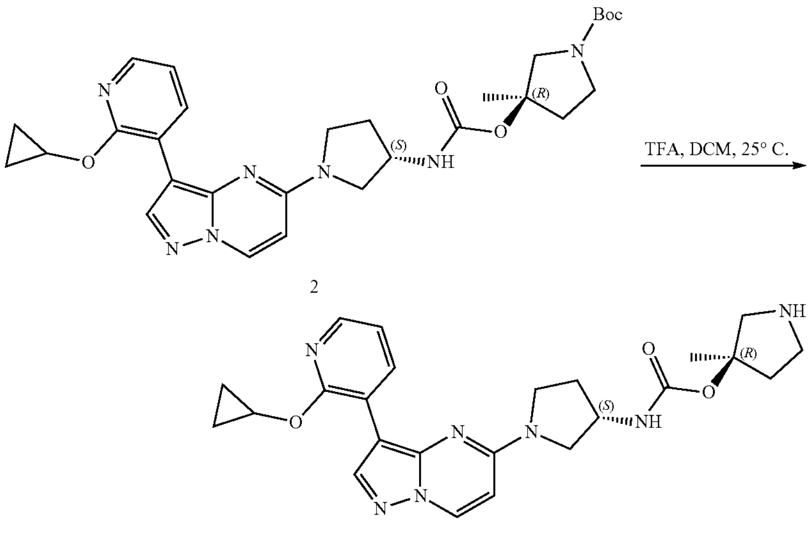

2

I-57

The product I-57 was prepared according to the synthesis method of I-56. Compound (R)-3-methylpyrrolidin-3-yl ((S)-1-(3-(2-cyclopropoxypyridin-3-yl)pyrazolo[1,5-a]pyrimidin-5-yl)pyrrolidin-3-yl)carbamate (18.09 mg, 38.39 μmol, 7.21% yield, 98.36% purity) was obtained as a solid.

LCMS m/z=464.2 $[M+H]^+$.

SFC $t_R$=1.598 min; 100%.

$^1$H NMR (400 MHz, DMSO-$d_6$) δ=8.92 (s, 1H), 8.66 (d, J=7.5 Hz, 1H), 8.33 (s, 1H), 8.03-7.92 (m, 1H), 7.54 (s, 1H), 7.12-7.04 (m, 1H), 6.46 (d, J=7.4 Hz, 1H), 4.44-4.38 (m, 1H), 4.25-4.17 (m, 1H), 3.75 (s, 2H), 3.69-3.55 (m, 2H), 3.46-3.26 (m, 2H), 3.07-2.91 (m, 3H), 2.25-2.09 (m, 2H), 1.99-1.90 (m, 1H), 1.88-1.80 (m, 1H), 1.55 (s, 3H), 0.85-0.74 (m, 4H).

Example 51: Synthesis of Compound I-58

Methyl 3-[(3-bromo-2-pyridyl)oxy]azetidine-1-carboxylate

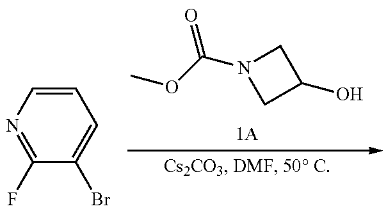

1

-continued

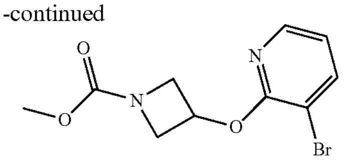

2

A mixture of 3-bromo-2-fluoro-pyridine (500 mg, 2.84 mmol, 1 eq), methyl 3-hydroxyazetidine-1-carboxylate (409.81 mg, 3.13 mmol, 1.1 eq), $Cs_2CO_3$ (1.85 g, 5.68 mmol, 2 eq) in DMF (10 mL) was degassed and purged with $N_2$ for 3 times, and then the mixture was stirred at 50° C. for 2 hr under $N_2$ atmosphere. The reaction mixture was diluted with $H_2O$ 10 mL and extracted with EtOAc 30 mL (10 mL×3). The combined organic layers were washed with $H_2O$ 30 mL (10 mL*3). The organic layers were concentrated under reduced pressure to give methyl 3-[(3-bromo-2-pyridyl)oxy]azetidine-1-carboxylate (800 mg, 2.73 mmol, 96.02% yield, 97.91% purity) as an oil.

LCMS m/z=287.0 $[M+H]^+$.

$^1$H NMR (400 MHz, DMSO-$d_6$) δ=8.15 (dd, J=1.6, 4.9 Hz, 1H), 8.09 (dd, J=1.6, 7.6 Hz, 1H), 7.02 (dd, J=4.8, 7.6 Hz, 1H), 5.42-5.33 (m, 1H), 4.36 (dd, J=7.2, 8.0 Hz, 2H), 3.97-3.85 (m, 2H), 3.58 (s, 3H).

Methyl 3-[[3-(4,4,5,5-tetramethyl-1,3,2-dioxaborolan-2-yl)-2-pyridyl]oxy]azetidine-1-carboxylate

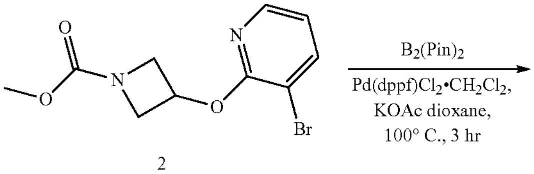

2

3

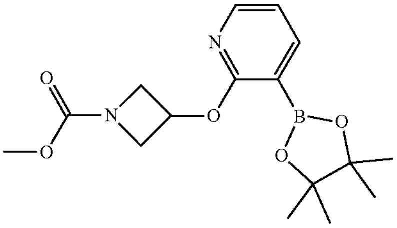

3

A mixture of methyl 3-[(3-bromo-2-pyridyl)oxy]azetidine-1-carboxylate (800 mg, 2.79 mmol, 1 eq), $B_2Pin_2$ (1.06 g, 4.18 mmol, 1.5 eq), KOAc (820.39 mg, 8.36 mmol, 3 eq), $Pd(dppf)Cl_2{\cdot}CH_2Cl_2$ (227.55 mg, 278.64 μmol, 0.1 eq) in dioxane (10 mL) was degassed and purged with $N_2$ for 3 times, and then the mixture was stirred at 100° C. for 3 hr under $N_2$ atmosphere. TLC indicated that (methyl 3-[(3-bromo-2-pyridyl)oxy]azetidine-1-carboxylate) was consumed. The reaction mixture was filtered and concentrated under reduced pressure to give methyl3-[[3-(4,4,5,5-tetramethyl-1,3,2-dioxaborolan-2-yl)-2-pyridyl]oxy]azetidine-1-carboxylate (800 mg, 2.39 mmol, 85.92% yield) as an oil.

LCMS m/z=335.0 [M+H]+.

Methyl 3-[[3-(5-piperazin-1-ylpyrazolo[1,5-a]pyrimidin-3-yl)-2-pyridyl]oxy]azetidine-1-carboxylate

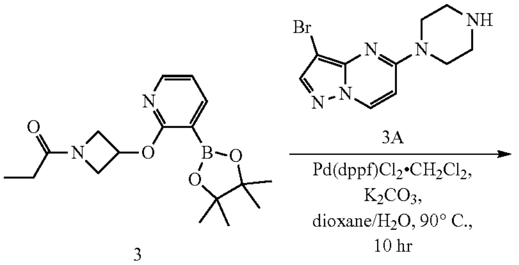

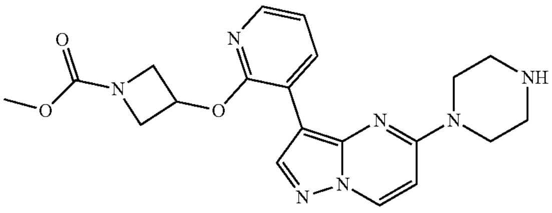

4

A mixture of methyl 3-[[3-(4,4,5,5-tetramethyl-1,3,2-dioxaborolan-2-yl)-2-pyridyl]oxy]azetidine-1-carboxylate (400 mg, 1.20 mmol, 1.5 eq), 3-bromo-5-piperazin-1-yl-pyrazolo[1,5-a]pyrimidine (225.14 mg, 797.99 μmol, 1 eq), $K_2CO_3$ (330.86 mg, 2.39 mmol, 3 eq), $Pd(dppf)Cl_2{\cdot}CH_2Cl_2$ (65.17 mg, 79.80 μmol, 0.1 eq) in dioxane (10 mL) $H_2O$ (1 mL) was degassed and purged with $N_2$ for 3 times, and then the mixture was stirred at 90° C. for 10 hr under $N_2$ atmosphere. The reaction mixture was concentrated under reduced pressure to give a residue. The residue was diluted with $H_2O$ (20 mL) and extracted with EtOAc (60 mL) (20 mL*3). The organic layers were concentrated under reduced pressure to give a residue. The residue was purified by column chromatography ($SiO_2$, DCM:MeOH=1/0 to 0/1) to afford methyl 3-[[3-(5-piperazin-1-ylpyrazolo[1,5-a]pyrimidin-3-yl)-2-pyridyl]oxy]azetidine-1-carboxylate (80 mg, 93.53 μmol, 11.72% yield, 47.87% purity) as an oil.

LCMS m/z=410.4 [M+H]+.

[(3S)-5-oxopyrrolidin-3-yl]-4-[3-[2-(1-methoxycarbonylazetidin-3-yl)oxy-3-pyridyl]pyrazolo[1,5-a]pyrimidin-5-yl]piperazine-1-carboxylate

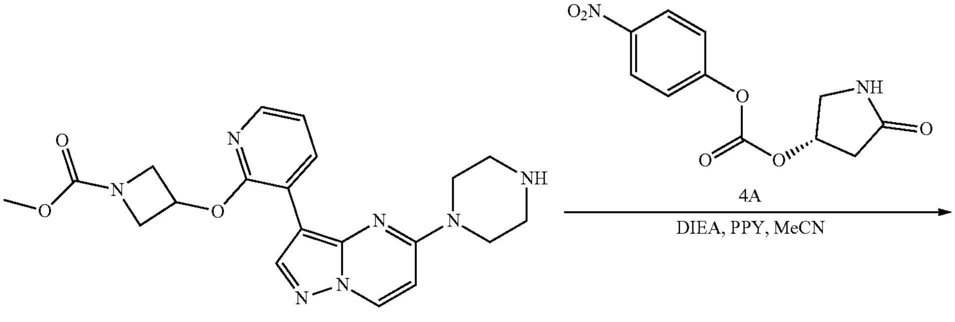

4

-continued

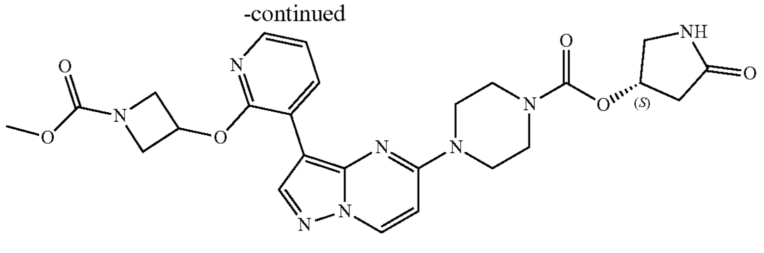

I-58

A mixture of methyl 3-[[3-(5-piperazin-1-ylpyrazolo[1,5-a]pyrimidin-3-yl)-2-pyridyl]oxy]azetidine-1-carboxylate (50 mg, 122.12 μmol, 1 eq), (4-nitrophenyl) [(3S)-5-oxopyrrolidin-3-yl]carbonate (39.01 mg, 146.54 μmol, 1.2 eq), DIEA (31.57 mg, 244.24 μmol, 42.54 μL, 2 eq), 4-pyrrolidin-1-ylpyridine (3.62 mg, 24.42 μmol, 0.2 eq) in MeCN (5 mL) was degassed and purged with $N_2$ for 3 times, and then the mixture was stirred at 25° C. for 2 hr under $N_2$ atmosphere. LCMS showed desired compound was detected. The reaction mixture was filtered and concentrated under reduced pressure to give a residue. The residue was purified by prep. HPLC (column: Waters Xbridge C18 150*50 mm*10 um; mobile phase: [water ($NH_3H_2O$)-MeCN]; gradient: 18%-48% B over 11 min) to give [(3S)-5-oxopyrrolidin-3-yl]-4-[3-[2-(1-methoxycarbonylazetidin-3-yl)oxy-3-pyridyl]pyrazolo[1,5-a]pyrimidin-5-yl]piperazine-1-carboxylate (13.36 mg, 24.81 μmol, 20.31% yield, 99.618% purity) as a solid.

LCMS m/z=537.2 $[M+H]^+$.

SFC $t_R$=1.866 min; 100%.

$^1$H NMR (400 MHz, $CDCl_3$) δ=8.76-8.71 (m, 1H), 8.62 (s, 1H), 8.42 (d, J=8.0 Hz, 1H), 7.98-7.93 (m, 1H), 7.06-7.02 (m, 1H), 6.42 (d, J=8.0 Hz, 1H), 5.61 (s, 1H), 5.54-5.48 (m, 1H), 5.44-5.39 (m, 1H), 4.50-4.44 (m, 2H), 4.17-4.13 (m, 2H), 3.84-3.80 (m, 1H), 3.79-3.75 (m, 4H), 3.70 (s, 3H), 3.69-3.60 (m, 4H), 3.49 (d, J=11.6 Hz, 1H), 2.79-2.72 (m, 1H), 2.50-2.44 (m, 1H).

Example 52: Synthesis of Compound I-59

1-(3-((3-bromopyridin-2-yl)oxy) azetidin-1-yl) ethan-1-one

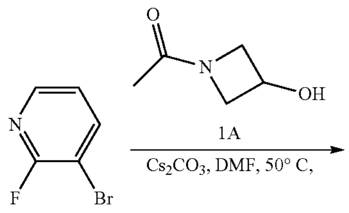

1

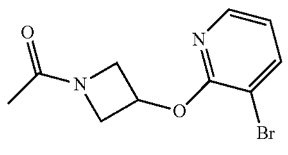

2

The product 2 was prepared according to the synthesis method of I-58. Compound 1-(3-((3-bromopyridin-2-yl) oxy) azetidin-1-yl) ethan-1-one was obtained as an oil.

LCMS m/z=272.9 $[M+H]^+$.

$^1$H NMR (400 MHz, $CDCl_3$) δ=8.01 (br s, 1H), 7.83-7.75 (m, 1H), 6.80 (ddd, J=1.1, 5.5, 6.8 Hz, 1H), 5.42-5.27 (m, 1H), 4.57-4.30 (m, 2H), 4.21-3.96 (m, 2H), 2.94 (br s, 3H).

1-(3-((3-(4,4,5,5-tetramethyl-1,3,2-dioxaborolan-2-yl)pyridin-2-yl)oxy) azetidin-1-yl) ethan-1-one

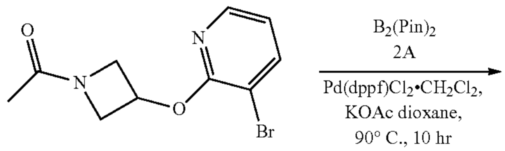

2

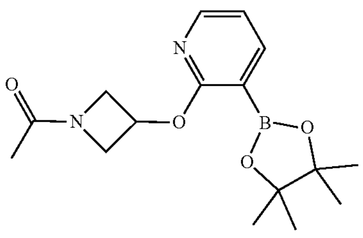

3

The product 3 was prepared according to the synthesis method of I-58. Compound 1-(3-((3-(4,4,5,5-tetramethyl-1,3,2-dioxaborolan-2-yl)pyridin-2-yl)oxy) azetidin-1-yl) ethan-1-one (1.05 g, 2.40 mmol, 65.19% yield) was obtained as oil.

$^1$H NMR (400 MHz, $CDCl_3$) δ=8.03-7.94 (m, 1H), 7.80 (dd, J=2.0, 7.1 Hz, 1H), 6.82-6.70 (m, 1H), 5.23-5.13 (m, 1H), 4.35 (dd, J=7.3, 8.9 Hz, 1H), 4.23 (dd, J=6.9, 10.9 Hz, 1H), 3.98-3.90 (m, 2H), 1.73 (s, 3H), 1.19 (s, 8H), 1.09 (s, 4H).

1-(3-((3-(5-(piperazin-1-yl)pyrazolo[1,5-a]pyrimidin-3-yl)pyridin-2-yl)oxy) azetidin-1-yl) ethan-1-one

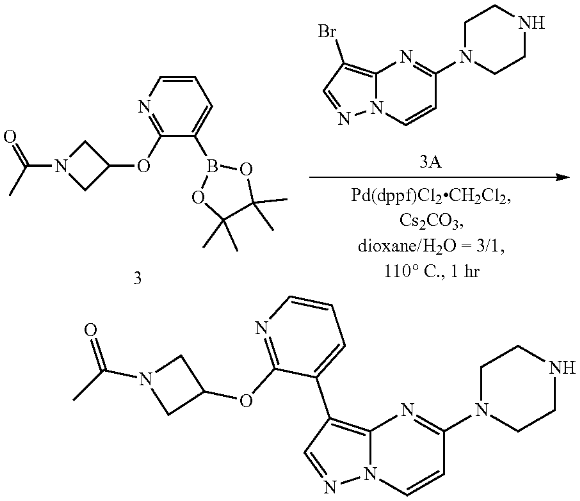

3

4

The product 4 was prepared according to the synthesis method of I-58 (The product 1-(3-((3-(5-(piperazin-1-yl) pyrazolo[1,5-a]pyrimidin-3-yl)pyridin-2-yl)oxy) azetidin-1-yl) ethan-1-one (0.368 g, 643.51 μmol, 40.95% yield) was obtained as a solid.

LCMS m/z=394.1 $[M+H]^+$.

$^1H$ NMR (400 MHz, $CDCl_3$) δ=8.79 (dd, J=1.8, 7.6 Hz, 1H), 8.59 (s, 1H), 8.34 (dd, J=7.8, 16.4 Hz, 2H), 7.88 (d, J=2.1 Hz, 1H), 6.33 (d, J=7.8 Hz, 1H), 6.13 (d, J=1.9 Hz, 1H), 5.51 (ddd, J=2.4, 4.3, 6.7 Hz, 1H), 4.60 (dd, J=6.9, 8.8 Hz, 1H), 4.49 (dd, J=7.1, 11.0 Hz, 1H), 4.27-4.16 (m, 2H), 3.77-3.74 (m, 4H), 3.72-3.68 (m, 4H), 1.92 (s, 3H).

(S)-5-oxopyrrolidin-3-yl 4-(3-(2-((1-acetylazetidin-3-yl)oxy)pyridin-3-yl)pyrazolo[1,5-a]pyrimidin-5-yl)piperazine-1-carboxylate

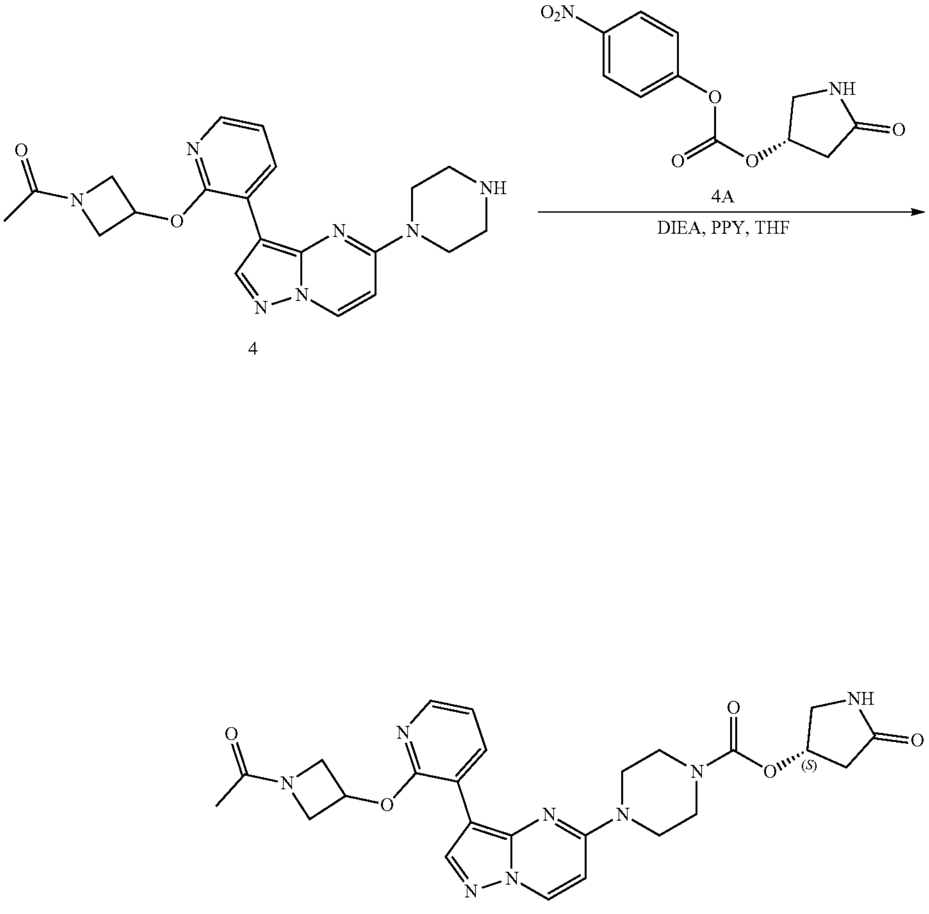

4

I-59

The product I-59 was prepared according to the synthesis method of I-58. The product (S)-5-oxopyrrolidin-3-yl 4-(3-(2-((1-acetylazetidin-3-yl)oxy)pyridin-3-yl)pyrazolo[1,5-a]pyrimidin-5-yl)piperazine-1-carboxylate (155.97 mg, 296.67 μmol, 38.91% yield) was obtained as a powder.

Compound I-59

LCMS m/z=521.3 $[M+H]^+$.

SFC $t_R$=1.051 min; 94.7%.

$^1$H NMR (400 MHz, DMSO-$d_6$) δ=8.87-8.82 (m, J=1.8, 7.6 Hz, 1H), 8.78 (d, J=7.9 Hz, 1H), 8.56 (s, 1H), 7.98-7.91 (m, J=1.9, 4.9 Hz, 1H), 7.73 (s, 1H), 7.17-7.10 (m, J=4.9, 7.6 Hz, 1H), 6.83 (d, J=7.9 Hz, 1H), 5.47-5.40 (m, 1H), 5.21 (t, J=6.1 Hz, 1H), 4.62-4.54 (m, J=7.1, 9.3 Hz, 1H), 4.33-4.20 (m, 2H), 3.96-3.88 (m, J=4.1, 10.6 Hz, 1H), 3.77 (d, J=5.1 Hz, 4H), 3.64-3.58 (m, J=5.6, 11.4 Hz, 1H), 3.53 (s, 4H), 3.25 (d, J=11.4 Hz, 1H), 2.68-2.59 (m, J=6.9, 17.5 Hz, 1H), 2.20-2.13 (m, J=1.9, 17.4 Hz, 1H), 1.80 (s, 3H).

Example 53: Synthesis of Compound I-60

N-[2-[(3-bromopyrazolo[1,5-a]pyrimidin-5-yl)amino]ethyl]-N-methyl-carbamate

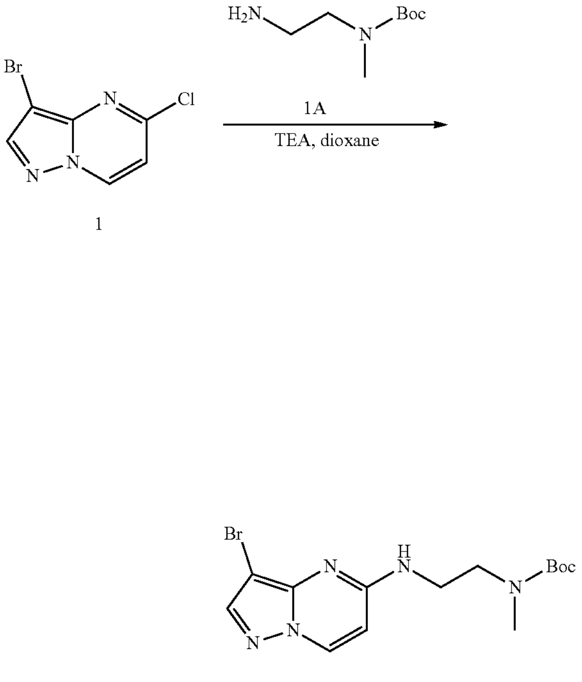

1

2

A mixture of 3-bromo-5-chloro-pyrazolo[1,5-a]pyrimidine (5 g, 21.51 mmol, 1 eq), tert-butyl N(2-aminoethyl)-N-methyl-carbamate (11.24 g, 64.53 mmol, 11.53 mL, 3 eq), TEA (6.53 g, 64.53 mmol, 8.98 mL, 3 eq) in dioxane (50 mL) was degassed and purged with $N_2$ for 3 times, and then the mixture was stirred at 90° C. for 1 hour under $N_2$ atmosphere. The reaction mixture was filtered and concentrated under reduced pressure to give a residue. The residue was purified by flash silica gel chromatography (ISCO®; 40 g SepaFlash® Silica Flash Column, eluent of 0~33% EA/PE gradient @ 80 mL/min) to give tert-butyl N-[2-[(3-bromopyrazolo[1,5-a]pyrimidin-5-yl)amino]ethyl]-N-methyl-carbamate (7.8 g, 21.07 mmol, 97.95% yield) as a powder.

LCMS m/z=372.1 $[C_{14}H_{18}{}^{81}BrN_5O_2+H]^+$.

Tert-butyl N-[2-[[3-[2-(cyclopropoxy)-3-pyridyl]pyrazolo[1,5-a]pyrimidin-5-yl]amino]ethyl]-N-methyl-carbamate

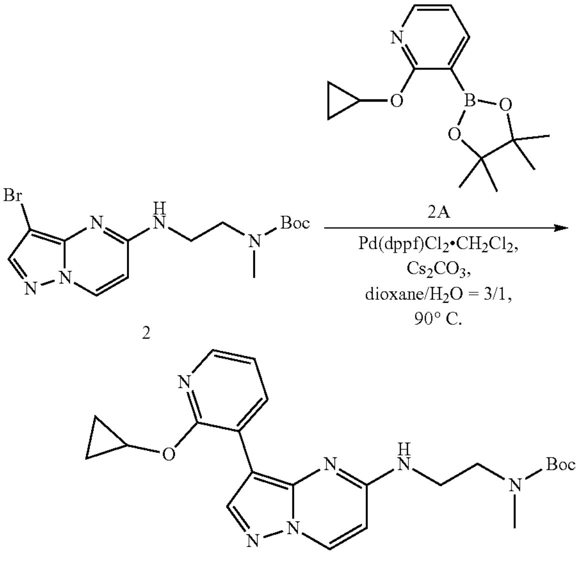

2

3

A mixture of tert-butyl N-[2-[(3-bromopyrazolo[1,5-a]pyrimidin-5-yl)amino]ethyl]-N-methyl-carbamate (2 g, 5.40 mmol, 1 eq), 2-(cyclopropoxy)-3-(4,4,5,5-tetramethyl-1,3,2-dioxaborolan-2-yl)pyridine (1.41 g, 5.40 mmol, 1 eq), $Cs_2CO_3$ (5.28 g, 16.21 mmol, 3 eq) in dioxane (15 mL) and $H_2O$ (5 mL), $Pd(dppf)Cl_2{\cdot}CH_2Cl_2$ (882.27 mg, 1.08 mmol, 0.2 eq) was degassed and purged with $N_2$ for 3 times, and then the mixture was stirred at 90° C. for 1 hour under $N_2$ atmosphere. The reaction mixture was filtered and concentrated under reduced pressure to give a residue. The residue was purified by flash silica gel chromatography (ISCO®; 40 g SepaFlash® Silica Flash Column, eluent of 0~37% EA/PE gradient @ 80 mL/min) to give tert-butyl N-[2-[[3-[2-(cyclopropoxy)-3-pyridyl]pyrazolo[1,5-a]pyrimidin-5-yl]amino]ethyl]-N-methyl-carbamate (1.47 g, 3.46 mmol, 64.11% yield) as a powder.

LCMS m/z=425.3 $[M+H]^+$.

N'-[3-[2-(cyclopropoxy)-3-pyridyl]pyrazolo[1,5-a]pyrimidin-5-yl]-N-methyl-ethane-1,2-diamine

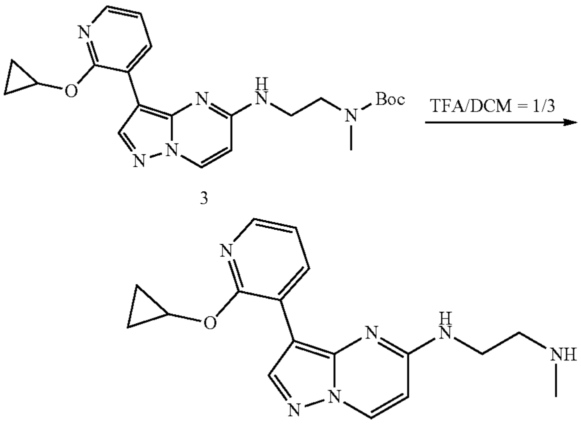

3

4

To a solution of tert-butyl N-[2-[[3-[2-(cyclopropoxy)-3-pyridyl]pyrazolo[1,5-a]pyrimidin-5-yl]amino]ethyl]-N-methyl-carbamate (300 mg, 706.72 μmol, 1 eq) in DCM (2.1 mL) was added TFA (1.07 g, 9.42 mmol, 0.7 mL, 13.33 eq). The mixture was stirred at 25° C. for 1 hour. The reaction mixture was filtered and concentrated under reduced pressure to give N'-[3-[2-(cyclopropoxy)-3-pyridyl]pyrazolo[1,5-a]pyrimidin-5-yl]-N-methyl-ethane-1,2-diamine (229 mg, 705.96 μmol, 99.89% yield) as an oil.

LCMS m/z=325.1 $[M+H]^+$.

[(3S)-5-oxopyrrolidin-3-yl] N-[2-[[3-[2-(cyclopropoxy)-3-pyridyl]pyrazolo[1,5-a]pyrimidin-5-yl]amino]ethyl]-N-methyl-carbamate

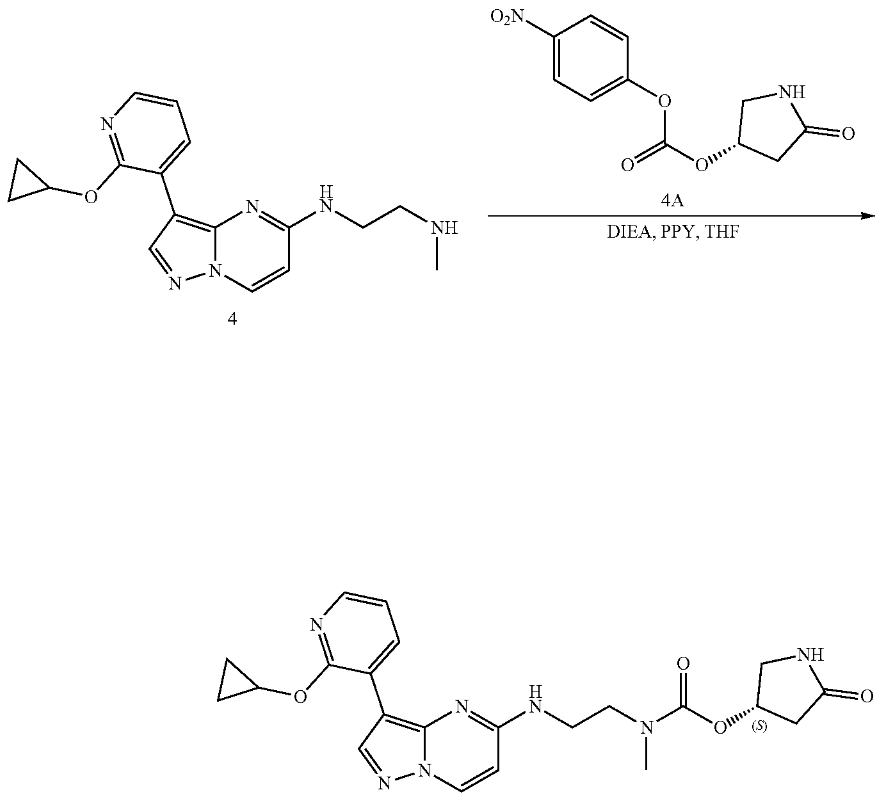

4

I-60

A mixture of N'-[3-[2-(cyclopropoxy)-3-pyridyl]pyrazolo[1,5-a]pyrimidin-5-yl]-N-methyl-ethane-1,2-diamine (199 mg, 613.48 μmol, 1 eq), (4-nitrophenyl) [(3S)-5-oxopyrrolidin-3-yl]carbonate (489.94 mg, 1.84 mmol, 3 eq), DIEA (237.86 mg, 1.84 mmol, 320.57 μL, 3 eq), 4-pyrrolidin-1-ylpyridine (18.18 mg, 122.70 μmol, 0.2 eq) in THF (2 mL) was degassed and purged with $N_2$ for 3 times, and then the mixture was stirred at 80° C. for 1 hour under $N_2$ atmosphere. The reaction mixture was filtered and concentrated under reduced pressure to give a residue. The crude was purified by prep. HPLC (column: Welch Xtimate C18 150*40 mm*10 um, Mobile Phase: water ($NH_3H_2O$+$NH_4HCO_3$)-MeCN, gradient: 10% B to 50% over 10 min) to give crude product. The crude was further purified by prep. HPLC (column: Xtimate C18 150*40 mm*10 um, Mobile Phase:water(HCOOH)-MeCN, gradient: 8% B to 46% over 10 min). The pure fractions were collected and the volatiles were removed under vacuum. The residue was partitioned between acetonitrile (10 mL) and water (30 mL). The solution was lyophilized to dryness to give [(3S)-5-oxopyrrolidin-3-yl]-N-[2-[[3-[2-(cyclopropoxy)-3-pyridyl]pyrazolo[1,5-a]pyrimidin-5-yl]amino]ethyl]-N-methyl-carbamate (19.76 mg, 43.39 μmol, 99.14% purity) as a powder.

LCMS m/z=452.2 $[M+H]^+$.

Compound I-60

LCMS m/z=452.4 $[M+H]^+$.

SFC $t_R$=1.428 min, 100%.

$^1H$ NMR (400 MHz, DMSO-$d_6$) δ=8.94-8.80 (m, 1H), 8.50 (d, J=6.0 Hz, 1H), 8.27 (s, 1H), 8.05-7.91 (m, 1H), 7.83 (d, J=3.4 Hz, 1H), 7.71-7.58 (m, 1H), 7.06 (s, 1H), 6.29 (d, J=7.4 Hz, 1H), 5.17-4.98 (m, 1H), 4.46-4.34 (m, 1H), 3.63-3.49 (m, 3H), 3.47 (d, J=5.0 Hz, 2H), 3.19-3.02 (m, 1H), 2.89 (d, J=2.4 Hz, 3H), 2.63-2.51 (m, 1H), 2.12-1.95 (m, 1H), 0.82-0.72 (m, 4H).

Example 54: Synthesis of Compound I-61

Tert-butyl (R)-3-(((2-((3-(2-cyclopropoxypyridin-3-yl)pyrazolo[1,5-a]pyrimidin-5-yl)amino)ethyl)(methyl)carbamoyl)oxy)-3-methylpyrrolidine-1-carboxylate

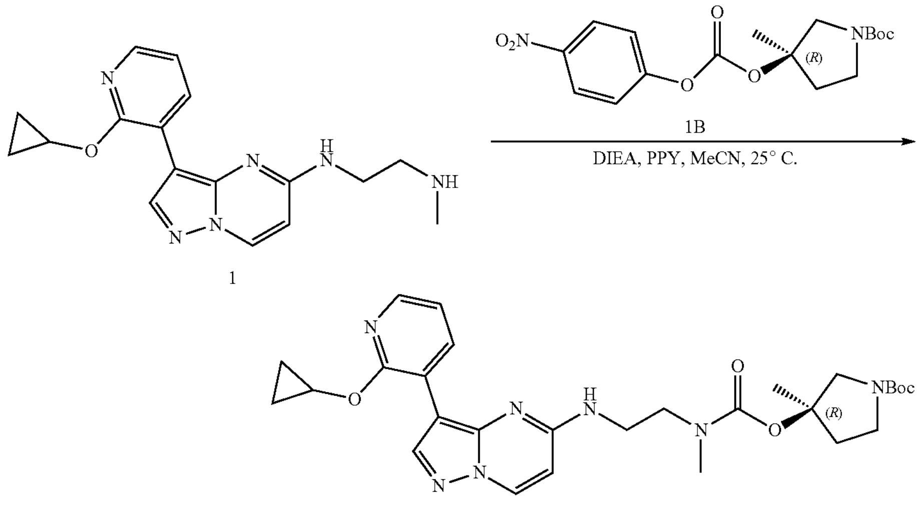

1

2

A mixture of $N^1$-(3-(2-cyclopropoxypyridin-3-yl)pyrazolo[1,5-a]pyrimidin-5-yl)-N2-methylethane-1,2-diamine (0.25 g, 770.70 μmol, 1 eq), tert-butyl (3R)-3-methyl-3-(4-nitrophenoxy)carbonyloxy-pyrrolidine-1-carboxylate (564.72 mg, 1.54 mmol, 2 eq), DIEA (298.82 mg, 2.31 mmol, 402.73 μL, 3 eq), 4-pyrrolidin-1-ylpyridine (22.84 mg, 154.14 μmol, 0.2 eq) in MeCN (6 mL) was degassed and purged with $N_2$ for 3 times, and then the mixture was stirred at 25° C. for 1 hr under $N_2$ atmosphere. The reaction mixture was filtered and concentrated under reduced pressure to give a residue. The residue was purified by flash silica gel chromatography (ISCO®; 40 g SepaFlash® Silica Flash Column, eluent of 0~33% ethyl acetate/petroleum ether gradient @ 80 mL/min) to give tert-butyl (R)-3-(((2-((3-(2-cyclopropoxypyridin-3-yl)pyrazolo[1,5-a]pyrimidin-5-yl)amino)ethyl)(methyl)carbamoyl)oxy)-3-methylpyrrolidine-1-carboxylate (300 mg, 543.84 umol, 70.56% yield, 67% purity) as a solid.

LCMS m/z=552.3 $[M+H]^+$.

(R)-3-methylpyrrolidin-3-yl (2-((3-(2-cyclopropoxypyridin-3-yl)pyrazolo[1,5-a]pyrimidin-5-yl)amino)ethyl)(methyl)carbamate

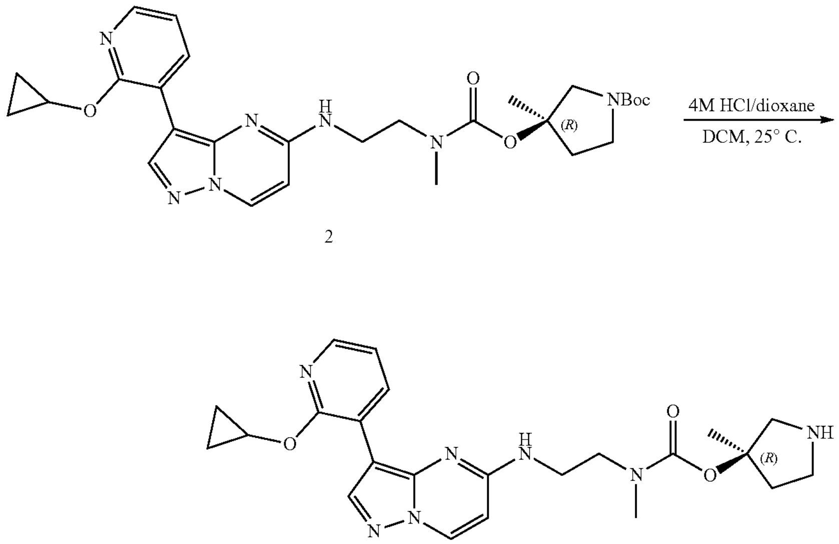

2

I-61

To a solution of tert-butyl (R)-3-(((2-((3-(2-cyclopropoxypyridin-3-yl)pyrazolo[1,5-a]pyrimidin-5-yl)amino)ethyl)(methyl)carbamoyl)oxy)-3-methylpyrrolidine-1-carboxylate (290 mg, 525.71 μmol, 1 eq) in DCM (3 mL) was added HCl/dioxane (4M, 3 mL, 22.83 eq). The mixture was stirred at 25° C. for 1 hr. The reaction mixture was concentrated under reduced pressure to remove solvent. The crude was purified by prep. HPLC (column: Welch Xtimate C18 150*40 mm*10 um, Mobile Phase A: water (HCOOH)-MeCN Mobile Phase B: acetonitrile, Flow rate: 25 mL/min, gradient condition from 0% B to 36% B over 10 min). The pure fractions were collected and the volatiles were removed under vacuum. The residue was partitioned between acetonitrile (2 mL) and water (10 mL). The solution was lyophilized to dryness to give (R)-3-methylpyrrolidin-3-yl-(2-((3-(2-cyclopropoxypyridin-3-yl)pyrazolo[1,5-a]pyrimidin-5-yl)amino)-ethyl)(methyl)carbamate (90.82 mg, 192.84 μmol, 36.68% yield, 95.87% purity) as an oil.

LCMS m/z=452.3 $[M+H]^+$

SFC $t_R$=1.019 min, 100%.

$^1H$ NMR (400 MHz, DMSO-$d_6$) δ=8.95-8.83 (m, 1H), 8.56-8.46 (m, 1H), 8.37 (s, 1H), 8.27 (s, 1H), 7.99 (d, J=4.1 Hz, 2H), 7.12-7.01 (m, 1H), 6.38-6.25 (m, 1H), 4.42-4.38 (m, 1H), 3.58-3.44 (m, 4H), 3.40-3.28 (m, 1H), 3.13-3.04 (m, 1H), 3.02-2.90 (m, 2H), 2.87 (d, J=11.8 Hz, 3H), 2.27-1.95 (m, 1H), 1.91-1.67 (m, 1H), 1.54-1.41 (m, 3H), 0.84-0.73 (m, 4H).

Example 55: Synthesis of Compound I-62

Tert-butyl 3-[[3-[5-[2-[tert-butoxycarbonyl(methyl)amino]ethylamino]pyrazolo[1,5-a]pyrimidin-3-yl]-2-pyridyl]oxy]azetidine-1-carboxylate A mixture of tert-butyl 3-[[3-(4,4,5,5-tetramethyl-1,3,2-dioxaborolan-2-yl)-2-pyridyl]oxy]azetidine-1-carboxylate (200 mg, 531.56 μmol, 1.1 eq), tert-butyl N-[2-[(3-bromopyrazolo[1,5-a]pyrimidin-5-yl)amino]ethyl]-N-methyl-carbamate (178.91 mg, 483.23 μmol, 1 eq), Pd(dppf)$Cl_2$·$CH_2Cl_2$ (78.93 mg, 96.65 μmol, 0.2 eq), $Cs_2CO_3$ (472.34 mg, 1.45 mmol, 3 eq) in dioxane (1.5 mL) and $H_2O$ (0.5 mL) was degassed and purged with $N_2$ for 3 times, and then the mixture was stirred at 110° C. for 1 hr under $N_2$ atmosphere. The reaction mixture was concentrated under reduced pressure to give a residue. The crude was purified by prep. HPLC (column: Waters xbridge 150*25 mm 10 um; mobile phase: [water ($NH_4HCO_3$)-MeCN]; gradient: 56%-86% B over 10 min). The pure fractions were collected and the volatiles were removed under vacuum. The residue was partitioned between acetonitrile (20 mL) and water (100 mL). The solution was lyophilized to dryness to give the product. The product tert-butyl 3-[[3-[5-[2-[tert-butoxycarbonyl(methyl)amino]ethylamino]pyrazolo[1,5-a]pyrimidin-3-yl]-2-pyridyl]oxy]azetidine-1-carboxylate (9.30 mg, 16.61 μmol, 3.44% yield, 96.398% purity) was obtained as a powder.

LCMS m/z=540.3 $[M+H]^+$.

SFC $t_R$=1.522 min; 100%.

$^1H$ NMR (400 MHz, DMSO-$d_6$) δ=9.03-8.83 (m, 1H), 8.62-8.41 (m, 2H), 7.98-7.73 (m, 2H), 7.14-6.99 (m, J=5.0, 7.3 Hz, 1H), 6.32 (s, 1H), 5.40 (d, J=3.8 Hz, 1H), 4.31 (d, J=7.3 Hz, 2H), 3.94 (d, J=6.1 Hz, 2H), 3.61-3.37 (m, 4H), 2.84 (br s, 3H), 1.42-1.37 (m, 9H), 1.37-1.17 (m, 9H).

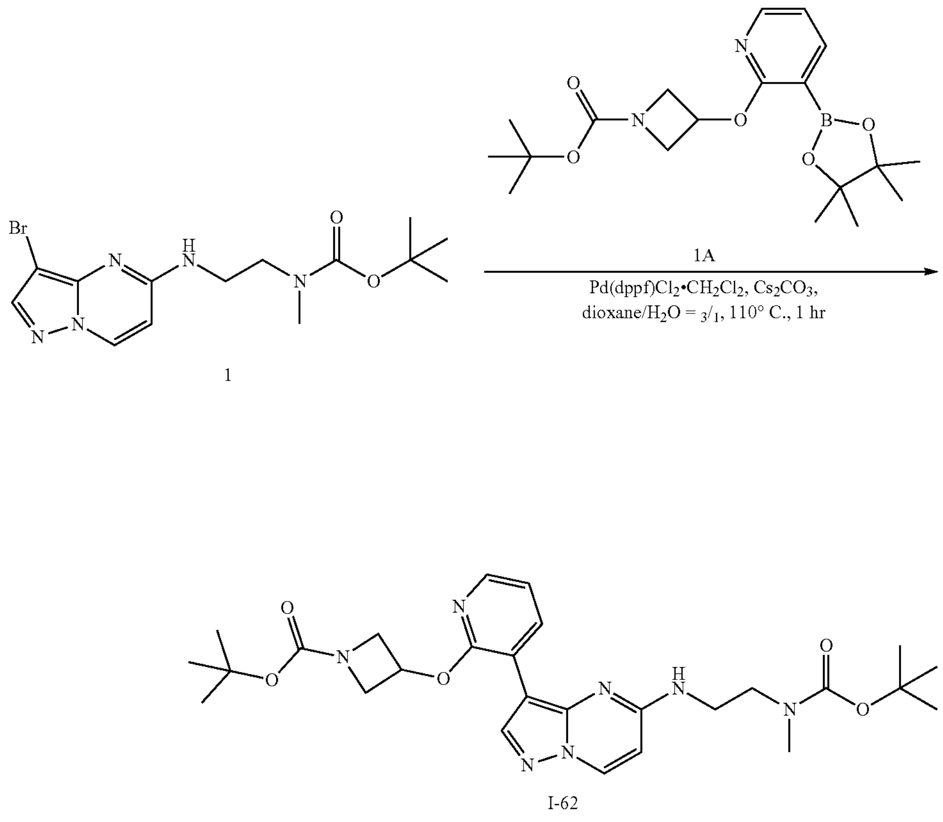

1

I-62

Example 56: Synthesis of Compound I-63

Tert-butyl (2-((3-(2-((1-acetylazetidin-3-yl)oxy)pyridin-3-yl)pyrazolo[1,5-a]pyrimidin-5-yl)amino)ethyl)(methyl)carbamate

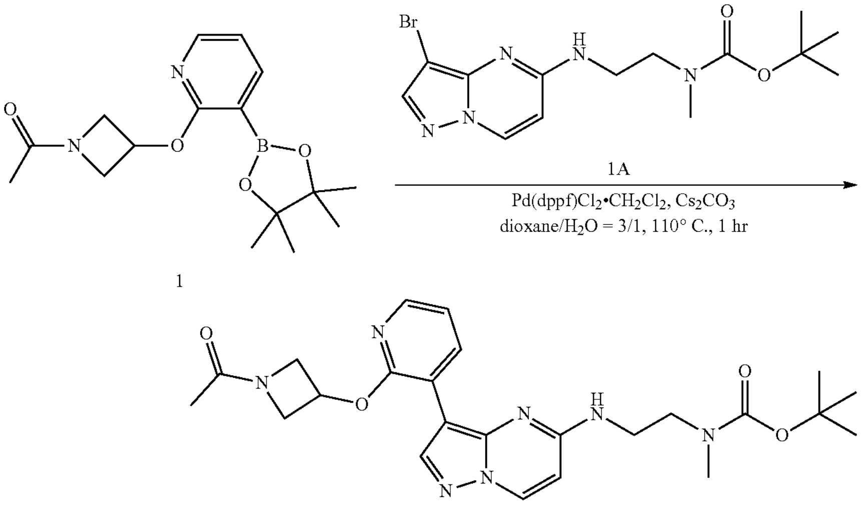

1

I-63

The product I-63 was prepared according to the synthesis method of I-62. Compound tert-butyl (2-((3-(2-((1-acetylazetidin-3-yl)oxy)pyridin-3-yl)pyrazolo[1,5-a]pyrimidin-5-yl)amino)ethyl)(methyl)carbamate (13.65 mg, 27.15 μmol, 4.32% yield, 95.771% purity) was obtained as a powder.

LCMS m/z=482.2 $[M+H]^+$.

$^1$H NMR (400 MHz, DMSO-$d_6$) δ=9.02-8.89 (m, 1H), 8.54 (s, 1H), 8.48 (s, 1H), 7.96-7.90 (m, 1H), 7.89-7.76 (m, 1H), 7.08 (s, 1H), 6.32 (s, 1H), 5.47-5.39 (m, 1H), 4.57 (s, 1H), 4.32-4.19 (m, 2H), 3.92 (s, 1H), 3.51 (d, J=4.5 Hz, 3H), 3.41 (s, 1H), 2.84 (s, 3H), 1.80 (s, 3H), 1.37-1.18 (m, 9H).

Example 57: Synthesis of Compound I-64

Methyl3-[[3-[5-[2-[tert-butoxycarbonyl(methyl)amino]ethylamino]pyrazolo[1,5-a]pyrimidin-3-yl]-2-pyridyl]oxy]azetidine-1-carboxylate

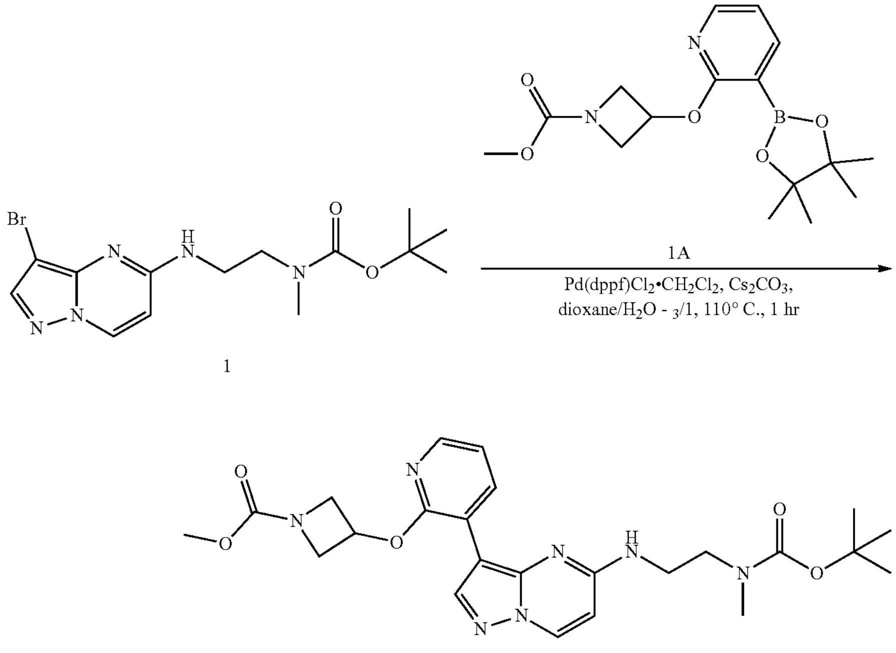

1

I-64

The product I-64 was prepared according to the synthesis method of I-62. Compound methyl3-[[3-[5-[2-[tert-butoxycarbonyl(methyl)amino]ethylamino]pyrazolo[1,5-a]pyrimidin-3-yl]-2-pyridyl]oxy]azetidine-1-carboxylate (9.13 mg, 18.22 μmol, 13.49% yield, 99.299% purity) was obtained as a solid.

Compound I-64

LCMS m/z=498.4 $[M+H]^+$.

SFC $t_R$=1.727 min; 100%.

$^1H$ NMR (400 MHz, DMSO-$d_6$) δ=9.00-8.87 (m, 1H), 8.59-8.51 (m, 1H), 8.48 (s, 1H), 7.94-7.89 (m, 1H), 7.88-7.77 (m, 1H), 7.11-7.05 (m, 1H), 6.37-6.27 (m, 1H), 5.51-5.40 (m, 1H), 4.42-4.31 (m, 2H), 4.09-3.94 (m, 2H), 3.58 (s, 3H), 3.55-3.39 (m, 4H), 2.90-2.81 (m, 3H), 1.38-1.18 (m, 9H).

Example 58: Synthesis of Compound I-65

3-(2-methoxypyridin-3-yl)-5-(piperazin-1-yl)pyrazolo[1,5-a]pyrimidine

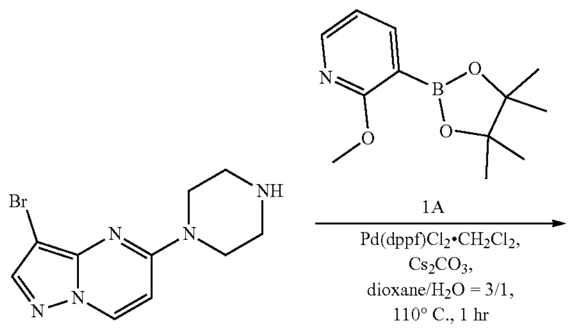

1

-continued

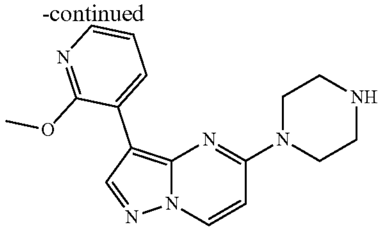

2

The product 2 was prepared according to the synthesis method of 0-58. Compound 3-(2-methoxypyridin-3-yl)-5-(piperazin-1-yl)pyrazolo[1,5-a]pyrimidine (500 mg, 1.35 mmol, 76.18% yield, 83.79% purity) was obtained as a solid.

$^1H$ NMR (400 MHz, $CDCl_3$) δ=8.78 (dd, J=1.6, 7.4 Hz, 1H), 8.62 (s, 1H), 8.40-8.28 (m, 1H), 8.01 (dd, J=1.6, 4.8 Hz, 1H), 6.99 (dd, J=5.0, 7.4 Hz, 1H), 6.47-6.33 (m, 1H), 4.09 (s, 3H), 3.76-3.69 (m, 4H), 3.68-3.62 (m, 1H), 3.06-3.00 (m, 4H).

(3R,3aS,6aR)-hexahydrofuro[2,3-b]furan-3-yl 4-(3-(2-methoxypyridin-3-yl)pyrazolo[1,5-a]pyrimidin-5-yl)piperazine-1-carboxylate

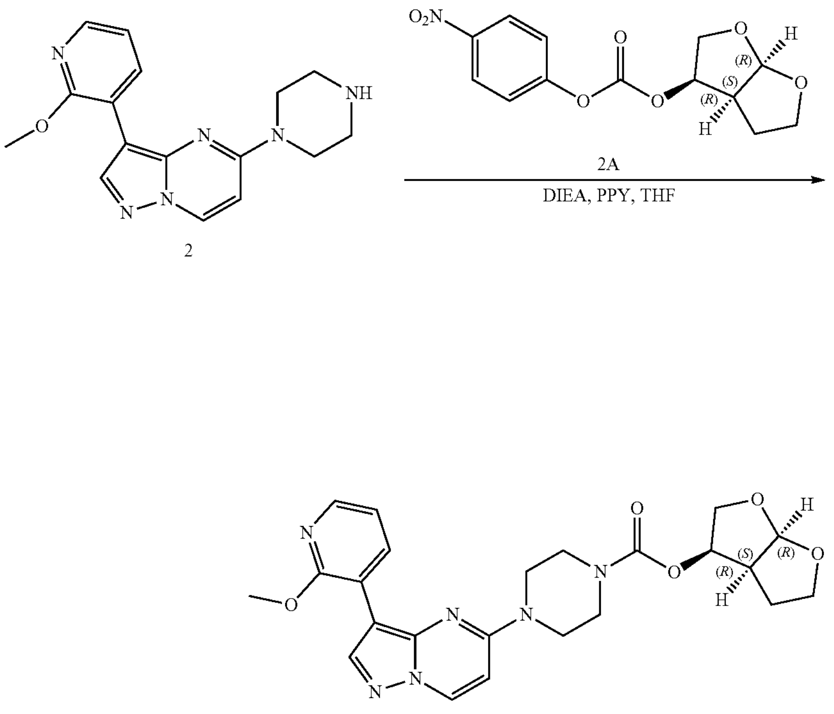

I-65

The product I-65 was prepared according to the synthesis method of I-58. Compound (3R,3aS,6aR)-hexahydrofuro[2,3-b]furan-3-yl 4-(3-(2-methoxypyridin-3-yl)pyrazolo[1,5-a]pyrimidin-5-yl)piperazine-1-carboxylate (24.18 mg, 51.74 μmol, 28.92% yield, 99.83% purity) was obtained as a solid. Compound I-65

LCMS m/z=467.2 $[M+H]^+$.

$^1$H NMR (400 MHz, DMSO-$d_6$) δ=8.87-8.79 (m, 1H), 8.76 (d, J=7.9 Hz, 1H), 8.50 (s, 1H), 8.02-7.92 (m, 1H), 7.14-6.96 (m, 1H), 6.81 (d, J=7.9 Hz, 1H), 5.62 (d, J=5.3 Hz, 1H), 5.16-4.97 (m, 1H), 3.99 (s, 3H), 3.98-3.94 (m, 1H), 3.92-3.85 (m, 1H), 3.82-3.77 (m, 4H), 3.77-3.73 (m, 1H), 3.71-3.65 (m, 1H), 3.58-3.52 (m, 4H), 3.10-2.96 (m, 1H), 2.04-1.93 (m, 1H), 1.90-1.73 (m, 1H).

SFC $t_R$=1.742, 0.450%; 1.946, 99.550%.

Example 59: Synthesis of Compound I-66

[(3aS,4R,6aR)-2,3,3a,4,5,6a-hexahydrofuro[2,3-b]furan-4-yl]-4-(3-bromopyrazolo[1,5-a]pyrimidin-5-yl)piperazine-1-carboxylate

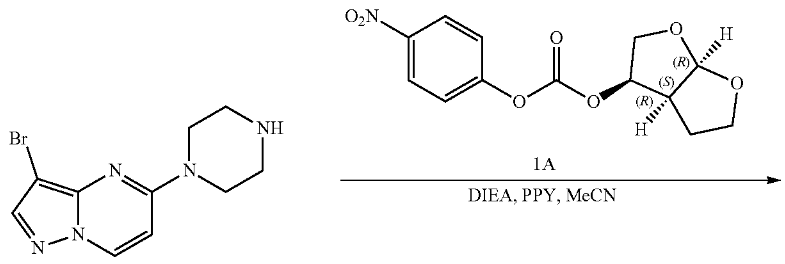

1

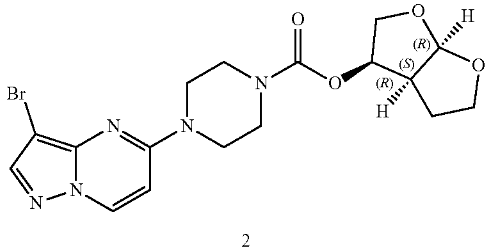

2

To a solution of 3-bromo-5-piperazin-1-yl-pyrazolo[1,5-a]pyrimidine (500 mg, 1.77 mmol, 1 eq), [(3aS,4R,6aR)-2,3,3a,4,5,6a-hexahydrofuro[2,3-b]furan-4-yl](4-nitrophenyl) carbonate (523.22 mg, 1.77 mmol, 1 eq) in MeCN (5 mL) was added DIEA (458.08 mg, 3.54 mmol, 617.36 μL, 2 eq) and 4-pyrrolidin-1-ylpyridine (52.53 mg, 354.43 μmol, 0.2 eq). The mixture was stirred at 25° C. for 1 hr. The reaction mixture was filtered with diatomite and concentrated under reduced pressure to give crude product. The crude was purified by FCC (ISCOR; 4 g SepaFlash® Silica Flash Column, eluent of 0~6% Methanol/Dichloromethane gradient @ 25 mL/min) to give [(3aS,4R,6aR)-2,3,3a,4,5,6a-hexahydrofuro[2,3-b]furan-4-yl] 4-(3-bromopyrazolo[1,5-a]pyrimidin-5-yl)piperazine-1-carboxylate (770 mg, 1.61 mmol, 90.81% yield, 91.599% purity) as an oil.

LCMS m/z=438.0 $[M+H]^+$.

$^1$H NMR (400 MHz, DMSO-$d_6$) δ=8.70 (d, J=7.9 Hz, 1H), 7.98 (s, 1H), 6.78 (d, J=7.9 Hz, 1H), 5.61 (d, J=5.1 Hz, 1H), 5.09 (q, J=6.5 Hz, 1H), 3.98-3.92 (m, 1H), 3.92-3.85 (m, 1H), 3.81-3.70 (m, 5H), 3.67 (br dd, J=6.1, 9.3 Hz, 1H), 3.52 (br s, 4H), 3.08-2.99 (m, 1H), 1.95 (br d, J=5.4 Hz, 1H), 1.89-1.74 (m, 1H).

[(3aS,4R,6aR)-2,3,3a,4,5,6a-hexahydrofuro[2,3-b]furan-4-yl]-4-(3-pyrazin-2-ylpyrazolo[1,5-a]pyrimidin-5-yl)piperazine-1-carboxylate

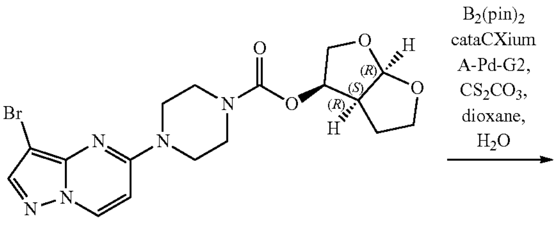

2

-continued

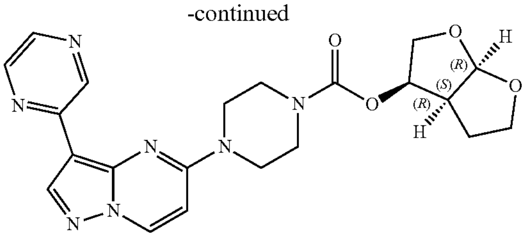

I-66

A mixture of [(3aS,4R,6aR)-2,3,3a,4,5,6a-hexahydrofuro[2,3-b]furan-4-yl] 4-(3-bromopyrazolo[1,5-a]pyrimidin-5-yl)piperazine-1-carboxylate (300 mg, 684.50 μmol, 1 eq), 2-iodopyrazine (141.00 mg, 684.50 μmol, 67.59 μL, 1 eq), 4,4,5,5-tetramethyl-2-(4,4,5,5-tetramethyl-1,3,2-dioxaborolan-2-yl)-1,3,2-dioxaborolane (347.64 mg) 1.37 mmol, 2 eq), $Cs_2CO_3$ (669.07 mg, 2.05 mmol, 3 eq) and [2-(2-aminophenyl)phenyl]-chloro-palladium; bis(1-adamantyl)-butyl-phosphane (91.54 mg, 136.90 μmol, 0.2 eq) in dioxane (3 mL) and $H_2O$ (0.3 mL) was degassed and purged with $N_2$ for 3 times, and then the mixture was stirred at 90° C. for 3 hr under $N_2$ atmosphere. The reaction mixture was diluted with $H_2O$ (10 mL) and extracted with EA (20 mL×3). The combined organic layers were dried over $Na_2SO_4$, filtered and concentrated under reduced pressure to give a residue. The residue was purified by prep-TLC ($SiO_2$, DCM: MeOH=10:1) to give crude product. Then the crude was further purified by prep. HPLC (column: Waters xbridge 150*25 mm 10 um; mobile phase: [water ($NH_4HCO_3$)-MeCN]; gradient: 17%-47% B over 14 min). The pure fractions were collected and the volatiles were removed under vacuum. The residue was partitioned between acetonitrile (20 mL) and water (100 mL). The solution was lyophilized to dryness to give the product. [(3aS,4R,6aR)-2,3,3a,4,5,6a-hexahydrofuro[2,3-b]furan-4-yl] 4-(3-pyrazin-2-ylpyrazolo[1,5-a]pyrimidin-5-yl)piperazine-1-carboxylate (1.39 mg, 2.92 μmol, 4.27e-1% yield, 91.884% purity) was obtained as a purple solid.

LCMS m/z=438.2 $[M+H]^+$.

Compound I-66

LCMS m/z=438.2 $[M+H]^+$.

SFC $t_R$=1.298, 100%.

$^1H$ NMR (400 MHz, methanol-$d_4$) δ=9.58 (s, 1H), 8.62-8.45 (m, 3H), 8.29 (d, J=1.8 Hz, 1H), 6.79 (d, J=8.0 Hz, 1H), 5.70 (d, J=5.0 Hz, 1H), 5.27-5.13 (m, 1H), 4.09-4.03 (m, 1H), 4.01-3.92 (m, 2H), 3.91-3.86 (m, 4H), 3.85-3.81 (m, 1H), 3.72-3.66 (m, 4H), 3.19-3.09 (m, 1H), 2.14-2.06 (m, 1H), 2.01-1.91 (m, 1H).

Example 60: Synthesis of Compound I-67

[(3aS,4R,6aR)-2,3,3a,4,5,6a-hexahydrofuro[2,3-b]furan-4-yl] 4-(3-pyrimidin-4-ylpyrazolo[1,5-a]pyrimidin-5-yl)piperazine-1-carboxylate

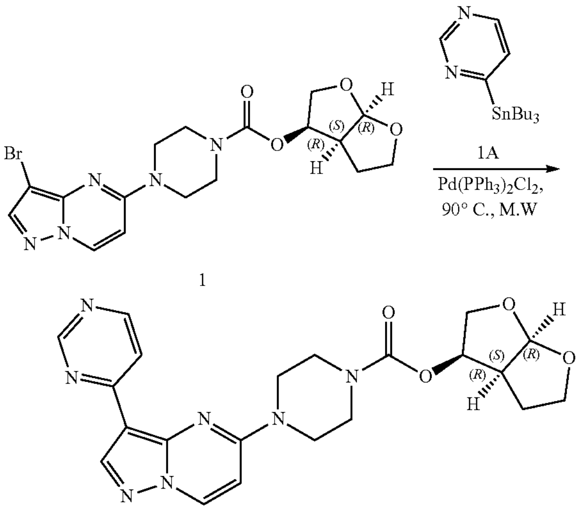

1

I-67

[(3aS,4R,6aR)-2,3,3a,4,5,6a-hexahydrofuro[2,3-b]furan-4-yl] 4-(3-bromopyrazolo[1,5-a]pyrimidin-5-yl)piperazine-1-carboxylate (100 mg, 228.17 μmol, 1 eq), tributyl(pyrimidin-4-yl) stannane (109.49 mg, 296.62 μmol, 1.3 eq) and $Pd(PPh_3)_2Cl_2$ (32.03 mg, 45.63 μmol, 0.4 eq) was added into a microwave tube in DMF (1 mL). The sealed tube was degassed and purged with $N_2$ for 3 times, and heated at 90° C. for 3 hr under microwave and $N_2$ atmosphere. The mixture was diluted with ethyl acetate (10 mL). The organic layer was washed with brine (2×10 mL), dried over $Na_2SO_4$ and evaporated under reduced pressure to afford the product. The residue was purified by prep-TLC ($SiO_2$, DCM: MeOH=10:1). Then the product was further purified by prep. HPLC (column: Waters xbridge 150*25 mm 10 um; mobile phase: [water ($NH_4HCO_3$)-MeCN]; gradient: 14%-44% B over 10 min). The pure fractions were collected and the volatiles were removed under vacuum. The residue was partitioned between acetonitrile (20 mL) and water (100 mL). The solution was lyophilized to dryness to give [(3aS,4R,6aR)-2,3,3a,4,5,6a-hexahydrofuro[2,3-b]furan-4-yl] 4-(3-pyrimidin-4-ylpyrazolo[1,5-a]pyrimidin-5-yl)piperazine-1-carboxylate (2.15 mg, 4.70 μmol, 2.06% yield, 95.686% purity) as a powder.

LCMS $t_R$=0.459 min 5-95CD_1 min, column: (Gemini@5umNX-C18 110A 2*30 mm, 5 um). m/z=438.1 $[M+H]^+$.

Compound I-67

LCMS m/z=438.1 $[M+H]^+$.

SFC $t_R$=1.150, 100%).

$^1H$ NMR (400 MHz, DMSO-$d_6$) δ=9.00 (d, J=1.3 Hz, 1H), 8.83 (d, J=7.9 Hz, 1H), 8.67 (d, J=5.5 Hz, 1H), 8.56 (s, 1H), 8.33-8.23 (m, 1H), 6.88 (d, J=7.9 Hz, 1H), 5.62 (d, J=5.1 Hz, 1H), 5.17-5.04 (m, 1H), 3.98-3.94 (m, 1H), 3.92-3.89 (m, 1H), 3.88-3.83 (m, 4H), 3.79-3.75 (m, 1H), 3.71-3.66 (m, 1H), 3.60-3.54 (m, 4H), 3.07-3.02 (m, 1H), 2.00-1.96 (m, 1H), 1.87-1.79 (m, 1H).

Example 61: Synthesis of Compound I-68

3-[2-(cyclopropoxy)phenyl]-5-piperazin-1-yl-pyrazolo[1,5-a]pyrimidine

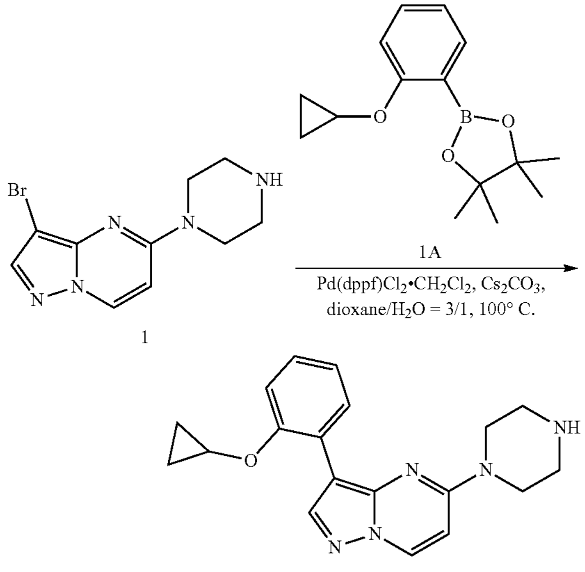

1

2

A mixture of 3-bromo-5-piperazin-1-yl-pyrazolo[1,5-a]pyrimidine (500 mg, 1.77 mmol, 1 eq), 2-[2-(cyclopropoxy)phenyl]-4,4,5,5-tetramethyl-1,3,2-dioxaborolane (461.01 mg, 1.77 mmol, 1 eq), $Cs_2CO_3$ (1.73 g, 5.32 mmol, 3 eq), $Pd(dppf)Cl_2{\cdot}CH_2Cl_2$ (289.44 mg, 354.43 μmol, 0.2 eq) in dioxane (9 mL) and $H_2O$ (3 mL) was degassed and purged with $N_2$ for 3 times, and then the mixture was stirred at 100°

C. for 1 hr under $N_2$ atmosphere. The mixture was concentrated to the crude product. The crude was purified by FCC (ISCO®; 12 g SepaFlash® Silica Flash Column, Eluent of 0~17% MeOH/DCM gradient @ 60 mL/min) to give 3-[2-(cyclopropoxy)phenyl]-5-piperazin-1-yl-pyrazolo[1,5-a]pyrimidine (450 mg, 1.21 mmol, 68.31% yield, 90.232% purity) as black gum.

LCMS m/z=336.4 $[M+H]^+$.

$^1$H NMR (400 MHz, DMSO-$d_6$) δ=8.64 (br d, J=7.9 Hz, 1H), 8.35 (br d, J=7.6 Hz, 1H), 8.30 (s, 1H), 7.36 (br d, J=8.1 Hz, 1H), 7.15 (br t, J=7.6 Hz, 1H), 7.02 (br t, J=7.4 Hz, 1H), 6.74 (br d, J=7.9 Hz, 1H), 3.89 (br s, 1H), 3.63 (br s, 4H), 3.30-3.17 (m, 1H), 2.80 (br s, 4H), 0.86-0.77 (m, 2H), 0.74 (br s, 2H).

[(3aS,4R,6aR)-2,3,3a,4,5,6a-hexahydrofuro[2,3-b]furan-4-yl] 4-[3-[2-(cyclopropoxy)phenyl]pyrazolo[1,5-a]pyrimidin-5-yl]piperazine-1-carboxylate

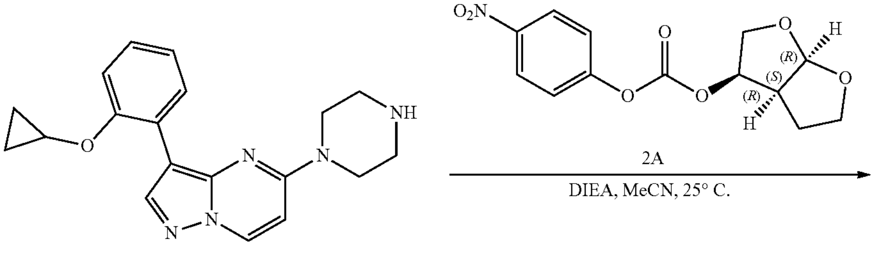

2

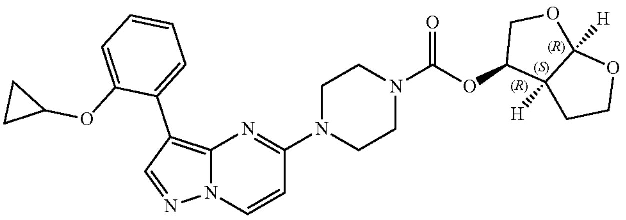

I-68

To a solution of 3-[2-(cyclopropoxy)phenyl]-5-piperazin-1-yl-pyrazolo[1,5-a]pyrimidine (200 mg, 596.30 μmol, 1 eq) and DIEA (154.13 mg, 1.19 mmol, 207.73 μL, 2 eq) in MeCN (2 mL) was added [(3aS,4R,6aR)-2,3,3a,4,5,6a-hexahydrofuro[2,3-b]furan-4-yl] (4-nitrophenyl) carbonate (176.05 mg, 596.30 μmol, 1 eq). The mixture was stirred at 25° C. for 1 hr. The mixture was concentrated to give crude product. The product was purified by prep. HPLC (Column: Waters xbridge 150*25 mm 10 um; mobile phase: [water ($NH_4HCO_3$)-MeCN]; gradient: 33%-63% B over 14 min) to give the product [(3aS,4R,6aR)-2,3,3a,4,5,6a-hexahydrofuro[2,3-b]furan-4-yl]-4-[3-[2-(cyclopropoxy)phenyl]pyrazolo[1,5-a]pyrimidin-5-yl]piperazine-1-carboxylate (108.59 mg, 219.78 μmol, 36.86% yield, 99.484% purity) as a solid. Compound I-68

LCMS m/z=492.2 $[M+H]^+$.

SFC $t_R$=2.112 min; 100%.

$^1$H NMR (400 MHz, DMSO-$d_6$) δ=8.71 (d, J=7.8 Hz, 1H), 8.36-8.32 (m, 1H), 8.31 (s, 1H), 7.37 (d, J=8.2 Hz, 1H), 7.21-7.13 (m, 1H), 7.09-6.98 (m, 1H), 6.77 (d, J=7.8 Hz, 1H), 5.61 (d, J=5.2 Hz, 1H), 5.13-5.05 (m, 1H), 3.98-3.84 (m, 3H), 3.82-3.71 (m, 5H), 3.71-3.64 (m, 1H), 3.60-3.47 (m, 4H), 3.11-2.95 (m, 1H), 2.01-1.92 (m, 1H), 1.88-1.75 (m, 1H), 0.91-0.67 (m, 4H).

Example 62: Synthesis of Compound I-69

3-(2-methoxyphenyl)-5-(piperazin-1-yl)pyrazolo[1,5-a]pyrimidine

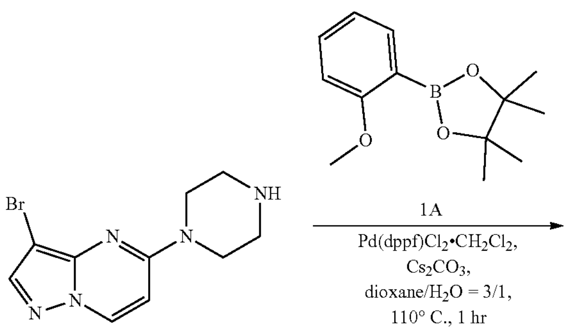

1

-continued

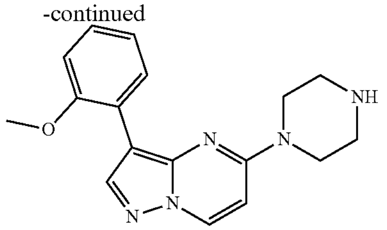

2

The product 2 was prepared according to the synthesis method of I-58. Compound 3-(2-methoxyphenyl)-5-(piperazin-1-yl)pyrazolo[1,5-a]pyrimidine (0.3 g, 601.23 μmol, 28.27% yield, 62% purity) was obtained as an oil.

$^1$H NMR (400 MHz, $CDCl_3$) δ=8.55 (s, 1H), 8.39 (dd, J=1.6, 7.6 Hz, 1H), 7.88 (d, J=2.1 Hz, 1H), 7.20 (dt, J=1.8, 7.8 Hz, 1H), 7.07 (dt, J=0.9, 7.5 Hz, 1H), 6.99 (d, J=8.3 Hz, 1H), 6.12 (d, J=1.8 Hz, 1H), 3.93 (s, 3H), 3.68 (br s, 4H), 3.00 (br d, J=5.0 Hz, 4H).

(3R,3aS,6aR)-hexahydrofuro[2,3-b]furan-3-yl 4-(3-(2-methoxyphenyl)pyrazolo[1,5-a]pyrimidin-5-yl)piperazine-1-carboxylate

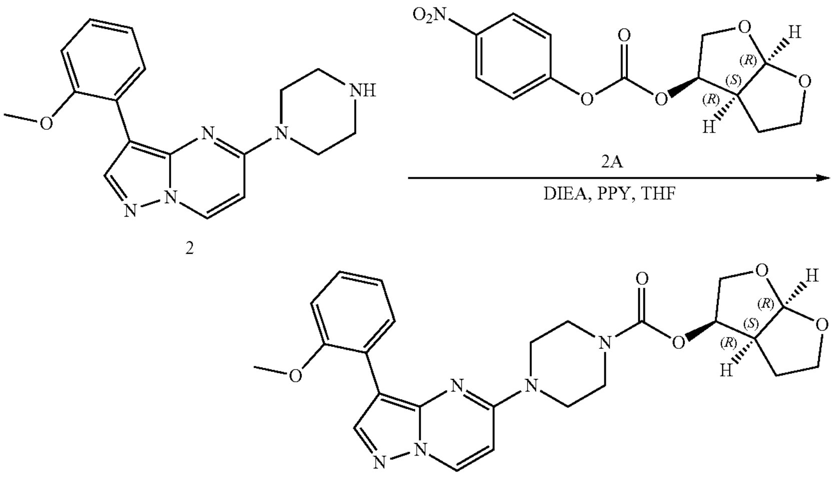

I-69

The product I-69 was prepared according to the synthesis method of I-58. Compound (3R,3aS,6aR)-hexahydrofuro[2,3-b]furan-3-yl 4-(3-(2-methoxyphenyl)pyrazolo[1,5-a]pyrimidin-5-yl)piperazine-1-carboxylate (97.48 mg, 200.83 μmol, 24.85% yield, 95.90% purity) was obtained.

Compound I-69

LCMS m/z=466.1 $[M+H]^+$.

SFC $t_R$=0.648 min; 100%).

$^1$H NMR (400 MHz, DMSO-$d_6$) δ=8.75-8.70 (m, 1H), 8.43 (s, 1H), 8.39-8.34 (m, J=1.6, 7.6 Hz, 1H), 7.19-7.13 (m, 1H), 7.08-6.98 (m, 2H), 6.78 (d, J=7.9 Hz, 1H), 5.61 (d, J=5.1 Hz, 1H), 5.12-5.06 (m, 1H), 3.98-3.92 (m, J=6.2, 9.4 Hz, 1H), 3.90-3.85 (m, 4H), 3.79-3.73 (m, 5H), 3.70-3.65 (m, J=6.2, 9.4 Hz, 1H), 3.54 (s, 4H), 3.07-2.99 (m, 1H), 2.02-1.93 (m, 1H), 1.88-1.74 (m, 1H).

Example 63: Synthesis of Compound I-70

Tert-butyl (2-((3-(2-methoxypyridin-3-yl)pyrazolo[1,5-a]pyrimidin-5-yl)amino)ethyl)(methyl)carbamate

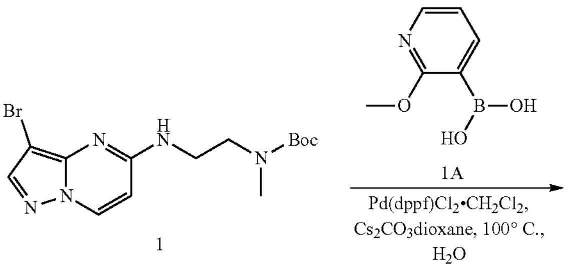

-continued

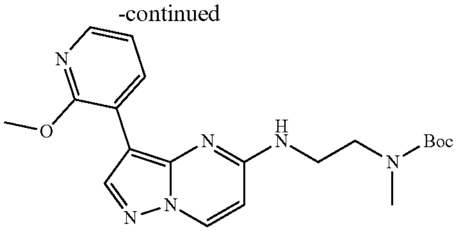

2

The product 2 was prepared according to the synthesis method of I-58. The product tert-butyl (2-((3-(2-methoxypyridin-3-yl)pyrazolo[1,5-a]pyrimidin-5-yl)amino)ethyl)-(methyl) carbamate (460 mg, 834.14 μmol, 61.77% yield, 72.254% purity) was obtained as black solid.

LCMS m/z=399.3 $[M+H]^+$.

$^1$H NMR (400 MHz, $CDCl_3$): δ=8.77 (br s, 1H), 8.50 (s, 1H), 8.14 (br d, J=4.8 Hz, 1H), 7.94 (br d, J=3.5 Hz, 1H), 7.19 (s, 1H), 6.89 (dd, J=5.0, 7.4 Hz, 1H), 5.97 (br d, J=7.5 Hz, 1H), 4.02 (s, 3H), 3.60 (br d, J=5.1 Hz, 2H), 3.53-3.48 (m, 2H), 2.86 (s, 3H), 1.38 (s, 9H).

N[1]-(3-(2-methoxypyridin-3-yl)pyrazolo[1,5-a]pyrimidin-5-yl)-N2-methylethane-1,2-diamine

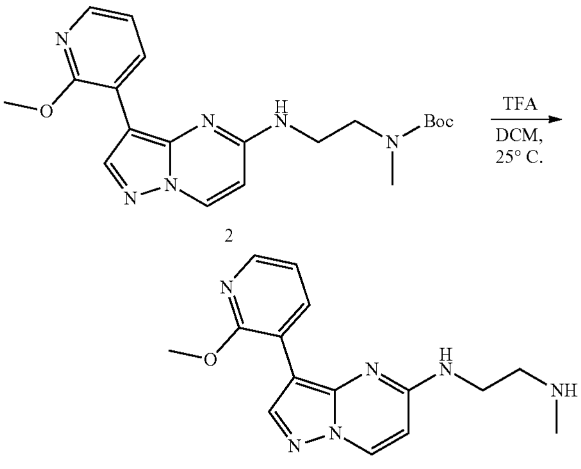

2

3

To a solution of tert-butyl (2-((3-(2-methoxypyridin-3-yl)pyrazolo[1,5-a]pyrimidin-5-yl)amino)ethyl)(methyl)carbamate (460 mg, 834.14 μmol, 1 eq) in DCM (6 mL) was added TFA (2 mL). The mixture was stirred at 25° C. for 1 hr. LCMS showed that desired MS was found. The mixture was concentrated to give N[1]-(3-(2-methoxypyridin-3-yl)pyrazolo[1,5-a]pyrimidin-5-yl)-N2-methylethane-1,2-diamine (500 mg, crude, TFA) as an oil.

LCMS m/z=299.0 $[M+H]^+$.

$^1$H NMR (400 MHz, DMSO-$d_6$): δ=8.69 (br d, J=7.4 Hz, 1H), 8.46 (br d, J=7.4 Hz, 2H), 8.31 (s, 1H), 7.85 (br d, J=4.4 Hz, 1H), 6.97-6.88 (m, 1H), 6.24 (br d, J=7.4 Hz, 1H), 3.87 (s, 3H), 3.58 (br s, 2H), 3.11 (br s, 2H), 3.06-2.97 (m, 1H), 2.38 (br s, 3H).

(3R,3aS,6aR)-hexahydrofuro[2,3-b]furan-3-yl (2-((3-(2-methoxypyridin-3-yl)pyrazolo[1,5-a]pyrimidin-5-yl)amino)ethyl)(methyl)carbamate

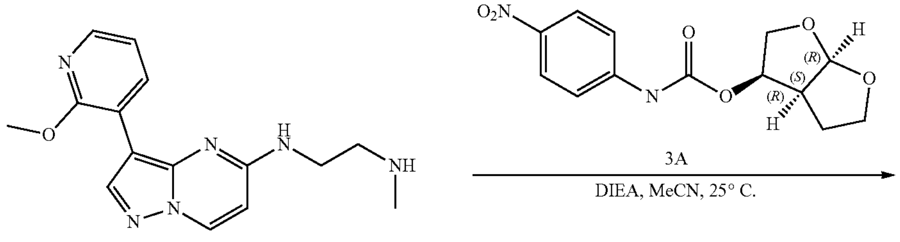

3

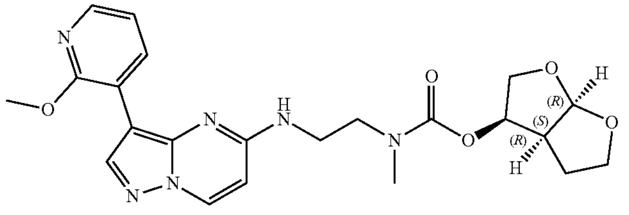

I-70

The product I-70 was prepared according to the synthesis method of I-58 (The product (3R,3aS,6aR)-hexahydrofuro[2,3-b]furan-3-yl (2-((3-(2-methoxypyridin-3-yl)pyrazolo[1,5-a]pyrimidin-5-yl)amino)ethyl)(methyl)carbamate (51.49 mg, 111.44 μmol, 45.96% yield, 98.365% purity) was obtained as a powder.

Compound I-70

LCMS m/z=455.2 $[M+H]^+$.

SFC $t_R$=1.435 min; 100%.

$^1$H NMR (400 MHz, DMSO-$d_6$): 8.99-8.79 (m, 1H), 8.58-8.47 (m, 1H), 8.42 (s, 1H), 7.99-7.92 (m, 1H), 7.90-7.75 (m, 1H), 7.09-6.98 (m, 1H), 6.36-6.25 (m, 1H), 5.58-5.44 (m, 1H), 5.01-4.87 (m, 1H), 3.99 (s, 3H), 3.89-3.64 (m, 2H), 3.63-3.46 (m, 5H), 3.45-3.33 (m, 1H), 2.91 (s, 3H), 2.89-2.80 (m, 1H), 1.85-1.42 (m, 2H).

Example 64: Synthesis of Compound I-71

Tert-butyl (2-((3-bromopyrazolo[1,5-a]pyrimidin-5-yl)amino)ethyl)(methyl)carbamate

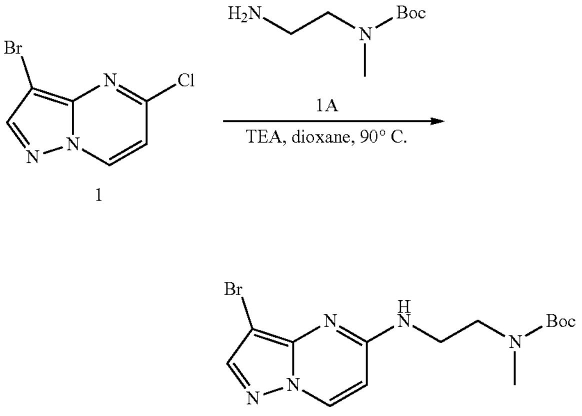

1

2

To a solution of 3-bromo-5-chloro-pyrazolo[1,5-a]pyrimidine (10 g, 43.02 mmol, 1 eq), tert-butyl N(2-amino-ethyl)-N-methyl-carbamate (7.50 g, 43.02 mmol, 7.69 mL, 1 eq) in dioxane (60 mL) was added TEA (8.71 g, 86.03 mmol, 11.98 mL, 2 eq). The mixture was stirred at 90° C. for 4 hr. The reaction mixture was concentrated under reduced pressure. The crude was purified by flash silica gel chromatography (ISCO®; 120 g SepaFlash® Silica Flash Column, eluent of 0~30% ethylacetate/petroleum ether gradient @ 100 mL/min) to give tert-butyl (2-((3-bromopyrazolo[1,5-a]pyrimidin-5-yl)amino)ethyl)(methyl)carbamate (10.01 g, 26.50 mmol, 61.59% yield, 98% purity) as a solid.

LCMS m/z=370.0 $[M+H]^+$.

Tert-butyl (2-((3-(2-cyclopropoxypyridin-3-yl)pyrazolo[1,5-a]pyrimidin-5-yl)amino)ethyl)(methyl)carbamate

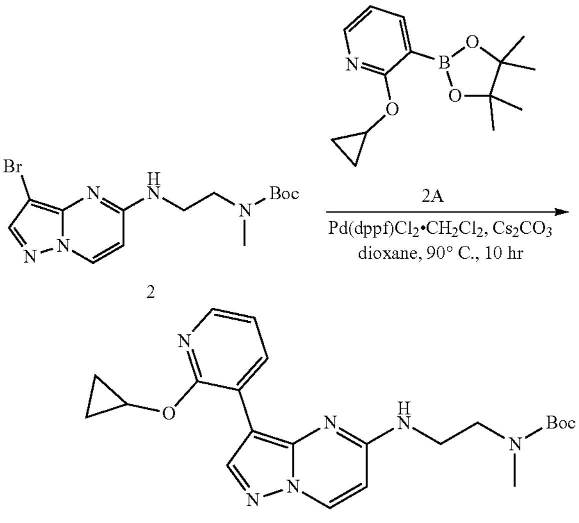

2

3

The product 3 was prepared according to the synthesis method of I-58. The product tert-butyl (2-((3-(2-cyclopropoxypyridin-3-yl)pyrazolo[1,5-a]pyrimidin-5-yl)amino)ethyl)(methyl)carbamate (412 mg, 463.93 μmol, 34.35% yield, 47.8% purity) was obtained as an oil).

$^1$H NMR (400 MHz, DMSO-$d_6$) δ=9.01-8.80 (m, 1H), 8.53-8.45 (m, 1H), 8.27 (s, 1H), 8.02-7.96 (m, 1H), 7.54-7.46 (m, 1H), 6.36-6.25 (m, 1H), 5.95 (s, 1H), 4.48-4.33 (m, 1H), 3.57-3.50 (m, 2H), 3.31 (s, 3H), 2.84 (br s, 2H), 1.24 (br s, 9H), 0.85-0.76 (m, 4H).

$N^1$-(3-(2-cyclopropoxypyridin-3-yl)pyrazolo[1,5-a]pyrimidin-5-yl)-N2-methylethane-1,2-diamine

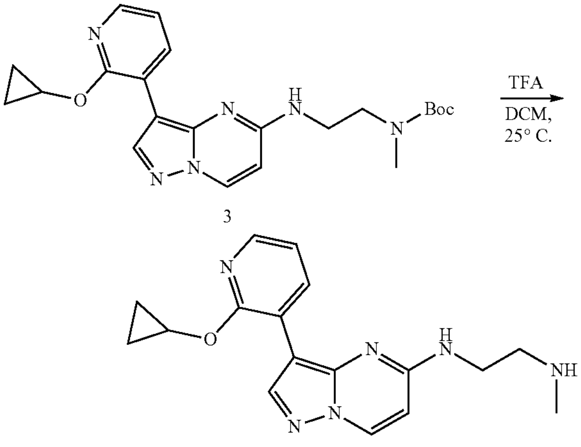

3

4

To a solution of tert-butyl (2-((3-(2-cyclopropoxypyridin-3-yl)pyrazolo[1,5-a]pyrimidin-5-yl)amino)ethyl)(methyl)carbamate (412 mg, 970.57 μmol, 1 eq) in DCM (3 mL) was added TFA (1.54 g, 13.46 mmol, 1 mL, 13.87 eq). The mixture was stirred at 25° C. for 1 hr. LCMS showed that desired MS was found. The reaction mixture was concentrated under reduced pressure to give $N^1$-(3-(2-cyclopropoxypyridin-3-yl)pyrazolo[1,5-a]pyrimidin-5-yl)-N2-methylethane-1,2-diamine (300 mg, crude) as an oil.

LCMS m/z=325.1 $[M+H]^+$.

(3R,3aS,6aR)-hexahydrofuro[2,3-b]furan-3-yl (2-((3-(2-cyclopropoxypyridin-3-yl)pyrazolo[1,5-a]pyrimidin-5-yl)amino)ethyl)(methyl)carbamate

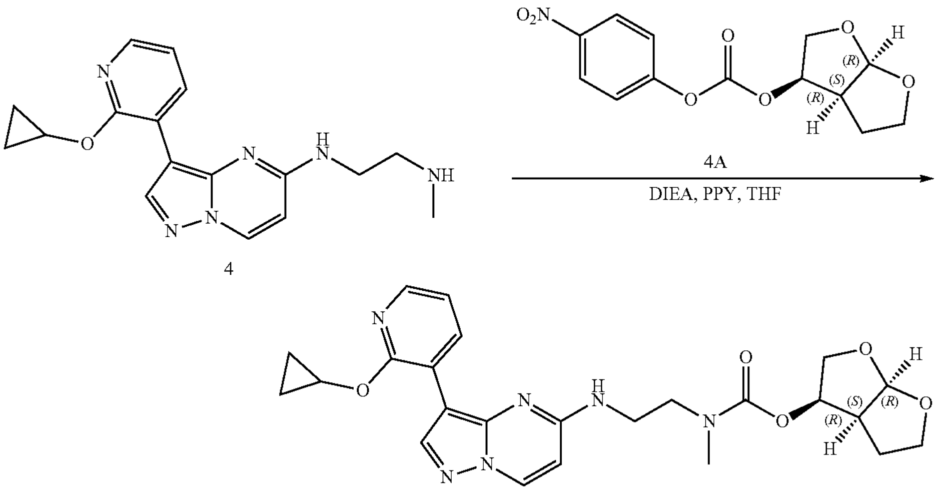

4

I-71

The product I-71 was prepared according to the synthesis method of I-58. The product (3R,3aS,6aR)-hexahydrofuro[2,3-b]furan-3-yl (2-((3-(2-cyclopropoxypyridin-3-yl)pyrazolo[1,5-a]pyrimidin-5-yl)amino)ethyl)(methyl)carbamate (24.29 mg, 49.92 μmol, 16.19% yield, 98.75% purity) was obtained as a solid.

Compound I-71

LCMS m/z=481.1 $[M+H]^+$.

SFC $t_R$=0.488 min; 100%.

$^1$H NMR (400 MHz, DMSO-$d_6$) δ=8.97-8.81 (m, 1H), 8.52 (t, J=7.3 Hz, 1H), 8.28 (s, 1H), 8.00 (s, 1H), 7.90-7.77 (m, 1H), 7.15-7.03 (m, 1H), 6.41-6.23 (m, 1H), 5.59-5.46 (m, 1H), 5.02-4.87 (m, 1H), 4.48-4.36 (m, 1H), 3.88-3.79 (m, 1H), 3.72-3.47 (m, 6H), 3.42 (s, 1H), 2.91 (s, 3H), 2.90-2.77 (m, 1H), 1.77-1.43 (m, 2H), 0.83-0.77 (m, 4H).

Example 65: Synthesis of Compound I-72

5-chloro-3-[2-(cyclopropoxy)-3-pyridyl]pyrazolo[1,5-a]pyrimidine

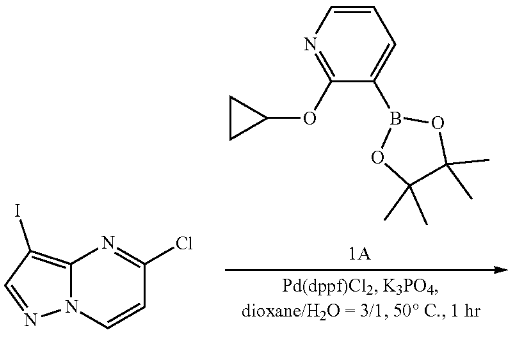

1

-continued

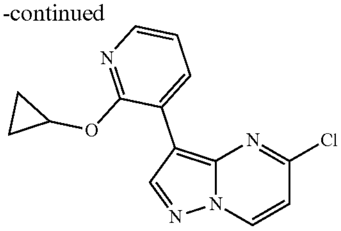

2

A mixture of 5-chloro-3-iodo-pyrazolo[1,5-a]pyrimidine (2.7 g, 9.66 mmol, 1 eq), 2-(cyclopropoxy)-3-(4,4,5,5-tetramethyl-1,3,2-dioxaborolan-2-yl)pyridine (2.52 g, 9.66 mmol, 1 eq), $K_3PO_4$ (6.15 g, 28.98 mmol, 3 eq), Pd(dppf)$Cl_2$ (1.41 g, 1.93 mmol, 0.2 eq) in dioxane/$H_2O$=3/1 (27 mL) was degassed and purged with $N_2$ for 3 times, and then the mixture was stirred at 50° C. for 1 hr under $N_2$ atmosphere. TLC (PE:EA=3:1, $R_f$=0.49) showed a new spot. The reaction mixture was concentrated under reduced pressure to give a residue. The residue was purified by flash silica gel chromatography (ISCO®; 40 g SepaFlash® Silica Flash Column, eluent of 0~8% Ethyl acetate/Petroleum ether gradient @ 70 mL/min). The product 5-chloro-3-[2-(cyclopropoxy)-3-pyridyl]pyrazolo[1,5-a]pyrimidine (856 mg, 2.99 mmol, 30.90% yield) was obtained as a solid.

LCMS m/z=286.9 $[M+H]^+$.

$^1$H NMR (400 MHz, $CDCl_3$) δ=8.70-8.58 (m, 3H), 8.18 (dd, J=1.9, 4.9 Hz, 1H), 7.08 (dd, J=4.9, 7.6 Hz, 1H), 6.85 (d, J=7.3 Hz, 1H), 4.46 (tt, J=3.2, 6.1 Hz, 1H), 0.89-0.84 (m, 4H).

[(3S)-5-oxopyrrolidin-3-yl] 4-[3-[2-(cyclopropoxy)-3-pyridyl]pyrazolo[1,5-a]pyrimidin-5-yl]-2,2,3,3,5,5,6,6-octadeuterio-piperazine-1-carboxylate

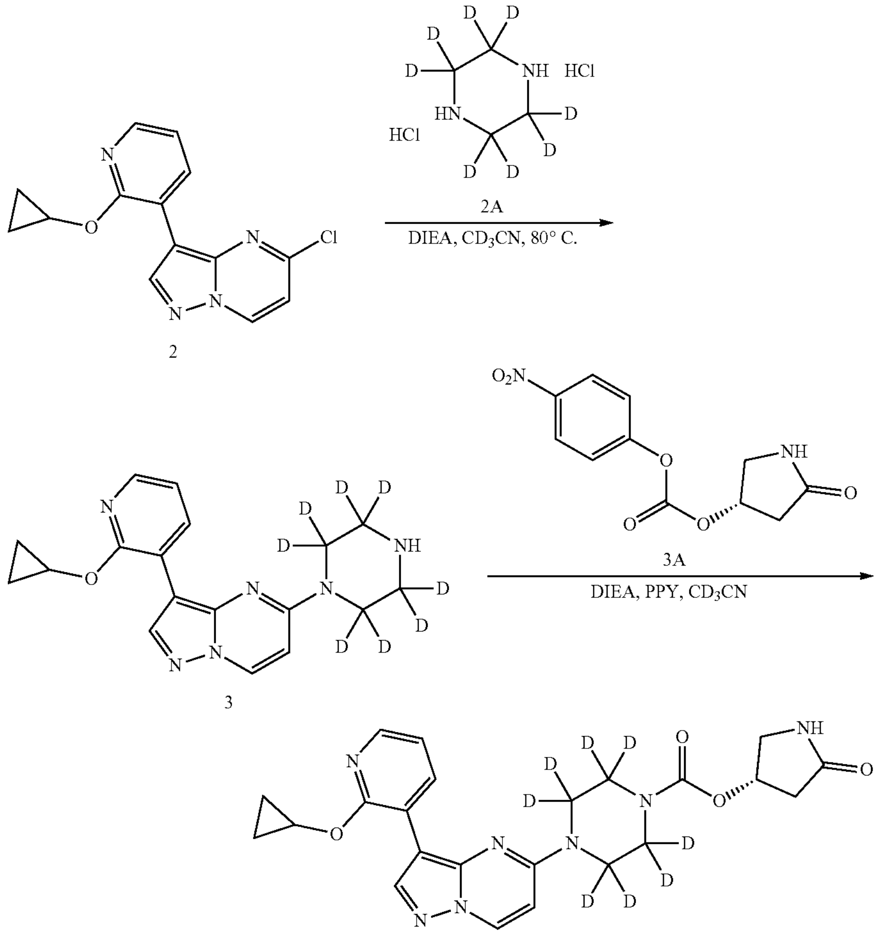

2

3

Compound I-72

To a solution of 5-chloro-3-[2-(cyclopropoxy)-3-pyridyl]pyrazolo[1,5-a]pyrimidine (460 mg, 1.60 mmol, 1 eq) in 2,2,2-trideuterioacetonitrile (5 mL) was added DIEA (829.42 mg, 6.42 mmol, 1.12 mL, 4 eq) and 2,2,3,3,5,5,6,6-octadeuteriopiperazine; dihydrochloride (294.91 mg, 1.76 mmol, 1.1 eq). The mixture was stirred at 80° C. for 0.3 hr. The deuterated ratio was tested by Special Analysis.

Then the mixture was added [(3S)-5-oxopyrrolidin-3-yl] carbonate (765.14 mg, 2.87 mmol, 1.8 eq) in 2,2,2-trideuterioacetonitrile (1 mL), DIEA (412.75 mg, 3.19 mmol, 556.27 μL, 2 eq) and 4-pyrrolidin-1-ylpyridine (47.33 mg, 319.36 μmol, 0.2 eq). The mixture was stirred at 25° C. for 1 hr. LCMS showed reactant 3 was consumed completely and desired mass was detected. The reaction mixture was filtered and concentrated under reduced pressure to give a residue. Then the product was further purified by prep. HPLC (column: Waters Xbridge BEH C18 250*50 mm*10 um; mobile phase: [water ($NH_4HCO_3$)-MeCN]; B %: 0%, isocratic elution mode) to give desired compound, which was further separated by prep. HPLC (column: Waters Xbridge BEH C18 250*50 mm*10 um; mobile phase: [water ($NH_4HCO_3$)-MeCN]; gradient: 19%-49% B over 10 min). The pure fractions were collected and the volatiles were removed under vacuum. The residue was partitioned between acetonitrile (2 mL) and water (10 mL). The solution was lyophilized to dryness to give the product. The product [(3S)-5-oxopyrrolidin-3-yl] 4-[3-[2-(cyclopropoxy)-3-pyridyl]pyrazolo[1,5-a]pyrimidin-5-yl]-2,2,3,3,5,5,6,6-octadeuterio-piperazine-1-carboxylate (290 mg, 605.35 μmol, 37.91% yield, 98.43% purity) was obtained as a solid.

Two batches were combined to give [(3S)-5-oxopyrrolidin-3-yl] 4-[3-[2-(cyclopropoxy)-3-pyridyl]pyrazolo[1,5-a]pyrimidin-5-yl]-2,2,3,3,5,5,6,6-octadeuterio-piperazine-1-carboxylate (377.91 mg, 782.05 μmol, 97.58% purity) as a solid.

LCMS $t_R$=0.291 min 5-95AB_0.8 min, column: (Kinetex® EVO C18 2.1×30 mm 5 um). m/z=345.2 $[M+H]^+$.

LCMS $t_R$=0.562 min 5-95N_1 min, column: (Shim-pack Scepter C18-120 2.1×33 mm 5 um). m/z=472.3 $[M+H]^+$.

Compound I-72

LCMS $t_R$=1.655 min 5-95AB_4 min, column: (Kinetex® EVO C18 3.0×50 mm 2.6 um) m/z=472.1 $[M+H]^+$.

SFC $t_R$=1.073 min; 100%).

$^1H$ NMR (400 MHz, DMSO-$d_6$) δ=8.79 (d, J=7.5 Hz, 1H), 8.74 (d, J=7.9 Hz, 1H), 8.34 (s, 1H), 8.04-7.98 (m, 1H), 7.73 (s, 1H), 7.11 (d, J=7.3 Hz, 1H), 6.80 (d, J=7.9 Hz, 1H), 5.20 (s, 1H), 4.44-4.36 (m, 1H), 3.61 (d, J=11.4 Hz, 1H), 3.24 (d, J=11.4 Hz, 1H), 2.64 (d, J=17.5 Hz, 1H), 2.16 (d, J=17.5 Hz, 1H), 0.82-0.75 (m, 4H).

Example 66: Synthesis of Compound I-73

[(3S)-1-methyl-5-oxo-pyrrolidin-3-yl]-4-[3-[2-(cyclopropoxy)-3-pyridyl]pyrazolo[1,5-a]pyrimidin-5-yl]-2,2,3,3,5,5,6,6-octadeuterio-piperazine-1-carboxylate

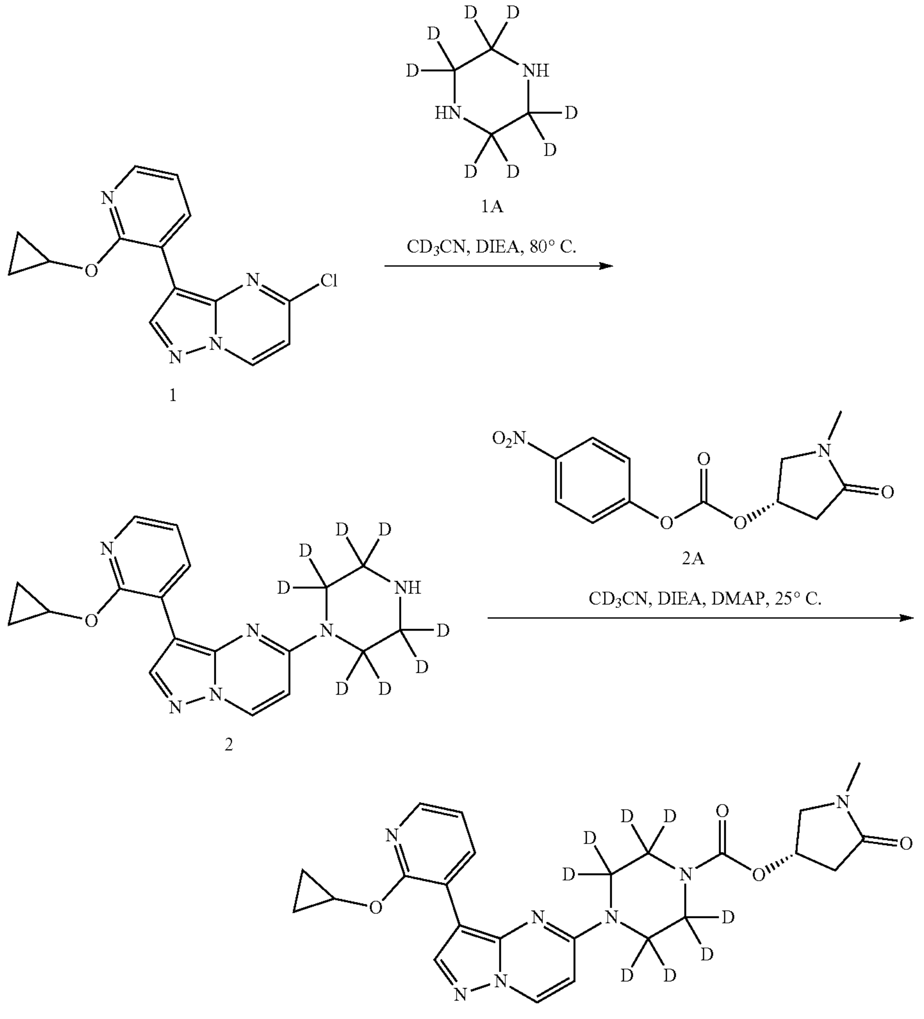

I-73

To a solution of 5-chloro-3-[2-(cyclopropoxy)-3-pyridyl]pyrazolo[1,5-a]pyrimidine (640 mg, 2.23 mmol, 1 eq) in 2,2,2-trideuterioacetonitrile (3 mL) was added DIEA (1.15 g, 8.93 mmol, 1.56 mL, 4 eq) and 2,2,3,3,5,5,6,6-octadeuteriopiperazine; dihydrochloride (410.31 mg, 2.46 mmol, 1.1 eq). The mixture was stirred at 80° C. for 0.5 hr. The mixture was stirred at 80° C. for 0.5 hr. LCMS showed reactant 1 was consumed completely and desired mass was detected.

Then the mixture was added [(3S)-1-methyl-5-oxo-pyrrolidin-3-yl](4-nitrophenyl) carbonate (618.33 mg, 2.21 mmol, 1 eq) in 2,2,2-trideuterioacetonitrile (3 mL) DIEA (570.34 mg, 4.41 mmol, 768.66 μL, 2 eq) and DMAP (53.91 mg, 441.30 μmol, 0.2 eq). The mixture was stirred at 25° C. for 0.5 hr. LCMS showed that desired MS was found. The mixture was concentrated to the crude product. The product was purified by prep. HPLC (column: Waters Xbridge BEH C18 250*50 mm*10 um; mobile phase: [water ($NH_4HCO_3$)-MeCN]; gradient: 22%-52% B over 10 min to give the product [(3S)-1-methyl-5-oxo-pyrrolidin-3-yl]-4-[3-[2-(cyclopropoxy)-3-pyridyl]pyrazolo[1,5-a]pyrimidin-5-yl]-2,2,3,3,5,5,6,6-octadeuterio-piperazine-1-carboxylate (314.98 mg, 647.92 μmol, 29.36% yield, 99.882% purity) as a powder.

Compound I-73

LCMS m/z=486.3 $[M+H]^+$.

SFC $t_R$=1.135 min; 100%.

$^1$H NMR (400 MHz, DMSO-$d_6$) δ=8.81-8.77 (m, 1H), 8.74 (d, J=7.8 Hz, 1H), 8.34 (s, 1H), 8.05-7.95 (m, 1H), 7.14-7.05 (m, 1H), 6.80 (d, J=7.8 Hz, 1H), 5.20-5.11 (m, 1H), 4.44-4.36 (m, 1H), 3.76-3.67 (m, 1H), 3.39-3.34 (m, 1H), 2.74 (s, 3H), 2.70 (d, J=7.4 Hz, 1H), 2.33-2.25 (m, 1H), 0.84-0.74 (m, 4H).

Example 67: Synthesis of Compound I-75

(4R)-4-[tert-butyl(diphenyl)silyl]oxy-1-(2-methoxyethyl)pyrrolidin-2-one

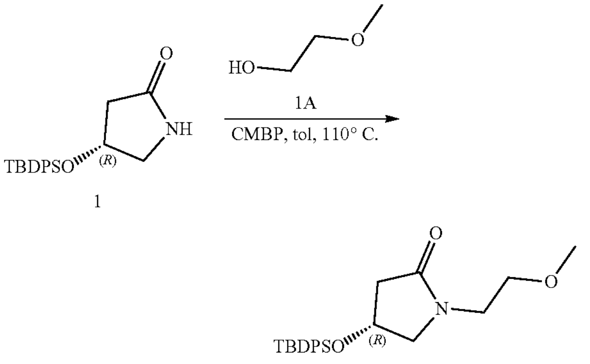

1

2

A mixture of (4R)-4-[tert-butyl(diphenyl)silyl]oxypyrrolidin-2-one (3 g, 8.84 mmol, 1 eq), 2-methoxyethanol (874.12 mg, 11.49 mmol, 1.3 eq), 2-(tributyl-phosphanylidene) acetonitrile (3.20 g, 13.25 mmol, 1.5 eq) in toluene (25 mL) was degassed and purged with $N_2$ for 3 times, and then the mixture was stirred at 110° C. for 2 hr under M.W. and N2 atmosphere. The reaction mixture was partitioned between DCM (25 mL) and $H_2O$ (50 mL). The organic phase was separated, and the inorganic phase was washed with DCM 150 mL (50 mL×3). The organic phases were combined and dried over $Na_2SO_4$, filtered and concentrated under reduced pressure to give a residue. The residue was purified by flash silica gel chromatography (ISCO®; 40 g SepaFlash® Silica Flash Column, eluent of 0~40% Ethyl acetate 1 Petroleum ether gradient @ 75 mL/min). Compound (4R)-4-[tert-butyl(diphenyl)silyl]oxy-1-(2-methoxyethyl)pyrrolidin-2-one (0.6 g, 1.51 mmol, 17.08% yield) was obtained as an oil.

LCMS m/z=398.1 $[M+H]^+$.

(4R)-4-hydroxy-1-(2-methoxyethyl)pyrrolidin-2-one

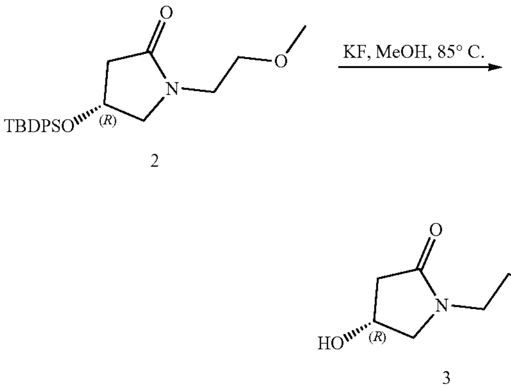

2

3

To a solution of (4R)-4-[tert-butyl(diphenyl)silyl]oxy-1-(2-methoxyethyl)pyrrolidin-2-one (600 mg, 1.51 mmol, 1 eq) in MeOH (6 mL) was added KF (438.38 mg, 7.55 mmol, 5 eq). The mixture was stirred at 85° C. for 10 hr. The reaction mixture was concentrated under reduced pressure to give a residue. The residue was purified by flash silica gel chromatography (ISCO®; 12 g SepaFlash® Silica Flash Column, eluent of 0~4% MeOH/DCM gradient @ 50 mL/min). Compound (4R)-4-hydroxy-1-(2-methoxyethyl) pyrrolidin-2-one (120 mg, 753.85 umol, 49.95% yield) was obtained as an oil.

LCMS m/z=160.1 $[M+H]^+$.

[(3R)-1-(2-methoxyethyl)-5-oxo-pyrrolidin-3-yl](4-nitrophenyl) carbonate

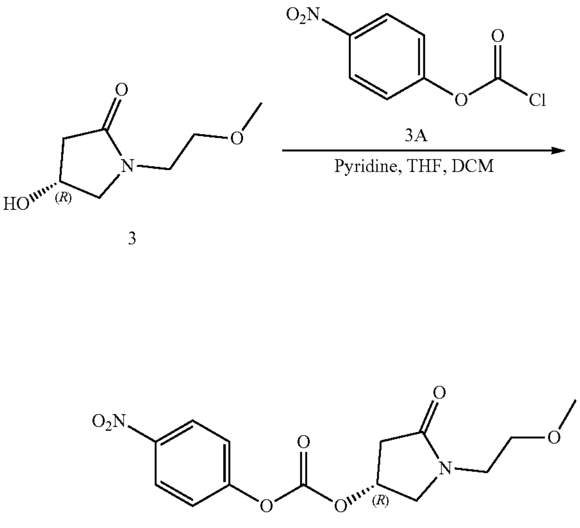

3

4

To a solution of (4R)-4-hydroxy-1-(2-methoxyethyl)pyrrolidin-2-one (120 mg, 753.85 μmol, 1 eq) and (4-nitrophenyl) carbonochloridate (455.85 mg, 2.26 mmol, 3 eq) in THF (0.6 mL) and DCM (2 mL) was added pyridine (178.89 mg, 2.26 mmol, 182.54 μL, 3 eq). The mixture was stirred at 25° C. for 1 hr. The reaction mixture was filtered and concentrated under reduced pressure to give a residue. The residue was purified by flash silica gel chromatography (ISCO®; 12 g SepaFlash® Silica Flash Column, eluent of 0~10% MeOH/DCM gradient @60 mL/min). Compound [(3R)-1-(2-methoxyethyl)-5-oxo-pyrrolidin-3-yl] (4-nitrophenyl) carbonate (200 mg, 616.74 μmol, 81.81% yield) was obtained as a solid.

LCMS m/z=325.0 $[M+H]^+$.

[(3R)-1-(2-methoxyethyl)-5-oxo-pyrrolidin-3-yl]-4-[3-[2-(cyclopropoxy)-3-pyridyl]pyrazolo[1,5-a]pyrimidin-5-yl]piperazine-1-carboxylate (I-75)

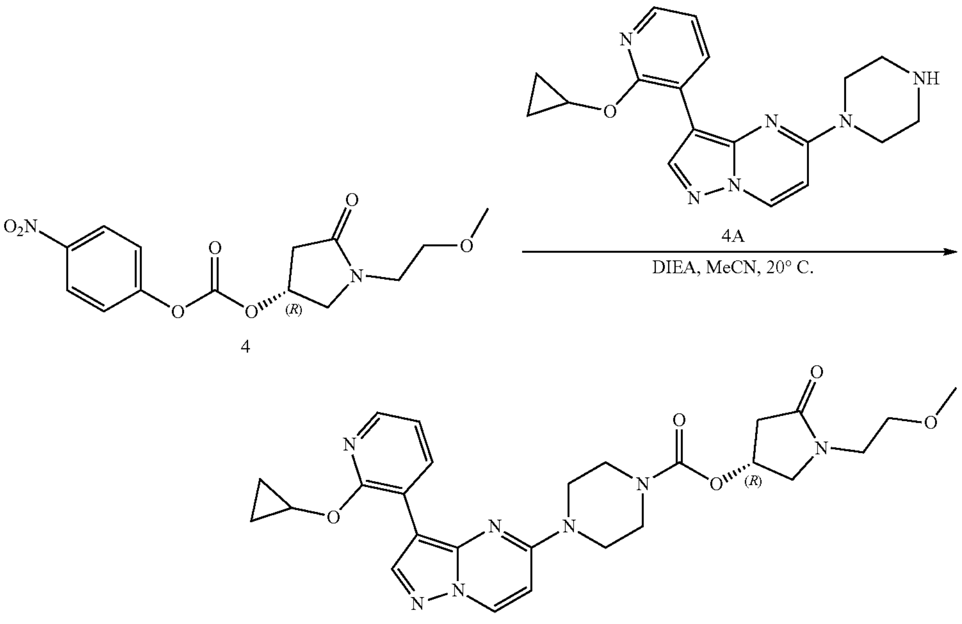

4

I-75

To a solution of [(3R)-1-(2-methoxyethyl)-5-oxo-pyrrolidin-3-yl](4-nitrophenyl) carbonate (180 mg, 555.07 μmol, 1 eq) and 3-[2-(cyclopropoxy)-3-pyridyl]-5-piperazin-1-yl-pyrazolo[1,5-a]pyrimidine (186.72 mg, 555.07 μmol, 1 eq) in MeCN (2 mL) was added DIEA (215.22 mg, 1.67 mmol, 290.05 μL, 3 eq). The mixture was stirred at 25° C. for 1 hr. The reaction mixture was concentrated under reduced pressure to give a residue. Then the residue was further purified by prep. HPLC (column: Welch Xtimate C18 250*50 mm*10 um; mobile phase: [water ($NH_3H_2O$+$NH_4HCO_3$)-MeCN]; gradient: 14%-54% B over 25 min). The pure fractions were collected and the volatiles were removed under vacuum. The residue was partitioned between acetonitrile (2 mL) and water (10 mL). The solution was lyophilized to dryness to give the product. Compound [(3R)-1-(2-methoxyethyl)-5-oxo-pyrrolidin-3-yl]-4-[3-[2-(cyclopropoxy)-3-pyridyl]pyrazolo[1,5-a]pyrimidin-5-yl]piperazine-1-carboxylate (70.59 mg, 135.34 μmol, 24.38% yield, 100% purity) was obtained as a solid.

Compound I-75

LCMS m/z=522.2 $[M+H]^+$.

SFC $t_R$=3.113 min; 100%.

$^1$H NMR (400 MHz, DMSO-$d_6$) δ=8.87-8.64 (m, 2H), 8.34 (s, 1H), 8.05-7.92 (m, 1H), 7.16-7.04 (m, 1H), 6.80 (d, J=7.9 Hz, 1H), 5.25-5.07 (m, 1H), 4.48-4.30 (m, 1H), 3.83-3.68 (m, 5H), 3.57-3.48 (m, 4H), 3.46-3.40 (m, 3H), 3.39-3.36 (m, 2H), 3.24 (s, 3H), 2.81-2.70 (m, 1H), 2.30 (d, J=17.4 Hz, 1H), 0.84-0.72 (m, 4H).

Example 68: Synthesis of Compound I-76

(4R)-4-[tert-butyl(diphenyl)silyl]oxy-1-isopropyl-pyrrolidin-2-one

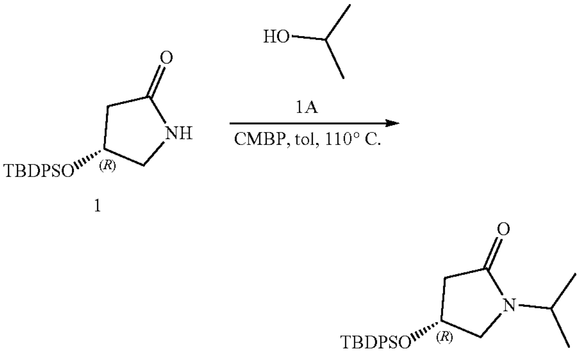

1

2

To a solution of propan-2-ol (354.02 mg, 5.89 mmol, 450.98 μL, 2 eq) in toluene (10 mL) was added 2-(tributylphosphanylidene) acetonitrile (1.07 g, 4.42 mmol, 1.5 eq) and (4R)-4-[tert-butyl(diphenyl)silyl]oxypyrrolidin-2-one (1 g, 2.95 mmol, 1 eq). The mixture was stirred at 110° C. for 3 hr under microwave and $N_2$ atmosphere. The reaction mixture was concentrated under reduced pressure to give a residue. The residue was purified by flash silica gel chromatography (ISCOR; 20 g SepaFlash® Silica Flash Column, eluent of 0~30% Ethyl acetate/Petroleum ether gradient to give (4R)-4-[tert-butyl(diphenyl)silyl]oxy-1-isopropyl-pyrrolidin-2-one (184 mg, 482.20 μmol, 16.37% yield) as a gum.

LCMS m/z=382.1 $M+1]^+$.

(4R)-4-hydroxy-1-isopropyl-pyrrolidin-2-one

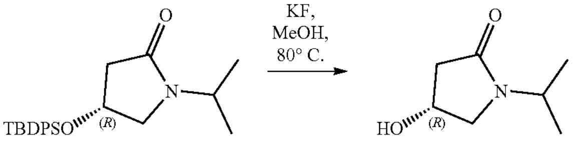

2 3

To a solution of (4R)-4-[tert-butyl(diphenyl)silyl]oxy-1-isopropyl-pyrrolidin-2-one (184 mg, 482.20 μmol, 1 eq) in MeOH (2 mL) was added KF (168.09 mg, 2.89 mmol, 6 eq). The mixture was stirred at 80° C. for 12 hr. TLC (DCM: MeOH=3:1) showed the new spot ($R_f$=0.18). The reaction mixture was concentrated under reduced pressure to give a residue. The residue was purified by flash silica gel chromatography (ISCO®; 4 g SepaFlash® Silica Flash Column, Eluent of 0~20% Methanol/Dichloromethane gradient @ 20 mL/min) to give (4R)-4-hydroxy-1-isopropyl-pyrrolidin-2-one (60 mg, 419.04 μmol, 86.90% yield) as a liquid.

$^1$H NMR (400 MHz, $CDCl_3$) δ=4.45 (ddd, J=2.5, 5.9, 8.8 Hz, 1H), 4.37-4.30 (m, 1H), 3.50 (dd, J=5.7, 10.8 Hz, 1H), 3.19 (dd, J=2.1, 10.9 Hz, 1H), 2.64 (dd, J=6.6, 17.3 Hz, 1H), 2.31 (dd, J=2.6, 17.3 Hz, 1H), 1.07 (dd, J=6.8, 15.9 Hz, 6H).

[(3R)-1-isopropyl-5-oxo-pyrrolidin-3-yl](4-nitrophenyl) carbonate

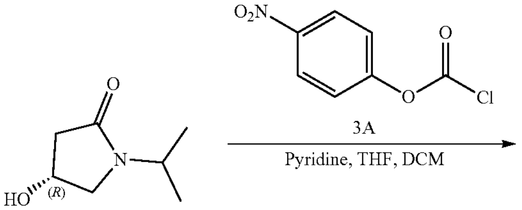

3

-continued

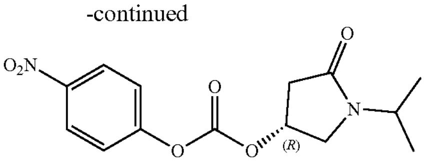

4

To a solution of (4R)-4-hydroxy-1-isopropyl-pyrrolidin-2-one (60 mg, 419.04 μmol, 1 eq) in DCM (0.5 mL) and THF (0.1 mL) was added pyridine (66.29 mg, 838.09 μmol, 67.65 μL, 2 eq) and (4-nitrophenyl) carbonochloridate (92.91 mg, 460.95 μmol, 1.1 eq). The mixture was stirred at 25° C. for 1 hr. LCMS showed reactant was consumed completely and desired mass was detected. The reaction mixture was concentrated under reduced pressure to give a residue. The residue was purified by flash silica gel chromatography (ISCO®; 4 g SepaFlash® Silica Flash Column, eluent of 0~100% Ethyl acetate/Petroleum ether gradient @ 20 mL/min) to give [(3R)-1-isopropyl-5-oxo-pyrrolidin-3-yl](4-nitrophenyl) carbonate (47 mg, 152.46 umol, 36.38% yield) as a liquid.

LCMS m/z=309.0 M+1]$^+$.

[(3R)-1-isopropyl-5-oxo-pyrrolidin-3-yl]-4-[3-[2-(cyclopropoxy)-3-pyridyl]pyrazolo[1,5-a]pyrimidin-5-yl]piperazine-1-carboxylate (I-76)

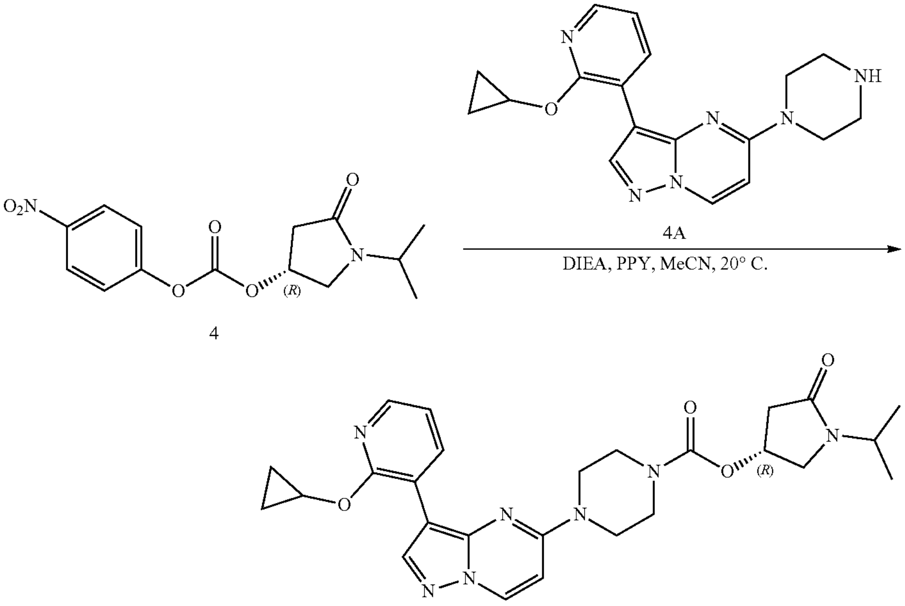

I-76

To a solution of 3-[2-(cyclopropoxy)-3-pyridyl]-5-piperazin-1-yl-pyrazolo[1,5-a]pyrimidine (61.54 mg, 182.95 µmol, 1.2 eq) in MeCN (1 mL) was added DIEA (59.11 mg, 457.37 µmol, 79.67 µL, 3 eq), [(3R)-1-isopropyl-5-oxo-pyrrolidin-3-yl](4-nitrophenyl) carbonate (47 mg, 152.46 µmol, 1 eq) and 4-pyrrolidin-1-ylpyridine (2.26 mg, 15.25 µmol, 0.1 eq). The mixture was stirred at 25° C. for 1 hr. The reaction mixture was concentrated under reduced pressure to give a residue. Then the product was further purified by prep. HPLC (Column: Waters Xbridge BEH C18 150*25 mm*5 um, Mobile Phase A: water ($NH_4HCO_3$), Mobile Phase B: acetonitrile, Flow rate: 25 mL/min, gradient condition from 27% B to 57%). The pure fractions were collected and the volatiles were removed under vacuum. The residue was partitioned between acetonitrile (2 mL) and water (10 mL). The solution was lyophilized to dryness give [(3R)-1-isopropyl-5-oxo-pyrrolidin-3-yl]-4-[3-[2-(cyclopropoxy)-3-pyridyl]pyrazolo[1,5-a]pyrimidin-5-yl]piperazine-1-carboxylate (54.65 mg, 105.31 µmol, 69.07% yield, 97.42% purity) as a solid.

Compound I-76

LCMS m/z=506.1 $[M+H]^+$.

SFC $t_R$=0.796 min; 100%.

$^1$H NMR (400 MHz, DMSO-$d_6$) δ=8.78 (d, J=7.6 Hz, 1H), 8.74 (d, J=7.9 Hz, 1H), 8.34 (s, 1H), 8.01 (d, J=4.9 Hz, 1H), 7.11 (d, J=7.6 Hz, 1H), 6.81 (d, J=7.9 Hz, 1H), 5.21-5.14 (m, 1H), 4.45-4.36 (m, 1H), 4.17 (t, J=13.6 Hz, 1H), 3.76 (s, 4H), 3.65 (d, J=11.4 Hz, 1H), 3.52 (t, J=5.2 Hz, 4H), 3.29 (d, J=1.6 Hz, 1H), 2.74 (d, J=17.4 Hz, 1H), 2.29 (d, J=17.4 Hz, 1H), 1.07 (d, J=7.7 Hz, 6H), 0.82-0.75 (m, 4H).

Example 69: Synthesis of Compound I-78

(4R)-4-[tert-butyl(diphenyl)silyl]oxy-1-methyl-pyrrolidin-2-one

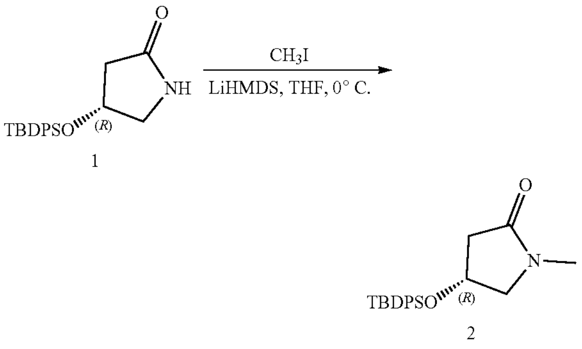

To a mixture of (4R)-4-[tert-butyl(diphenyl)silyl]oxypyrrolidin-2-one (6 g, 17.67 mmol, 1 eq) in THF (80 mL) was added [bis(trimethylsilyl)amino]lithium (1 M, 26.51 mL, 1.5 eq) at 0° C. for 30 min under $N_2$ atmosphere. Then iodomethane (7.53 g, 53.02 mmol, 3.30 mL, 3 eq) was added at 0° C. under $N_2$ atmosphere. The mixture was stirred at 25° C. for 1 hr. The mixture was quenched by saturation $NH_4Cl$ (aq.) (150 mL), and then extracted with EA (150 mL*3). The organic layers were combined and concentrated to give a residue. The residue was purified by flash silica gel chromatography (ISCO®; 80 g SepaFlash® Silica Flash Column, eluent of 0~30% Ethyl acetate/Petroleum ether gradient @ 100 mL/min). Compound (4R)-4-[tert-butyl(diphenyl)silyl]oxy-1-methyl-pyrrolidin-2-one (4.7 g, 13.29 mmol, 75.23% yield) was obtained as a solid.

LCMS m/z=354.1 $[M+H]^+$.

$^1$H NMR (400 MHz, DMSO-$d_6$) δ=7.60 (br d, J=6.8 Hz, 4H), 7.54-7.42 (m, 6H), 4.45 (br s, 1H), 3.46 (dd, J=5.8, 10.4 Hz, 1H), 3.21 (br d, J=10.4 Hz, 1H), 2.69 (s, 3H), 2.44 (br dd, J=6.7, 16.9 Hz, 1H), 2.15 (br d, J=16.6 Hz, 1H), 1.01 (s, 9H).

(4R)-4-hydroxy-1-methyl-pyrrolidin-2-one

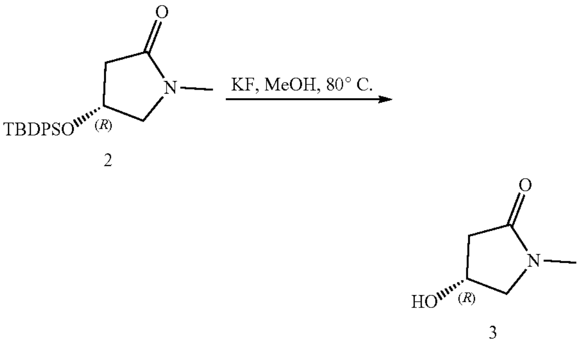

To a solution of (4R)-4-[tert-butyl(diphenyl)silyl]oxy-1-methyl-pyrrolidin-2-one (9.4 g, 26.59 mmol, 1 eq) in MeOH (100 mL) was added KF (9.27 g, 159.53 mmol, 3.74 mL, 6 eq). The mixture was stirred at 80° C. for 5 hr. TLC (DCM:MeOH=10:1, $R_f$=0.33) showed a new spot. The reaction mixture was concentrated under reduced pressure to give a residue. The residue was purified by flash silica gel chromatography (ISCO®; 120 g SepaFlash® Silica Flash Column, eluent of 0~10% Methanol/Dichloromethane gradient @ 100 mL/min). Compound (4R)-4-hydroxy-1-methyl-pyrrolidin-2-one (2.59 g, 22.50 mmol, 84.61% yield) was obtained as a liquid.

$^1$H NMR (400 MHz, DMSO-$d_6$) δ=5.33-5.04 (m, 1H), 4.25 (br t, J=6.0 Hz, 1H), 3.53 (dd, J=5.6, 10.4 Hz, 1H), 3.09 (dd, J=1.6, 10.4 Hz, 1H), 2.70 (s, 3H), 2.01 (br d, J=16.9 Hz, 1H).

[(3R)-1-methyl-5-oxo-pyrrolidin-3-yl](4-nitrophenyl) carbonate

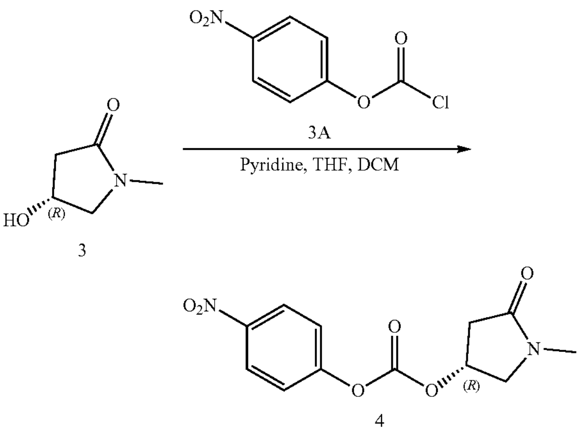

To a solution of (4R)-4-hydroxy-1-methyl-pyrrolidin-2-one (2.59 g, 22.50 mmol, 1 eq) in DCM (20 mL) and THF (4 mL) was added pyridine (3.56 g, 44.99 mmol, 3.63 mL, 2 eq) and (4-nitrophenyl) carbonochloridate (4.99 g, 24.75 mmol, 1.1 eq). The mixture was stirred at 25° C. for 1 hr. LCMS showed reactant was consumed completely and desired mass was detected. The reaction mixture was concentrated under reduced pressure to give a residue. The residue was purified by flash silica gel chromatography (ISCO®; 40 g SepaFlash® Silica Flash Column, eluent of 0~50% Ethyl acetate/Petroleum ether gradient @ 100 mL/min). Compound [(3R)-1-methyl-5-oxo-pyrrolidin-3-yl](4-nitrophenyl) carbonate (5 g, 17.84 mmol, 79.31% yield) was obtained as a solid.

LCMS m/z=280.9 $[M+H]^+$.

SFC $t_R$=1.014 min; 100%.

$^1$H NMR (400 MHz, DMSO-d) δ=8.39-8.26 (m, 2H), 7.69-7.54 (m, 2H), 5.30 (t, J=6.0 Hz, 1H), 3.78 (dd, J=5.5, 11.9 Hz, 1H), 3.57 (d, J=11.8 Hz, 1H), 2.86-2.78 (m, 1H), 2.77 (s, 3H), 2.45 (s, 1H).

[(3R)-1-methyl-5-oxo-pyrrolidin-3-yl]-4-[3-[2-(1-tert-butoxycarbonylazetidin-3-yl)oxy-3-pyridyl] pyrazolo[1,5-a]pyrimidin-5-yl]piperazine-1-carboxylate

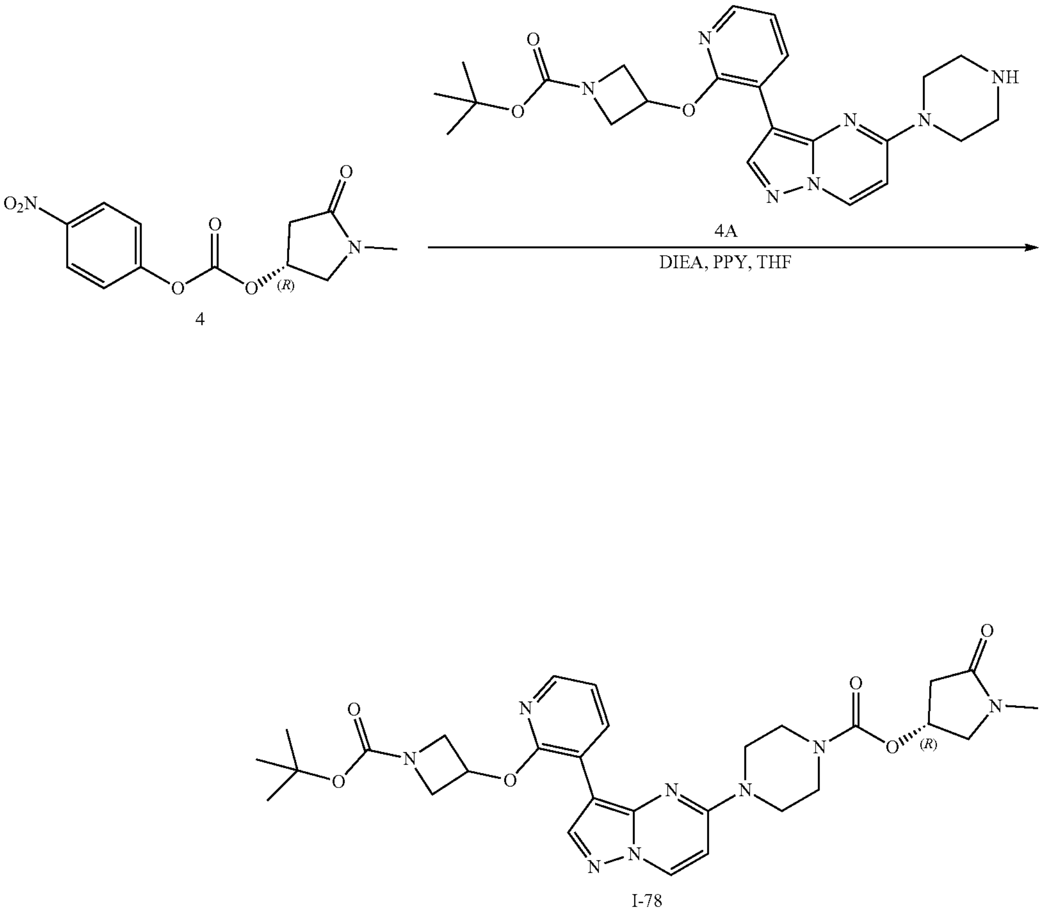

4

4A

I-78

To a solution of tert-butyl 3-[[3-(5-piperazin-1-ylpyrazolo [1,5-a]pyrimidin-3-yl)-2-pyridyl]oxy]azetidine-1-carboxylate (150 mg, 332.21 μmol, 1 eq) in THF (2 mL) was added DIEA (64.40 mg, 498.32 μmol, 86.80 μL, 1.5 eq), PPY (10.22 mg, 66.44 μmol, 0.2 eq) and [(3R)-1-methyl-5-oxo-pyrrolidin-3-yl](4-nitrophenyl) carbonate (111.72 mg, 398.65 μmol, 1.2 eq). The mixture was stirred at 25° C. for 1 hr. The reaction mixture was concentrated under reduced pressure to remove solvent. The product was further purified by prep. HPLC (column: Waters Xbridge 150*25 mm*5 um; mobile phase: [water ($NH_3H_2O$)-MeCN]; gradient: 30%-60% B over 10 min). The pure fractions were collected and the volatiles were removed under vacuum. The residue was partitioned between acetonitrile (2 mL) and water (10 mL). The solution was lyophilized to dryness to give [(3R)-1-methyl-5-oxo-pyrrolidin-3-yl] 4-[3-[2-(1-tert-butoxycarbonylazetidin-3-yl)oxy-3-pyridyl]pyrazolo[1,5-a]pyrimidin-5-yl]piperazine-1-carboxylate (30.66 mg, 49.43 μmol, 48.82% yield, 95.545% purity) as a powder.

Compound I-78

LCMS m/z=593.2 $[M+H]^+$.

SFC $t_R$=1.530 min; 100%.

$^1$H NMR (400 MHz, DMSO-$d_6$) δ=8.82 (d, J=1.6 Hz, 1H), 8.78 (d, J=7.8 Hz, 1H), 8.54 (s, 1H), 7.97-7.91 (m, 1H), 7.17-7.07 (m, J=4.9, 7.5 Hz, 1H), 6.83 (d, J=7.9 Hz, 1H), 5.45-5.35 (m, 1H), 5.19-5.11 (m, J=6.4, 6.4 Hz, 1H), 4.34-4.26 (m, 2H), 3.94 (d, J=6.5 Hz, 2H), 3.82-3.74 (m, 4H), 3.73-3.68 (m, 1H), 3.58-3.46 (m, 4H), 3.36 (d, J=11.3 Hz, 1H), 2.76-2.67 (m, 4H), 2.28 (d, J=18.0 Hz, 1H), 1.42-1.34 (m, 9H).

Example 70: Synthesis of Compound I-79

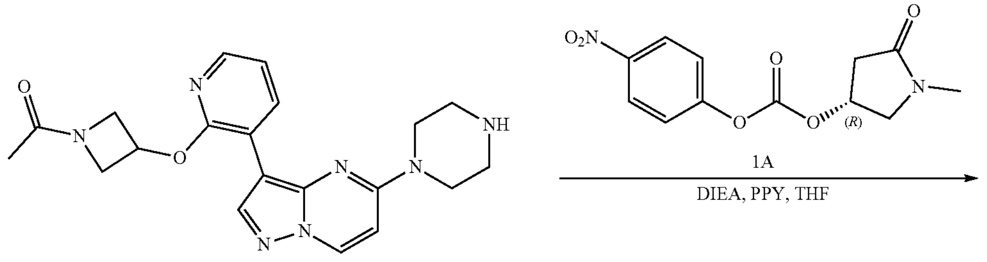

1

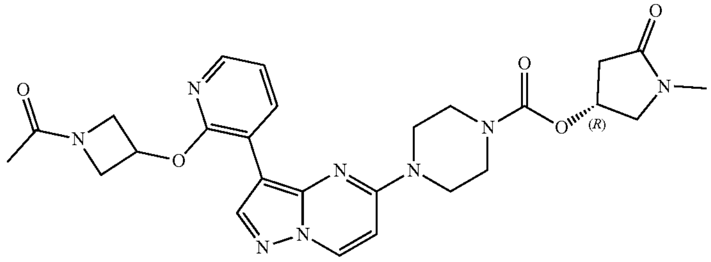

I-79

To a solution of [(3R)-1-methyl-5-oxo-pyrrolidin-3-yl](4-nitrophenyl) carbonate (142.45 mg, 508.33 μmol, 1 eq) in THF (2 mL) was added DIEA (131.39 mg, 1.02 mmol, 177.08 μL, 2 eq), 1-[3-[[3-(5-piperazin-1-ylpyrazolo[1,5-a]pyrimidin-3-yl)-2-pyridyl]oxy]azetidin-1-yl]ethanone (200 mg, 508.33 μmol, 1 eq) and 4-pyrrolidin-1-ylpyridine (15.07 mg, 101.67 μmol, 0.2 eq). The mixture was stirred at 25° C. for 1 hr. The reaction mixture was concentrated under reduced pressure to give a residue. Then the residue was further purified by prep. HPLC (column: Phenomenex luna C18 150*25 mm*10 um; mobile phase: [water (HCOOH)-MeCN]; gradient: 18%-48% B over 10 min). The pure fractions were collected and the volatiles were removed under vacuum. The residue was partitioned between acetonitrile (2 mL) and water (10 mL). The solution was lyophilized to dryness to give [(3R)-1-methyl-5-oxo-pyrrolidin-3-yl]-4-[3-[2-(1-acetylazetidin-3-yl)oxy-3-pyridyl]pyrazolo[1,5-a]pyrimidin-5-yl]piperazine-1-carboxylate (46.88 mg, 83.22 μmol, 16.37% yield, 94.89% purity) as a powder.

Compound I-79

LCMS m/z=535.2 $[M+H]^+$.

SFC $t_R$=1.460 min; 100%.

$^1H$ NMR (400 MHz, DMSO-$d_6$) δ=8.83 (d, J=7.5 Hz, 1H), 8.78 (d, J=7.8 Hz, 1H), 8.56 (s, 1H), 7.98-7.90 (m, 1H), 7.14 (d, J=7.4 Hz, 1H), 6.83 (d, J=7.9 Hz, 1H), 5.44 (s, 1H), 5.16 (t, J=5.6 Hz, 1H), 4.57 (t, J=7.9 Hz, 1H), 4.32-4.19 (m, 2H), 3.93 (d, J=10.6 Hz, 1H), 3.77 (s, 4H), 3.74-3.69 (m, 1H), 3.53 (s, 4H), 3.36 (d, J=11.8 Hz, 1H), 2.77-2.69 (m, 4H), 2.28 (d, J=17.4 Hz, 1H), 1.80 (s, 3H).

Example 71: Synthesis of Compound I-80

3-bromo-2-(cyclopropoxy)-5-methoxy-pyridine

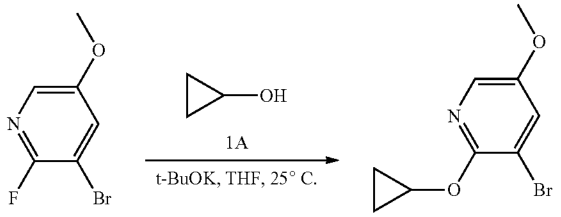

1 2

To a mixture of 3-bromo-2-fluoro-5-methoxy-pyridine (300 mg, 1.46 mmol, 1 eq) and cyclopropanol (169.15 mg, 2.91 mmol, 2 eq) in THF (2 mL) was added t-BuOK (1 M, 2.18 mL, 1.5 eq). The mixture was stirred at 25° C. for 10 hr. The reaction mixture was filtered with diatomite and concentrated under reduced pressure to give crude product. The crude was purified by FCC (ISCO®; 4 g SepaFlash® Silica Flash Column, eluent of 0~3% Ethyl acetate/Petroleum ether gradient @ 35 mL/min) to give 3-bromo-2-(cyclopropoxy)-5-methoxy-pyridine (290 mg, 932.07 μmol, 64.01% yield, 78.450% purity) as a liquid.

LCMS m/z=243.8 $[M+H]^+$.

$^1H$ NMR (400 MHz, DMSO-$d_6$) δ=7.93 (br s, 1H), 7.75 (s, 1H), 4.21 (br d, J=1.6 Hz, 1H), 3.79 (s, 3H), 0.79-0.70 (m, 2H), 0.65 (br s, 2H).

2-(cyclopropoxy)-5-methoxy-3-(4,4,5,5-tetramethyl-1,3,2-dioxaborolan-2-yl)pyridine

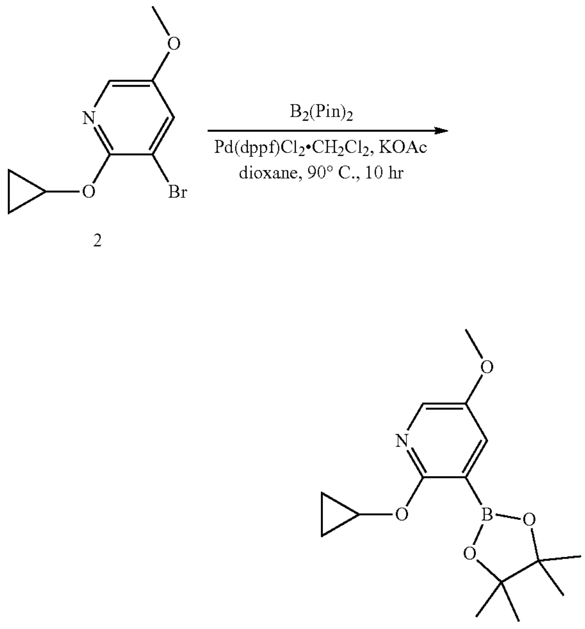

2

3

A mixture of 3-bromo-2-(cyclopropoxy)-5-methoxy-pyridine (290 mg, 1.19 mmol, 1 eq), 4,4,5,5-tetramethyl-2-(4,4,5,5-tetramethyl-1,3,2-dioxaborolan-2-yl)-1,3,2-dioxaborolane (452.56 mg, 1.78 mmol, 1.5 eq), KOAc (233.21 mg, 2.38 mmol, 2 eq), Pd(dppf)$Cl_2$·$CH_2Cl_2$ (194.05 mg, 237.62 μmol, 0.2 eq) in dioxane (3 mL) was degassed and purged with $N_2$ for 3 times, and then the mixture was stirred at 90° C. for 10 hr under $N_2$ atmosphere. The reaction mixture was concentrated under reduced pressure to give a residue. The crude was purified by FCC (ISCO®; 4 g SepaFlash® Silica Flash Column, Eluent of 0~10% Ethyl acetate/Petroleum ether gradient @ 35 mL/min) to give 2-(cyclopropoxy)-5-methoxy-3-(4,4,5,5-tetramethyl-1,3,2-dioxaborolan-2-yl)pyridine (130 mg, 330.35 μmol, 27.80% yield, 73.986% purity) as a liquid.

LCMS m/z=291.9 $[M+H]^+$.

$^1$H NMR (400 MHz, DMSO-$d_6$) δ=8.02-7.87 (m, 1H), 7.53-7.34 (m, 1H), 4.34-4.04 (m, 1H), 3.77 (s, 3H), 1.38-1.14 (m, 12H), 0.70-0.53 (m, 4H).

3-[2-(cyclopropoxy)-5-methoxy-3-pyridyl]-5-piperazin-1-yl-pyrazolo[1,5-a]pyrimidine

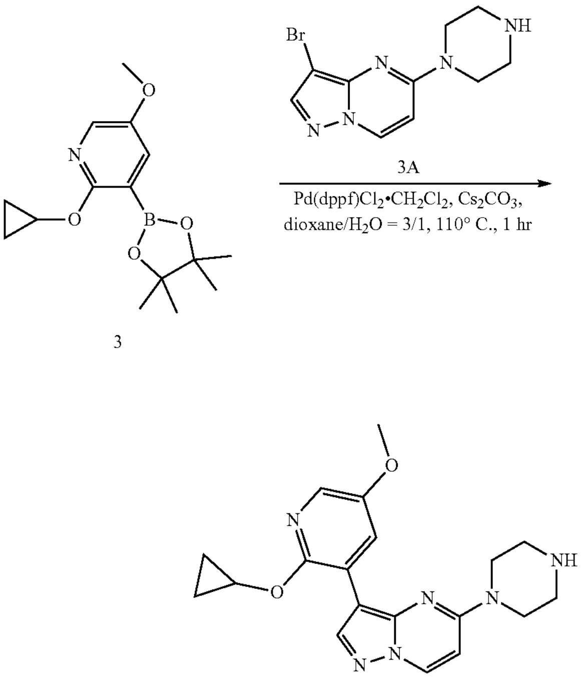

3

4

A mixture of 2-(cyclopropoxy)-5-methoxy-3-(4,4,5,5-tetramethyl-1,3,2-dioxaborolan-2-yl)pyridine (130 mg, 446.51 μmol, 1 eq), 3-bromo-5-piperazin-1-yl-pyrazolo[1,5-a]pyrimidine (125.98 mg, 446.51 μmol, 1 eq), $Cs_2CO_3$ (436.44 mg, 1.34 mmol, 3 eq), Pd(dppf)$Cl_2$·$CH_2Cl_2$ (14.59 mg, 17.86 μmol, 0.04) in dioxane (3 mL) and $H_2O$ (1 mL) was degassed and purged with $N_2$ for 3 times, and then the mixture was stirred at 110° C. for 1 hr under $N_2$ atmosphere. The reaction mixture was filtered with diatomite and concentrated under reduced pressure to give a residue. The crude was purified by FCC (ISCO®; 4 g SepaFlash® Silica Flash Column, eluent of 0~5% Methanol/Dichloromethane gradient @ 25 mL/min) to give 3-[2-(cyclopropoxy)-5-methoxy-3-pyridyl]-5-piperazin-1-yl-pyrazolo[1,5-a]pyrimidine (66 mg, 86.36 μmol, 19.34% yield, 47.947% purity) as a solid.

LCMS m/z=367.0 $[M+H]^+$.

[(3R)-1-methyl-5-oxo-pyrrolidin-3-yl]-4-[3-[2-(cyclopropoxy)-5-methoxy-3-pyridyl]pyrazolo[1,5-a]pyrimidin-5-yl]piperazine-1-carboxylate

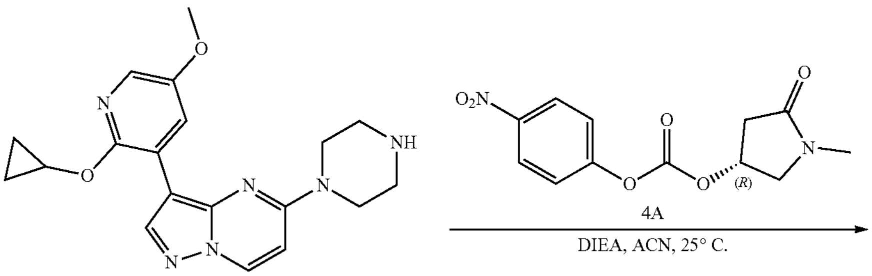

4

-continued

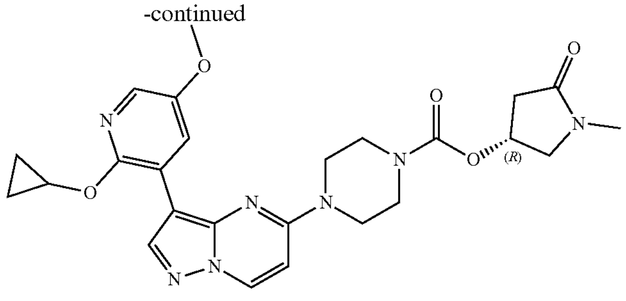

I-80

To a mixture of 3-[2-(cyclopropoxy)-5-methoxy-3-pyridyl]-5-piperazin-1-yl-pyrazolo[1,5-a]pyrimidine (66 mg, 180.12 μmol, 1 eq) and [(3R)-1-methyl-5-oxo-pyrrolidin-3-yl](4-nitrophenyl) carbonate (50.48 mg, 180.12 μmol, 1 eq) in MeCN (0.5 mL) was added DIEA (69.84 mg, 540.37 μmol, 94.12 μL, 3 eq). The mixture was stirred at 25° C. for 1 hr. LCMS showed that desired MS was found. The reaction mixture was filtered with diatomite and concentrated under reduced pressure to give crude product. The product was purified by prep. HPLC (Column: Waters Xbridge 150*25 mm*5 um; mobile phase: [water ($NH_3H_2O$)-MeCN]; gradient: 22%-52% B over 10 min). The pure fractions were collected and the volatiles were removed under vacuum. The residue was partitioned between acetonitrile (20 mL) and water (100 mL). The solution was lyophilized to dryness to give [(3R)-1-methyl-5-oxo-pyrrolidin-3-yl] 4-[3-[2-(cyclopropoxy)-5-methoxy-3-pyridyl]pyrazolo[1,5-a]pyrimidin-5-yl]piperazine-1-carboxylate (17.26 mg, 32.01 μmol, 17.77% yield, 94.118% purity) as a powder.

Compound I-80

LCMS m/z=508.1 $[M+H]^+$.

SFC $t_R$=1.150 min; 100%.

$^1H$ NMR (400 MHz, DMSO-$d_6$) δ=8.76 (d, J=7.9 Hz, 1H), 8.56 (d, J=2.8 Hz, 1H), 8.37 (s, 1H), 7.70 (d, J=2.8 Hz, 1H), 6.82 (d, J=7.9 Hz, 1H), 5.15 (t, J=5.9 Hz, 1H), 4.42-4.22 (m, 1H), 3.84 (s, 3H), 3.82-3.75 (m, 4H), 3.74-3.70 (m, 1H), 3.58-3.48 (m, 4H), 3.36 (d, J=11.4 Hz, 1H), 2.74 (s, 3H), 2.72-2.65 (m, 1H), 2.30 (d, J=18.0 Hz, 1H), 0.79-0.72 (m, 4H).

Example 72: Synthesis of Compound I-81

3-bromo-2-(cyclopropoxy)-5-fluoro-pyridine

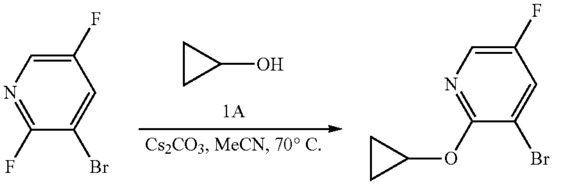

1 2

The product 2 was prepared according to the synthesis method of I-58. 3-bromo-2-(cyclopropoxy)-5-fluoro-pyridine (350 mg, 1.51 mmol, 58.52% yield) was obtained as colorless oil.

$^1H$ NMR (400 MHz, DMSO-$d_6$) δ=8.32-8.06 (m, 2H), 4.25 (tt, J=3.0, 6.1 Hz, 1H), 0.82-0.65 (m, 4H).

2-(cyclopropoxy)-5-fluoro-3-(4,4,5,5-tetramethyl-1,3,2-dioxaborolan-2-yl)pyridine

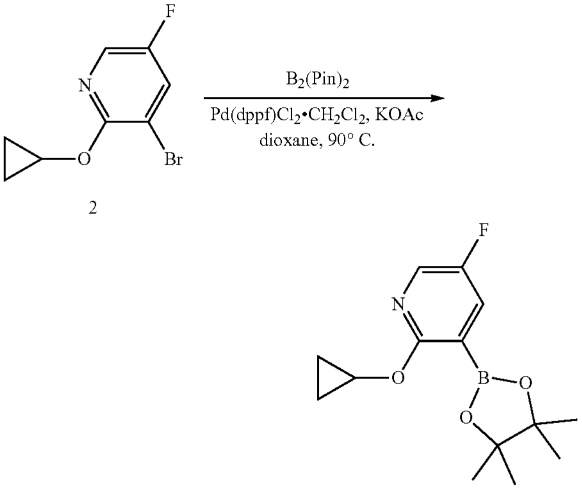

2

3

The product 3 was prepared according to the synthesis method of I-58. The product 2-(cyclopropoxy)-5-fluoro-3-(4,4,5,5-tetramethyl-1,3,2-dioxaborolan-2-yl)pyridine (270 mg, 967.35 μmol, 64.13% yield) was obtained as colorless oil.

$^1H$ NMR (400 MHz, DMSO-$d_6$) δ=8.25 (d, J=3.1 Hz, 1H), 7.67 (dd, J=3.2, 8.1 Hz, 1H), 4.18 (dt, J=3.1, 6.2 Hz, 1H), 1.26 (s, 12H), 0.74-0.71 (m, 2H), 0.62-0.56 (m, 2H).

3-[2-(cyclopropoxy)-5-fluoro-3-pyridyl]-5-piperazin-1-yl-pyrazolo[1,5-a]pyrimidine

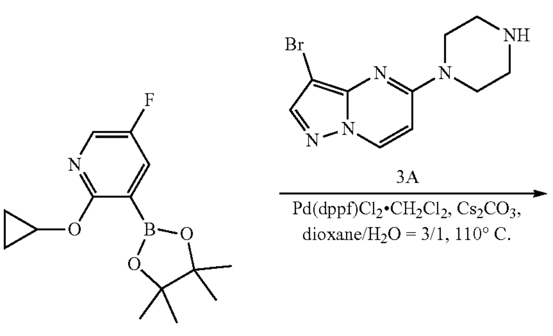

3

-continued

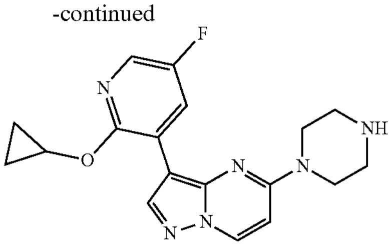

4

The product 4 was prepared according to the synthesis method of I-58. The product 3-[2-(cyclopropoxy)-5-fluoro-3-pyridyl]-5-piperazin-1-yl-pyrazolo[1,5-a]pyrimidine (149 mg, 341.73 μmol, 35.33% yield, 81.278% purity) was obtained as an oil.

LCMS m/z=355.2 $[M+H]^+$.

[(3R)-1-methyl-5-oxo-pyrrolidin-3-yl] 4-[3-[2-(cyclopropoxy)-5-fluoro-3-pyridyl]pyrazolo[1,5-a]pyrimidin-5-yl]piperazine-1-carboxylate To a mixture of 3-[2-(cyclopropoxy)-5-fluoro-3-pyridyl]-5-piperazin-1-yl-pyrazolo[1,5-a]pyrimidine (149 mg, 341.73 μmol, 1 eq) and [(3R)-1-methyl-5-oxo-pyrrolidin-3-yl](4-nitrophenyl) carbonate (95.77 mg, 341.73 μmol, 1 eq) in MeCN (2 mL) was added DIEA (88.33 mg, 683.47 μmol, 119.05 μL, 2 eq). The mixture was stirred at 25° C. for 1 hr. LCMS showed that desired MS was found. The mixture was concentrated to give the crude product. The crude was purified by prep. HPLC (column: Phenomenex luna C18 150*25 mm*10 um; mobile phase: [water (HCOOH)-MeCN]; gradient: 30%-60% B over 8 min) to give [(3R)-1-methyl-5-oxo-pyrrolidin-3-yl]-4-[3-[2-(cyclopropoxy)-5-fluoro-3-pyridyl]pyrazolo[1,5-a]pyrimidin-5-yl]piperazine-1-carboxylate (122.92 mg, 243.29 μmol, 71.19% yield, 98.073% purity) as a powder.

Compound I-81

LCMS m/z=496.2 $[M+H]^+$.

SFC $t_R$=1.423 min; 100%.

$^1$H NMR (400 MHz, DMSO-$d_6$) δ=8.77 (d, J=7.8 Hz, 1H), 8.72-8.62 (m, 1H), 8.38 (s, 1H), 7.96 (d, J=4.0 Hz, 1H), 6.84 (d, J=7.8 Hz, 1H), 5.21-5.10 (m, 1H), 4.41-4.31 (m, 1H), 3.81-3.69 (m, 5H), 3.60-3.48 (m, 4H), 3.40-3.35 (m,

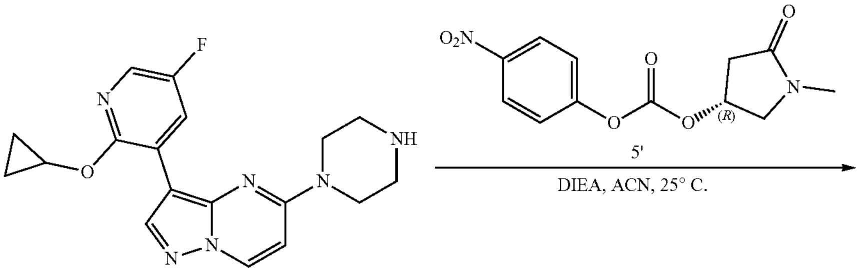

4

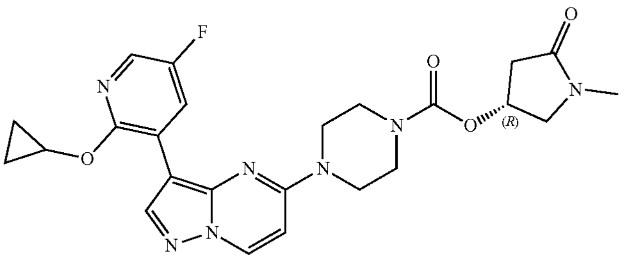

I-81

1H), 2.76-2.75 (m, 0.3H), 2.74 (s, 3H), 2.70 (d, J=7.2 Hz, 0.6H), 2.35-2.26 (m, 1H), 0.86-0.74 (m, 4H).

Example 73: Synthesis of Compound I-82

3-bromo-2-(cyclopropoxy)-5-(trifluoromethoxy) pyridine

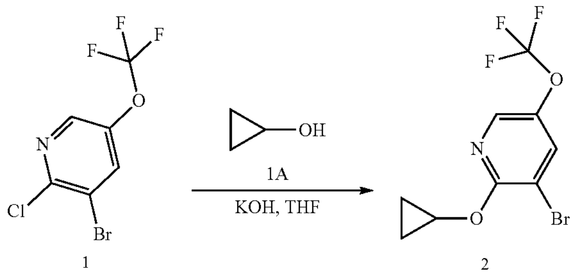

1 2

To a solution of 3-bromo-2-chloro-5-(trifluoromethoxy) pyridine (500 mg, 1.81 mmol, 1 eq) in THF (5 mL) was added KOH (202.96 mg, 3.62 mmol, 2 eq) and cyclopropanol (210.10 mg, 3.62 mmol, 2 eq). The mixture was stirred at 25° C. for 4 hr. The reaction mixture was concentrated under reduced pressure to give a residue. The residue was purified by flash silica gel chromatography (ISCO®; 12 g SepaFlash® Silica Flash Column, eluent of 0~2% Ethyl acetate/Petroleum ether gradient @ 40 mL/min) to give 3-bromo-2-(cyclopropoxy)-5-(trifluoromethoxy)pyridine (149 mg, 499.91 μmol, 27.64% yield) as a gum.

LCMS m/z=297.8 M+1]$^+$.

2-(cyclopropoxy)-3-(4,4,5,5-tetramethyl-1,3,2-dioxaborolan-2-yl)-5-(trifluoromethoxy)pyridine

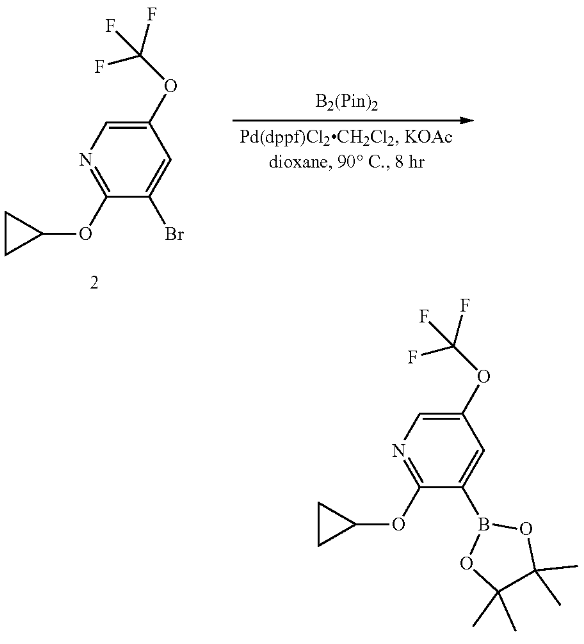

2

3

To a solution of 3-bromo-2-(cyclopropoxy)-5-(trifluoromethoxy)pyridine (149 mg, 499.91 μmol, 1 eq) in dioxane (2 mL) was added KOAc (98.12 mg, 999.81 μmol, 2 eq), 4,4,5,5-tetramethyl-2-(4,4,5,5-tetramethyl-1,3,2-dioxaborolan-2-yl)-1,3,2-dioxaborolane (152.33 mg, 599.89 μmol, 1.2 eq) and $Pd(dppf)Cl_2 \cdot CH_2Cl_2$ (61.24 mg, 74.99 umol, 0.15 eq) under $N_2$ atmosphere. The mixture was stirred at 90° C. for 8 hr under $N_2$ atmosphere. TLC (PE:EA=5:1, $R_f$=0.6) showed a new spot. The reaction mixture was concentrated under reduced pressure to give a residue. The residue was purified by flash silica gel chromatography (ISCOR; 4 g SepaFlash® Silica Flash Column, Eluent of 0~10% Ethyl acetate/Petroleum ether gradient @ 20 mL/min) to give 2-(cyclopropoxy)-3-(4,4,5,5-tetramethyl-1,3,2-dioxaborolan-2-yl)-5-(trifluoromethoxy)pyridine (80 mg, 231.80 umol, 46.37% yield) as a gum.

LCMS m/z=345.8 M+1]$^+$.

3-[2-(cyclopropoxy)-5-(trifluoromethoxy)-3-pyridyl]-5-piperazin-1-yl-pyrazolo[1,5-a]pyrimidine

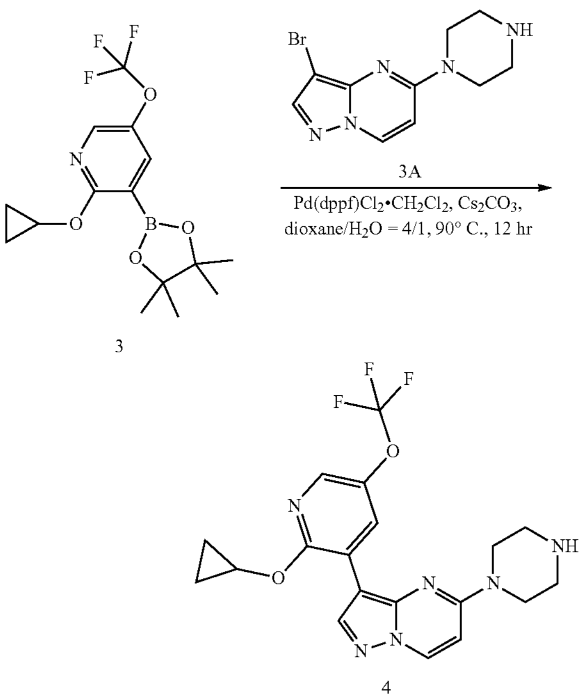

3

4

A mixture of 2-(cyclopropoxy)-3-(4,4,5,5-tetramethyl-1,3,2-dioxaborolan-2-yl)-5-(trifluoromethoxy)pyridine (80 mg, 231.80 μmol, 1 eq), 3-bromo-5-piperazin-1-yl-pyrazolo [1,5-a]pyrimidine (78.48 mg, 278.16 μmol, 1.2 eq), $Cs_2CO_3$ (151.05 mg, 463.61 μmol, 2 eq), $Pd(dppf)Cl_2 \cdot CH_2Cl_2$ (28.39 mg, 34.77 μmol, 0.15 eq) in dioxane (0.8 mL) and $H_2O$ (0.2 mL) was degassed and purged with $N_2$ for 3 times, and then the mixture was stirred at 90° C. for 12 hr under $N_2$ atmosphere. LCMS showed reactant was consumed completely and desired mass was detected. TLC (DCM: MeOH=10:1, $R_f$=0.28) showed a new spot. The reaction mixture was concentrated under reduced pressure to give a residue. The residue was purified by flash silica gel chromatography (ISCO®; 4 g SepaFlash® Silica Flash Column, eluent of 0~7% Methanol/Dichloromethane gradient @ 20 mL/min) to give 3-[2-(cyclopropoxy)-5-(trifluoromethoxy)-3-pyridyl]-5-piperazin-1-yl-pyrazolo[1,5-a]pyrimidine (24 mg, 57.09 μmol, 24.63% yield) as a gum.

LCMS m/z=420.9 M+1]$^+$.

[(3R)-1-methyl-5-oxo-pyrrolidin-3-yl]-4-[3-[2-(cyclopropoxy)-5-(trifluoromethoxy)-3-pyridyl]pyrazolo[1,5-a]pyrimidin-5-yl]piperazine-1-carboxylate

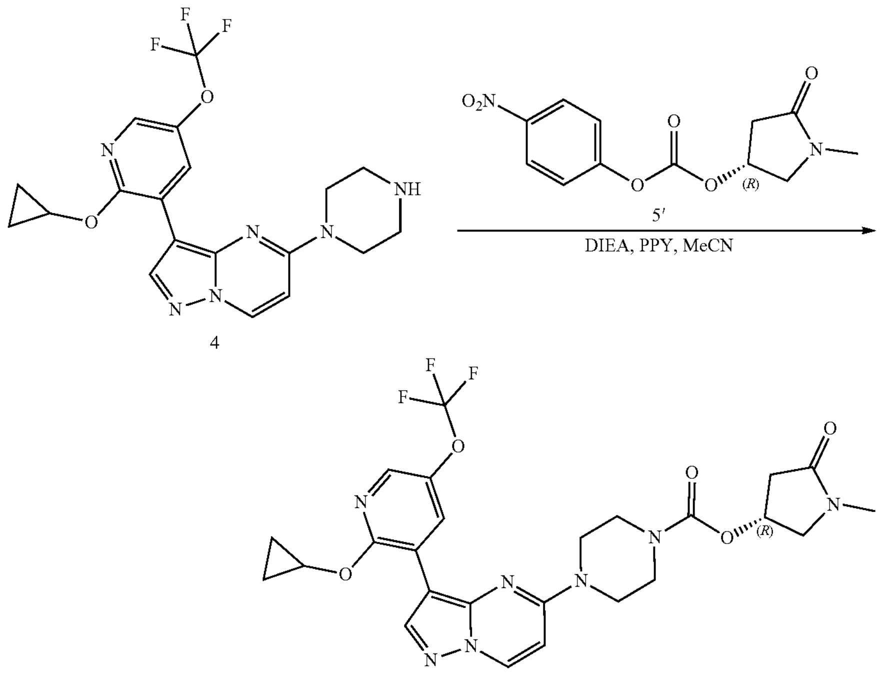

4

5′

I-82

To a solution of 3-[2-(cyclopropoxy)-5-(trifluoromethoxy)-3-pyridyl]-5-piperazin-1-yl-pyrazolo[1,5-a]pyrimidine (24 mg, 57.09 μmol, 1 eq) in MeCN (0.5 mL) was added DIEA (22.14 mg, 171.27 μmol, 29.83 μL, 3 eq), [(3R)-1-methyl-5-oxo-pyrrolidin-3-yl](4-nitrophenyl) carbonate (19.20 mg, 68.51 μmol, 1.2 eq) and 4-pyrrolidin-1-ylpyridine (846.10 μg, 5.71 μmol, 0.1 eq). The mixture was stirred at 25° C. for 1 hr. The reaction mixture was concentrated under reduced pressure to give a residue. Then the product was further purified by prep. HPLC (column: Waters Xbridge BEH C18 150*25 mm*5 um; mobile phase: [water ($NH_4HCO_3$)-MeCN]; gradient: 37%-67% B over 10 min). The pure fractions were collected and the volatiles were removed under vacuum. The residue was partitioned between acetonitrile (2 mL) and water (10 mL). The solution was lyophilized to dryness to give [(3R)-1-methyl-5-oxo-pyrrolidin-3-yl]-4-[3-[2-(cyclopropoxy)-5-(trifluoromethoxy)-3-pyridyl]pyrazolo[1,5-a]pyrimidin-5-yl]piperazine-1-carboxylate (16.19 mg, 27.54 μmol, 48.25% yield, 95.53% purity) as a solid.

Compound I-82

LCMS m/z=562.1 $[M+H]^+$.

SFC $t_R$=1.175 min; 100%.

$^1$H NMR (400 MHz, DMSO-$d_6$) δ=8.97-8.86 (m, 1H), 8.79 (d, J=7.9 Hz, 1H), 8.39 (s, 1H), 8.08 (d, J=2.9 Hz, 1H), 6.86 (d, J=7.9 Hz, 1H), 5.20-5.11 (m, 1H), 4.45-4.38 (m, 1H), 3.81-3.69 (m, 5H), 3.51 (s, 4H), 3.36 (d, J=11.5 Hz, 1H), 2.74 (s, 3H), 2.70 (d, J=7.3 Hz, 1H), 2.34-2.25 (m, 1H), 0.85-0.81 (m, 4H).

Example 74: Synthesis of Compounds I-95, I-98, and I-103

3-bromo-5-piperazin-1-yl-pyrazolo[1,5-a]pyrimidine (I-103)

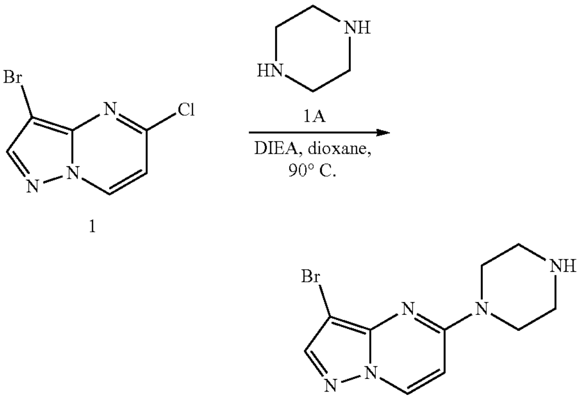

1

1A

I-103

To a solution of 3-bromo-5-chloro-pyrazolo[1,5-a]pyrimidine (40 g, 172.07 mmol, 1 eq) and TEA (52.23 g, 516.21 mmol, 71.85 mL, 3 eq) in dioxane (400 mL) was added piperazine (44.46 g, 516.21 mmol, 3 eq). The mixture was stirred at 90° C. for 0.5 hr. LCMS showed that desired MS was found. The reaction mixture was diluted with water and extracted with EA (3×300 mL). The combined organic layers were washed with brine solution, dried over sodium sulfate, concentrated under reduced pressure to give 3-bromo-5-piperazin-1-yl-pyrazolo[1,5-a]pyrimidine (48 g, 170.13 mmol, 98.87% yield) as a solid, which was checked by 1H.

The product was purified by pre-HPLC (Column: Waters Xbridge BEH C18 150*25*10 um; mobile phase: [water ($NH_3H_2O$)-ACN]; gradient: 12%-42% B over 13 min): The pure fractions were collected and the volatiles were removed under vacuum. The residue was partitioned between acetonitrile (20 mL) and water (100 mL). The solution was lyophilized to dryness to give 3-bromo-5-piperazin-1-yl-pyrazolo[1,5-a]pyrimidine (138.95 mg, 489.84 umol, 46.07% yield, 99.462% purity) as a solid.

LCMS m/z=281.8 $[M+H]^+$.

$^1H$ NMR (400 MHz, DMSO-$d_6$) δ=8.61 (d, J=7.9 Hz, 1H), 7.93 (s, 1H), 6.73 (d, J=8.0 Hz, 1H), 3.65-3.57 (m, 4H), 3.17 (s, 1H), 2.81-2.69 (m, 4H).

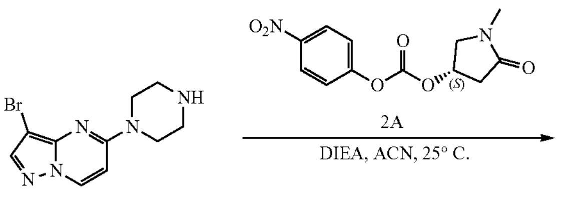

I-103

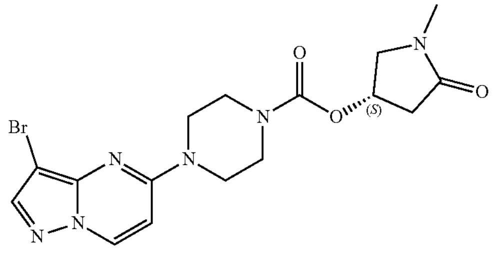

I-95

To a solution of 3-bromo-5-piperazin-1-yl-pyrazolo[1,5-a]pyrimidine (4 g, 14.18 mmol, 1 eq) and DIEA (I-103, 3.66 g, 28.35 mmol, 4.94 mL, 2 eq) in ACN (40 mL) was added [(3S)-1-methyl-5-oxo-pyrrolidin-3-yl](4-nitrophenyl) carbonate (4.77 g, 17.01 mmol, 1.2 eq). The mixture was stirred at 25° C. for 1 hr. LCMS showed desired compound was detected. The reaction mixture was concentrated under reduced pressure to remove solvent. The crude was purified by FCC (ISCO®; 40 g SepaFlash® Silica Flash Column, Eluent of 0~8% Methanol/Dichloromethane ether gradient @ 25 mL/min) to give [(3S)-1-methyl-5-oxo-pyrrolidin-3-yl] 4-(3-bromopyrazolo[1,5-a]pyrimidin-5-yl)piperazine-1-carboxylate (I-95, 6 g, 13.46 mmol, 94.93% yield, 94.938% purity) as a solid.

The product was purified by pre-HPLC (Column: Waters Xbridge BEH C18 250*25*10 um; mobile phase: [water ($NH_4HCO_3$)-ACN]; gradient: 15%-45% B over 15 min). The pure fractions were collected and the volatiles were removed under vacuum. The residue was partitioned between acetonitrile (20 mL) and water (100 mL). The solution was lyophilized to dryness to give [(3S)-1-methyl-5-oxo-pyrrolidin-3-yl]-4-(3-bromopyrazolo[1,5-a]pyrimidin-5-yl)piperazine-1-carboxylate (197.9 mg, 467.56 μmol, 49.47% yield, 100.000% purity) as a solid.

LCMS m/z=422.9 $[M+H]^+$.

$^1H$ NMR (400 MHz, DMSO-$d_6$) δ=8.69 (d, J=7.9 Hz, 1H), 8.10 (br d, J=9.0 Hz, 1H), 8.02-7.93 (m, 1H), 6.89 (br d, J=9.0 Hz, 1H), 6.78 (br d, J=7.9 Hz, 1H), 5.15 (br t, J=5.8 Hz, 1H), 3.76-3.69 (m, 4H), 3.49 (br s, 4H), 3.36 (br d, J=11.3 Hz, 1H), 2.74 (s, 3H), 2.28 (br d, J=17.8 Hz, 1H).

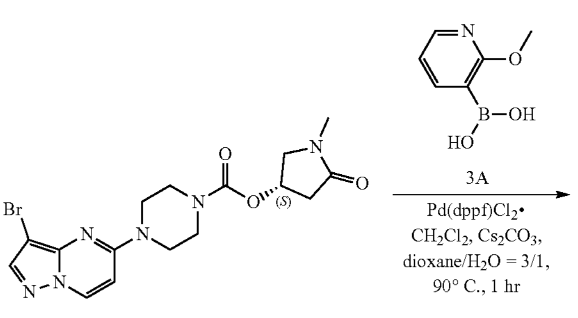

I-95

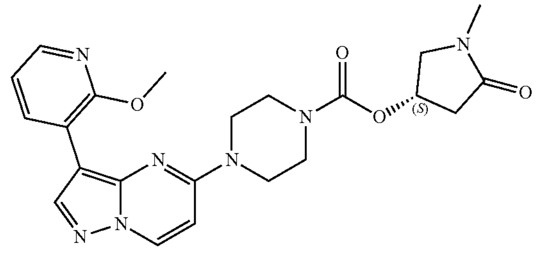

4

A mixture of [(3S)-1-methyl-5-oxo-pyrrolidin-3-yl]-4-(3-bromopyrazolo[1,5-a]pyrimidin-5-yl)piperazine-1-carboxylate (800 mg, 1.89 mmol, 1 eq), (2-methoxy-3-pyridyl) boronic acid (346.89 mg, 2.27 mmol, 1.2 eq), $Cs_2CO_3$ (1.85 g, 5.67 mmol, 3 eq) and Pd(dppf)$Cl_2$·$CH_2Cl_2$ (92.61 mg, 113.40 μmol, 0.06 eq) in dioxane (9 mL) and $H_2O$ (3 mL) was degassed and purged with $N_2$ for 3 times, and the mixture was stirred at 90° C. for 0.5 hr under $N_2$ atmosphere. LCMS showed that desired MS was found. The mixture was filtered and the filtrate was concentrated to the crude product. The crude was purified by FCC (ISCO®; 20 g SepaFlash® Silica Flash Column, Eluent of 0~5% MeOH/DCM ether gradient @ 45 mL/min) to give [(3S)-1-methyl-5-oxo-pyrrolidin-3-yl]-4-[3-(2-methoxy-3-pyridyl)pyrazolo[1,5-a]pyrimidin-5-yl]piperazine-1-carboxylate (4, 500 mg, 466.60 μmol, 24.69% yield, 42.132% purity) as a solid.

LCMS m/z=452.0 $[M+H]^+$).

$^1H$ NMR (400 MHz, DMSO-$d_6$) δ=8.76 (d, J=7.9 Hz, 1H), 7.97 (dd, J=1.7, 4.8 Hz, 1H), 7.55 (br dd, J=6.7, 10.4 Hz, 1H), 7.51-7.44 (m, 1H), 7.08 (dd, J=4.9, 7.4 Hz, 1H), 6.82 (d, J=7.9 Hz, 1H), 5.18-5.13 (m, 1H), 3.99 (s, 3H), 3.79-3.73 (m, 4H), 3.71 (br dd, J=2.9, 5.8 Hz, 2H), 3.53 (br s, 4H), 3.39-3.34 (m, 3H), 2.70 (dd, J=2.3, 7.1 Hz, 1H), 2.33-2.28 (m, 1H).

[(3S)-1-methyl-5-oxo-pyrrolidin-3-yl]-4-[3-(2-hydroxy-3-pyridyl)pyrazolo[1,5-a]pyrimidin-5-yl]piperazine-1-carboxylate (I-98)

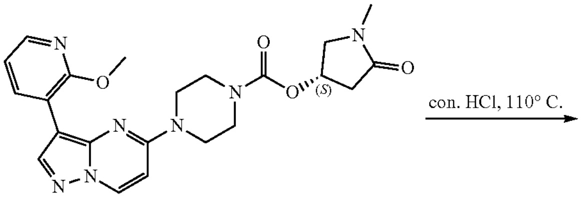

-continued

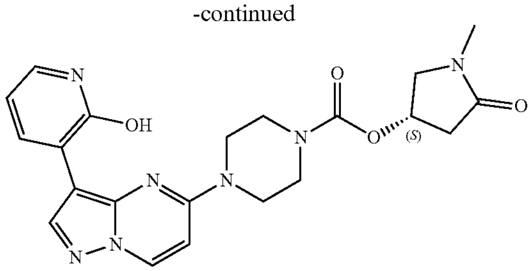

I-98

HCl (12 M, 1 mL, 11.29 eq) was added to [(3S)-1-methyl-5-oxo-pyrrolidin-3-yl] 4-[3-(2-methoxy-3-pyridyl)pyrazolo[1,5-a]pyrimidin-5-yl]piperazine-1-carboxylate (480 mg, 1.06 mmol, 1 eq). The mixture was stirred at 110° C. for 1 hr. LCMS showed that desired MS was found. The mixture was filtered and the filtrate was concentrated to the crude product. The crude product was purified by pre-HPLC (Column: Phenomenex luna C18 150*40*10 um; mobile phase: [water (FA)-ACN]; gradient: 7%-37% B over 10 min). The pure fractions were collected and the volatiles were removed under vacuum. The residue was partitioned between acetonitrile (20 mL) and water (100 mL). The solution was lyophilized to dryness to give [(3S)-1-methyl-5-oxo-pyrrolidin-3-yl]-4-[3-(2-hydroxy-3-pyridyl)pyrazolo[1,5-a]pyrimidin-5-yl]piperazine-1-carboxylate (I-98, 83.02 mg, 189.39 μmol, 17.81% yield, 99.794% purity) as a powder.

LCMS m/z=438.2 $[M+H]^+$).

SFC $t_R$=1.502 min; 100%.

$^1$H NMR (400 MHz, DMSO-$d_6$) δ=11.59 (s, 1H), 8.89 (s, 1H), 8.69 (d, J=7.9 Hz, 1H), 8.63-8.56 (m, 1H), 7.20-7.10 (m, 1H), 6.75 (d, J=8.0 Hz, 1H), 6.29 (t, J=6.8 Hz, 1H), 5.16-5.07 (m, 1H), 3.76-3.70 (m, 4H), 3.69-3.65 (m, 1H), 3.53-3.42 (m, 4H), 3.34 (d, J=1.4 Hz, 1H), 2.70 (s, 3H), 2.70-2.64 (m, 1H), 2.30-2.20 (m, 1H).

Example 75: Synthesis of Compounds I-96, 1-100, and I-104

3-chloropyrazolo[1,5-a]pyrimidin-5-ol

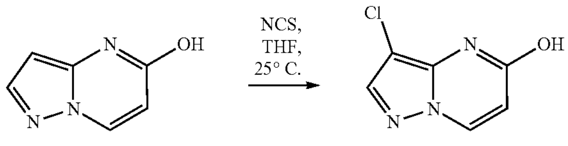

1 2

To a stirred solution of pyrazolo[1,5-a]pyrimidin-5-ol (1 g, 7.40 mmol, 1 eq) in THF (10 mL) was added NCS (988.23 mg, 7.40 mmol, 1 eq) at −78° C. The reaction mixture was allowed to warmed to 25° C. for 12 hr. Then the reaction was heated to 50° C. and stirred for another 5 hr. LCMS showed the starting material was consumed completely and desired compound was detected. The reaction mixture was concentrated under reduced pressure to give a residue. The residue was purified by trituration with water (20 mL) and concentrated to give desired product 3-chloropyrazolo[1,5-a]pyrimidin-5-ol (1 g, 5.90 mmol, 79.69% yield, N/A purity) as a solid.

LCMS m/z=170.0 $[M+H]^+$.

$^1$H NMR (400 MHz, DMSO-$d_6$) δ=12.63-12.43 (m, 1H), 8.48 (d, J=5.8 Hz, 1H), 7.97-7.83 (m, 1H), 6.11-5.96 (m, 1H).

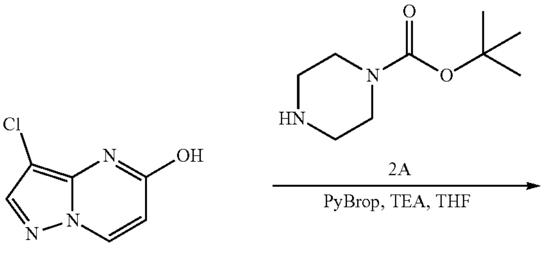

2

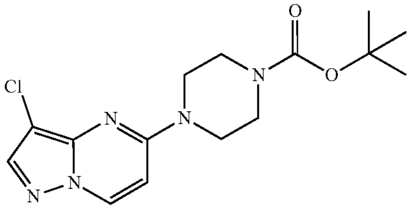

I-100

To a solution of 3-chloropyrazolo[1,5-a]pyrimidin-5-ol (200 mg, 1.18 mmol, 1 eq) in THF (3 mL) was added PYBROP (824.77 mg, 1.77 mmol, 1.5 eq), TEA (238.70 mg, 2.36 mmol, 328.33 μL, 2 eq) and tert-butyl piperazine-1-carboxylate (285.58 mg, 1.53 mmol, 1.3 eq). The mixture was stirred at 50° C. for 12 hr. LCMS showed the starting material was consumed completely and the desired compound was detected. The reaction mixture was filtered and filter cake was triturated with MeCN (10 mL) to give a product, and the filtration was concentrated to give a residue. The residue was purified by prep-HPLC (column: Waters Xbridge BEH C18 150*25*10 um; mobile phase: [water ($NH_3 \cdot H_2O$)-AON]; gradient: 38%-68% B over 10 min) and lyophilized to give tert-butyl 4-(3-chloropyrazolo[1,5-a]pyrimidin-5-yl)piperazine-1-carboxylate (I-100, 55.09 mg, 162.41 μmol, 13.77% yield, 99.59% purity) as a white solid.

LCMS m/z=337.9 $[M+H]^+$).

$^1$H NMR (400 MHz, DMSO-$d_6$) δ=8.39 (d, J=7.9 Hz, 1H), 7.83 (s, 1H), 6.70 (d, J=8.0 Hz, 1H), 3.80-3.76 (m, 4H), 3.56 (m, 4H), 1.49 (s, 9H).

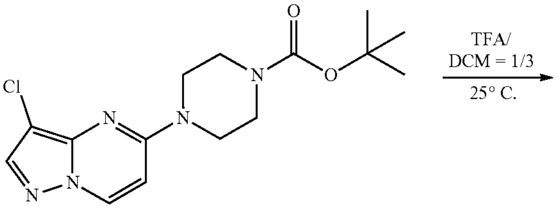

I-100

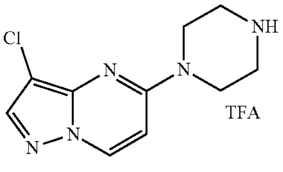

I-104

To a solution of tert-butyl 4-(3-chloropyrazolo[1,5-a]pyrimidin-5-yl)piperazine-1-carboxylate (0.36 g, 1.07 mmol, 1 eq) in DCM (3 mL) was added TFA (1.54 g, 13.46 mmol, 1 mL, 12.63 eq) at 0° C. The mixture was stirred at 25° C. for 1 hr. LCMS showed the starting material was consumed completely and desired compound was detected. The reaction mixture was concentrated under reduced pressure to give a residue. The residue was purified by prep-HPLC (column: CD01-Phenomenex luna C18 150*25*10 um; mobile phase: [water (TFA)-ACN]; gradient: 3%-33% B over 10 min) and lyophilized to give desired product 3-chloro-5-piperazin-1-yl-pyrazolo[1,5-a]pyrimidine (292.30 mg, 827.34 μmol, 77.63% yield, 99.55% purity, TFA) as a solid.

LCMS m/z=238.1 $[M+H]^+$).

$^1$H NMR (400 MHz, DMSO-$d_6$) δ=8.98 (d, J=19.4 Hz, 2H), 8.77 (d, J=7.9 Hz, 1H), 8.03 (s, 1H), 6.85 (d, J=7.9 Hz, 1H), 3.94-3.87 (m, 4H), 3.25-3.19 (m, 4H).

[(3S)-1-methyl-5-oxo-pyrrolidin-3-yl]-4-(3-chloropyrazolo[1,5-a]pyrimidin-5-yl)piperazine-1-carboxylate (I-96)

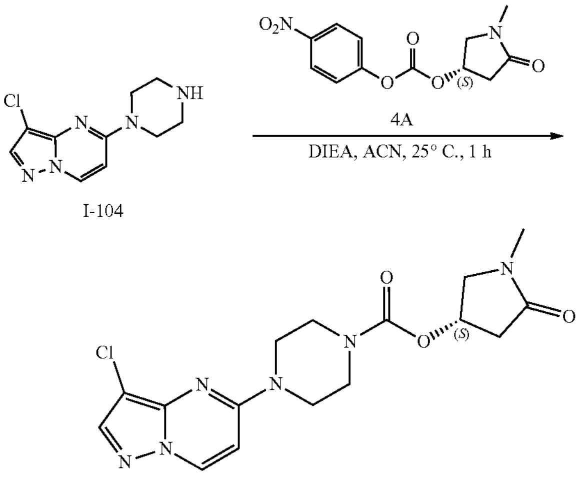

I-104

I-96

To a solution of 3-chloro-5-piperazin-1-yl-pyrazolo[1,5-a]pyrimidine (166 mg, 471.98 μmol, 1 eq, TFA) in ACN (2 mL) was added DIEA (305.00 mg, 2.36 mmol, 411.05 μL, 5 eq) and (4-nitrophenyl) [rac-(3S)-1-methyl-5-oxo-pyrrolidin-3-yl]carbonate (158.72 mg, 566.37 μmol, 1.2 eq). The mixture was stirred at 1 hr for 30° C. LCMS showed the starting material was consumed completely and desired compound was detected. The reaction mixture was concentrated under reduced pressure to give a residue. The residue was purified by prep-HPLC (column: Waters Xbridge BEH C18 150*25*10 um; mobile phase: [water ($NH_3H_2O$)-ACN]; gradient: 19%-39% B over 10 min) and lyophilized to give [(3S)-1-methyl-5-oxo-pyrrolidin-3-yl] 4-(3-chloropyrazolo[1,5-a]pyrimidin-5-yl)piperazine-1-carboxylate (I-96, 177.53 mg, 464.99 μmol, 98.52% yield, 99.22% purity) as a solid.

LCMS m/z=378.9 $[M+H]^+$).

SFC $t_R$=2.152 min; 100%.

$^1$H NMR (400 MHz, DMSO-$d_6$) δ=8.68 (d, J=7.9 Hz, 1H), 7.98 (s, 1H), 6.78 (d, J=7.9 Hz, 1H), 5.17-5.10 (m, 1H), 3.76-3.68 (m, 5H), 3.48 (m, 4H), 3.35 (m, 1H), 2.73 (s, 3H), 2.70 (m, 1H), 2.31-2.24 (m, 1H).

Example 76: Synthesis of Compounds I-97 and I-105

5-piperazin-1-ylpyrazolo[1,5-a]pyrimidine

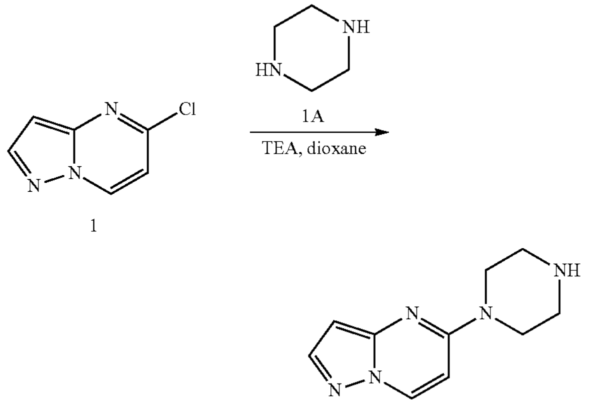

1

I-105

To a solution of 5-chloropyrazolo[1,5-a]pyrimidine (1 g, 6.51 mmol, 1 eq) 5-chloropyrazolo[1,5-a]pyrimidine (1 g, 6.51 mmol, 1 eq) and TEA (1.98 g, 19.54 mmol, 2.72 mL, 3 eq) in dioxane (20 mL) was added piperazine (1.68 g, 19.54 mmol, 3 eq). The mixture was stirred at 90° C. for 0.5 hr. LCMS showed that desired MS was found. The reaction mixture was diluted with water and extracted with EA (3×50 mL). The combined organic layers were washed with brine solution, dried over sodium sulfate, concentrated to give the P1 (5-piperazin-1-ylpyrazolo[1,5-a]pyrimidine (760 mg, 3.74 mmol, 57.42% yield) as a yellow solid. The water phase was concentrated and purified by pre-HPLC (Column: Waters Xbridge BEH C18 150*25*10 um; mobile phase: [water ($NH_4HCO_3$)-ACN]; gradient: 0%-30% B over 10 min). The pure fractions were collected and the volatiles were removed under vacuum. The residue was partitioned between acetonitrile (2 mL) and water (10 mL). The solution was lyophilized to dryness to give the P2 5-piperazin-1-ylpyrazolo[1,5-a]pyrimidine (185 mg, 898.95 μmol, 13.81% yield, 98.76% purity) as a powder.

[(3S)-1-methyl-5-oxo-pyrrolidin-3-yl]-4-pyrazolo[1,5-a]pyrimidin-5-ylpiperazine-1-carboxylate (I-97)

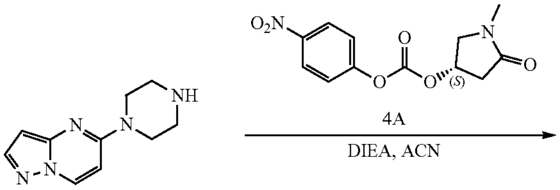

I-105

-continued

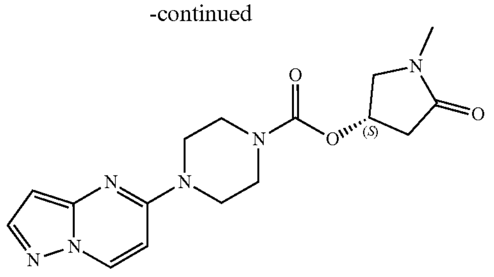

I-97

To a mixture of 5-(piperazin-1-yl)pyrazolo[1,5-a]pyrimidine (300 mg, 1.48 mmol, 1 eq) and [(3S)-1-methyl-5-oxo-pyrrolidin-3-yl](4-nitrophenyl) carbonate (413.64 mg, 1.48 mmol, 1 eq) in ACN (3 mL) was added DIEA (381.54 mg, 2.95 mmol, 514.21 μL, 2 eq). The mixture was stirred at 25° C. for 1 hr. LCMS showed that desired MS was found. The mixture was concentrated to the crude product. The product was purified by pre. HPLC (Column: Waters Xbridge BEH C18 250*25*10 um; mobile phase: [water ($NH_4HCO_3$)-ACN]; gradient: 8%-38% B over 15 min). The pure fractions were collected and the volatiles were removed under vacuum. The residue was partitioned between acetonitrile (2 mL) and water (10 mL). The solution was lyophilized to dryness to give the product. The product was purified by pre. HPLC (Column: Daisogel SP-100-8-ODS-PK 150*25*10 um; mobile phase: [water ($NH_4HCO_3$)-ACN]; gradient: 1%-31% B over 12 min), the pure fractions were collected and the volatiles were removed under vacuum. The residue was partitioned between acetonitrile (2 mL) and water (10 mL). The solution was lyophilized to dryness to give the product. Then the product was purified further by pre. HPLC (Column: Waters Xbridge BEH C18 150*25*10 um; mobile phase: [water ($NH_4HCO_3$)-ACN]; gradient: 4%-34% B over 10 min), the pure fractions were collected and the volatiles were removed under vacuum. The residue was partitioned between acetonitrile (2 mL) and water (10 mL). The solution was lyophilized to dryness to give [(3S)-1-methyl-5-oxo-pyrrolidin-3-yl] 4-pyrazolo[1,5-a]pyrimidin-5-ylpiperazine-1-carboxylate (201.74 mg, 565.97 μmol, 92.95% yield, 96.61% purity) as a solid.

LCMS m/z=345.1 $[M+H]^+$).

SFC $t_R$=0.828 min; 100%.

$^1H$ NMR (400 MHz, DMSO-$d_6$) δ=8.67 (d, J=7.8 Hz, 1H), 7.86 (d, J=2.2 Hz, 1H), 6.70 (d, J=7.8 Hz, 1H), 6.10-5.98 (m, 1H), 5.19-5.10 (m, 1H), 3.75-3.69 (m, 1H), 3.69-3.62 (m, 4H), 3.51-3.42 (m, 4H), 3.37-3.33 (m, 1H), 2.76-2.74 (m, 0.3H), 2.73 (s, 3H), 2.71-2.69 (m, 0.6H), 2.32-2.23 (m, 1H).

Example 77: Synthesis of Compounds I-102, I-102-2, and I-106

3-(2-methoxy-3-pyridyl)-5-piperazin-1-yl-pyrazolo[1,5-a]pyrimidine

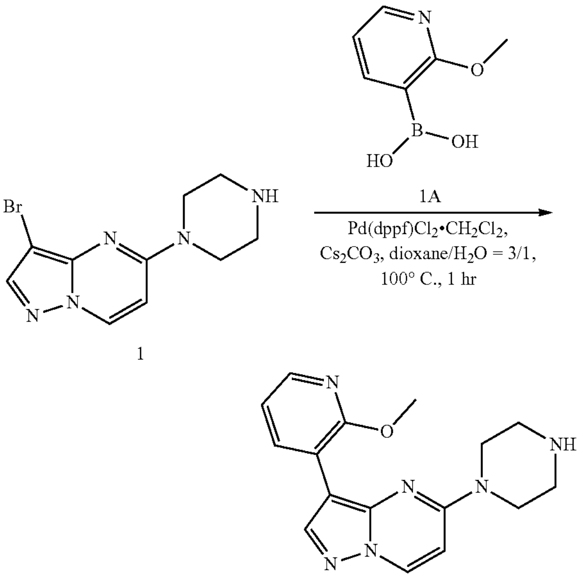

1

I-102-2

A mixture of 3-bromo-5-piperazin-1-yl-pyrazolo[1,5-a]pyrimidine (0.7 g, 2.48 mmol, 1 eq), (2-methoxy-3-pyridyl)boronic acid (417.40 mg, 2.73 mmol, 1.1 eq), Pd(dppf)$Cl_2$·$CH_2Cl_2$ (405.22 mg, 496.21 μmol, 0.2 eq), $Cs_2CO_3$ (2.43 g, 7.44 mmol, 2.35 mL, 3 eq) in dioxane (6 mL) and $H_2O$ (2 mL) was degassed and purged with $N_2$ for 3 times, and then the mixture was stirred at 100° C. for 2 h under $N_2$ atmosphere. LCMS showed desired mass was detected. The reaction mixture was concentrated under reduced pressure to remove solvent. The residue was purified by flash silica gel chromatography (ISCO®; 4 g SepaFlash®| Silica Flash Column, Eluent of 0~10% MeOH/DCM gradient @ 40 mL/min). Then the product was further purified by prep. HPLC (column: Waters Xbridge BEH C18 150*25*10 um; mobile phase: [water ($NH_4HCO_3$)-MeCN]; gradient: 40%-70% B over 10 min). The pure fractions were collected and the volatiles were removed under vacuum. The residue was partitioned between acetonitrile (2 mL) and water (10 mL). The solution was lyophilized to dryness to give 3-(2-methoxy-3-pyridyl)-5-piperazin-1-yl-pyrazolo[1,5-a]pyrimidine (I-102-2, 14.02 mg, 44.56 μmol, 34.57% yield, 98.634% purity) as a solid.

LCMS m/z=311.1 $[M+H]^+$.

$^1H$ NMR (400 MHz, DMSO-$d_6$) δ=8.81 (d, J=7.5 Hz, 1H), 8.68 (d, J=7.9 Hz, 1H), 8.48 (s, 1H), 7.96 (d, J=4.8 Hz, 1H), 7.13-7.01 (m, 1H), 6.79 (d, J=7.9 Hz, 1H), 3.99 (s, 3H), 3.68-3.62 (m, 4H), 2.85-2.75 (m, J=4.1 Hz, 4H).

3-(5-piperazin-1-ylpyrazolo[1,5-a]pyrimidin-3-yl)pyridin-2-ol

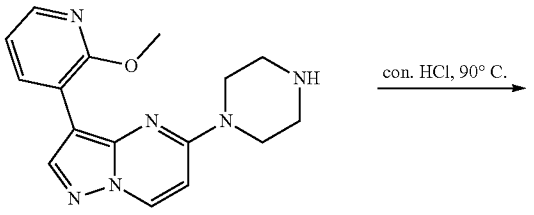

I-102-2

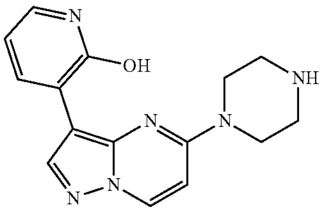

I-106

HCl (12 M, 13.99 mL, 229.66 eq) was added to tert-butyl 3-(2-methoxy-3-pyridyl)-5-piperazin-1-yl-pyrazolo[1,5-a]pyrimidine (0.3 g, 730.87 μmol, 1 eq). The mixture was stirred at 90° C. for 1 hr. LCMS showed desired mass was detected. The reaction mixture was quenched by addition of saturated $Na_2CO_3$ aq. at 25° C., and extracted with CHCl3/i-PrOH (3:1) (30 mL×3). The combined organic layers were washed with brine (30 mL), dried over $Na_2SO_4$, filtered and concentrated under reduced pressure to give a residue. Then the product was purified by prep. HPLC (column: Waters Xbridge BEH C18 150*25*10 um; mobile phase: [water ($NH_3H_2O$)-MeCN]; gradient: 2%-32% B over 10 min). The pure fractions were collected and the volatiles were removed under vacuum. The residue was partitioned between acetonitrile (2 mL) and water (10 mL). The solution was lyophilized to dryness to give 3-(5-piperazin-1-ylpyrazolo[1,5-a]pyrimidin-3-yl)pyridine-2-ol (I-102, 20.47 mg, 66.22 μmol, 9.06% yield, 95.854% purity) as a off-white solid.

LCMS m/z=297.0 $[M+H]^+$).

$^1$H NMR (400 MHz, DMSO-$d_6$) δ=11.85-11.39 (m, 1H), 8.91 (s, 1H), 8.69-8.56 (m, 2H), 7.21-7.16 (m, 1H), 6.75 (d, J=7.9 Hz, 1H), 6.33 (t, J=6.8 Hz, 1H), 3.67-3.60 (m, 4H), 2.88-2.74 (m, 4H).

tert-butyl 4-[3-(2-hydroxy-3-pyridyl)pyrazolo[1,5-a]pyrimidin-5-yl]piperazine-1-carboxylate (I-102)

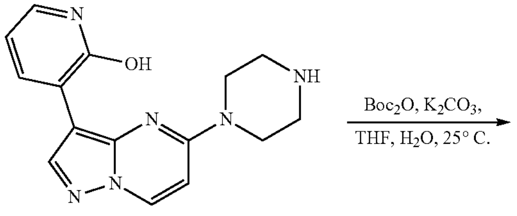

I-106

-continued

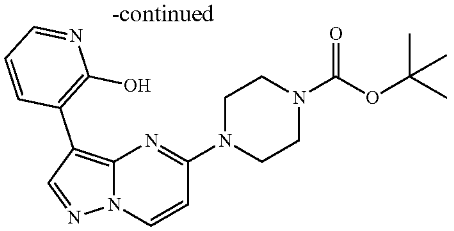

I-102

To a solution of 3-(5-piperazin-1-yl-pyrazolo[1,5-a]pyrimidin-3-yl)pyridine-2-ol (0.3 g, 731.08 μmol, 1 eq, TFA) in THF (3 mL) and $H_2O$ (3 mL) was added BoczO (159.56 mg, 731.08 μmol, 167.95 μL, 1 eq) and $K_2CO_3$ (202.08 mg, 1.46 mmol, 2 eq). The mixture was stirred at 25° C. for 10 hr. LCMS showed desired product was detected. The reaction mixture was concentrated under reduced pressure to remove solvent. Then the product was further purified by prep. HPLC (column: Waters Xbridge BEH C18 150*25*10 um; mobile phase: [water ($NH_3H_2O$)-MeCN]; gradient: 24%-54% B over 10 min). The pure fractions were collected and the volatiles were removed under vacuum. The residue was partitioned between acetonitrile (2 mL) and water (10 mL). The solution was lyophilized to dryness to give tert-butyl 4-[3-(2-hydroxy-3-pyridyl)pyrazolo[1,5-a]pyrimidin-5-yl]piperazine-1-carboxylate (I-102, 49.93 mg, 122.12 μmol, 16.70% yield, 96.96% purity) as a solid.

LCMS m/z=397.9 $[M+H]^+$).

$^1$H NMR (400 MHz, DMSO-$d_6$) δ=8.93 (s, 1H), 8.72 (d, J=7.9 Hz, 1H), 8.62 (dd, J=2.1, 7.1 Hz, 1H), 7.20 (dd, J=2.0, 6.4 Hz, 1H), 6.78 (d, J=7.9 Hz, 1H), 6.34 (t, J=6.8 Hz, 1H), 3.79-3.68 (m, 4H), 3.49 (br d, J=4.9 Hz, 4H), 1.44 (s, 9H).

Example 79: Synthesis of Compound I-107

3-bromo-5-piperazin-1-yl-pyrazolo[1,5-a]pyrimidine

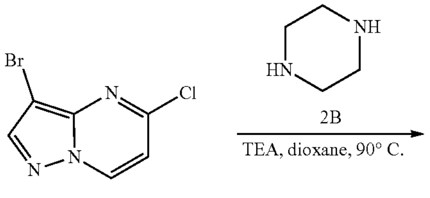

2C

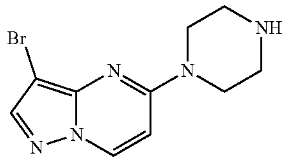

2A

To a solution of 3-bromo-5-chloro-pyrazolo[1,5-a]pyrimidine (40 g, 172.07 mmol, 1 eq) and TEA (52.23 g, 516.21 mmol, 71.85 mL, 3 eq) in dioxane (400 mL) was added piperazine (44.46 g, 516.21 mmol, 3 eq). The mixture was stirred at 90° C. for 0.5 hr. LCMS showed that desired MS was found. The reaction mixture was diluted with water and extracted with EA (3×300 mL). The combined organic layers were washed with brine, dried over sodium sulphate, concentrated under reduced pressure to give 3-bromo-5-piperazin-1-yl-pyrazolo[1,5-a]pyrimidine (48 g, 170.13 mmol, 98.87% yield) as a solid.

LCMS m/z=281.9 [M+H]+.

$^1$H NMR (400 MHz, DMSO-$d_6$) δ=8.61 (d, J=7.9 Hz, 1H), 7.93 (s, 1H), 6.73 (d, J=8.0 Hz, 1H), 3.65-3.57 (m, 4H), 3.17 (s, 1H), 2.81-2.69 (m, 4H).

3-bromo-2-(cyclopropoxy)pyridine

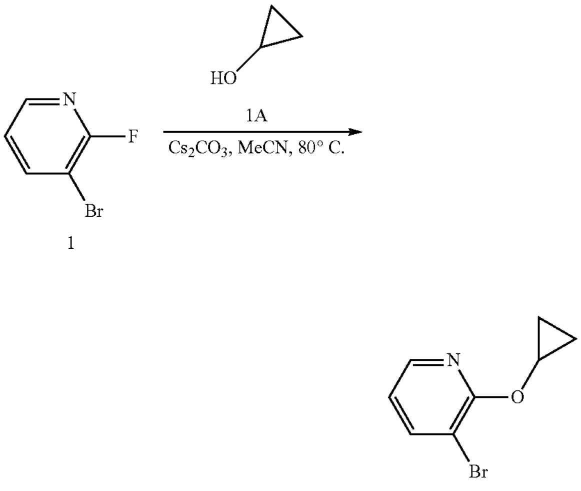

1

2

A mixture of cyclopropanol (24.75 g, 426.15 mmol, 1.5 eq), 3-bromo-2-fluoro-pyridine (50 g, 284.10 mmol, 1 eq), $Cs_2CO_3$ (138.85 g, 426.15 mmol, 1.5 eq) in ACN (500 mL) was degassed and purged with $N_2$ for 3 times, and then the mixture was stirred at 80° C. for 10 hr under $N_2$ atmosphere. LCMS showed desired compound was detected. The reaction mixture was concentrated under reduced pressure to give a residue. the residue was purified by column chromatography ($SiO_2$, Petroleum ether/Ethyl acetate=1/0 to 5/1) to give 3-bromo-2-(cyclopropoxy)pyridine (31 g, 123.10 mmol, 43.33% yield, 85% purity) as an oil.

LCMS m/z=215.9 [M+H]+).

$^1$H NMR (400 MHz, DMSO-$d_6$) δ=11.85-11.39 (m, 1H), 8.91 (s, 1H), 8.69-8.56 (m, 2H), 7.21-7.16 (m, 1H), 6.75 (d, J=7.9 Hz, 1H), 6.33 (t, J=6.8 Hz, 1H), 3.67-3.60 (m, 4H), 2.88-2.74 (m, 4H).

2-(cyclopropoxy)-3-(4,4,5,5-tetramethyl-1,3,2-dioxaborolan-2-yl)pyridine

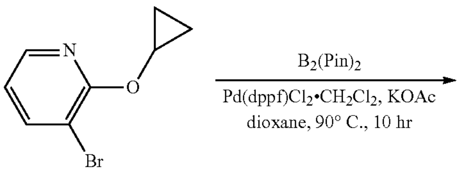

2

-continued

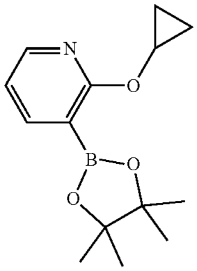

3

A mixture of 3-bromo-2-(cyclopropoxy)pyridine (15 g, 70.07 mmol, 1 eq), 4,4,5,5-tetramethyl-2-(4,4,5,5-tetramethyl-1,3,2-dioxaborolan-2-yl)-1,3,2-dioxaborolane (26.69 g, 105.11 mmol, 1.5 eq), KOAc (20.63 g, 210.22 mmol, 3 eq), $Pd(dppf)Cl_2 \cdot CH_2Cl_2$ (1.14 g, 1.40 mmol, 0.02 eq) in dioxane (200 mL) was degassed and purged with $N_2$ for 3 times, and then the mixture was stirred at 90° C. for 10 hr under $N_2$ atmosphere. LCMS showed desired compound was detected. The reaction mixture was filtered and concentrated under reduced pressure to give a residue, The residue was purified by column chromatography ($SiO_2$, Petroleum ether/Ethyl acetate=1/0 to 10/1) to give 2-(cyclopropoxy)-3-(4,4,5,5-tetramethyl-1,3,2-dioxaborolan-2-yl)pyridine (9 g, 34.47 mmol, 49.19% yield) as an oil.

LCMS m/z=261.7 [M+H]+).

$^1$H NMR (400 MHz, DMSO-$d_6$) δ=8.27 (dd, J=2.0, 4.8 Hz, 1H), 7.90-7.79 (m, 1H), 6.98 (dd, J=4.8, 7.2 Hz, 1H), 4.22 (tt, J=3.0, 6.2 Hz, 1H), 1.26 (s, 12H), 0.77-0.69 (m, 2H), 0.61-0.55 (m, 2H).

3-[2-(cyclopropoxy)-3-pyridyl]-5-piperazin-1-yl-pyrazolo[1,5-a]pyrimidine (1-107)

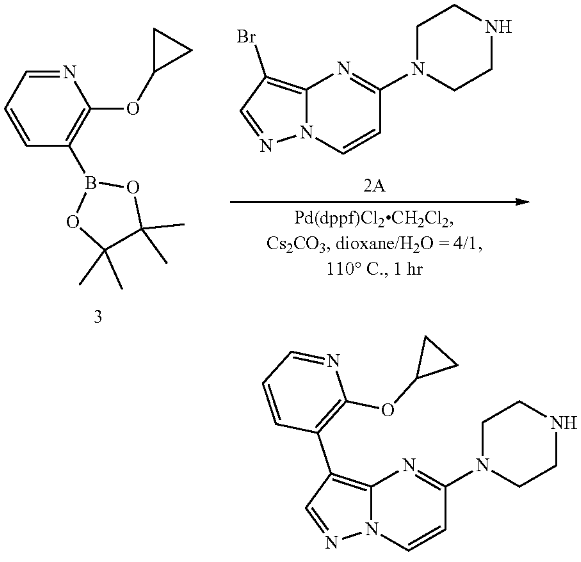

3

I-107

A mixture of 2-(cyclopropoxy)-3-(4,4,5,5-tetramethyl-1,3,2-dioxaborolan-2-yl)pyridine (9 g, 34.47 mmol, 1.2 eq), 3-bromo-5-piperazin-1-yl-pyrazolo[1,5-a]pyrimidine (8.10 g, 28.72 mmol, 1 eq), $Cs_2CO_3$ (18.72 g, 57.44 mmol, 2 eq)

and Pd(dppf)$Cl_2$·$CH_2Cl_2$ (1.17 g, 1.44 mmol, 0.05 eq) in dioxane (200 mL) and $H_2O$ (50 mL). was degassed and purged with $N_2$ for 3 times, and then the mixture was stirred at 110° C. for 1 hr under $N_2$ atmosphere. LCMS showed desired compound was detected. The reaction mixture was concentrated under reduced pressure to give a residue. The residue of all batches was combined together for purification. The residue was purified by column chromatography ($SiO_2$, $CH_2Cl_2$:MeOH=1:0 to 10/1) to give 3-[2-(cyclopropoxy)-3-pyridyl]-5-piperazin-1-yl-pyrazolo[1,5-a]pyrimidine (I-107, 18 g, 42.27 mmol, 58.87% yield, 79% purity) as an oil.

The product (1 g) was purified by prep-HPLC (column: Phenomenex luna C18 150*40*10 um; mobile phase: [water (FA)-ACN]; gradient: 0%-25% B over 10 min). The pure fractions were collected and the volatiles were removed under vacuum. The residue was partitioned between acetonitrile (2 mL) and water (10 mL). The solution was lyophilized to dryness to give 3-[2-(cyclopropoxy)-3-pyridyl]-5-piperazin-1-yl-pyrazolo[1,5a]pyrimidine (595.33 mg, 1.31 mmol, 44.19% yield, 99.395% purity, TFA) as a solid.

LCMS m/z=337.0 $[M+H]^+$).

$^1H$ NMR (400 MHz, DMSO-$d_6$) δ=8.98 (s, 2H), 8.87-8.80 (m, 1H), 8.77-8.71 (m, 1H), 8.37 (s, 1H), 8.07-7.99 (m, 1H), 7.15-7.06 (m, 1H), 6.87 (d, J=8.0 Hz, 1H), 4.44-4.36 (m, 1H), 3.98-3.91 (m, 4H), 3.38-3.16 (m, 4H), 0.88-0.68 (m, 4H).

Example 80: Synthesis of Compound I-108

3-iodo-2-methyl-pyrazolo[1,5-a]pyrimidin-5-ol

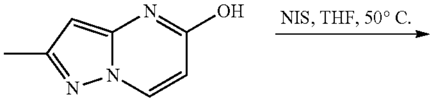

1

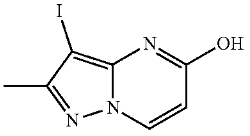

2

To a solution of 2-methylpyrazolo[1,5-a]pyrimidin-5-ol (1.00 g, 6.70 mmol, 1 eq) in THF (10 mL) was added NIS (1.51 g, 6.70 mmol, 1 eq) at 0° C., which was stirred at 50° C. for 12 hr. LCMS showed 85.26% of desired product. The suspension was filtered to give the filter cake. The filter cake was washed with petroleum ether (30 mL). The crude product was used into the next step without further purification. Compound 3-iodo-2-methyl-pyrazolo[1,5-a]pyrimidin-5-ol (1.51 g, 5.15 mmol, 76.75% yield, 93.73% purity) was obtained as a white solid.

LCMS m/z=275.9 $[M+H]^+$.

$^1H$ NMR (400 MHz, DMSO-$d_6$) δ=12.10 (br s, 1H), 8.35 (br d, J=7.8 Hz, 1H), 5.92 (br d, J=7.6 Hz, 1H), 2.18 (s, 3H).

tert-butyl 4-(3-iodo-2-methyl-pyrazolo[1,5-a]pyrimidin-5-yl)piperazine-1-carboxylate

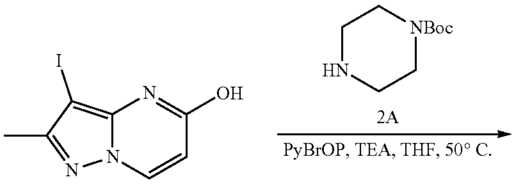

2

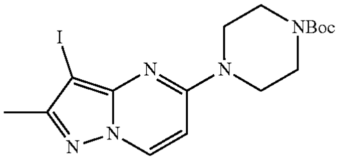

3

To a solution of 3-iodo-2-methyl-pyrazolo[1,5-a]pyrimidin-5-ol (1 g, 3.64 mmol, 1 eq) and tert-butyl piperazine-1-carboxylate (744.88 mg, 4.00 mmol, 1.1 eq) in THF (15 mL) was added PYBROP (2.54 g, 5.45 mmol, 1.5 eq) and TEA (1.10 g, 10.91 mmol, 1.52 mL, 3 eq), which was stirred at 50° C. for 12 hr. LCMS showed 88.86% of desired product. The suspension was filtered to give the filtrate. The filtrate was concentrated to the crude product. The crude product was purified by re-crystallization with ACN (12 mL) at 25° C. The solid was precipitated, filtered by suction, washed twice, and then dried. Compound tert-butyl 4-(3-iodo-2-methyl-pyrazolo[1,5-a]pyrimidin-5-yl)piperazine-1-carboxylate (1.5 g, 3.29 mmol, 90.39% yield, 97.12% purity) was obtained as a yellow solid.

LCMS m/z=444.0 $[M+H]^+$).

$^1H$ NMR (400 MHz, DMSO-$d_6$) δ=8.56 (d, J=7.8 Hz, 1H), 6.66 (d, J=7.9 Hz, 1H), 3.71-3.65 (m, 4H), 3.46-3.41 (m, 4H), 2.25 (s, 3H), 1.42 (s, 9H).

tert-butyl 4-[3-[2-(cyclopropoxy)-3-pyridyl]-2-methyl-pyrazolo[1,5-a]pyrimidin-5-yl]piperazine-1-carboxylate

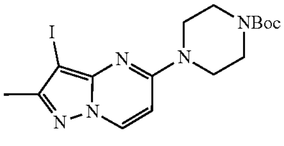

3

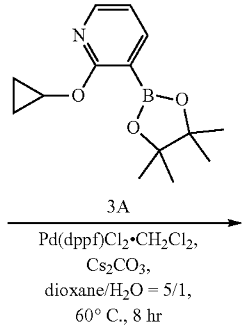

-continued

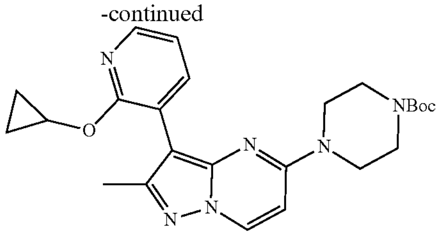

4

A mixture of tert-butyl 4-(3-iodo-2-methyl-pyrazolo[1,5-a]pyrimidin-5-yl)piperazine-1-carboxylate (1 g, 2.26 mmol, 1 eq), 2-(cyclopropoxy)-3-(4,4,5,5-tetramethyl-1,3,2-dioxaborolan-2-yl)pyridine (589.07 mg, 2.26 mmol, 1 eq), $Cs_2CO_3$ (2.21 g, 6.77 mmol, 3 eq) in dioxane (10 mL) and $H_2O$ (2 mL) was degassed and purged with $N_2$ for 3 times, $Pd(dppf)Cl_2 \cdot CH_2Cl_2$ (184.23 mg, 225.59 μmol, 0.1 eq) was added. The reaction mixture was degassed and purged with $N_2$ for 3 times and stirred at 60° C. for 8 hr under $N_2$ atmosphere. LCMS showed 46.63% of desired product. The reaction was concentrated to dryness under reduced pressure to give the crude product. The crude product was purified by column chromatography ($SiO_2$, Petroleum ether:Ethyl acetate=1/0 to 1/1) to give tert-butyl 4-[3-[2-(cyclopropoxy)-3-pyridyl]-2-methyl-pyrazolo[1,5-a]pyrimidin-5-yl]piperazine-1-carboxylate (398 mg, 615.64 μmol, 27.29% yield, 69.69% purity) as a solid.

LCMS m/z=451.2 $[M+H]^+$).

$^1$H NMR (400 MHz, DMSO-$d_6$) δ=8.58 (d, J=7.8 Hz, 1H), 8.14 (dd, J=1.8, 4.9 Hz, 1H), 7.72 (dd, J=1.8, 7.3 Hz, 1H), 7.59-7.53 (m, 1H), 6.65 (d, J=7.9 Hz, 1H), 4.26-4.22 (m, 1H), 3.61-3.56 (m, 4H), 3.40 (br d, J=3.0 Hz, 4H), 2.16 (s, 3H), 1.41 (s, 9H), 0.78-0.69 (m, 2H), 0.63-0.55 (m, 2H).

3-[2-(cyclopropoxy)-3-pyridyl]-2-methyl-5-piperazin-1-yl-pyrazolo[1,5-a]pyrimidine

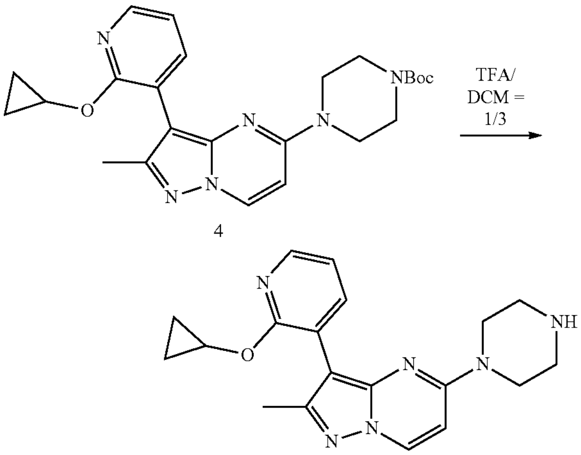

4

5

To a solution of tert-butyl 4-[3-[2-(cyclopropoxy)-3-pyridyl]-2-methyl-pyrazolo[1,5-a]pyrimidin-5-yl]piperazine-1-carboxylate (395 mg, 876.74 μmol, 1 eq) in DCM (2 mL) was added TFA (0.5 mL), which was stirred at 25° C. for 2 hr. LCMS showed 50.43% of desired product. The reaction was concentrated to give 3-[2-(cyclopropoxy)-3-pyridyl]-2-methyl-5-piperazin-1-yl-pyrazolo[1,5-a]pyrimidine (400 mg, crude, TFA) as a yellow oil.

LCMS m/z=351.2 $[M+H]^+$).

[(3S)-1-methyl-5-oxo-pyrrolidin-3-yl]-4-[3-[2-(cyclopropoxy)-3-pyridyl]-2-methyl-pyrazolo[1,5-a]pyrimidin-5-yl]piperazine-1-carboxylate (1-108)

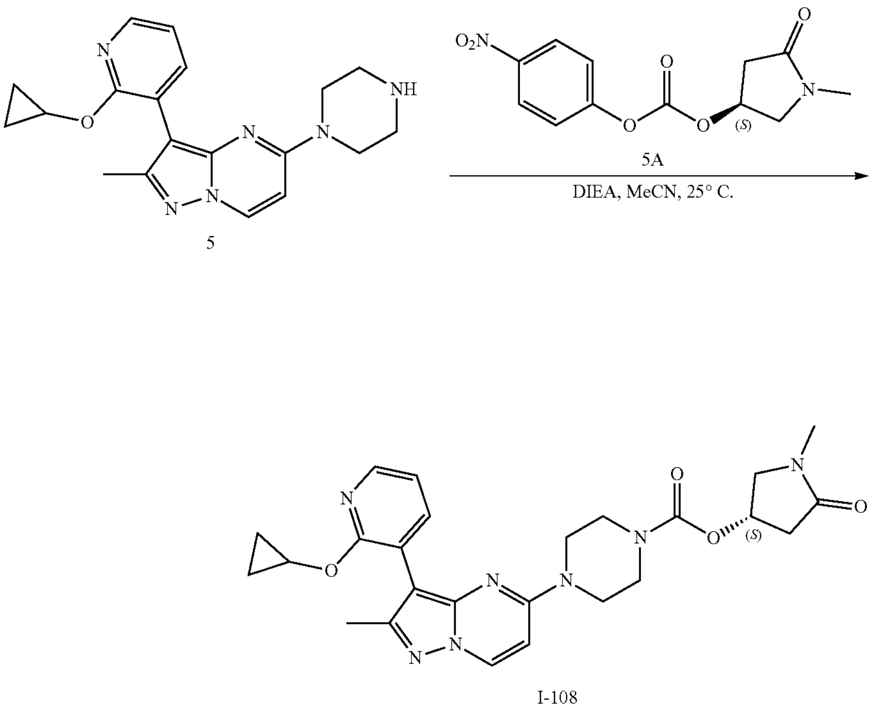

5

I-108

To a solution of 3-[2-(cyclopropoxy)-3-pyridyl]-2-methyl-5-piperazin-1-yl-pyrazolo[1,5-a]pyrimidine (400 mg, 861.25 μmol, 1 eq, TFA) and [(3S)-1-methyl-5-oxo-pyrrolidin-3-yl](4-nitrophenyl) carbonate (289.62 mg, 1.03 mmol, 1.2 eq) in MeCN (2 mL) was added DIEA (556.55 mg, 4.31 mmol, 750.07 μL, 5 eq), which was stirred at 25° C. for 12 hr. LCMS showed 44.13% of desired product. The reaction was concentrated to a residue.

The crude product was purified by column chromatography ($SiO_2$, Dichloromethane:Methanol=1/0 to 10/1) to the product, then the product was purified by reversed-phase HPLC (column: Waters Xbridge BEH C18 150*25*10 um; mobile phase: [water ($NH_3H_2O$)—I]; gradient: 22%-42% B over 10 min) and lyophilized to give the product. The product was purified by reversed-phase HPLC (column: Waters Xbridge BEH C18 150*25*10 um; mobile phase: [water ($NH_4HCO_3$)—I]; gradient: 19%-49% B over 10 min) and lyophilized to give [(3S)-1-methyl-5-oxo-pyrrolidin-3-yl]-4-[3-[2-(cyclopropoxy)-3-pyridyl]-2-methyl-pyrazolo[1,5-a]pyrimidin-5-yl]piperazine-1-carboxylate (I-108, 81.63 mg, 164.28 μmol, 19.07% yield, 98.92% purity) as a solid.

LCMS m/z=492.1 $[M+H]^+$).

$^1$H NMR (400 MHz, DMSO-$d_6$) δ=8.59 (d, J=8.0 Hz, 1H), 8.20-8.07 (m, 1H), 7.78-7.67 (m, 1H), 7.15-7.01 (m, 1H), 6.66 (d, J=8.0 Hz, 1H), 5.17-5.07 (m, 1H), 4.30-4.18 (m, 1H), 3.73-3.67 (m, 1H), 3.64-3.57 (m, 4H), 3.46-3.40 (m, 4H), 3.34-3.29 (m, 1H), 2.74-2.72 (m, 3H), 2.71-2.65 (m, 1H), 2.30-2.22 (m, 1H), 2.16 (s, 3H), 0.77-0.69 (m, 2H), 0.63-0.55 (m, 2H).

Example 81: Synthesis of Compound I-109

Ethyl 6-fluoro-5,7-dihydroxy-pyrazolo[1,5-a]pyrimidine-3-carboxylate

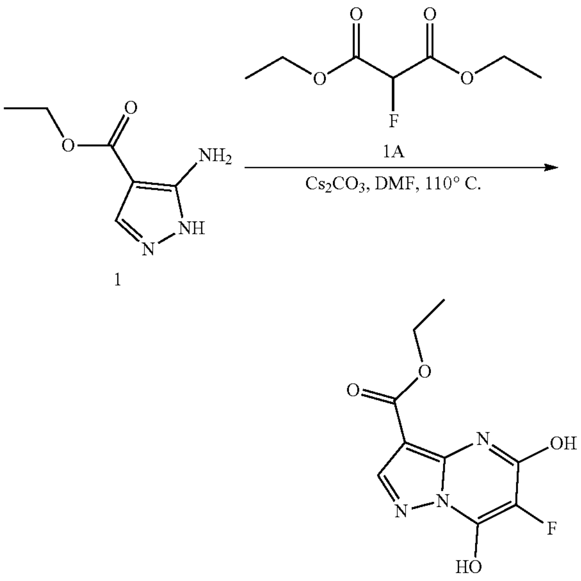

1 1A 2

To a solution of ethyl 3-amino-1H-pyrazole-4-carboxylate (5 g, 32.23 mmol, 1 eq) in DMF (20 mL) was added $Cs_2CO_3$ (15.75 g, 48.34 mmol, 1.5 eq) and diethyl 2-fluoropropanedioate (8.61 g, 48.34 mmol, 1.5 eq). The mixture was stirred at 110° C. for 12 hr. LCMS showed the starting material was consumed completely and desired compound was detected. The mixture was diluted with water (80 mL), acidified to pH=5 by 5 M HCl aqueous solution and then lots of solid was formed. The mixture was filtered, the filter cake was washed with MeOH (10 mL×2) and concentrated in vacuum to remove the solvent to afford ethyl 6-fluoro-5,7-dihydroxy-pyrazolo[1,5-a]pyrimidine-3-carboxylate (5.76 g, 23.88 mmol, 74.11% yield, N/A purity) as a solid.

LCMS m/z=242.0 $[M+H]^+$.

$^1$H NMR (400 MHz, DMSO-$d_6$) ¿=9.35 (s, 1H), 7.82 (s, 1H), 4.22 (q, J=7.0 Hz, 2H), 1.27 (t, J=7.1 Hz, 3H).

Ethyl 5,7-dichloro-6-fluoro-pyrazolo[1,5-a]pyrimidine-3-carboxylate

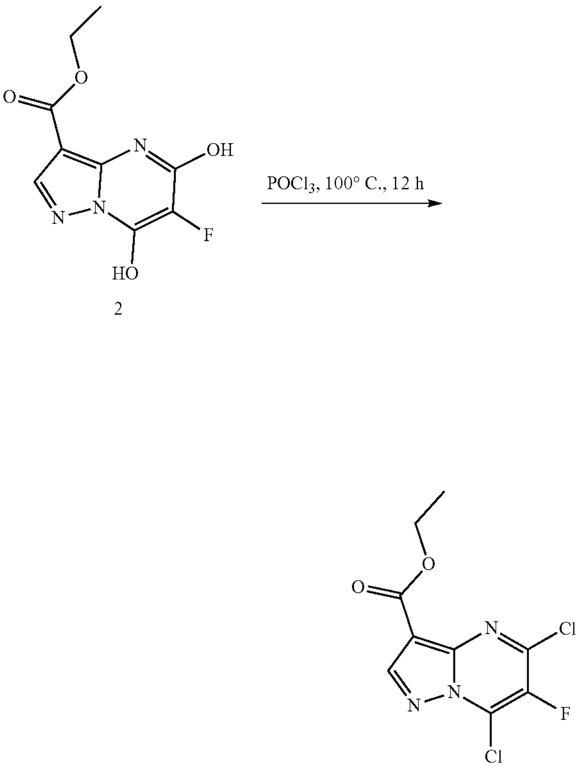

2 3

Ethyl 6-fluoro-5,7-dihydroxy-pyrazolo[1,5-a]pyrimidine-3-carboxylate (3 g, 12.44 mmol, 1 eq) was added to $POCl_3$ (16.45 g, 107.28 mmol, 10 mL, 8.62 eq). The mixture was stirred at 100° C. for 12 hr. LCMS showed the starting material was consumed completely and desired compound was detected. The reaction mixture was concentrated under reduced pressure to give a residue. The residue was purified by flash silica gel chromatography (ISCO®; 20 g SepaFlash® Silica Flash Column, Eluent of 15~20% Ethyl acetate/Petroleum ether gradient 80 mL/min) to give desired product ethyl 5,7-dichloro-6-fluoro-pyrazolo[1,5-a]pyrimidine-3-carboxylate (1.6 g, 5.00 mmol, 40.23% yield, 86.98% purity) as a solid.

LCMS m/z=277.9 $[M+H]^+$.

Ethyl 5-chloro-6-fluoro-pyrazolo[1,5-a]pyrimidine-3-carboxylate

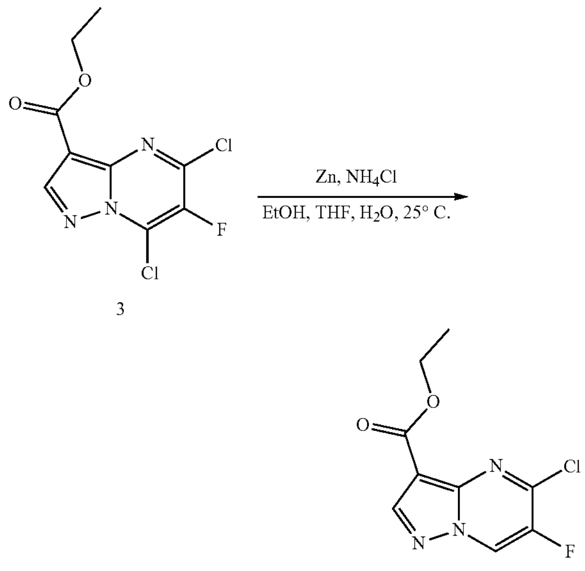

3

4

To a solution of ethyl 5,7-dichloro-6-fluoro-pyrazolo[1,5-a]pyrimidine-3-carboxylate (3.3 g, 11.87 mmol, 1 eq) in EtOH (15 mL), THF (5 mL) and $H_2O$ (10 mL) was added $NH_4Cl$ (1.59 g, 29.67 mmol, 2.5 eq) and Zn (1.16 g, 17.80 mmol, 1.5 eq). The mixture was stirred at 25° C. for 0.5 hr. TLC (petroleum ether:ethyl acetate=3:1) showed the starting material (Rr-0.55) was consumed completely and a mainly new spot (Rr=0.5) was formed. The zinc powder was removed by filtration, and the filter cake was washed with DCM (3 mL). The filtrate was concentrated in vacuum to remove the solvent. The residue was purified by flash silica gel chromatography (ISCO®; 40 g SepaFlash® Silica Flash Column, Eluent of 18~25% Ethyl acetate/Petroleum ether gradient @ 100 mL/min) to give desired product ethyl 5-chloro-6-fluoro-pyrazolo[1,5-a]pyrimidine-3-carboxylate (1.99 g, 7.81 mmol, 65.84% yield, 95.65% purity) as a solid.

LCMS m/z=244.0 $[M+H]^+$.

$^1H$ NMR (400 MHz, DMSO-$d_6$) δ=9.92 (d, J=4.3 Hz, 1H), 8.68 (s, 1H), 4.32 (q, J=7.0 Hz, 2H), 1.32 (t, J=7.1 Hz, 3H)

Ethyl 5-(4-tert-butoxycarbonylpiperazin-1-yl)-6-fluoro-pyrazolo[1,5-a]pyrimidine-3-carboxylate

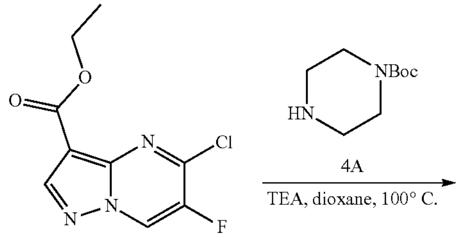

4

4A

-continued

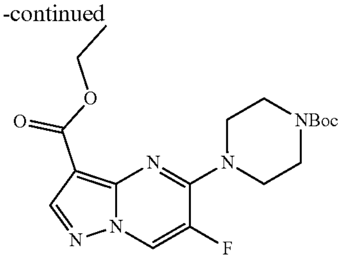

5

To a solution of ethyl 5-chloro-6-fluoro-pyrazolo[1,5-a]pyrimidine-3-carboxylate (1.9 g, 7.80 mmol, 1 eq) in dioxane (20 mL) was added TEA (2.37 g, 23.40 mmol, 3.26 mL, 3 eq) and tert-butyl piperazine-1-carboxylate (4.36 g, 23.40 mmol, 3 eq). The mixture was stirred at 100° C. for 12 hr. TLC (petroleum ether:ethyl acetate=3:1) showed the starting material ($R_f$=0.50) was consumed completely and a mainly new spot ($R_f$=0.35) was formed. The reaction mixture was concentrated under reduced pressure to give a residue. The residue was purified by flash silica gel chromatography (ISCO®; 40 g SepaFlash® Silica Flash Column, Eluent of 43~55% Ethyl acetate/Petroleum ether gradient 100 mL/min) to give ethyl 5-(4-tert-butoxycarbonylpiperazin-1-yl)-6-fluoro-pyrazolo[1,5-a]pyrimidine-3-carboxylate (3 g, 7.30 mmol, 93.55% yield, 95.68% purity) as a solid.

LCMS m/z=393.9 $[M+H]^+$.

$^1H$ NMR (400 MHz, DMSO-$d_6$) δ=9.29 (d, J=8.8 Hz, 1H), 8.30 (s, 1H), 4.21 (q, J=7.1 Hz, 2H), 3.81-3.76 (m, 4H), 3.53-3.48 (m, 4H), 1.43 (s, 9H), 1.29 (t, J=7.1 Hz, 3H).

5-(4-tert-butoxycarbonylpiperazin-1-yl)-6-fluoro-pyrazolo[1,5-a]pyrimidine-3-carboxylic acid

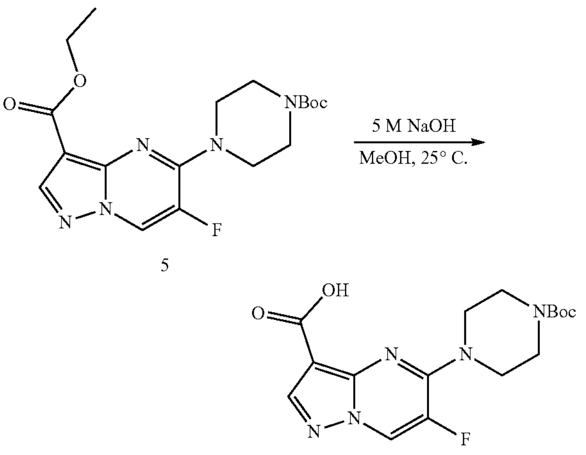

5

6

To a solution of ethyl 5-(4-tert-butoxycarbonylpiperazin-1-yl)-6-fluoro-pyrazolo[1,5-a]pyrimidine-3-carboxylate (3 g, 7.63 mmol, 1 eq) in MeOH (21 mL) was added NaOH (5 M, 7 mL, 4.59 eq). The mixture was stirred at 70° C. for 0.5 hr. TLC (petroleum ether:ethyl acetate=1:1) showed the starting material ($R_f$=0.60) was consumed completely and a mainly new spot (R=0.00) was formed. The reaction mixture was concentrated in vacuo to give a residue. The mixture was diluted with water (50 mL). The water phase was acidified to pH=5 with citric aqueous solution and lots of solid was precipitated, the solid was collected to give 5-(4-tert-butoxycarbonylpiperazin-1-yl)-6-fluoro-pyrazolo[1,5-a]pyrimidine-3-carboxylic acid (1.85 g, 2.90 mmol, 38.02% yield, 57.26% purity) as a solid.

LCMS m/z=366.1 [M+H]$^+$.

$^1$H NMR (400 MHz, DMSO-$d_6$) δ=9.28 (d, J=8.8 Hz, 1H), 8.26 (s, 1H), 3.78-3.75 (m, 4H), 3.52-3.49 (m, 4H), 1.43 (s, 9H)

Tert-butyl 4-(6-fluoro-3-iodo-pyrazolo[1,5-a]pyrimidin-5-yl)piperazine-1-carboxylate

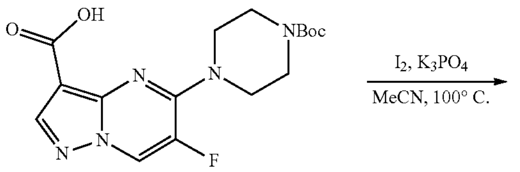

6

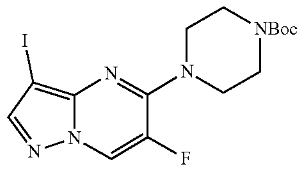

7

To a solution of 5-(4-tert-butoxycarbonylpiperazin-1-yl)-6-fluoro-pyrazolo[1,5-a]pyrimidine-3-carboxylic acid (1.29 g, 3.53 mmol, 1 eq) in ACN (10 mL) was added $K_3PO_4$ (1.50 g, 7.06 mmol, 694.28 μL, 2 eq) and $I_2$ (896.15 mg, 3.53 mmol, 711.23 μL, 1 eq). The mixture was stirred at 100° C. for 1 hr. TLC (petroleum ether:ethyl acetate=1:1) showed the starting material (Rr-0.00) was consumed completely and a mainly new spot ($R_f$=0.60) was formed. The reaction solution was diluted with water (100 mL) and then extracted with ethyl acetate (100 mL×2). The combined organic layers were washed with brine (80 mL), dried over anhydrous sodium sulfate, filtered and concentrated in vacuo to give residue. The residue was purified by flash silica gel chromatography (ISCO®; 12 g SepaFlash® Silica Flash Column, Eluent of 22~30% Ethyl acetate/Petroleum ether gradient @ 50 mL/min) to give tert-butyl 4-(6-fluoro-3-iodo-pyrazolo[1,5-a]pyrimidin-5-yl)piperazine-1-carboxylate (535 mg, 1.18 mmol, 33.31% yield, 98.33% purity) as a solid.

LCMS m/z=448.0 [M+H]$^+$.

$^1$H NMR (400 MHz, DMSO-$d_6$) δ=9.23 (d, J=8.6 Hz, 1H), 7.99 (s, 1H), 3.68-3.62 (m, 4H), 3.52-3.46 (m, 4H), 1.42 (s, 9H).

tert-butyl 4-[3-[2-(cyclopropoxy)-3-pyridyl]-6-fluoro-pyrazolo[1,5-a]pyrimidin-5-yl]piperazine-1-carboxylate

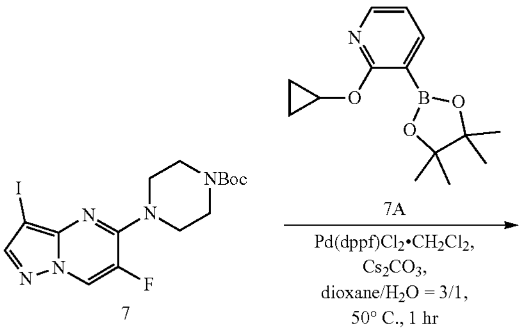

7

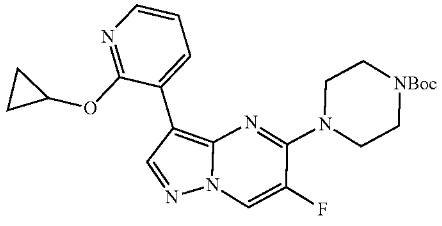

8

A mixture of tert-butyl 4-(6-fluoro-3-iodo-pyrazolo[1,5-a]pyrimidin-5-yl)piperazine-1-carboxylate (78 mg, 174.40 μmol, 1 eq), 2-(cyclopropoxy)-3-(4,4,5,5-tetramethyl-1,3,2-dioxaborolan-2-yl)pyridine (54.65 mg, 209.28 μmol, 1.2 eq), $Cs_2CO_3$ (170.47 mg, 523.20 umol, 3 eq) and Pd(dppf)$Cl_2$·$CH_2Cl_2$ (7.12 mg, 8.72 μmol, 0.05 eq) in dioxane (3.5 mL) and $H_2O$ (0.7 mL) was degassed and purged with $N_2$ for 3 times, and then the mixture was stirred at 50° C. for 1 h under $N_2$ atmosphere. LCMS showed desired compound was detected. The reaction mixture was concentrated under reduced pressure to give a residue. The residue was purified by flash silica gel chromatography (ISCO®; 4 g SepaFlash® Silica Flash Column, Eluent of 25~30% Ethyl acetate/Petroleum ether gradient @ 20 mL/min) to give tert-butyl 4-[3-[2-(cyclopropoxy)-3-pyridyl]-6-fluoro-pyrazolo[1,5-a]pyrimidin-5-yl]piperazine-1-carboxylate (70 mg, 96.85 μmol, 55.53% yield, 62.88% purity) as an oil.

LCMS m/z=455.1 [M+H]$^+$.

3-[2-(cyclopropoxy)-3-pyridyl]-6-fluoro-5-piperazin-1-yl-pyrazolo[1,5-a]pyrimidine

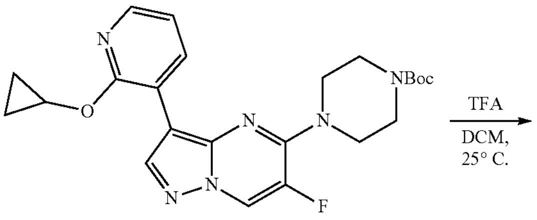

8

-continued

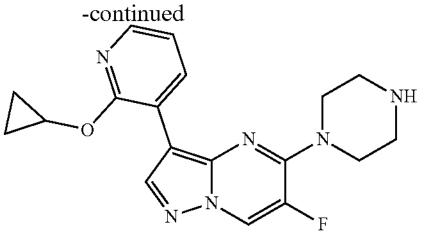

9

To a solution of tert-butyl 4-[3-[2-(cyclopropoxy)-3-pyridyl]-6-fluoro-pyrazolo[1,5-a]pyrimidin-5-yl]piperazine-1-carboxylate (120 mg, 264.03 μmol, 1 eq) in DCM (3 mL) was added TFA (1.54 g, 13.46 mmol, 1 mL, 50.99 eq). The mixture was stirred at 25° C. for 0.5 hr. LCMS showed the starting material was consumed completely and desired compound was detected. The reaction mixture was concentrated under reduced pressure to give 3-[2-(cyclopropoxy)-3-pyridyl]-6-fluoro-5-piperazin-1-yl-pyrazolo[1,5-a]pyrimidine (120 mg, 256.19 μmol, 97.03% yield, N/A purity, TFA) as an oil.

LCMS m/z=355.1 [M+H]+.

[(3S)-1-methyl-5-oxo-pyrrolidin-3-yl] 4-[3-[2-(cyclopropoxy)-3-pyridyl]-6-fluoro-pyrazolo[1,5-a]pyrimidin-5-yl]piperazine-1-carboxylate (I-109)

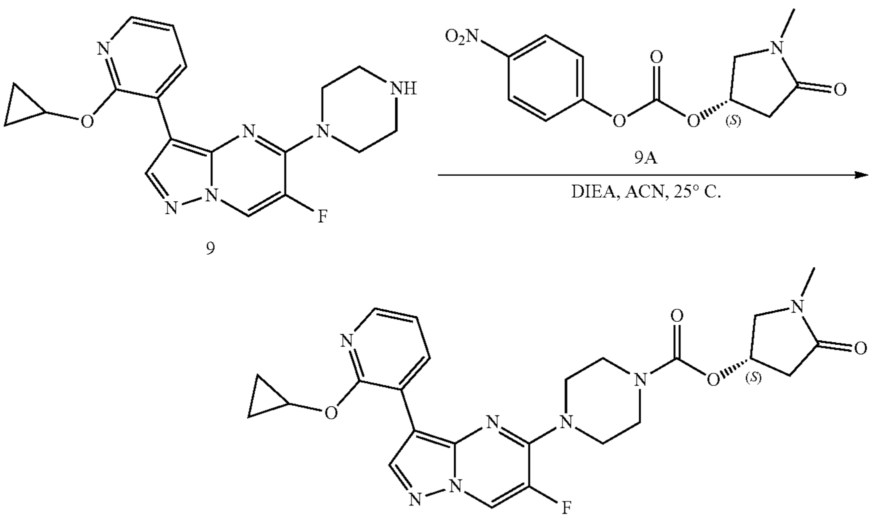

9

I-109

To a solution of 3-[2-(cyclopropoxy)-3-pyridyl]-6-fluoro-5-piperazin-1-yl-pyrazolo[1,5-a]pyrimidine (120 mg, 256.19 μmol, 1 eq, TFA) in ACN (2 mL) was added DIEA (165.55 mg, 1.28 mmol, 223.11 μL, 5 eq) and [(3S)-1-methyl-5-oxo-pyrrolidin-3-yl](4-nitrophenyl) carbonate (71.79 mg, 256.19 μmol, 1 eq). The reaction mixture was stirred at 25° C. for 1 hr. LCMS showed the starting material was consumed completely and desired compound was detected. The reaction mixture was concentrated in vacuo to give crude product. The crude product was purified by prep-HPLC (column: CD02-Waters Xbridge BEH C18 150*25*10 um; mobile phase: [water ($NH_4HCO_3$)-ACN]; gradient: 22%-52% B over 10 min) and lyophilized to give desired [(3S)-1-methyl-5-oxo-pyrrolidin-3-yl]-4-[3-[2-(cyclopropoxy)-3-pyridyl]-6-fluoro-pyrazolo[1,5-a]pyrimidin-5-yl]piperazine-1-carboxylate (58.38 mg, 117.50 umol, 45.86% yield, 99.73% purity) as a solid.

LCMS m/z=496.6 $[M+H]^+$.

SFC $t_R$=0.993 min; 100%

$^1$H NMR (400 MHz, DMSO-$d_6$) δ=9.24 (d, J=8.6 Hz, 1H), 8.73-8.68 (m, 1H), 8.38 (s, 1H), 8.06-8.01 (m, 1H), 7.14-7.09 (m, 1H), 5.18-5.12 (m, 1H), 4.42-4.37 (m, 1H), 3.75-3.72 (m, 1H), 3.72-3.67 (m, 4H), 3.60-3.54 (m, 4H), 3.38-3.35 (m, 1H), 2.74 (s, 3H), 2.73-2.68 (m, 1H), 2.32-2.26 (m, 1H), 0.82-0.75 (m, 4H).

Example 82: Synthesis of Compound I-110 and I-110-9

Methyl (E)-2,3-dimethoxyprop-2-enoate

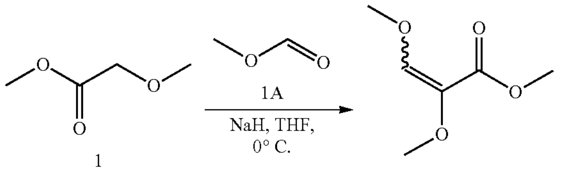

1 2

To a solution of methyl 2-methoxyacetate (5 g, 48.03 mmol, 4.75 mL, 1 eq) and methyl formate (3.46 g, 57.63 mmol, 3.50 mL, 1.2 eq) in THF (45 mL) was slowly added NaH (2.69 g, 67.24 mmol, 60% purity, 1.4 eq) under $N_2$, keep the temperature of the reaction system below 0° C. throughout the feeding process, and stirred at 25° C. for 2 hours. TLC (petroleum ether:ethyl acetate=5:1) showed the starting material (Rr=0.60) was consumed completely and a mainly new spot (Rr=0.70) was formed. Methyl tert-butyl ether was added to the reaction mixture and stir at 25° C. for 30 min, filtered, and the filter cake was vacuum-dried to obtain product methyl (E)-2,3-dimethoxyprop-2-enoate (3 g, crude) as a solid.

Ethyl 5-hydroxy-6-methoxy-pyrazolo[1,5-a]pyrimidine-3-carboxylate

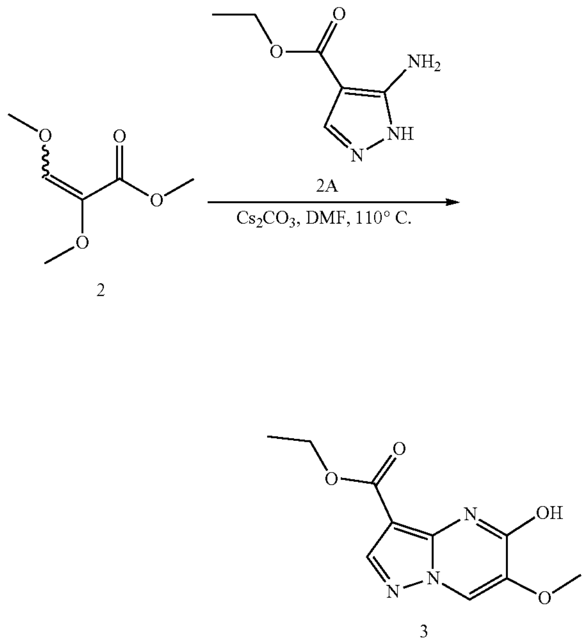

To a solution of ethyl 5-amino-1H-pyrazole-4-carboxylate (707.78 mg, 4.56 mmol, 1 eq) in DMF (5 mL) was added $Cs_2CO_3$ (2.23 g, 6.84 mmol, 1.5 eq) and methyl (E)-2,3-dimethoxyprop-2-enoate (1 g, 6.84 mmol, 1.5 eq). The mixture was stirred at 110° C. for 6 hr. LCMS showed the starting material was consumed completely and desired compound was detected. The mixture was diluted with water (5 mL), acidified to pH-5 by 5 M HCl aqueous solution and then lots of solid was formed. The mixture was filtered, the filter cake was washed with MeOH (5 mL×2) and concentrated in vacuum to remove the solvent to afford ethyl 5-hydroxy-6-methoxy-pyrazolo[1,5-a]pyrimidine-3-carboxylate (450 mg, 1.90 mmol, 41.59% yield, N/A purity) as a solid.

LCMS m/z=237.8 $[M+H]^+$.

$^1H$ NMR (400 MHz, DMSO-$d_6$) δ=11.95 (s, 1H), 8.33-8.19 (m, 1H), 8.09-7.55 (m, 1H), 4.34-4.23 (m, 2H), 3.78 (d, J=3.6 Hz, 3H), 1.33-1.25 (m, 3H).

Ethyl 5-(4-tert-butoxycarbonylpiperazin-1-yl)-6-methoxy-pyrazolo[1,5-a]pyrimidine-3-carboxylate

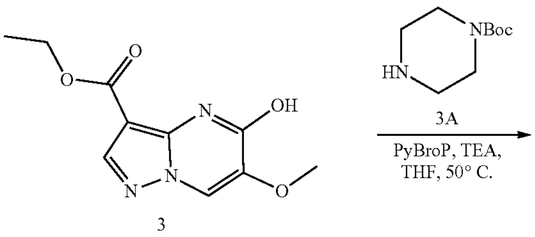

-continued

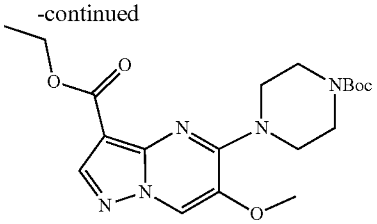

4

To a solution of ethyl 5-hydroxy-6-methoxy-pyrazolo[1,5-a]pyrimidine-3-carboxylate (450 mg, 1.90 mmol, 1 eq) in DMF (5 mL) was added PYBROP (1.33 g, 2.85 mmol, 1.5 eq), TEA (575.88 mg, 5.69 mmol, 792.13 μL, 3 eq) and tert-butyl piperazine-1-carboxylate (353.33 mg, 1.90 mmol, 1 eq). The mixture was stirred at 50° C. for 12 hr. LCMS showed the starting material was consumed completely and the desired compound was detected. The reaction mixture was added acetonitrile, then filtered and the filter cake was washed with MeCN (5 mL×2) and concentrated in vacuum to remove the solvent to afford ethyl 5-(4-tert-butoxycarbonylpiperazin-1-yl)-6-methoxy-pyrazolo[1,5-a]pyrimidine-3-carboxylate (350 mg, 863.24 μmol, 45.50% yield, N/A purity) as a solid.

LCMS m/z=406.0 $[M+H]^+$.

$^1H$ NMR (400 MHz, METHANOL-$d_4$) δ=8.33 (s, 1H), 8.21 (s, 1H), 4.37-4.26 (m, 2H), 3.94 (s, 3H), 3.92-3.87 (m, 4H), 3.63-3.55 (m, 4H), 1.51 (s, 9H), 1.43-1.36 (m, 3H).

5-(4-tert-butoxycarbonylpiperazin-1-yl)-6-methoxy-pyrazolo[1,5-a]pyrimidine-3-carboxylic acid

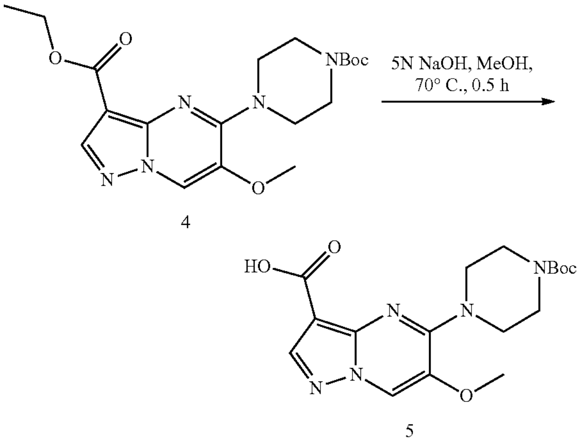

To a solution of ethyl 5-(4-tert-butoxycarbonylpiperazin-1-yl)-6-methoxy-pyrazolo[1,5-a]pyrimidine-3-carboxylate (350 mg, 863.24 μmol, 1 eq) in MeOH (3 mL) was added NaOH (5 M, 1 mL, 5.79 eq). The mixture was stirred at 70° C. for 0.5 hr. LCMS showed the starting material was consumed completely and desired compound was detected. The reaction solution was concentrated in vacuum to remove the solvent. The mixture was diluted with water (5 mL), the water phase was acidified to pH=5 with citric aqueous solution and lots of solid was precipitated, the solid was collected to give 5-(4-tert-butoxycarbonylpiperazin-1-yl)-6-methoxy-pyrazolo[1,5-a]pyrimidine-3-carboxylic acid (157 mg, 361.93 μmol, 41.93% yield, 87% purity) as a solid.

LCMS m/z=377.8 $[M+H]^+$.

$^1$H NMR (400 MHz, DMSO-$d_6$) ¿=12.03-11.75 (m, 1H), 8.60 (s, 1H), 8.16 (s, 1H), 3.87 (s, 3H), 3.75-3.69 (m, 4H), 3.49-3.43 (m, 4H), 1.42 (s, 9H).

tert-butyl-4-(3-iodo-6-methoxy-pyrazolo[1,5-a]pyrimidin-5-yl)piperazine-1-carboxylate

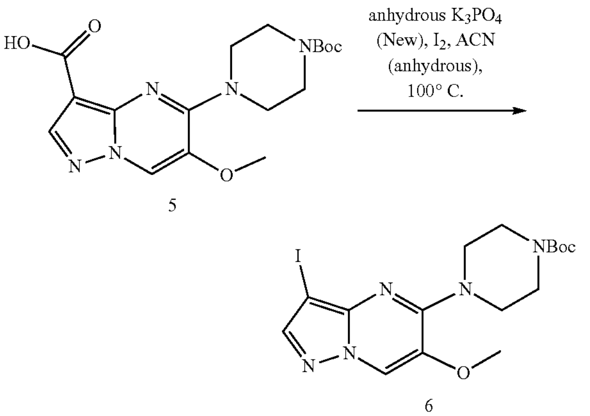

5

6

To a solution of 5-(4-tert-butoxycarbonylpiperazin-1-yl)-6-methoxy-pyrazolo[1,5-a]pyrimidine-3-carboxylic acid (100 mg, 264.97 μmol, 1 eq) in ACN (1 mL) was added $K_3PO_4$ (112.49 mg, 529.95 μmol, 52.10μ, 2 eq) and $I_2$ (67.25 mg, 264.97 μmol, 53.38μ, 1 eq). The mixture was stirred at 100° C. for 2 hr. LCMS showed the starting material was consumed completely and desired compound was detected. The reaction solution was diluted with water (30 mL) and then extracted with ethyl acetate (20 mL×3). The combined organic layers were washed with brine (20 mL), dried over anhydrous sodium sulfate, filtered and concentrated in vacuo to give tert-butyl 4-(3-iodo-6-methoxy-pyrazolo[1,5-a]pyrimidin-5-yl)piperazine-1-carboxylate (100 mg, 205.58 μmol, 77.59% yield, 94.42% purity) as a solid.

LCMS m/z=460.0 [M+H]$^+$.

$^1$H NMR (400 MHz, DMSO-$d_6$) δ=8.59 (s, 1H), 7.88 (s, 1H), 3.86 (s, 3H), 3.64-3.59 (m, 4H), 3.49-3.43 (m, 4H), 1.42 (s, 9H).

Tert-butyl-4-[3-[2-(cyclopropoxy)-3-pyridyl]-6-methoxy-pyrazolo[1,5-a]pyrimidin-5-yl]piperazine-1-carboxylate

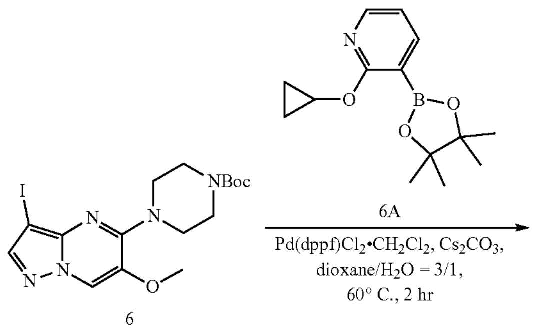

6

-continued

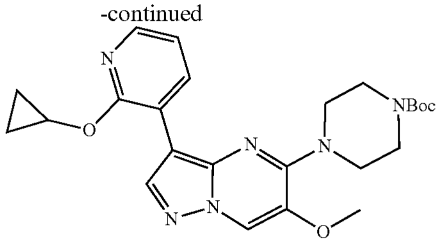

7

A mixture of tert-butyl 4-(3-iodo-6-methoxy-pyrazolo[1,5-a]pyrimidin-5-yl)piperazine-1-carboxylate (140 mg, 304.82 μmol, 1 eq), 2-(cyclopropoxy)-3-(4,4,5,5-tetramethyl-1,3,2-dioxaborolan-2-yl)pyridine (95.52 mg, 365.79 μmol, 1.2 eq) $Cs_2CO_3$ (297.95 mg, 914.47 μmol, 3 eq) and Pd(dppf)$Cl_2$·$CH_2Cl_2$ (12.45 mg, 15.24 μmol, 0.05 eq) in dioxane (3 mL) and $H_2O$ (1 mL) was degassed and purged with $N_2$ for 3 times, and then the mixture was stirred at 50° C. for 2 hr under $N_2$ atmosphere. LCMS showed desired compound was detected. The reaction mixture was concentrated under reduced pressure to give a residue. The residue was purified by flash silica gel chromatography (ISCO®; 4 g SepaFlash® Silica Flash Column, Eluent of 48~55% Ethyl acetate/Petroleum ether gradient @ 20 mL/min) to give tert-butyl 4-[3-[2-(cyclopropoxy)-3-pyridyl]-6-methoxy-pyrazolo[1,5-a]pyrimidin-5-yl]piperazine-1-carboxylate (100 mg, 188.30 μmol, 61.77% yield, 87.85% purity) as a solid.

LCMS m/z=467.1 [M+H]$^+$.

$^1$H NMR (400 MHz, DMSO-$d_6$) δ=8.81-8.75 (m, 1H), 8.62 (s, 1H), 8.30 (s, 1H), 8.03-7.99 (m, 1H), 7.15-7.09 (m, 1H), 4.45-4.37 (m, 1H), 3.89 (s, 3H), 3.68-3.62 (m, 4H), 3.53-3.48 (m, 4H), 1.43 (s, 9H), 0.83-0.76 (m, 4H).

3-[2-(cyclopropoxy)-3-pyridyl]-6-methoxy-5-piperazin-1-yl-pyrazolo[1,5-a]pyrimidine

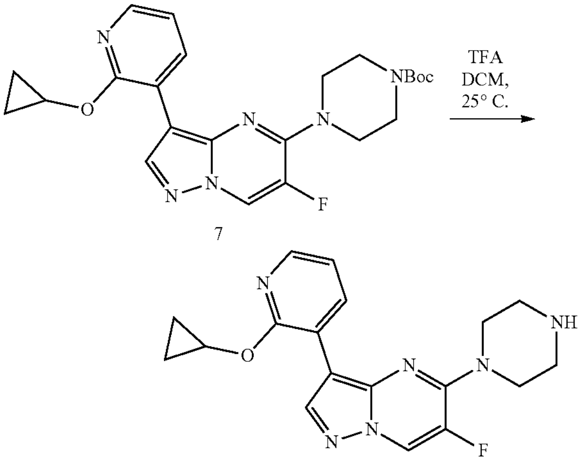

7

8

To a solution of tert-butyl 4-[3-[2-(cyclopropoxy)-3-pyridyl]-6-methoxy-pyrazolo[1,5-a]pyrimidin-5-yl]piperazine-1-carboxylate (100 mg, 214.35 μmol, 1 eq) in DCM (1.5 mL) was added TFA (767.50 mg, 6.73 mmol, 0.5 mL, 31.40 eq). The mixture was stirred at 25° C. for 0.5 hr. LCMS showed the starting material was consumed completely and desired compound was detected. The reaction mixture was concentrated under reduced pressure to give 3-[2-(cyclopropoxy)-3-pyridyl]-6-methoxy-5-piperazin-1-yl-pyrazolo[1,5-a]pyrimidine (100 mg, 208.14 μmol, 97.11% yield, N/A purity, TFA) as an oil.

LCMS m/z=367.1 [M+H]$^+$.

[(3S)-1-methyl-5-oxo-pyrrolidin-3-yl]-4-[3-[2-(cyclopropoxy)-3-pyridyl]-6-methoxy-pyrazolo[1,5-a]pyrimidin-5-yl]piperazine-1-carboxylate (I-110-9)

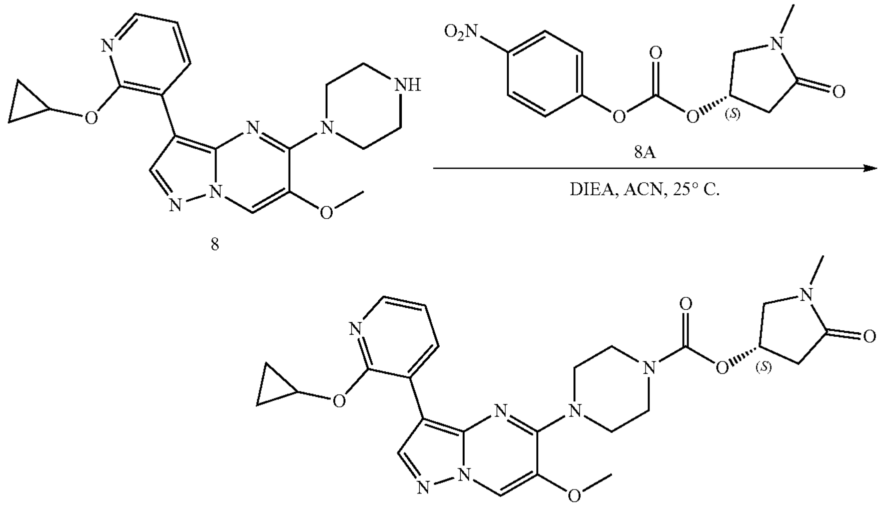

I-110-9

To a solution of 3-[2-(cyclopropoxy)-3-pyridyl]-6-methoxy-5-piperazin-1-yl-pyrazolo[1,5-a]pyrimidine (100 mg, 208.14 μmol, 1 eq, TFA) in I (2 mL), was added DIEA (134.50 mg, 1.04 mmol, 181.27 μL, 5 eq) and [(3S)-1-methyl-5-oxo-pyrrolidin-3-yl](4-nitrophenyl) carbonate (58.33 mg, 208.14 μmol, 1 eq). The reaction mixture was stirred at 25° C. for 2 hr. LCMS showed the starting material was consumed completely and desired compound was detected. The reaction mixture was filtered and filter cake was washed Petroleum ether (2 mL*2) to give a white solid (P1). Then the filtrate was concentrated in vacuum to give a residue (P2). The residue (P2) was purified by prep-HPLC (column: Waters Xbridge BEH C18 150*25*10 um; mobile phase: [water ($NH_4HCO_3$)—I]; gradient: 20%-50% B over 10 min) and lyophilized to give [(3S)-1-methyl-5-oxo-pyrrolidin-3-yl]-4-[3-[2-(cyclopropoxy)-3-pyridyl]-6-methoxy-pyrazolo[1,5-a]pyrimidin-5-yl]piperazine-1-carboxylate (I-110-9, 29.07 mg, 56.52 μmol, 57.37% yield, 98.68% purity) as a white solid LCMS m/z=508.4 $[M+H]^+$.

SFC $t_R$=1.308 min; 100%.

$^1$H NMR (400 MHz, DMSO-$d_6$) δ=8.80-8.76 (m, 1H), 8.62 (s, 1H), 8.30 (s, 1H), 8.03-8.00 (m, 1H), 7.14-7.08 (m, 1H), 5.18-5.12 (m, 1H), 4.44-4.37 (m, 1H), 3.88 (s, 3H), 3.74-3.70 (m, 1H), 3.70-3.64 (m, 4H), 3.57-3.52 (m, 4H), 3.38-3.36 (m, 1H), 2.74 (s, 3H), 2.73-2.68 (m, 1H), 2.31-2.25 (m, 1H), 0.82-0.77 (m, 4H).

[(3S)-1-methyl-5-oxo-pyrrolidin-3-yl]-4-[3-[2-(cyclopropoxy)-3-pyridyl]-6-hydroxy-pyrazolo[1,5-a]pyrimidin-5-yl]piperazine-1-carboxylate (I-110)

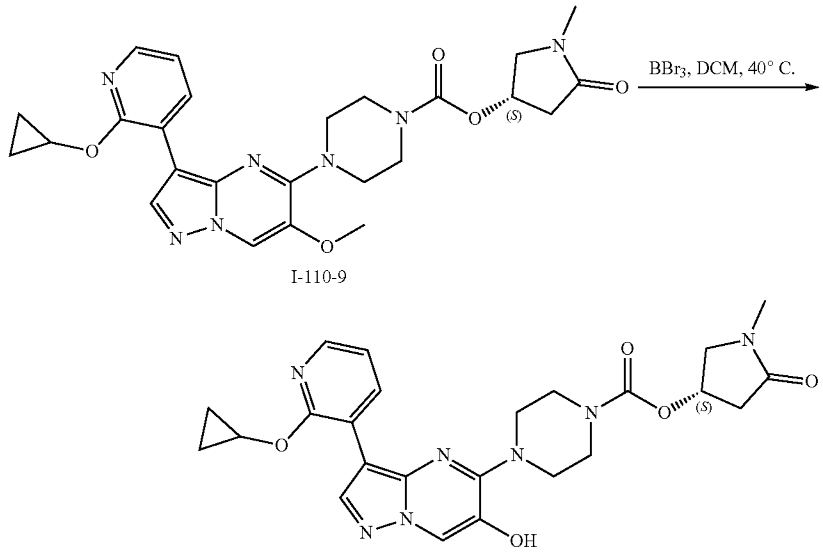

I-110

To a solution [(3S)-1-methyl-5-oxo-pyrrolidin-3-yl] 4-[3-[2-(cyclopropoxy)-3-pyridyl]-6-methoxy-pyrazolo[1,5-a]pyrimidin-5-yl]piperazine-1-carboxylate (100 mg, 165.43 umol, 1 eq) in DCM (2 mL) was added $BBr_3$ (2 M, 1 mL, 12.09 eq) at 0° C. under $N_2$. The mixture was stirred at 40° C. for 2 hr. LCMS showed desired compound was detected. The reaction was slowly poured into water (10 mL) at room temperature and stirred for 0.5 h. Then the reaction mixture was basified to pH=8 by $NaHCO_3$, and concentrated in vacuo to give a residue. The residue was purified by prep-HPLC (column: CD24-XPT C18 150*25*7 um; mobile phase: [water ($NH_4HCO_3$)-ACN]; gradient: 17%-47% B over 11 min) and second prep-HPLC (column: CD04-Welch Xtimate C18 150*25*7 um; mobile phase: [water (FA)-ACN]; gradient: 21%-51% B over 10 min) then lyophilized to give [(3S)-1-methyl-5-oxo-pyrrolidin-3-yl] 4-[3-[2-(cyclopropoxy)-3-pyridyl]-6-hydroxy-pyrazolo[1,5-a]pyrimidin-5-yl]piperazine-1-carboxylate (I-110, 9.71 mg, 19.25 μmol, 23.75% yield, 97.84% purity) as a solid, LCMS m/z=494.0 $[M+H]^+$.

SFC $t_R$=1.934 min; 100%.

$^1H$ NMR (400 MHz, DMSO-$d_6$) δ=8.82-8.78 (m, 1H), 8.23 (s, 1H), 8.14 (s, 1H), 8.02-7.97 (m, 1H), 7.13-7.08 (m, 1H), 5.18-5.10 (m, 1H), 4.44-4.36 (m, 1H), 3.77-3.69 (m, 5H), 3.58-3.53 (m, 4H), 3.38-3.37 (m, 1H), 2.74 (s, 3H), 2.73-2.68 (m, 1H), 2.31-2.25 (m, 1H), 0.83-0.74 (m, 4H).

Example 83: Synthesis of Compound I-111

6-methylpyrazolo[1,5-a]pyrimidine-5,7-diol

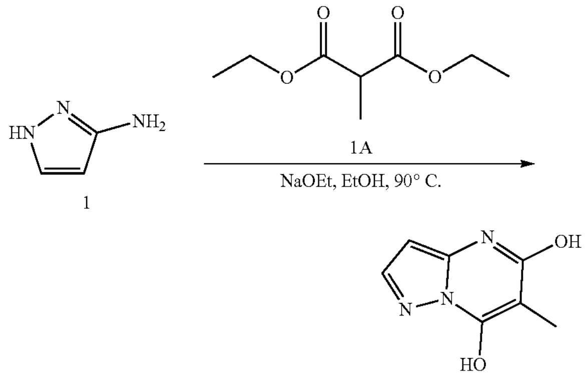

1
2

To a solution of 1H-pyrazol-3-amine (10 g, 120.35 mmol, 1 eq) in EtOH (50 mL) was added NaOEt (40.95 g, 120.35 mmol, 20% purity, 1 eq) and diethyl 2-methylpropanedioate (25.16 g, 144.42 mmol, 24.62 mL, 1.2 eq). The mixture was stirred at 90° C. for 12 hr. TLC showed one new spot was formed. The reaction mixture was quenched by addition HCl (10 mL, 6N) and filtered by suction. The filter cake was washed twice and then dried to give 6-methylpyrazolo[1,5-a]pyrimidine-5,7-diol (17.5 g, 105.96 mmol, 88.05% yield) as a solid.

$^1H$ NMR (400 MHz, DMSO-$d_6$) δ=7.72 (d, J=1.5 Hz, 1H), 5.89 (br s, 1H), 1.87 (s, 3H).

5,7-dichloro-6-methyl-pyrazolo[1,5-a]pyrimidine

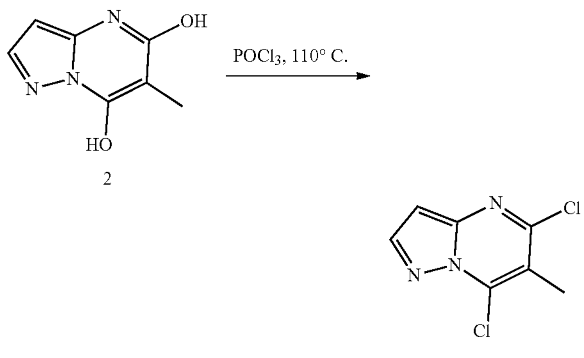

2
3

To a solution of 6-methylpyrazolo[1,5-a]pyrimidine-5,7-diol (10 g, 60.55 mmol, 1 eq) in $POCl_3$ (20 mL) was stirred at 110° C. for 5 hr. LCMS showed desired MS was detected. The reaction mixture was concentrated under reduced pressure to remove solvent. The residue was basified with 3N NaOH solution (pH=9-10) and extracted with ethyl acetate (3×200 ml). The combined organic layers were dried over anhydrous $Na_2SO_4$, filtered, and concentrated under vacuum to give 5,7-dichloro-6-methyl-pyrazolo[1,5-a]pyrimidine (2.7 g, 11.49 mmol, 18.98% yield, 86% purity) as a solid.

LCMS m/z=201.7 $[M+H]^+$.

$^1H$ NMR (400 MHz, DMSO-$d_6$) δ=8.32 (d, J=2.3 Hz, 1H), 6.84 (d, J=2.3 Hz, 1H), 2.46 (s, 3H).

5-chloro-6-methyl-pyrazolo[1,5-a]pyrimidine

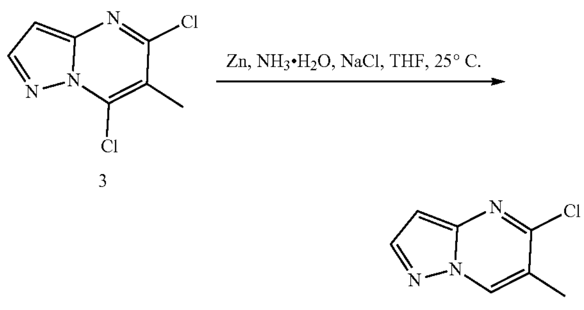

3
4

To a solution of 5,7-dichloro-6-methyl-pyrazolo[1,5-a]pyrimidine (3.7 g, 18.31 mmol, 1 eq) in THF (15 mL) was added Zn (3.59 g, 54.94 mmol, 3 eq), $NH_3·H_2O$ (4.28 g, 36.63 mmol, 4.70 mL, 30% purity, 2 eq) and sat. NaCl (5.38 M, 13.62 mL, 4 eq). The mixture was stirred at 25° C. for 12 hr. LCMS showed desired MS was detected. The mixture was filtered and extracted with ethyl acetate (100 ml×3). The residue was purified by flash silica gel chromatography (ISCO®; 40 g SepaFlash® Silica Flash Column, Eluent of 0~50% Ethyl acetate/Petroleum ether gradient @40 mL/min) to give 5-chloro-6-methyl-pyrazolo[1,5-a]pyrimidine (1.6 g, 9.26 mmol, 50.57% yield, 97% purity) as a solid.

LCMS m/z=167.7 $[M+H]^+$.

$^1H$ NMR (400 MHz, CHLOROFORM-d) δ=8.56-8.41 (m, 1H), 8.05 (d, J=2.3 Hz, 1H), 6.58 (dd, J=0.7, 2.3 Hz, 1H), 2.38 (d, J=1.1 Hz, 3H).

5-chloro-3-iodo-6-methyl-pyrazolo[1,5-a]pyrimidine

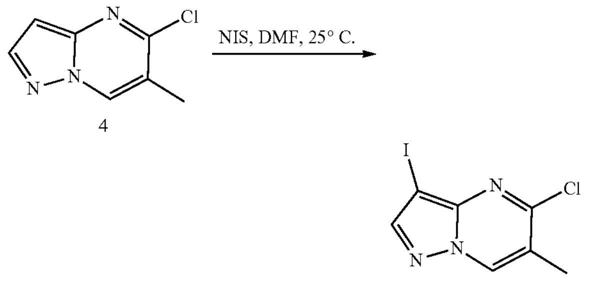

4

5

To a solution of 5-chloro-6-methyl-pyrazolo[1,5-a]pyrimidine (1.6 g, 9.55 mmol, 1 eq) in DMF (5 mL) was added NIS (3.22 g, 14.32 mmol, 1.5 eq). The mixture was stirred at 25° C. for 10 hr. LCMS showed desired MS was detected. The reaction mixture was concentrated under reduced pressure to remove solvent. The residue was purified by flash silica gel chromatography (ISCO®; 5 g SepaFlash® Silica Flash Column, Eluent of 0~30% Ethyl acetate/Petroleum ether gradient @ 25 mL/min) to give 5-chloro-3-iodo-6-methyl-pyrazolo[1,5-a]pyrimidine (1.05 g, 3.47 mmol, 36.35% yield, 97% purity) as a solid.

LCMS m/z=293.6 $[M+H]^+$.

$^1$H NMR (400 MHz, DMSO-$d_6$) δ=9.21 (d, J=0.9 Hz, 1H), 8.29 (s, 1H), 2.33 (d, J=0.8 Hz, 3H).

tert-butyl 4-(3-iodo-6-methyl-pyrazolo[1,5-a]pyrimidin-5-yl)piperazine-1-carboxylate

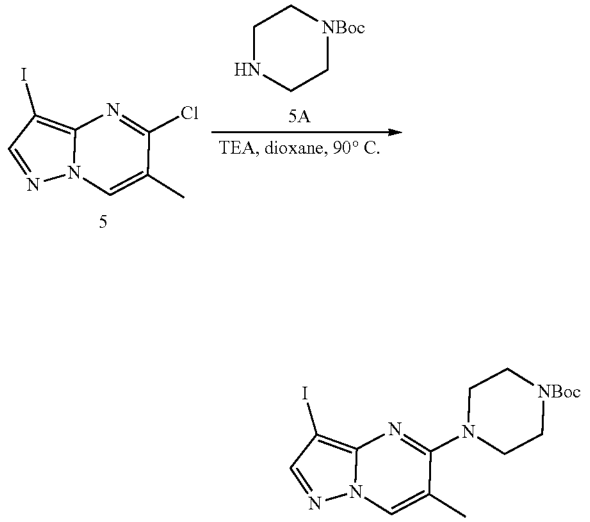

5

6

To a solution of 5-chloro-3-iodo-6-methyl-pyrazolo[1,5-a]pyrimidine (1 g, 3.41 mmol, 1 eq) in dioxane (10 mL) was added TEA (689.56 mg, 6.81 mmol, 948.50 μL, 2 eq) and tert-butyl piperazine-1-carboxylate (1.90 g, 10.22 mmol, 3 eq). The mixture was stirred at 90° C. for 12 hr. LCMS showed desired MS was detected. The reaction mixture was concentrated under reduced pressure to remove solvent. The residue was purified by flash silica gel chromatography (ISCO®; 5 g SepaFlash® Silica Flash Column, Eluent of 0~20% Ethyl acetate/Petroleum ether gradient @25 mL/min) to give tert-butyl 4-(3-iodo-6-methyl-pyrazolo[1,5-a]pyrimidin-5-yl)piperazine-1-carboxylate (0.65 g, 1.47 mmol, 43.04% yield, 100% purity) as a solid.

LCMS m/z=443.8 $[M+H]^+$.

$^1$H NMR (400 MHz, DMSO-$d_6$) δ=8.74 (s, 1H), 7.99 (s, 1H), 3.50 (br s, 4H), 3.36 (br s, 4H), 2.27 (s, 3H), 1.44 (s, 9H).

tert-butyl-4-[3-[2-(cyclopropoxy)-3-pyridyl]-6-methyl-pyrazolo[1,5-a]pyrimidin-5-yl]piperazine-1-carboxylate

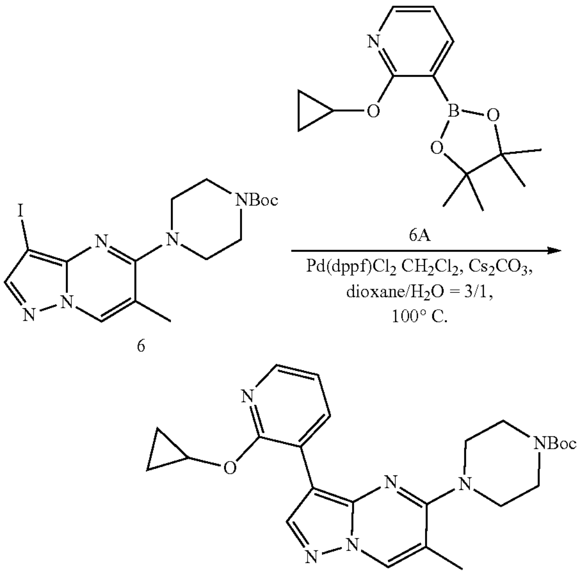

6

7

A mixture of tert-butyl 4-(3-iodo-6-methyl-pyrazolo[1,5-a]pyrimidin-5-yl)piperazine-1-carboxylate (0.35 g, 789.57 μmol, 1 eq), 2-(cyclopropoxy)-3-(4,4,5,5-tetramethyl-1,3,2-dioxaborolan-2-yl)pyridine (247.41 mg, 947.48 μmol, 1.2 eq), Pd(dppf)$Cl_2$·$CH_2Cl_2$ (128.96 mg, 157.91 μmol, 0.2 eq) and $Cs_2CO_3$ (771.77 mg, 2.37 mmol, 3 eq) in dioxane (3 mL) and $H_2O$ (1 mL) was degassed and purged with $N_2$ for 3 times, and then the mixture was stirred at 100° C. for 1 hr under $N_2$ atmosphere. LCMS showed desired MS was detected. The reaction mixture was concentrated under reduced pressure to remove solvent. The residue was purified by flash silica gel chromatography (ISCO®; 5 g SepaFlash® Silica Flash Column, Eluent of 0~40% Ethyl acetate/Petroleum ether gradient @ 25 mL/min) to give tert-butyl 4-[3-[2-(cyclopropoxy)-3-pyridyl]-6-methyl-pyrazolo[1,5-a]pyrimidin-5-yl]piperazine-1-carboxylate (0.16 g, 301.87 μmol, 38.23% yield, 85% purity) as a solid.

LCMS m/z=451.2 $[M+H]^+$.

$^1$H NMR (400 MHz, DMSO-$d_6$) δ=8.83 (dd, J=1.9, 7.6 Hz, 1H), 8.79 (d, J=1.0 Hz, 1H), 8.39 (s, 1H), 8.04 (dd, J=1.8, 4.8 Hz, 1H), 7.14 (dd, J=4.9, 7.5 Hz, 1H), 4.54-4.32 (m, 1H), 3.53 (br s, 4H), 3.38 (br d, J=6.1 Hz, 4H), 2.30 (s, 3H), 1.44 (s, 9H), 0.83-0.77 (m, 4H).

3-[2-(cyclopropoxy)-3-pyridyl]-6-methyl-5-piperazin-1-yl-pyrazolo[1,5-a]pyrimidine

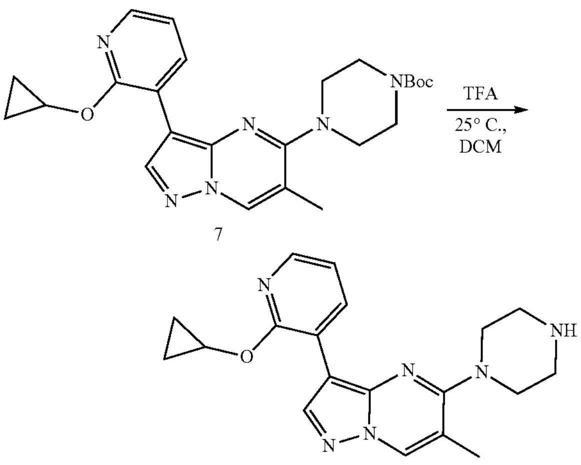

7

8

To a solution of tert-butyl 4-[3-[2-(cyclopropoxy)-3-pyridyl]-6-methyl-pyrazolo[1,5-a]pyrimidin-5-yl]piperazine-1-carboxylate (0.16 g, 355.14 μmol, 1 eq) in DCM (2 mL) was added TFA (767.50 mg, 6.73 mmol, 0.5 mL, 18.95 eq). The mixture was stirred at 25° C. for 1 hr. LCMS showed desired mass was detected. The reaction mixture was concentrated under reduced pressure to give 3-[2-(cyclopropoxy)-3-pyridyl]-6-methyl-5-piperazin-1-yl-pyrazolo[1,5-a]pyrimidine (0.2 g, crude, TFA) as an oil.

LCMS m/z=350.9 [M+H]$^+$.

[(3S)-1-methyl-5-oxo-pyrrolidin-3-yl]-4-[3-[2-(cyclopropoxy)-3-pyridyl]-6-methyl-pyrazolo[1,5-a]pyrimidin-5-yl]piperazine-1-carboxylate (I-111)

To a solution of 3-[2-(cyclopropoxy)-3-pyridyl]-6-methyl-5-piperazin-1-yl-pyrazolo[1,5-a]pyrimidine (0.17 g, 366.03 μmol, 1 eq, TFA) in MeCN (4 mL) was added DIEA (236.53 mg, 1.83 mmol, 318.78 μL, 5 eq) and [(3S)-1-methyl-5-oxo-pyrrolidin-3-yl](4-nitrophenyl) carbonate (123.09 mg, 439.24 μmol, 1.2 eq). The mixture was stirred at 25° C. for 2 hr. LCMS showed desired mass was detected. The reaction mixture was concentrated under reduced pressure to remove solvent. Then the product was further purified by prep. HPLC (column: CD02-Waters Xbridge BEH C18 150*25*10 um; mobile phase: [water ($NH_3H_2O$)-MeCN]; gradient: 25%-55% B over 10 min). The pure fractions were collected and the volatiles were removed under vacuum. The residue was partitioned between acetonitrile (2 mL) and water (10 mL). The solution was lyophilized to dryness to give [(3S)-1-methyl-5-oxo-pyrrolidin-3-yl]-4-[3-[2-(cyclopropoxy)-3-pyridyl]-6-methyl-pyrazolo[1,5-a]pyrimidin-5-yl]piperazine-1-carboxylate (I-111, 70.09 mg, 141.91 μmol, 38.77% yield, 99.522% purity) as a powder.

LCMS m/z=492.1 [M+H]$^+$.

SFC $t_R$=0.707 min; 100%.

$^1$H NMR (400 MHz, DMSO-$d_6$) δ=8.84-8.77 (m, 2H), 8.38 (s, 1H), 8.10-8.00 (m, J=1.8 Hz, 1H), 7.17-7.09 (m, 1H), 5.15 (t, J=6.4 Hz, 1H), 4.45-4.37 (m, 1H), 3.77-3.69 (m, 1H), 3.57 (s, 4H), 3.44-3.34 (m, 5H), 2.77-2.67 (m, 4H), 2.32-2.24 (m, 4H), 0.84-0.74 (m, 4H).

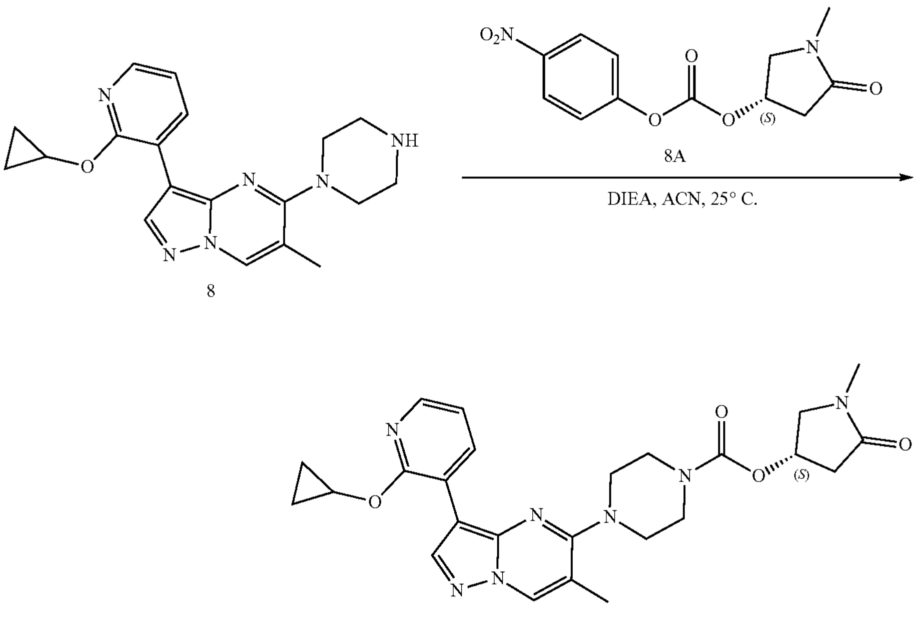

8

I-111

Example 84: Synthesis of Compound I-113

(4S)-4-[tert-butyl(diphenyl)silyl]oxy-1-(trideuteriomethyl)pyrrolidin-2-one

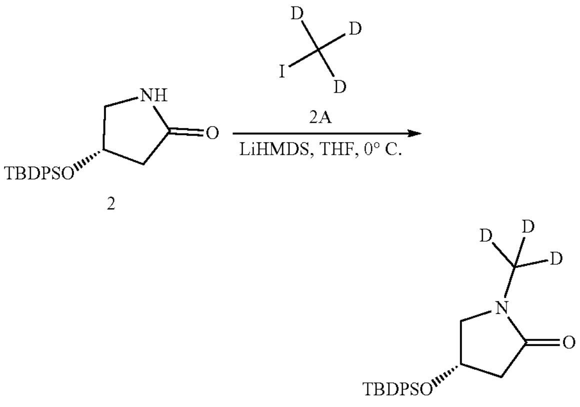

2

3

To a solution of (4S)-4-[tert-butyl(diphenyl)silyl]oxypyrrolidin-2-one (5 g, 14.73 mmol, 1 eq) in THF (50 mL) was added dropwise LiHMDS (1 M, 29.45 mL, 2 eq) at 0° C. After addition, the mixture was stirred at 0° C. for 0.5 hr, and then trideuterio (iodo) methane (8.54 g, 58.91 mmol, 3.67 mL, 4 eq) was added dropwise at 0° C. The resulting mixture was stirred at 25° C. for 12 hr. LCMS showed the starting material was consumed completely and desired compound was detected. The reaction mixture was quenched by addition saturated ammonium chloride solution (100 mL) at 25° C., and then extracted with ethyl acetate (80 mL×2). The combined organic layers were washed with brine (50 mL), dried over anhydrous sodium sulfate, filtered and concentrated in vacuum. The residue was purified by flash silica gel chromatography (ISCO®; 40 g SepaFlash® Silica Flash Column, Eluent of 25~45% Ethyl acetate/Petroleum ether gradient @ 80 mL/min) to give (4S)-4-[tert-butyl(diphenyl)silyl]oxy-1-(trideuteriomethyl)pyrrolidin-2-one (4.7 g, 13.18 mmol, 89.51% yield, 100% purity) as a gum.

LCMS m/z=357.2 $[M+H]^+$.

$^1H$ NMR (400 MHz, DMSO-$d_6$) δ=7.59 (d, J=6.3 Hz, 4H), 7.52-7.38 (m, 6H), 4.49-4.41 (m, 1H), 3.45 (dd, J=5.8, 10.4 Hz, 1H), 3.20 (dd, J=2.4, 10.4 Hz, 1H), 2.43 (dd, J=6.7, 16.8 Hz, 1H), 2.15 (dd, J=2.9, 16.8 Hz, 1H), 1.00 (s, 9H).

(4S)-4-hydroxy-1-(trideuteriomethyl)pyrrolidin-2-one

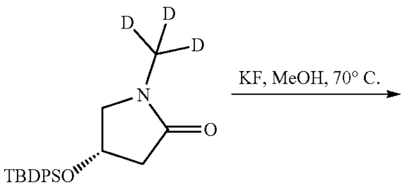

3

-continued

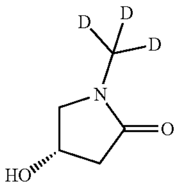

4

To a solution of (4S)-4-[tert-butyl(diphenyl)silyl]oxy-1-(trideuteriomethyl)pyrrolidin-2-one (1 g, 2.80 mmol, 1 eq) in MeOH (5 mL) was added KF (1.63 g, 28.05 mmol, 10 eq). The mixture was stirred at 70° C. for 12 hr. LCMS showed the starting material was consumed completely and desired compound was detected. The reaction mixture was concentrated under reduced pressure to give a residue. The residue was purified by flash silica gel chromatography (ISCO®; 20 g SepaFlash® Silica Flash Column, Eluent of 10~25% Methanol/Dichloromethane gradient @ 80 mL/min), and concentrated in vacuum to give (4S)-4-hydroxy-1-(trideuteriomethyl)pyrrolidin-2-one (300 mg, 2.54 mmol, 90.53% yield, N/A purity) as a solid.

LCMS m/z=118.9 $[M+H]^+$.

$^1H$ NMR (400 MHz, DMSO-$d_6$) δ=5.15 (d, J=4.0 Hz, 1H), 4.29-4.22 (m, 1H), 3.52 (dd, J=5.6, 10.5 Hz, 1H), 3.09 (dd, J=2.1, 10.4 Hz, 1H), 2.49-2:44 (m, 1H), 2.00 (dd, J=2.4, 16.8 Hz, 1H).

(4-nitrophenyl) [(3S)-5-oxo-1-(trideuteriomethyl)pyrrolidin-3-yl]carbonate

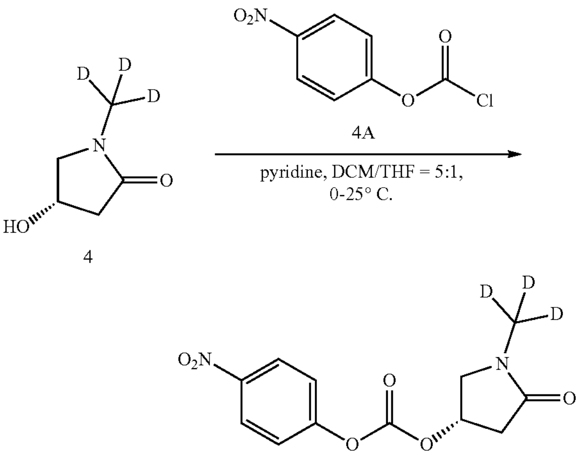

4

5

To a solution of ((4S)-4-hydroxy-1-(trideuteriomethyl)pyrrolidin-2-one (100 mg, 846.39 μmol, 1 eq) in DCM (1.5 mL) and THF (0.5 mL) was added pyridine (133.90 mg, 1.69 mmol, 136.63 μL, 2 eq) (4-nitrophenyl), and then (4-nitrophenyl) carbonochloridate (187.66 mg, 931.03 μmol, 1.1 eq) was slowly added at 0° C. The reaction mixture was stirred at 25° C. for 12 h. LCMS and Deuterated ratio showed the starting material was consumed completely and desired compound was detected. The reaction mixture was filtered. The filtrate was concentrated in vacuum to give a crude product (4-nitrophenyl) [(3S)-5-oxo-1-(trideuteriomethyl)pyrrolidin-3-yl]carbonate (120 mg, 423.65 μmol, 50.05% yield, N/A purity) as an oil.

LCMS m/z=283.8 $[M+H]^+$.

[(3S)-5-oxo-1-(trideuteriomethyl)pyrrolidin-3-yl] 4-[3-[2-(cyclopropoxy)-3-pyridyl]pyrazolo[1,5-a] pyrimidin-5-yl]piperazine-1-carboxylate (I-113)

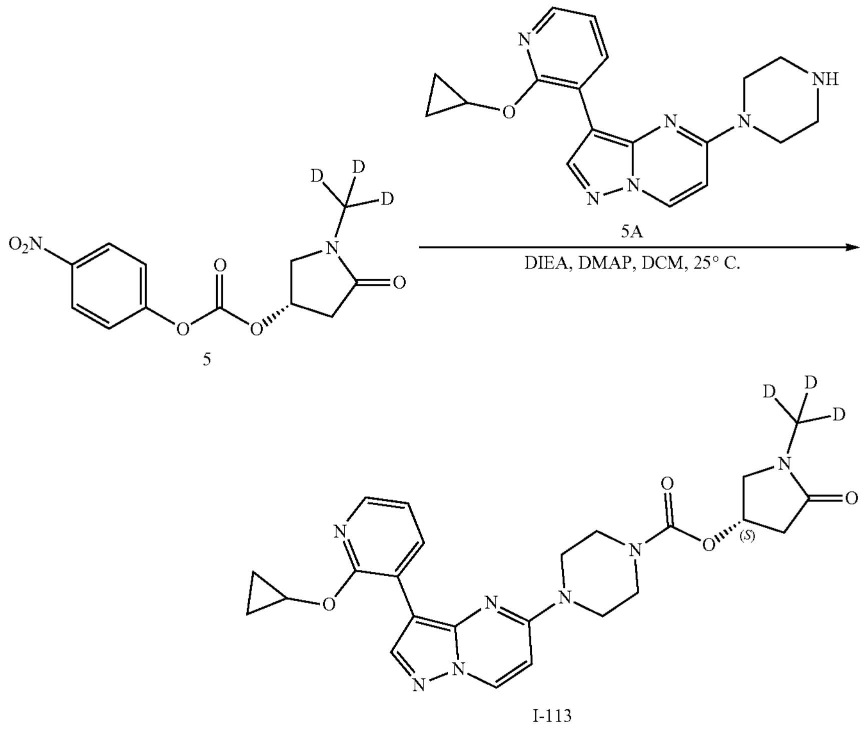

To a solution of 3-[2-(cyclopropoxy)-3-pyridyl]-5-piperazin-1-yl-pyrazolo[1,5-a]pyrimidine (95.01 mg, 282.43 μmol, 1 eq) in ACN (1 mL), was added DIEA (73.01 mg, 564.87 μmol, 98.39 μL, 2 eq) and (4-nitrophenyl) [(3S)-5-oxo-1-(trideuteriomethyl)pyrrolidin-3-yl]carbonate (120 mg, 423.65 μmol, 1.5 eq). The reaction mixture was stirred at 25° C. for 2 hr. LCMS showed the starting material was consumed completely and desired compound was detected. The reaction mixture was concentrated under reduced pressure to give a residue. The residue was purified by prep-HPLC (column: Waters Xbridge BEH C18 150*25*10 um; mobile phase: [water ($NH_3H_2O$)—I]; gradient: 22%-52% B over 10 min) and lyophilized to give [(3S)-5-oxo-1-(trideuteriomethyl) 344yrrolidine-3-yl]-4-[3-[2-(cyclopropoxy)-3-pyridyl]pyrazolo[1,5-a]pyrimidin-5-yl]piperazine-1-carboxylate (I-113, 26.58 mg, 53.51 μmol, 18.95% yield, 96.74% purity) as a solid.

LCMS m/z=480.9 $[M+H]^+$.

SFC $t_R$=1.474 min; 100%.

$^1H$ NMR (400 MHz, DMSO-$d_6$) δ=8.80-8.77 (m, 1H), 8.74 (d, J=7.9 Hz, 1H), 8.34 (s, 1H), 8.02-7.99 (m, 1H), 7.13-7.08 (m, 1H), 6.81 (d, J=7.9 Hz, 1H), 5.18-5.13 (m, 1H), 4.42-4.37 (m, 1H), 3.78-3.74 (m, 4H), 3.73-3.69 (m, 1H), 3.56-3.50 (m, 4H), 3.39-3.36 (m, 1H), 2.76-2.68 (m, 1H), 2.31-2.25 (m, 1H), 0.81-0.77 (m, 4H).

Example 85: Synthesis of Compound I-114

(4S)-4-[tert-butyl(diphenyl)silyl]oxy-1-isopropyl-pyrrolidin-2-one

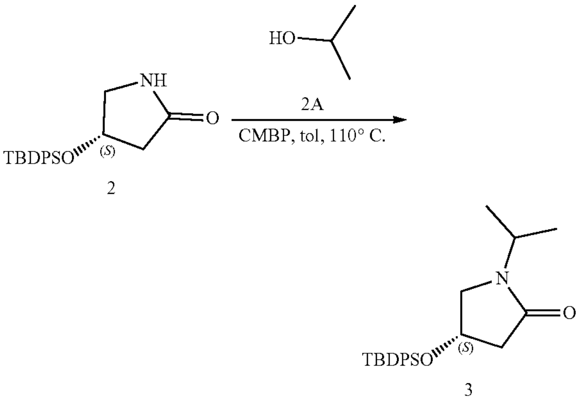

To a mixture of (4S)-4-[tert-butyl(diphenyl)silyl]oxypyrrolidin-2-one (5 g, 14.73 mmol, 1 eq) in Tol. (50 mL) was added propan-2-ol (1.77 g, 29.45 mmol, 2.25 mL, 2 eq) and 2-(tributyl-phosphanylidene) acetonitrile (7.11 g, 29.45 mmol, 2 eq) under $N_2$ atmosphere. The mixture was stirred at 110° C. for 10 hr under $N_2$ atmosphere. LCMS showed that desired MS was found. The mixture was filtered and the filtrate was concentrated to the crude product. The crude product was purified by FCC (ISCO®; 120 g SepaFlash® Silica Flash Column, Eluent of 0~46% Ethyl acetate/Petroleum ether gradient @ 25 mL/min) to give (4S)-4-[tert-butyl (diphenyl)silyl]oxy-1-isopropyl-pyrrolidin-2-one (410 mg, 880.53 μmol, 5.98% yield, 81.950% purity) as an oil.

LCMS m/z=382.3 $[M+H]^+$.

$^1$H NMR (400 MHz, DMSO-$d_6$) δ=7.55 (ddd, J=1.6, 3.3, 7.8 Hz, 4H), 7.47-7.37 (m, 6H), 4.47-4.30 (m, 1H), 4.12 (td, J=6.8, 13.6 Hz, 1H), 3.36-3.30 (m, 1H), 3.10 (dd, J=1.9, 10.5 Hz, 1H), 2.40 (dd, J=6.1, 16.6 Hz, 1H), 2.07 (dd, J=2.4, 16.6 Hz, 1H), 1.01 (d, J=6.8 Hz, 3H), 0.96 (s, 9H), 0.95-0.91 (m, 3H).

(4S)-4-hydroxy-1-isopropyl-pyrrolidin-2-one

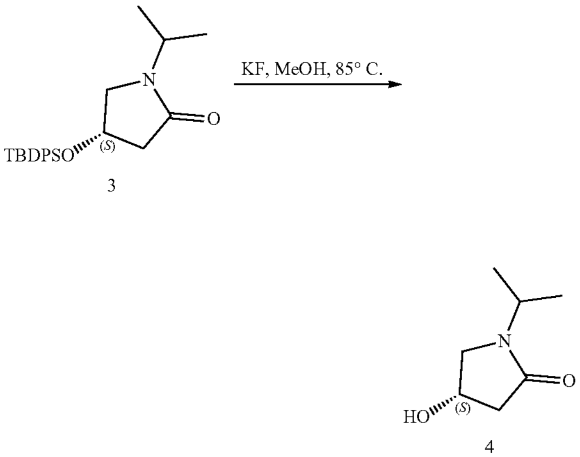

3

4

To a solution of (4S)-4-[tert-butyl(diphenyl)silyl]oxy-1-isopropyl-pyrrolidin-2-one (410 mg, 1.07 mmol, 1 eq) in MeOH (3 mL) was added KF (374.54 mg, 6.45 mmol, 6 eq). The mixture was stirred at 85° C. for 10 hr. LCMS showed that desired MS was found. The reaction mixture was concentrated under reduced pressure to remove solvent. The crude was purified by FCC (ISCO®; 4 g SepaFlash® Silica Flash Column, Eluent of 0~15% Methanol/Dichloromethane ether gradient @ 25 mL/min), and concentrated in vacuum to give (4S)-4-hydroxy-1-isopropyl-pyrrolidin-2-one (130 mg, 495.24 μmol, 31.35% yield, 54.546% purity) as a liquid.

LCMS m/z=143.8 $[M+H]^+$.

$^1$H NMR (400 MHz, DMSO-$d_6$) δ=5.11 (d, J=3.9 Hz, 1H), 4.32-4.21 (m, 1H), 4.20-4.04 (m, 1H), 3.43 (dd, J=5.5, 10.3 Hz, 1H), 3.05 (dd, J=2.1, 10.4 Hz, 1H), 2.49-2.43 (m, 1H), 2.02 (dd, J=2.5, 16.8 Hz, 1H), 1.03 (dd, J=6.9, 8.0 Hz, 6H).

[(3S)-1-isopropyl-5-oxo-pyrrolidin-3-yl](4-nitrophenyl) carbonate

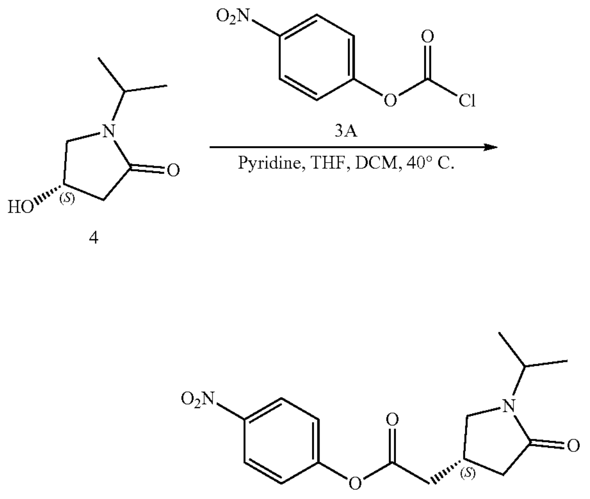

4

5

To a solution of (4S)-4-hydroxy-1-isopropyl-pyrrolidin-2-one (60 mg, 419.04 μmol, 1 eq) in DCM (0.2 mL) and THF (1 mL) was added pyridine (165.73 mg, 2.10 mmol, 169.11 μL, 5 eq) and (4-nitrophenyl) carbonochloridate (101.36 mg, 502.85 μmol, 1.2 eq). The mixture was stirred at 40° C. for 1 hr under $N_2$ atmosphere. LCMS showed that desired MS was found. The mixture was filtered and the filtrate was concentrated to the crude product. The crude was purified by FCC (ISCO®; 4 g SepaFlash® Silica Flash Column, Eluent of 0~70% Ethyl acetate/Petroleum ether gradient @ 25 mL/min), and concentrated in vacuum to give [(3S)-1-isopropyl-5-oxo-pyrrolidin-3-yl](4-nitrophenyl) carbonate (90 mg, 269.02 μmol, 64.20% yield, 92.149% purity) was obtained as an oil.

LCMS m/z=308.8 $[M+H]^+$.

$^1$H NMR (400 MHz, DMSO-$d_6$) δ=8.41-8.25 (m, 2H), 7.68-7.49 (m, 2H), 5.32 (t, J=6.1 Hz, 1H), 4.17 (qd, J=6.7, 13.4 Hz, 1H), 3.75-3.70 (m, 1H), 3.50 (d, J=11.9 Hz, 1H), 2.83-2.74 (m, 1H), 2.54 (s, 1H), 1.09 (dd, J=6.8, 11.2 Hz, 6H).

[(3S)-1-isopropyl-5-oxo-pyrrolidin-3-yl]-4-[3-[2-(cyclopropoxy)-3-pyridyl]pyrazolo[1,5-a]pyrimidin-5-yl]piperazine-1-carboxylate (I-114)

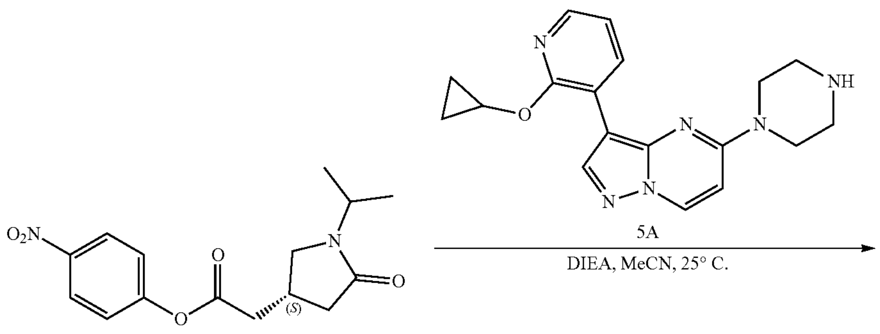

5

-continued

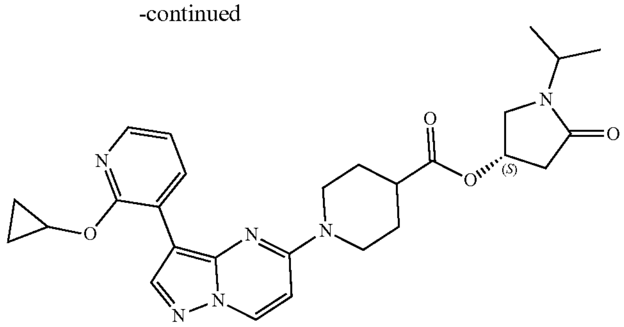

I-114

To a solution of [(3S)-1-isopropyl-5-oxo-pyrrolidin-3-yl] (4-nitrophenyl) carbonate (90 mg, 291.94 μmol, 1 eq) in ACN (1 mL) was added DIEA (113.19 mg, 875.81 μmol, 152.55 μL, 3 eq) and 3-[2-(cyclopropoxy)-3-pyridyl]-5-piperazin-1-yl-pyrazolo[1,5-a]pyrimidine (98.20 mg, 291.94 μmol, 1 eq). The mixture was stirred at 25° C. for 10 hr. LCMS showed the starting material was consumed completely and desired compound was detected. The mixture was filtered and the filtrate was concentrated to the crude product. The product was purified by pre-HPLC (Column: Waters Xbridge BEH C18 150*25*10 um; mobile phase: [water ($NH_3H_2O$)-ACN]; gradient: 27%-57% B over 10 min). The pure fractions were collected and the volatiles were removed under vacuum. The residue was partitioned between acetonitrile (20 mL) and water (100 mL). The solution was lyophilized to dryness to give [(3S)-1-isopropyl-5-oxo-pyrrolidin-3-yl] 4-[3-[2-(cyclopropoxy)-3-pyridyl]pyrazolo[1,5-a]pyrimidin-5-yl]piperazine-1-carboxylate (I-114, 56.29 mg, 110.54 μmol, 37.87% yield, 99.284% purity) as a powder.

LCMS m/z=506.3 $[M+H]^+$.

SFC $t_R$=1.138 min; 100%.

$^1H$ NMR (400 MHz, DMSO-$d_6$) δ=8.86-8.69 (m, 2H), 8.34 (s, 1H), 8.04-7.95 (m, 1H), 7.15-7.05 (m, 1H), 6.81 (d, J=7.9 Hz, 1H), 5.23-5.12 (m, 1H), 4.46-4.35 (m, 1H), 4.25-4.10 (m, 1H), 3.83-3.71 (m, 4H), 3.69-3.60 (m, 1H), 3.56-3.46 (m, 4H), 3.32-3.28 (m, 1H), 2.79-2.68 (m, 1H), 2.33-2.24 (m, 1H), 1.12-1.02 (m, 6H), 0.83-0.73 (m, 4H).

Example 86: Synthesis of Compound I-115

(4S)-4-[tert-butyl(diphenyl)silyl]oxy-1-(2-methoxyethyl)pyrrolidin-2-one

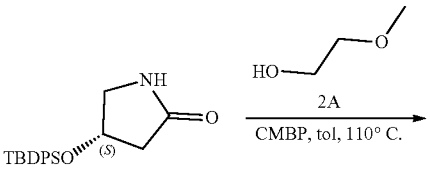

2

-continued

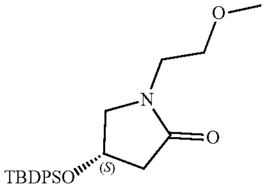

3

To a mixture of (4S)-4-[tert-butyl(diphenyl)silyl]oxypyrrolidin-2-one (5 g, 14.73 mmol, 1 eq) in Tol. (50 mL) was added 2-(tributyl-phosphanylidene) acetonitrile (7.11 g, 29.45 mmol, 2 eq) and 2-methoxyethanol (1.34 g, 17.67 mmol, 1.2 eq) at 0° C. under $N_2$ atmosphere, the mixture was stirred at 110° C. for 8 hr. LCMS showed 14.67% of desired product. The reaction was concentrated to product residue. The crude product was purified by column chromatography ($SiO_2$, Petroleum ether:Ethyl acetate=1/0 to 0/1) to give (4S)-4-[tert-butyl(diphenyl)silyl]oxy-1-(2-methoxyethyl)pyrrolidin-2-one (1.62 g, 2.97 mmol, 20.19% yield, 72.96% purity) as an oil.

LCMS m/z=398.1 $[M+H]^+$.

$^1H$ NMR (400 MHz, DMSO-$d_6$) δ=7.60-7.58 (m, 4H), 7.47-7.44 (m, 6H), 4.46-4.41 (m, 1H), 3.50-3.46 (m, 1H), 3.37 (dd, J=1.7, 2.4 Hz, 2H), 3.35 (br d, J=4.1 Hz, 1H), 3.31-3.27 (m, 2H), 3.20 (s, 3H), 2.48-2.42 (m, 1H), 2.15 (dd, J=2.8, 16.8 Hz, 1H), 1.00 (s, 9H).

(4S)-4-hydroxy-1-(2-methoxyethyl)pyrrolidin-2-one

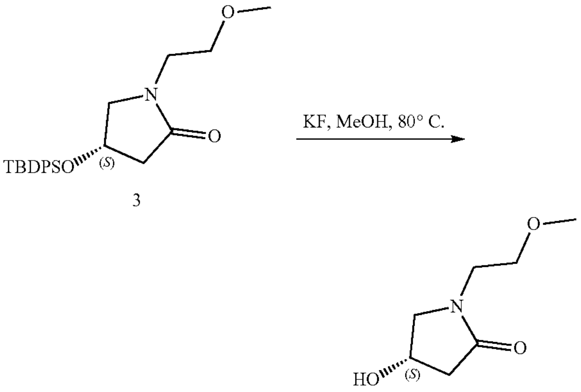

3

4

To a solution of (4S)-4-[tert-butyl(diphenyl)silyl]oxy-1-(2-methoxyethyl)pyrrolidin-2-one (1.1 g, 2.77 mmol, 1 eq) in MeOH (10 mL) was added KF (1.61 g, 27.67 mmol, 10 eq), which was stirred at 80° C. for 12 hr. LCMS showed 95.88% of desired product. The reaction was concentrated to product residue. The crude product was purified by column chromatography ($SiO_2$, Dichloromethane:Methanol=1/0 to 10/1) to give (4S)-4-hydroxy-1-(2-methoxyethyl)pyrrolidin-2-one (456 mg, 2.23 mmol, 55.50% yield, 77.73% purity) as a solid.

LCMS m/z=159.8 $[M+H]^+$.

$^1$H NMR (400 MHz, DMSO-$d_6$) δ=4.26 (dq, J=2.6, 6.1 Hz, 1H), 3.57 (dd, J=5.6, 10.4 Hz, 1H), 3.42-3.32 (m, 4H), 3.31-3.25 (m, 1H), 3.23 (s, 3H), 3.16 (dd, J=2.1, 10.4 Hz, 1H), 2.55-2.45 (m, 2H).

[(3S)-1-(2-methoxyethyl)-5-oxo-pyrrolidin-3-yl](4-nitrophenyl) carbonate

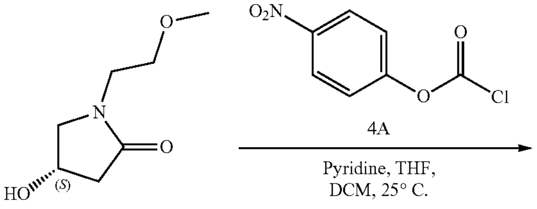

4

-continued

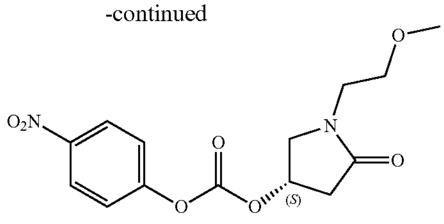

5

To a solution of (4S)-4-hydroxy-1-(2-methoxyethyl)pyrrolidin-2-one (450 mg, 2.83 mmol, 1 eq), (4-nitrophenyl) carbonochloridate (683.77 mg, 3.39 mmol, 1.2 eq) in DCM (1.5 mL) and THF (0.3 mL) was added pyridine (670.83 mg, 8.48 mmol, 684.52 μL, 3 eq), which was stirred at 40° C. for 12 hr. LCMS showed 56.41% of desired product. The reaction was concentrated to product residue. The crude product was purified by column chromatography ($SiO_2$, Dichloromethane/Methanol=1/0 to 10/1) to give (3S)-1-(2-methoxyethyl)-5-oxo-pyrrolidin-3-yl] (4-nitrophenyl) carbonate (425 mg, 1.28 mmol, 45.41% yield, 97.96% purity) as a solid.

LCMS m/z=325.1 $[M+H]^+$.

$^1$H NMR (400 MHz, DMSO-$d_6$) δ=8.37-8.29 (m, 2H), 7.63-7.56 (m, 2H), 5.35-5.26 (m, 1H), 3.83 (dd, J=5.5, 12.0 Hz, 1H), 3.62 (d, J=11.9 Hz, 1H), 3.46-3.40 (m, 4H), 3.25 (s, 3H), 2.84 (dd, J=6.7, 17.8 Hz, 1H), 2.55-2.51 (m, 1H).

[(3S)-1-(2-methoxyethyl)-5-oxo-pyrrolidin-3-yl]-4-[3-[2-(cyclopropoxy)-3-pyridyl]pyrazolo[1,5-a]pyrimidin-5-yl]piperazine-1-carboxylate (I-115)

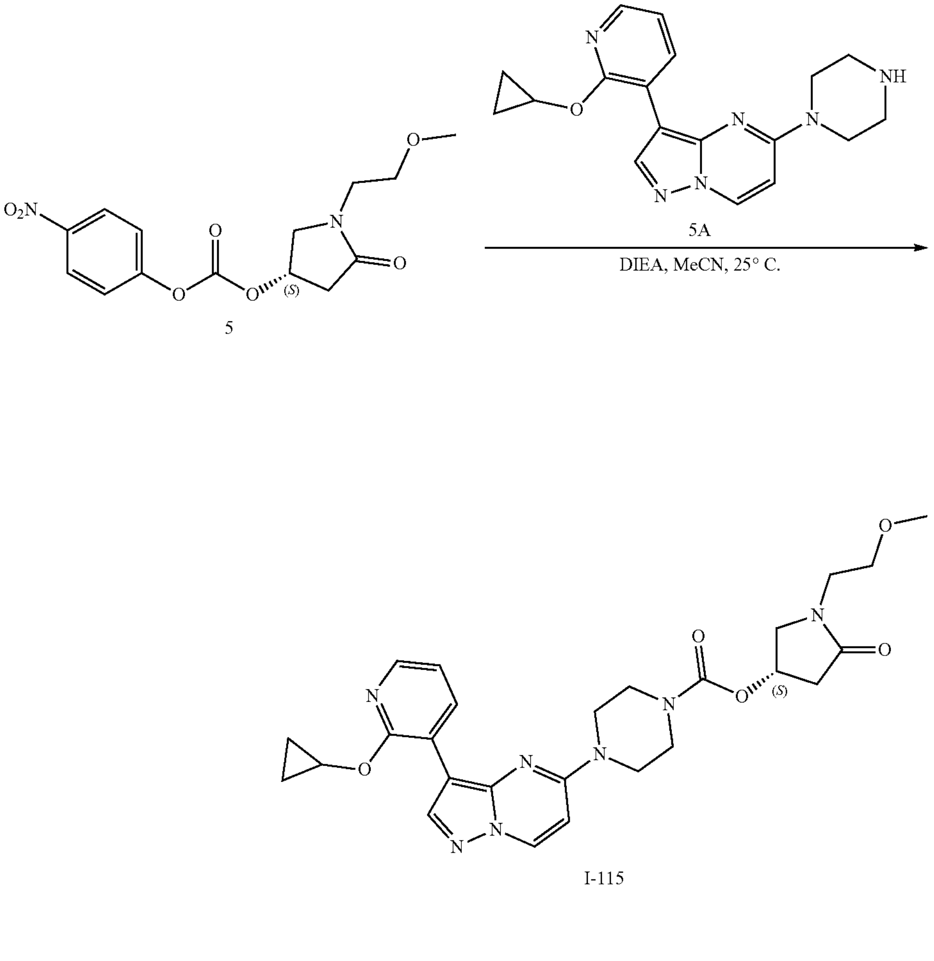

I-115

To a solution of [(3S)-1-(2-methoxyethyl)-5-oxo-pyrrolidin-3-yl](4-nitrophenyl) carbonate (200 mg, 616.74 μmol, 1 eq) and 3-[2-(cyclopropoxy)-3-pyridyl]-5-piperazin-1-yl-pyrazolo[1,5-a]pyrimidine (248.96 mg, 740.09 μmol, 1.2 eq) in MeCN (2 mL) was added DIEA (398.55 mg, 3.08 mmol, 537.12 μL, 5 eq), which was stirred at 25° C. for 12 hr. LCMS showed 47.71% of desired product. The reaction was concentrated to dryness under reduced pressure to give the crude product. The crude product was purified by column chromatography ($SiO_2$, Dichloromethane:Methanol=1/0 to 10/1), then the product was purified by reversed-phase HPLC (column: Waters Xbridge BEH C18 150*25*10 um; mobile phase: [water ($NH_3H_2O$)-ACN]; gradient: 22%-52% B over 10 min) and lyophilized to give [(3S)-1-(2-methoxyethyl)-5-oxo-pyrrolidin-3-yl]-4-[3-[2-(cyclopropoxy)-3-pyridyl]pyrazolo[1,5-a]pyrimidin-5-yl]piperazine-1-carboxylate (I-115, 60.91 mg, 116.44 umol, 18.88% yield, 99.71% purity) as a solid.

LCMS m/z=522.2 $[M+H]^+$.

SFC $t_R$=0.758 min; 100%.

$^1$H NMR (400 MHz, DMSO-$d_6$) δ=8.81-8.77 (m, 1H), 8.75 (d, J=7.6 Hz, 1H), 8.34 (s, 1H), 8.02-7.99 (m, 1H), 7.13-7.07 (m, 1H), 6.81 (d, J=7.6 Hz, 1H), 5.19-5.13 (m, 1H), 4.43-4.37 (m, 1H), 3.80-3.73 (m, 5H), 3.55-3.49 (m, 4H), 3.45-3.40 (m, 3H), 3.38-3.35 (m, 2H), 3.24 (s, 3H), 2.80-2.71 (m, 1H), 2.34-2.27 (m, 1H), 0.82-0.76 (m, 4H).

Example 87: Synthesis of Compound I-116

(4S)-4-hydroxy-1-(trideuteriomethyl)pyrrolidin-2-one

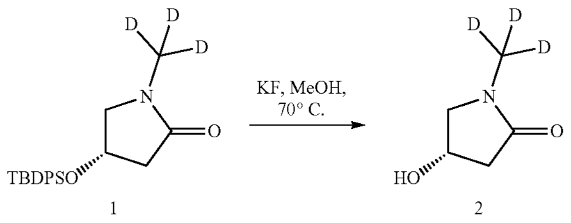

A mixture of (4S)-4-[tert-butyl(diphenyl)silyl]oxy-1-(trideuteriomethyl)pyrrolidin-2-one (2.2 g, 6.17 mmol, 1 eq) and KF (3.58 g, 61.70 mmol, 10 eq) in MeOH (20 mL) was degassed and purged with $N_2$ for 3 times, then the mixture was stirred at 70° C. for 10 hr under $N_2$ atmosphere. LCMS showed desired compound was detected. The reaction mixture was concentrated to a residue. The residue was purified by column chromatography ($SiO_2$, DCM:MeOH=1/0 to 10/1) to give (4S)-4-hydroxy-1-(trideuteriomethyl)pyrrolidin-2-one (700 mg, 5.92 mmol, 96.02% yield) as an oil.

LCMS m/z=119.3 $[M+H]^+$.

$^1$H NMR (400 MHz, DMSO-$d_6$) δ=4.60-4.39 (m, 1H), 3.67-3.60 (m, 1H), 3.46 (s, 1H), 3.34-3.28 (m, 1H), 2.69-2.62 (m, 1H), 2.39-2.32 (m, 1H).

(4-nitrophenyl) [(3S)-5-oxo-1-(trideuteriomethyl)pyrrolidin-3-yl]carbonate

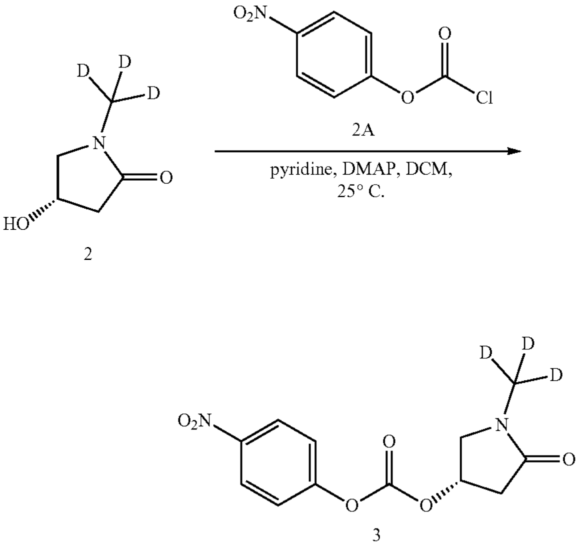

A mixture of (4S)-4-hydroxy-1-(trideuteriomethyl)pyrrolidin-2-one (100 mg, 846.39 μmol, 1 eq), (4-nitrophenyl) carbonochloridate (204.72 mg, 1.02 mmol, 1.2 eq), DMAP (51.70 mg, 423.20 μmol, 0.5 eq) and pyridine (334.75 mg, 4.23 mmol, 341.58 μL, 5 eq) in DCM (5 mL) was degassed and purged with $N_2$ for 3 times, and then the mixture was stirred at 25° C. for 2 hr under $N_2$ atmosphere. LCMS showed desired compound was detected. The reaction mixture was concentrated to a residue. The residue was purified by column chromatography ($SiO_2$, Petroleum ether/Ethyl acetate=1/0 to 0/1) to give (4-nitrophenyl) [(3S)-5-oxo-1-(trideuteriomethyl)pyrrolidin-3-yl]carbonate (120 mg, 403.04 μmol, 47.62% yield, 95.134% purity) as a solid.

LCMS m/z=284.0 $[M+H]^+$.

[(3S)-5-oxo-1-(trideuteriomethyl)pyrrolidin-3-yl] 4-[3-[2-(cyclopropoxy)-3-pyridyl]-6-fluoro-pyrazolo[1,5-a]pyrimidin-5-yl]piperazine-1-carboxylate (I-116)

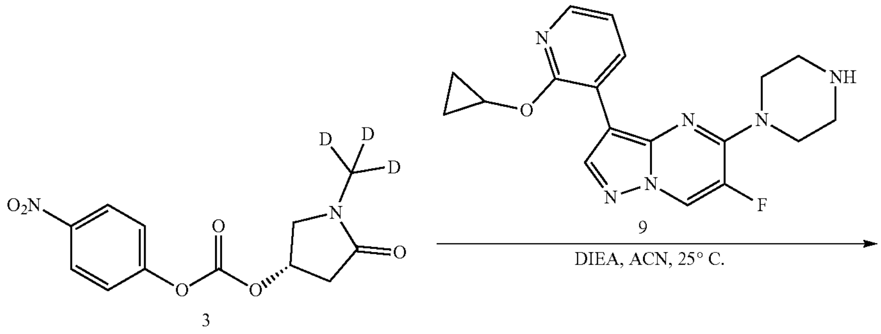

-continued

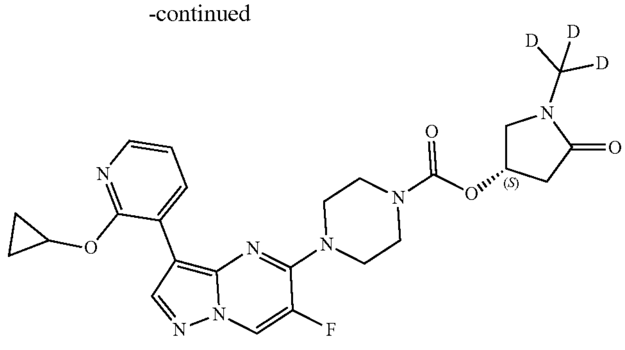

I-116

A mixture of (4-nitrophenyl) [(3S)-5-oxo-1-(trideuteriomethyl)pyrrolidin-3-yl] carbonate (60 mg, 211.83 μmol, 1 eq), 3-[2-(cyclopropoxy)-3-pyridyl]-6-fluoro-5-piperazin-1-yl-pyrazolo[1,5-a]pyrimidine (128.99 mg, 275.37 μmol, 1.3 eq, TFA) and DIEA (136.88 mg, 1.06 mmol, 184.48 μL, 5 eq) in ACN (1 mL) was degassed and purged with $N_2$ for 3 times, and then the mixture was stirred at 25° C. for 1 hr under $N_2$ atmosphere. LCMS showed desired compound was detected. The reaction mixture was concentrated a residue. The residue was purified by prep-HPLC (column: XPT PHS C18 150*25*10 um; mobile phase: [water (FA)-ACN]; gradient: 27%-57% B over 10 min). The pure fractions were collected and the volatiles were removed under vacuum. The residue was partitioned between acetonitrile (2 mL) and water (10 mL). The solution was lyophilized to dryness to give [(3S)-5-oxo-1-(trideuteriomethyl)pyrrolidin-3-yl]-4-[3-[2-(cyclopropoxy)-3-pyridyl]-6-fluoro-pyrazolo[1,5-a]pyrimidin-5-yl]piperazine-1-carboxylate (I-116, 48.54 mg, 96.80 μmol, 45.70% yield, 99.413% purity) as a solid.

LCMS m/z=499.2 $[M+H]^+$.

SFC $t_R$=2.245 min; 100%.

$^1H$ NMR (400 MHz, DMSO-$d_6$) δ=9.28-9.22 (m, 1H), 8.74-8.67 (m, 1H), 8.38 (s, 1H), 8.06-8.00 (m, 1H), 7.16-7.08 (m, 1H), 5.20-5.11 (m, 1H), 4.44-4.36 (m, 1H), 3.77-3.66 (m, 5H), 3.63-3.50 (m, 4H), 3.38-3.36 (m, 1H), 2.78-2.67 (m, 1H), 2.34-2.23 (m, 1H), 0.84-0.73 (m, 4H).

Example 88: Synthesis of Compound I-117 tert-butyl 4-[3-[2-(cyclopropoxy)-5-methoxy-3-pyridyl]-6-fluoro-pyrazolo[1,5-a]pyrimidin-5-yl]piperazine-1-carboxylate

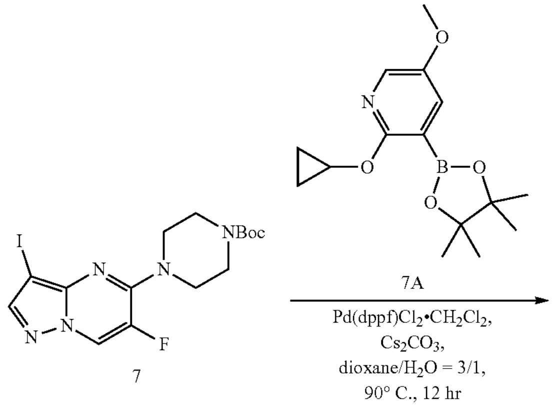

-continued

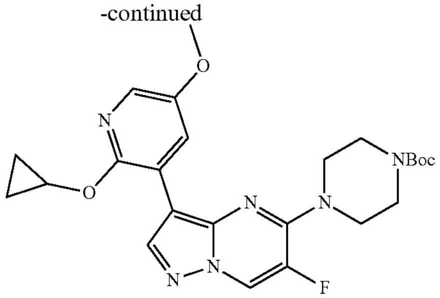

8

A mixture of tert-butyl 4-(6-fluoro-3-iodo-pyrazolo[1,5-a]pyrimidin-5-yl)piperazine-1-carboxylate (80 mg, 178.87 μmol, 1 eq), 2-(cyclopropoxy)-5-methoxy-3-(4,4,5,5-tetramethyl-1,3,2-dioxaborolan-2-yl)pyridine (62.49 mg, 214.65 μmol, 1.2 eq), $Cs_2CO_3$ (174.84 mg, 536.62 μmol, 3 eq) and Pd(dppf)$Cl_2 \cdot CH_2Cl_2$ (14.61 mg, 17.89 μmol, 0.1 eq) in dioxane (2.5 mL) and $H_2O$ (0.5 mL) was degassed and purged with $N_2$ for 3 times, and then the mixture was stirred at 90° C. for 12 hr under $N_2$ atmosphere. LCMS showed desired compound was detected. The reaction mixture was concentrated under reduced pressure to give a residue. The residue was purified by flash silica gel chromatography (ISCO®; 4 g SepaFlash®Silica Flash Column, Eluent of 22~30% Ethyl acetate/Petroleum ether gradient @ 20 mL/min), and concentrated in vacuum to give tert-butyl 4-[3-[2-(cyclopropoxy)-5-methoxy-3-pyridyl]-6-fluoro-pyrazolo[1,5-a]pyrimidin-5-yl]piperazine-1-carboxylate (81 mg, 130.06 umol, 72.71% yield, 77.8% purity) as a solid.

LCMS m/z=485.3 $[M+H]^+$.

3-[2-(cyclopropoxy)-5-methoxy-3-pyridyl]-6-fluoro-5-piperazin-1-yl-pyrazolo[1,5-a]pyrimidine

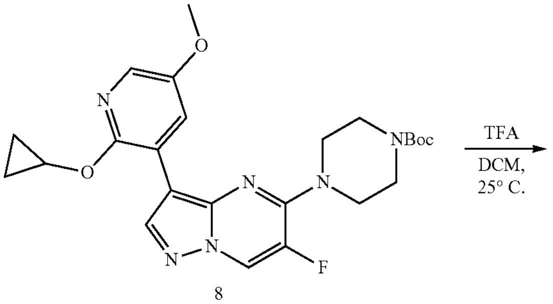

8

-continued

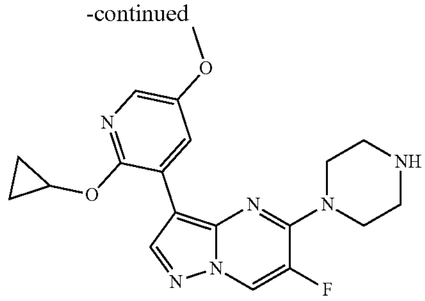

9

To a solution of tert-butyl 4-[3-[2-(cyclopropoxy)-5-methoxy-3-pyridyl]-6-fluoro-pyrazolo[1,5-a]pyrimidin-5-yl]piperazine-1-carboxylate (81 mg, 167.18 μmol, 1 eq) in DCM (3 mL) was added TFA (1.54 g, 13.46 mmol, 1 mL, 80.53 eq). The mixture was stirred at 25° C. for 1 hr. LCMS showed the starting material was consumed completely and desired compound was detected. The reaction mixture was concentrated under reduced pressure to give 3-[2-(cyclopropoxy)-5-methoxy-3-pyridyl]-6-fluoro-5-piperazin-1-yl-pyrazolo[1,5-a]pyrimidine (80 mg, 160.50 μmol, 96.01% yield, N/A purity, TFA) as an oil.

LCMS m/z=385.1 $[M+H]^+$.

[(3S)-5-oxo-1-(trideuteriomethyl)pyrrolidin-3-yl] 4-[3-[2-(cyclopropoxy)-5-methoxy-3-pyridyl]-6-fluoro-pyrazolo[1,5-a]pyrimidin-5-yl]piperazine-1-carboxylate (I-117)

To a solution of 3-[2-(cyclopropoxy)-5-methoxy-3-pyridyl]-6-fluoro-5-piperazin-1-yl-pyrazolo[1,5-a]pyrimidine (70 mg, 140.44 μmol, 1 eq, TFA) in ACN (2 mL) was added DIEA (90.75 mg, 702.21 μmol, 122.31 μL, 5 eq) and (4-nitrophenyl) [(3S)-5-oxo-1-(trideuteriomethyl)pyrrolidin-3-yl]carbonate (43.76 mg, 154.49 μmol, 1.1 eq). The reaction mixture was stirred at 25° C. for 2 hr. LCMS showed the starting material was consumed completely and desired compound was detected. The reaction mixture was concentrated under reduced pressure to give a residue. The residue was purified by prep-HPLC (column: Waters Xbridge BEH C18 150*25*10 um; mobile phase: [water ($NH_3H_2O$)-ACN]; gradient: 26%-56% B over 10 min) and lyophilized to give [(3S)-5-oxo-1-(trideuteriomethyl)pyrrolidin-3-yl]-4-[3-[2-(cyclopropoxy)-5-methoxy-3-pyridyl]-6-fluoro-pyrazolo[1,5-a]pyrimidin-5-yl]piperazine-1-carboxylate (I-117, 47.51 mg, 89.46 μmol, 63.70% yield, 99.52% purity) as a solid.

LCMS m/z=529.2 $[M+H]^+$.

SFC $t_R$=1.337 min; 100%.

$^1H$ NMR (400 MHz, DMSO-$d_6$) ¿=8.80-8.77 (m, 1H), 8.74 (d, J=7.9 Hz, 1H), 8.34 (s, 1H), 8.02-7.99 (m, 1H), 7.13-7.08 (m, 1H), 6.81 (d, J=7.9 Hz, 1H), 5.18-5.13 (m, 1H), 4.42-4.37 (m, 1H), 3.78-3.74 (m, 4H), 3.73-3.69 (m, 1H), 3.56-3.50 (m, 4H), 3.39-3.36 (m, 1H), 2.76-2.68 (m, 1H), 2.31-2.25 (m, 1H), 0.81-0.77 (m, 4H).

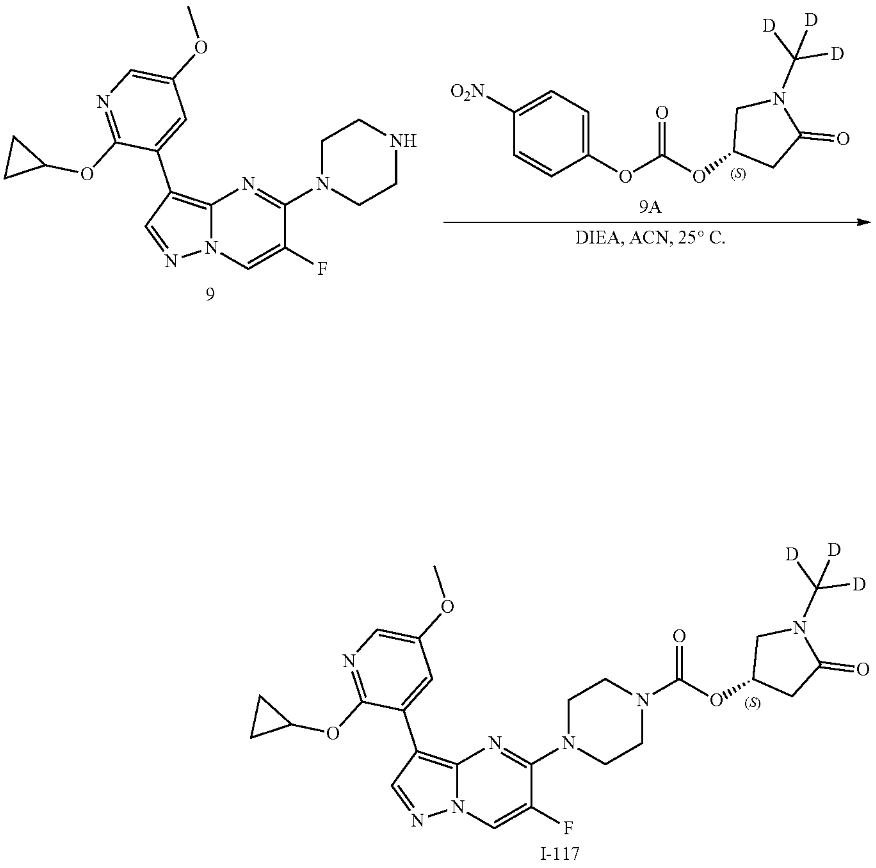

Example 89: Synthesis of Compound I-118

3-bromo-2-(cyclopropoxy)-5-fluoro-pyridine

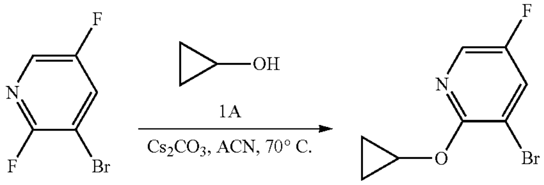

1 2

To a mixture of cyclopropanol (419.18 mg, 7.22 mmol, 1.4 eq) in dry ACN (5 mL) was added $Cs_2CO_3$ (3.36 g, 10.31 mmol, 2 eq) at 0° C. The mixture was stirred at this temperature for 10 min. 3-bromo-2,5-difluoro-pyridine (1 g, 5.16 mmol, 1 eq) was added at 0° C. The mixture was warmed to 70° C. and stirred for 2 hr under $N_2$ atmosphere. LCMS showed that desired MS was found. The mixture was concentrated to the crude product. The crude was purified by FCC (ISCO®; 20 g SepaFlash® Silica Flash Column, Eluent of 0~17% Ethyl acetate/Petroleum ether gradient @ 35 mL/min) to give 3-bromo-2-(cyclopropoxy)-5-fluoro-pyridine (590 mg, 2.54 mmol, 49.32% yield) as an oil.

LCMS m/z=232.0 $[M+H]^+$.

$^1H$ NMR (400 MHz, DMSO-$d_6$) δ=8.23 (d, J=2.6 Hz, 1H), 8.16 (dd, J=2.8, 7.6 Hz, 1H), 4.25 (tt, J=3.0, 6.1 Hz, 1H), 0.81-0.75 (m, 2H), 0.72-0.65 (m, 2H).

2-(cyclopropoxy)-5-fluoro-3-(4,4,5,5-tetramethyl-1,3,2-dioxaborolan-2-yl)pyridine

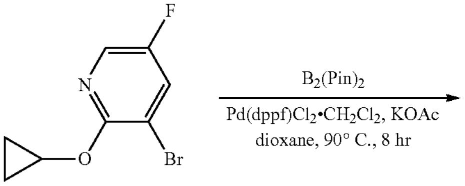

2

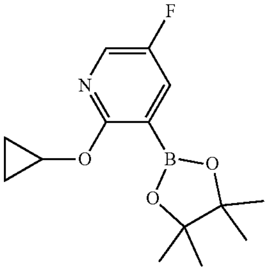

3

A mixture of 3-bromo-2-(cyclopropoxy)-5-fluoro-pyridine (590 mg, 2.54 mmol, 1 eq), 4,4,5,5-tetramethyl-2-(4,4,5,5-tetramethyl-1,3,2-dioxaborolan-2-yl)-1,3,2-dioxaborolane (774.78 mg, 3.05 mmol, 1.2 eq), KOAc (499.05 mg, 5.09 mmol, 2 eq) and $Pd(dppf)Cl_2 \cdot CH_2Cl_2$ (207.64 mg, 254.26 μmol, 0.1 eq) in dioxane (6 mL) was degassed and purged with $N_2$ for 3 times, and then the mixture was stirred at 90° C. for 8 hr under $N_2$ atmosphere. LCMS showed that desired MS was found. The mixture was concentrated to the crude product. The crude was purified by FCC (ISCO®; 20 g SepaFlash® Silica Flash Column, Eluent of 0~17% Ethyl acetate/Petroleum ether gradient @ 20 mL/min) to give 2-(cyclopropoxy)-5-fluoro-3-(4,4,5,5-tetramethyl-1,3,2-dioxaborolan-2-yl)pyridine (500 mg, 1.79 mmol, 70.46% yield) as an oil.

LCMS m/z=280.2 $[M+H]^+$.

$^1H$ NMR (400 MHz, DMSO-$d_6$) δ=8.25 (d, J=3.1 Hz, 1H), 7.67 (br dd, J=2.5, 5.5 Hz, 1H), 4.19 (td, J=2.8, 6.0 Hz, 1H), 1.26 (s, 12H), 0.71 (br d, J=3.6 Hz, 2H), 0.61-0.56 (m, 2H).

tert-butyl 4-[3-[2-(cyclopropoxy)-5-fluoro-3-pyridyl]-6-fluoro-pyrazolo[1,5-a]pyrimidin-5-yl]piperazine-1-carboxylate

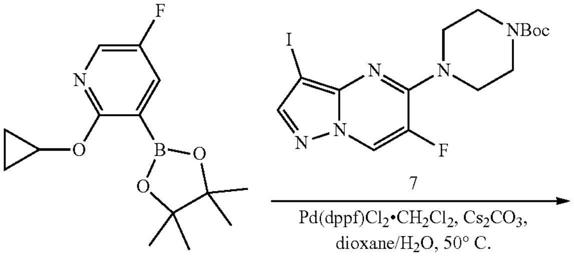

3

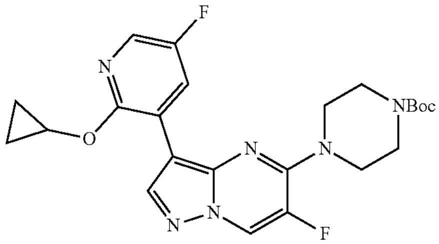

8

A mixture of tert-butyl 4-(6-fluoro-3-iodo-pyrazolo[1,5-a]pyrimidin-5-yl)piperazine-1-carboxylate (65 mg, 145.33 μmol, 1 eq), 2-(cyclopropoxy)-5-fluoro-3-(4,4,5,5-tetramethyl-1,3,2-dioxaborolan-2-yl)pyridine (60.85 mg, 218.00 μmol, 1.5 eq), $Pd(dppf)Cl_2 \cdot CH_2Cl_2$ (23.74 mg, 29.07 μmol, 0.2 eq) and $Cs_2CO_3$ (94.71 mg, 290.67 μmol, 2 eq) in dioxane (1.5 mL) and $H_2O$ (0.5 mL) was degassed and purged with $N_2$ for 3 times, and then the mixture was stirred at 50° C. for 0.5 hr under $N_2$ atmosphere. LCMS showed that desired MS was found. The mixture was concentrated to the crude product. The crude was purified by FCC (ISCO®; 4 g SepaFlash® Silica Flash Column, Eluent of 0~25% Ethyl acetate/Petroleum ether gradient @ 18 mL/min) to give tert-butyl-4-[3-[2-(cyclopropoxy)-5-fluoro-3-pyridyl]-6-fluoro-pyrazolo[1,5-a]pyrimidin-5-yl]piperazine-1-carboxylate (88 mg, 143.43 μmol, 98.69% yield, 77.009% purity) as a solid.

LCMS m/z=473.1 $[M+H]^+$.

3-[2-(cyclopropoxy)-5-fluoro-3-pyridyl]-6-fluoro-5-piperazin-1-yl-pyrazolo[1,5-a]pyrimidine

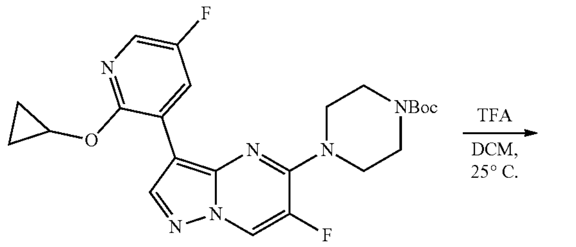

8

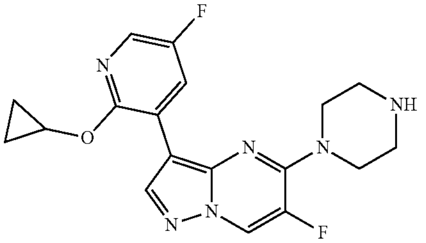

9

To a mixture of tert-butyl 4-[3-[2-(cyclopropoxy)-5-fluoro-3-pyridyl]-6-fluoro-pyrazolo[1,5-a]pyrimidin-5-yl]piperazine-1-carboxylate (88 mg, 143.43 μmol, 1 eq) in DCM (1.5 mL) was added TFA (0.5 mL). The mixture was stirred at 25° C. for 0.5 hr. LCMS showed that desired MS was found. The mixture was concentrated to give 3-[2-(cyclopropoxy)-5-fluoro-3-pyridyl]-6-fluoro-5-piperazin-1-yl-pyrazolo[1,5-a]pyrimidine (70 mg, crude, TFA) as an oil. LCMS m/z=373.2 $[M+H]^+$.

[(3S)-5-oxo-1-(trideuteriomethyl)pyrrolidin-3-yl] 4-[3-[2-(cyclopropoxy)-5-fluoro-3-pyridyl]-6-fluoro-pyrazolo[1,5-a]pyrimidin-5-yl]piperazine-1-carboxylate (I-118)

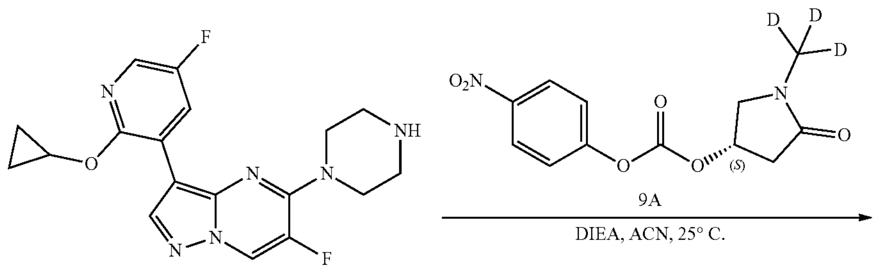

9

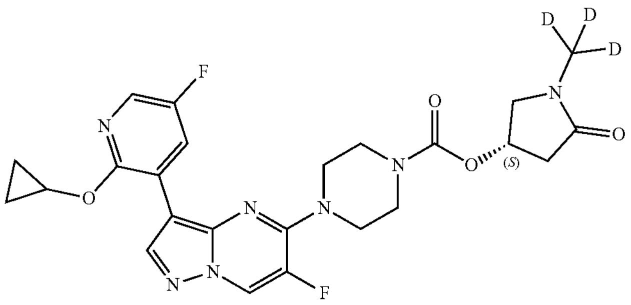

I-118

To a mixture of 3-[2-(cyclopropoxy)-5-fluoro-3-pyridyl]-6-fluoro-5-piperazin-1-yl-pyrazolo[1,5-a]pyrimidine (35 mg, 71.96 µmol, 1 eq, TFA) and DIEA (27.90 mg, 215.87 µmol, 37.60 µL, 3 eq) in ACN (0.5 mL) was added (4-nitrophenyl) [(3S)-5-oxo-1-(trideuteriomethyl)pyrrolidin-3-yl]carbonate (18.34 mg, 64.76 µmol, 0.9 eq). The mixture was stirred at 25° C. for 0.5 hr. LCMS showed that desired MS was found. The mixture was concentrated to the crude product. The crude product was purified by prep-HPLC (Column: Waters Xbridge BEH C18 250*25*10 um; mobile phase: [water ($NH_4HCO_3$)-ACN];

gradient: 27%-57% B over 15 min to give [(3S)-5-oxo-1-(trideuteriomethyl)pyrrolidin-3-yl] 4-[3-[2-(cyclopropoxy)-5-fluoro-3-pyridyl]-6-fluoro-pyrazolo[1,5-a]pyrimidin-5-yl]piperazine-1-carboxylate (I-118, 19.69 mg, 37.34 µmol, 51.88% yield, 97.939% purity) as a powder.

LCMS m/z=517.1 $[M+H]^+$

SFC $t_R$=2.011 min; 100%.

$^1$H NMR (400 MHz, DMSO-$d_6$) δ=9.30 (d, J=8.6 Hz, 1H), 8.64-8.58 (m, 1H), 8.43 (s, 1H), 8.02 (d, J=4.0 Hz, 1H), 5.20-5.11 (m, 1H), 4.41-4.34 (m, 1H), 3.75-3.71 (m, 4H), 3.64-3.55 (m, 4H), 3.39 (d, J=1.6 Hz, 1H), 3.36 (d, J=1.6 Hz, 1H), 2.77-2.69 (m, 1H), 2.34-2.24 (m, 1H), 0.85-0.77 (m, 4H).

Example 90: Synthesis of Compound I-83

[(3R)-1-methyl-5-oxo-pyrrolidin-3-yl] 4-[3-[2-(1-methoxycarbonylazetidin-3-yl)oxy-3-pyridyl]pyrazolo[1,5-a]pyrimidin-5-yl]piperazine-1-carboxylate LCMS m/z=551.3 $[M+H]^+$.

SFC $t_R$=1.818 min; 100%.

$^1$H NMR (400 MHz, DMSO-$d_6$) δ=8.85-8.80 (m, 1H), 8.77 (d, J=7.9 Hz, 1H), 8.57-8.54 (m, 1H), 7.96-7.91 (m, 1H), 7.13 (s, 1H), 6.83 (d, J=7.9 Hz, 1H), 5.50-5.41 (m, 1H), 5.16 (t, J=6.3 Hz, 1H), 4.37 (t, J=7.3 Hz, 2H), 4.02 (d, J=6.8 Hz, 2H), 3.79-3.74 (m, 4H), 3.74-3.70 (m, 1H), 3.58 (s, 3H), 3.55-3.49 (m, 4H), 3.35 (s, 1H), 2.74 (s, 3H), 2.70 (d, J=7.1 Hz, 1H), 2.29 (d, J=17.9 Hz, 1H).

Example 91: Synthesis of Compound I-84 and I-84-6

(4R)-1-(2-benzyloxyethyl)-4-[tert-butyl(diphenyl)silyl]oxy-pyrrolidin-2-one

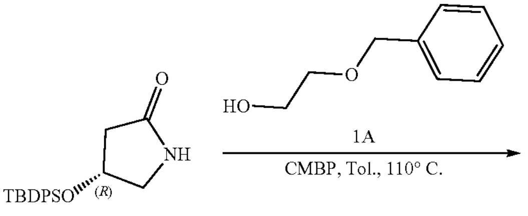

1

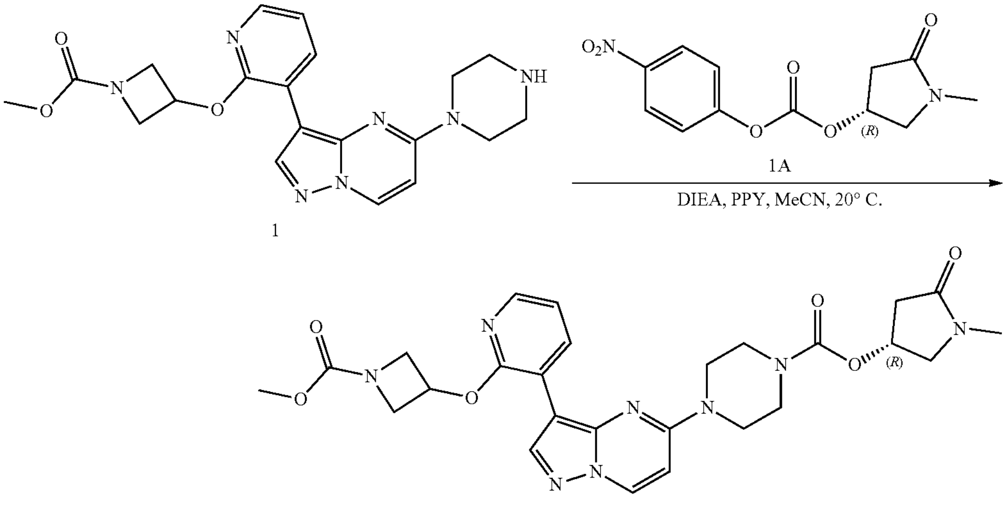

1

I-83

The product I-83 was prepared according to the synthesis method of I-58. Then the product was further purified by prep. HPLC (column: Waters Xbridge 150*25 mm*5 um; mobile phase: [water ($NH_3H_2O$)-ACN]; gradient: 18%-48% B over 10 min). The pure fractions were collected and the volatiles were removed under vacuum. The residue was partitioned between acetonitrile (2 mL) and water (10 mL). The solution was lyophilized to dryness to give [(3R)-1-methyl-5-oxo-pyrrolidin-3-yl]-4-[3-[2-(1-methoxycarbonylazetidin-3-yl)oxy-3-pyridyl]pyrazolo-[1,5-a]pyrimidin-5-yl]piperazine-1-carboxylate (I-83, 116.41 mg, 207.71 umol, 61.75% yield, 98.239% purity) as a powder.

-continued

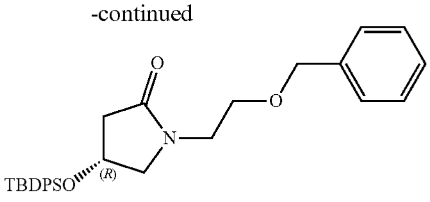

2

The product 2 was prepared according to the synthesis method of I-35. The crude was purified by FCC (ISCO®; 80 g SepaFlash® Silica Flash Column, eluent of 0~30% Petroleum ether/Ethyl acetate gradient @ 80 mL/min) to give (4R)-1-(2-benzyloxyethyl)-4-[tert-butyl(diphenyl)silyl]oxy-pyrrolidin-2-one (2.5 g, 5.26 mmol, 17.86% yield, 99.661% purity) as a liquid.

LCMS m/z=474.2 $[M+H]^+$.

$^1H$ NMR (400 MHz, DMSO-$d_6$) δ=7.58 (br d, J=7.5 Hz, 4H), 7.48-7.40 (m, 5H), 7.33-7.25 (m, 6H), 4.44 (s, 2H), 3.59-3.38 (m, 7H), 2.48-2.39 (m, 1H), 2.17 (dd, J=2.8, 16.8 Hz, 1H), 0.99 (s, 9H).

(4R)-1-(2-benzyloxyethyl)-4-hydroxy-pyrrolidin-2-one

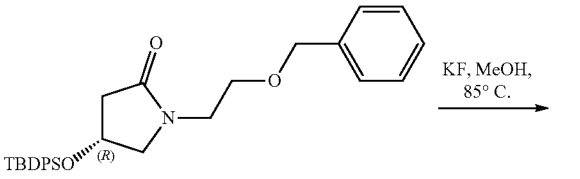

2

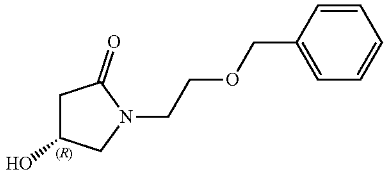

3

The product 3 was prepared according to the synthesis method of I-35. The crude was purified by FCC (ISCO®; 12 g SepaFlash® Silica Flash Column, eluent of 0~12% Methanol/Dichloromethane gradient @ 25 mL/min) to give (4R)-1-(2-benzyloxyethyl)-4-hydroxy-pyrrolidin-2-one (840 mg, 3.11 mmol, 58.92% yield, 87.108% purity) as a liquid.

LCMS m/z=236.1 $[M+H]^+$.

$^1H$ NMR (400 MHz, DMSO-$d_6$) δ=7.49-7.23 (m, 5H), 5.18 (d, J=3.9 Hz, 1H), 4.50 (s, 2H), 4.29 (dq, J=2.7, 6.1 Hz, 1H), 3.62 (dd, J=5.6, 10.4 Hz, 1H), 3.58-3.51 (m, 2H), 3.50-3.42 (m, 1H), 3.38 (s, 1H), 3.23 (dd, J=2.1, 10.4 Hz, 1H), 2.56 (s, 1H), 2.07 (dd, J=2.5, 16.9 Hz, 1H).

[(3R)-1-(2-benzyloxyethyl)-5-oxo-pyrrolidin-3-yl] (4-nitrophenyl) carbonate

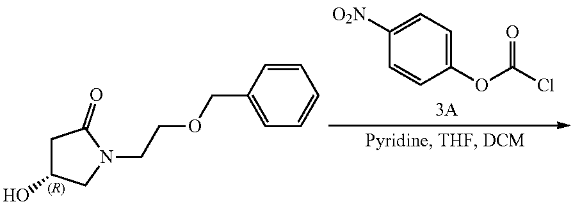

3

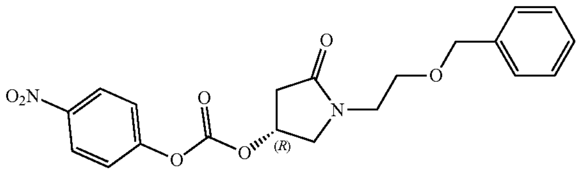

4

The product 4 was prepared according to the synthesis method of I-35. The crude was purified by FCC (ISCO®; 4 g SepaFlash® Silica Flash Column, eluent of 0~50% Petroleum ether/Ethyl acetate gradient @ 35 mL/min) to give [(3R)-1-(2-benzyloxyethyl)-5-oxo-pyrrolidin-3-yl](4-nitrophenyl) carbonate (520 mg, 1.29 mmol, 75.72% yield, 99.114% purity) as a liquid.

LCMS m/z=401.0 $[M+H]^+$.

$^1H$ NMR (400 MHz, DMSO-$d_6$) δ=8.40-8.24 (m, 2H), 7.64-7.54 (m, 2H), 7.39-7.23 (m, 5H), 5.31 (t, J=5.9 Hz, 1H), 4.49 (s, 2H), 3.85 (dd, J=5.4, 12.0 Hz, 1H), 3.66 (d, J=11.9 Hz, 1H), 3.59-3.54 (m, 2H), 3.49-3.42 (m, 2H), 2.84 (dd, J=6.7, 17.8 Hz, 1H), 2.52 (br s, 1H).

[(3R)-1-(2-benzyloxyethyl)-5-oxo-pyrrolidin-3-yl]-4-[3-[2-(1-methoxycarbonyl-azetidin-3-yl)oxy-3-pyridyl]pyrazolo[1,5-a]pyrimidin-5-yl]piperazine-1-carboxylate

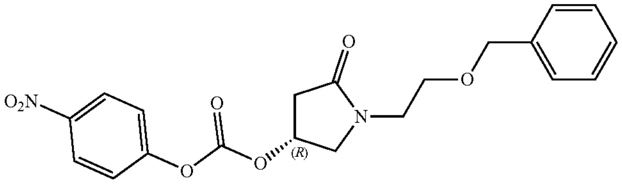

4

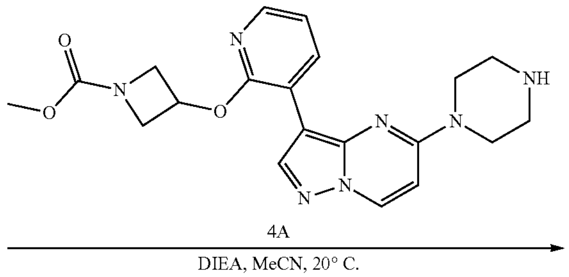

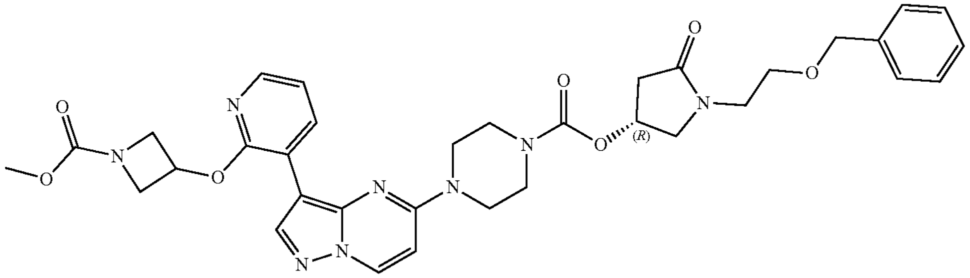

I-84-6

To a solution of methyl 3-[[3-(5-piperazin-1-ylpyrazolo[1,5-a]pyrimidin-3-yl)-2-pyridyl]oxy]azetidine-1-carboxylate (150 mg, 366.35 μmol, 1 eq) in MeCN (1 mL) was added DIEA (142.05 mg, 1.10 mmol, 191.44 μL, 3 eq) and [(3R)-1-(2-benzyloxyethyl)-5-oxo-pyrrolidin-3-yl](4-nitrophenyl) carbonate (146.68 mg, 366.35 μmol, 1 eq). The mixture was stirred at 25° C. for 1 hr. LCMS showed that desired MS was found. The reaction mixture was concentrated under reduced pressure to give a residue. The crude was purified by FCC (ISCO®; 4 g SepaFlash® Silica Flash Column, eluent of 0~9% Methanol/Dichloromethane gradient @ 25 mL/min) to give [(3R)-1-(2-benzyloxyethyl)-5-oxo-pyrrolidin-3-yl]-4-[3-[2-(1-methoxycarbonyl-azetidin-3-yl)oxy-3-pyridyl]pyrazolo[1,5-a]pyrimidin-5-yl]piperazine-1-carboxylate (I-84-6, 240 mg, 262.12 μmol, 71.55% yield, 73.254% purity) as an oil.

LCMS m/z=671.4 $[M+H]^+$.

SFC $t_R$=1.767 min; 100%.

$^1$H NMR (400 MHz, DMSO-$d_6$) ¿=8.85-8.71 (m, 2H), 8.55 (s, 1H), 7.98-7.87 (m, 1H), 7.38-7.20 (m, 5H), 7.15-7.06 (m, 1H), 6.80 (d, J=8.0 Hz, 1H), 5.54-5.39 (m, 1H), 5.22-5.10 (m, 1H), 4.47 (s, 2H), 4.43-4.32 (m, 2H), 4.08-3.95 (m, 2H), 3.81-3.75 (m, 2H), 3.74-3.69 (m, 4H), 3.58 (s, 3H), 3.56-3.51 (m, 4H), 3.49-3.47 (m, 4H), 2.79-2.72 (m, 1H), 2.34-2.27 (m, 1H).

[(3R)-1-(2-hydroxyethyl)-5-oxo-pyrrolidin-3-yl] 4-[3-[2-(1-methoxycarbonylazetidin-3-yl)oxy-3-pyridyl]pyrazolo[1,5-a]pyrimidin-5-yl]piperazine-1-carboxylate To a solution of [(3R)-1-(2-benzyloxyethyl)-5-oxo-pyrrolidin-3-yl] 4-[3-[2-(1-methoxycarbonylazetidin-3-yl)oxy-3-pyridyl]pyrazolo[1,5-a]pyrimidin-5-yl]piperazine-1-carboxylate (100 mg, 149.09 μmol, 1 eq) in MeOH (5 mL) was added $Pd(OH)_2$ (100 mg, 142.41 μmol, 20% purity) under $N_2$ atmosphere. The suspension was degassed under vacuum and purged with $H_2$ several times. The mixture was stirred under $H_2$ atmosphere (300.55 μg, 149.09 μmol) (50 psi) at 25° C. for 10 hr. LCMS showed that desired MS was found. The reaction mixture was concentrated under reduced pressure to give a residue. The residue was purified by prep. HPLC (Column: Phenomenex luna C18 150*25 mm*10 um; mobile phase: [water(HCOOH)-MeCN]; gradient: 20%-50% B over 8 min). The pure fractions were collected and the volatiles were removed under vacuum. The residue was partitioned between acetonitrile (20 mL) and water (100 mL). The solution was lyophilized to dryness to give [(3R)-1-(2-hydroxyethyl)-5-oxo-pyrrolidin-3-yl]-4-[3-[2-(1-methoxycarbonylazetidin-3-yl)oxy-3-pyridyl]pyrazolo[1,5-a]pyrimidin-5-yl]piperazine-1-carboxylate (I-84, 2.46 mg, 4.14 μmol, 2.78% yield, 97.678% purity) as a powder.

LCMS m/z=581.3 $[M+H]^+$.

SFC $t_R$=1.679 min; 100%.

$^1$H NMR (400 MHz, DMSO-$d_6$) δ=8.85-8.72 (m, 2H), 8.55 (s, 1H), 8.00-7.89 (m, 1H), 7.21-7.09 (m, 1H), 6.83 (d, J=8.0 Hz, 1H), 5.56-5.40 (m, 1H), 5.22-5.11 (m, 1H), 4.72 (t, J=5.4 Hz, 1H), 4.42-4.30 (m, 2H), 4.07-3.97 (m, 2H), 3.84-3.80 (m, 1H), 3.79-3.75 (m, 4H), 3.58 (s, 3H), 3.55-3.51 (m, 4H), 3.50-3.48 (m, J=5.5 Hz, 2H), 3.47-3.42 (m, 2H), 3.25-3.22 (m, 1H), 2.78-2.70 (m, 1H), 2.33-2.28 (m, 1H).

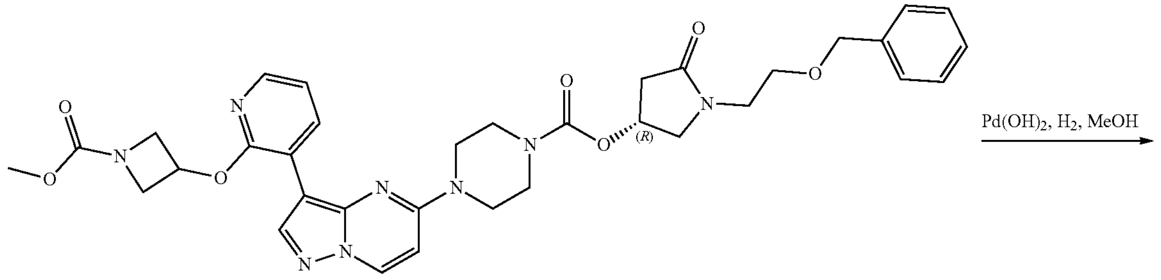

I-84-6

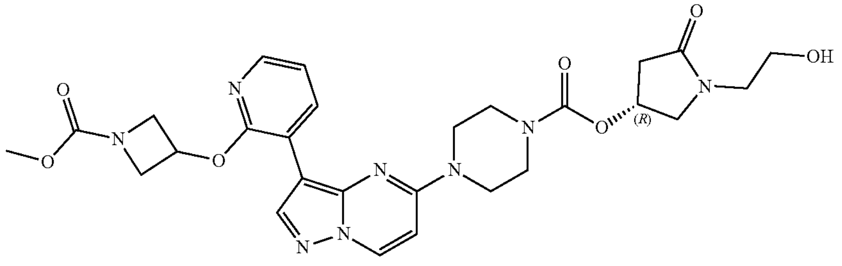

I-84

Example 92: Synthesis of Compound I-85

(4R)-4-[tert-butyl(diphenyl)silyl]oxy-1-(oxetan-3-yl) pyrrolidin-2-one

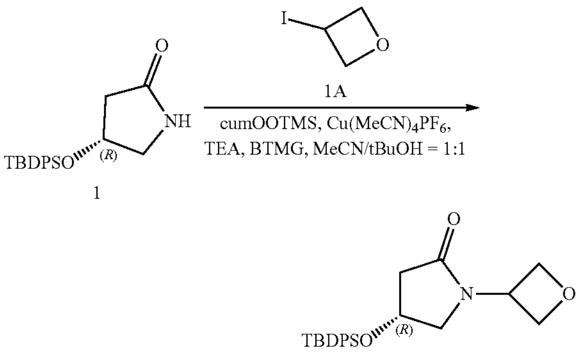

1 1A 2

A mixture of 3-iodooxetane (1.30 g, 7.07 mmol, 1.2 eq), (4R)-4-[tert-butyl(diphenyl)silyl]oxypyrrolidin-2-one (2 g, 5.89 mmol, 1 eq) and cuprous; acetonitrile; hexafluorophosphate (219.57 mg, 589.10 μmol, 0.1 eq) in MeCN (0.2 mL) and t-BuOH (0.2 mL) was degassed and purged with $N_2$ for 3 times, TEA (2.98 g, 29.45 mmol, 4.10 mL, 5 eq) and 2-tert-butyl-1,1,3,3-tetramethylguanidine (2.02 g, 11.78 mmol, 2.37 mL, 2 eq) was added, followed by trimethyl-(1-methyl-1-phenyl-ethyl) peroxy-silane (6.61 g, 29.45 mmol, 5 eq). The mixture was stirred at 25° C. for 1 hr under $N_2$ atmosphere. LCMS showed desired mass was detected. The reaction mixture was concentrated under reduced pressure to remove solvent. The residue was purified by flash silica gel chromatography (ISCO®; 20 g SepaFlash® Silica Flash Column, Eluent of 0~30% Ethyl acetate/Petroleum ether gradient @ 40 mL/min) to give (4R)-4-[tert-butyl(diphenyl)silyl]oxy-1-(oxetan-3-yl)pyrrolidin-2-one (1.5 g, 3.41 mmol, 57.93% yield, 90% purity) as an oil.

LCMS m/z=396.1 $[M+H]^+$.

$^1H$ NMR (400 MHz, CHLOROFORM-d) δ=7.57 (br d, J=6.8 Hz, 4H), 7.43-7.28 (m, 6H), 5.28 (br d, J=7.0 Hz, 1H), 4.78 (t, J=7.3 Hz, 1H), 4.71 (t, J=7.4 Hz, 1H), 4.65-4.59 (m, 1H), 4.52 (s, 1H), 4.46-4.40 (m, 1H), 3.60-3.46 (m, 2H), 2.39 (d, J=4.6 Hz, 2H), 0.99 (s, 9H).

(4R)-4-hydroxy-1-(oxetan-3-yl)pyrrolidin-2-one

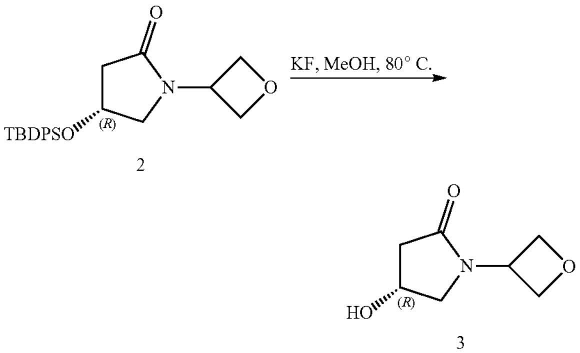

2 3

To a solution of (4R)-4-[tert-butyl(diphenyl)silyl]oxy-1-(oxetan-3-yl)pyrrolidin-2-one (1.5 g, 3.79 mmol, 1 eq) in MeOH (4 mL) was added KF (3.30 g, 56.88 mmol, 15 eq). The mixture was stirred at 80° C. for 12 hr. LCMS showed desired mass was detected. The reaction mixture was concentrated under reduced pressure to remove solvent. The residue was purified by flash silica gel chromatography (ISCO®; 12 g SepaFlash® Silica Flash Column, eluent of 0~30% MeOH/DCM gradient @ 40 mL/min) to give (4R)-4-hydroxy-1-(oxetan-3-yl)pyrrolidin-2-one (0.523 g, 3.29 mmol, 86.88% yield, 99% purity) as an oil.

LCMS m/z=158.0 $[M+H]^+$.

$^1H$ NMR (400 MHz, CHLOROFORM-d) δ=5.30 (quin, J=7.0 Hz, 1H), 4.79 (td, J=7.4, 11.3 Hz, 2H), 4.73-4.68 (m, 1H), 4.68-4.61 (m, 1H), 4.57-4.51 (m, 1H), 3.81 (dd, J=5.4, 10.6 Hz, 1H), 3.60 (dd, J=1.8, 10.7 Hz, 1H), 2.65 (dd, J=6.4, 17.4 Hz, 1H), 2.35 (dd, J=2.3, 17.5 Hz, 1H).

(4-nitrophenyl) [(3R)-1-(oxetan-3-yl)-5-oxo-pyrrolidin-3-yl]carbonate

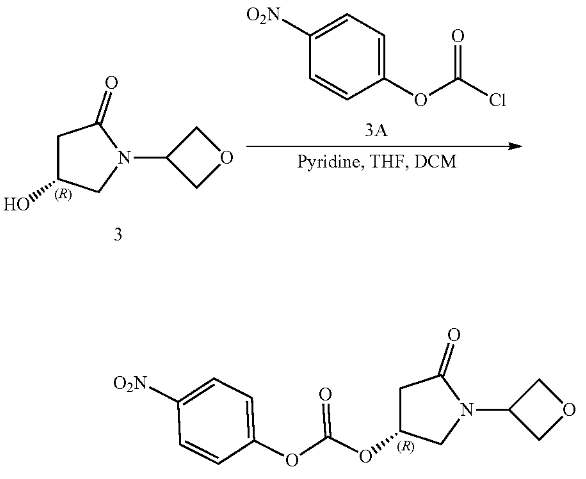

3 3A 4

To a solution of (4R)-4-hydroxy-1-(oxetan-3-yl)pyrrolidin-2-one (0.12 g, 763.52 μmol, 1 eq) in THF (5 mL) was added pyridine (120.79 mg, 1.53 mmol, 123.25 μL, 2 eq) and (4-nitrophenyl) carbonochloridate (615.59 mg, 3.05 mmol, 4 eq). The mixture was stirred at 25° C. for 1 hr. LCMS showed desired mass was detected. The reaction mixture was concentrated under reduced pressure to remove solvent. The residue was purified by flash silica gel chromatography (ISCO®; 5 g SepaFlash® Silica Flash Column, eluent of 0~100% Ethyl acetate/Petroleum gradient @ 18 mL/min) to give (4-nitrophenyl) [(3R)-1-(oxetan-3-yl)-5-oxo-pyrrolidin-3-yl]carbonate (0.163 g, 343.94 μmol, 45.05% yield, 68% purity) as an oil.

LCMS m/z=323.2 $[M+H]^+$.

$^1H$ NMR (400 MHz, CHLOROFORM-d) δ=8.26-8.18 (m, 2H), 7.37-7.29 (m, 2H), 5.43-5.36 (m, 1H), 5.34-5.26 (m, 1H), 4.93-4.75 (m, 2H), 4.74-4.61 (m, 2H), 4.07-3.99 (m, 1H), 3.89-3.82 (m, 1H), 2.84 (dd, J=6.9, 18.1 Hz, 1H), 2.64 (dd, J=2.0, 18.1 Hz, 1H).

[(3R)-1-(oxetan-3-yl)-5-oxo-pyrrolidin-3-yl]-4-[3-[2-(1-methoxycarbonylazetidin-3-yl)oxy-3-pyridyl]pyrazolo[1,5-a]pyrimidin-5-yl]piperazine-1-carboxylate

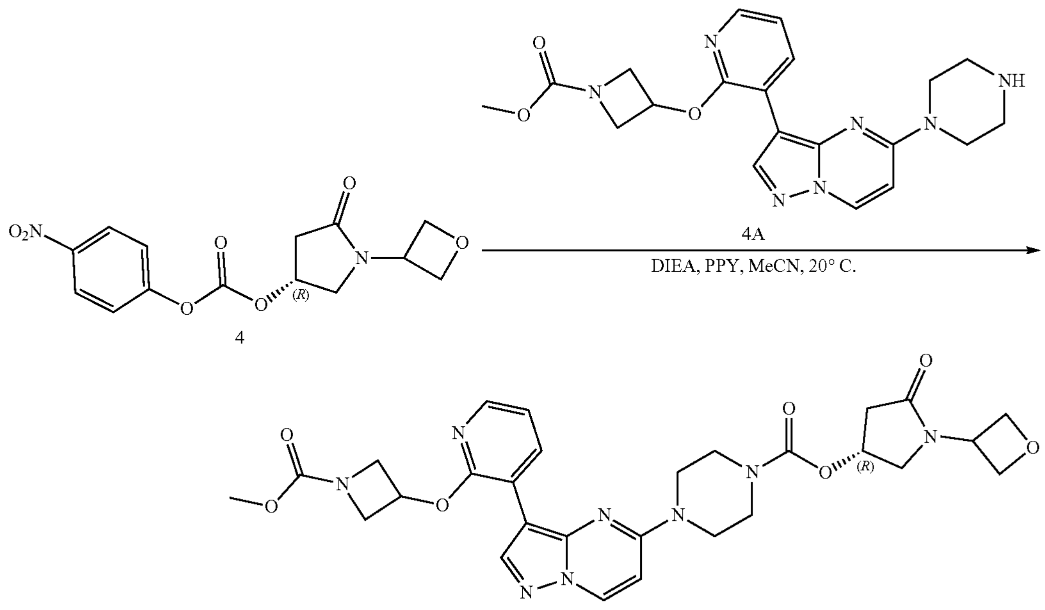

4

I-85

To a solution of methyl 3-[3-(5-piperazin-1-ylpyrazolo[1,5-a]pyrimidin-3-yl)-2-pyridyl]oxy]azetidine-1-carboxylate (0.15 g, 336.40 μmol, 1 eq, HCl) in MeCN (2 mL) was added DIEA (173.91 mg, 1.35 mmol, 234.38 μL, 4 eq) and PPY (10.35 mg, 67.28 μmol, 0.2 eq) (4-nitrophenyl) [(3R)-1-(oxetan-3-yl)-5-oxo-pyrrolidin-3-yl]carbonate (162.62 mg, 504.60 umol, 1.5 eq). The mixture was stirred at 25° C. for 1 hr. LCMS showed desired mass was detected. The reaction mixture was concentrated under reduced pressure to remove solvent. Then the product was further purified by prep. HPLC (column: Waters Xbridge 150*25 mm*5 um; mobile phase: [water ($NH_3H_2O$)-MeCN]; gradient: 18%-48% B over 14 min). The pure fractions were collected and the volatiles were removed under vacuum. The residue was partitioned between acetonitrile (2 mL) and water (10 mL). The solution was lyophilized to dryness to give [(3R)-1-(oxetan-3-yl)-5-oxo-pyrrolidin-3-yl]-4-[3-[2-(1-methoxycarbonylazetidin-3-yl)oxy-3-pyridyl]pyrazolo[1,5-a]pyrimidin-5-yl]piperazine-1-carboxylate (I-85, 40.12 mg, 65.55 μmol, 19.49% yield, 96.82% purity) as a solid.

LCMS m/z=593.3 $[M+H]^+$

SFC $t_R$=2.107 min; 100%.

$^1H$ NMR (400 MHz, DMSO-$d_6$) δ=8.84-8.81 (m, 1H), 8.78 (d, J=7.9 Hz, 1H), 8.56 (s, 1H), 7.94 (d, J=1.3 Hz, 1H), 7.17-7.11 (m, 1H), 6.83 (d, J=8.0 Hz, 1H), 5.49-5.42 (m, 1H), 5.25 (t, J=6.2 Hz, 1H), 5.15 (t, J=7.1 Hz, 1H), 4.73-4.65 (m, 4H), 4.42-4.33 (m, 2H), 4.05-3.96 (m, 3H), 3.82-3.74 (m, 4H), 3.70 (d, J=10.9 Hz, 1H), 3.59 (s, 3H), 3.57-3.49 (m, 4H), 2.84-2.75 (m, 1H), 2.36 (s, 1H).

Example 93: Synthesis of Compound I-119

3-bromo-2-tetrahydrofuan-3-yloxy-pyridine

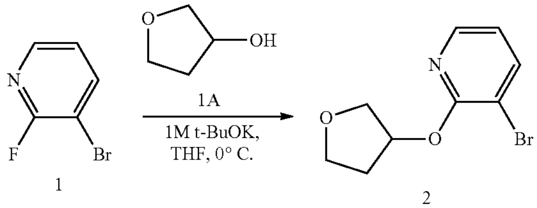

1

2

To a mixture of tetrahydrofuran-3-ol (1.50 g, 17.05 mmol, 1.38 mL, 1 eq) and t-BuOK (1 M, 25.57 mL, 1.5 eq) in THF (20 mL) was added 3-bromo-2-fluoro-pyridine (3 g, 17.05 mmol, 1 eq) at 0° C. The mixture was stirred at 0° C. for 1 hr. LCMS showed that desired MS was found. The reaction mixture was concentrated under reduced pressure to remove solvent. The residue was diluted with $H_2O$ (100 mL) and extracted with EtOAc (100 mL×3). The combined organic layers were dried over $Na_2SO_4$, filtered and concentrated under reduced pressure to give 3-bromo-2-tetrahydrofuran-3-yloxy-pyridine (3.7 g, 14.83 mmol, 87.00% yield, 97.833% purity) as a liquid.

LCMS m/z=244.0 $[M+H]^+$.

$^1H$ NMR (400 MHz, DMSO-$d_6$) δ=8.15 (dd, J=1.6, 4.9 Hz, 1H), 8.03 (dd, J=1.6, 7.6 Hz, 1H), 6.95 (dd, J=4.9, 7.6 Hz, 1H), 5.52 (m, 1H), 3.96-3.89 (m, 1H), 3.88-3.82 (m, 1H), 3.80-3.73 (m, 2H), 2.31-2.14 (m, 1H), 2.07-1.90 (m, 1H).

2-tetrahydrofuran-3-yloxy-3-(4,4,5,5-tetramethyl-1,3,2-dioxaborolan-2-yl)pyridine

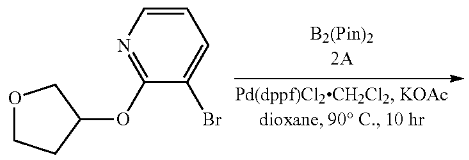

2

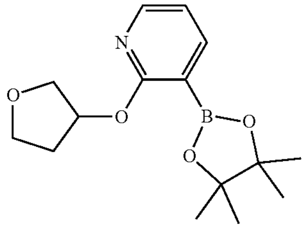

3

A mixture of 3-bromo-2-tetrahydrofuran-3-yloxy-pyridine (3.7 g, 15.16 mmol, 1 eq), 4,4,5,5-tetramethyl-2-(4,4,5,5-tetramethyl-1,3,2-dioxaborolan-2-yl)-1,3,2-dioxaborolane (3.85 g, 15.16 mmol, 1 eq), KOAc (2.98 g, 30.32 mmol, 2 eq) and $Pd(dppf)Cl_2 \cdot CH_2Cl_2$ (618.96 mg, 757.93 μmol, 0.05 eq) in dioxane (40 mL) was degassed and purged with $N_2$ for 3 times, and then the mixture was stirred at 90° C. for 10 hr under $N_2$ atmosphere. LCMS showed that desired MS was found. The reaction mixture was concentrated under reduced pressure to give a residue. The residue was purified by FCC (ISCO®; 20 g SepaFlash® Silica Flash Column, Eluent of 0~11% Ethyl acetate/Petroleum ether gradient @ 25 mL/min) to give 2-tetrahydrofuran-3-yloxy-3-(4,4,5,5-tetramethyl-1,3,2-dioxaborolan-2-yl)pyridine (3.8 g, 4.29 mmol, 28.29% yield, 32.856% purity) as a liquid.

LCMS m/z=292.2 $[M+H]^+$.

$^1H$ NMR (400 MHz, DMSO-$d_6$) δ=8.21 (dd, J=2.1, 4.9 Hz, 1H), 7.85 (dd, J=2.1, 7.1 Hz, 1H), 6.95 (dd, J=5.0, 7.0 Hz, 1H), 5.50-5.38 (m, 1H), 3.96-3.92 (m, 1H), 3.88-3.82 (m, 1H), 3.77 (m, 1H), 3.71 (m, 1H), 2.20-2.11 (m, 1H), 2.01-1.95 (m, 1H), 1.27 (s, 12H).

5-piperazin-1-yl-3-(2-tetrahydrofuran-3-yloxy-3-pyridyl)pyrazolo[1,5-a]pyrimidine

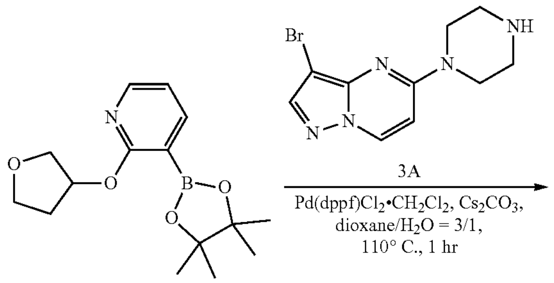

3

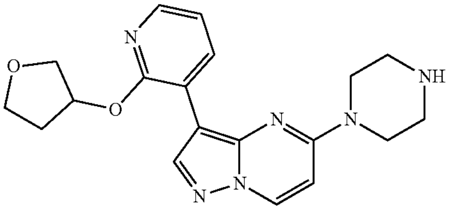

4

A mixture of 2-(tetrahydrofuran-3-yloxy)-3-(4,4,5,5-tetramethyl-1,3,2-dioxaborolan-2-yl)pyridine (300 mg, 1.03 mmol, 1 eq), 3-bromo-5-piperazin-1-yl-pyrazolo[1,5-a]pyrimidine (290.72 mg, 1.03 mmol, 1 eq), Pd(dppf)$Cl_2 \cdot CH_2Cl_2$ (42.07 mg, 51.52 μmol, 0.05 eq) and $Cs_2CO_3$ (671.45 mg, 2.06 mmol, 2 eq) in dioxane (3 mL) and $H_2O$ (1 mL) was degassed and purged with $N_2$ for 3 times, and then the mixture was stirred at 110° C. for 1 hr under $N_2$ atmosphere. LCMS showed that desired MS was found. The reaction mixture was filtered and concentrated under reduced pressure to give a residue. The residue was purified by FCC (ISCOR; 4 SepaFlash® Silica Flash Column, Eluent of 0~8% Methanol/Dichloromethane ether gradient @ 25 mL/min) to give 5-(piperazin-1-yl)-3-(2-tetrahydrofuran-3-yloxy)-3-pyridyl)pyrazolo[1,5-a]pyrimidine (99 mg, 234.48 μmol, 22.76% yield, 86.785% purity) as a liquid.

LCMS m/z=367.2 $[M+H]^+$.

$^1H$ NMR (400 MHz, CHLOROFORM-d) δ=8.26-8.18 (m, 2H), 7.37-7.29 (m, 2H), 5.43-5.36 (m, 1H), 5.34-5.26 (m, 1H), 4.93-4.75 (m, 2H), 4.74-4.61 (m, 2H), 4.07-3.99 (m, 1H), 3.89-3.82 (m, 1H), 2.84 (dd, J=6.9, 18.1 Hz, 1H), 2.64 (dd, J=2.0, 18.1 Hz, 1H).

[(3S)-1-methyl-5-oxo-pyrrolidin-3-yl]-4-[3-(2-tetrahydrofuran-3-yloxy]-3-pyridyl)pyrazolo[1,5-a]pyrimidin-5-yl]piperazine-1-carboxylate

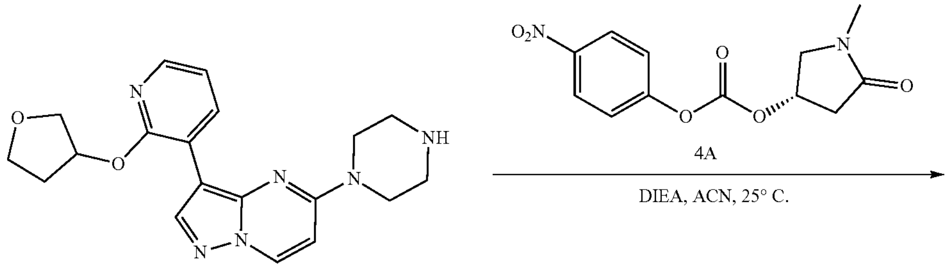

4

-continued

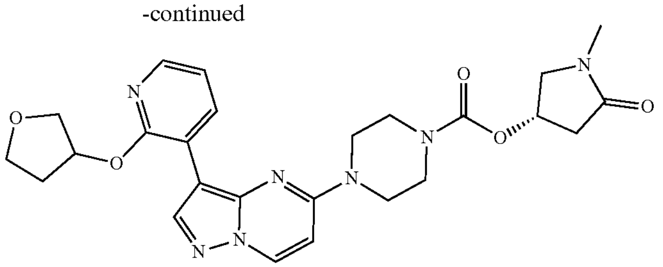

I-119

To a mixture of 5-piperazin-1-yl-3-(2-tetrahydrofuran-3-yloxy-3-pyridyl)pyrazolo[1,5-a]pyrimidine (99 mg, 270.18 μmol, 1 eq) and DIEA (104.76 mg, 810.55 umol, 141.18 μL, 3 eq) in ACN (1 mL) was added [(3S)-1-methyl-5-oxo-pyrrolidin-3-yl](4-nitrophenyl) carbonate (75.71 mg, 270.18 μmol, 1 eq) at 25° C. The mixture was stirred at 25° C. for 1 hr. LCMS showed that desired MS was found. The reaction mixture was concentrated under reduced pressure to give a residue. The residue was purified by pre-HPLC (Column: WePure Biotech XPT PHS C18 150*25*7 um; mobile phase: [$H_2O$ (0.225% FA)-ACN]; gradient: 14%-44% B over 10.0 min). The pure fractions were collected and the volatiles were removed under vacuum. The residue was partitioned between acetonitrile (20 mL) and water (100 mL). The solution was lyophilized to dryness to give [(3S)-1-methyl-5-oxo-pyrrolidin-3-yl] 4-[3-(2-tetrahydrofuran-3-yloxy-3-pyridyl)pyrazolo[1,5-a]pyrimidin-5-yl]piperazine-1-carboxylate (I-119, 31.34 mg, 60.98 μmol, 69.04% yield, 98.754% purity) as a gum.

LCMS m/z=507.8 $[M+H]^+$.

SFC $t_R$=1.501 min, 1.892 min; 49.54%, 50.45%.

$^1H$ NMR (400 MHz, DMSO-$d_6$): 8.84-8.79 (m, 1H), 8.76 (d, J=7.6 Hz, 1H), 8.47 (s, 1H), 8.02-7.92 (m, 1H), 7.13-7.03 (m, 1H), 6.82 (d, J=7.6 Hz, 1H), 5.79-5.58 (m, 1H), 5.20-5.12 (m, 1H), 4.01-3.95 (m, 1H), 3.94-3.89 (m, 1H), 3.89-3.85 (m, 1H), 3.85-3.81 (m, 1H), 3.81-3.74 (m, 4H), 3.74-3.69 (m, 1H), 3.62-3.46 (m, 4H), 3.38-3.35 (m, 1H), 2.78-2.75 (m, 0.4H), 2.74 (s, 3H), 2.70 (m, 0.5H), 2.35-2.22 (m, 2H), 2.18-2.08 (m, 1H).

Example 94: Synthesis of Compound I-120

Ethyl 6-fluoro-5,7-dihydroxy-pyrazolo[1,5-a]pyrimidine-3-carboxylate

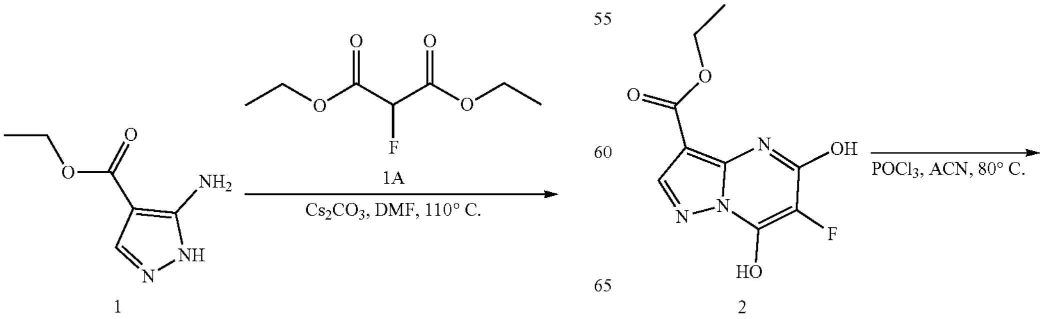

-continued

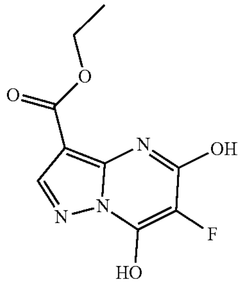

2

To a solution of ethyl 3-amino-1H-pyrazole-4-carboxylate (10 g, 64.45 mmol, 1 eq) in DMF (30 mL) was added $Cs_2CO_3$ (31.50 g, 96.68 mmol, 1.5 eq) and diethyl 2-fluoropropanedioate (17.22 g, 96.68 mmol, 1.5 eq), the mixture was stirred at 110° C. for 12 hr. LCMS showed the starting material was consumed completely and desired compound was detected. The mixture was diluted with water (150 mL), acidified to pH=5 by 5 M HCl aqueous solution and then lots of solid was formed. The mixture was filtered, the filter cake was washed with MeOH (10 mL×2) and dried in vacuum to give ethyl 6-fluoro-5,7-dihydroxy-pyrazolo[1,5-a]pyrimidine-3-carboxylate (8.1 g, 33.31 mmol, 51.68% yield, 99.180% purity) as a solid.

LCMS m/z=242.1 $[M+H]^+$.

Ethyl 5,7-dichloro-6-fluoro-pyrazolo[1,5-a]pyrimidine-3-carboxylate

-continued

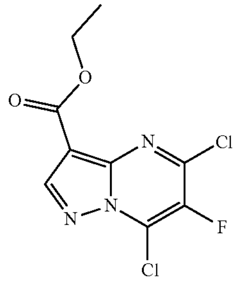

3

A mixture of ethyl 6-fluoro-5,7-dihydroxy-pyrazolo[1,5-a]pyrimidine-3-carboxylate (8 g, 33.17 mmol, 1 eq) and $POCl_3$ (15.26 g, 99.51 mmol, 9.28 mL, 3 eq) in ACN (50 mL) was degassed and purged with $N_2$ for 3 times, and then the mixture was stirred at 80° C. for 12 hr under $N_2$ atmosphere. LCMS indicated reactant was consumed completely. The reaction mixture was concentrated under reduced pressure to give a residue. The residue was quenched by addition of $H_2O$ (50 mL) at 0° C. Then the mixture was diluted with $H_2O$ (80 mL) and extracted with EtOAc (50 mL×3). The combined organic layers were washed with 1 N NaOH (30 mL×2), dried over $Na_2SO_4$, filtered and concentrated to a residue. The residue was purified by column chromatography ($SiO_2$, Petroleum ether/Ethyl acetate=1/0 to 5/1) to give ethyl 5,7-dichloro-6-fluoro-pyrazolo[1,5-a]pyrimidine-3-carboxylate (3.8 g, 8.05 mmol, 24.26% yield, 58.887% purity) as a solid.

LCMS m/z=277.9 $[M+H]^+$.

Ethyl 5-chloro-6-fluoro-pyrazolo[1,5-a]pyrimidine-3-carboxylate

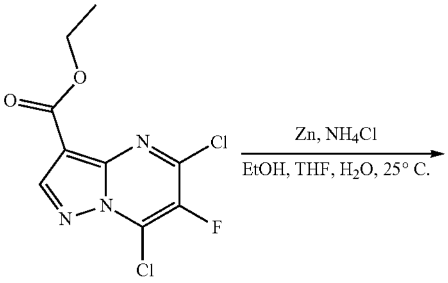

3

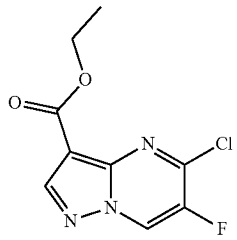

4

To a solution of ethyl 5,7-dichloro-6-fluoro-pyrazolo[1,5-a]pyrimidine-3-carboxylate (3.8 g, 13.67 mmol, 1 eq) in EtOH (18 mL), THF (6 mL) and $H_2O$ (12 mL) was added Zn (1.32 g, 20.19 mmol, 1.48 eq) and $NH_4Cl$ (1.10 g, 20.50 mmol, 1.5 eq) under $N_2$ atmosphere, then the mixture was degassed and purged with $N_2$ for 3 times. The mixture was stirred at 25° C. for 1 hr under $N_2$ atmosphere. LCMS showed reactant was consumed completely. The reaction mixture was filtered through celite and the filter cake was washed with DCM (20 mL). The filtrate was concentrated under reduced pressure to give a residue. The residue was purified by column chromatography ($SiO_2$, Petroleum ether/Ethyl acetate=1/0 to 3/1) to give ethyl 5-chloro-6-fluoro-pyrazolo[1,5-a]pyrimidine-3-carboxylate (2.1 g, 7.51 mmol, 54.93% yield, 87.085% purity) as a solid.

LCMS m/z=244.0 $[M+H]^+$.

$^1H$ NMR (400 MHz, DMSO-$d_6$) δ=9.90 (d, J=4.4 Hz, 1H), 8.67 (s, 1H), 4.47-4.14 (m, 2H), 1.45-1.20 (m, 3H).

Ethyl 5-(4-tert-butoxycarbonylpiperazin-1-yl)-6-fluoro-pyrazolo[1,5-a]pyrimidine-3-carboxylate

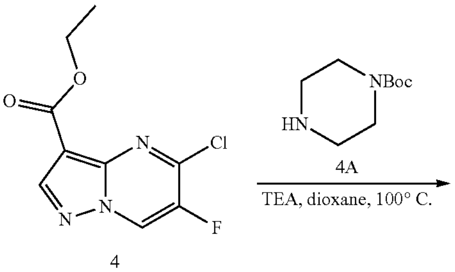

4

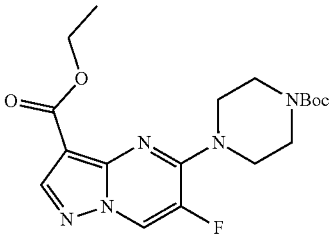

5

A mixture of ethyl 5-chloro-6-fluoro-pyrazolo[1,5-a]pyrimidine-3-carboxylate (2.1 g, 8.62 mmol, 1 eq), tert-butyl piperazine-1-carboxylate (4.82 g, 25.86 mmol, 3 eq), TEA (2.62 g, 25.86 mmol, 3.60 mL, 3 eq) in dioxane (30 mL) was degassed and purged with $N_2$ for 3 times, and then the mixture was stirred at 100° C. for 12 hr under $N_2$ atmosphere. LCMS showed reactant 4 was consumed completely. The reaction mixture was concentrated under reduced pressure to give a residue. The residue was purified by column chromatography ($SiO_2$, Petroleum ether/Ethyl acetate=1/0 to 3/1) to give ethyl 5-(4-tert-butoxycarbonylpiperazin-1-yl)-6-fluoro-pyrazolo[1,5-a]pyrimidine-3-carboxylate (2.9 g, 5.31 mmol, 61.57% yield, 72% purity) as a solid.

LCMS m/z=394.3 $[M+H]^+$.

5-(4-tert-butoxycarbonylpiperazin-1-yl)-6-fluoro-pyrazolo[1,5-a]pyrimidine-3-carboxylic acid

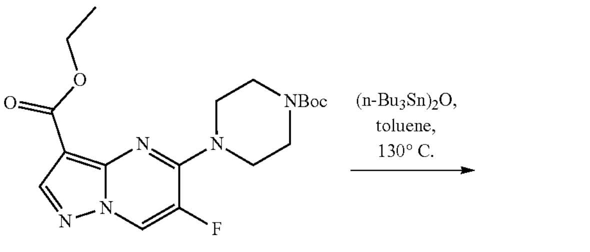

5

6

A mixture of ethyl 5-(4-tert-butoxycarbonylpiperazin-1-yl)-6-fluoro-pyrazolo[1,5-a]pyrimidine-3-carboxylate (2.48 g, 6.30 mmol, 1 eq) and bis(tributyltin) oxide (7.930 g, 13.30 mmol, 6.76 mL, 2.11 eq) in toluene (10 mL) was degassed and purged with $N_2$ for 3 times, and then the mixture was stirred at 130° C. for 12 hr under $N_2$ atmosphere. LCMS indicated reactant 5 was consumed completely. The reaction mixture was quenched by addition of saturated KF aqueous (20 mL) at 0° C., diluted with EtOAc (50 mL), basified with saturated $NaHCO_3$ aqueous to PH=8, and extracted with EtOAc (30 mL×3). The combined organic layers were concentrated under reduced pressure to give a residue. The residue was purified by column chromatography ($SiO_2$, Petroleum ether/Ethyl acetate=1/0 to 0/1) to give 5-(4-tert-butoxycarbonylpiperazin-1-yl)-6-fluoro-pyrazolo[1,5-a]pyrimidine-3-carboxylic acid (1.56 g, 3.80 mmol, 60.28% yield, 88.998% purity) as a solid.

LCMS m/z=366.1 [M+H]$^+$.

tert-butyl-4-(6-fluoro-3-iodo-pyrazolo[1,5-a]pyrimidin-5-yl)piperazine-1-carboxylate

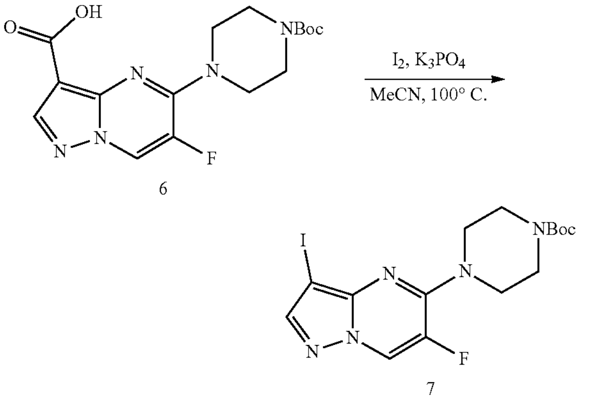

6

7

A mixture of 5-(4-tert-butoxycarbonylpiperazin-1-yl)-6-fluoro-pyrazolo[1,5-a]pyrimidine-3-carboxylic acid (1.56 g, 4.27 mmol, 1 eq), $I_2$ (1.08 g, 4.27 mmol, 860.08 µL, 1 eq) and $K_3PO_4$ (1.81 g, 8.54 mmol, 2 eq) in ACN (20 mL) was degassed and purged with $N_2$ for 3 times, and then the mixture was stirred at 100° C. for 1 hr under $N_2$ atmosphere. LCMS showed reactant 6 was consumed completely. The reaction mixture was filtered and concentrated under reduced pressure to give a residue. The residue was purified by column chromatography ($SiO_2$, Petroleum ether/Ethyl acetate=1/0 to 5/1) to give tert-butyl 4-(6-fluoro-3-iodo-pyrazolo[1,5-a]pyrimidin-5-yl)piperazine-1-carboxylate (1.5 g, 3.09 mmol, 72.37% yield, 92.137% purity) as an oil.

LCMS m/z=448.0 [M+H]$^+$.

$^1$H NMR (400 MHz, DMSO-$d_6$) δ=9.50-9.08 (m, 1H), 7.99 (s, 1H), 3.73-3.55 (m, 4H), 3.54-3.47 (m, 4H), 1.42 (s, 9H).

tert-butyl-4-[6-fluoro-3-(2-tetrahydrofuran-3-yloxy-3-pyridyl)pyrazolo[1,5-a]pyrimidin-5-yl]piperazine-1-carboxylate

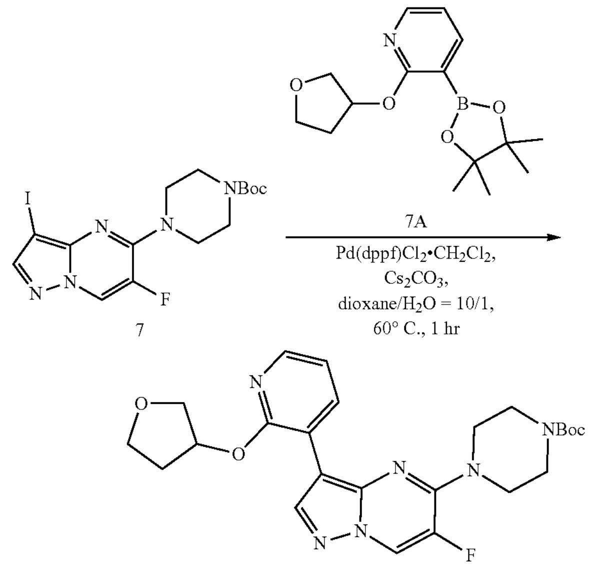

7

8

A mixture of tert-butyl 4-(6-fluoro-3-iodo-pyrazolo[1,5-a]pyrimidin-5-yl)piperazine-1-carboxylate (200 mg, 447.18 µmol, 1 eq), 2-tetrahydrofuran-3-yloxy-3-(4,4,5,5-tetramethyl-1,3,2-dioxaborolan-2-yl)pyridine (300 mg, 1.03 mmol, 2.30 eq), $Cs_2CO_3$ (291.40 mg, 894.36 µmol, 2 eq) and Pd(dppf)$Cl_2$·$CH_2Cl_2$ (36.52 mg, 44.72 µmol, 0.1 eq) in dioxane (2 mL) and $H_2O$ (0.2 mL) was degassed and purged with $N_2$ for 3 times, and then the mixture was stirred at 60° C. for 1 hr under $N_2$ atmosphere. LCMS showed Reactant 1 was consumed completely. The reaction mixture was filtered and concentrated under reduced pressure to give a residue. The residue was purified by column chromatography ($SiO_2$, Petroleum ether/Ethyl acetate=1/0 to 0/1). Compound tert-butyl 4-[6-fluoro-3-(2-tetrahydrofuran-3-yloxy-3-pyridyl)pyrazolo[1,5-a]pyrimidin-5-yl]piperazine-1-carboxylate (170 mg, 320.26 µmol, 71.62% yield, 91.279% purity) was obtained as an oil.

LCMS m/z=485.3 [M+H]$^+$.

6-fluoro-5-piperazin-1-yl-3-(2-tetrahydrofuran-3-yloxy-3-pyridyl)pyrazolo[1,5-a]pyrimidine

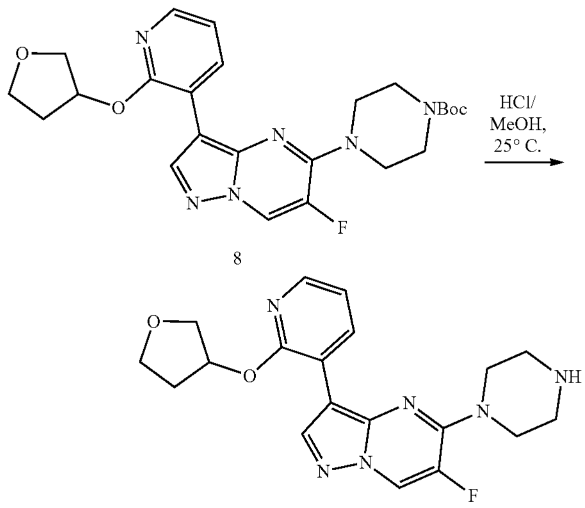

8

9

To a solution of tert-butyl 4-[6-fluoro-3-(2-tetrahydrofuran-3-yloxy-3-pyridyl)pyrazolo[1,5-a]pyrimidin-5-yl]piperazine-1-carboxylate (170 mg, 350.86 μmol, 1 eq) in MeOH (2 mL) was added HCl/MeOH (2 M, 3.51 mL, 20 eq). The mixture was stirred at 25° C. for 30 min. TLC indicated Reactant 8 was consumed completely. The reaction mixture was concentrated under reduced pressure to give 6-fluoro-5-piperazin-1-yl-3-(2-tetrahydrofuran-3-yloxy-3-pyridyl)pyrazolo[1,5-a]pyrimidine hydrochloride (170 mg, crude, hydrochloride) as an oil.

LCMS m/z=385.2 $[M+H]^+$.

[(3S)-1-methyl-5-oxo-pyrrolidin-3-yl] 4-[6-fluoro-3-(2-tetrahydrofuran-3-yloxy-3-pyridyl)pyrazolo[1,5-a]pyrimidin-5-yl]piperazine-1-carboxylate

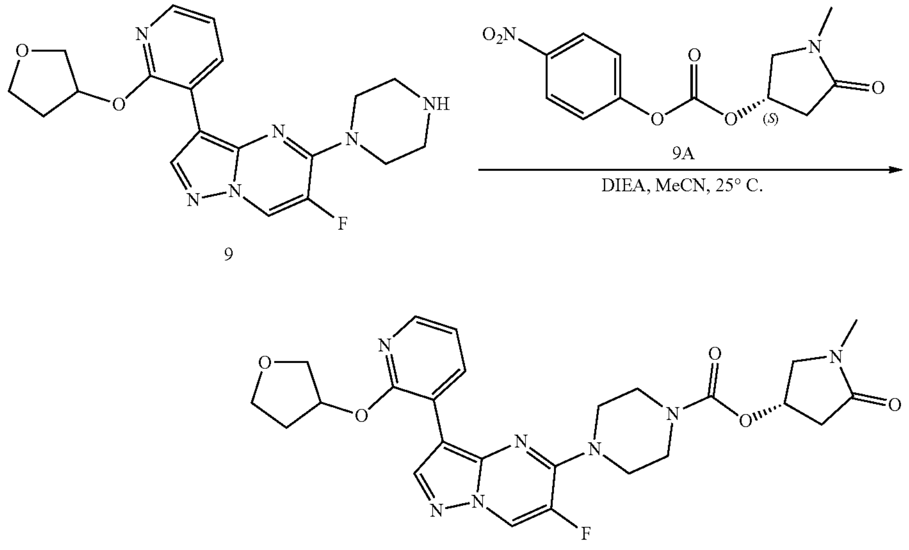

9

I-120

A mixture of 6-fluoro-5-piperazin-1-yl-3-(2-tetrahydrofuran-3-yloxy-3-pyridyl)pyrazolo[1,5-a]pyrimidine hydrochloride (170 mg, 403.93 μmol, 1 eq), [(3S)-1-methyl-5-oxo-pyrrolidin-3-yl](4-nitrophenyl) carbonate (147.15 mg, 525.11 μmol, 1.3 eq), DIEA (156.61 mg, 1.21 mmol, 211.07 μL, 3 eq) in ACN (3 mL) was degassed and purged with $N_2$ for 3 times, and then the mixture was stirred at 25° C. for 1 hr under $N_2$ atmosphere. LCMS showed Reactant 9 was consumed completely. The reaction mixture was concentrated under reduced pressure to give a residue. The residue was purified by prep-HPLC (column: Waters Xbridge BEH C18 100*25 mm*10 um; mobile phase: [$H_2O$ (0.05% $NH_3H_2O$)-ACN]; gradient: 21%-51% B over 10.0 min) to give [(3S)-1-methyl-5-oxo-pyrrolidin-3-yl] 4-[6-fluoro-3-(2-tetrahydrofuran-3-yloxy-3-pyridyl)pyrazolo[1,5-a]pyrimidin-5-yl]piperazine-1-carboxylate (I-120, 45.99 mg, 86.58 μmol, 21.44% yield, 98.94% purity) as a solid.

LCMS m/z=526.2 $[M+H]^+$.

SFC $t_{R1}$=1.390 min, 42.36%, $t_{R2}$=1.693 min; 57.64%.

$^1$H NMR (400 MHz, DMSO-$d_6$) δ=9.29-9.23 (m, 1H), 8.76-8.69 (m, 1H), 8.49 (s, 1H), 8.01-7.95 (m, 1H), 7.18-7.00 (m, 1H), 5.70-5.63 (m, 1H), 5.19-5.12 (m, 1H), 3.99-3.92 (m, 1H), 3.91-3.84 (m, 2H), 3.83-3.77 (m, 1H), 3.75-3.66 (m, 5H), 3.60-3.53 (m, 4H), 3.38-3.33 (m, 1H), 2.76-2.68 (m, 4H), 2.31-2.22 (m, 2H), 2.17-2.07 (m, 1H).

Example 95: Synthesis of Compound I-121

3-bromo-2-(cyclopentoxy)pyridine

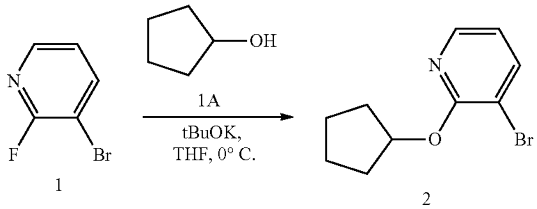

1

2

To a solution of 3-bromo-2-fluoro-pyridine (5 g, 28.41 mmol, 1 eq) and cyclopentanol (2.94 g, 34.09 mmol, 3.09 mL, 1.2 eq) in THF (10 mL) was added tBuOK (1 M, 56.82 mL, 2 eq), the mixture was stirred at 0° C. for 2 hr. TLC showed Reactant 1 was consumed completely. The reaction mixture was concentrated under reduced pressure to a residue. The residue was diluted with $H_2O$ (100 mL) and extracted with EtOAc (100 mL×3). The combined organic layers were dried over $Na_2SO_4$, filtered and concentrated under reduced pressure to give 3-bromo-2-(cyclopentoxy) pyridine (6.6 g, 27.26 mmol, 95.95% yield) as a solid.

$^1$H NMR (400 MHz, CHLOROFORM-d) 8=8.18-7.99 (m, 1H), 7.94-7.63 (m, 1H), 6.78-6.63 (m, 1H), 5.61-5.29 (m, 1H), 2.03-1.75 (m, 6H), 1.68-1.59 (m, 2H).

2-(cyclopentoxy)-3-(4,4,5,5-tetramethyl-1,3,2-dioxaborolan-2-yl)pyridine

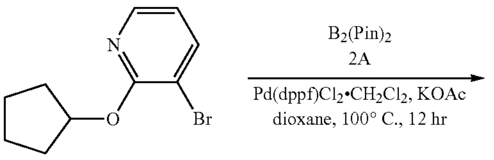

2

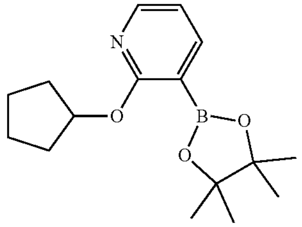

3

A mixture of 3-bromo-2-(cyclopentoxy)pyridine (3 g, 12.39 mmol, 1 eq), $B_2Pin_2$ (4.72 g, 18.59 mmol, 1.5 eq), KOAc (2.43 g, 24.78 mmol, 2 eq) and Pd(dppf)$Cl_2$ (453.33 mg, 619.55 μmol, 0.05 eq) in dioxane (30 mL) was degassed and purged with $N_2$ for 3 times, then the mixture was stirred at 100° C. for 12 hr under $N_2$ atmosphere. TLC showed Reactant 2 was consumed completely. The reaction mixture was concentrated under reduced pressure to give a residue. The residue was purified by column chromatography ($SiO_2$, Petroleum ether/Ethyl acetate=1/0 to 15/1) to give 2-(cyclopentoxy)-3-(4,4,5,5-tetramethyl-1,3,2-dioxaborolan-2-yl) pyridine (3 g, 10.37 mmol, 83.72% yield) as an oil.

LCMS m/z=290.1 $[M+H]^+$.

$^1$H NMR (400 MHz, DMSO-$d_6$) ¿=8.29-8.14 (m, 1H), 7.85-7.70 (m, 1H), 6.97-6.84 (m, 1H), 5.47-5.29 (m, 1H), 1.82-1.65 (m, 6H), 1.61-1.53 (m, 2H), 1.26 (s, 12H).

tert-butyl 4-[3-[2-(cyclopentoxy)-3-pyridyl]-6-fluoro-pyrazolo[1,5-a]pyrimidin-5-yl]piperazine-1-carboxylate

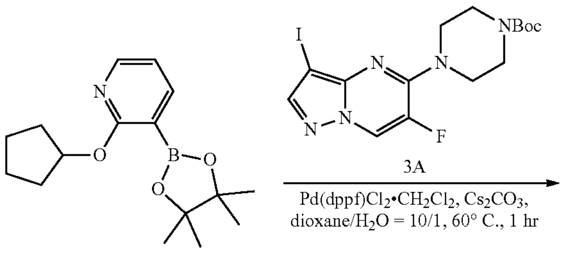

3

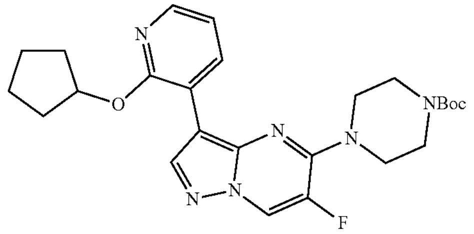

4

A mixture of 2-(cyclopentoxy)-3-(4,4,5,5-tetramethyl-1,3,2-dioxaborolan-2-yl)pyridine (200 mg, 691.62 μmol, 1.55 eq), tert-butyl 4-(6-fluoro-3-iodo-pyrazolo[1,5-a]pyrimidin-5-yl)piperazine-1-carboxylate (200 mg, 447.18 μmol, 1 eq), $Cs_2CO_3$ (291.40 mg, 894.36 μmol, 2 eq) and Pd(dppf)$Cl_2$ (32.72 mg, 44.72 μmol, 0.1 eq) in dioxane (2 mL) and $H_2O$ (0.2 mL) was degassed and purged with $N_2$ for 3 times, then the mixture was stirred at 60° C. for 1 hr under $N_2$ atmosphere. LCMS showed desired compound was detected. The reaction mixture was filtered and concentrated under reduced pressure to give a residue. The residue was purified by column chromatography ($SiO_2$, Petroleum ether/Ethyl acetate=1/0 to 3/1) to give tert-butyl 4-[3-[2-(cyclopentoxy)-3-pyridyl]-6-fluoro-pyrazolo[1,5-a]pyrimidin-5-yl]piperazine-1-carboxylate (90 mg, 170.22 μmol, 38.06% yield, 91.266% purity) as a yellow oil.

LCMS m/z=483.3 $[M+H]^+$.

3-[2-(cyclopentoxy)-3-pyridyl]-6-fluoro-5-piperazin-1-yl-pyrazolo[1,5-a]pyrimidine

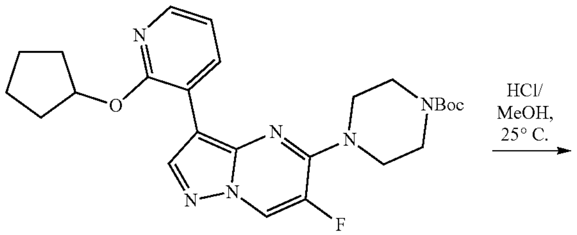

4

-continued

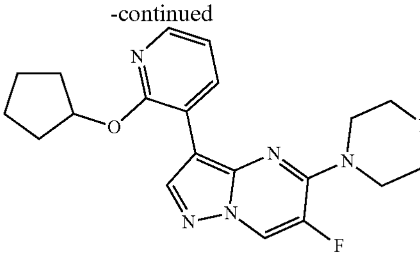

5

A mixture of tert-butyl 4-[3-[2-(cyclopentoxy)-3-pyridyl]-6-fluoro-pyrazolo[1,5-a]pyrimidin-5-yl]piperazine-1-carboxylate (90 mg, 186.51 μmol, 1 eq) and HCl/MeOH (2 M, 1.87 mL, 20 eq) in MeOH (2 mL) was degassed and purged with $N_2$ for 3 times, then the mixture was stirred at 25° C. for 1 hr under $N_2$ atmosphere. TLC indicated Reactant 4 was consumed completely. The reaction mixture was concentrated under reduced pressure to give 3-[2-(cyclopentoxy)-3-pyridyl]-6-fluoro-5-piperazin-1-yl-pyrazolo[1,5-a]pyrimidine hydrochloride (100 mg, crude, hydrochloride) as an oil.

LCMS m/z=383.2 $[M+H]^+$.

[(3S)-1-methyl-5-oxo-pyrrolidin-3-yl]-4-[3-[2-(cyclopentoxy)-3-pyridyl]-6-fluoro-pyrazolo[1,5-a]pyrimidin-5-yl]piperazine-1-carboxylate

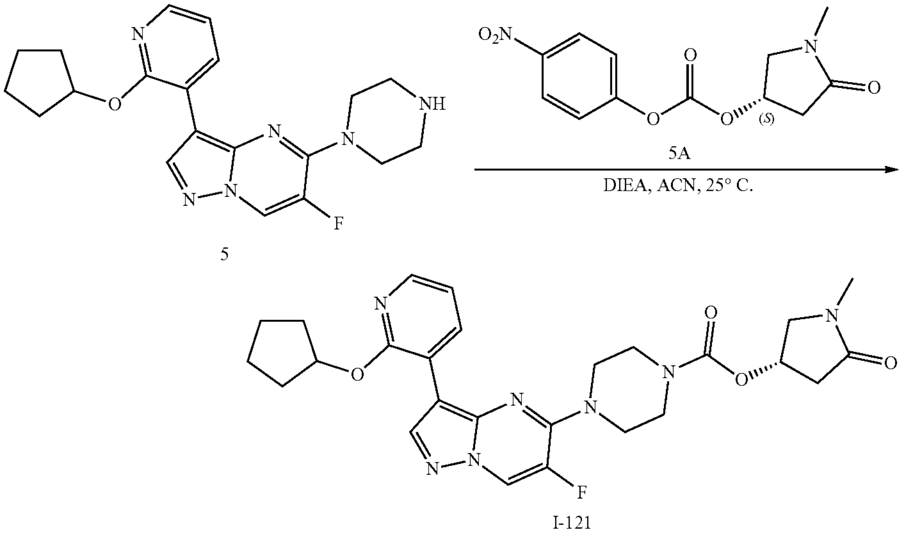

5

I-121

A mixture of [(3S)-1-methyl-5-oxo-pyrrolidin-3-yl](4-nitrophenyl) carbonate (100.35 mg, 358.09 μmol, 1.5 eq), 3-[2-(cyclopentoxy)-3-pyridyl]-6-fluoro-5-piperazin-1-yl-pyrazolo[1,5-a]pyrimidine hydrochloride (100 mg, 238.72 μmol, 1 eq) and DIEA (92.56 mg, 716.17 μmol, 124.74 μL, 3 eq) in ACN (3 mL) was degassed and purged with $N_2$ for 3 times, then the mixture was stirred at 25° C. for 1 hr under $N_2$ atmosphere. LCMS showed Reactant 5 was consumed completely, the reaction mixture was concentrated under reduced pressure to give a residue. The residue was purified by prep-HPLC (column: Waters Xbridge BEH C18 100*25 mm*10 um; mobile phase: [$H_2O$ (0.05% $NH_3H_2O$)-ACN]; gradient: 37%-67% B over 10.0 min). The pure fractions were lyophilized to dryness to give [(3S)-1-methyl-5-oxo-pyrrolidin-3-yl] 4-[3-[2-(cyclopentoxy)-3-pyridyl]-6-fluoro-pyrazolo[1,5-a]pyrimidin-5-yl]piperazine-1-carboxylate (I-121, 34.40 mg, 65.51 μmol, 27.44% yield, 99.70% purity) as a solid.

LCMS m/z=524.2 $[M+H]^+$.

SFC $t_R$=1.425 min, 100%.

$^1H$ NMR (400 MHz, DMSO-$d_6$) δ=9.28-9.22 (m, 1H), 8.75-8.69 (m, 1H), 8.49 (s, 1H), 8.03-7.95 (m, 1H), 7.09-7.01 (m, 1H), 5.59-5.52 (m, 1H), 5.19-5.10 (m, 1H), 3.76-3.68 (m, 5H), 3.61-3.52 (m, 4H), 3.39-3.35 (m, 1H), 2.77-2.69 (m, 4H), 2.32-2.25 (m, 1H), 2.03-1.91 (m, 2H), 1.87-1.73 (m, 4H), 1.69-1.60 (m, 2H).

Example 96: Synthesis of Compound I-122

3-bromo-2-tetrahydropyran-4-yloxy-pyridine

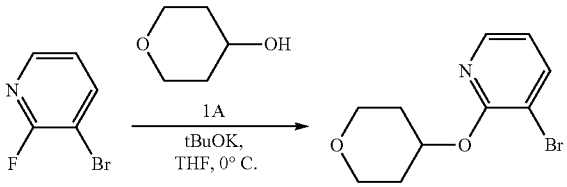

1

2

A mixture of 3-bromo-2-fluoro-pyridine (3 g, 17.05 mmol, 1 eq), tetrahydropyran-4-ol (1.74 g, 17.05 mmol, 1.70 mL, 1 eq) and tBuOK (1 M, 25.57 mL, 1.5 eq) in THF (20 mL) was degassed and purged with $N_2$ for 3 times, and then the mixture was stirred at 0° C. for 1 hr under $N_2$ atmosphere. LCMS showed Reactant 1 was consumed completely, the reaction mixture was concentrated under reduced pressure to a residue. The residue was diluted with $H_2O$ (100 mL) and extracted with EtOAc (100 mL×3). The combined organic layers were dried over $Na_2SO_4$, filtered and concentrated under reduced pressure to give 3-bromo-2-tetrahydropyran-4-yloxy-pyridine (3.7 g, 14.33 mmol, 84.09% yield) as an oil.

LCMS m/z=258.2 $[M+H]^+$).

2-(tetrahydropyran-4-yloxy)-3-(4,4,5,5-tetramethyl-1,3,2-dioxaborolan-2-yl)pyridine

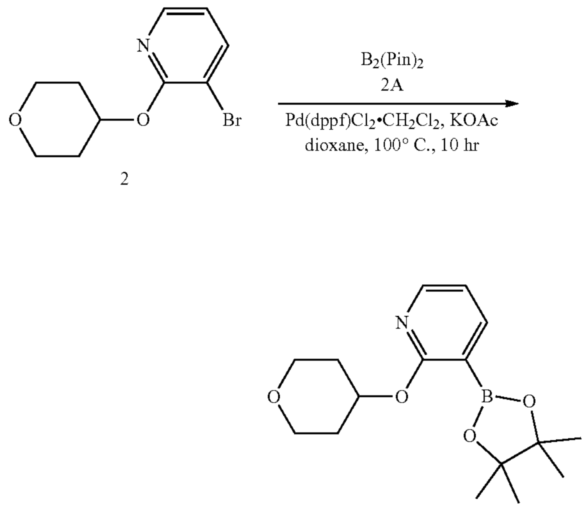

2

3

A mixture of 3-bromo-2-tetrahydropyran-4-yloxy-pyridine (2 g, 7.75 mmol, 1 eq), $B_2Pin_2$ (2.95 g, 11.62 mmol, 1.5 eq), KOAc (1.52 g, 15.50 mmol, 2 eq) and Pd(dppf)$Cl_2$·$CH_2Cl_2$ (316.39 mg, 387.43 μmol, 0.05 eq) in dioxane (30 mL) was degassed and purged with $N_2$ for 3 times, and then the mixture was stirred at 100° C. for 10 hr under $N_2$ atmosphere. LCMS showed Reactant 2 was consumed completely. The reaction mixture was filtered and concentrated under reduced pressure to give a residue. The residue was purified by column chromatography ($SiO_2$, Petroleum ether/Ethyl acetate=1/0 to 10/1) to give 2-tetrahydropyran-4-yloxy-3-(4,4,5,5-tetramethyl-1,3,2-dioxaborolan-2-yl)pyridine (2.1 g, 2.34 mmol, 30.19% yield, 34% purity) as an oil.

LCMS m/z=306.2 $[M+H]^+$).

$^1H$ NMR (400 MHz, DMSO-$d_6$) δ=8.25-8.19 (m, 1H), 7.90-7.83 (m, 1H), 6.96-6.91 (m, 1H), 5.33-5.24 (m, 1H), 3.90-3.81 (m, 2H), 3.59-3.47 (m, 2H), 1.99-1.86 (m, 2H), 1.68-1.58 (m, 2H), 1.30 (s, 9H), 1.17 (s, 3H).

tert-butyl4-[6-fluoro-3-(2-tetrahydropyran-4-yloxy-3-pyridyl)pyrazolo[1,5-a]pyrimidin-5-yl]piperazine-1-carboxylate

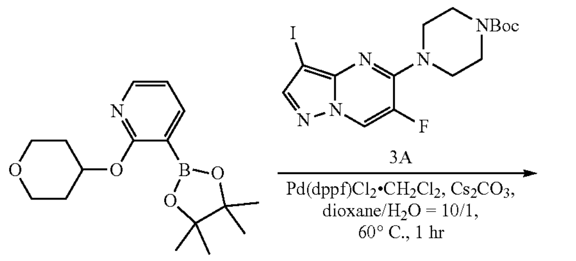

3A

3

-continued

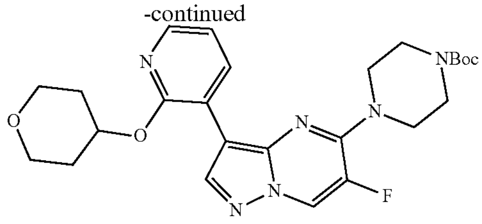

4

A mixture of 2-tetrahydropyran-4-yloxy-3-(4,4,5,5-tetramethyl-1,3,2-dioxaborolan-2-yl)pyridine (300 mg, 983.04 μmol, 2.20 eq), tert-butyl 4-(6-fluoro-3-iodo-pyrazolo[1,5-a]pyrimidin-5-yl)piperazine-1-carboxylate (200 mg, 447.18 μmol, 1 eq), $Cs_2CO_3$ (291.40 mg, 894.36 μmol, 2 eq) and Pd(dppf)$Cl_2$·$CH_2Cl_2$ (36.52 mg, 44.72 μmol, 0.1 eq) in dioxane (2 mL) and $H_2O$ (0.2 mL) was degassed and purged with $N_2$ for 3 times, and then the mixture was stirred at 60° C. for 1 hr under $N_2$ atmosphere. LCMS showed desired compound was detected. The reaction mixture was filtered and concentrated under reduced pressure to give a residue. The residue was purified by column chromatography ($SiO_2$, Petroleum ether/Ethyl acetate=1/0 to 0/1) to give tert-butyl 4-[6-fluoro-3-(2-tetrahydropyran-4-yloxy-3-pyridyl)pyrazolo[1,5-a]pyrimidin-5-yl]piperazine-1-carboxylate (170 mg, 302.04 μmol, 67.54% yield, 88.577% purity) as an oil.

LCMS m/z=499.4 $[M+H]^+$).

6-fluoro-5-piperazin-1-yl-3-(2-tetrahydropyran-4-yloxy-3-pyridyl)pyrazolo[1,5-a]pyrimidine

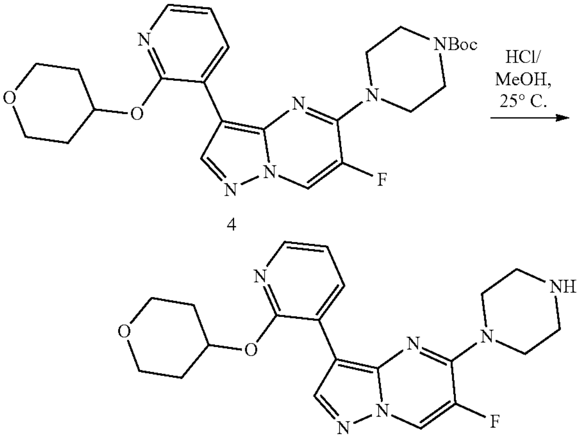

4

5

A mixture of tert-butyl 4-[6-fluoro-3-(2-tetrahydropyran-4-yloxy-3-pyridyl)pyrazolo[1,5-a]pyrimidin-5-yl]piperazine-1-carboxylate (170 mg, 340.99 μmol, 1 eq) and HCl/MeOH (2 M, 3.41 mL, 20 eq) in MeOH (2 mL) was degassed and purged with $N_2$ for 3 times, and then the mixture was stirred at 25° C. for 30 min under $N_2$ atmosphere.

LCMS showed Reactant 4 was consumed completely. The reaction mixture was concentrated under reduced pressure to give 6-fluoro-5-piperazin-1-yl-3-(2-tetrahydropyran-4-yloxy-3-pyridyl)pyrazolo[1,5-a]pyrimidine hydrochloride (170 mg, crude, hydrochloride) as an oil.

LCMS m/z=399.2 $[M+H]^+$).

[(3S)-1-methyl-5-oxo-pyrrolidin-3-yl] 4-[6-fluoro-3-(2-tetrahydropyran-4-yloxy-3-pyridyl)pyrazolo[1,5-a]pyrimidin-5-yl]piperazine-1-carboxylate

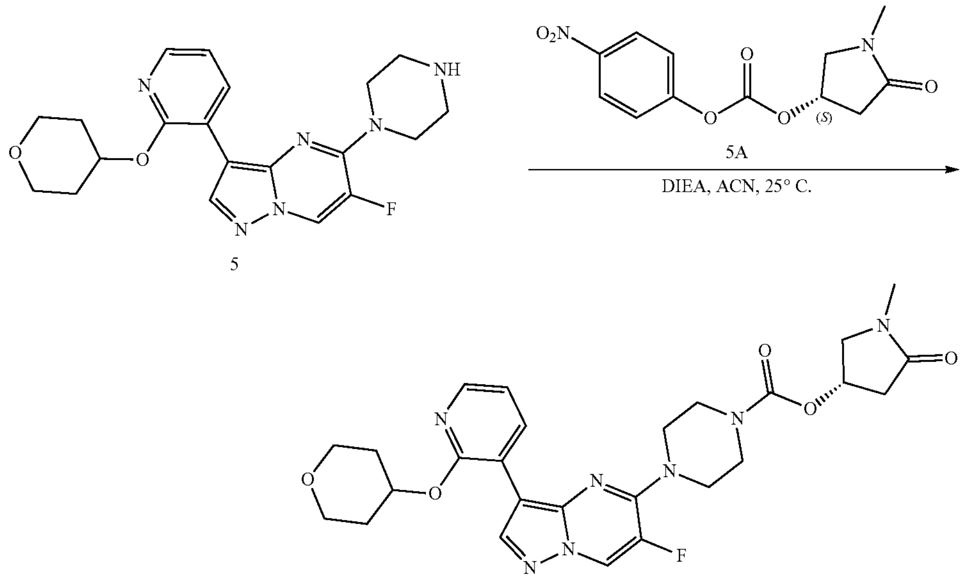

5

I-122

To a solution of 6-fluoro-5-piperazin-1-yl-3-(2-tetrahydropyran-4-yloxy-3-pyridyl)pyrazolo[1,5-a]pyrimidine hydrochloride (170 mg, 390.90 μmol, 1 eq) and [(3S)-1-methyl-5-oxo-pyrrolidin-3-yl](4-nitrophenyl) carbonate (142.41 mg, 508.17 μmol, 1.3 eq) in ACN (3 mL) was added DIEA (151.56 mg, 1.17 mmol, 204.26 μL, 3 eq). The mixture was stirred at 25° C. for 1 hr. LCMS showed Reactant 5 was consumed completely. The reaction mixture was concentrated under reduced pressure to give a residue. The residue was purified by prep-HPLC (column: WePure Biotech XPT C18 150*25*7 um; mobile phase: [$H_2O$ (10 mM $NH_4HCO_3$)-ACN]; gradient: 24%-54% B over 11.0 min). The pure fractions were lyophilized to dryness to give [(3S)-1-methyl-5-oxo-pyrrolidin-3-yl]-4-[6-fluoro-3-(2-tetrahydropyran-4-yloxy-3-pyridyl)pyrazolo[1,5-a]pyrimidin-5-yl]piperazine-1-carboxylate (I-122, 87.39 mg, 160.02 μmol, 40.94% yield, 98.80% purity) as a solid, LCMS m/z=540.1 $[M+H]^+$).

SFC $t_R$=1.519, 100%.

$^1$H NMR (400 MHz, DMSO-$d_6$) δ=9.30-9.22 (m, 1H), 8.75-8.68 (m, 1H), 8.58-8.51 (m, 1H), 8.03-7.95 (m, 1H), 7.12-7.03 (m, 1H), 5.41-5.32 (m, 1H), 5.20-5.11 (m, 1H), 3.93-3.82 (m, 2H), 3.79-3.66 (m, 5H), 3.64-3.50 (m, 6H), 3.39-3.34 (m, 1H), 2.74 (s, 3H), 2.73-2.65 (m, 1H), 2.37-2.22 (m, 1H), 2.15-2.01 (m, 2H), 1.82-1.67 (m, 2H).

Example 97: Synthesis of Compound I-123

3-bromo-2-(cyclohexoxy)pyridine

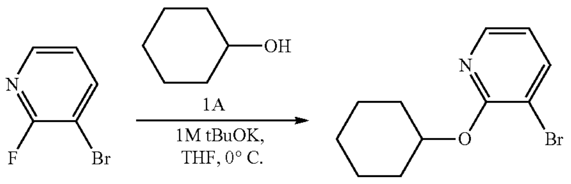

1

2

To a mixture of cyclohexanol (2.05 g, 20.46 mmol, 2.13 mL, 1.2 eq) and t-BuOK (1 M, 22.16 mL, 1.3 eq) in THF (30 mL) was added 3-bromo-2-fluoro-pyridine (3 g, 17.05 mmol, 1 eq) at 0° C. The mixture was stirred at 0° C. for 1 hr. TLC (Petroleum ether:Ethyl acetate=10:1, $R_f$=0.7) showed that the reaction was completed. The reaction mixture was concentrated under reduced pressure to give a residue. The residue was purified by FCC (ISCO®; 4 g SepaFlash® Silica Flash Column, Eluent of 0~2% Ethyl acetate/Petroleum ether gradient @ 25 mL/min) to give 3-bromo-2-(cyclohexoxy)pyridine (3.9 g, 15.23 mmol, 89.32% yield) as a liquid.

$^1$H NMR (400 MHz, DMSO-$d_6$) δ=8.13 (dd, J=1.7, 4.8 Hz, 1H), 7.99 (dd, J=1.6, 7.6 Hz, 1H), 6.90 (dd, J=4.9, 7.6 Hz, 1H), 5.13-4.98 (m, 1H), 1.88 (m, 2H), 1.80-1.63 (m, 2H), 1.61-1.47 (m, 3H), 1.44-1.28 (m, 3H).

2-(cyclohexoxy)-3-(4,4,5,5-tetramethyl-1,3,2-dioxaborolan-2-yl)pyridine

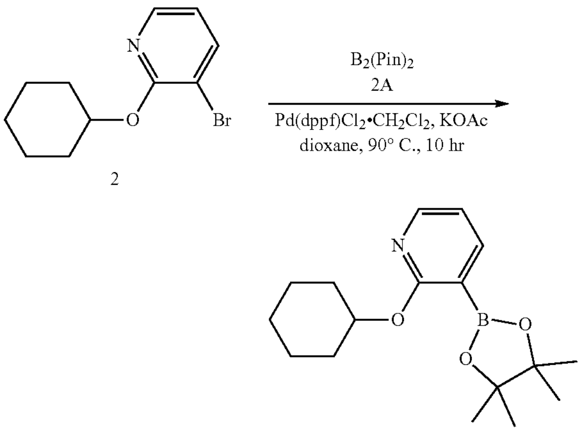

2

3

A mixture of 3-bromo-2-(cyclohexoxy)pyridine (3.9 g, 15.23 mmol, 1 eq), 4,4,5,5-tetramethyl-2-(4,4,5,5-tetramethyl-1,3,2-dioxaborolan-2-yl)-1,3,2-dioxaborolane (3.87 g, 15.23 mmol, 1 eq), KOAc (2.99 g, 30.45 mmol, 2 eq), $Pd(dppf)Cl_2 \cdot CH_2Cl_2$ (621.71 mg, 761.31 umol, 0.05 eq) in dioxane (40 mL) was degassed and purged with $N_2$ for 3 times, and then the mixture was stirred at 90° C. for 10 hr under $N_2$ atmosphere. LCMS showed that desired MS was found. The reaction mixture was concentrated under reduced pressure to give a residue. The residue was purified by FCC (ISCO®; 20 g SepaFlash® Silica Flash Column, Eluent of 0~2% Ethyl acetate/Petroleum ether gradient @ 25 mL/min) to give 2-(cyclohexoxy)-3-(4,4,5,5-tetramethyl-1,3,2-dioxaborolan-2-yl)pyridine (4 g, 8.64 mmol, 56.75% yield, 65.498% purity) as a liquid.

LCMS m/z=304.2 $[M+H]^+$).

$^1H$ NMR (400 MHz, CHLOROFORM-d) δ=8.06 (dd, J=1.8, 4.9 Hz, 1H), 7.78 (dd, J=1.7, 7.6 Hz, 1H), 6.72 (dd, J=4.8, 7.6 Hz, 1H), 5.12 (t, J=3.9 Hz, 1H), 1.98-1.94 (m, 2H), 1.83 (m, 3H), 1.68-1.63 (m, 3H), 1.46 (m, 2H), 1.38-1.23 (m, 12H).

tert-butyl 4-[3-[2-(cyclohexoxy)-3-pyridyl]-6-fluoro-pyrazolo[1,5-a]pyrimidin-5-yl]piperazine-1-carboxylate

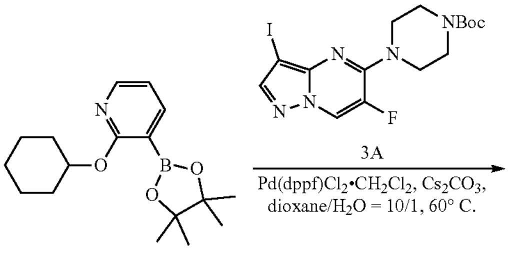

3

-continued

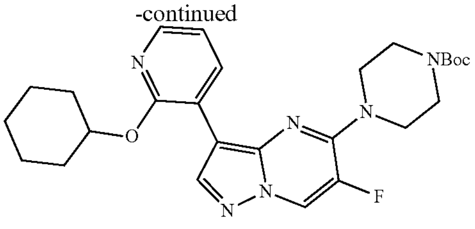

4

A mixture of tert-butyl 4-(6-fluoro-3-iodo-pyrazolo[1,5-a]pyrimidin-5-yl)piperazine-1-carboxylate (200 mg, 447.18 μmol, 1 eq), 2-(cyclohexoxy)-3-(4,4,5,5-tetramethyl-1,3,2-dioxaborolan-2-yl)pyridine (406.76 mg, 1.34 mmol, 3 eq), $Pd(dppf)Cl_2 \cdot CH_2Cl_2$ (73.04 mg, 89.44 μmol, 0.2 eq) and $Cs_2CO_3$ (291.40 mg, 894.36 μmol, 2 eq) in dioxane (4 mL) and $H_2O$ (0.4 mL) was degassed and purged with $N_2$ for 3 times, and then the mixture was stirred at 60° C. for 5 hr under $N_2$ atmosphere. LCMS showed that desired MS was found. The mixture was concentrated to the crude product. The crude was purified by flash silica gel chromatography (ISCO®; 12 g SepaFlash® Silica Flash Column, Eluent of 0~17% Ethyl acetate/Petroleum ether gradient @ 30 mL/min) to tert-butyl 4-[3-[2-(cyclohexoxy)-3-pyridyl]-6-fluoro-pyrazolo[1,5-a]pyrimidin-5-yl]piperazine-1-carboxylate (130 mg, 206.50 μmol, 46.18% yield, 78.879% purity) as a gum.

LCMS m/z=497.4 $[M+H]^+$).

3-[2-(cyclohexoxy)-3-pyridyl]-6-fluoro-5-piperazin-1-yl-pyrazolo[1,5-a]pyrimidine

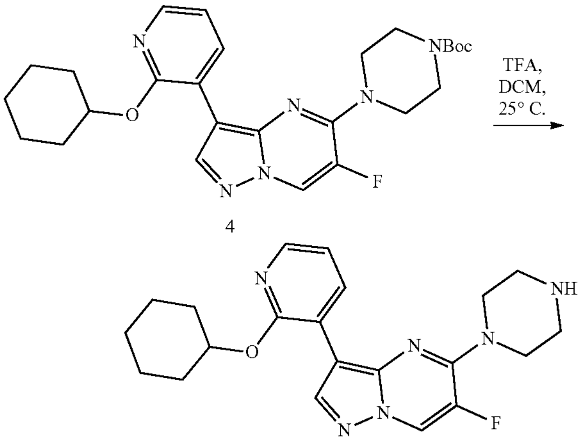

4

5

A mixture of tert-butyl 4-[3-[2-(cyclohexoxy)-3-pyridyl]-6-fluoro-pyrazolo[1,5-a]pyrimidin-5-yl]piperazine-1-carboxylate (130 mg, 206.50 μmol, 1 eq) in DCM (1.5 mL) was added TFA (0.5 mL) and the mixture was stirred at 25° C. for 0.5 hr. LCMS showed that desired MS was found. The mixture was concentrated to 3-[2-(cyclohexoxy)-3-pyridyl]-6-fluoro-5-piperazin-1-yl-pyrazolo[1,5-a]pyrimidine trifluoroacetate (120 mg, crude, trifluoroacetate) as a gum.

LCMS m/z=397.2 $[M+H]^+$).

[(3S)-1-methyl-5-oxo-pyrrolidin-3-yl]-4-[3-[2-(cyclohexoxy)-3-pyridyl]-6-fluoro-pyrazolo[1,5-a]pyrimidin-5-yl]piperazine-1-carboxylate

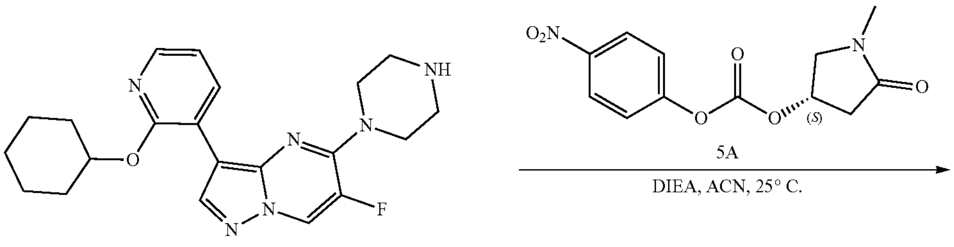

5

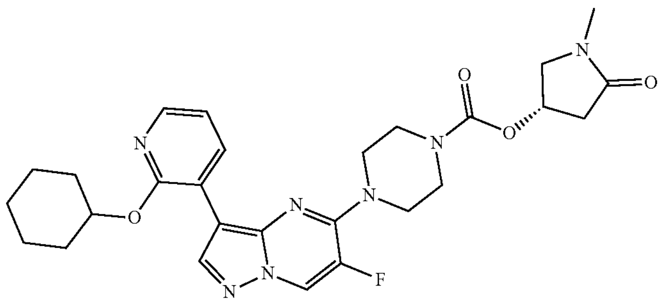

I-123

To a mixture of 3-[2-(cyclohexoxy)-3-pyridyl]-6-fluoro-5-piperazin-1-yl-pyrazolo[1,5-a]pyrimidine trifluoroacetate (120 mg, 235.07 μmol, 1 eq) and DIEA (91.14 mg, 705.21 μmol, 122.83 μL, 3 eq) in ACN (2 mL) was added [(3S)-1-methyl-5-oxo-pyrrolidin-3-yl] (4-nitrophenyl) carbonate (65.87 mg, 235.07 μmol, 1 eq) at 25° C. The mixture was stirred at 25° C. for 1 hr. LCMS showed that desired MS was found. The mixture was concentrated to the crude product. The crude was purified by prep-HPLC (column: Daisogel SP-100-8-ODS-PK 150*25*10 um; mobile phase: [$H_2O$ (10 mM $NH_4HCO_3$)-ACN]; gradient: 43%-73% B over 10.0 min). The pure fractions were lyophilized to dryness to give [(3S)-1-methyl-5-oxo-pyrrolidin-3-yl] 4-[3-[2-(cyclohexoxy)-3-pyridyl]-6-fluoro-pyrazolo[1,5-a]pyrimidin-5-yl]piperazine-1-carboxylate (I-123, 54.54 mg, 101.25 μmol, 43.07% yield, 99.80% purity) as a powder.

LCMS m/z=538.2 $[M+H]^+$).

SFC $t_R$=1.432, 100%.

$^1H$ NMR (400 MHz, DMSO-$d_6$): 9.26 (d, J=8.6 Hz, 1H), 8.76-8.67 (m, 1H), 8.55 (s, 1H), 8.09-7.86 (m, 1H), 7.14-6.99 (m, 1H), 5.27-5.10 (m, 2H), 3.79-3.66 (m, 5H), 3.63-3.53 (m, 4H), 3.39-3.37 (m, 1H), 2.77-2.75 (m, 0.4H), 2.74 (s, 3H), 2.70 (m, 0.5H), 2.32-2.24 (m, 1H), 2.08-1.94 (m, 2H), 1.79-1.68 (m, 2H), 1.66-1.50 (m, 3H), 1.49-1.29 (m, 3H).

Example 98: Synthesis of Compound I-124

Ethyl 5-[2-(tert-butoxycarbonylamino)ethylamino]-6-fluoro-pyrazolo[1,5-a]pyrimidine-3-carboxylate

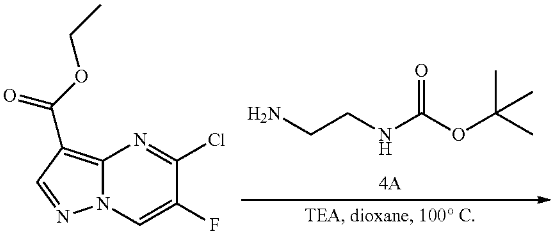

4

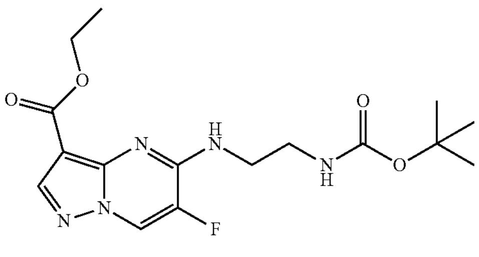

5

To a solution of ethyl 5-chloro-6-fluoro-pyrazolo[1,5-a]pyrimidine-3-carboxylate (1.8 g, 7.39 mmol, 1 eq) and tert-butyl N-(2-aminoethyl)carbamate (2.37 g, 14.78 mmol, 2.33 mL, 2 eq) in dioxane (10 mL) was added TEA (1.50 g, 14.78 mmol, 2.06 mL, 2 eq), the mixture was stirred at 100° C. for 12 hr. LCMS showed Reactant 4 was consumed completely. The reaction mixture was concentrated under reduced pressure to give a residue. The residue was purified by column chromatography ($SiO_2$, DCM:MeOH=1/0 to 10/1) to give ethyl 5-[2-(tert-butoxycarbonylamino)ethylamino]-6-fluoro-pyrazolo[1,5-a]pyrimidine-3-carboxylate (2.5 g, 6.10 mmol, 82.60% yield, 89.685% purity) as a solid.

LCMS m/z=368.1 $[M+H]^+$.

$^1H$ NMR (400 MHz, DMSO-$d_6$) δ=9.12-9.05 (m, 1H), 8.28-8.13 (m, 1H), 8.12-8.01 (m, 1H), 6.89 (s, 1H), 4.24-4.13 (m, 2H), 3.57-3.47 (m, 2H), 3.29-3.22 (m, 2H), 1.35 (s, 9H), 1.30-1.25 (m, 3H).

5-[2-(tert-butoxycarbonylamino)ethylamino]-6-fluoro-pyrazolo[1,5-a]pyrimidine-3-carboxylic acid

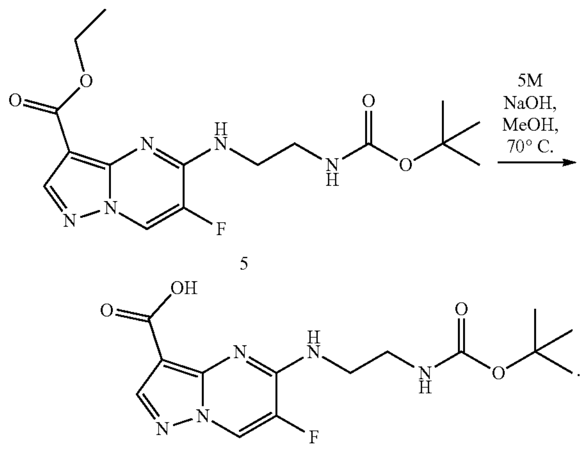

5

6

To a solution of ethyl 5-[2-(tert-butoxycarbonylamino)ethylamino]-6-fluoro-pyrazolo[1,5-a]pyrimidine-3-carboxylate (600 mg, 1.63 mmol, 1 eq) in MeOH (10 mL) was added NaOH (5 M, 2 mL, 6.12 eq). The mixture was stirred at 70° C. for 0.5 hr. LCMS showed that desired MS was found. The reaction solution was concentrated in vacuum to remove the solvent. The mixture was diluted with water (50 mL). The water phase was adjusted to pH=5 and extracted with DCM (80 mL×3). The organic phase was dried with $Na_2SO_4$, filtered and concentrated to give 5-[2-(tert-butoxycarbonylamino)ethylamino]-6-fluoro-pyrazolo[1,5-a]pyrimidine-3-carboxylic acid (680 mg, 1.56 mmol, 95.33% yield, 77.691% purity) as a gum.

LCMS m/z=340.0 $[M+H]^+$).

tert-butyl N-[2-[(6-fluoro-3-iodo-pyrazolo[1,5-a]pyrimidin-5-yl)amino]ethyl]carbamate

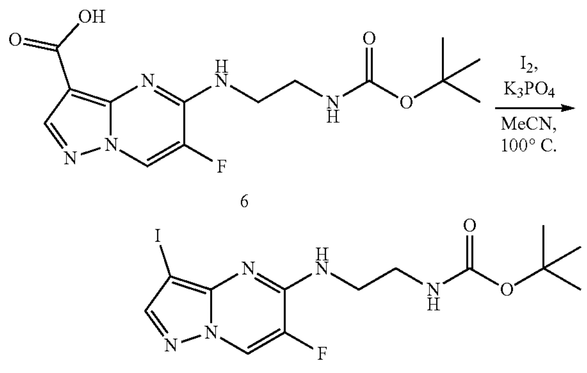

6

7

A mixture of 5-[2-(tert-butoxycarbonylamino)ethylamino]-6-fluoro-pyrazolo[1,5-a]pyrimidine-3-carboxylic acid (640 mg, 1.89 mmol, 1 eq), $K_3PO_4$ (800.72 mg, 3.77 mmol, 2 eq) and $I_2$ (478.71 mg, 1.89 mmol, 379.93 μL, 1 eq) in ACN (10 mL) was degassed and purged with $N_2$ for 3 times, and then the mixture was stirred at 100° C. for 1 hr under $N_2$ atmosphere. TLC indicated Reactant 6 was consumed completely. The reaction mixture was concentrated under reduced pressure to give a residue. The residue was purified by column chromatography ($SiO_2$, Petroleum ether/Ethyl acetate=1/0 to 1/1) to give tert-butyl N-[2-[(6-fluoro-3-iodo-pyrazolo[1,5-a]pyrimidin-5-yl)amino]ethyl]carbamate (500 mg, 1.09 mmol, 57.77% yield, 91.79% purity) as a solid.

LCMS m/z=422.0 $[M+H]^+$).

$^1H$ NMR (400 MHz, DMSO-$d_6$) δ=9.08-8.97 (m, 1H), 7.87 (s, 1H), 7.78 (s, 1H), 6.90 (s, 1H), 3.49-3.44 (m, 2H), 3.27-3.20 (m, 2H), 1.37 (s, 9H).

tert-butyl N-[2-[3-[2-(cyclopropoxy)-3-pyridyl]-6-fluoro-pyrazolo[1,5-a]pyrimidin-5-yl]amino]ethyl]carbamate

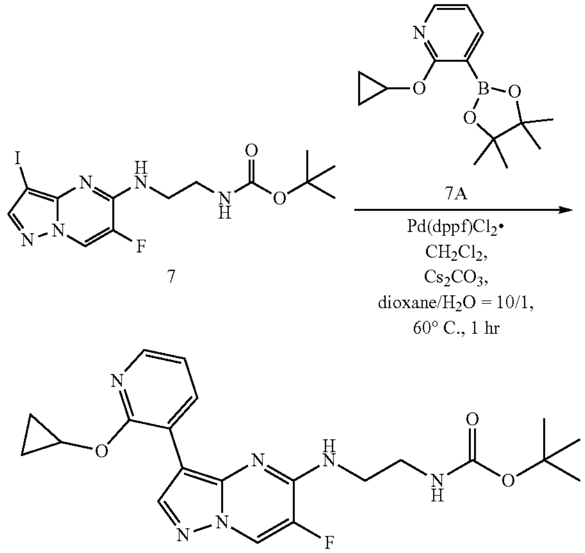

7

I-124

A mixture of tert-butyl N-[2-[(6-fluoro-3-iodo-pyrazolo[1,5-a]pyrimidin-5-yl)amino]ethyl]carbamate (80 mg, 189.93 μmol, 1 eq), 2-(cyclopropoxy)-3-(4,4,5,5-tetramethyl-1,3,2-dioxaborolan-2-yl)pyridine (123.99 mg, 474.82 μmol, 2.5 eq), $Cs_2CO_3$ (123.77 mg, 379.86 μmol, 2 eq) and $Pd(dppf)Cl_2 \cdot CH_2Cl_2$ (15.51 mg, 18.99 μmol, 0.1 eq) in dioxane (1 mL) and $H_2O$ (0.1 mL) was degassed and purged with $N_2$ for 3 times, and then the mixture was stirred at 60° C. for 1 hr under $N_2$ atmosphere. LCMS showed desired compound was detected. The reaction mixture was filtered and concentrated under reduced pressure to give a residue. The residue was purified by prep-HPLC (column: Phenomenex luna C18 250 mm*100 mm*10 um; mobile phase: [$H_2O$ (10 mM $NH_4HCO_3$)-ACN]; gradient: 37%-67% B over 10.0 min). The pure fractions were lyophilized to dryness to give tert-butyl N-[2-[[3-[2-(cyclopropoxy)-3-pyridyl]-6-fluoro-pyrazolo[1,5-a]pyrimidin-5-yl]amino]ethyl]carbamate (I-124, 22.85 mg, 53.33 μmol, 28.08% yield, 100% purity) as a solid.

LCMS m/z=429.2 $[M+H]^+$).

$^1H$ NMR (400 MHz, DMSO-$d_6$) δ=9.12-9.00 (m, 1H), 8.91-8.84 (m, 1H), 8.31 (s, 1H), 8.03-7.99 (m, 1H), 7.95-

7.88 (m, 1H), 7.15-7.09 (m, 1H), 7.03-6.95 (m, 1H), 4.44-4.37 (m, 1H), 3.54-3.47 (m, 2H), 3.30-3.23 (m, 2H), 1.37 (s, 9H), 0.82-0.76 (m, 4H).

Example 99: Synthesis of Compound I-125 tert-butyl N-[2-[[6-fluoro-3-(2-tetrahydrofuran-3-yloxy-3-pyridyl)pyrazolo[1,5-a]pyrimidin-5-yl]amino]ethyl]carbamate

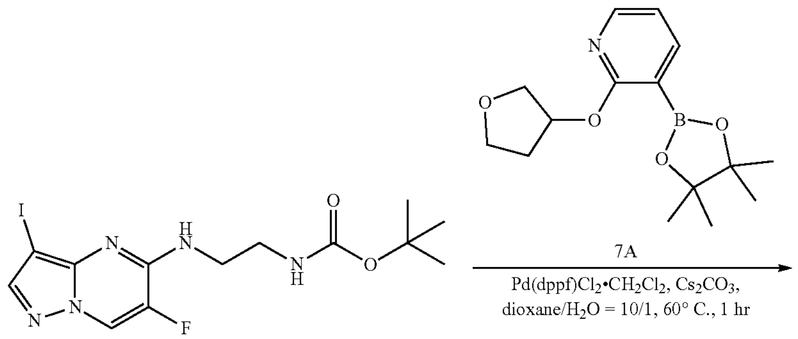

7

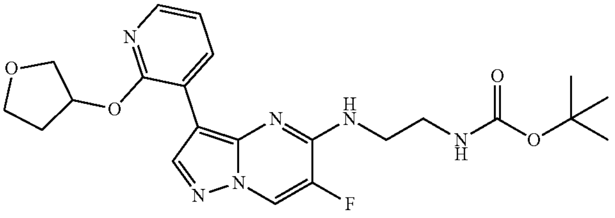

I-125

A mixture of tert-butyl N-[2-[(6-fluoro-3-iodo-pyrazolo[1,5-a]pyrimidin-5-yl)amino]ethyl]carbamate (80 mg, 189.93 μmol, 1 eq), 2-tetrahydrofuran-3-yloxy-3-(4,4,5,5-tetramethyl-1,3,2-dioxaborolan-2-yl)pyridine (165.89 mg, 569.79 μmol, 3 eq), $Cs_2CO_3$ (123.77 mg, 379.86 μmol, 2 eq) and Pd(dppf)$Cl_2$·$CH_2Cl_2$ (15.51 mg, 18.99 μmol, 0.1 eq) in dioxane (1 mL) and $H_2O$ (0.1 mL) was degassed and purged with $N_2$ for 3 times, and then the mixture was stirred at 60° C. for 1 hr under $N_2$ atmosphere. LCMS showed Reactant 7 was consumed completely. The reaction mixture was concentrated under reduced pressure to give a residue. The residue was purified by prep-HPLC (column: Waters Xbridge BEH C18 100*25 mm*10 um; mobile phase: [$H_2O$ (0.05% $NH_3H_2O$)-ACN]; gradient: 34%-64% B over 10.0 min) and lyophilized to dryness to give tert-butyl N-[2-[[6-fluoro-3-(2-tetrahydrofuran-3-yloxy-3-pyridyl)pyrazolo[1,5-a]pyrimidin-5-yl]amino]ethyl]carbamate (I-125, 33.83 mg, 73.60 μmol, 38.75% yield, 99.743% purity) as a solid. LCMS m/z=459.3 $[M+H]^+$.

SFC $t_{R1}$=1.608 min; 49.718%, $t_{R2}$=1.776 min; 50.282%. $^1$H NMR 400 MHz, DMSO-$d_6$) δ=9.10-9.02 (m, 1H), 8.94-8.85 (m, 1H), 8.43 (s, 1H), 7.98-7.88 (m, 2H), 7.13-7.05 (m, 1H), 7.01-6.93 (m, 1H), 5.71-5.64 (m, 1H), 4.00-3.89 (m, 2H), 3.88-3.79 (m, 2H), 3.55-3.46 (m, 2H), 3.29-3.23 (m, 2H), 2.33-2.20 (m, 1H), 2.17-2.06 (m, 1H), 1.37 (s, 9H).

Example 100: Synthesis of Compound I-127 tert-butyl N-[2-[[6-fluoro-3-(2-tetrahydropyran-4-yloxy-3-pyridyl)pyrazolo[1,5-a]pyrimidin-5-yl]amino]ethyl]carbamate

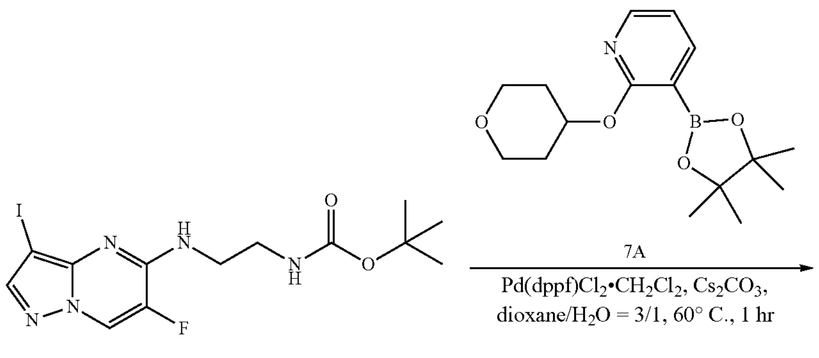

7

-continued

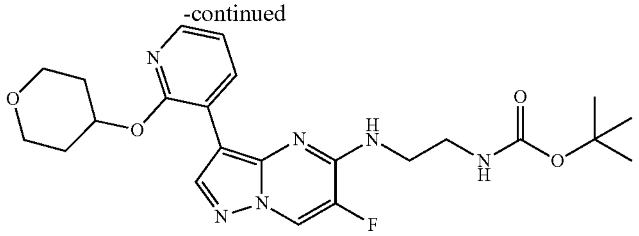

I-127

A mixture of tert-butyl N-[2-[(6-fluoro-3-iodo-pyrazolo[1,5-a]pyrimidin-5-yl)amino]ethyl]carbamate (80 mg, 189.93 μmol, 1 eq), 2-tetrahydropyran-4-yloxy-3-(4,4,5,5-tetramethyl-1,3,2-dioxaborolan-2-yl)pyridine (173.89 mg, 569.79 μmol, 3 eq) Pd(dppf)$Cl_2$·$CH_2Cl_2$ (31.02 mg, 37.99 μmol, 0.2 eq) and $Cs_2CO_3$ (185.65 mg, 569.79 μmol, 3 eq) in dioxane (1.8 mL) and $H_2O$ (0.6 mL) was degassed and purged with $N_2$ for 3 times, and then the mixture was stirred at 60° C. for 2 hr under $N_2$ atmosphere. LCMS showed that desired MS was found. The reaction mixture was concentrated under reduced pressure to give a residue. The residue was purified by FCC (ISCO®; 4 g SepaFlash® Silica Flash Column, Eluent of 0~40% Ethyl acetate/Petroleum ether gradient @ 25 mL/min) to give the product. Then the product was further purified by pre-HPLC (Column: Phenomenex luna C18 150*25*10 um; mobile phase: [$H_2O$ (0.225% FA)-ACN]; gradient: 39%-69% B over 10.0 min). The pure fractions were collected and the volatiles were removed under vacuum. The residue was partitioned between acetonitrile (20 mL) and water (100 mL). The solution was lyophilized to dryness to give tert-butyl N-[2-[[6-fluoro-3-(2-tetrahydropyran-4-yloxy]-3-pyridyl)pyrazolo[1,5-a]pyrimidin-5-yl]amino]ethyl]carbamate (I-127, 42.57 mg, 90.09 μmol, 47.43% yield, 100% purity) as a powder.

LCMS m/z=473.3 $[M+H]^+$).

$^1H$ NMR (400 MHz, DMSO-$d_6$) δ=9.06 (d, J=6.4 Hz, 1H), 8.92-8.82 (m, 1H), 8.47 (s, 1H), 7.98-7.94 (m, 1H), 7.93-7.86 (m, 1H), 7.10-7.02 (m, 1H), 7.01-6.94 (m, 1H), 5.44 -5.30 (m, 1H), 3.91-3.81 (m, 2H), 3.58-3.49 (m, 4H), 3.28-3.22 (m, 2H), 2.11-2.05 (m, 2H), 1.82-1.71 (m, 2H), 1.36 (s, 9H).

Example 101: Synthesis of Compound I-129

6-chloro-3-[2-(cyclopropoxy)-3-pyridyl]imidazo[1,2-b]pyridazine

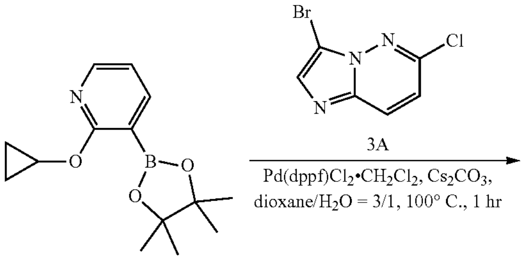

3

-continued

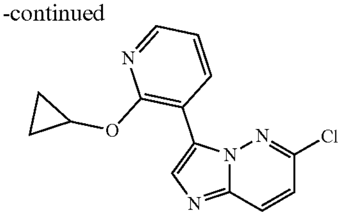

4

A mixture of 2-(cyclopropoxy)-3-(4,4,5,5-tetramethyl-1,3,2-dioxaborolan-2-yl)pyridine (400 mg, 1.53 mmol, 1 eq), 3-bromo-6-chloro-imidazo[1,2-b]pyridazine (356.10 mg, 1.53 mmol, 1 eq), Pd(dppf)$Cl_2$·$CH_2Cl_2$ (62.55 mg, 76.59 μmol, 0.05 eq) and $Cs_2CO_3$ (1.50 g, 4.60 mmol, 3 eq) in dioxane (3 mL)/$H_2O$ (1 mL) was degassed and purged with $N_2$ for 3 times, and then the mixture was stirred at 100° C. for 1 hr under $N_2$ atmosphere. LCMS showed that desired MS was found. The reaction mixture was concentrated under reduced pressure to give a residue. The residue was purified by FCC (ISCO®; 4 g SepaFlash® Silica Flash Column, Eluent of 0~20% Ethyl acetate/Petroleum ether gradient @ 25 mL/min) to give 6-chloro-3-[2-(cyclopropoxy)-3-pyridyl]imidazo[1,2-b]pyridazine (260 mg, 737.53 μmol, 48.15% yield, 81.331% purity) as a solid.

LCMS m/z=287.1 $[M+H]^+$.

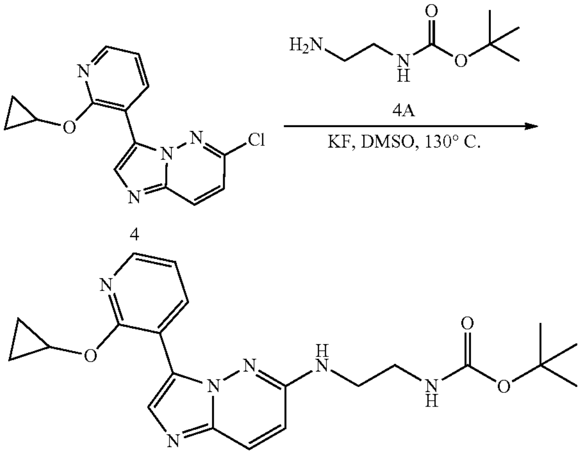

I-129

To a mixture of 6-chloro-3-[2-(cyclopropoxy)-3-pyridyl]imidazo[1,2-b]pyridazine (115 mg, 401.09 μmol, 1 eq) and KF (46.60 mg, 802.19 μmol, 2 eq) in DMSO (0.5 mL) was added tert-butyl N-(2-aminoethyl)carbamate (77.11 mg, 481.31 μmol, 75.90 μL, 1.2 eq). The mixture was stirred at 130° C. for 1 hr. LCMS showed that desired MS was found. The reaction mixture was concentrated under reduced pressure to give a residue. The residue was purified by pre-HPLC (Column: WePure Biotech XPT PHS C18 150*25*7 um; mobile phase: [$H_2O$ (0.225% FA)-ACN]; gradient: 14%-44% B over 10.0 min). The pure fractions were collected and the volatiles were removed under vacuum. The residue was partitioned between acetonitrile (20 mL) and water (100 mL). The solution was lyophilized to dryness to give tert-butyl N-[2-[[3-[2-(cyclopropoxy)-3-pyridyl]imidazo[1,2-b]pyridazin-6-yl]amino]ethyl]carbamate (I-129, 46.76 mg, 111.82 μmol, 27.88% yield, 98.155% purity) as a solid.

LCMS m/z=411.0 $[M+H]^+$).

$^1$H NMR (400 MHz, DMSO-$d_6$) δ=8.87 (d, J=7.4 Hz, 1H), 8.19-8.10 (m, 1H), 7.84-7.71 (m, 2H), 7.23-7.14 (m, 1H), 7.08 (t, J=4.8 Hz, 1H), 6.89 (t, J=5.0 Hz, 1H), 6.70 (d, J=9.8 Hz, 1H), 4.45-4.34 (m, 1H), 3.31-3.28 (m, 2H), 3.23-3.18 (m, 2H), 1.37 (s, 9H), 0.82-0.70 (m, 4H).

Compounds I-86, I-87, I-88, I-89, I-90, I-91, I-92, I-93, and I-94 were prepared according to the procedures described above.

Example 102: Evaluation of the Biological Activity of Compounds Disclosed Herein Expression and Purification of AAK1, BIKE and GAK Kinase Domain Proteins DNA fragments encoding the kinase domain of human AAK1 (amino acids T27-A365), BIKE (amino acids S38-E345) (K320A, K321A) and GAK (amino acids Q25-N335) sequences were independently cloned into pET24a with an N-terminal 6His-tag followed by a TEV cleavage and Avi site.

The recombinant proteins were independently expressed in *Escherichia coli* BL21(DE3) cells cultured in Luria-Bertani (LB) medium until OD600 reached 0.6-0.8, then cooled to 15° C. and supplemented with 0.5 mM isopropyl 1-thio-D-galactopyranoside (IPTG) induce protein expression 16 h. Cells were harvested and resuspended in lysis buffer (50 mM HEPES pH 7.5, 500 mM NaCl, 5 mM imidazole, 5% glycerol, 0.5 mM Tris (2-carboxyethyl) phosphine (TCEP), complete Protease Inhibitor Tablet (Roche)) and lysed by microfluidics high pressure homogenizer (UH-06, Union-Biotech). Proteins were purified using Ni-Affinity chromatography (His FF column, Bestchrom) and eluted stepwise in binding buffer with 20-300 mM imidazole. Removal of the hexahistidine tag was performed at 4° C. overnight using recombinant TEV protease and reacted with BirA to obtain the corresponsing biotinylated-AAK1, BIKE or GAK proteins. Further separated in the reverse Strep column (Strep-Tactin®XT, IBA). The Biotin elution sample was collected containing untagged biotinylated protein was then purified by Ion-exchange chromatography (Mono Q 10/100 GL, Cytiva) and Size-exclusion chromatography (HiLoad 16/600 Superdex 200 pg, Cytiva). The pure protein was stored in a storage buffer 50 mM HEPES (pH 7.5), 300 mM NaCl, 5% glycerol at −80° C. Protein were characterized by SDS-PAGE, LC-MS and aSEC.

SPR Assay: Kinetics of AAK1 Kinase Inhibition

Surface plasmon resonance (SPR) experiments were carried out using a Biacore 8K+ with a SA chip at 25° C. (GE Healthcare). SPR assays were performed in the running buffer contains 10 mM HEPES (pH7.4), 150 mM NaCl, 2 mM MgCl2, 0.05% Tween-20, 2% DMSO. SPR assays of small molecule binding used biotinylated AAK1 (T27-A365) protein captured on SA chip. The protein was diluted to 50 μg/ml using running buffer. Before immobilization of protein, the sensor surface was conditioned with three one-minute injections of 1 M NaCl in 0.05 M NaOH with the rate of 10 μl/min. Then, the protein was injected over the chip at the rate of 5 l/min for 72 s. The sensor surface was blocked by injecting 50 M biocytin at the flow rate of 10 μl/min for 120 s. The Immobilization levels were typically 4800-5200 RU. Solvent correction solutions (running buffer with 1%-3% DMSO) were injected over sensor surface and the sensorgrams were recorded to get the solvent correction curve. Analytes were serially diluted to various concentrations with running buffer and injected for 180 s. The reasonable dissociation time was set according to the dissociation speed. The flow rate for binding assay is 30 μl/min. Binding sensorgrams were processed, solvent-corrected, and double-referenced using Biacore software. 1:1 binding kinetic model or steady state affinity model was used to fit the single-cycle kinetic curves to determine binding data (ka, kd, KD values).

AAK1 Psens Assay:

This example describes one illustrative method for determining the IC50 of the compounds of the present invention against AAK1 (amino acids T27-A365). AAK1 protein was dissolved at 20 nM in 1× enzyme solution (50 mM HEPES pH7.5, 10 mM MgCl2, 1 mM DTT, 1% glycerol, 0.5 mM EGTA, 0.01% Briji35, 0.02% BSA) and 12.5 ul was incubated with 250 nl DMSO or 250 nl compound in DMSO at 25° C. for 15 min. The reaction was started by addition of 12.5 ul of 30 uM AQT0759 (Assayquant, CSKS-AQT0759B) and 70 uM ATP which were diluted in 1× substrate dilution buffer (50 mM HEPES pH7.5, 10 mM MgCl2, 1 mM DTT, 1% glycerol, 0.5 mM EGTA, 0.01% Briji35). The rate of product formation (fluorescence signal with Excitation at 360 nm and Emission at 486 nm, Molecular Devices SpectraMax Paradigm) was measured every 2 minutes for 120 minutes at 25° C. and the RFU data was analyzed by linear regression. For IC50 determination, rates normalized relative to uninhibited controls were plotted against compound concentration and fitted using a 4 parameter non-linear regression curve fit (Y=Bottom+((Top−Bottom)/(1+((IC50/X)^Slope))), XLfit Model 205).

Bike Psens Assay:

This example describes one illustrative method for determining the IC50 of the compounds of the present invention against BIKE (amino acids S38-E345) (K320A, K321A). BIKE protein was dissolved at 20 nM in 1× enzyme solution (50 mM HEPES pH7.5, 10 mM MgCl2, 1 mM DTT, 1% glycerol, 0.5 mM EGTA, 0.01% Briji35, 0.02%, BSA) and 12.5 ul was incubated with 250 nl DMSO or 250 nl compound in DMSO at 25° C. for 15 min. The reaction was started by addition of 12.5 ul of 30 uM AQT0759 (Assayquant, CSKS-AQT0759B) and 40 uM ATP which were diluted in 1× substrate dilution buffer (50 mM HEPES pH7.5, 10 mM MgCl2, 1 mM DTT, 1% glycerol, 0.5 mM EGTA, 0.01% Briji35). The rate of product formation (fluorescence signal with Excitation at 360 nm and Emission at 486 nm, Molecular Devices SpectraMax Paradigm) was measured every 2 minutes for 120 minutes at 25° C. and the RFU data was analyzed by linear regression. For IC50 determination, rates normalized relative to uninhibited controls were plotted against compound concentration and fitted using a 4 parameter non-linear regression curve fit (Y=Bottom+((Top−Bottom)/(1+((IC50/X)^Slope))), XLfit Model 205).

GAK Psens Assay:

This example describes one illustrative method for determining the IC50 of the compounds of the present invention against GAK (amino acids Q25-N335). GAK protein was dissolved at 160 nM in 1× enzyme solution (50 mM HEPES pH7.5, 10 mM MgCl2, 1 mM DTT, 1% glycerol, 0.5 mM EGTA, 0.01% Briji35, 0.02% BSA) and 12.5 ul was incubated with 250 nl DMSO or 250 nl compound in DMSO at 25° C. for 15 min. The reaction was started by addition of 12.5 ul of 30 uM AQT0766 (Assayquant, CSKS-AQT0766B) and 140 uM ATP which were diluted in 1× substrate dilution buffer (50 mM HEPES pH7.5, 10 mM MgCl2, 1 mM DTT, 1% glycerol, 0.5 mM EGTA, 0.01% Briji35). The rate of product formation (fluorescence signal with Excitation at 360 nm and Emission at 486 nm, Molecular Devices SpectraMax Paradigm) was measured every 2 minutes for 120 minutes at 25° C. and the RFU data was analyzed by linear regression. For IC50 determination, rates normalized relative to uninhibited controls were plotted against compound concentration and fitted using a 4 parameter non-linear regression curve fit (Y=Bottom+((Top−Bottom)/(1+((IC50/X)^Slope))), XLfit Model 205).

pAP2M1 Cell-Based Assay (In-Cell Western):

Hela cells (ATCC #CRM-CCL-2) were transiently co-transfected with pLenti6.3-AP2M1 and pLenti6.3-AAK1 constructs (Plasmid ration @5:5) using FuGENE® HD Transfection Reagent (Promega #E2312) and were plated in 384-w plate (Corning #3764) at 5,500 cells/well in Dulbecco's Modified Eagle's Medium (Gibco #12100) supplemented with 10% fetal bovine serum (Invitrogen #10091148). 48 hr after transfection, cells were treated with compounds which with 3 folds dilution from top dose 10 uM for 11 doses or vehicle (DMSO) for 3 hr. After 3 hr treatment, the cells were fixed in 4% paraformaldehyde (Thermofisher #28908) for 30 min at room temperature (RT) and run on in-cell western. Antibodies used in ICW were Phospho-AP2M1 (Thr156) (D4F3) (CST #7399) (1:50 dilution), IRDye® 800CW Goat anti-Rabbit IgG Secondary Antibody (Li—COR #926-32211) (1:500 dilution). CellTag 700 Stain (Li—COR #926-41090) (1:500 dilution) was used as internal standard. The plate was read on Licor Odyssey CLx imaging system (LICOR) to acquire fluorescence intensity at 700 channel and 800 channel.

Data analysis: Fluorescence intensity at 700 channel served as internal standard and 800 channel were normalized with 700 channel. For IC50 determination, rates normalized relative to uninhibited controls were plotted against compound concentration and fitted using a 4 parameter non-linear regression curve fit (Y=Bottom+((Top−Bottom)/(1+((IC50/X)^Slope))), XLfit Model 205). The results are provided in Table 2.

TABLE 2

Biological Activity of Evaluated Compounds

| Compound ID | AAK1 pSENs:$EIC_{50}$ (nM)[1] | AAK1 In-cell Western:$IC_{50}$ (nM)[1] | BIKE pSENs:$IC_{50}$ (nM)[1] | GAK pSENs:$IC_{50}$ (nM)[1] | AAK1:GAK pSENs Selectivity[2] |
|---|---|---|---|---|---|
| RC-1 | 8.68 | 157 | 84.6 | 1050 | 0.0083 |
| LP-935509 | 5.07 | | 33.3 | 720 | 0.0070 |
| I-1 | B | D | D | E | A |
| I-2 | A | B | C | E | A |
| I-3 | A | D | B | D | B |
| I-4 | B | D | D | D | C |
| I-5 | A | C | A | D | B |
| I-6 | A | D | A | E | A |
| I-8 | A | A | A | C | B |
| I-9 | A | B | A | C | B |
| I-10 | A | D | C | E | A |
| I-11 | A | C | C | E | A |
| I-12 | A | C | B | D | A |
| I-13 | A | A | A | B | B |
| I-13-5 | A | A | B | C | B |
| I-14 | A | C | C | D | A |
| I-15 | A | B | C | C | B |
| I-16 | A | A | A | B | B |
| I-16-7 | A | A | B | B | B |
| I-17 | A | D | E | E | B |
| I-18 | A | C | D | E | A |
| I-19 | C | E | E | E | D |
| I-20 | C | E | E | D | D |
| I-21 | B | E | E | D | B |
| I-21-5 | A | C | C | C | B |
| I-22 | A | B | B | B | B |
| I-23 | B | E | E | E | B |
| I-24 | B | E | E | E | B |
| I-25 | A | E | C | E | A |
| I-26 | A | D | D | E | A |
| I-27 | A | C | C | E | A |
| I-28 | A | E | B | E | A |
| I-29 | B | E | E | D | B |
| I-30 | B | E | D | E | A |
| I-31 | C | E | C | D | D |
| I-32 | A | E | B | E | A |
| I-33 | E | E | E | E | D |
| I-34 | A | C | C | E | A |
| I-35 | B | E | E | E | B |
| I-36 | A | D | B | E | A |
| I-37 | A | D | D | D | A |
| I-38 | A | E | C | E | A |
| I-39 | A | D | C | E | A |

TABLE 2-continued

| Biological Activity of Evaluated Compounds | | | | | |
|---|---|---|---|---|---|
| Compound ID | AAK1 pSENs:$EIC_{50}$ (nM)[1] | AAK1 In-cell Western:$IC_{50}$ (nM)[1] | BIKE pSENs:$IC_{50}$ (nM)[1] | GAK pSENs:$IC_{50}$ (nM)[1] | AAK1:GAK pSENs Selectivity[2] |
| I-40 | C | E | E | E | B |
| I-41 | C | E | E | E | B |
| I-41-4C | E | E | E | E | D |
| I-41-5 | C | E | E | E | C |
| I-41-6 | C | E | E | E | B |
| I-42 | A | D | C | E | A |
| I-43 | E | E | E | E | D |
| I-44 | E | E | E | E | D |
| I-45 | E | E | E | E | E |
| I-46 | E | E | E | D | E |
| I-47 | E | E | E | E | E |
| I-48 | D | E | E | E | D |
| I-49 | E | E | E | | |
| I-50 | A | C | D | E | A |
| I-51 | A | C | D | D | A |
| I-52 | A | C | D | E | A |
| I-53 | A | C | D0 | E | A |
| I-54 | D | E | E | E | C |
| I-55 | C | E | E | E | D |
| I-56 | C | E | E | E | C |
| I-57 | B | E | E | D | C |
| I-58 | A | D | C | E | A |
| I-59 | A | E | D | E | A |
| I-60 | B | E | D | E | C |
| I-61 | A | D | B | C | B |
| I-62 | A | E | C | E | A |
| I-63 | A | B | B | E | A |
| I-64 | A | B | B | E | A |
| I-65 | A | C | C | E | A |
| I-66 | C | D | E | D | D |
| I-67 | D | E | E | E | C |
| I-68 | B | D | E | E | A |
| I-69 | A | D | C | E | A |
| I-70 | A | D | B | D | B |
| I-71 | A | D | D | D | B |
| I-72 | A | D | C | E | A |
| I-73 | A | D | D | E | A |
| I-83 | A | D | | E | A |
| I-84 | C | E | | E | B |
| I-84-6 | C | E | E | E | B |
| I-85 | D | E | E | E | C |
| I-86 | A | C | C | E | A |
| I-87 | A | C | B | D | A |
| I-88 | A | E | C | D | B |
| I-89 | A | D | C | E | A |
| I-90 | A | D | B | D | A |
| I-91 | A | D | C | E | A |
| I-92 | E | E | E | E | E |
| I-93 | E | E | E | E | E |
| I-94 | A | D | C | E | A |
| I-95 | E | E | E | E | E |
| I-96 | E | E | E | E | E |
| I-97 | E | E | E | E | E |
| I-98 | C | E | D | E | C |
| I-99 | C | E | E | E | C |
| I-100 | D | E | E | E | D |
| I-101 | E | E | E | E | E |
| I-102 | A | D | B | E | A |
| I-102-2 | E | E | E | E | E |
| I-103 | E | E | E | E | E |
| I-104 | E | E | E | E | E |
| I-105 | E | E | E | E | E |
| I-106 | D | E | C | E | C |
| I-107 | E | E | E | E | E |
| I-108 | E | E | E | E | E |
| I-109 | A | C | B | E | A |
| I-110 | E | E | E | E | E |
| I-110-9 | E | E | E | E | E |
| I-111 | D | E | E | E | C |
| I-113 | A | C | D | E | A |
| I-114 | B | E | D | E | B |
| I-115 | A | D | D | E | A |
| I-116 | A | | B | E | A |
| I-117 | A | | A | D | A |

TABLE 2-continued

| Biological Activity of Evaluated Compounds | | | | | |
|---|---|---|---|---|---|
| Compound ID | AAK1 pSENs:$EIC_{50}$ (nM)[1] | AAK1 In-cell Western:$IC_{50}$ (nM)[1] | BIKE pSENs:$IC_{50}$ (nM)[1] | GAK pSENs:$IC_{50}$ (nM)[1] | AAK1:GAK pSENs Selectivity[2] |
| I-118 | A | | B | E | A |
| I-119 | B | E | D | E | B |
| I-120 | B | E | C | E | B |
| I-121 | B | E | D | E | B |
| I-122 | B | D | C | E | A |
| I-123 | C | E | E | E | C |
| I-124 | B | D | D | D | C |
| I-129 | A | D | B | C | C |

[1]A: 1-50 nM; B: 51-150 nM; C: 151-500 nM; D: 501-1500 nM; E: >1500 nM

[2]A: ≤0.015; B: 0.016-0.075; C: 0.076-0.15; D: 0.16-1.00; E: >1.00

Chemiluminescent Western Blotting (WB) Assay for hPBMCs

Frozen PBMCs from human (Sailybio) were thawed in a 37° C. water bath. The cells were resuspended in RPMI1640 medium (Invitrogen #11875) supplemented with heat inactivated 10% fetal bovine serum (Invitrogen #10091148). $2\times10^6$ cells were treated with compounds with final concentration at 10/1/0.1/0.01 uM or vehicle (DMSO) for 1 to 24 hr. After treatment, cells were harvested and lysed with RIPA lysis buffer (Beyotime #P0013B) containing protease inhibitor cocktail (Roche #04693132001) and Phosphatase inhibitor (Roche #4906837001). The total protein concentration was measured using a BCA protein assay kit (Thermofisher #23225). Samples were run on pre-cast 4-12% Bis-Tris gels (Thermofisher #WG1403BOX) with separation using the XCell4 SureLock gel apparatus (ThermoFisher). Antibodies used in WB were AAK1 (E8M3P) (CST #61527) (1:1000 dilution), Phospho-AP2M1 (Thr156) (D4F3) (CST #7399) (1:1000 dilution), AP2M1 (E5X6F) (CST #68196) (1:1000 dilution), GAPDH (CST, #2118) (1:3000 dilution). Images were acquired on ChemiDoc™ XRS+ System (BIO RAD).

Data analysis: The Image J software s (Version 1.8.0) was used for quantification. GAPDH served as loading controls and the other targets were normalized with GAPDH. For IC50 determination, % inh were calculated and fitted using a four parameter non-linear regression curve fit (Y=Bottom+((Top−Bottom)/(1+((IC50/X)^Slope))), GraphPad Prism (version 9)).

Several compounds of the disclosure demonstrated dose dependent reductions in pAP2M1 levels after 1 and 4 hrs of treatment, when normalized to DMSO vehicle control.

Example 75: Crystallization and Structure Determination

Co-crystallization of AAK1 (T27-A365) was often compound dependent; therefore, crystal structures with compounds of interest were obtained by co-crystallizing AAK1 (T27-A365) with a compound of AKK1-IN-1 that resulted in robust crystal growth. This compound is referred to as the parent compound. The complex was incubated on ice for 0.5 h and was then clarified by centrifugation. Crystallization experiments were carried out at 20° C. using the Sitting-drop, vapor-diffusion method. The Sitting drop consisted of 0.2 uL of protein overlaid with 0.2 μL of the reservoir solution (22% PEG 3350, 0.1 M Bis-Tris pH 6.75). Crystals appeared after 14 d. To promote crystal nucleation, some large crystals were crushed and used for streak seeding. Crystals of hAAK1 with the parent compound were transferred to a soaking drop consisting of a stabilizing solution (22% PEG 3350, 0.1 M Bis-Tris|pH 6.75) and 2-5 mM compound of interest. The crystals were harvested after 16 h and transferred briefly into the stabilizing solution plus 15% Glycerol and flash-cooled for cryodata collection.

Multiple compounds of the instant invention co-crystallized with AKK1 at resolutions of 1.5 to 3 angstroms (Å).

Example 76: Evaluation of Disclosed Compounds in Animal Models of DMD

Spontaneous disease models in mice can play a role in the discovery of novel therapies for the treatment of patients. For example, the dystrophin-deficient mdx mouse on the C57BL/10 genetic background (B10.mdx) and a more severe muscle disease is observed when the mdx mutation is crossed onto the DBA/2J genetic background (D2.mdx) (see: Hammers D W, Hart C C, Matheny M K, Wright L A, Armellini M, Barton E R, Sweeney H L. The D2.mdx mouse as a preclinical model of the skeletal muscle pathology associated with Duchenne muscular dystrophy. Sci Rep. 2020 Aug. 21; 10 (1): 14070.doi:10.1038/s41598-020-70987-y. PMID: 32826942; PMCID: PMC7442653).

The spontaneous B10:Dmd$^{mdx}$ mutant mouse, like DMD patients, does not express dystrophin. In addition to being dystrophic, the mdx mouse also shows a deficit in muscle regeneration, with the hallmark increase in total number of satellite cells that is observed in DMD patients. Thus, the B10:Dmd$^{mdx}$ mutant mouse is a useful model for studying Duchenne muscular dystrophy (DMD).

Based on this utility, the mdx mouse model is used to screen for compounds, which in combination with damaged muscle, re-initiate the regeneration process and increase muscle strength and function.

Compounds of the present disclosure have demonstrated activity in the spontaneous B10:Dmd$^{mdx}$ mutant mouse dosed either IP or PO.

What is claimed is:

1. A compound of Formula (IA'-3):

(IA'-3)

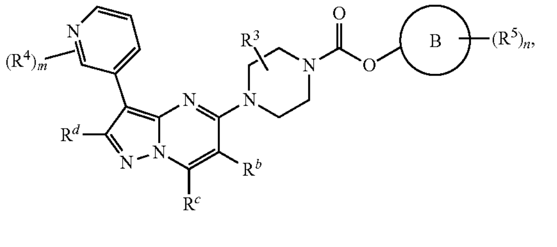

or pharmaceutically acceptable salt, deuterated form, or stereoisomer thereof, wherein:

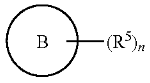 is 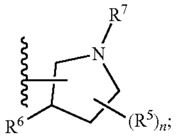;

$R^b$, $R^c$, and $R^d$ are each independently H, halogen, $C_{1-6}$ alkyl, —OH, —O—($C_{1-6}$ alkyl), —$NH_2$, —NH—($C_{1-6}$ alkyl), or —NH—($C_{1-6}$ alkyl)$_2$;

$R^3$ is H, halogen, $C_{1-6}$ alkyl, —CN, —C(O)$NH_2$, —C(O)OEt, or —C(O)OH;

each $R^4$ is independently halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N($C_{1-6}$ alkyl)$_2$, —NH-(cycloalkyl), or —NH-(heterocyclyl);

each $R^5$ is independently H, halogen, $C_{1-6}$ alkyl, $C_{1-6}$ heteroalkyl, O—$C_{1-6}$ alkyl, $C_{1-5}$ alkylene-cycloalkyl, or $C_{1-5}$ alkylene-heterocyclyl, or two $R^5$ form an oxo;

$R^6$ is H, $C_{1-6}$ alkyl, $C_{2-6}$ alkenyl, or $C_{2-6}$ alkynyl;

$R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2Ph$, $C_{1-5}$ alkylene-$NH_2$, $C_{1-5}$ alkylene-NH—($C_{1-6}$ alkyl), $C_{1-3}$ alkylene-N($C_{1-6}$ alkyl)$_2$, $C_{1-5}$ alkylene-NH—($CH_2Ph$), $C_{1-5}$ alkylene-C(O)—$NH_2$, $C_{1-5}$ alkylene-C(O)—NH—($C_{1-6}$ alkyl), $C_{1-5}$ alkylene-C(O)—N($C_{1-6}$ alkyl)$_2$, or 4- to 8-membered heterocyclyl;

m is 0, 1, 2, or 3; and n is 0, 1, or 2.

2. The compound of claim 1, wherein

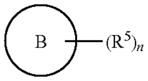 is 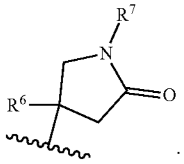.

3. The compound of claim 1, wherein $R^b$ is H, F, —OH, —OMe, or Me.

4. The compound of claim 1, wherein $R^c$ is H.

5. The compound of claim 1, wherein $R^d$ is H.

6. The compound of claim 1, wherein $R^3$ is H.

7. The compound of claim 1, wherein $R^4$ is —O—($C_{1-5}$ alkyl), —O—($C_{3-6}$ cycloalkyl), —O-(4- to 8-membered heterocyclyl), —NH—($C_{1-5}$ alkyl), —NH—($C_{3-4}$ cycloalkyl), or —NH-(4- to 8-membered heterocyclyl).

8. The compound of claim 7, wherein $R^4$ is:

—OH, 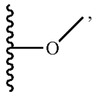, 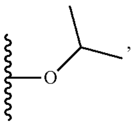, 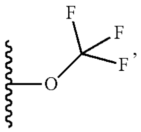, 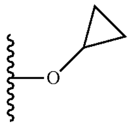, 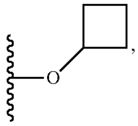, 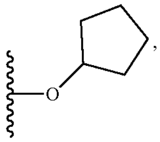, -continued

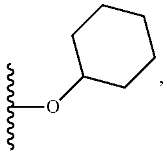, 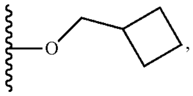, 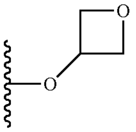,

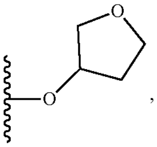, 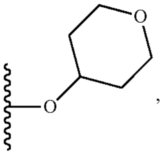, 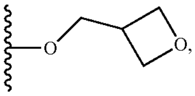,

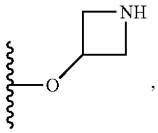, 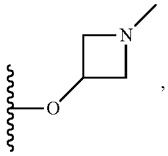,

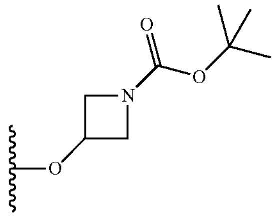, 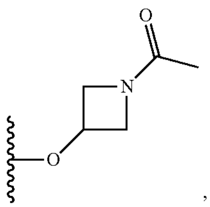,

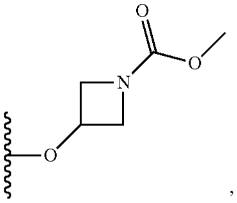, 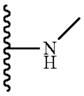, 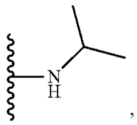,

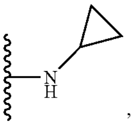, 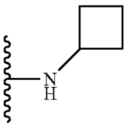, 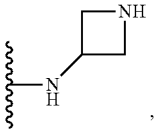,

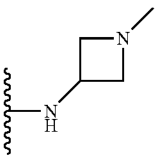, or 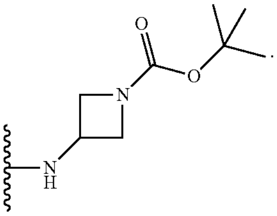.

9. The compound of claim 7, wherein $R^4$ is:

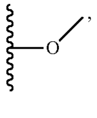, 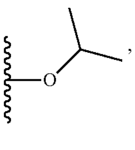, 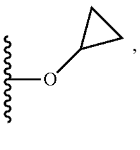,

-continued

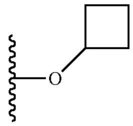, 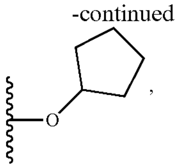, or 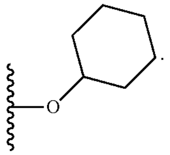.

10. The compound of claim 1, wherein two $R^5$ form an oxo.

11. The compound of claim 1, wherein each $R^5$ is H.

12. The compound of claim 1, wherein $R^6$ is H, Me, or —C≡CH.

13. The compound of claim 12, wherein $R^6$ is H or Me.

14. The compound of claim 1, wherein $R_7$ is H, $CH_3$, $CH_2CH_3$, i-Pr,

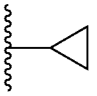,

—$CH_2CH_2$—OH, —$CH_2CH_2$—$OCH_3$, —$CH_2CH_2$—OBn, —$CH_2CH_2$—$NH_2$, —$CH_2CH_2$—NH—($CH_3$), —$CH_2CH_2$—N$(CH_3)_2$, —$CH_2C(O)$—$NH_2$, —$CH_2C(O)$—NH—($CH_3$), —$CH_2C(O)$—N$(CH_3)_2$,

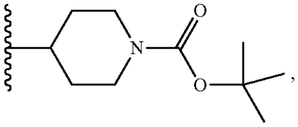,

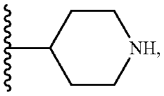, 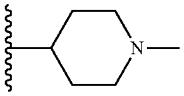,

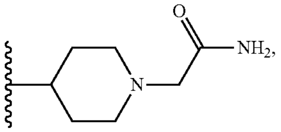, or 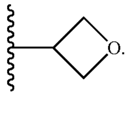.

15. The compound of claim 14, wherein $R^7$ is H or Me.

16. The compound of claim 1, wherein m is 1.

17. The compound of claim 1, wherein m is 2.

18. The compound of claim 1, wherein the compound has the structure of Formula (IA'-5):

(IA'-5)

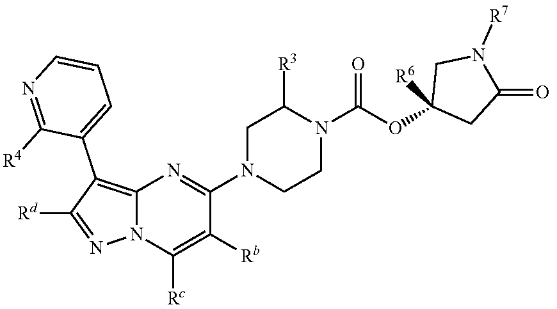

or pharmaceutically acceptable salt or deuterated form thereof, wherein:

$R^b$, $R^c$, and $R^d$ are each independently H, halogen, $C_{1-6}$ alkyl, —OH, —O—($C_{1-6}$ alkyl), —$NH_2$, —NH—($C_{1-6}$ alkyl), or —NH—$(C_{1-6}$ alkyl$)_2$;

$R^3$ is H, halogen, $C_{1-6}$ alkyl, —CN, —C(O)$NH_2$, —C(O)OEt, or —C(O)OH;

$R^4$ is halogen, OH, O—$C_{1-6}$ alkyl, O—$C_{1-6}$ haloalkyl, O-cycloalkyl, O-heterocyclyl, O—($C_{1-5}$ alkylene)-cycloalkyl, O—($C_{1-5}$ alkylene)-heterocyclyl, —NH—($C_{1-6}$ alkyl), —N$(C_{1-6}$ alkyl$)_2$, —NH-(cycloalkyl), or —NH-(heterocyclyl);

Reis H, $C_{1-6}$ alkyl, $C_{2-6}$ alkenyl, or $C_{2-6}$ alkynyl; and $R^7$ is H, $C_{1-6}$ alkyl, $C_{1-5}$ alkylene-OH, $C_{1-5}$ alkylene-O—($C_{1-6}$ alkyl), $C_{1-5}$ alkylene-O—$CH_2$Ph, $C_{1-5}$ alkylene-$NH_2$, $C_{1-5}$ alkylene-NH—($C_{1-6}$ alkyl), $C_{1-5}$ alkylene-N$(C_{1-6}$ alkyl$)_2$, $C_{1-5}$ alkylene-NH—($CH_2$Ph), $C_{1-5}$ alkylene-C(O)—$NH_2$, $C_{1-5}$ alkylene-C(O)—NH—($C_{1-6}$ alkyl), $C_{1-5}$ alkylene-C(O)—N$(C_{1-6}$ alkyl$)_2$, or 4- to 8-membered heterocyclyl.

19. The compound of claim 18, wherein $R^b$, $R^c$, and $R^d$ are each H.

20. The compound of claim 19, wherein $R^3$ is H.

21. The compound of claim 20, wherein $R^4$ is:

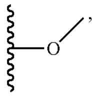, 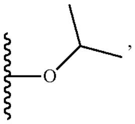, 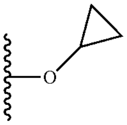,

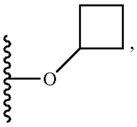, 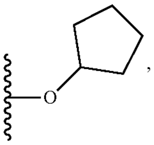, or

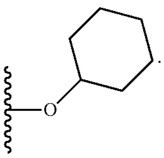.

22. The compound of claim 21, wherein $R^4$ is

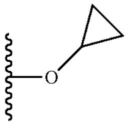 or 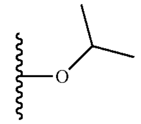.

23. The compound of claim 20, wherein $R^6$ is H and $R^7$ is H or Me.

24. The compound of claim 1, wherein the compound has the structure:
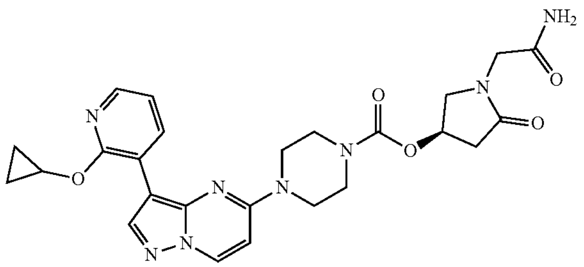
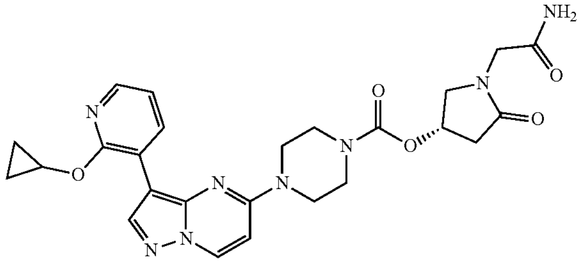
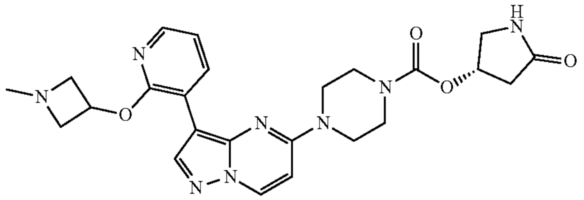
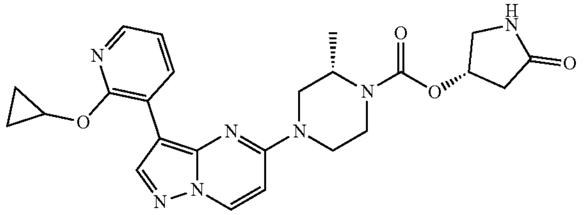
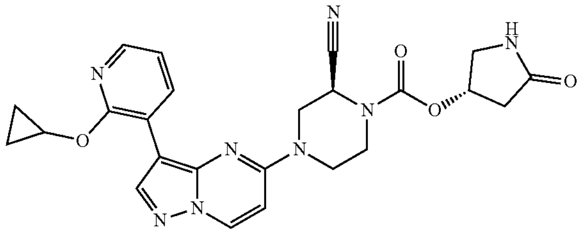
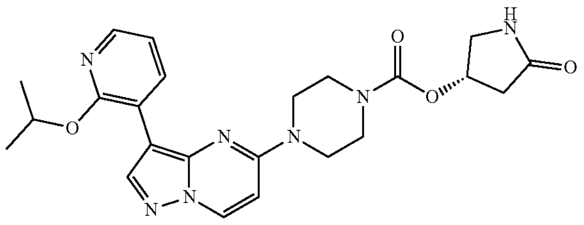
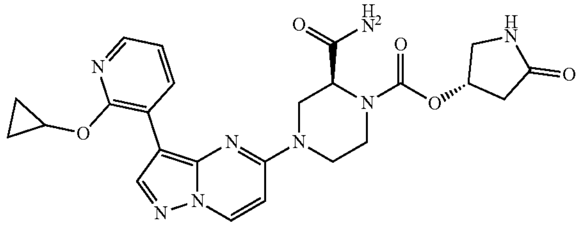
-continued
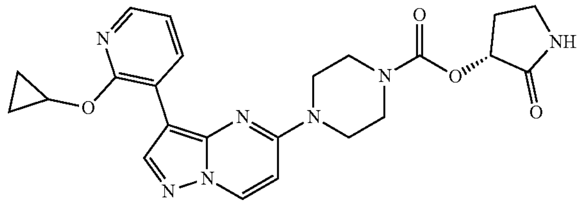
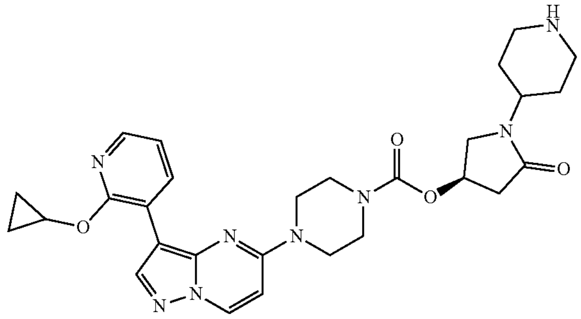
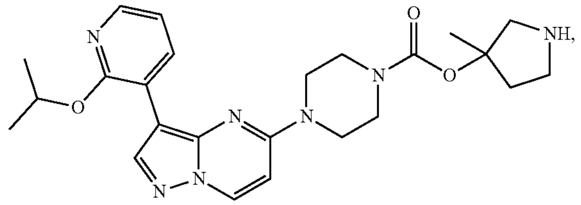
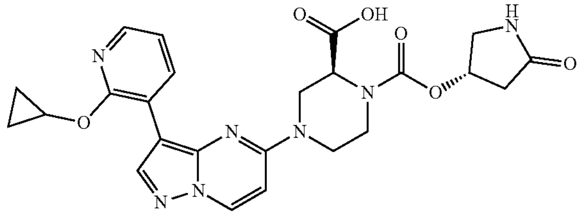
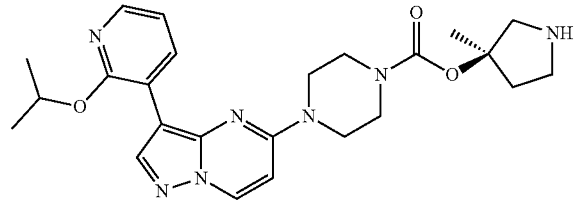
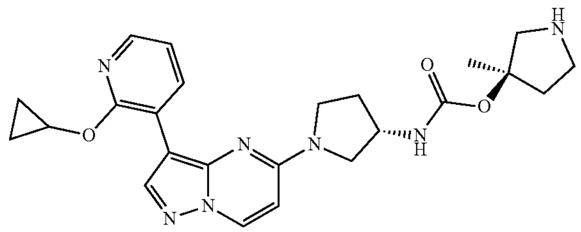
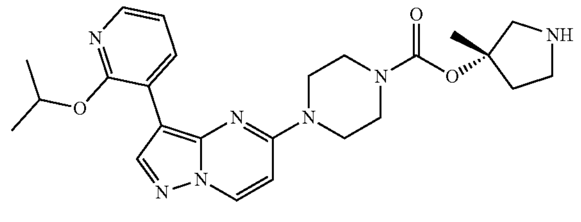

-continued
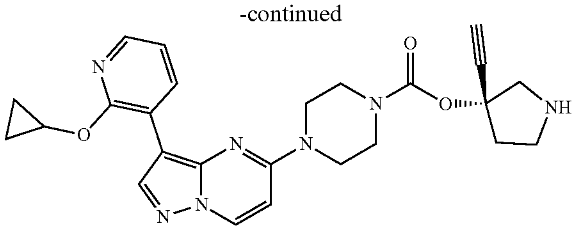
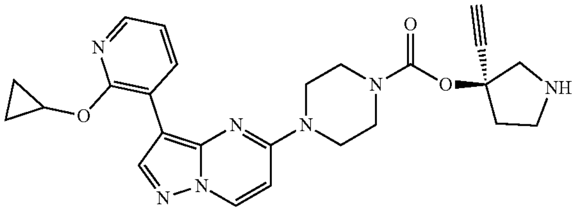
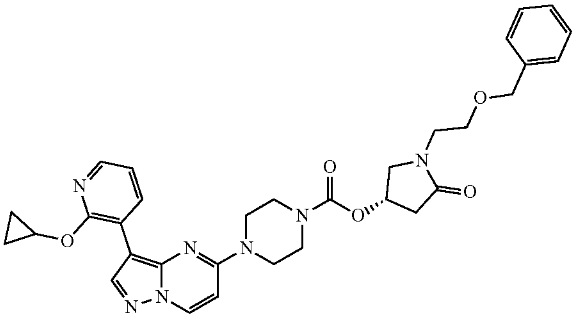
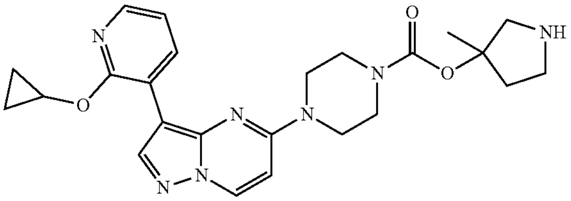
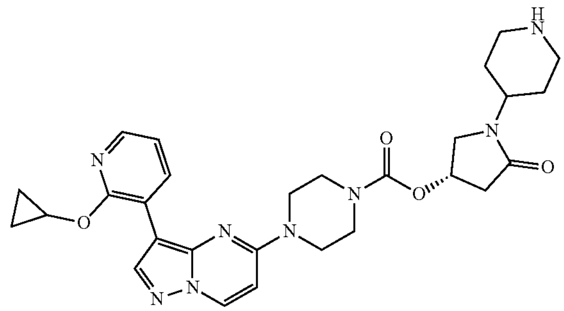
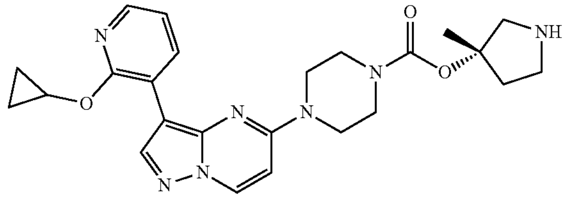
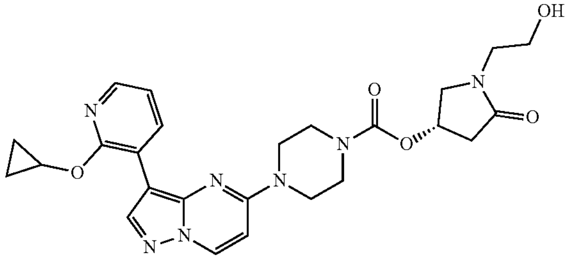
-continued
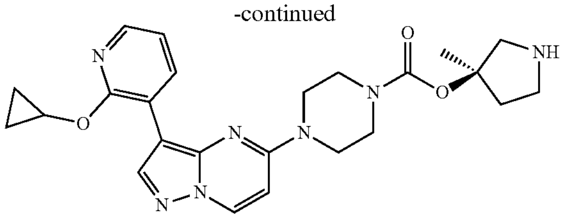
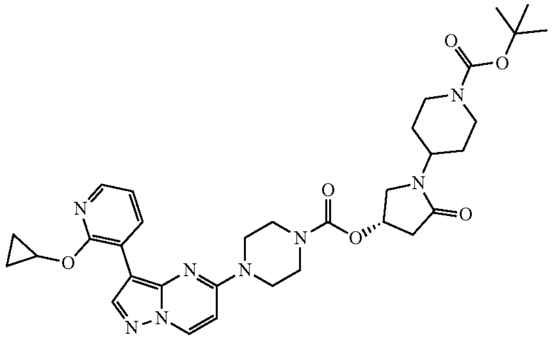
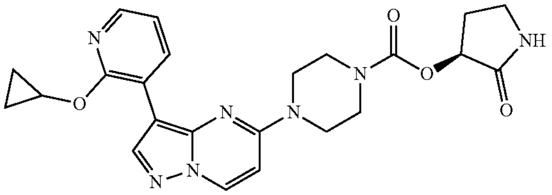
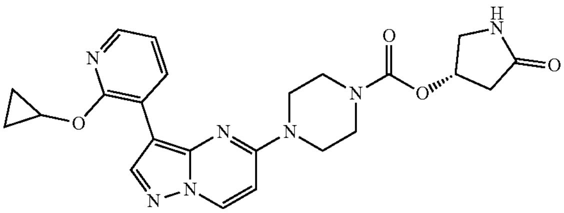
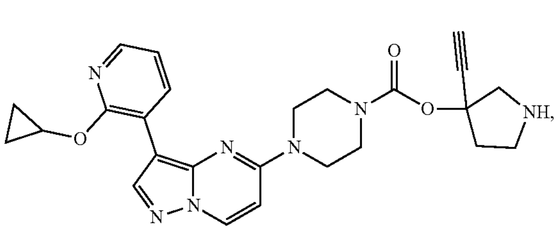
,
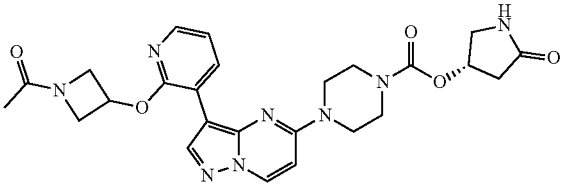
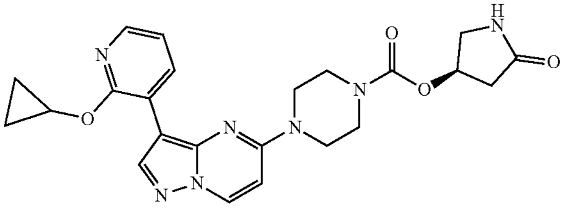

-continued
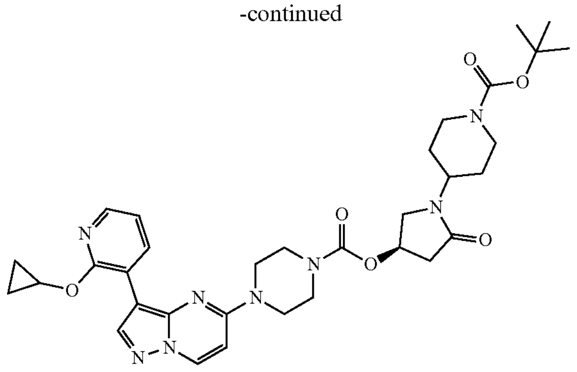
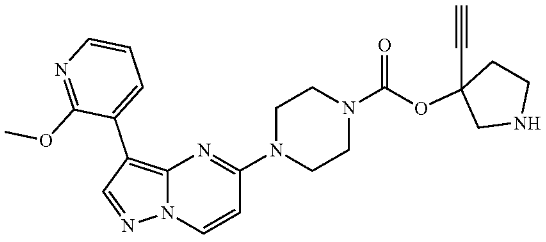
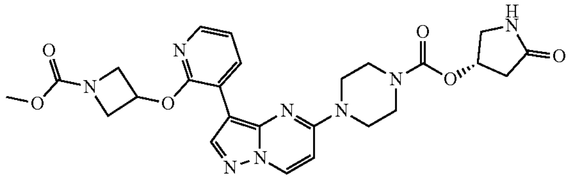
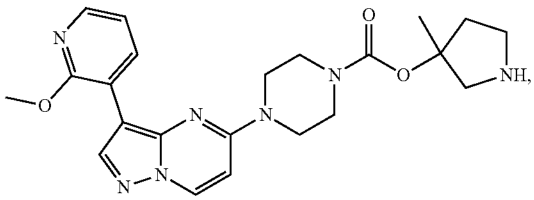
,
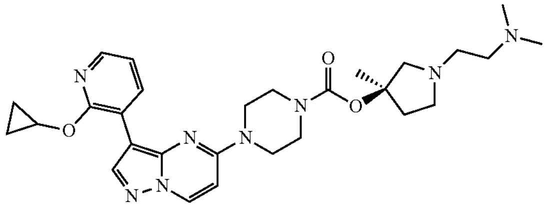
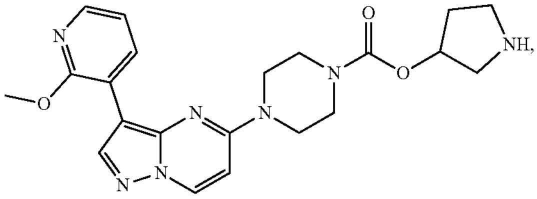
,
or a pharmaceutically acceptable salt thereof.
25. The compound of claim 24, wherein the compound has the structure:
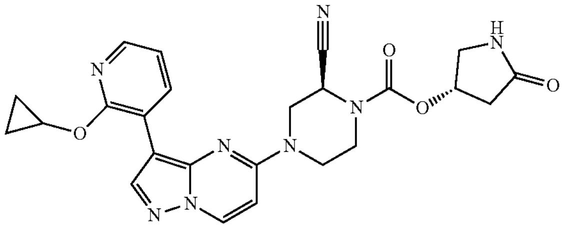
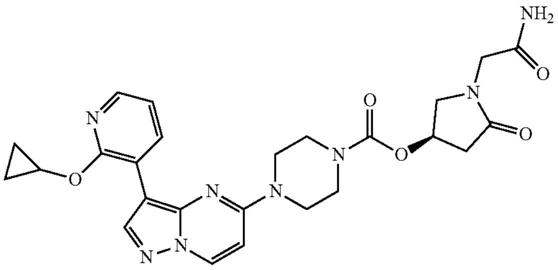
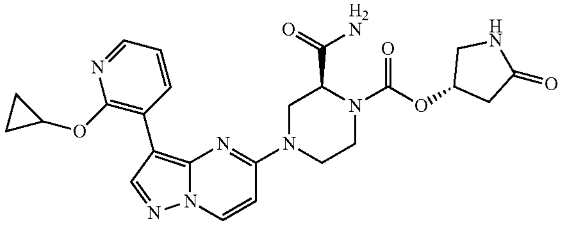
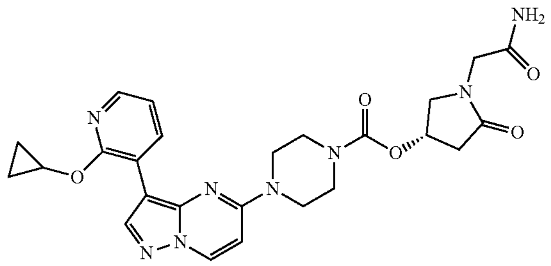
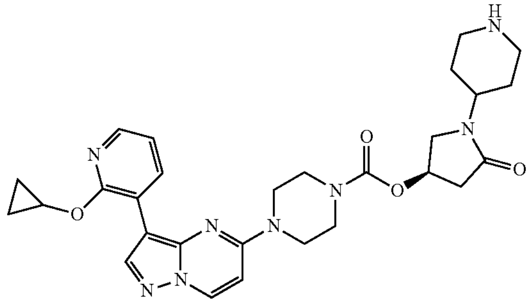
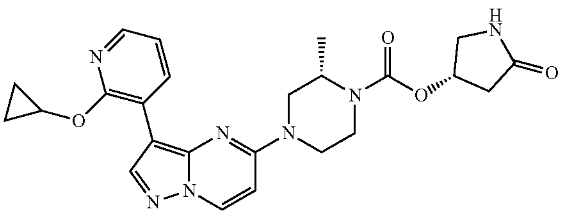

-continued
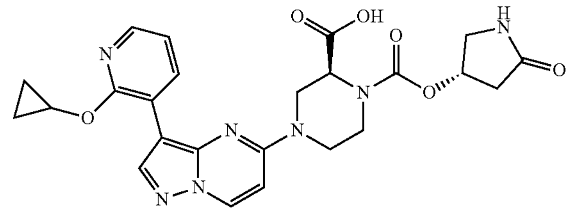
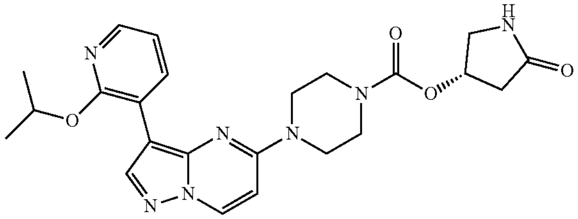
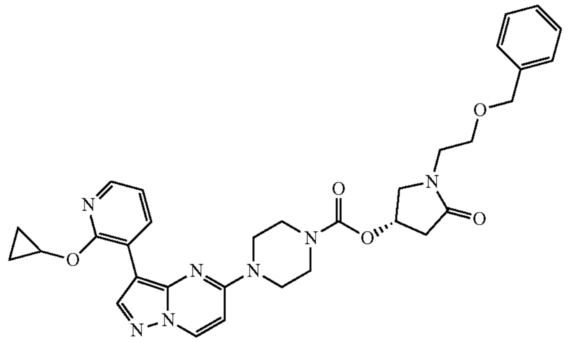
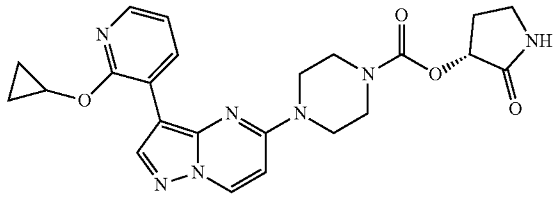
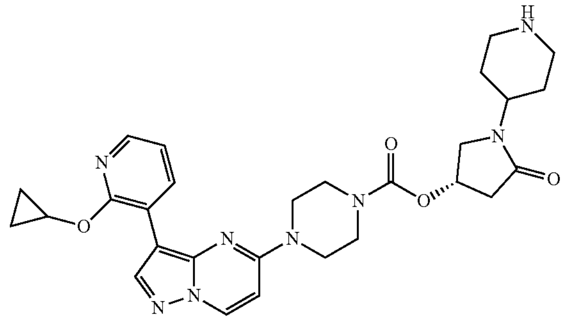
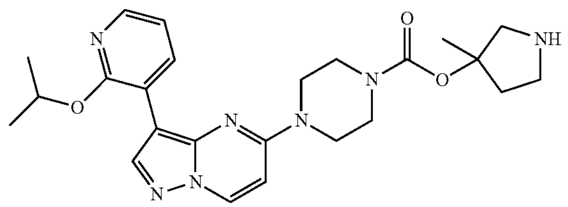
-continued
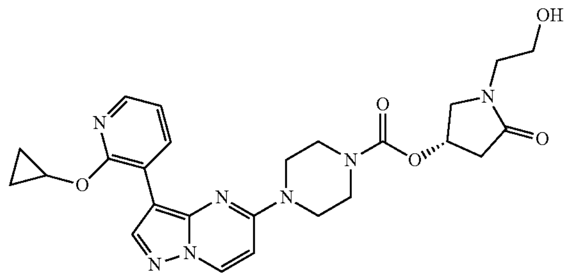
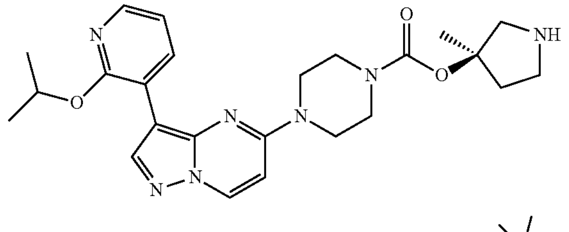
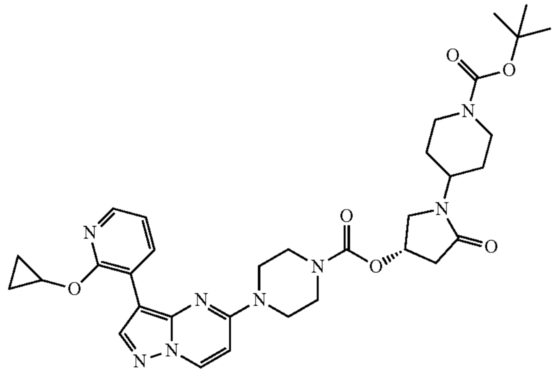
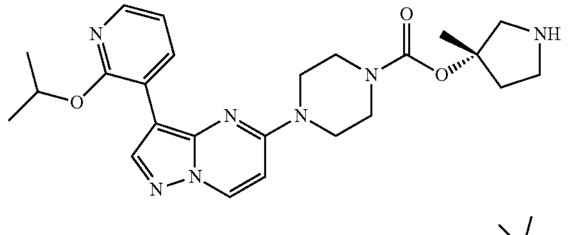
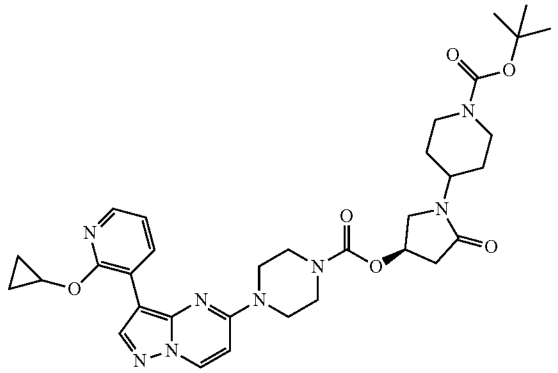
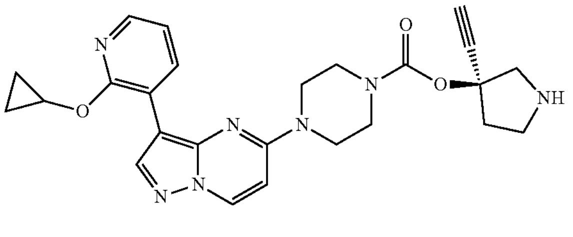
or a pharmaceutically acceptable salt thereof.

26. A pharmaceutical composition comprising the compound of claim 1, or a pharmaceutically acceptable salt thereof, and a pharmaceutically acceptable carrier or excipient.

27. Thecompound of claim 25, wherein the compound is:

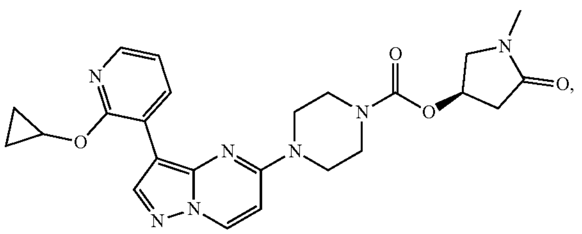 [SMILES: CN1C[C@H](OC(=O)N2CCN(c3ccn4ncc(-c5cccnc5OC5CC5)c4n3)CC2)CC1=O]

or a pharmaceutically acceptable salt thereof.

28. The compound of claim 25, wherein the compound is:

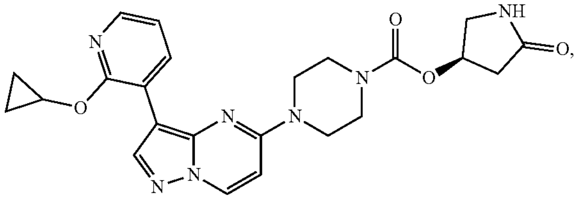 [SMILES: O=C1C[C@@H](OC(=O)N2CCN(c3ccn4ncc(-c5cccnc5OC5CC5)c4n3)CC2)CN1]

or a pharmaceutically acceptable saltthereof.

29. The compound of claim 25, wherein the compound is:

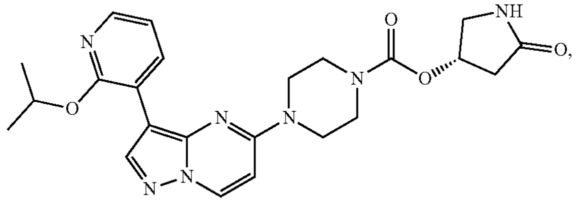 [SMILES: CC(C)Oc1ncccc1-c1cnn2ccc(N3CCN(C(=O)O[C@@H]4CNC(=O)C4)CC3)nc12]

or a pharmaceutically acceptable salt thereof.

30. The compound of claim 25, wherein the compound is:

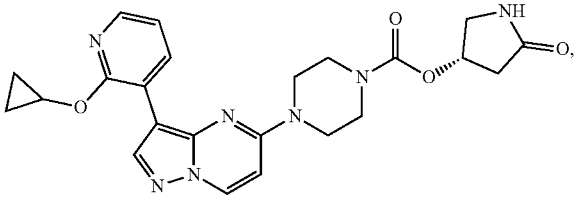 [SMILES: O=C1C[C@H](OC(=O)N2CCN(c3ccn4ncc(-c5cccnc5OC5CC5)c4n3)CC2)CN1]

or a pharmaceutically acceptable salt thereof.

31. The compound of claim 25, wherein the compound is:

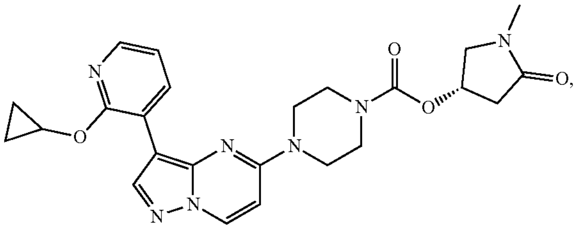 [SMILES: CN1C[C@@H](OC(=O)N2CCN(c3ccn4ncc(-c5cccnc5OC5CC5)c4n3)CC2)CC1=O]

or a pharmaceutically acceptable salt thereof.

32. The compound of claim 25, wherein the compound is:

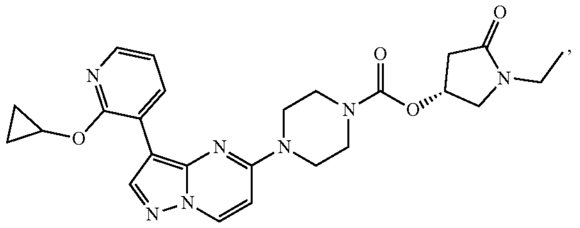 [SMILES: CCN1C[C@H](OC(=O)N2CCN(c3ccn4ncc(-c5cccnc5OC5CC5)c4n3)CC2)CC1=O]

or a pharmaceutically acceptable salt thereof.

33. The compound of claim 25, wherein the compound is:

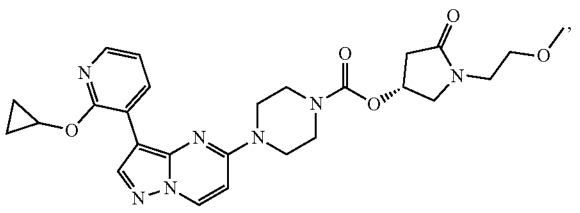 [SMILES: COCCN1C[C@H](OC(=O)N2CCN(c3ccn4ncc(-c5cccnc5OC5CC5)c4n3)CC2)CC1=O]

or a pharmaceutically acceptable salt thereof.

34. The compound of claim 25, wherein the compound is:

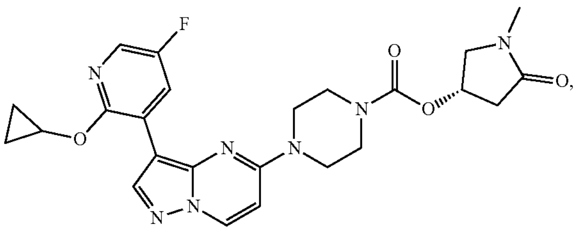 [SMILES: CN1C[C@@H](OC(=O)N2CCN(c3ccn4ncc(-c5cc(F)cnc5OC5CC5)c4n3)CC2)CC1=O]

or a pharmaceutically acceptable salt thereof.

35. The compound of claim 25, wherein the compound is:

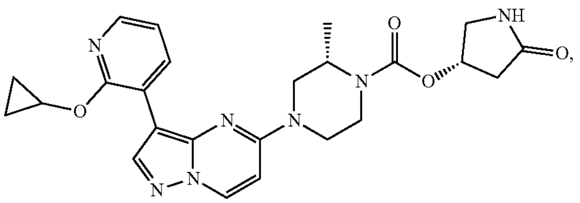 [SMILES: C[C@H]1CN(c2ccn3ncc(-c4cccnc4OC4CC4)c3n2)CCN1C(=O)O[C@@H]1CNC(=O)C1]

or a pharmaceutically acceptable salt thereof.

36. The compound of claim 25, wherein the compound is:
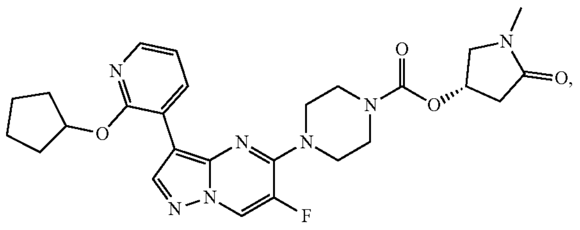 [SMILES: CN1C[C@@H](OC(=O)N2CCN(c3nc4c(-c5cccnc5OC5CCCC5)cnn4cc3F)CC2)CC1=O]
or a pharmaceutically acceptable salt thereof.
37. A pharmaceutically composition comprising the compound of claim 25, or a pharmaceutically acceptable salt thereof, and a pharmaceutically acceptable carrier or excipient.
* * * * *